United States Patent
Gardner et al.

(10) Patent No.: US 10,294,229 B2
(45) Date of Patent: May 21, 2019

(54) HETEROARYL SUBSTITUTED AMINOPYRIDINE COMPOUNDS

(71) Applicant: BRISTOL-MYERS SQUIBB COMPANY, Princeton, NJ (US)

(72) Inventors: Daniel S. Gardner, Furlong, PA (US); Joseph B. Santella, Springfield, PA (US); Venkatram Reddy Paidi, Bangalore (IN); Hong Wu, New Hope, PA (US); John V. Duncia, Newtown, PA (US); Satheesh Kesavan Nair, Bangalore (IN); John Hynes, Washington Crossing, PA (US); Xiao Zhu, Potomac, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/738,362

(22) PCT Filed: Jun. 23, 2016

(86) PCT No.: PCT/US2016/038858
§ 371 (c)(1),
(2) Date: Dec. 20, 2017

(87) PCT Pub. No.: WO2016/210034
PCT Pub. Date: Dec. 29, 2016

(65) Prior Publication Data
US 2018/0186799 A1    Jul. 5, 2018

(30) Foreign Application Priority Data

Jun. 24, 2015    (IN) .......................... 1877/DEL/2015

(51) Int. Cl.
*A61K 31/437* (2006.01)
*A61K 31/519* (2006.01)
*A61P 29/00* (2006.01)
*C07D 487/04* (2006.01)
*C07D 471/04* (2006.01)

(52) U.S. Cl.
CPC ......... *C07D 487/04* (2013.01); *C07D 471/04* (2013.01)

(58) Field of Classification Search
CPC .. A61K 31/437; A61K 31/519; C07D 487/04; C07D 471/04
See application file for complete search history.

(56) References Cited

U.S. PATENT DOCUMENTS

| | | |
|---|---|---|
| 8,575,153 B2 | 11/2013 | Kitamura et al. |
| 8,586,751 B2 | 11/2013 | De Lucca et al. |
| 9,242,976 B2 | 1/2016 | Paidi et al. |
| 9,663,467 B2 | 5/2017 | Moslin et al. |

| | | |
|---|---|---|
| 2005/0272753 A1 | 12/2005 | Nagashima et al. |
| 2006/0148800 A1 | 7/2006 | Stadtmueller et al. |
| 2009/0082329 A1 | 3/2009 | Halley et al. |

(Continued)

FOREIGN PATENT DOCUMENTS

| | | |
|---|---|---|
| EP | 2 532 656 A1 | 12/2012 |
| GB | 2 388 596 A | 11/2003 |
| WO | WO 02/102800 A1 | 12/2002 |

(Continued)

OTHER PUBLICATIONS

Buckley, George M., "IRAK-4 inhibitors. Part 1: A series of amides", ScienceDirect, Bioorganic & Medicinal Chemistry Letters, 2008, vol. 18, pp. 3211-3214.
Buckley, George M., et al., "IRAK-4 inhibitors. Part II: A structure-based assessment of imidazo[1,2-α]pyridine binding", ScienceDirect, Bioorganic & Medicinal Chemistry Letters, 2008, vol. 18, pp. 3291-3295.
Buckley, George M., et al., "IRAK-4 inhibitors. Part III: A series of imidazo[1,2-a]pyridines", Bioorganic & Medicinal Chemistry Letters, 2008, vol. 18, No. 12, pp. 3656-3660.
Hynes, John, et al., Annual Reports in Medicinal Chemistry, 2014, vol. 49, pp. 117-133.
Seganish, W. Michael, "Inhibitors of interleukin-1 receptor-associated kinase 4 (IRAK4): a patent review (2012-2015)", Expert Opinion on Therapeutic Patents, 2016, vol. 26, No. 8, pp. 917-932.
International Preliminary Report on Patentability, International application No. PCT/US2016/038858, dated Dec. 26, 2017.

*Primary Examiner* — Brenda L Coleman
(74) *Attorney, Agent, or Firm* — Gary Greenblatt

(57) ABSTRACT

Disclosed are compounds of Formula (I) or salts thereof, wherein HET is a heteroaryl selected from pyrrolo[2,3-b]pyridinyl, pyrrolo[2,3 d]pyrimidinyl, pyrazolo[3,4 b]pyridinyl, pyrazolo[3,4 d]pyrimidinyl, imidazolo[4,5 b]pyridinyl, and imidazolo[4,5 d]pyrimidinyl, wherein said heteroaryl is attached to the pyridinyl group in the compound of Formula (I) by a nitrogen ring atom in said heteroaryl and wherein said heteroaryl is substituted with zero to 2 $R_b$; A is pyrazolyl, imidazolyl, triazolyl, isoxazolyl, oxadiazolyl or dihydroisoxazolyl, each substituted with zero or 1 $R_a$; and $R_3$, $R_a$, and $R_b$ are define herein. Also disclosed are methods of using such compounds as modulators of IRAK4, and pharmaceutical compositions comprising such compounds. These compounds are useful in treating, preventing, or slowing inflammatory and autoimmune diseases, or in the treatment of cancer.

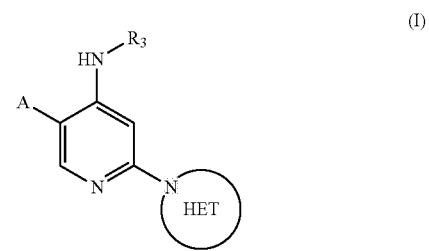

(I)

13 Claims, No Drawings

(56) References Cited

U.S. PATENT DOCUMENTS

2011/0230467 A1  9/2011  Shirakami et al.

FOREIGN PATENT DOCUMENTS

| WO | WO 03/013523 A1 | 2/2003 |
|----|----|----|
| WO | WO 2004/065378 A1 | 8/2004 |
| WO | WO 2005/007646 A1 | 1/2005 |
| WO | WO 2005/075468 A2 | 8/2005 |
| WO | WO 2008/148889 A1 | 12/2008 |
| WO | WO 2009/046416 A1 | 4/2009 |
| WO | WO 2011/053701 A1 | 5/2011 |
| WO | WO 2012/149567 A1 | 11/2012 |
| WO | WO 2013/106612 A1 | 7/2013 |
| WO | WO 2013/106614 A1 | 7/2013 |
| WO | WO 2014/074657 A1 | 5/2014 |
| WO | WO 2014/074660 A1 | 5/2014 |
| WO | WO 2014/074675 A1 | 5/2014 |
| WO | WO 2015/103453 A1 | 7/2015 |
| WO | WO 2016/210037 A1 | 12/2016 |

HETEROARYL SUBSTITUTED AMINOPYRIDINE COMPOUNDS

CROSS-REFERENCE TO RELATED APPLICATIONS

This application claims the benefit of Indian Provisional Patent Application Serial No. 1877/DEL/15, filed Jun. 24, 2015, which is incorporated herein in its entirety.

DESCRIPTION

The present invention generally relates to heteroaryl substituted aminopyridine compounds useful as kinase inhibitors, including the modulation of IRAK-4. Provided herein are heteroaryl substituted aminopyridine compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including IRAK-4 in a mammal.

Toll/IL-1 receptor family members are important regulators of inflammation and host resistance. The Toll like receptor (TLR) family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Members of the IRAK family of serine/threonine kinases are recruited to the receptor via interactions with MyD88. The family consists of four members. Several lines of evidence indicate that IRAK4 plays a critical and non-redundant role in initiating signaling via MyD88 dependent TLRs and IL-1R family members. Structural data confirms that IRAK4 directly interacts with MyD88 and subsequently recruits either IRAK1 or IRAK2 to the receptor complex to facilitate downstream signaling (Lin, S. et al., *Nature*, 465:885-890 (2010)). IRAK4 directly phosphorylates IRAK1 to facilitate downstream signaling to the E3 ubiquitin ligase TRAF6, resulting in activation of the serine/threonine kinase TAK1 with subsequent activation of the NFκB pathway and MAPK cascade (Flannery, S. et al., *Biochem. Pharmacol.*, 80:1981-1991 (2010)). A subset of human patients was identified who lack IRAK4 expression (Picard, C. et al., *Science*, 299:2076-2079 (2003)). Cells from these patients fail to respond to all TLR agonists with the exception of TLR3 as well as to members of the IL-1 family including IL-113 and IL-18 (Ku, C. et al., *J. Exp. Med.*, 204:2407-2422 (2007)). Deletion of IRAK4 in mice results in a severe block in IL-1, IL-18 and all TLR dependent responses with the exception of TLR3 (Suzuki, N. et al., *Nature*, 416:750-754 (2002)). In contrast, deletion of either IRAK1 (Thomas, J. A. et al., *J. Immunol.*, 163:978-984 (1999); Swantek, J. L. et al., *J. Immunol.*, 164:4301-4306 (2000) or IRAK2 (Wan, Y. et al., *J. Biol. Chem.*, 284:10367-10375 (2009)) results in partial loss of signaling. Furthermore, IRAK4 is the only member of the IRAK family whose kinase activity has been shown to be required for initiation of signaling. Replacement of wild type IRAK4 in the mouse genome with a kinase inactive mutant (KDKI) impairs signaling via all MyD88 dependent receptors including IL-1, IL-18 and all TLRs with the exception of TLR3 (Koziczak-Holbro, M. et al., *J. Biol. Chem.*, 282:13552-13560 (2007); Kawagoe, T. et al., *J. Exp. Med.*, 204:1013-1024 (2007); and Fraczek, J. et al., *J. Biol. Chem.*, 283:31697-31705 (2008)).

As compared to wild type animals, IRAK4 KDKI mice show greatly reduced disease severity in mouse models of multiple sclerosis (Staschke, K. A. et al., *J. Immunol.*, 183:568-577 (2009)), rheumatoid arthritis (Koziczak-Holbro, M. et al., *Arthritis Rheum.*, 60:1661-1671 (2009)), atherosclerosis (Kim, T. W. et al., *J. Immunol.*, 186:2871-2880 (2011) and Rekhter, M. et al., *Biochem. Biophys. Res. Comm.*, 367:642-648 (2008)), and myocardial infarction (Maekawa, Y. et al., *Circulation*, 120:1401-1414 (2009)). As described, IRAK4 inhibitors will block all MyD88 dependent signaling. MyD88 dependent TLRs have been shown to contribute to the pathogenesis of multiple sclerosis, rheumatoid arthritis, cardiovascular disease, metabolic syndrome, sepsis, systemic lupus erythematosus, inflammatory bowel diseases including Crohn's disease and ulcerative colitis, autoimmune uveitis, asthma, allergy, type I diabetes, and allograft rejection (Keogh, B. et al., *Trends Pharmacol. Sci.*, 32:435-442 (2011); Mann, D. L., *Circ. Res.*, 108:1133-1145 (2011); Horton, C. G. et al., *Mediators Inflamm.*, Article ID 498980 (2010), doi:10.1155/2010/498980; Goldstein, D. R. et al., *J Heart Lung Transplant.*, 24:1721-1729 (2005); and Cario, E., *Inflamm. Bowel Dis.*, 16:1583-1597 (2010)). Oncogenically active MyD88 mutations in diffuse large B cell lymphomas have been identified that are sensitive to IRAK4 inhibition (Ngo, V. N. et al., *Nature*, 470:115-121 (2011)). Whole genome sequencing also identified mutations in MyD88 associated with chronic lymphatic leukemia suggesting that IRAK4 inhibitors may also have utility in treating leukemia (Puente, X. S. et al., *Nature*, 475:101-105 (2011)).

In addition to blocking TLR signaling, IRAK4 inhibitors will also block signaling by members of the IL-1 family. Neutralization of IL-1 has been shown to be efficacious in multiple diseases including gout; gouty arthritis; type 2 diabetes; auto-inflammatory diseases including Cryopyrin-Associated Periodic Syndromes (CAPS), TNF Receptor Associated Periodic Syndrome (TRAPS), Familial Mediterranean Fever (FMF), adult onset stills; systemic onset juvenile idiopathic arthritis; stroke; Graft-versus-Host Disease (GVHD); smoldering multiple myeloma; recurrent pericarditis; osteoarthritis; emphysema (Dinarello, C. A., *Eur. J. Immunol.*, 41:1203-1217 (2011) and Couillin, I. et al., *J Immunol.*, 183:8195-8202 (2009)). In a mouse model of Alzheimer's disease, blockade of IL-1 receptor improved cognitive defects, attenuated tau pathology and reduced oligomeric forms of amyloid-β (Kitazawa, M. et al., *J. Immunol.*, 187:6539-6549 (2011)). IL-1 has also been shown to be a critical link to adaptive immunity, driving differentiation of the TH17 effector T cell subset (Chung, Y. et al., *Immunity*, 30:576-587 (2009)). Therefore, IRAK4 inhibitors are predicted to have efficacy in TH17 associated diseases including multiple sclerosis, psoriasis, inflammatory bowel diseases, autoimmune uveitis, and rheumatoid arthritis (Wilke, C. M. et al., *Trends Immunol.*, 32:603-661 (2011)).

WO2013/106612, WO2013/106614, WO2013/106641, WO2014/074657, and WO2014/074675 disclose substituted pyridyl compounds useful as kinase inhibitors, including the modulation of IRAK4.

In view of the conditions that may benefit by treatment involving modulation of protein kinases, it is immediately apparent that new compounds capable of modulating protein kinases such as IRAK-4 and methods of using these compounds could provide substantial therapeutic benefits to a wide variety of patients.

The present invention relates to a new class of heteroaryl substituted aminopyridine compounds found to be effective inhibitors of protein kinases including IRAK-4. These compounds are provided to be useful as pharmaceuticals with desirable stability, bioavailability, therapeutic index, and toxicity values that are important to their drugability.

SUMMARY OF THE INVENTION

The present invention provides to compounds of Formula (I) that are useful as inhibitors of IRAK-4, and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of IRAK-4 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

One embodiment provides a method for treating inflammatory and autoimmune diseases wherein the treatment of inflammatory diseases is even more preferred. Particular, inflammatory and autoimmune diseases include, but are not limited to, Crohn's disease, ulcerative colitis, asthma, graft versus host disease, allograft rejection, chronic obstructive pulmonary disease, Graves' disease, rheumatoid arthritis, systemic lupus erythematosus, lupus nephritis, cutaneous lupus, psoriasis, cryopyrin-associated periodic syndromes (CAPS), TNF receptor associated periodic syndrome (TRAPS), familial Mediterranean fever (FMF), adult onset stills, systemic onset juvenile idiopathic arthritis, multiple sclerosis, neuropathic pain, gout, and gouty arthritis.

One embodiment provides a method for treating gout and gouty arthritis.

An alternate preferred embodiment is a method for treating metabolic diseases, including type 2 diabetes and atherosclerosis.

One embodiment provides a method for treating cancer comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancer.

The present invention also provides a compound of Formula (I) or a pharmaceutical composition in a kit with instructions for using the compound or composition.

The present invention also provides processes and intermediates for making the compounds of the present invention or stereoisomers, tautomers, pharmaceutically acceptable salts, solvates, or prodrugs thereof.

These and other features of the invention will be set forth in the expanded form as the disclosure continues.

DETAILED DESCRIPTION

The first aspect of the present invention provides at least one compound of Formula (I):

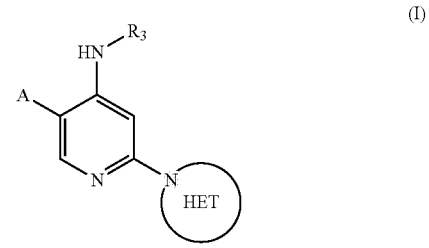

(I)

or a salt thereof, wherein:

HET is a heteroaryl selected from pyrrolo[2,3-b]pyridinyl, pyrrolo[2,3-d]pyrimidinyl, pyrazolo[3,4-b]pyridinyl, pyrazolo[3,4-d]pyrimidinyl, imidazolo[4,5-b]pyridinyl, and imidazolo[4,5-d]pyrimidinyl, wherein said heteroaryl is attached to the pyridinyl group in the compound of Formula (I) by a nitrogen ring atom in said heteroaryl and wherein said heteroaryl is substituted with zero to 2 $R_b$;

A is pyrazolyl, imidazolyl, triazolyl, isoxazolyl, oxadiazolyl or dihydroisoxazolyl, each substituted with $R_a$;

$R_3$ is $C_{2-3}$ alkyl, $C_{2-3}$ fluoroalkyl, $C_{3-4}$ hydroxyalkyl, or a cyclic group selected from $C_{3-6}$ cycloalkyl, oxetanyl, tetrahydrofuranyl, tetrahydropyranyl, and pyrazolyl, wherein said cyclic group is substituted with zero to 2 substituents independently selected from F, —OH, $C_{1-2}$ alkyl, and —CH$_2$CHF$_2$;

$R_a$ is:

(i) H, F, $C_1$, —OH, —CN, $C_{1-6}$ alkyl, $C_{1-6}$ fluoroalkyl, $C_{1-4}$ cyanoalkyl, $C_{1-6}$ hydroxyalkyl, $C_{1-5}$ hydroxy-fluoroalkyl, $C_{2-4}$ alkenyl, $C_{1-6}$ aminoalkyl, —(CH$_2$)$_{1-3}$NHR$_y$, —(CH$_2$)$_{1-3}$NR$_y$R$_y$, —CH$_2$CH(OH)(phenyl), —CH(CH$_2$OH)(phenyl), —CH$_2$CH(OH)CH$_2$(phenyl), —CH$_2$CH(OH)CH$_2$O(methoxyphenyl), —CH$_2$CH(NH$_2$)CH$_2$(phenyl), —(CH$_2$CH$_2$O)$_4$H, —(CH$_2$)$_{1-3}$O(C$_{1-3}$ alkyl), —CH$_2$CH(OH)CH$_2$O(C$_{1-3}$ alkyl), —CH$_2$C(O)(C$_{1-3}$ alkyl), —CH$_2$C(O)NR$_y$R$_y$, —(CH$_2$)$_{1-3}$NR$_y$C(O)(C$_{1-3}$ alkyl), —CH$_2$C(O)O(C$_{1-3}$ alkyl), —C(O)NH$_2$, —CH$_2$NR$_y$C(O)NH$_2$, —(CH$_2$)$_{1-2}$NR$_y$C(O)O(C$_{1-2}$ alkyl), —(CR$_y$R$_y$)$_{1-5}$OC(O)CH$_2$NR$_y$R$_y$, —CH$_2$CH$_2$S(O)$_2$CH$_3$, —CH$_2$S(O)$_2$(C$_{1-3}$ alkyl), —CH$_2$S(O)$_2$(phenyl), or —NH(aminocyclohexyl); or (ii) —(CH$_2$)$_{0-3}$R$_z$ or —(CH$_2$)$_{0-1}$C(O)R$_z$, wherein R$_z$ is $C_{3-6}$ cycloalkyl, azetidinyl, oxetanyl, tetrahydrofuranyl, tetrahydropyranyl, piperidinyl, piperazinyl, pyrrolyl, pyrrolidinonyl, morpholinyl, pyrrolidinyl, phenyl, pyrazolyl, imidazolyl, pyridinyl, pyrimidinyl, dioxopyrimidinyl, benzo[d]imidazolyl, benzo[d]thiazolyl, 1,3-dioxolanyl, or 8-azabicyclo[3.2.1]octanyl, each substituted with zero to 4 substituents independently from F, —CN, —OH, —NR$_y$R$_y$, C$_{1-3}$ alkyl, C$_{1-3}$ fluoroalkyl, C$_{1-3}$ hydroxyalkyl, —CH(phenyl)$_2$, —O(C$_{1-4}$ alkyl), —C(O)(C$_{1-4}$ alkyl), —C(O)(C$_{1-4}$ deuteroalkyl), —C(O)(C$_{1-5}$ hydroxyalkyl), —C(O)(C$_{1-3}$ fluoroalkyl), —C(O)(C$_{3-6}$ cycloalkyl), —C(O)O(C$_{1-3}$ alkyl), —C(O)NR$_y$R$_y$, —C(O)(phenyl), —C(O)(pyridinyl), —C(O)CH$_2$(C$_{3-6}$ cycloalkyl), —C(O)O(C$_{1-4}$ alkyl), —NH(C$_{1-4}$ alkyl), —NH(C$_{1-3}$ fluoroalkyl), —NHC(O)CH$_3$, —NHC(O)O(C$_{1-3}$ alkyl), —NHC(O)OC(CH$_3$)$_3$, —S(O)$_2$(C$_{1-3}$ alkyl), —OS(O)$_2$(C$_{1-3}$ alkyl), methyl oxadiazolyl, and pyrimidinyl;

each R$_b$ is independently selected from H, Cl, —CN, —NH$_2$, and —C(O)NH$_2$, wherein said heteroaryl is attached to the pyridinyl group by a nitrogen atom in said heteroaryl; and each R$_y$ is independently H or C$_{1-2}$ alkyl.

One embodiment provides a compound of Formula (I) or a salt thereof, wherein:

HET is a heteroaryl selected from pyrrolo[2,3-b]pyridinyl, pyrrolo[2,3-d]pyrimidinyl, pyrazolo[3,4-b]pyridinyl, pyrazolo[3,4-d]pyrimidinyl, imidazolo[4,5-b]pyridinyl, and imidazolo[4,5-d]pyrimidinyl, wherein said heteroaryl is attached to the pyridinyl group in the compound of Formula (I) by a nitrogen ring atom in said heteroaryl and wherein said heteroaryl is substituted with zero to 2 R$_b$;

A is pyrazolyl, imidazolyl, or triazolyl, each substituted with R$_a$;

R$_3$ is —CH$_2$CH$_3$, —CH(CH$_3$)$_2$, —CH$_2$CHF$_2$, —CH(CH$_3$)CH$_2$OH, cyclopropyl, oxetanyl, tetrahydropyranyl, ethyl pyrazolyl, or 2,2-difluoroethyl pyrazolyl;

R$_a$ is:
(i) H, F, C$_1$, —OH, —CN, C$_{1-6}$ alkyl, C$_{1-4}$ fluoroalkyl, C$_{1-4}$ cyanoalkyl, C$_{1-6}$ hydroxyalkyl, C$_{1-4}$ hydroxy-fluoroalkyl, C$_{2-4}$ alkenyl, C$_{1-6}$ aminoalkyl, —(CH$_2$)$_{1-3}$NHR$_y$, —(CH$_2$)$_{1-3}$NR$_y$R$_y$, —CH$_2$CH(OH)(phenyl), —CH(CH$_2$OH)(phenyl), —CH$_2$CH(OH)CH$_2$(phenyl), —CH$_2$CH(OH)CH$_2$O(methoxyphenyl), —CH$_2$CH(NH$_2$)CH$_2$(phenyl), —(CH$_2$CH$_2$O)$_4$H, —(CH$_2$)$_{1-3}$O(C$_{1-3}$ alkyl), —CH$_2$CH(OH)CH$_2$O(C$_{1-3}$ alkyl), —CH$_2$C(O)(C$_{1-3}$ alkyl), —CH$_2$C(O)NR$_y$R$_y$, —CH$_2$C(O)O(C$_{1-3}$ alkyl), —C(O)NH$_2$, —CH$_2$NHC(O)NH$_2$, —CH$_2$CH$_2$S(O)$_2$CH$_3$, —CH$_2$S(O)$_2$(C$_{1-3}$ alkyl), or —CH$_2$S(O)$_2$(phenyl); or
(ii) —(CH$_2$)$_{0-3}$R$_z$ or —CH$_2$C(O)R$_z$, wherein R$_z$ is C$_{3-6}$ cycloalkyl, azetidinyl, oxetanyl, tetrahydrofuranyl, tetrahydropyranyl, piperidinyl, piperazinyl, pyrrolyl, pyrrolidinonyl, morpholinyl, pyrrolidinyl, phenyl, pyrazolyl, imidazolyl, pyridinyl, pyrimidinyl, dioxopyrimidinyl, benzo[d]imidazolyl, or benzo[d]thiazolyl, each substituted with zero to 4 substituents independently from F, —CN, —OH, —NR$_y$R$_y$, C$_{1-3}$ alkyl, C$_{1-3}$ fluoroalkyl, —CH(phenyl)$_2$, —O(C$_{1-4}$ alkyl), —C(O)(C$_{1-4}$ alkyl), —C(O)(C$_{1-4}$ deuteroalkyl), —C(O)(C$_{3-6}$ cycloalkyl), —C(O)O(C$_{1-3}$ alkyl), —C(O)NR$_y$R$_y$, —C(O)(phenyl), —C(O)(pyridinyl), —C(O)CH$_2$(C$_{3-6}$ cycloalkyl), —C(O)O(C$_{1-4}$ alkyl), —NHCH(CH$_3$)$_2$, —NHC(O)CH$_3$, —NHC(O)OCH$_3$, —NHC(O)OC(CH$_3$)$_3$, —S(O)$_2$(C$_{1-3}$ alkyl), —OS(O)$_2$(C$_{1-3}$ alkyl), methyl oxadiazolyl, and pyrimidinyl;

each R$_b$ is independently selected from H, Cl, —CN, —NH$_2$, and —C(O)NH$_2$, wherein said heteroaryl is attached to the pyridinyl group by a nitrogen atom in said heteroaryl; and each R$_y$ is independently H or C$_{1-2}$ alkyl.

One embodiment provides a compound of Formula (I) or a salt thereof wherein A is

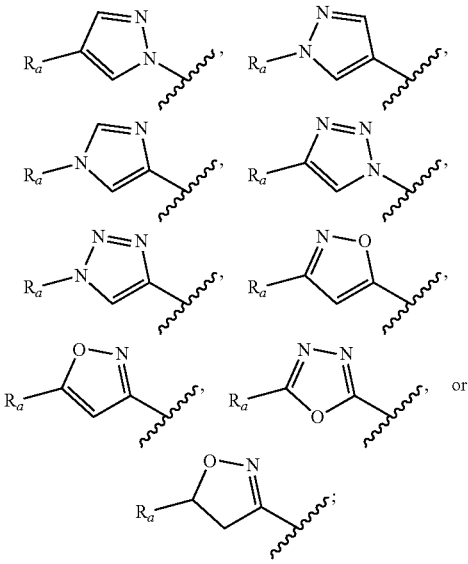

R$_a$ is:
(i) H, —CN, C$_{1-5}$ alkyl, C$_{1-5}$ fluoroalkyl, C$_{1-3}$ cyanoalkyl, C$_{1-5}$ hydroxyalkyl, —CH$_2$CH(OH)CF$_3$, —CH$_2$CHFC(CH$_3$)$_2$OH, —CH$_2$CH(OH)(phenyl), —CH(CH$_2$OH)(phenyl), —CH$_2$CH(OH)CH$_2$(phenyl), —CH$_2$CH(OH)CH$_2$O(methoxyphenyl), —CH=CH$_2$, —CH$_2$NH$_2$, —CH$_2$NHCH$_3$, —CH$_2$N(CH$_3$)$_2$, —CH$_2$CH$_2$NH$_2$, —CH$_2$CH$_2$N(CH$_3$)$_2$, —CH$_2$CH$_2$CH$_2$NHR$_y$, —C(CH$_3$)$_2$NH$_2$, —(CH$_2$)$_5$NH$_2$, —CH$_2$CH(NH$_2$)CH$_2$(phenyl), —CH$_2$N(CH$_2$CH$_3$)$_2$, —(CH$_2$CH$_2$O)$_4$H, —CH$_2$OCH$_3$, —CH$_2$CH$_2$OCH$_3$, —CH$_2$CH$_2$OCH$_2$CH$_3$, —CH$_2$CH(OH)CH$_2$OCH$_3$, —CH$_2$CH(OH)CH$_2$OCH$_2$CH$_3$, —CH$_2$C(O)CH$_3$, —CH$_2$C(O)NH$_2$, —CH$_2$C(O)NHCH$_3$, —CH$_2$C(O)OCH$_2$CH$_3$, —C(O)NH$_2$, —CH$_2$NHC(O)NH$_2$, —CH$_2$NR$_y$C(O)NH$_2$, —(CH$_2$)$_{1-2}$NR$_y$C(O)O(C$_{1-2}$ alkyl), —CH$_2$CH$_2$CH$_2$N(CH$_3$)C(O)CH$_3$, —CH$_2$CH$_2$NHC(O)OCH$_3$, —CH$_2$CH$_2$C(CH$_3$)$_2$OC(O)CH$_2$NR$_y$R, —(CH$_2$)$_{1-5}$OC(O)CH$_2$NR$_y$R$_y$, or —CH$_2$CH$_2$S(O)$_2$CH$_3$;
(ii) cyclopropyl, cyclopentyl, hydroxycyclopentyl, oxetanyl, or cyclohexyl substituted with zero or one substituent selected from —OH, C$_{1-2}$ alkyl, —NH$_2$, —NHCH(CH$_3$)$_2$, —NHC(O)CH$_3$, —NHC(O)O(C$_{1-3}$ alkyl), and —NHCH$_2$CHF$_2$;
(iii) phenyl substituted with zero to 2 substituents independently selected from F, —CN, —OH, —OCH$_3$, and —C(O)OCH$_3$;
(iv) —CH$_2$(cyclopropyl), —CH$_2$(difluorocyclopropyl), —CH$_2$(cyclobutyl), —CH$_2$(oxetanyl), —CH$_2$(hydroxyoxetanyl), —CH$_2$(morpholinyl), —CH$_2$(phenyl), —CH$_2$(fluorophenyl), —CH$_2$(methoxyphenyl), —CH$_2$(pyridinyl), —CH$_2$(butoxycarbonyl, hydroxypiperidinyl), —CH$_2$(butoxycarbonyl pyrrolidinyl), —CH$_2$(acetylazetidinyl), —CH$_2$(benzo[d]imidazolyl), —CH$_2$(methyl benzo[d]thiazolyl), —CH$_2$CH$_2$(morpholinyl), —CH$_2$CH$_2$(phenyl), —CH$_2$CH$_2$(pyridinyl), —CH$_2$CH$_2$(dimethylpyrazolyl), —CH$_2$CH$_2$CH$_2$(phenyl), —CH$_2$CH$_2$(pyrrolidinyl), —CH$_2$C(O)(morpholinyl), —CH$_2$C(O)(piperazinyl), —CH$_2$C(O)(acetylpiperazinyl), —CH$_2$C(O)(methylsulfonyl piperazinyl), —CH$_2$CH ($NH_2$)$CH_2$(phenyl), —$CH_2S(O)_2$(phenyl), —C(O)(morpholinyl), or —NH(aminocyclohexyl);

(v) pyridinyl, tetrahydrofuranyl, tetrahydropyranyl, pyrrolidinyl, morpholinyl, pyrrolidinonyl, dioxopyrimidinyl, imidazolyl, 1,3-dioxolanyl, 8-azabicyclo[3.2.1]octanyl, or azetidinyl substituted with zero to 4 substituents independently selected from —CN, —OH, —$CH_3$, —$CH_2CH_3$, —$CH(CH_3)_2$, —$CH_2OH$, —C(O)cyclopropyl, —C(O)phenyl, —C(O)$CH_3$, —C(O)$CD_3$, —C(O)CH($CH_3)_2$, —C(O)C($CH_3)_3$, —C(O)$CH_2$(cyclopropyl), —C(O)O$CH_3$, —C(O)OC($CH_3)_3$, —CH(phenyl)$_2$, methyl oxadiazolyl, and pyrimidinyl; or (vi) piperidinyl substituted with zero to 3 substituents independently selected from F, —OH, —$CH_3$, —CH($CH_3)_2$, —$CH_2CHF_2$, —C(O)$NH_2$, —C(O)$CH_3$, —C(O)$CH_2CH_3$, —C(O)C($CH_3)_3$, —C(O)$CH_2$C($CH_3)_2$OH, —C(O)$CF_3$, —C(O)O$CH_3$, —C(O)O$CH_2CH_3$, —C(O)OC($CH_3)_3$, —C(O)(pyridinyl), —S(O)$_2$($C_{1-2}$ alkyl), and —OS(O)$_2CH_3$; and HET and $R_3$ are defined in the first aspect.

One embodiment provides a compound of Formula (I) or a salt thereof wherein $R_a$ is:

(i) H, —CN, $C_{1-5}$ alkyl, $C_{1-3}$ fluoroalkyl, $C_{1-3}$ cyanoalkyl, $C_{1-5}$ hydroxyalkyl, —$CH_2CH(OH)CF_3$, —$CH_2CH(OH)$(phenyl), —CH($CH_2OH$)(phenyl), —$CH_2CH(OH)CH_2$(phenyl), —$CH_2CH(OH)CH_2$O(methoxyphenyl), —CH=$CH_2$, —$CH_2NH_2$, —$CH_2NHCH_3$, —$CH_2N(CH_3)_2$, —$CH_2CH_2NH_2$, —$CH_2CH_2N(CH_3)_2$, —$CH_2CH_2CH_2NH_2$, —C($CH_3)_2NH_2$, —($CH_2)_5NH_2$, —$CH_2CH(NH_2)CH_2$(phenyl), —$CH_2N(CH_2CH_3)_2$, —($CH_2CH_2O)_4H$, —$CH_2OCH_3$, —$CH_2CH_2OCH_3$, —$CH_2CH_2OCH_2CH_3$, —$CH_2CH(OH)CH_2OCH_3$, —$CH_2CH(OH)CH_2OCH_2CH_3$, —$CH_2C(O)CH_3$, —$CH_2C(O)NH_2$, —$CH_2C(O)NHCH_3$, —$CH_2C(O)OCH_2CH_3$, —C(O)$NH_2$, —$CH_2NHC(O)NH_2$, or —$CH_2CH_2S(O)_2CH_3$;

(ii) cyclopropyl, cyclopentyl, hydroxycyclopentyl, oxetanyl, or cyclohexyl substituted with zero or one substituent selected from —OH, —$CH_3$, —$NH_2$, —NHCH($CH_3)_2$, —NHC(O)$CH_3$, —NHC(O)O$CH_3$, and —NHC(O)OC($CH_3)_3$;

(iii) phenyl substituted with zero to 2 substituents independently selected from F, —CN, —OH, —$OCH_3$, and —C(O)O$CH_3$;

(iv) —$CH_2$(cyclopropyl), —$CH_2$(difluorocyclopropyl), —$CH_2$(cyclobutyl), —$CH_2$(oxetanyl), —$CH_2$(hydroxyoxetanyl), —$CH_2$(morpholinyl), —$CH_2$(phenyl), —$CH_2$(fluorophenyl), —$CH_2$(methoxyphenyl), —$CH_2$(pyridinyl), —$CH_2$(butoxycarbonyl, hydroxypiperidinyl), —$CH_2$(butoxycarbonyl pyrrolidinyl), —$CH_2$(acetylazetidinyl), —$CH_2$(benzo[d]imidazolyl), —$CH_2$(methyl benzo[d]thiazolyl), —$CH_2CH_2$(morpholinyl), —$CH_2CH_2$(phenyl), —$CH_2CH_2$(pyridinyl), —$CH_2CH_2$(dimethylpyrazolyl), —$CH_2CH_2CH_2$(phenyl), —$CH_2CH_2CH_2$(pyrrolidinyl), —$CH_2C(O)$(morpholinyl), —$CH_2C(O)$(piperazinyl), —$CH_2C(O)$(acetylpiperazinyl), —$CH_2C(O)$(methylsulfonyl piperazinyl), —$CH_2CH(NH_2)CH_2$(phenyl), or —$CH_2S(O)_2$(phenyl);

(v) pyridinyl, cyanopyridinyl, tetrahydrofuranyl, tetrahydropyranyl, hydroxytetrahydrofuranyl, trihydroxy-hydroxymethyltetrahydropyranyl, acetopyrrolidinyl, methylpyrrolidinonyl, dioxopyrimidinyl, methylimidazolyl, or azetidinyl substituted with zero to 1 substituent selected from —CN, —$CH_3$, —$CH_2CH_3$, —CH($CH_3)_2$, —C(O)cyclopropyl, —C(O)phenyl, —C(O)$CH_3$, —C(O)$CD_3$, —C(O)CH($CH_3)_2$, —C(O)C($CH_3)_3$, —C(O)$CH_2$(cyclopropyl), —C(O)O$CH_3$, —C(O)OC($CH_3)_3$, —CH(phenyl)$_2$, methyl oxadiazolyl, and pyrimidinyl; or (vi) piperidinyl substituted with zero to 3 substituents independently selected from F, —OH, —$CH_3$, —CH($CH_3)_2$, —$CH_2CHF_2$, —C(O)$NH_2$, —C(O)$CH_3$, —C(O)$CH_2CH_3$, —C(O)C($CH_3)_3$, —C(O)O$CH_3$, —C(O)O$CH_2CH_3$, —C(O)OC($CH_3)_3$, —C(O)(pyridinyl), —S(O)$_2CH_3$, and —OS(O)$_2CH_3$;

and HET, A, and $R_3$ are defined in the first aspect.

One embodiment provides a compound of Formula (I) or a salt thereof wherein $R_a$ is:

(i) H, —CN, —$CH_3$, —$CH_2CH_3$, —$CH_2CH_2CH_3$, —CH($CH_3)_2$, —$CH_2CH_2CH_2CH_3$, —$CH_2CH(CH_3)_2$, —C($CH_3)_3$, —$CH_2CH_2CH(CH_3)_2$, —$CH_2F$, —$CHF_2$, —$CF_3$, —$CH_2CHF_2$, —$CH_2CF_3$, —$CH_2CHFCH_3$, —$CH_2CH_2CH_2F$, —$CH_2CH_2C(CH_3)_2F$, —$CH_2CN$, —$CH_2CH_2CN$, —$CH_2CH_2CH_2CN$, —$CH_2OH$, —$CH_2CH_2OH$, —$CH_2C(CH_3)_2OH$, —C($CH_3)_2OH$, —$CH_2CH(CH_3)OH$, —$CH_2CH(OH)CH_3$, —$CH_2CH_2CH_2OH$, —($CH_2)_4OH$, —C($CH_3)(OH)CH_2CH_3$, —$CH_2CH(OH)CH_2OH$, —$CH_2CH(CH_3)CH_2OH$, —$CH_2CH(OH)CH_2CH_3$, —CH($CH_3)CH(CH_3)OH$, —$CH_2CH_2C(CH_3)_2OH$, —$CH_2CH_2C(CH_3)(OH)CH_2OH$, —$CH_2CH(OH)CH(CH_3)_2$, —$CH_2C(CH_3)(OH)CH_2CH_3$, —$CH_2C(CH_3)(OH)CH_2OH$, —CH($CH_2OH)_2$, —$CH_2CH(OH)CF_3$, —$CH_2CHFC(CH_3)_2OH$, —$CH_2CH(OH)$(phenyl), —CH($CH_2OH$)(phenyl), —$CH_2CH(OH)CH_2$(phenyl), —$CH_2CH(OH)CH_2O$(methoxyphenyl), —CH=$CH_2$, —$CH_2NH_2$, —$CH_2NHCH_3$, —$CH_2N(CH_3)_2$, —$CH_2CH_2NH_2$, —$CH_2CH_2N(CH_3)_2$, —$CH_2CH_2CH_2NH_2$, —C($CH_3)_2NH_2$, —$CH_2CH_2CH_2NHCH_3$, —($CH_2)_5NH_2$, —$CH_2CH(NH_2)CH_2$(phenyl), —$CH_2N(CH_2CH_3)_2$, —($CH_2CH_2O)_4H$, —$CH_2OCH_3$, —$CH_2CH_2OCH_3$, —$CH_2CH_2OCH_2CH_3$, —$CH_2CH(OH)CH_2OCH_3$, —$CH_2CH(OH)CH_2OCH_2CH_3$, —$CH_2C(O)CH_3$, —$CH_2C(O)NH_2$, —$CH_2C(O)NHCH_3$, —$CH_2C(O)OCH_2CH_3$, —C(O)$NH_2$, —$CH_2NHC(O)NH_2$, —$CH_2NHC(O)OCH_3$, —$CH_2CH_2NHC(O)OCH_3$, —$CH_2CH_2CH_2N(CH_3)C(O)CH_3$, —$CH_2CH_2C(CH_3)_2OC(O)CH_2NH_2$, —$CH_2CH_2C(CH_3)_2OC(O)CH_2N(CH_3)_2$, or —$CH_2CH_2S(O)_2CH_3$;

(ii) cyclopropyl, cyclopentyl, oxetanyl, or cyclohexyl substituted with zero or one substituent selected from —OH, —$CH_3$, —$NH_2$, —NHCH$_2CH_3$, —NHCH($CH_3)_2$, —NHCH$_2CHF_2$, —NHC(O)$CH_3$, —NHC(O)O$CH_3$, —NHC(O)O$CH_2CH_3$, and —NHC(O)OC($CH_3)_3$;

(iii) phenyl substituted with zero to 2 substituents independently selected from F, —CN, —OH, —$OCH_3$, and —C(O)O$CH_3$;

(iv) —$CH_2$(cyclopropyl), —$CH_2$(difluorocyclopropyl), —$CH_2$(cyclobutyl), —$CH_2$(oxetanyl), —$CH_2$(hydroxyoxetanyl), —$CH_2$(morpholinyl), —$CH_2$(phenyl), —$CH_2$(fluorophenyl), —$CH_2$(methoxyphenyl), —$CH_2$(pyridinyl), —$CH_2$(butoxycarbonyl, hydroxypiperidinyl), —$CH_2$(butoxycarbonyl pyrrolidinyl), —$CH_2$(acetylazetidinyl), —$CH_2$(benzo[d]imidazolyl), —$CH_2$(methyl benzo[d]thiazolyl), —$CH_2CH_2$(morpholinyl), —$CH_2CH_2$(phenyl), —$CH_2CH_2$(pyridinyl), —$CH_2CH_2$(dimethylpyrazolyl), —$CH_2CH_2CH_2$(phenyl), —$CH_2CH_2CH_2$(pyrrolidinyl), —C(O)(morpholinyl), —$CH_2C(O)$(morpholinyl), —$CH_2C(O)$(piperazinyl), —$CH_2C(O)$(acetylpiperazinyl), —$CH_2C(O)$(methylsulfonyl piperazinyl), —$CH_2CH(NH_2)CH_2$(phenyl), or —$CH_2S(O)_2$(phenyl);

(v) pyridinyl, tetrahydrofuranyl, tetrahydropyranyl, pyrrolidinyl, pyrrolidinonyl, morpholinyl, dioxopyrimidinyl, imidazolyl, azetidinyl, 1,3-dioxolanyl, or 8-azabicyclo[3.2.1]octanyl, each substituted with zero to 4 substituents independently selected from —OH, —CN, —CH$_3$, —CH$_2$CH$_3$, —CH(CH$_3$)$_2$, —CH$_2$OH, —C(O)cyclopropyl, —C(O)phenyl, —C(O)CH$_3$, —C(O)CD$_3$, —C(O)CH(CH$_3$)$_2$, —C(O)C(CH$_3$)$_3$, —C(O)CH$_2$(cyclopropyl), —C(O)OCH$_3$, —C(O)OC(CH$_3$)$_3$, —CH(phenyl)$_2$, methyl oxadiazolyl, and pyrimidinyl; or (vi) piperidinyl substituted with zero to 3 substituents independently selected from F, —OH, —CH$_3$, —CH(CH$_3$)$_2$, —CH$_2$CHF$_2$, —C(O)NH$_2$, —C(O)CH$_3$, —C(O)CH$_2$CH$_3$, —C(O)C(CH$_3$)$_3$, —C(O)CF$_3$, —C(O)OCH$_3$, —C(O)OCH$_2$CH$_3$, —C(O)OC(CH$_3$)$_3$, —C(O)CH$_2$C(CH$_3$)$_2$OH, —C(O)(pyridinyl), —S(O)$_2$CH$_3$, —S(O)$_2$CH$_2$CH$_3$, and —OS(O)$_2$CH$_3$;

and HET, A, and R$_3$ are defined in the first aspect.

One embodiment provides a compound of Formula (I) or a salt thereof wherein R$_a$ is:

(i) H, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$CH(CH$_3$)$_2$, —CH$_2$F, —CHF$_2$, —CF$_3$, —CH$_2$CHF$_2$, —CH$_2$CF$_3$, —CH$_2$CHFCH$_3$, —CH$_2$CH$_2$CH$_2$F, —CH$_2$CN, —CH$_2$CH$_2$CN, —CH$_2$CH$_2$CH$_2$CN, —CH$_2$OH, —CH$_2$CH$_2$OH, —CH$_2$C(CH$_3$)$_2$OH, —C(CH$_3$)$_2$OH, —CH$_2$CH(CH$_3$)OH, —CH$_2$CH(OH)CH$_3$, —CH$_2$CH$_2$CH$_2$OH, —(CH$_2$)$_4$OH, —(CH$_2$)$_5$OH, —C(CH$_3$)(OH)CH$_2$CH$_3$, —CH$_2$CH(OH)CH$_2$OH, —CH$_2$CH(CH$_3$)CH$_2$OH, —CH$_2$CH(OH)CH$_2$CH$_3$, —CH(CH$_3$)CH(CH$_3$)OH, —CH$_2$CH$_2$C(CH$_3$)$_2$OH, —CH$_2$CH(OH)CH(CH$_3$)$_2$, —CH$_2$C(CH$_3$)(OH)CH$_2$CH$_3$, —CH$_2$CH(OH)CF$_3$, —CH$_2$CH(OH)(phenyl), —CH(CH$_2$OH)(phenyl), —CH$_2$CH(OH)CH$_2$(phenyl), —CH$_2$CH(OH)CH$_2$O(methoxyphenyl), —CH=CH$_2$, —CH$_2$NH$_2$, —CH$_2$NHCH$_3$, —CH$_2$N(CH$_3$)$_2$, —CH$_2$CH$_2$NH$_2$, —CH$_2$CH$_2$N(CH$_3$)$_2$, —CH$_2$CH$_2$CH$_2$NH$_2$, —C(CH$_3$)$_2$NH$_2$, —(CH$_2$)$_5$NH$_2$, —CH$_2$CH(NH$_2$)CH$_2$(phenyl), —CH$_2$N(CH$_2$CH$_3$)$_2$, —(CH$_2$CH$_2$O)$_4$H, —CH$_2$OCH$_3$, —CH$_2$CH$_2$OCH$_3$, —CH$_2$CH$_2$OCH$_2$CH$_3$, —CH$_2$CH(OH)CH$_2$OCH$_3$, —CH$_2$CH(OH)CH$_2$OCH$_2$CH$_3$, —CH$_2$C(O)CH$_3$, —CH$_2$C(O)NH$_2$, —CH$_2$C(O)NHCH$_3$, —CH$_2$C(O)OCH$_2$CH$_3$, —C(O)NH$_2$, —CH$_2$NHC(O)NH$_2$, or —CH$_2$CH$_2$S(O)$_2$CH$_3$;

(ii) cyclopropyl, cyclopentyl, hydroxycyclopentyl, oxetanyl, or cyclohexyl substituted with zero or one substituent selected from —OH, —CH$_3$, —NH$_2$, —NHCH(CH$_3$)$_2$, —NHC(O)CH$_3$, —NHC(O)OCH$_3$, and —NHC(O)OC(CH$_3$)$_3$;

(iii) phenyl substituted with zero to 2 substituents independently selected from F, —CN, —OH, —OCH$_3$, and —C(O)OCH$_3$;

(iv) —CH$_2$(cyclopropyl), —CH$_2$(difluorocyclopropyl), —CH$_2$(cyclobutyl), —CH$_2$(oxetanyl), —CH$_2$(hydroxyoxetanyl), —CH$_2$(morpholinyl), —CH$_2$(phenyl), —CH$_2$(fluorophenyl), —CH$_2$(methoxyphenyl), —CH$_2$(pyridinyl), —CH$_2$(butoxycarbonyl, hydroxypiperidinyl), —CH$_2$(butoxycarbonyl pyrrolidinyl), —CH$_2$(acetylazetidinyl), —CH$_2$(benzo[d]imidazolyl), —CH$_2$(methyl benzo[d]thiazolyl), —CH$_2$CH$_2$(morpholinyl), —CH$_2$CH$_2$(phenyl), —CH$_2$CH$_2$(pyridinyl), —CH$_2$CH$_2$(dimethylpyrazolyl), —CH$_2$CH$_2$CH$_2$(phenyl), —CH$_2$CH$_2$CH$_2$(pyrrolidinyl), —CH$_2$C(O)(morpholinyl), —CH$_2$C(O)(piperazinyl), —CH$_2$C(O)(acetylpiperazinyl), —CH$_2$C(O)(methylsulfonyl piperazinyl), —CH$_2$CH(NH$_2$)CH$_2$(phenyl), or —CH$_2$S(O)$_2$(phenyl);

(v) pyridinyl, cyanopyridinyl, tetrahydrofuranyl, tetrahydropyranyl, hydroxytetrahydrofuranyl, trihydroxy-hydroxymethyltetrahydropyranyl, acetopyrrolidinyl, methylpyrrolidinonyl, dioxopyrimidinyl, methylimidazolyl, or azetidinyl substituted with zero to 1 substituent selected from —CN, —CH$_3$, —CH$_2$CH$_3$, —CH(CH$_3$)$_2$, —C(O)cyclopropyl, —C(O)phenyl, —C(O)CH$_3$, —C(O)CD$_3$, —C(O)CH(CH$_3$)$_2$, —C(O)C(CH$_3$)$_3$, —C(O)CH$_2$(cyclopropyl), —C(O)OCH$_3$, —C(O)OC(CH$_3$)$_3$, —CH(phenyl)$_2$, methyl oxadiazolyl, and pyrimidinyl; or (vi) piperidinyl substituted with zero to 3 substituents independently selected from F, —OH, —CH$_3$, —CH(CH$_3$)$_2$, —CH$_2$CHF$_2$, —C(O)NH$_2$, —C(O)CH$_3$, —C(O)CH$_2$CH$_3$, —C(O)C(CH$_3$)$_3$, —C(O)OCH$_3$, —C(O)OCH$_2$CH$_3$, —C(O)OC(CH$_3$)$_3$, —C(O)(pyridinyl), —S(O)$_2$CH$_3$, and —OS(O)$_2$CH$_3$;

and HET, A, and R$_3$ are defined in the first aspect.

One embodiment provides a compound of Formula (I) or a salt thereof, wherein HET is:

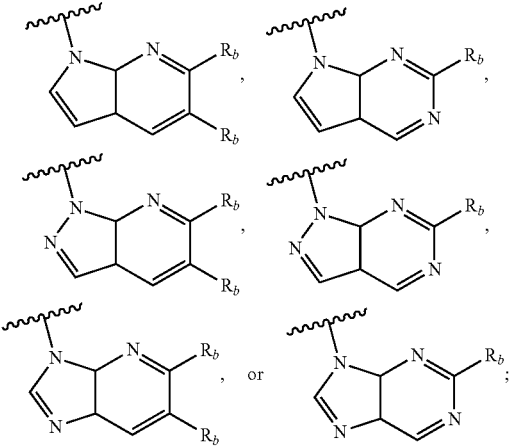

and A, R$_3$, and R$_b$ are defined in the first aspect. Included in this embodiment are compounds in which each R$_b$ is independently selected from H, Cl, —CN, and —NH$_2$.

One embodiment provides a compound of Formula (I) or a salt thereof, wherein wherein HET is

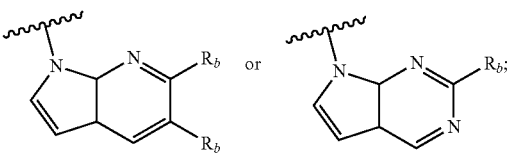

and A, R$_3$, and R$_b$ are defined in the first aspect. Included in this embodiment are compounds in which each R$_b$ is independently selected from H, Cl, —CN, and —NH$_2$. Also included are compounds in which each R$_b$ is independently selected from H and —CN.

One embodiment provides a compound of Formula (I) or a salt thereof, wherein wherein HET is

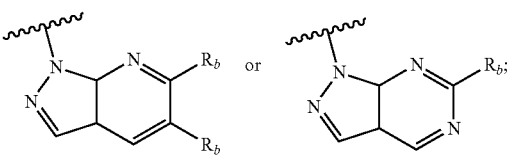

and A, $R_3$, and $R_b$ are defined in the first aspect. Included in this embodiment are compounds in which each $R_b$ is independently selected from H, Cl, —CN, and —NH$_2$. Also included are compounds in which each $R_b$ is independently selected from H, —CN, and —NH$_2$.

One embodiment provides a compound of Formula (I) or a salt thereof, wherein wherein HET is

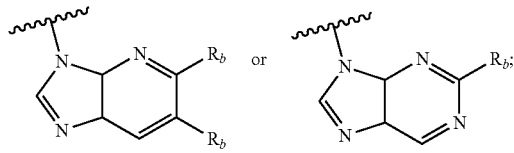

and A, $R_3$, and $R_b$ are defined in the first aspect. Included in this embodiment are compounds in which each $R_b$ is independently selected from H, Cl, —CN, and —NH$_2$. Also included are compounds in which each $R_b$ is independently selected from H, —CN, and —NH$_2$.

One embodiment provides a compound of Formula (I) or a salt thereof, wherein HET is

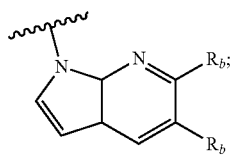

and A, $R_3$, and $R_b$ are defined in the first aspect. Included in this embodiment are compounds in which each $R_b$ is independently selected from H, Cl, —CN, and —NH$_2$. Also included are compounds in which one $R_b$ is H and the other $R_b$ is —CN.

One embodiment provides a compound of Formula (I) or a salt thereof, wherein HET is

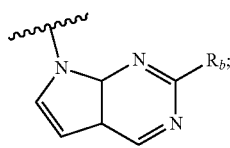

and A, $R_3$, and $R_b$ are defined in the first aspect. Included in this embodiment are compounds in which $R_b$ is selected from H, Cl, —CN, and —NH$_2$. Also included are compounds in which $R_b$ is H.

One embodiment provides a compound of Formula (I) or a salt thereof, wherein HET is

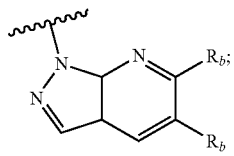

and A, $R_3$, and $R_b$ are defined in the first aspect. Included in this embodiment are compounds in which each $R_b$ is independently selected from H, —CN, and —NH$_2$. Also included are compounds in which one $R_b$ is H and the other $R_b$ is —CN.

One embodiment provides a compound of Formula (I) or a salt thereof, wherein HET is

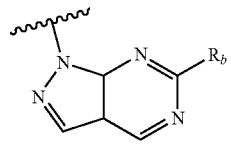

and A, $R_3$, and $R_b$ are defined in the first aspect. Included in this embodiment are compounds in which $R_b$ is selected from H, Cl, —CN, and —NH$_2$. Also included are compounds in which each $R_b$ is H.

One embodiment provides a compound of Formula (I) or a salt thereof, wherein HET is:

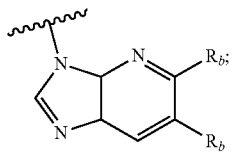

and A, $R_3$, and $R_b$ are defined in the first aspect. Included in this embodiment are compounds in which each $R_b$ is independently selected from H, Cl, —CN, and —NH$_2$. Also included are compounds in which each $R_b$ is independently selected from H, —CN, and —NH$_2$.

One embodiment provides a compound of Formula (I) or a salt thereof, wherein HET is:

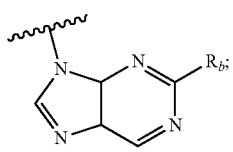

and A, $R_3$, and $R_b$ are defined in the first aspect. Included in this embodiment are compounds in which $R_b$ is selected from H, Cl, —CN, and —NH$_2$. Also included are compounds in which $R_b$ is —NH$_2$.

One embodiment provides a compound of Formula (I) or a salt thereof, wherein A is pyrazolyl or imidazolyl, each substituted with $R_a$; and HET, $R_3$, and $R_a$ are defined in the first aspect. Included in this embodiment are compounds in which A is

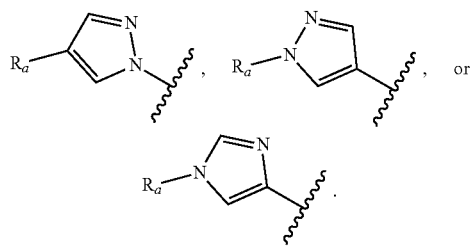

One embodiment provides a compound of Formula (I) or a salt thereof, wherein A is pyrazolyl substituted with $R_a$; and HET, $R_3$, and $R_a$ are defined in the first aspect. Included in this embodiment are compounds in which A is

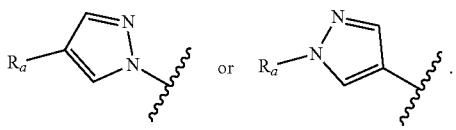 or 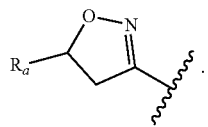

One embodiment provides a compound of Formula (I) or a salt thereof, wherein A is imidazolyl substituted with $R_a$; and HET, $R_3$, and $R_a$ are defined in the first aspect. Included in this embodiment are compounds in which A is

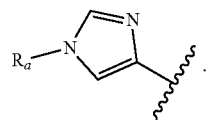

One embodiment provides a compound of Formula (I) or a salt thereof, wherein A is triazolyl substituted with $R_a$; and HET, $R_3$, and $R_a$ are defined in the first aspect. Included in this embodiment are compounds in which A is

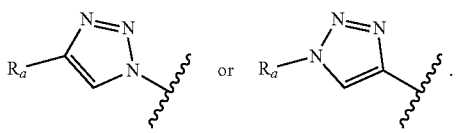

One embodiment provides a compound of Formula (I) or a salt thereof, wherein A is pyrazolyl or triazolyl, each substituted with $R_a$; and HET, $R_3$, and $R_a$ are defined in the first aspect.

One embodiment provides a compound of Formula (I) or a salt thereof, wherein A is isoxazolyl substituted with $R_a$; and HET, $R_3$, and $R_a$ are defined in the first aspect. Included in this embodiment are compounds in which A is

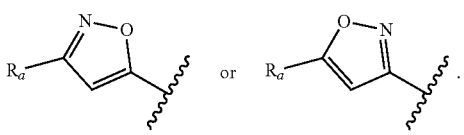

One embodiment provides a compound of Formula (I) or a salt thereof, wherein A is oxadiazolyl substituted with $R_a$; and HET, $R_3$, and $R_a$ are defined in the first aspect. Included in this embodiment are compounds in which A is

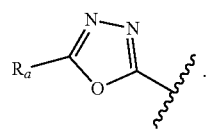

One embodiment provides a compound of Formula (I) or a salt thereof, wherein A is dihydroisoxazolyl substituted with $R_a$; and HET, $R_3$, and $R_a$ are defined in the first aspect. Included in this embodiment are compounds in which A is One embodiment provides a compound of Formula (I) or a salt thereof, wherein A is isoxazolyl or dihydroisoxazolyl, each substituted with $R_a$; and HET, $R_3$, and $R_a$ are defined in the first aspect. Included in this embodiment are compounds in which A is

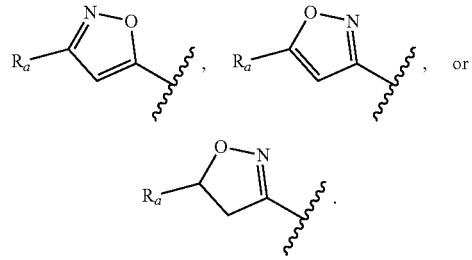

One embodiment provides a compound of Formula (I) or a salt thereof, wherein A is

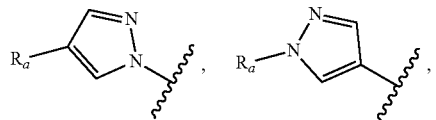

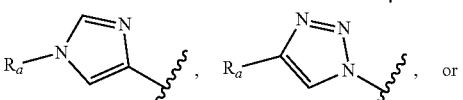

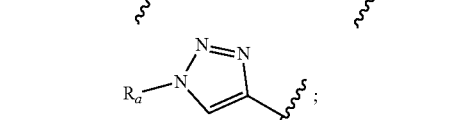

and HET, $R_3$, and $R_a$ are defined in the first aspect.

One embodiment provides a compound of Formula (I) or a salt thereof, wherein A is

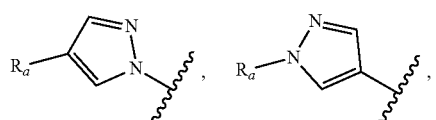

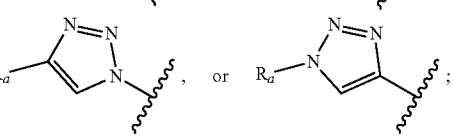

and HET, $R_3$, and $R_a$ are defined in the first aspect.

One embodiment provides a compound of Formula (I) or a salt thereof, wherein A is

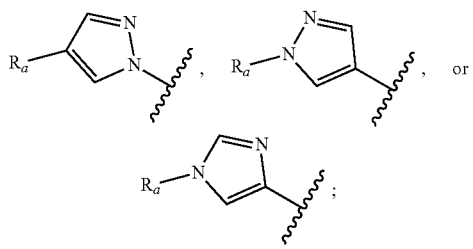

and HET, $R_3$, and $R_a$ are defined in the first aspect.

One embodiment provides a compound of Formula (I) or a salt thereof, wherein $R_3$ is —$CH_2CH_3$, —$CH(CH_3)_2$, —$CH_2CHF_2$, —$CH(CH_3)CH_2OH$, cyclopropyl, oxetanyl, tetrahydropyranyl,

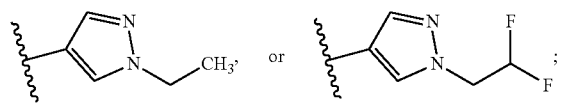

and HET and A are defined in the first aspect.

One embodiment provides a compound of Formula (I) or a salt thereof, wherein $R_3$ is —$CH_2CH_3$, —$CH(CH_3)_2$, —$CH_2CHF_2$, or —$CH(CH_3)CH_2OH$; and HET and A are defined in the first aspect. Included in this embodiment are compounds in which $R_3$ is —$CH(CH_3)_2$ or —$CH(CH_3)CH_2OH$. Also included in this embodiment are compounds in which $R_3$ is —$CH(CH_3)_2$.

One embodiment provides a compound of Formula (I) or a salt thereof, wherein $R_3$ is cyclopropyl, oxetanyl, tetrahydropyranyl, ethyl pyrazolyl, or 2,2-difluoroethyl pyrazolyl; and HET and A are defined in the first aspect. Included in this embodiment are compounds in which $R_3$ is cyclopropyl, oxetanyl, tetrahydropyranyl,

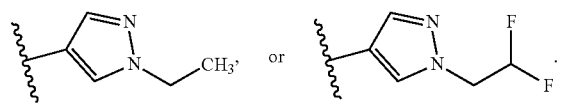

One embodiment provides a compound of Formula (I) or a salt thereof, wherein: $R_3$ is —$CH(CH_3)_2$, cyclopropyl, or

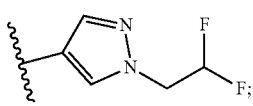 [SMILES: *c1cnn(CC(F)F)c1]

HET is

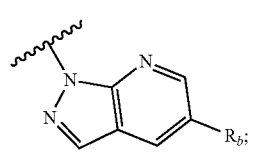

and A, $R_a$, and $R_b$ are defined in the first aspect. Included in this embodiment are compounds in which A is

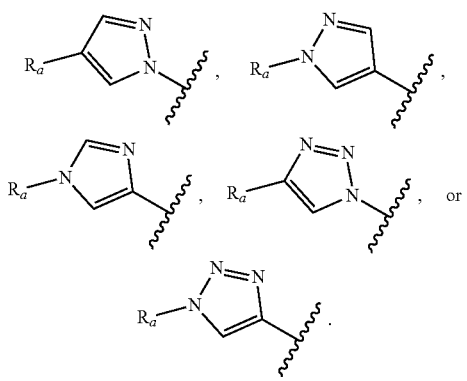

One embodiment provides a compound of Formula (I) or a salt thereof, wherein: A is pyrazolyl; HET is a heteroaryl selected from pyrazolo[3,4-b]pyridinyl and pyrazolo[3,4-d]pyrimidinyl, wherein said heteroaryl is attached to the pyridinyl group in the compound of Formula (I) by a nitrogen ring atom in said heteroaryl and wherein said heteroaryl is substituted with zero to 2 $R_b$; $R_3$ is —$CH(CH_3)_2$ or $CH_2CHF_2$; and each $R_b$ is independently H or —CN. Included in this embodiment are compounds in which A is

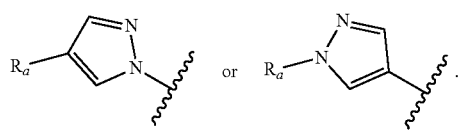

Also included in this embodiment are compounds in which HET is pyrazolo[3,4-b]pyridinyl.

One embodiment provides a compound of Formula (I) or a salt thereof, wherein: A is

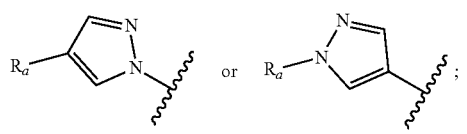

HET is

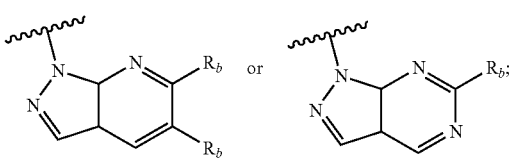

$R_3$ is —$CH(CH_3)_2$ or —$CH_2CHF_2$; $R_a$ is —CN, —$CH_3$, —$CH_2CH_3$, —$CH_2CH_2CH_3$, —$CH(CH_3)_2$, —$CH_2CH(CH_3)_2$, —$CH_2CN$, —$CH_2CH_2CH_2CN$, —$CHF_2$, —$CF_3$, —$CH_2CF_3$, —$CH_2CH_2OH$, —$CH_2$(phenyl), —$CH_2$(oxetanyl), cyclopropyl, tetrahydropyranyl, or pyridinyl; and each $R_b$ is independently H or —CN.

One embodiment provides a compound of Formula (I) or a salt thereof, wherein: A is HET is

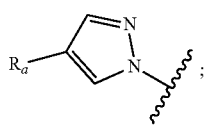

$R_3$ is —CH(CH$_3$)$_2$; $R_a$ is —CN, —CH$_3$, —CH(CH$_3$)$_2$, —CH$_2$CN, —CH$_2$CH$_2$CH$_2$CN, —CF$_3$, —CH$_2$CH$_2$OH, —CH$_2$(phenyl), or pyridinyl; and each $R_b$ is independently H or —CN.

One embodiment provides a compound of Formula (I) or a salt thereof, wherein: A is

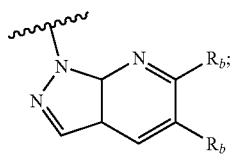

HET is

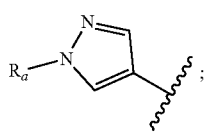

$R_3$ is —CH(CH$_3$)$_2$ or —CH$_2$CHF$_2$; $R_a$ is —CH$_2$CH$_3$, —CH$_2$CH$_2$CH$_3$, —CH$_2$CH(CH$_3$)$_2$, —CHF$_2$, —CH$_2$CF$_3$, —CH$_2$CH$_2$OH, —CH$_2$(oxetanyl), cyclopropyl, or tetrahydropyranyl; and each $R_b$ is independently H or —CN.

One embodiment provides a compound of Formula (I) or a salt thereof, wherein: A is

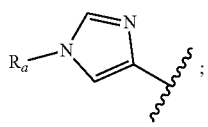

HET is

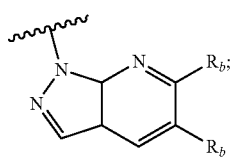

$R_3$ is —CH(CH$_3$)$_2$; $R_a$ is H, —CH$_2$CH$_3$, —CH$_2$CH$_2$CH$_3$, —CH(CH$_3$)$_2$, —CH$_2$CH(CH$_3$)$_2$, —CH$_2$CHF$_2$, —CH$_2$CH(OH)CH$_3$, —CH$_2$CH(CH$_3$)CH$_2$OH, —CH$_2$CH$_2$C(CH$_3$)$_2$OH, —CH$_2$C(O)NH$_2$, —CH$_2$C(O)NHCH$_3$, —CH$_2$(C$_{3-4}$ cycloalkyl), —CH$_2$(phenyl), —CH$_2$(pyridinyl), —CH$_2$(oxetanyl), —CH$_2$(hydroxyoxetanyl), —CH$_2$(acetylazetidinyl), —CH$_2$C(O)(morpholinyl), —CH$_2$CH$_2$CH$_2$(phenyl), acetylazetidinyl, or pyridinyl; and each $R_b$ is independently H or —CN.

One embodiment provides a compound of Formula (I) or a salt thereof, wherein A is

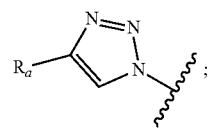

HET is:

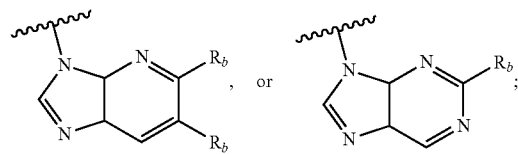

$R_3$ is —CH(CH$_3$)$_2$, —CH$_2$C(CH$_3$)$_2$OH, —CH(CH$_3$)CH$_2$OH, —CH(CH$_3$)CH$_2$OH, cyclopropyl, oxetanyl, tetrahydropyranyl, or difluoroethyl pyrazolyl; $R_a$ is —CH$_2$CH$_3$, —CH$_2$CH$_2$CH$_3$, —CH$_2$CH$_2$CH$_2$CH$_3$, —CH$_2$CH(CH$_3$)$_2$, —CH$_2$CH$_2$CH(CH$_3$)$_2$, —CH$_2$OH, —CH$_2$CH$_2$OH, —CH$_2$CH$_2$CH$_2$OH, —CH$_2$CH(OH)CH$_3$, —C(CH$_3$)$_2$OH, —(CH$_2$)$_4$OH, —CH$_2$C(CH$_3$)$_2$OH, —CH$_2$CH(OH)CH$_2$CH$_3$, —C(CH$_3$)(OH)CH$_2$CH$_3$, —CH$_2$C(CH$_3$)(OH)CH$_2$CH$_3$, —CH$_2$CH$_2$C(CH$_3$)$_2$OH, —CH$_2$F, —CH$_2$CHFCH$_3$, —CH$_2$CH$_2$CN, —CH$_2$CH$_2$CH$_2$CN, —CH$_2$NH$_2$, —CH$_2$NHCH$_3$, —CH$_2$N(CH$_3$)$_2$, —CH$_2$CH$_2$NH$_2$, —C(CH$_3$)$_2$NH$_2$, —CH$_2$N(CH$_2$CH$_3$)$_2$, —CH$_2$OCH$_3$, —CH$_2$C(O)CH$_3$, —CH$_2$NHC(O)NH$_2$, —C(O)NH$_2$, —CH=CH$_2$, —CH$_2$(morpholinyl), —CH$_2$CH$_2$(phenyl), —CH$_2$CH(OH)(phenyl), —CH$_2$S(O)$_2$(phenyl), acetylazetidinyl, cyclopropyl, cyclopentyl, phenyl, dimethoxyphenyl, pyridinyl, cyclohexyl substituted with —NH$_2$, —NHC(O)CH$_3$, —NHCH(CH$_3$)$_2$, —NHC(O)OCH$_3$, or —NHC(O)OC(CH$_3$)$_3$; or piperidinyl substituted with zero or 1 substituent selected from —CH(CH$_3$)$_2$, —CH$_2$CHF$_2$, —C(O)NH$_2$, —C(O)OCH$_3$, and —C(O)OC(CH$_3$)$_3$; and each $R_b$ is independently H, —CN, or —NH$_2$.

One embodiment provides a compound of Formula (I) or a salt thereof, wherein A is

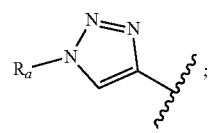

19

HET is

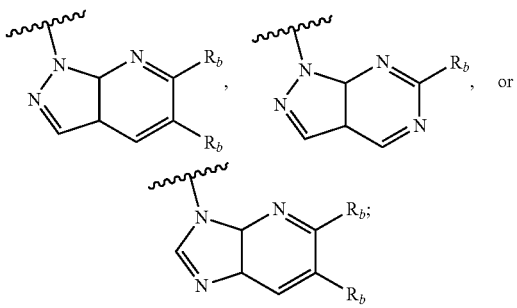

$R_3$ is —$CH_2CH_3$, —$CH(CH_3)_2$, —$CH(CH_3)CH_2OH$, cyclopropyl, tetrahydropyranyl, ethyl pyrazolyl, or difluoroethyl pyrazolyl; $R_a$ is (i) H, $C_{1-5}$ alkyl, $C_{2-3}$ fluoroalkyl, —$CH_2CN$, $C_{1-5}$ hydroxyalkyl, —$CH_2CH(OH)CF_3$, —$CH_2CH(OH)(phenyl)$, —$CH(CH_2OH)(phenyl)$, —$CH_2CH(OH)CH_2(phenyl)$, —$CH_2CH(OH)CH_2O$ (methoxyphenyl), —$CH_2CH_2NH_2$, —$CH_2CH_2N(CH_3)_2$, —$CH_2CH_2CH_2NH_2$, —$(CH_2)_5NH_2$, —$CH_2CH(NH_2)CH_2$ (phenyl), —$(CH_2CH_2O)_4H$, —$CH_2OCH_3$, —$CH_2CH_2OCH_3$, —$CH_2CH_2OCH_2CH_3$, —$CH_2CH(OH)CH_2OCH_3$, —$CH_2CH(OH)CH_2OCH_2CH_3$, —$CH_2C(O)OCH_2CH_3$, or —$CH_2CH_2S(O)_2CH_3$; (ii) hydroxycyclopentyl, oxetanyl, or cyclohexyl substituted with zero or one substituent selected from —OH and —$CH_3$; (iii) phenyl substituted with zero to 2 substituents independently selected from F, —CN, —OH, and —$C(O)OCH_3$; (iv) —$CH_2(cyclopropyl)$, —$CH_2(difluorocyclopropyl)$, —$CH_2$(cyclobutyl), —$CH_2(oxetanyl)$, —$CH_2(phenyl)$, —$CH_2$(fluorophenyl), —$CH_2(methoxyphenyl)$, —$CH_2(butoxycarbonyl, hydroxypiperidinyl)$, —$CH_2$(butoxycarbonyl pyrrolidinyl), —$CH_2(benzo[d]imidazolyl)$, —$CH_2(methyl benzo[d]thiazolyl)$, —$CH_2CH_2(morpholinyl)$, —$CH_2CH_2$(phenyl), —$CH_2CH_2(pyridinyl)$, —$CH_2CH_2(dimethylpyrazolyl)$, —$CH_2CH_2CH_2(phenyl)$, —$CH_2CH_2CH_2(pyrrolidinyl)$, —$CH_2C(O)(morpholinyl)$, —$CH_2C(O)(piperazinyl)$, —$CH_2C(O)(acetylpiperazinyl)$, —$CH_2C(O)(acetylpiperazinyl)$, or —$CH_2C(O)(methylsulfonyl piperazinyl)$; (v) pyridinyl, cyanopyridinyl, tetrahydrofuranyl, tetrahydropyranyl, hydroxytetrahydrofuranyl, trihydroxy-hydroxymethyltetrahydropyranyl, acetopyrrolidinyl, methylpyrrolidinonyl, dioxopyrimidinyl, or azetidinyl substituted with zero to 1 substituent selected from —CN, —$CH_3$, —$CH_2CH_3$, —$CH(CH_3)_2$, —$C(O)cyclopropyl$, —$C(O)phenyl$, —$C(O)CH_3$, —$C(O)CD_3$, —$C(O)CH(CH_3)_2$, —$C(O)C(CH_3)_3$, —$C(O)CH_2(cyclopropyl)$, —$C(O)OCH_3$, —$C(O)OC(CH_3)_3$, —$CH(phenyl)_2$, methyl oxadiazolyl, and pyrimidinyl; or (vi) piperidinyl substituted with zero to 3 substituents independently selected from F, —OH, —$CH_3$, —$C(O)CH_3$, —$C(O)OCH_3$, —$C(O)OCH_2CH_3$, —$C(O)OC(CH_3)_3$, —$C(O)(pyridinyl)$, —$S(O)_2CH_3$, and —$OS(O)_2CH_3$; and each $R_b$ is independently H, Cl, —CN, —$NH_2$, or —$C(O)NH_2$.

One embodiment provides a compound of Formula (I) or a salt thereof, wherein A is

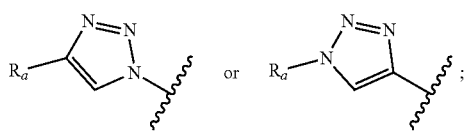

20

HET is

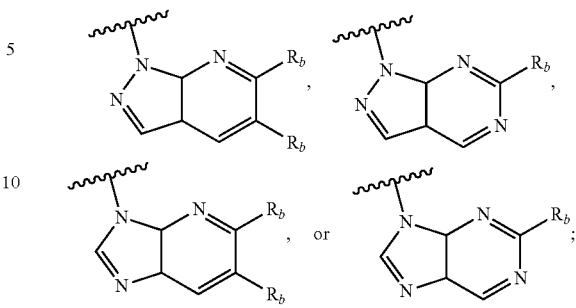

$R_3$ is —$CH_2CH_3$, —$CH(CH_3)_2$, —$CH_2C(CH_3)_2OH$, —$CH(CH_3)CH_2OH$, —$CH(CH_3)CH_2OH$, cyclopropyl, oxetanyl, tetrahydropyranyl, ethyl pyrazolyl, or difluoroethyl pyrazolyl; $R_a$ is H, $C_{1-5}$ alkyl, $C_{1-3}$ fluoroalkyl, $C_{1-5}$ hydroxyalkyl, —$CH_2CN$, —$CH_2CH_2CN$, —$CH_2CH_2CH_2CN$, —$CH_2NH_2$, —$CH_2NHCH_3$, —$CH_2N(CH_3)_2$, —$CH_2CH_2NH_2$, —$CH_2CH_2N(CH_3)_2$, —$C(CH_3)_2NH_2$, —$CH_2CH_2CH_2NH_2$, —$(CH_2)_5NH_2$, —$CH_2N(CH_2CH_3)_2$, —$CH_2CH(OH)CF_3$, —$(CH_2CH_2O)_4H$, —$CH_2OCH_3$, —$CH_2C(O)CH_3$, —$CH_2CH_2OCH_3$, —$CH_2CH_2OCH_2CH_3$, —$CH_2CH(OH)CH_2OCH_3$, —$CH_2CH(OH)CH_2OCH_2CH_3$, —$CH_2C(O)OCH_2CH_3$, or —$CH_2CH_2S(O)_2CH_3$, —$CH_2NHC(O)NH_2$, —$C(O)NH_2$, —CH=$CH_2$, —$CH_2$(cyclopropyl), —$CH_2(difluorocyclopropyl)$, —$CH_2(cyclobutyl)$, —$CH_2(oxetanyl)$, —$CH_2(morpholinyl)$, —$CH_2(phenyl)$, —$CH_2(fluorophenyl)$, —$CH_2(methoxyphenyl)$, —$CH_2$(butoxycarbonyl, hydroxypiperidinyl), —$CH_2$(butoxycarbonyl pyrrolidinyl), —$CH_2(benzo[d]imidazolyl)$, —$CH_2(methyl benzo[d]thiazolyl)$, —$CH_2CH_2(morpholinyl)$, —$CH_2CH_2(phenyl)$, —$CH_2CH(OH)(phenyl)$, —$CH_2CH_2(pyridinyl)$, —$CH_2CH_2(dimethylpyrazolyl)$, —$CH(CH_2OH)(phenyl)$, —$CH_2CH_2CH_2(phenyl)$, —$CH_2CH_2(pyrrolidinyl)$, —$CH_2CH(OH)CH_2(phenyl)$, —$CH_2CH(OH)CH_2O(methoxyphenyl)$, —$CH_2CH(NH_2)CH_2(phenyl)$, —$CH_2C(O)(morpholinyl)$, —$CH_2C(O)(piperazinyl)$, —$CH_2C(O)(acetylpiperazinyl)$, —$CH_2C(O)(acetylpiperazinyl)$, —$CH_2C(O)(methylsulfonyl piperazinyl)$, —$CH_2S(O)_2(phenyl)$, acetylazetidinyl, cyclopropyl, cyclopentyl, hydroxycyclopentyl, phenyl, oxetanyl, dimethoxyphenyl, pyridinyl; cyclohexyl substituted with —OH, —$CH_3$, —$NH_2$, —$NHC(O)CH_3$, —$NHCH(CH_3)_2$, —$NHC(O)OCH_3$, or —$NHC(O)OC(CH_3)_3$; pyridinyl, cyanopyridinyl, tetrahydrofuranyl, tetrahydropyranyl, hydroxytetrahydrofuranyl, trihydroxy-hydroxymethyltetrahydropyranyl, acetopyrrolidinyl, methylpyrrolidinonyl, dioxopyrimidinyl; phenyl substituted with zero to 2 substituents independently selected from F, —CN, —OH, and —$C(O)OCH_3$; or piperidinyl substituted with zero to 3 substituents independently selected from F, —OH, —$CH_3$, —$CH(CH_3)_2$, —$CH_2CHF_2$, —$C(O)NH_2$, —$C(O)CH_3$, —$C(O)OCH_3$, —$C(O)OCH_2CH_3$, —$C(O)OC(CH_3)_3$, —$C(O)(pyridinyl)$, —$S(O)_2CH_3$, and —$OS(O)_2CH_3$; or azetidinyl substituted with zero to 1 substituent selected from —CN, —$CH_3$, —$CH_2CH_3$, —$CH(CH_3)_2$, —$C(O)cyclopropyl$, —$C(O)phenyl$, —$C(O)CH_3$, —$C(O)CD_3$, —$C(O)CH(CH_3)_2$, —$C(O)C(CH_3)_3$, —$C(O)CH_2(cyclopropyl)$, —$C(O)OCH_3$, —$C(O)OC(CH_3)_3$, —$CH(phenyl)_2$, methyl oxadiazolyl, and pyrimidinyl; and each $R_b$ is independently H, $C_1$, —CN, —$NH_2$, or —$C(O)NH_2$.

One embodiment provides a compound of Formula (I) or a salt thereof wherein: HET is a heteroaryl selected from pyrazolo[3,4-b]pyridinyl, wherein said heteroaryl is attached to the pyridinyl group in the compound of Formula (I) by a nitrogen ring atom in said heteroaryl and wherein said heteroaryl is substituted with $R_b$; A is

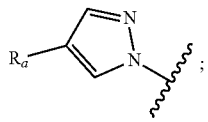

$R_3$ is —CH(CH$_3$)$_2$; $R_a$ is —CN, —CH$_3$, —CH(CH$_3$)$_2$, —CF$_3$, —CH$_2$CH$_2$OH, —CH$_2$CH$_2$C(CH$_3$)$_2$OH, —CH$_2$CN, —CH$_2$CH$_2$CH$_2$CN, —CH$_2$(phenyl), or pyridinyl; and $R_b$ is —CN. Included in this embodiment are compounds in which HET is

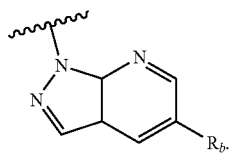

One embodiment provides a compound of Formula (I) or a salt thereof wherein: HET is a heteroaryl selected from pyrazolo[3,4-b]pyridinyl, pyrazolo[3,4-d]pyrimidinyl, imidazolo[4,5-b]pyridinyl, and imidazolo[4,5-d]pyrimidinyl, wherein said heteroaryl is attached to the pyridinyl group in the compound of Formula (I) by a nitrogen ring atom in said heteroaryl and wherein said heteroaryl is substituted with zero to 2 $R_b$; A is

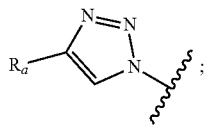

$R_3$ is —CH$_2$CH$_3$, —CH$_2$CH$_2$CH$_3$, —CH(CH$_3$)$_2$, —CH(CH$_3$)CH$_2$OH, —C(CH$_3$)$_2$CH$_2$OH, —CH$_2$C(CH$_3$)$_2$OH, —CH$_2$CH$_2$CH$_2$F, —CH(CH$_2$F)$_2$, —CH$_2$CH$_2$CF$_3$, cyclopropyl, methylcyclopropyl, difluorocyclobutyl, fluorocyclopentyl, difluorocyclopentyl, fluorocyclohexyl, hydroxycyclohexyl, oxetanyl, tetrahydrofuranyl, fluorotetrahydrofuranyl, tetrahydropyranyl, and difluoroethylpyrazolyl; $R_a$ is (i) —CH$_2$F, —CH$_2$OH, —CH$_2$NH$_2$, —CH$_2$CH$_3$, —CH$_2$CH$_2$OH, —CH$_2$CH$_2$CN, —CH$_2$CH$_2$CH$_3$, —CH$_2$CHFCH$_3$, —CH$_2$CH$_2$CH$_2$CN, —CH$_2$CH(OH)CH$_3$, —CH$_2$CH$_2$CH$_2$OH, —CH$_2$CH$_2$CH$_2$CH$_3$, —CH$_2$CH(OH)CH$_2$CH$_3$, —C(CH$_3$)$_2$OH, —C(CH$_3$)$_2$NH$_2$, —CH$_2$CH(CH$_3$)$_2$, —(CH$_2$)$_4$OH, —CH$_2$C(CH$_3$)$_2$OH, —C(CH$_3$)(OH)CH$_2$CH$_3$, —CH$_2$CH$_2$CH(CH$_3$)$_2$, —CH$_2$C(CH$_3$)(OH)CH$_2$CH$_3$, —CH$_2$CH$_2$C(CH$_3$)$_2$OH, —CH=CH$_2$, —CH$_2$CH$_2$C(CH$_3$)$_2$F, —CH$_2$CHFC(CH$_3$)$_2$OH, —CH$_2$CH$_2$C(CH$_3$)(OH)CH$_2$OH, —CH$_2$CH$_2$C(CH$_3$)$_2$OC(O)CH$_2$NH$_2$, —CH$_2$CH$_2$C(CH$_3$)$_2$OC(O)CH$_2$N(CH$_3$)$_2$, —CH$_2$NHCH$_3$, —CH$_2$N(CH$_3$)$_2$, —CH$_2$N(CH$_2$CH$_3$)$_2$, —CH$_2$CH$_2$NH$_2$, —CH$_2$OCH$_3$, —CH$_2$C(O)CH$_3$, —CH$_2$NHC(O)NH$_2$, —CH$_2$CH$_2$NHC(O)OCH$_3$, or —C(O)NH$_2$; (ii) cyclopropyl, cyclopentyl, or cyclohexyl substituted with —NH$_2$, —NHC(O)CH$_3$, —NHC(O)OC(CH$_3$)$_3$, —NHC(O)OCH$_3$, —NHC(CH$_3$)$_2$, —NHCH$_2$CH$_3$, or —NHCH$_2$CHF$_2$; (iii) phenyl or dimethoxyphenyl; (iv) —CH$_2$(morpholinyl), —CH$_2$CH$_2$(phenyl), —CH$_2$S(O)$_2$(phenyl), —CH$_2$CH$_2$(morpholinyl), or —CH$_2$CH(OH)(phenyl); (v) acetoazetidinyl, methylimidazolyl, pyridinyl, or tetrahydropyranyl; or (vi) piperidinyl substituted with zero to 1 substituent selected from —C(O)NH$_2$, —C(O)CF$_3$, —C(O)CH$_2$C(CH$_3$)$_2$OH, —C(O)OC(CH$_3$)$_3$, —C(O)OCH$_3$, —CH(CH$_3$)$_2$, —CH$_2$CHF$_2$, —S(O)$_2$CH$_2$CH$_3$, or —S(O)$_2$CH$_3$; and each $R_b$ is independently selected from $C_1$, —CN, and —NH$_2$. Included in this embodiment are compounds in which HET is:

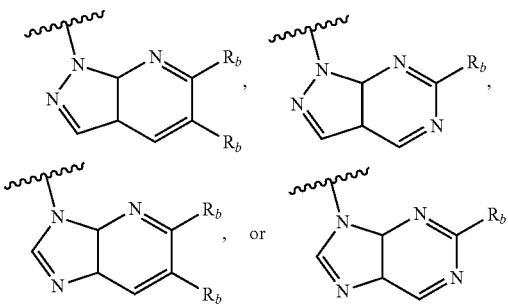

One embodiment provides a compound of Formula (I) or a salt thereof wherein: HET is a heteroaryl selected from pyrazolo[3,4-b]pyridinyl, wherein said heteroaryl is attached to the pyridinyl group in the compound of Formula (I) by a nitrogen ring atom in said heteroaryl and wherein said heteroaryl is substituted with $R_b$; A is

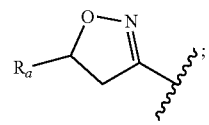

$R_3$ is —CH$_2$CH$_3$, CH(CH$_3$)$_2$, or —CH$_2$CHF$_2$; $R_a$ is —CH$_2$CH$_2$C(CH$_3$)$_2$OH or —CH$_2$NHC(O)OCH$_3$; and $R_b$ is —CN. Included in this embodiment are compounds in which HET is

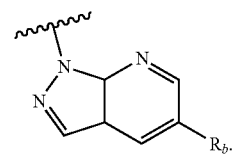

One embodiment provides a compound of Formula (I) or a salt thereof wherein: HET is a heteroaryl selected from pyrazolo[3,4-b]pyridinyl, wherein said heteroaryl is attached to the pyridinyl group in the compound of Formula (I) by a nitrogen ring atom in said heteroaryl and wherein said heteroaryl is substituted with $R_b$; A is

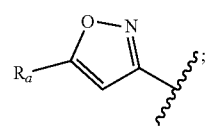

$R_3$ is —CH(CH$_3$)$_2$; $R_a$ is —CH$_2$C(CH$_3$)$_2$OH, —CH$_2$CH$_2$C(CH$_3$)$_2$OH, morpholinyl, ethylmorpholinyl, piperidinyl, or methylsulfonylpiperidinyl; and $R_b$ is —CN. Included in this embodiment are compounds in which HET is

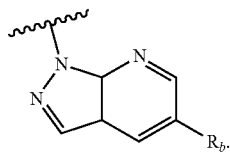

One embodiment provides a compound of Formula (I) or a salt thereof wherein: HET is a heteroaryl selected from pyrazolo[3,4-b]pyridinyl, wherein said heteroaryl is attached to the pyridinyl group in the compound of Formula (I) by a nitrogen ring atom in said heteroaryl and wherein said heteroaryl is substituted with $R_b$; A is

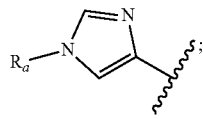

$R_3$ is —CH(CH$_3$)$_2$; $R_a$ is H, —CH$_2$CH$_3$, —CH$_2$CH$_2$CH$_3$, —CH(CH$_3$)$_2$, —CH$_2$CH(CH$_3$)$_2$, —CH$_2$CHF$_2$, —CH$_2$C(O)NH$_2$, —CH$_2$CH(OH)CH$_3$, —CH$_2$CH(CH$_3$)CH$_2$OH, —CH$_2$CH$_2$C(CH$_3$)$_2$OH, —CH$_2$C(O)NHCH$_3$, pyridinyl, acetylazetidinyl, —CH$_2$(acetylazetidinyl), —CH$_2$(cyclopropyl), —CH$_2$(cyclobutyl), —CH$_2$(oxetanyl), —CH$_2$(hydroxyoxetanyl), —CH$_2$(phenyl), —CH$_2$(pyridinyl), —CH$_2$CH$_2$CH$_2$(phenyl), or —CH$_2$C(O)(morpholinyl); and $R_b$ is —CN. Included in this embodiment are compounds in which HET is

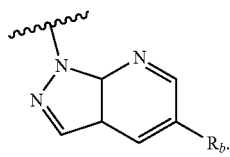

One embodiment provides a compound of Formula (I) or a salt thereof wherein:

HET is a heteroaryl selected from pyrazolo[3,4-b]pyridinyl and pyrazolo[3,4-d]pyrimidinyl, wherein said heteroaryl is attached to the pyridinyl group in the compound of Formula (I) by a nitrogen ring atom in said heteroaryl and wherein said heteroaryl is substituted with zero to one $R_b$; A is

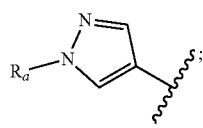

$R_3$ is —CH(CH$_3$)$_2$ or difluoroethyl pyrazolyl; $R_a$ is —CH$_2$CH$_3$, —CH$_2$CH$_2$CH$_3$, —CH$_2$CH(CH$_3$)$_2$, —CHF$_2$, —CH$_2$CF$_3$, —CH$_2$CH$_2$OH, —CH$_2$(oxetanyl), cyclopropyl, or tetrahydropyranyl; and $R_b$ is —CN. Included in this embodiment are compounds in which HET is

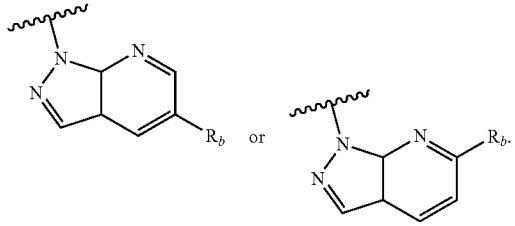

One embodiment provides a compound of Formula (I) or a salt thereof wherein: HET is a heteroaryl selected from pyrrolo[2,3-b]pyridinyl, pyrrolo[2,3-d]pyrimidinyl, pyrazolo[3,4-b]pyridinyl, and imidazolo[4,5-b]pyridinyl, wherein said heteroaryl is attached to the pyridinyl group in the compound of Formula (I) by a nitrogen ring atom in said heteroaryl and wherein said heteroaryl is substituted with zero to 2 $R_b$; A is

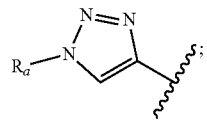

a $R_3$ is —CH$_2$CH$_3$, —CH(CH$_3$)$_2$, —CH(CH$_3$)CH$_2$OH, cyclopropyl, tetrahydropyranyl, ethyl pyrazolyl, and difluoroethyl pyrazolyl; $R_a$ is: (i) —CH$_3$, —CH$_2$CN, —CH$_2$CH$_3$, —CH$_2$CH$_2$OH, —CH$_2$CHF$_2$, —CH$_2$CH$_2$NH$_2$, —CH$_2$CH$_2$S(O)$_2$CH$_3$, —CH$_2$CH$_2$OCH$_3$, —CH$_2$CH$_2$OCH$_2$CH$_3$, —CH$_2$CH$_2$N(CH$_3$)$_2$, —CH$_2$CH$_2$CH$_3$, —CH(CH$_3$)$_2$, —C(CH$_3$)$_3$, —CH$_2$CH(OH)CH$_3$, —CH$_2$CH$_2$CH$_2$OH, —CH$_2$CH(CH$_3$)OH, —CH$_2$CH(OH)CH$_2$OH, —CH$_2$CHFCH$_3$, —CH$_2$CH$_2$CH$_2$F, —CH$_2$CH(OH)CF$_3$, —CH$_2$CH(OH)CH$_2$OCH$_2$CH$_3$, —CH$_2$CH$_2$CH$_2$NH$_2$, —CH$_2$CH(OH)CH$_2$OCH$_3$, —CH$_2$C(CH$_3$)$_2$OH, —(CH$_2$)$_4$OH, —CH(CH$_3$)CH(CH$_3$)OH, —CH$_2$CH$_2$CH(CH$_3$)$_2$, —CH$_2$C(CH$_3$)(OH)CH$_2$CH$_3$, —CH$_2$CH(OH)CH(CH$_3$)$_2$, —CH$_2$CH$_2$C(CH$_3$)$_2$OH, —(CH$_2$)$_5$NH$_2$, —CH$_2$C(O)CH$_3$, —CH$_2$C(O)OCH$_2$CH$_3$, —CH$_2$CH(OH)(phenyl), —CH(CH$_2$OH)(phenyl), —CH$_2$CH(OH)CH$_2$(phenyl), —CH$_2$CH(OH)CH$_2$O(methoxyphenyl), or —(CH$_2$CH$_2$O)$_4$H; (ii) oxetanyl or C$_{5-6}$ cycloalkyl substituted with zero to 2 substituents independently selected from —OH, —CH$_3$, —NH$_2$, —NHCH$_2$CHF$_2$, —NHC(O)OCH$_3$, and —NHC(O)OCH$_2$CH$_3$; (iii) phenyl substituted with zero to 2 substituents independently selected from F, —OH, —CN, —C(O)OCH$_3$, and —NHC(O)OC(CH$_3$)$_3$; (iv) —CH$_2$(cyclopropyl), —CH$_2$(difluorocyclopropyl), —CH$_2$(cyclobutyl), —CH$_2$(oxetanyl), —CH$_2$(phenyl), —CH$_2$(fluorophenyl), —CH$_2$(methoxyphenyl), —CH$_2$(butoxycarbonylpyrrolidinyl), —CH$_2$(butoxycarbonyl, hydroxypiperidinyl), —CH$_2$(benzo[d]imidazolyl), —CH$_2$(methylbenzo[d]thiazolyl), —CH$_2$CH$_2$(morpholinyl), —CH$_2$CH$_2$(phenyl), —CH$_2$CH$_2$(dimethylpyrazolyl), —CH$_2$CH$_2$(pyridinyl), —CH$_2$CH$_2$CH$_2$(phenyl), —CH$_2$CH$_2$CH$_2$(pyrrolidinyl), —CH$_2$C(O)(morpholinyl), —CH$_2$C(O)(piperazinyl), —CH$_2$C(O)(acetopiperazinyl), —CH$_2$C(O)(methylsulfonylpiperazinyl), or —CH$_2$CH(NH$_2$)CH$_2$(phenyl); (v) pyridinyl, cyanopyridinyl, tetrahydrofuranyl, tetrahydropyranyl, hydroxytetrahydrofuranyl, trihydroxy-hydroxymethyltetrahydropyranyl, acetopyrrolidinyl, methylpyrrolidinonyl, dioxopyrimidinyl, or azetidinyl substituted with zero to 1 substituent selected from —CN, —CH$_3$, —CH$_2$CH$_3$, —CH(CH$_3$)$_2$, —C(O)(cyclopropyl), —C(O)(phenyl), —C(O)

CH$_3$, —C(O)CD$_3$, —C(O)CH(CH$_3$)$_2$, —C(O)C(CH$_3$)$_3$, —C(O)CH$_2$(cyclopropyl), —C(O)OCH$_3$, —C(O)OC(CH$_3$)$_3$, —CH(phenyl)$_2$, methyloxadiazolyl, and pyrimidinyl; or (vi) piperidinyl substituted with zero to 3 substituents independently selected from F, —OH, —CH$_3$, —C(O)CH$_3$, —C(O)CH$_2$CH$_3$, —C(O)C(CH$_3$)$_3$, —C(O)OCH$_3$, —C(O)OCH$_2$CH$_3$, —C(O)OC(CH$_3$)$_3$, —C(O)(pyridinyl), —S(O)$_2$CH$_3$, and —OS(O)$_2$CH$_3$; and R$_b$ is C$_1$, —CN, —NH$_2$, or —C(O)NH$_2$. Included in this embodiment are compounds in which HET is:

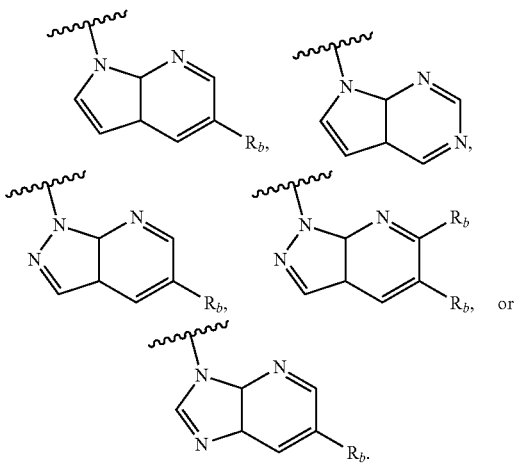

One embodiment provides a compound of Formula (I) or a salt thereof wherein: HET is a heteroaryl selected from pyrazolo[3,4-b]pyridinyl, wherein said heteroaryl is attached to the pyridinyl group in the compound of Formula (I) by a nitrogen ring atom in said heteroaryl and wherein said heteroaryl is substituted with R$_b$; A is

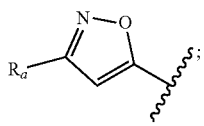

R$_3$ is —CH(CH$_3$)$_2$; R$_a$ is —CH(CH$_2$OH)$_2$, —CH$_2$CH$_2$C(CH$_3$)$_2$OH, —CH$_2$CH$_2$CH$_2$NHCH$_3$, —CH$_2$CH$_2$CH$_2$N(CH$_3$)C(O)CH$_3$, morpholinyl, piperidinyl, acetylpiperidinyl, acetamidocyclohexyl, ((methoxycarbonyl)amino)cyclohexyl, difluoropiperidinyl, hydroxypiperidinyl, dimethylmorpholinyl, tetrahydropyranyl, pyrrolidinyl, acetylpyrrolidinyl, fluoro-acetylpiperidinyl, methoxycarbonylpiperidinyl, azetidinyl, acetylazetidinyl, methoxycarbonylazetidinyl, dimethyl-1,3-dioxolanyl, or acetyl-8-azabicyclo[3.2.1]octanyl; and R$_b$ is —CN. Included in this embodiment are compounds in which HET is

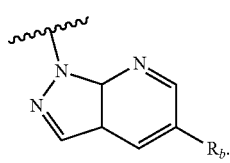

One embodiment provides a compound of Formula (I) or a salt thereof wherein: HET is a heteroaryl selected from pyrazolo[3,4-b]pyridinyl, wherein said heteroaryl is attached to the pyridinyl group in the compound of Formula (I) by a nitrogen ring atom in said heteroaryl and wherein said heteroaryl is substituted with R$_b$; A is

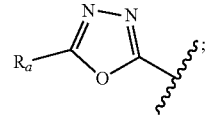

R$_3$ is —CH(CH$_3$)$_2$; R$_a$ is —C(O)(morpholinyl) or —NH(aminocyclohexyl); and R$_b$ is —CN. Included in this embodiment are compounds in which HET is

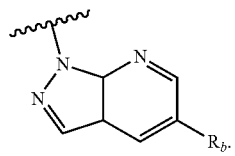

One embodiment provides a compound of Formula (I) or a salt thereof, wherein said compound is selected from: 2-(4-(4-(isopropylamino)-6-(7H-pyrrolo[2,3-d]pyrimidin-7-yl)pyridin-3-yl)-1H-1,2,3-triazol-1-yl)ethanol (1); ethyl 2-(4-(4-(isopropylamino)-6-(7H-pyrrolo[2,3-d]pyrimidin-7-yl)pyridin-3-yl)-1H-1,2,3-triazol-1-yl)acetate (2); N-isopropyl-5-(1-(2-morpholinoethyl)-1H-1,2,3-triazol-4-yl)-2-(7H-pyrrolo[2,3-d]pyrimidin-7-yl)pyridin-4-amine (3); (3R,4R)-4-(4-(4-(isopropylamino)-6-(7H-pyrrolo[2,3-d]pyrimidin-7-yl) pyridin-3-yl)-1H-1,2,3-triazol-1-yl)piperidin-3-ol (4); 5-(1-(5-aminopentyl)-1H-1,2,3-triazol-4-yl)-N-isopropyl-2-(7H-pyrrolo[2,3-d]pyrimidin-7-yl)pyridin-4-amine (5); (3R,4S)-4-(4-(4-(isopropylamino)-6-(7H-pyrrolo[2,3-d]pyrimidin-7-yl)pyridin-3-yl)-1H-1,2,3-triazol-1-yl)piperidin-3-ol (6); (3S,4R)-4-(4-(4-(isopropylamino)-6-(7H-pyrrolo[2,3-d]pyrimidin-7-yl)pyridin-3-yl)-1H-1,2,3-triazol-1-yl)piperidin-3-ol (7); 6-((4-(4-(isopropylamino)-6-(7H-pyrrolo[2,3-d]pyrimidin-7-yl) pyridin-3-yl)-1H-1,2,3-triazol-1-yl)methyl)pyrimidine-2,4(1H,3H)-dione (8); 2-(2-(2-(2-(4-(4-(isopropylamino)-6-(7H-pyrrolo[2,3-d]pyrimidin-7-yl) pyridin-3-yl)-1H-1,2,3-triazol-1-yl)ethoxy)ethoxy)ethoxy) ethanol (9); 1-(5-(1-isopentyl-1H-1,2,3-triazol-4-yl)-4-(isopropylamino)pyridin-2-yl)-1H-pyrazolo[3,4-b]pyridine-5-carbonitrile, TFA (10); 1-(5-(1-(2-hydroxyethyl)-1H-1,2,3-triazol-4-yl)-4-(isopropylamino)pyridin-2-yl)-1H-pyrazolo[3,4-b]pyridine-5-carbonitrile (11); 1-(4-(isopropylamino)-5-(1-(2-morpholinoethyl)-1H-1,2,3-triazol-4-yl)pyridin-2-yl)-1H-pyrazolo[3,4-b]pyridine-5-carbonitrile (12); 1-(4-(cyclopropylamino)-5-(1-(2-morpholinoethyl)-1H-1,2,3-triazol-4-yl)pyridin-2-yl)-1H-pyrazolo[3,4-b]pyridine-5-carbonitrile (13); 1-(4-(cyclopropylamino)-5-(1-(2-hydroxyethyl)-1H-1,2,3-triazol-4-yl) pyridin-2-yl)-1H-pyrazolo[3,4-b]pyridine-5-carbonitrile (14); 1-(4-(isopropylamino)-5-(1-(oxetan-3-yl)-1H-1,2,3-triazol-4-yl) pyridin-2-yl)-1H-pyrazolo[3,4-b]pyridine-5-carbonitrile (15); 1-(5-(1-(cyclopropylmethyl)-1H-1,2,3-triazol-4-yl)-4-(isopropylamino) pyridin-2-yl)-1H-pyrazolo[3,4-b]pyridine-5-carbonitrile (16); 1-(5-(1-cyclohexyl-1H-1,2,3-triazol-4-yl)-4-(isopropylamino)pyridin-2-yl)-1H-pyrazolo[3,4-b]pyridine-5-carbonitrile (17); 1-(5-(1-(tert-butyl)-1H-1,2,3-triazol-4-yl)-4-(isopropylamino)pyridin-2-yl)-1H-pyrazolo[3,4-b]pyridine-5-carbonitrile (18); 1-(4-(isopropylamino)-5-(1-(tetrahydro-2H-pyran-4-yl)-1H-1,2, 3-triazol-4-yl)pyridin-2-yl)-1H-pyrazolo[3,4-b]pyridine-5-carbonitrile (19); 1-(5-(1-(2-fluorophenyl)-1H-1,2,3-triazol-4-yl)-4-(isopropylamino)pyridin-2-yl)-1H-pyrazolo [3,4-b]pyridine-5-carbonitrile (20); 1-(4-(isopropylamino)-5-(1-(1-methyl-2-oxopyrrolidin-3-yl)-1H-1,2,3-triazol-4-yl)pyridin-2-yl)-1H-pyrazolo[3,4-b]pyridine-5-carbonitrile (21 and 22); 3-(5-(1-(tert-butyl)-1H-1,2,3-triazol-4-yl)-4-(isopropylamino) pyridin-2-yl)-3H-imidazo[4,5-b]pyridine-6-carbonitrile (23); 3-(4-(isopropylamino)-5-(1-(tetrahydro-2H-pyran-4-yl)-1H-1,2,3-triazol-4-yl) pyridin-2-yl)-3H-imidazo[4,5-b]pyridine-6-carbonitrile (24); 6-amino-1-(5-(1-cyclohexyl-1H-1,2,3-triazol-4-yl)-4-(isopropylamino) pyridin-2-yl)-1H-pyrazolo[3,4-b]pyridine-5-carbonitrile (25); 2-(5-chloro-1H-pyrazolo[3,4-b]pyridin-1-yl)-N-isopropyl-5-(1-(oxetan-3-yl)-1H-1,2,3-triazol-4-yl)pyridin-4-amine (26); 2-(5-chloro-1H-pyrazolo [3,4-b]pyridin-1-yl)-5-(1-(cyclopropylmethyl)-1H-1,2,3-triazol-4-yl)-N-isopropylpyridin-4-amine (27); 1-(5-(1-(3-hydroxypropyl)-1H-1,2,3-triazol-4-yl)-4-(isopropylamino) pyridin-2-yl)-1H-pyrazolo [3,4-b]pyridine-5-carbonitrile (28); 6-amino-1-(5-(1-(3-hydroxypropyl)-1H-1,2,3-triazol-4-yl)-4-(isopropylamino)pyridin-2-yl)-1H-pyrazolo[3,4-b]pyridine-5-carbonitrile (29); 1-(4-(isopropylamino)-5-(1-propyl-1H-1,2,3-triazol-4-yl) pyridin-2-yl)-1H-pyrazolo[3,4-b]pyridine-5-carbonitrile (30); 1-(5-(1-((2,2-difluorocyclopropyl)methyl)-1H-1,2,3-triazol-4-yl)-4-(isopropylamino)pyridin-2-yl)-1H-pyrazolo[3,4-b]pyridine-5-carbonitrile (31 and 32); 6-amino-1-(4-(isopropylamino)-5-(1-propyl-1H-1,2,3-triazol-4-yl)pyridin-2-yl)-1H-pyrazolo[3,4-b]pyridine-5-carbonitrile (33); 1-(4-(cyclopropylamino)-5-(1-propyl-1H-1,2,3-triazol-4-yl) pyridin-2-yl)-1H-pyrazolo[3,4-b]pyridine-5-carbonitrile (34); 6-amino-1-(4-(cyclopropylamino)-5-(1-propyl-1H-1,2,3-triazol-4-yl)pyridin-2-yl)-1H-pyrazolo [3,4-b]pyridine-5-carbonitrile (35); 2-(5-chloro-1H-pyrazolo[3,4-b]pyridin-1-yl)-N-cyclopropyl-5-(1-propyl-1H-1,2,3-triazol-4-yl)pyridin-4-amine (36); 1-(5-(1-ethyl-1H-1,2,3-triazol-4-yl)-4-(isopropylamino)pyridin-2-yl)-1H-pyrazolo[3,4-b]pyridine-5-carbonitrile (37); 3-(5-(1-ethyl-1H-1,2,3-triazol-4-yl)-4-(isopropylamino)pyridin-2-yl)-3H-imidazo[4,5-b]pyridine-6-carbonitrile (38); 2-(5-chloro-1H-pyrazolo[3,4-b]pyridin-1-yl)-5-(1-ethyl-1H-1,2,3-triazol-4-yl)-N-isopropylpyridin-4-amine (39); 3-(4-(isopropylamino)-5-(1-propyl-1H-1,2,3-triazol-4-yl)pyridin-2-yl)-3H-imidazo[4,5-b]pyridine-6-carbonitrile (40); 1-(4-(isopropylamino)-5-(1-(3,3,3-trifluoropropyl)-1H-1,2,3-triazol-4-yl)pyridin-2-yl)-1H-pyrazolo[3,4-b]pyridine-5-carbonitrile (41); 3-(4-(isopropylamino)-5-(1-(3,3,3-trifluoropropyl)-1H-1,2,3-triazol-4-yl)pyridin-2-yl)-3H-imidazo[4,5-b]pyridine-6-carbonitrile (42); 3-(4-(cyclopropylamino)-5-(1-propyl-1H-1,2,3-triazol-4-yl)pyridin-2-yl)-3H-imidazo[4,5-b]pyridine-6-carbonitrile (43); 1-(5-(1-(3-fluoropropyl)-1H-1,2,3-triazol-4-yl)-4-(isopropylamino)pyridin-2-yl)-1H-pyrazolo [3,4-b]pyridine-5-carbonitrile (44); 3-(5-(1-(3-fluoropropyl)-1H-1,2,3-triazol-4-yl)-4-(isopropylamino)pyridin-2-yl)-3H-imidazo[4,5-b]pyridine-6-carbonitrile (45); 6-amino-1-(5-(1-(3-fluoropropyl)-1H-1,2,3-triazol-4-yl)-4-(isopropylamino)pyridin-2-yl)-1H-pyrazolo[3,4-b]pyridine-5-carbonitrile (46); 1-(5-(1-(cyanomethyl)-1H-1,2,3-triazol-4-yl)-4-(isopropylamino) pyridin-2-yl)-1H-pyrazolo[3,4-b]pyridine-5-carbonitrile (47); 1-(5-(1-(4-fluorobutyl)-1H-1,2,3-triazol-4-yl)-4-(isopropylamino)pyridin-2-yl)-1H-pyrazolo[3,4-b]pyridine-5-carbonitrile (48); 1-(5-(1-propyl-1H-1,2,3-triazol-4-yl)-4-((tetrahydro-2H-pyran-4-yl) amino)pyridin-2-yl)-1H-pyrazolo[3,4-b]pyridine-5-carbonitrile (49); 3-(5-(1-propyl-1H-1,2,3-triazol-4-yl)-4-((tetrahydro-2H-pyran-4-yl) amino)pyridin-2-yl)-3H-imidazo[4,5-b]pyridine-6-carbonitrile (50); 6-amino-1-(5-(1-propyl-1H-1,2,3-triazol-4-yl)-4-((tetrahydro-2H-pyran-4-yl)amino)pyridin-2-yl)-1H-pyrazolo[3,4-b]pyridine-5-carbonitrile (51); (S)-1-(4-((1-hydroxypropan-2-yl)amino)-5-(1-propyl-1H-1,2,3-triazol-4-yl)pyridin-2-yl)-1H-pyrazolo[3,4-b]pyridine-5-carbonitrile (52); (S)-3-(4-((1-hydroxypropan-2-yl)amino)-5-(1-propyl-1H-1,2,3-triazol-4-yl)pyridin-2-yl)-3H-imidazo[4,5-b]pyridine-6-carbonitrile (53); 1-(4-(ethylamino)-5-(1-propyl-1H-1,2,3-triazol-4-yl) pyridin-2-yl)-1H-pyrazolo[3,4-b]pyridine-5-carbonitrile (54); 3-(4-(ethylamino)-5-(1-propyl-1H-1,2,3-triazol-4-yl)pyridin-2-yl)-3H-imidazo[4,5-b]pyridine-6-carbonitrile (55); 1-(4-(isopropylamino)-5-(1-phenethyl-1H-1,2,3-triazol-4-yl) pyridin-2-yl)-1H-pyrazolo [3,4-b]pyridine-5-carbonitrile (56); 3-(4-(isopropylamino)-5-(1-phenethyl-1H-1,2,3-triazol-4-yl)pyridin-2-yl)-3H-imidazo[4,5-b]pyridine-6-carbonitrile (57); 1-(4-((1-ethyl-1H-pyrazol-4-yl)amino)-5-(1-propyl-1H-1,2,3-triazol-4-yl)pyridin-2-yl)-1H-pyrazolo [3,4-b]pyridine-5-carbonitrile (58); 3-(4-((1-ethyl-1H-pyrazol-4-yl) amino)-5-(i-propyl-1H-1,2,3-triazol-4-yl)pyridin-2-yl)-3H-imidazo[4,5-b]pyridine-6-carbonitrile (59); 1-(4-((1-(2,2-difluoroethyl)-1H-pyrazol-4-yl)amino)-5-(1-propyl-1H-1,2,3-triazol-4-yl) pyridin-2-yl)-1H-pyrazolo[3,4-b]pyridine-5-carbonitrile (60); 3-(4-((1-(2,2-difluoroethyl)-1H-pyrazol-4-yl)amino)-5-(1-propyl-1H-1,2,3-triazol-4-yl)pyridin-2-yl)-3H-imidazo[4,5-b]pyridine-6-carbonitrile (61); 9-(4-(isopropylamino)-5-(1-propyl-1H-1,2,3-triazol-4-yl)pyridin-2-yl)-9H-purin-2-amine (62); 1-(5-(1-(2-hydroxy-2-methylpropyl)-1H-1,2,3-triazol-4-yl)-4-(isopropylamino)pyridin-2-yl)-1H-pyrazolo[3,4-b]pyridine-5-carbonitrile (63); 1-(5-(1-((1R,2R)-2-hydroxy-2-methylcyclohexyl)-1H-1,2,3-triazol-4-yl)-4-(isopropylamino)pyridin-2-yl)-1H-pyrazolo[3,4-b]pyridine-5-carbonitrile (64); (S)-1-(5-(1-(2-hydroxypropyl)-1H-1,2,3-triazol-4-yl)-4-(isopropylamino)pyridin-2-yl)-1H-pyrazolo[3,4-b]pyridine-5-carbonitrile (65); (R)-1-(5-(1-(2-hydroxypropyl)-1H-1,2,3-triazol-4-yl)-4-(isopropylamino) pyridin-2-yl)-1H-pyrazolo[3,4-b]pyridine-5-carbonitrile (66); 3-(5-(1-(2-hydroxy-2-methylpropyl)-1H-1,2,3-triazol-4-yl)-4-(isopropylamino)pyridin-2-yl)-3H-imidazo[4,5-b]pyridine-6-carbonitrile (67); (R)-3-(5-(1-(2-hydroxypropyl)-1H-1,2,3-triazol-4-yl)-4-(isopropylamino)pyridin-2-yl)-3H-imidazo[4,5-b]pyridine-6-carbonitrile (68); (S)-3-(5-(1-(2-hydroxypropyl)-1H-1,2,3-triazol-4-yl)-4-(isopropylamino)pyridin-2-yl)-3H-imidazo[4,5-b]pyridine-6-carbonitrile (69); (S)-6-amino-1-(5-(1-(2-hydroxypropyl)-1H-1,2,3-triazol-4-yl)-4-(isopropylamino)pyridin-2-yl)-1H-pyrazolo[3,4-b]pyridine-5-carbonitrile (70); (S)-1-(4-(ethylamino)-5-(1-(2-hydroxypropyl)-1H-1,2,3-triazol-4-yl) pyridin-2-yl)-1H-pyrazolo[3,4-b]pyridine-5-carbonitrile (71); (S)-3-(4-(ethylamino)-5-(1-(2-hydroxypropyl)-1H-1,2,3-triazol-4-yl)pyridin-2-yl)-3H-imidazo [4,5-b]pyridine-6-carbonitrile (72); 3-(5-(1-((3R,4S)-4-hydroxytetrahydrofuran-3-yl)-1H-1,2,3-triazol-4-yl)-4-(isopropylamino) pyridin-2-yl)-3H-imidazo[4,5-b]pyridine-6-carbonitrile (74); 3-(5-(1-((3R,4S)-4-hydroxytetrahydrofuran-3-yl)-1H-1,2,3-triazol-4-yl)-4-(isopropylamino) pyridin-2-yl)-3H-imidazo[4,5-b]pyridine-6-carbonitrile (73 and 75); 1-(5-(1-(2-hydroxy-3-phenylpropyl)-1H-1,2,3-triazol-4-yl)-4-(isopropylamino)pyridin-2-yl)-1H-pyrazolo [3,4-b] pyridine-5-carbonitrile (76 and 77); 3-(5-(1-(2-hydroxy-3-phenylpropyl)-1H-1,2,3-triazol-4-yl)-4-(isopropylamino) pyridin-2-yl)-3H-imidazo[4,5-b]pyridine-6-carbonitrile (78 and 79); 1-(5-(1-((1R,2R)-2-hydroxycyclopentyl)-1H-1,2,3-triazol-4-yl)-4-(isopropylamino)pyridin-2-yl)-1H-pyrazolo [3,4-b]pyridine-5-carbonitrile (80 and 82); 3-(5-(1-((1R,2R)-2-hydroxycyclopentyl)-1H-1,2,3-triazol-4-yl)-4-

(isopropylamino)pyridin-2-yl)-3H-imidazo[4,5-b]pyridine-6-carbonitrile (81 and 83); (S)-1-(5-(1-(2-hydroxy-2-phenylethyl)-1H-1,2,3-triazol-4-yl)-4-(isopropylamino)pyridin-2-yl)-1H-pyrazolo[3,4-b]pyridine-5-carbonitrile (84); (R)-1-(5-(1-(2-hydroxy-2-phenylethyl)-1H-1,2,3-triazol-4-yl)-4-(isopropylamino)pyridin-2-yl)-1H-pyrazolo[3,4-b]pyridine-5-carbonitrile (85); (R)-1-(5-(1-(2-hydroxy-1-phenylethyl)-1H-1,2,3-triazol-4-yl)-4-(isopropylamino)pyridin-2-yl)-1H-pyrazolo[3,4-b]pyridine-5-carbonitrile (86); (S)-1-(5-(1-(2-hydroxy-1-phenylethyl)-1H-1,2,3-triazol-4-yl)-4-(isopropylamino)pyridin-2-yl)-1H-pyrazolo[3,4-b]pyridine-5-carbonitrile (87); 1-(5-(1-((2R,3S)-3-hydroxybutan-2-yl)-1H-1,2,3-triazol-4-yl)-4-(isopropylamino)pyridin-2-yl)-1H-pyrazolo[3,4-b]pyridine-5-carbonitrile (88 and 89); 1-(5-(1-((2S,3S)-3-hydroxybutan-2-yl)-1H-1,2,3-triazol-4-yl)-4-(isopropylamino) pyridin-2-yl)-1H-pyrazolo[3,4-b]pyridine-5-carbonitrile (90 and 91); 1-(5-(1-(2-hydroxy-2-methylbutyl)-1H-1,2,3-triazol-4-yl)-4-(isopropylamino)pyridin-2-yl)-1H-pyrazolo[3,4-b]pyridine-5-carbonitrile (92 and 93); 3-(5-(1-(2-hydroxy-2-methylbutyl)-1H-1,2,3-triazol-4-yl)-4-(isopropylamino)pyridin-2-yl)-3H-imidazo[4,5-b]pyridine-6-carbonitrile (94 and 95); 1-(5-(1-((1R,2R)-2-hydroxycyclohexyl)-1H-1,2,3-triazol-4-yl)-4-(isopropylamino)pyridin-2-yl)-1H-pyrazolo[3,4-b]pyridine-5-carbonitrile (96); 6-amino-4-(5-(1-(2-hydroxy-2-methylpropyl)-1H-1,2,3-triazol-4-yl)-4-(isopropylamino)pyridin-2-yl)-1H-pyrazolo[3,4-b]pyridine-5-carbonitrile (97); Ethyl 2-(4-(6-(5-cyano-1H-pyrazolo[3,4-b]pyridin-1-yl)-4-(isopropylamino)pyridin-3-yl)-1H-1,2,3-triazol-1-yl)acetate (98); (R)-tert-butyl 2-((4-(6-(5-cyano-1H-pyrazolo[3,4-b]pyridin-1-yl)-4-(isopropylamino)pyridin-3-yl)-1H-1,2,3-triazol-1-yl) methyl)pyrrolidine-1-carboxylate (99); 1-(5-(1-(1-benzhydrylazetidin-3-yl)-1H-1,2,3-triazol-4-yl)-4-(isopropylamino)pyridin-2-yl)-1H-pyrazolo[3,4-b]pyridine-5-carbonitrile (100); 1-(4-(isopropylamino)-5-(1-(2-morpholino-2-oxoethyl)-1H-1,2,3-triazol-4-yl)pyridin-2-yl)-1H-pyrazolo[3,4-b]pyridine-5-carbonitrile (101); 1-(5-(1-(2-(3,5-dimethyl-1H-pyrazol-4-yl)ethyl)-1H-1,2,3-triazol-4-yl)-4-(isopropylamino)pyridin-2-yl)-1H-pyrazolo[3,4-b]pyridine-5-carbonitrile (102); 1-(5-(1-(3-hydroxyphenyl)-1H-1,2,3-triazol-4-yl)-4-(isopropylamino)pyridin-2-yl)-1H-pyrazolo[3,4-b]pyridine-5-carbonitrile (103); 1-(5-(1-(3-cyano-4-fluorophenyl)-1H-1,2,3-triazol-4-yl)-4-(isopropylamino)pyridin-2-yl)-1H-pyrazolo[3,4-b]pyridine-5-carbonitrile (104); 1-(4-(isopropylamino)-5-(1-((2R,3R,4S,5R,6R)-3,4,5-trihydroxy-6-(hydroxymethyl)tetrahydro-2H-pyran-2-yl)-1H-1,2,3-triazol-4-yl)pyridin-2-yl)-1H-pyrazolo[3,4-b]pyridine-5-carbonitrile (105); 1-(4-(isopropylamino)-5-(1-((2-methylbenzo[d]thiazol-5-yl)methyl)-1H-1,2,3-triazol-4-yl)pyridin-2-yl)-1H-pyrazolo[3,4-b]pyridine-5-carbonitrile (106); 1-(5-(1-benzyl-1H-1,2,3-triazol-4-yl)-4-(isopropylamino) pyridin-2-yl)-1H-pyrazolo[3,4-b]pyridine-5-carbonitrile (107); 1-(5-(1-((1H-benzo[d]imidazol-2-yl)methyl)-1H-1,2,3-triazol-4-yl)-4-(isopropylamino)pyridin-2-yl)-1H-pyrazolo[3,4-b]pyridine-5-carbonitrile (108); 1-(5-(1-(4-fluorophenyl)-1H-1,2,3-triazol-4-yl)-4-(isopropylamino)pyridin-2-yl)-1H-pyrazolo[3,4-b]pyridine-5-carbonitrile (109); 1-(4-(isopropylamino)-5-(1-(4-methoxybenzyl)-1H-1,2,3-triazol-4-yl)pyridin-2-yl)-1H-pyrazolo[3,4-b]pyridine-5-carbonitrile (110); 1-(5-(1-(2-cyanopyridin-3-yl)-1H-1,2,3-triazol-4-yl)-4-(isopropylamino)pyridin-2-yl)-1H-pyrazolo[3,4-b]pyridine-5-carbonitrile (111); 1-(5-(1-(4-fluorobenzyl)-1H-1,2,3-triazol-4-yl)-4-(isopropylamino)pyridin-2-yl)-1H-pyrazolo[3,4-b]pyridine-5-carbonitrile (112); tert-butyl 3-(4-(6-(5-cyano-1H-pyrazolo [3,4-b]pyridin-1-yl)-4-(isopropylamino)pyridin-3-yl)-1H-1,2,3-triazol-1-yl)azetidine-1-carboxylate (113); 1-(5-(1-(5-aminopentyl)-1H-1,2,3-triazol-4-yl)-4-(isopropylamino) pyridin-2-yl)-1H-pyrazolo[3,4-b]pyridine-5-carbonitrile (114); 1-(4-(isopropylamino)-5-(1-phenyl-1H-1,2,3-triazol-4-yl) pyridin-2-yl)-1H-pyrazolo[3,4-b]pyridine-5-carbonitrile (115); 1-(4-(isopropylamino)-5-(1-(2-(methylsulfonyl)ethyl)-1H-1,2,3-triazol-4-yl) pyridin-2-yl)-1H-pyrazolo[3,4-b]pyridine-5-carbonitrile (116); 1-(5-(1-(cyclobutylmethyl)-1H-1,2,3-triazol-4-yl)-4-(isopropylamino)pyridin-2-yl)-1H-pyrazolo [3,4-b]pyridine-5-carbonitrile (117); 1-(4-(isopropylamino)-5-(1-(2-(pyridin-2-yl)ethyl)-1H-1,2,3-triazol-4-yl)pyridin-2-yl)-1H-pyrazolo[3,4-b]pyridine-5-carbonitrile (118); 1-(4-(isopropylamino)-5-(1-(2-(pyridin-3-yl)ethyl)-1H-1,2,3-triazol-4-yl)pyridin-2-yl)-1H-pyrazolo [3,4-b]pyridine-5-carbonitrile (119); 1-(4-(isopropylamino)-5-(1-(2-(pyridin-4-yl)ethyl)-1H-1,2,3-triazol-4-yl)pyridin-2-yl)-1H-pyrazolo[3,4-b]pyridine-5-carbonitrile (120); 1-(4-(isopropylamino)-5-(1-(2-methoxyethyl)-1H-1,2,3-triazol-4-yl)pyridin-2-yl)-1H-pyrazolo[3,4-b]pyridine-5-carbonitrile (121); 1-(5-(1-(2-ethoxyethyl)-1H-1,2,3-triazol-4-yl)-4-(isopropylamino)pyridin-2-yl)-1H-pyrazolo[3,4-b]pyridine-5-carbonitrile (122); 1-(4-(isopropylamino)-5-(1-(oxetan-2-ylmethyl)-1H-1,2,3-triazol-4-yl)pyridin-2-yl)-1H-pyrazolo[3,4-b]pyridine-5-carbonitrile (123); 1-(5-(1-(4-hydroxybutyl)-1H-1,2,3-triazol-4-yl)-4-(isopropylamino)pyridin-2-yl)-1H-pyrazolo[3,4-b]pyridine-5-carbonitrile (124); 1-(5-(1-(5-hydroxypentyl)-1H-1,2,3-triazol-4-yl)-4-(isopropylamino)pyridin-2-yl)-1H-pyrazolo [3,4-b]pyridine-5-carbonitrile (125); 1-(5-(1-(2-(dimethylamino)ethyl)-1H-1,2,3-triazol-4-yl)-4-(isopropylamino)pyridin-2-yl)-1H-pyrazolo[3,4-b]pyridine-5-carbonitrile (126); 1-(4-(isopropylamino)-5-(1-(3-(pyrrolidin-1-yl)propyl)-1H-1,2,3-triazol-4-yl)pyridin-2-yl)-1H-pyrazolo[3,4-b]pyridine-5-carbonitrile (127); 1-(5-(1-(3-hydroxy-3-methylbutyl)-1H-1,2,3-triazol-4-yl)-4-(isopropylamino)pyridin-2-yl)-1H-pyrazolo[3,4-b]pyridine-5-carbonitrile (128); 1-(4-(isopropylamino)-5-(1-(3,3,3-trifluoro-2-hydroxypropyl)-1H-1,2,3-triazol-4-yl)pyridin-2-yl)-1H-pyrazolo[3,4-b]pyridine-5-carbonitrile (129); 1-(4-(isopropylamino)-5-(1-(3-phenylpropyl)-1H-1,2,3-triazol-4-yl) pyridin-2-yl)-1H-pyrazolo[3,4-b]pyridine-5-carbonitrile (130); 1-(5-(1-(2,3-dihydroxypropyl)-1H-1,2,3-triazol-4-yl)-4-(isopropylamino)pyridin-2-yl)-1H-pyrazolo [3,4-b]pyridine-5-carbonitrile (131); tert-butyl 4-((4-(6-(5-cyano-1H-pyrazolo[3,4-b]pyridin-1-yl)-4-(isopropylamino)pyridin-3-yl)-1H-1,2,3-triazol-1-yl)methyl)-4-hydroxypiperidine-1-carboxylate (132); 1-(5-(1-(2-hydroxy-3-methoxypropyl)-1H-1,2,3-triazol-4-yl)-4-(isopropylamino)pyridin-2-yl)-1H-pyrazolo[3,4-b]pyridine-5-carbonitrile (133); (S)-1-(5-(1-(2-hydroxybutyl)-1H-1,2,3-triazol-4-yl)-4-(isopropylamino)pyridin-2-yl)-1H-pyrazolo[3,4-b]pyridine-5-carbonitrile (134); 1-(5-(1-(2-hydroxy-3-methylbutyl)-1H-1,2,3-triazol-4-yl)-4-(isopropylamino)pyridin-2-yl)-1H-pyrazolo[3,4-b]pyridine-5-carbonitrile (135); 1-(5-(1-(2-hydroxy-3-(4-methoxyphenoxy)propyl)-1H-1,2,3-triazol-4-yl)-4-(isopropylamino)pyridin-2-yl)-1H-pyrazolo[3,4-b]pyridine-5-carbonitrile (136); 1-(5-(1-(3-ethoxy-2-hydroxypropyl)-1H-1,2,3-triazol-4-yl)-4-(isopropylamino)pyridin-2-yl)-1H-pyrazolo[3,4-b]pyridine-5-carbonitrile (137); 1-(5-(1-(azetidin-3-yl)-1H-1,2,3-triazol-4-yl)-4-(isopropylamino)pyridin-2-yl)-1H-pyrazolo[3,4-b]pyridine-5-carbonitrile (138); 1-(5-(1-(1-(2-cyclopropylacetyl)azetidin-3-yl)-1H-1,2,3-triazol-4-yl)-4-(isopropylamino)pyridin-2-yl)-1H-pyrazolo[3,4-b]pyridine-5-carbonitrile (139); 1-(5-(1-(1-trideuteroacetylazetidin-3-yl)-1H-1,2,3-triazol-4-yl)-4-(isopropylamino)pyridin-2-yl)-1H-pyrazolo[3,4-b]pyridine-5-carbonitrile (140); 1-(5-(1-(1-cyanoazetidin-3- yl)-1H-1,2,3-triazol-4-yl)-4-(isopropylamino)pyridin-2-yl)-1H-pyrazolo[3,4-b]pyridine-5-carbonitrile (141); methyl 3-(4-(6-(5-cyano-1H-pyrazolo[3,4-b]pyridin-1-yl)-4-(isopropylamino)pyridin-3-yl)-1H-1,2,3-triazol-1-yl)azetidine-1-carboxylate (142); 1-(5-(1-(1-benzoylazetidin-3-yl)-1H-1,2,3-triazol-4-yl)-4-(isopropylamino)pyridin-2-yl)-1H-pyrazolo[3,4-b]pyridine-5-carbonitrile (143); 1-(5-(1-(1-isobutyrylazetidin-3-yl)-1H-1,2,3-triazol-4-yl)-4-(isopropylamino)pyridin-2-yl)-1H-pyrazolo[3,4-b]pyridine-5-carbonitrile (144); 1-(5-(1-(1-(cyclopropanecarbonyl)azetidin-3-yl)-1H-1,2,3-triazol-4-yl)-4-(isopropylamino)pyridin-2-yl)-1H-pyrazolo[3,4-b]pyridine-5-carbonitrile (145); 1-(4-(isopropylamino)-5-(1-(1-pivaloylazetidin-3-yl)-1H-1,2,3-triazol-4-yl)pyridin-2-yl)-1H-pyrazolo[3,4-b]pyridine-5-carbonitrile (146); 1-(4-(isopropylamino)-5-(1-(1-(pyrimidin-2-yl)azetidin-3-yl)-1H-1,2,3-triazol-4-yl)pyridin-2-yl)-1H-pyrazolo[3,4-b]pyridine-5-carbonitrile (147); 1-(4-(isopropylamino)-5-(1-(1-(5-methyl-1,3,4-oxadiazol-2-yl)azetidin-3-yl)-1H-1,2,3-triazol-4-yl)pyridin-2-yl)-1H-pyrazolo[3,4-b]pyridine-5-carbonitrile (148); 1-(5-(1-(1-ethylazetidin-3-yl)-1H-1,2,3-triazol-4-yl)-4-(isopropylamino)pyridin-2-yl)-1H-pyrazolo[3,4-b]pyridine-5-carbonitrile (149); 1-(4-(isopropylamino)-5-(1-(1-isopropylazetidin-3-yl)-1H-1,2,3-triazol-4-yl)pyridin-2-yl)-1H-pyrazolo[3,4-b]pyridine-5-carbonitrile (150); 1-(4-(isopropylamino)-5-(1-(1-methylazetidin-3-yl)-1H-1,2,3-triazol-4-yl)pyridin-2-yl)-1H-pyrazolo[3,4-b]pyridine-5-carbonitrile, 2TFA (151); 3-(4-(isopropylamino)-5-(1-(1-methylazetidin-3-yl)-1H-1,2,3-triazol-4-yl)pyridin-2-yl)-3H-imidazo[4,5-b]pyridine-6-carbonitrile (152); 3-(5-(1-(1-(2,2-difluoroethyl)azetidin-3-yl)-1H-1,2,3-triazol-4-yl)-4-(isopropylamino)pyridin-2-yl)-3H-imidazo[4,5-b]pyridine-6-carbonitrile (153); 1-(5-(1-(1-acetylazetidin-3-yl)-1H-1,2,3-triazol-4-yl)-4-(isopropylamino)pyridin-2-yl)-1H-pyrazolo[3,4-b]pyridine-5-carbonitrile (154); 1-(3-(4-(6-(5-chloro-1H-pyrazolo[3,4-b]pyridin-1-yl)-4-(isopropylamino)pyridin-3-yl)-1H-1,2,3-triazol-1-yl)azetidin-1-yl)ethanone (155); 3-(5-(1-(1-acetylazetidin-3-yl)-1H-1,2,3-triazol-4-yl)-4-(isopropylamino)pyridin-2-yl)-3H-imidazo[4,5-b]pyridine-6-carbonitrile (156); 1-(5-(1-(1-acetylpyrrolidin-3-yl)-1H-1,2,3-triazol-4-yl)-4-(isopropylamino)pyridin-2-yl)-1H-pyrazolo[3,4-b]pyridine-5-carbonitrile (157 and 158); 1-(5-(1-(1-acetylpiperidin-4-yl)-1H-1,2,3-triazol-4-yl)-4-(isopropylamino)pyridin-2-yl)-1H-pyrazolo[3,4-b]pyridine-5-carbonitrile (159); 1-(5-(1-(1-acetylpiperidin-3-yl)-1H-1,2,3-triazol-4-yl)-4-(isopropylamino)pyridin-2-yl)-1H-pyrazolo[3,4-b]pyridine-5-carbonitrile (160 and 161); 1-(5-(1-(1-acetylazetidin-3-yl)-1H-1,2,3-triazol-4-yl)-4-(isopropylamino)pyridin-2-yl)-1H-pyrrolo[2,3-b]pyridine-5-carbonitrile, TFA (162); 1-(4-(isopropylamino)-5-(1-(2-morpholinoethyl)-1H-1,2,3-triazol-4-yl)pyridin-2-yl)-1H-pyrrolo[2,3-b]pyridine-5-carbonitrile, 2TFA (163); 1-(4-(isopropylamino)-5-(1-methyl-1H-1,2,3-triazol-4-yl)pyridin-2-yl)-1H-pyrazolo[3,4-b]pyridine-5-carbonitrile (164); 2-(5-chloro-1H-pyrazolo[3,4-b]pyridin-1-yl)-N-isopropyl-5-(1-methyl-1H-1,2,3-triazol-4-yl)pyridin-4-amine (165); 1-(5-(1-(2-fluoropropyl)-1H-1,2,3-triazol-4-yl)-4-(isopropylamino)pyridin-2-yl)-1H-pyrazolo[3,4-b]pyridine-5-carbonitrile (166 and 167); (S)-1-(5-(1-(2-amino-3-phenylpropyl)-1H-1,2,3-triazol-4-yl)-4-(isopropylamino)pyridin-2-yl)-1H-pyrazolo[3,4-b]pyridine-5-carbonitrile (168); (R)-1-(5-(1-(2-amino-3-phenylpropyl)-1H-1,2,3-triazol-4-yl)-4-(isopropylamino)pyridin-2-yl)-1H-pyrazolo[3,4-b]pyridine-5-carbonitrile (169); 1-(4-(isopropylamino)-5-(1-(2-oxopropyl)-1H-1,2,3-triazol-4-yl)pyridin-2-yl)-1H-pyrazolo[3,4-b]pyridine-5-carbonitrile (170); 1-(5-(1-(3-aminopropyl)-1H-1,2,3-triazol-4-yl)-4-(isopropylamino)pyridin-2-yl)-1H-pyrazolo[3,4-b]pyridine-5-carbonitrile (171); 1-(5-(1-(2-aminoethyl)-1H-1,2,3-triazol-4-yl)-4-(isopropylamino)pyridin-2-yl)-1H-pyrazolo[3,4-b]pyridine-5-carbonitrile (172); 1-(5-(1-(2-cyanophenyl)-1H-1,2,3-triazol-4-yl)-4-(isopropylamino)pyridin-2-yl)-1H-pyrazolo[3,4-b]pyridine-5-carbonitrile (173); 1-(4-(isopropylamino)-5-(1-(pyridin-3-yl)-1H-1,2,3-triazol-4-yl)pyridin-2-yl)-1H-pyrazolo[3,4-b]pyridine-5-carbonitrile (174); methyl 2-(4-(6-(5-cyano-1H-pyrazolo[3,4-b]pyridin-1-yl)-4-(isopropylamino)pyridin-3-yl)-1H-1,2,3-triazol-1-yl)benzoate (175); (3R,4S)-tert-butyl 4-(4-(6-(5-cyano-1H-pyrazolo[3,4-b]pyridin-1-yl)-4-(isopropylamino)pyridin-3-yl)-1H-1,2,3-triazol-1-yl)-3-hydroxypiperidine-1-carboxylate (176); 1-(5-(1-((3R,4S)-3-hydroxypiperidin-4-yl)-1H-1,2,3-triazol-4-yl)-4-(isopropylamino)pyridin-2-yl)-1H-pyrazolo[3,4-b]pyridine-5-carbonitrile (177); 1-(5-(1-((3R,4S)-1-acetyl-3-hydroxypiperidin-4-yl)-1H-1,2,3-triazol-4-yl)-4-(isopropylamino)pyridin-2-yl)-1H-pyrazolo[3,4-b]pyridine-5-carbonitrile (178); 1-(5-(1-((3R,4S)-3-hydroxy-1-pivaloylpiperidin-4-yl)-1H-1,2,3-triazol-4-yl)-4-(isopropylamino)pyridin-2-yl)-1H-pyrazolo[3,4-b]pyridine-5-carbonitrile (179); (3R,4S)-ethyl 4-(4-(6-(5-cyano-1H-pyrazolo[3,4-b]pyridin-1-yl)-4-(isopropylamino)pyridin-3-yl)-1H-1,2,3-triazol-1-yl)-3-hydroxypiperidine-1-carboxylate (180); 1-(5-(1-((3R,4S)-3-hydroxy-1-(methylsulfonyl)piperidin-4-yl)-1H-1,2,3-triazol-4-yl)-4-(isopropylamino)pyridin-2-yl)-1H-pyrazolo[3,4-b]pyridine-5-carbonitrile (181); (3R,4S)-4-(4-(6-(5-cyano-1H-pyrazolo[3,4-b]pyridin-1-yl)-4-(isopropylamino)pyridin-3-yl)-1H-1,2,3-triazol-1-yl)-1-(methylsulfonyl)piperidin-3-yl methanesulfonate (182); 1-(5-(1-((3R,4S)-3-hydroxy-1-picolinoylpiperidin-4-yl)-1H-1,2,3-triazol-4-yl)-4-(isopropylamino)pyridin-2-yl)-1H-pyrazolo[3,4-b]pyridine-5-carbonitrile (183); 1-(5-(1-((3R,4S)-3-hydroxy-1-nicotinoylpiperidin-4-yl)-1H-1,2,3-triazol-4-yl)-4-(isopropylamino)pyridin-2-yl)-1H-pyrazolo[3,4-b]pyridine-5-carbonitrile (184); 1-(5-(1-((3R,4S)-3-hydroxy-1-isonicotinoylpiperidin-4-yl)-1H-1,2,3-triazol-4-yl)-4-(isopropylamino)pyridin-2-yl)-1H-pyrazolo[3,4-b]pyridine-5-carbonitrile (185); 1-(5-(1-((3S,4R)-3-hydroxypiperidin-4-yl)-1H-1,2,3-triazol-4-yl)-4-(isopropylamino)pyridin-2-yl)-1H-pyrazolo[3,4-b]pyridine-5-carbonitrile (186); 1-(5-(1-((3S,4R)-3-hydroxypiperidin-4-yl)-1H-1,2,3-triazol-4-yl)-4-(isopropylamino)pyridin-2-yl)-1H-pyrazolo[3,4-b]pyridine-5-carboxamide (187); 1-(5-(1-((3S,4R)-3-hydroxy-1-(methylsulfonyl)piperidin-4-yl)-1H-1,2,3-triazol-4-yl)-4-(isopropylamino)pyridin-2-yl)-1H-pyrazolo[3,4-b]pyridine-5-carbonitrile (188); (3S,4R)-ethyl 4-(4-(6-(5-cyano-1H-pyrazolo[3,4-b]pyridin-1-yl)-4-(isopropylamino)pyridin-3-yl)-1H-1,2,3-triazol-1-yl)-3-hydroxypiperidine-1-carboxylate (189); 1-(5-(1-((3S,4R)-3-hydroxy-1-pivaloylpiperidin-4-yl)-1H-1,2,3-triazol-4-yl)-4-(isopropylamino)pyridin-2-yl)-1H-pyrazolo[3,4-b]pyridine-5-carbonitrile (190); 1-(5-(1-((3S,4R)-1-acetyl-3-hydroxypiperidin-4-yl)-1H-1,2,3-triazol-4-yl)-4-(isopropylamino)pyridin-2-yl)-1H-pyrazolo[3,4-b]pyridine-5-carbonitrile (191); 1-(4-(isopropylamino)-5-(1-(2-oxo-2-(piperazin-1-yl)ethyl)-1H-1,2,3-triazol-4-yl)pyridin-2-yl)-1H-pyrazolo[3,4-b]pyridine-5-carbonitrile (192); 1-(4-(isopropylamino)-5-(1-(2-(4-(methylsulfonyl)piperazin-1-yl)-2-oxoethyl)-1H-1,2,3-triazol-4-yl)pyridin-2-yl)-1H-pyrazolo[3,4-b]pyridine-5-carbonitrile (193); 1-(5-(1-(2-(4-acetylpiperazin-1-yl)-2-oxoethyl)-1H-1,2,3-triazol-4-yl)-4-(isopropylamino)pyridin-2-yl)-1H-pyrazolo[3,4-b]pyridine-5-carbonitrile (194); 1-(4-(isopropylamino)-5-(1-(piperidin-4-yl)-1H-1,2,3-triazol-4-yl)pyridin-2-yl)-1H-pyrazolo[3,4-b]pyridine-5-carbonitrile (195); 1-(4-(isopropylamino)-5-

(1-(1-(methylsulfonyl) piperidin-4-yl)-1H-1,2,3-triazol-4-yl)pyridin-2-yl)-1H-pyrazolo[3,4-b]pyridine-5-carbonitrile (196); 1-(5-(1-((trans)-1-acetyl-3-hydroxypiperidin-4-yl)-1H-1,2,3-triazol-4-yl)-4-(isopropylamino)pyridin-2-yl)-1H-pyrazolo[3,4-b]pyridine-5-carbonitrile (197); 1-(5-(1-((3R,4R)-1-acetyl-3-hydroxypiperidin-4-yl)-1H-1,2,3-triazol-4-yl)-4-(isopropylamino)pyridin-2-yl)-1H-pyrazolo[3,4-b]pyridine-5-carbonitrile (198 and 203); 1-(5-(1-((3R,4R)-3-hydroxy-1-(methylsulfonyl)piperidin-4-yl)-1H-1,2,3-triazol-4-yl)-4-(isopropylamino)pyridin-2-yl)-1H-pyrazolo[3,4-b]pyridine-5-carbonitrile (199 and 204); 1-(5-(1-((3R,4R)-3-hydroxy-1-pivaloylpiperidin-4-yl)-1H-1,2,3-triazol-4-yl)-4-(isopropylamino)pyridin-2-yl)-1H-pyrazolo[3,4-b]pyridine-5-carbonitrile (200 and 206); 1-(4-(cyclopropylamino)-5-(1-((trans)-4-hydroxypiperidin-3-yl)-1H-1,2,3-triazol-(3R,4R)-methyl 4-(4-(6-(5-cyano-1H-pyrazolo[3,4-b]pyridin-1-yl)-4-(isopropylamino) pyridin-3-yl)-1H-1,2,3-triazol-1-yl)-3-hydroxypiperidine-1-carboxylate (201 and 205); (3R,4R)-4-(4-(6-(5-cyano-1H-pyrazolo[3,4-b]pyridin-1-yl)-4-(isopropylamino)pyridin-3-yl)-1H-1,2,3-triazol-1-yl)-1-(methylsulfonyl)piperidin-3-yl methanesulfonate (202); 4-yl)pyridin-2-yl)-1H-pyrazolo[3,4-b]pyridine-5-carbonitrile (207); 1-(5-(1-((3R,4R)-3-hydroxy-1-pivaloylpiperidin-4-yl)-1H-1,2,3-triazol-4-yl)-4-(isopropylamino)pyridin-2-yl)-1H-pyrazolo[3,4-b]pyridine-5-carbonitrile (205 and 206); 1-(4-(cyclopropylamino)-5-(1-((trans)-4-hydroxypiperidin-3-yl)-1H-1,2,3-triazol-4-yl)pyridin-2-yl)-1H-pyrazolo [3,4-b]pyridine-5-carbonitrile (207); (trans)-methyl 4-(4-(6-(5-cyano-1H-pyrazolo[3,4-b]pyridin-1-yl)-4-(cyclopropylamino) pyridin-3-yl)-1H-1,2,3-triazol-1-yl)-3-hydroxy-3-methylpiperidine-1-carboxylate (208); 1-(5-(1-((cis)-3-fluoropiperidin-4-yl)-1H-1,2,3-triazol-4-yl)-4-(isopropylamino)pyridin-2-yl)-1H-pyrazolo[3,4-b]pyridine-5-carbonitrile (209); 1-(5-(1-((trans)-3-fluoro-1-(methylsulfonyl)piperidin-4-yl)-1H-1,2,3-triazol-4-yl)-4-(isopropylamino)pyridin-2-yl)-1H-pyrazolo[3,4-b]pyridine-5-carbonitrile (210 and 211); tert-butyl ((trans)-4-(4-(6-(5-cyano-1H-pyrazolo[3,4-b]pyridin-1-yl)-4-(isopropylamino) pyridin-3-yl)-1H-1,2,3-triazol-1-yl)cyclohexyl)carbamate (212); 1-(5-(1-isopropyl-1H-1,2,3-triazol-4-yl)-4-(isopropylamino)pyridin-2-yl)-1H-pyrazolo[3,4-b]pyridine-5-carbonitrile (213); 1-(4-(isopropylamino)-5-(1-(tetrahydrofuran-3-yl)-1H-1,2,3-triazol-4-yl)pyridin-2-yl)-1H-pyrazolo[3,4-b]pyridine-5-carbonitrile (214 and 215); 1-(5-(1-((1S,2R)-2-hydroxycyclohexyl)-1H-1,2,3-triazol-4-yl)-4-(isopropylamino) pyridin-2-yl)-1H-pyrazolo[3,4-b]pyridine-5-carbonitrile (216); 2-(5-chloro-1H-pyrazolo[3,4-b]pyridin-1-yl)-5-(1-isopentyl-1H-1,2,3-triazol-4-yl)-N-isopropylpyridin-4-amine (217); 2-(5-chloro-1H-pyrazolo[3,4-b]pyridin-1-yl)-N-isopropyl-5-(1-propyl-1H-1,2,3-triazol-4-yl)pyridin-4-amine (218); 1-(4-(Isopropylamino)-5-(1-propyl-1H-imidazol-4-yl)pyridin-2-yl)-1H-indazole-5-carbonitrile (219); 1-(5-(1H-imidazol-4-yl)-4-(isopropylamino)pyridin-2-yl)-1H-indazole-5-carbonitrile (220); 1-(5-(1-isobutyl-1H-imidazol-4-yl)-4-(isopropylamino)pyridin-2-yl)-1H-pyrazolo[3,4-b]pyridine-5-carbonitrile (221); (S)-1-(5-(1-(2-hydroxypropyl)-1H-imidazol-4-yl)-4-(isopropylamino) pyridin-2-yl)-1H-pyrazolo[3,4-b]pyridine-5-carbonitrile (222); 1-(5-(1-(1-acetylazetidin-3-yl)-1H-imidazol-4-yl)-4-(isopropylamino)pyridin-2-yl)-1H-pyrazolo[3,4-b]pyridine-5-carbonitrile (223); 1-(4-(isopropylamino)-5-(1-(pyridin-3-yl)-1H-imidazol-4-yl)pyridin-2-yl)-1H-pyrazolo[3,4-b]pyridine-5-carbonitrile (224); 1-(5-(1-isopropyl-1H-imidazol-4-yl)-4-(isopropylamino)pyridin-2-yl)-1H-pyrazolo[3,4-b]pyridine-5-carbonitrile (225); 1-(5-(1-(2,2-difluoroethyl)-1H-imidazol-4-yl)-4-(isopropylamino)pyridin-2-yl)-1H-pyrazolo[3,4-b]pyridine-5-carbonitrile (226); 1-(5-(1-ethyl-1H-imidazol-4-yl)-4-(isopropylamino)pyridin-2-yl)-1H-pyrazolo[3,4-b]pyridine-5-carbonitrile (227); (S)-1-(5-(1-(3-hydroxy-2-methylpropyl)-1H-imidazol-4-yl)-4-(isopropylamino) pyridin-2-yl)-1H-pyrazolo[3,4-b]pyridine-5-carbonitrile (228); 1-(5-(1-(cyclopropylmethyl)-1H-imidazol-4-yl)-4-(isopropylamino)pyridin-2-yl)-1H-pyrazolo[3,4-b]pyridine-5-carbonitrile (229); 1-(5-(1-benzyl-1H-imidazol-4-yl)-4-(isopropylamino)pyridin-2-yl)-1H-pyrazolo[3,4-b]pyridine-5-carbonitrile (330); 1-(4-(isopropylamino)-5-(1-(2-morpholino-2-oxoethyl)-1H-imidazol-4-yl)pyridin-2-yl)-1H-pyrazolo[3,4-b]pyridine-5-carbonitrile (331); 1-(5-(1-((3-hydroxyoxetan-3-yl)methyl)-1H-imidazol-4-yl)-4-(isopropylamino)pyridin-2-yl)-1H-pyrazolo[3,4-b]pyridine-5-carbonitrile (332); 1-(5-(1-(cyclobutylmethyl)-1H-imidazol-4-yl)-4-(isopropylamino)pyridin-2-yl)-1H-pyrazolo[3,4-b]pyridine-5-carbonitrile (333); 1-(5-(1-((1-acetylazetidin-3-yl)methyl)-1H-imidazol-4-yl)-4-(isopropylamino)pyridin-2-yl)-1H-pyrazolo[3,4-b]pyridine-5-carbonitrile (334); 1-(4-(isopropylamino)-5-(1-(pyridin-3-ylmethyl)-1H-imidazol-4-yl)pyridin-2-yl)-1H-pyrazolo[3,4-b]pyridine-5-carbonitrile (335); 1-(4-(isopropylamino)-5-(1-(oxetan-3-ylmethyl)-1H-imidazol-4-yl) pyridin-2-yl)-1H-pyrazolo[3,4-b]pyridine-5-carbonitrile (336); 2-(4-(6-(5-cyano-1H-pyrazolo[3,4-b]pyridin-1-yl)-4-(isopropylamino)pyridin-3-yl)-1H-imidazol-1-yl) acetamide (337); 2-(4-(6-(5-cyano-1H-pyrazolo[3,4-b]pyridin-1-yl)-4-(isopropylamino) pyridin-3-yl)-1H-imidazol-1-yl)-N-methylacetamide (238); 1-(4-(isopropylamino)-5-(1-(pyridin-2-ylmethyl)-1H-imidazol-4-yl)pyridin-2-yl)-1H-pyrazolo[3,4-b]pyridine-5-carbonitrile (239); 1-(5-(1-(3-hydroxy-3-methylbutyl)-1H-imidazol-4-yl)-4-(isopropylamino)pyridin-2-yl)-1H-pyrazolo[3,4-b]pyridine-5-carbonitrile (240); 1-(4-(isopropylamino)-5-(1-(3-phenylpropyl)-1H-imidazol-4-yl)pyridin-2-yl)-1H-pyrazolo[3,4-b]pyridine-5-carbonitrile (241); 1-(5-(4-(2-hydroxyethyl)-1H-pyrazol-1-yl)-4-(isopropylamino)pyridin-2-yl)-1H-pyrazolo[3,4-b]pyridine-5-carbonitrile (242); 1-(5-(4-benzyl-1H-pyrazol-1-yl)-4-(isopropylamino)pyridin-2-yl)-1H-pyrazolo[3,4-b]pyridine-5-carbonitrile (243); 1-(5-(4-isopropyl-1H-pyrazol-1-yl)-4-(isopropylamino)pyridin-2-yl)-1H-pyrazolo[3,4-b]pyridine-5-carbonitrile (244); 1-(4-(isopropylamino)-5-(4-(pyridin-2-yl)-1H-pyrazol-1-yl)pyridin-2-yl)-1H-pyrazolo[3,4-b]pyridine-5-carbonitrile (245); 1-(4-(isopropylamino)-5-(3-methyl-1H-pyrazol-1-yl)pyridin-2-yl)-1H-pyrazolo[3,4-b] pyridine-5-carbonitrile (246); 1-(4-(isopropylamino)-5-(3-(trifluoromethyl)-1H-pyrazol-1-yl)pyridin-2-yl)-1H-pyrazolo[3,4-b]pyridine-5-carbonitrile (247); 1-(5-(3-cyano-1H-pyrazol-1-yl)-4-(isopropylamino)pyridin-2-yl)-1H-pyrazolo[3,4-b]pyridine-5-carbonitrile (248); 1-(4-(isopropylamino)-5-(3-(pyridin-3-yl)-1H-pyrazol-1-yl)pyridin-2-yl)-1H-pyrazolo[3,4-b]pyridine-5-carbonitrile (249); 1-(5-(3-(cyanomethyl)-1H-pyrazol-1-yl)-4-(isopropylamino)pyridin-2-yl)-1H-pyrazolo[3,4-b]pyridine-5-carbonitrile (250); 1-(5-(4-(3-aminopropyl)-1H-pyrazol-1-yl)-4-(isopropylamino)pyridin-2-yl)-1H-pyrazolo[3,4-b]pyridine-5-carbonitrile (251); 1-(5-(1-(2-hydroxyethyl)-1H-pyrazol-4-yl)-4-(isopropylamino)pyridin-2-yl)-1H-pyrazolo[3,4-b]pyridine-5-carbonitrile (252); 1-(5-(1-ethyl-1H-pyrazol-4-yl)-4-(isopropylamino)pyridin-2-yl)-1H-pyrazolo[3,4-b]pyridine-5-carbonitrile (253); 1-(4-(isopropylamino)-5-(1-(oxetan-3-ylmethyl)-1H-pyrazol-4-yl) pyridin-2-yl)-1H-pyrazolo[3,4-b]pyridine-5-carbonitrile (254); 1-(4-(isopropylamino)-5-(1-(2,2,2-trifluoroethyl)-1H-pyrazol-4-yl)pyridin-2-yl)-1H-pyrazolo[3,4-b]pyridine-5-carbonitrile (255); 1-(4-((1-(2,2-difluoroethyl)-1H-pyrazol-4-yl)amino)-5-(1-propyl-1H- pyrazol-4-yl) pyridin-2-yl)-1H-pyrazolo[3,4-b]pyridine-5-carbonitrile (256); 1-(4-(isopropylamino)-5-(1-(tetrahydro-2H-pyran-4-yl)-1H-pyrazol-4-yl)pyridin-2-yl)-1H-pyrazolo [3,4-b]pyridine-5-carbonitrile (257); 1-(5-(1-isobutyl-1H-pyrazol-4-yl)-4-(isopropylamino)pyridin-2-yl)-1H-pyrazolo [3,4-b]pyridine-5-carbonitrile (258); 1-(5-(1-cyclopropyl-1H-pyrazol-4-yl)-4-(isopropylamino)pyridin-2-yl)-1H-pyrazolo[3,4-b]pyridine-5-carbonitrile (259); 1-(5-(1-(difluoromethyl)-1H-pyrazol-4-yl)-4-(isopropylamino) pyridin-2-yl)-1H-pyrazolo[3,4-b]pyridine-5-carbonitrile (260); 1-(4-(isopropylamino)-5-(1-propyl-1H-pyrazol-4-yl)pyridin-2-yl)-1H-pyrazolo[3,4-b]pyridine-5-carbonitrile (261); N-isopropyl-2-(1H-pyrazolo[3,4-d]pyrimidin-1-yl)-5-(1-(2,2,2-trifluoroethyl)-1H-pyrazol-4-yl)pyridin-4-amine (262); 1-(4-(isopropylamino)-5-(4-propyl-1H-1,2,3-triazol-1-yl)pyridin-2-yl)-1H-pyrazolo[3,4-b]pyridine-5-carbonitrile (263); 1-(4-((2-hydroxy-2-methylpropyl)amino)-5-(4-(2-hydroxypropyl)-1H-1,2,3-triazol-1-yl)pyridin-2-yl)-1H-pyrazolo[3,4-b]pyridine-5-carbonitrile (264); 1-(5-(4-(2-hydroxypropyl)-1H-1,2,3-triazol-1-yl)-4-(isopropylamino) pyridin-2-yl)-1H-pyrazolo[3,4-b]pyridine-5-carbonitrile (265 and 268); 1-(5-(4-cyclopentyl-1H-1,2,3-triazol-1-yl)-4-(isopropylamino)pyridin-2-yl)-1H-pyrazolo[3,4-b]pyridine-5-carbonitrile (266); 1-(4-(isopropylamino)-5-(4-(methoxymethyl)-1H-1,2,3-triazol-1-yl)pyridin-2-yl)-1H-pyrazolo [3,4-b]pyridine-5-carbonitrile (267); 1-(4-((1-(2,2-difluoroethyl)-1H-pyrazol-4-yl) amino)-5-(4-propyl-1H-1,2,3-triazol-1-yl)pyridin-2-yl)-1H-pyrazolo[3,4-b]pyridine-5-carbonitrile (269); N-(1-(2,2-difluoroethyl)-1H-pyrazol-4-yl)-5-(4-propyl-1H-1,2,3-triazol-1-yl)-2-(1H-pyrazolo[3,4-d]pyrimidin-1-yl)pyridin-4-amine (270 and 271); (R)-1-(4-((1-hydroxypropan-2-yl)amino)-5-(4-propyl-1H-1,2,3-triazol-1-yl)pyridin-2-yl)-1H-pyrazolo[3,4-b]pyridine-5-carbonitrile (272); (S)-1-(4-((1-hydroxypropan-2-yl)amino)-5-(4-propyl-1H-1,2,3-triazol-1-yl)pyridin-2-yl)-1H-pyrazolo[3,4-b]pyridine-5-carbonitrile (273); 1-(4-(cyclopropylamino)-5-(4-(2-hydroxypropyl)-1H-1,2,3-triazol-1-yl)pyridin-2-yl)-1H-pyrazolo[3,4-b]pyridine-5-carbonitrile (274 and 275); 1-(4-(oxetan-3-ylamino)-5-(4-propyl-1H-1,2,3-triazol-1-yl)pyridin-2-yl)-1H-pyrazolo[3,4-b]pyridine-5-carbonitrile (276); 3-(4-(oxetan-3-ylamino)-5-(4-propyl-1H-1,2,3-triazol-1-yl)pyridin-2-yl)-3H-imidazo[4,5-b]pyridine-6-carbonitrile (277); 3-(4-(isopropylamino)-5-(4-propyl-1H-1,2,3-triazol-1-yl)pyridin-2-yl)-3H-imidazo[4,5-b]pyridine-6-carbonitrile (278); 9-(4-(isopropylamino)-5-(4-propyl-1H-1,2,3-triazol-1-yl)pyridin-2-yl)-9H-purin-2-amine (279); 6-amino-1-(4-(isopropylamino)-5-(4-propyl-1H-1,2,3-triazol-1-yl)pyridin-2-yl)-1H-pyrazolo[3,4-b] pyridine-5-carbonitrile (280); 6-amino-1-(4-(oxetan-3-ylamino)-5-(4-propyl-1H-1,2,3-triazol-1-yl)pyridin-2-yl)-1H-pyrazolo[3,4-b]pyridine-5-carbonitrile (281); 2-(5-chloro-1H-pyrazolo[3,4-b]pyridin-1-yl)-N-isopropyl-5-(4-propyl-1H-1,2,3-triazol-1-yl)pyridin-4-amine (282); 1-(5-(4-propyl-1H-1,2,3-triazol-1-yl)-4-((tetrahydro-2H-pyran-4-yl)amino)pyridin-2-yl)-1H-pyrazolo[3,4-b]pyridine-5-carbonitrile (283); 3-(4-(isopropylamino)-5-(4-(methoxymethyl)-1H-1,2,3-triazol-1-yl)pyridin-2-yl)-3H-imidazo[4,5-b]pyridine-6-carbonitrile (284); (S)-3-(4-((1-hydroxypropan-2-yl)amino)-5-(4-propyl-1H-1,2,3-triazol-1-yl)pyridin-2-yl)-3H-imidazo[4,5-b]pyridine-6-carbonitrile (285); (R)-3-(4-((1-hydroxypropan-2-yl) amino)-5-(4-propyl-1H-1,2,3-triazol-1-yl) pyridin-2-yl)-3H-imidazo[4,5-b]pyridine-6-carbonitrile (286); 1-(4-((2-hydroxy-2-methylpropyl)amino)-5-(4-propyl-1H-1,2,3-triazol-1-yl)pyridin-2-yl)-1H-pyrazolo[3,4-b]pyridine-5-carbonitrile (287); 3-(5-(4-(3-hydroxypropyl)-1H-1,2,3-triazol-1-yl)-4-(isopropylamino)pyridin-2-yl)-3H-imidazo [4,5-b]pyridine-6-carbonitrile (288); 1-(5-(4-(2-fluoropropyl)-1H-1,2,3-triazol-1-yl)-4-(isopropylamino) pyridin-2-yl)-1H-pyrazolo [3,4-b]pyridine-5-carbonitrile (289); 3-(5-(4-(2-fluoropropyl)-1H-1,2,3-triazol-1-yl)-4-(isopropylamino)pyridin-2-yl)-3H-imidazo[4,5-b]pyridine-6-carbonitrile (290); 3-(5-(4-(2-fluoropropyl)-1H-1,2,3-triazol-1-yl)-4-(isopropylamino)pyridin-2-yl)-3H-imidazo[4,5-b]pyridine-6-carbonitrile (291); 1-(5-(4-(2-fluoropropyl)-1H-1,2,3-triazol-1-yl)-4-(isopropylamino)pyridin-2-yl)-1H-pyrazolo[3,4-b]pyridine-5-carbonitrile (292); 9-(5-(4-(2-fluoropropyl)-1H-1,2,3-triazol-1-yl)-4-(isopropylamino)pyridin-2-yl)-9H-purin-2-amine (293); 1-(5-(4-(2-fluoropropyl)-1H-1,2,3-triazol-1-yl)-4-(isopropylamino)pyridin-2-yl)-1H-pyrazolo[3,4-b]pyridine-5-carbonitrile (294); 1-(5-(4-(hydroxymethyl)-1H-1,2,3-triazol-1-yl)-4-(isopropylamino)pyridin-2-yl)-1H-pyrazolo[3,4-b]pyridine-5-carbonitrile (295); 1-(5-(4-(3-hydroxypropyl)-1H-1,2,3-triazol-1-yl)-4-(isopropylamino) pyridin-2-yl)-1H-pyrazolo [3,4-b]pyridine-5-carbonitrile (296); 1-(4-(isopropylamino)-5-(4-phenyl-1H-1,2,3-triazol-1-yl)pyridin-2-yl)-1H-pyrazolo[3,4-b]pyridine-5-carbonitrile (297); 1-(5-(4-(2-hydroxypropan-2-yl)-1H-1,2,3-triazol-1-yl)-4-(isopropylamino)pyridin-2-yl)-1H-pyrazolo[3,4-b]pyridine-5-carbonitrile (298); 1-(4-(isopropylamino)-5-(4-(pyridin-3-yl)-1H-1,2,3-triazol-1-yl)pyridin-2-yl)-1H-pyrazolo[3,4-b]pyridine-5-carbonitrile (299); 1-(5-(4-cyclopropyl-1H-1,2,3-triazol-1-yl)-4-(isopropylamino)pyridin-2-yl)-1H-pyrazolo[3,4-b]pyridine-5-carbonitrile (300); 1-(4-(isopropylamino)-5-(4-(morpholinomethyl)-1H-1,2,3-triazol-1-yl)pyridin-2-yl)-1H-pyrazolo[3,4-b]pyridine-5-carbonitrile (301); 1-(5-(4-(2-hydroxyethyl)-1H-1,2,3-triazol-1-yl)-4-(isopropylamino) pyridin-2-yl)-1H-pyrazolo [3,4-b]pyridine-5-carbonitrile (302); 1-(5-(4-(2-hydroxybutyl)-1H-1,2,3-triazol-1-yl)-4-(isopropylamino) pyridin-2-yl)-1H-pyrazolo[3,4-b]pyridine-5-carbonitrile (303); 1-(4-(isopropylamino)-5-(4-(pyridin-2-yl)-1H-1,2,3-triazol-1-yl) pyridin-2-yl)-1H-pyrazolo[3,4-b]pyridine-5-carbonitrile (304); 1-(5-(4-isobutyl-1H-1,2,3-triazol-1-yl)-4-(isopropylamino)pyridin-2-yl)-1H-pyrazolo[3,4-b] pyridine-5-carbonitrile (305); 1-(5-(4-(2-hydroxy-2-methylpropyl)-1H-1,2,3-triazol-1-yl)-4-(isopropylamino) pyridin-2-yl)-1H-pyrazolo[3,4-b]pyridine-5-carbonitrile (306); 1-(5-(4-isopentyl-1H-1,2,3-triazol-1-yl)-4-(isopropylamino)pyridin-2-yl)-1H-pyrazolo[3,4-b]pyridine-5-carbonitrile (307); 1-(5-(4-((dimethylamino)methyl)-1H-1,2,3-triazol-1-yl)-4-(isopropylamino)pyridin-2-yl)-1H-pyrazolo[3,4-b]pyridine-5-carbonitrile (308); 1-(6-(5-cyano-1H-pyrazolo[3,4-b]pyridin-1-yl)-4-(isopropylamino)pyridin-3-yl)-1H-1,2,3-triazole-4-carboxamide (309); 1-(5-(4-(aminomethyl)-1H-1,2,3-triazol-1-yl)-4-(isopropylamino) pyridin-2-yl)-1H-pyrazolo[3,4-b]pyridine-5-carbonitrile (310); 1-(5-(4-(4-hydroxybutyl)-1H-1,2,3-triazol-1-yl)-4-(isopropylamino)pyridin-2-yl)-1H-pyrazolo [3,4-b]pyridine-5-carbonitrile (311); 1-(5-(4-(2-aminopropan-2-yl)-1H-1,2,3-triazol-1-yl)-4-(isopropylamino)pyridin-2-yl)-1H-pyrazolo[3,4-b]pyridine-5-carbonitrile (312); 1-((1-(6-(5-cyano-1H-pyrazolo[3,4-b]pyridin-1-yl)-4-(isopropylamino)pyridin-3-yl)-1H-1,2,3-triazol-4-yl)methyl)urea (313); 1-(4-(isopropylamino)-5-(4-((methylamino)methyl)-1H-1,2,3-triazol-1-yl)pyridin-2-yl)-1H-pyrazolo[3,4-b]pyridine-5-carbonitrile (314); (R)-1-(5-(4-(2-hydroxy-2-phenylethyl)-1H-1,2,3-triazol-1-yl)-4-(isopropylamino)pyridin-2-yl)-1H-pyrazolo[3,4-b]pyridine-5-carbonitrile (315); 1-(5-(4-(3,5-dimethoxyphenyl)-1H-1,2,3-triazol-1-yl)-4-(isopropylamino)pyridin-2-yl)-1H-pyrazolo[3,4-b]pyridine-5-carbonitrile (316); 1-(4-(isopropylamino)-5-(4-(1-methyl-1H-imidazol-5-yl)-1H-1,2,3-triazol-1-yl)pyridin-2-yl)-1H- pyrazolo[3,4-b]pyridine-5-carbonitrile (317); 1-(5-(4-(2-hydroxy-2-methylbutyl)-1H-1,2,3-triazol-1-yl)-4-(isopropylamino)pyridin-2-yl)-1H-pyrazolo[3,4-b]pyridine-5-carbonitrile (318); 1-(4-(isopropylamino)-5-(4-phenethyl-1H-1,2,3-triazol-1-yl)pyridin-2-yl)-1H-pyrazolo[3,4-b]pyridine-5-carbonitrile (319); 1-(5-(4-butyl-1H-1,2,3-triazol-1-yl)-4-(isopropylamino)pyridin-2-yl)-1H-pyrazolo[3,4-b]pyridine-5-carbonitrile (320); 1-(5-(4-(2-cyanoethyl)-1H-1,2,3-triazol-1-yl)-4-(isopropylamino)pyridin-2-yl)-1H-pyrazolo[3,4-b]pyridine-5-carbonitrile (321); 1-(5-(4-(2-hydroxybutan-2-yl)-1H-1,2,3-triazol-1-yl)-4-(isopropylamino)pyridin-2-yl)-1H-pyrazolo[3,4-b]pyridine-5-carbonitrile (322); 1-(5-(4-(3-cyanopropyl)-1H-1,2,3-triazol-1-yl)-4-(isopropylamino)pyridin-2-yl)-1H-pyrazolo[3,4-b]pyridine-5-carbonitrile (323); 1-(5-(4-((diethylamino)methyl)-1H-1,2,3-triazol-1-yl)-4-(isopropylamino)pyridin-2-yl)-1H-pyrazolo[3,4-b]pyridine-5-carbonitrile (324); 1-(5-(4-ethyl-1H-1,2,3-triazol-1-yl)-4-(isopropylamino)pyridin-2-yl)-1H-pyrazolo[3,4-b]pyridine-5-carbonitrile (325); 1-(4-(isopropylamino)-5-(4-(pyridin-4-yl)-1H-1,2,3-triazol-1-yl)pyridin-2-yl)-1H-pyrazolo [3,4-b]pyridine-5-carbonitrile (326); 1-(5-(4-(3-hydroxy-3-methylbutyl)-1H-1,2,3-triazol-1-yl)-4-(isopropylamino)pyridin-2-yl)-1H-pyrazolo[3,4-b]pyridine-5-carbonitrile (327); 1-(5-(4-(2-aminoethyl)-1H-1,2,3-triazol-1-yl)-4-(isopropylamino)pyridin-2-yl)-1H-pyrazolo[3,4-b]pyridine-5-carbonitrile (328); 1-(5-(4-(fluoromethyl)-1H-1,2,3-triazol-1-yl)-4-(isopropylamino)pyridin-2-yl)-1H-pyrazolo[3,4-b]pyridine-5-carbonitrile (329); 1-(5-(4-allyl-1H-1,2,3-triazol-1-yl)-4-(isopropylamino)pyridin-2-yl)-1H-pyrazolo[3,4-b]pyridine-5-carbonitrile (330); 1-(4-(isopropylamino)-5-(4-(2-oxopropyl)-1H-1,2,3-triazol-1-yl)pyridin-2-yl)-1H-pyrazolo[3,4-b]pyridine-5-carbonitrile (331); 1-(4-(isopropylamino)-5-(4-((phenylsulfonyl)methyl)-1H-1,2,3-triazol-1-yl)pyridin-2-yl)-1H-pyrazolo[3,4-b]pyridine-5-carbonitrile (332); tert-butyl 4-(1-(6-(5-cyano-1H-pyrazolo[3,4-b]pyridin-1-yl)-4-(isopropylamino)pyridin-3-yl)-1H-1,2,3-triazol-4-yl)piperidine-1-carboxylate (333); 1-(4-(isopropylamino)-5-(4-(piperidin-4-yl)-1H-1,2,3-triazol-1-yl)pyridin-2-yl)-1H-pyrazolo[3,4-b]pyridine-5-carbonitrile, 2 HCl (334); 1-(5-(4-(1-acetylpiperidin-4-yl)-1H-1,2,3-triazol-1-yl)-4-(isopropylamino)pyridin-2-yl)-1H-pyrazolo[3,4-b]pyridine-5-carbonitrile (335); 1-(5-(4-(1-(2,2-difluoroethyl)piperidin-4-yl)-1H-1,2,3-triazol-1-yl)-4-(isopropylamino)pyridin-2-yl)-1H-pyrazolo[3,4-b]pyridine-5-carbonitrile (336); 1-(4-(isopropylamino)-5-(4-(1-isopropylpiperidin-4-yl)-1H-1,2,3-triazol-1-yl)pyridin-2-yl)-1H-pyrazolo[3,4-b]pyridine-5-carbonitrile (337); methyl 4-(1-(6-(5-cyano-1H-pyrazolo[3,4-b]pyridin-1-yl)-4-(isopropylamino)pyridin-3-yl)-1H-1,2,3-triazol-4-yl)piperidine-1-carboxylate (338); 1-(5-(4-(1-acetylazetidin-3-yl)-1H-1,2,3-triazol-1-yl)-4-(isopropylamino)pyridin-2-yl)-1H-pyrazolo[3,4-b]pyridine-5-carbonitrile (339); 1-(5-(4-((1s,4s)-4-aminocyclohexyl)-1H-1,2,3-triazol-1-yl)-4-(isopropylamino) pyridin-2-yl)-1H-pyrazolo[3,4-b]pyridine-5-carbonitrile (340); N-((1s,4s)-4-(1-(6-(5-cyano-1H-pyrazolo[3,4-b]pyridin-1-yl)-4-(isopropylamino)pyridin-3-yl)-1H-1,2,3-triazol-4-yl)cyclohexyl)acetamide (341); tert-butyl ((1s,4s)-4-(1-(6-(5-cyano-1H-pyrazolo[3,4-b]pyridin-1-yl)-4-(isopropylamino)pyridin-3-yl)-1H-1,2,3-triazol-4-yl) cyclohexyl) carbamate (342); 1-(4-(isopropylamino)-5-(4-((1s,4s)-4-(isopropylamino) cyclohexyl)-1H-1,2,3-triazol-1-yl)pyridin-2-yl)-1H-pyrazolo[3,4-b]pyridine-5-carbonitrile (343); methyl ((1s,4s)-4-(1-(6-(5-cyano-1H-pyrazolo[3,4-b]pyridin-1-yl)-4-(isopropylamino)pyridin-3-yl)-1H-1,2,3-triazol-4-yl)cyclohexyl)carbamate (344); (±)-1-(5-(4-(2-fluoro-3-hydroxy-3-methylbutyl)-1H-1,2,3-triazol-1-yl)-4-(isopropylamino)pyridin-2-yl)-1H-pyrazolo[3,4-b]pyridine-5-carbonitrile (345); 1-(5-(4-(1-(ethylsulfonyl)piperidin-4-yl)-1H-1,2,3-triazol-1-yl)-4-(isopropylamino)pyridin-2-yl)-1H-pyrazolo[3,4-b]pyridine-5-carbonitrile (346); 1-(4-((3,3-difluorocyclopentyl)amino)-5-(4-(3-hydroxy-3-methylbutyl)-1H-1,2,3-triazol-1-yl)pyridin-2-yl)-1H-pyrazolo[3,4-b]pyridine-5-carbonitrile (347); 1-(4-(cyclopropylamino)-5-(4-(tetrahydro-2H-pyran-4-yl)-1H-1,2,3-triazol-1-yl)pyridin-2-yl)-1H-pyrazolo[3,4-b]pyridine-5-carbonitrile (348); 1-(4-(isopropylamino)-5-(4-(2-morpholinoethyl)-1H-1,2,3-triazol-1-yl)pyridin-2-yl)-1H-pyrazolo[3,4-b]pyridine-5-carbonitrile (349); 4-(1-(6-(6-amino-1H-pyrazolo[3,4-d]pyrimidin-1-yl)-4-(isopropylamino)pyridin-3-yl)-1H-1,2,3-triazol-4-yl)-2-methylbutan-2-ol (350); 1-(5-(4-(3-fluoro-3-methylbutyl)-1H-1,2,3-triazol-1-yl)-4-(isopropylamino) pyridin-2-yl)-1H-pyrazolo[3,4-d]pyrimidin-6-amine (351); methyl (2-(1-(6-(5-cyano-1H-pyrazolo[3,4-b]pyridin-1-yl)-4-(isopropylamino)pyridin-3-yl)-1H-1,2,3-triazol-4-yl) ethyl) carbamate (352); 1-(4-(cyclopropylamino)-5-(4-(2-fluoropropyl)-1H-1,2,3-triazol-1-yl)pyridin-2-yl)-1H-pyrazolo[3,4-b]pyridine-5-carbonitrile (353 and 354); 1-(4-(isopropylamino)-5-(4-(tetrahydro-2H-pyran-4-yl)-1H-1,2,3-triazol-1-yl)pyridin-2-yl)-1H-pyrazolo[3,4-b]pyridine-5-carbonitrile (355); 1-(5-(4-((1s,4s)-4-(ethylamino)cyclohexyl)-1H-1,2,3-triazol-1-yl)-4-(isopropylamino)pyridin-2-yl)-1H-pyrazolo[3,4-b]pyridine-5-carbonitrile (356); 4-(1-(6-(5-amino-1H-pyrazolo[3,4-b]pyridin-1-yl)-4-(isopropylamino)pyridin-3-yl)-1H-1,2,3-triazol-4-yl)-2-methylbutan-2-ol (357); 1-(5-(4-((1s,4s)-4-((2,2-difluoroethyl)amino)cyclohexyl)-1H-1,2,3-triazol-1-yl)-4-(isopropylamino)pyridin-2-yl)-1H-pyrazolo[3,4-b]pyridine-5-carbonitrile (358); 1-(5-(4-(3-hydroxy-3-methylbutyl)-1H-1,2,3-triazol-1-yl)-4-(oxetan-3-ylamino)pyridin-2-yl)-1H-pyrazolo[3,4-b]pyridine-5-carbonitrile (359); 1-(5-(4-(1-(3-hydroxy-3-methylbutanoyl) piperidin-4-yl)-1H-1,2,3-triazol-1-yl)-4-(isopropylamino)pyridin-2-yl)-1H-pyrazolo[3,4-b]pyridine-5-carbonitrile (360); 1-(4-(isopropylamino)-5-(4-(1-(methylsulfonyl)piperidin-4-yl)-1H-1,2,3-triazol-1-yl)pyridin-2-yl)-1H-pyrazolo[3,4-b]pyridine-5-carbonitrile (361); 1-(5-(4-(3-hydroxy-3-methylbutyl)-1H-1,2,3-triazol-1-yl)-4-((3,3,3-trifluoropropyl)amino)pyridin-2-yl)-1H-pyrazolo[3,4-b]pyridine-5-carbonitrile (362); 1-(5-(4-(3-fluoro-3-methylbutyl)-1H-1,2,3-triazol-1-yl)-4-(oxetan-3-ylamino)pyridin-2-yl)-1H-pyrazolo[3,4-b]pyridine-5-carbonitrile (363); 1-(4-((3-fluorocyclopentyl)amino)-5-(4-(3-hydroxy-3-methylbutyl)-1H-1,2,3-triazol-1-yl)pyridin-2-yl)-1H-pyrazolo[3,4-b]pyridine-5-carbonitrile (364); (S)-1-(5-(4-(3-hydroxy-3-methylbutyl)-1H-1,2,3-triazol-1-yl)-4-((tetrahydrofuran-3-yl)amino)pyridin-2-yl)-1H-pyrazolo[3,4-b]pyridine-5-carbonitrile (365); (S)-1-(5-(4-(3-hydroxy-3-methylbutyl)-1H-1,2,3-triazol-1-yl)-4-((tetrahydrofuran-3-yl)amino)pyridin-2-yl)-1H-pyrazolo[3,4-b]pyridine-5-carbonitrile (366); 1-(4-((3,3-difluorocyclobutyl)amino)-5-(4-(3-hydroxy-3-methylbutyl)-1H-1,2,3-triazol-1-yl)pyridin-2-yl)-1H-pyrazolo[3,4-b]pyridine-5-carbonitrile (367); 1-(4-(((1S,3S)-3-fluorocyclopentyl)amino)-5-(4-(3-hydroxy-3-methylbutyl)-1H-1,2,3-triazol-1-yl)pyridin-2-yl)-1H-pyrazolo[3,4-b]pyridine-5-carbonitrile (368); 1-(4-(ethylamino)-5-(4-(3-hydroxy-3-methylbutyl)-1H-1,2,3-triazol-1-yl)pyridin-2-yl)-1H-pyrazolo[3,4-b]pyridine-5-carbonitrile (369); 1-(4-((3-fluoropropyl)amino)-5-(4-(3-hydroxy-3-methylbutyl)-1H-1,2,3-triazol-1-yl)pyridin-2-yl)-1H-pyrazolo[3,4-b]pyridine-5-carbonitrile (370); 6-amino-1-(5-(4-(3-hydroxy-3-methylbutyl)-1H-1,2,3-triazol-1-yl)-4-(isopropylamino)pyridin-2-yl)-1H-pyrazolo[3,4-b]pyridine-5-carbonitrile (371); 1-(4-(((1S,3R)-3-fluorocyclopentyl)amino)-5-(4-(3-hydroxy-3-methylbutyl)-1H-1,2,3-triazol-1-yl)pyridin-2-yl)-1H-pyrazolo[3,4-b]pyridine-5-carbonitrile (372); (R)-1-(5-(4-(3-fluoro-3-methylbutyl)-1H-1,2,3-triazol-1-yl)-4-((tetrahydrofuran-3-yl)amino)pyridin-2-yl)-1H-pyrazolo[3,4-b]pyridine-5-carbonitrile (373); 1-(4-(((1r,4r)-4-fluorocyclohexyl) amino)-5-(4-(3-hydroxy-3-methylbutyl)-1H-1,2,3-triazol-1-yl)pyridin-2-yl)-1H-pyrazolo[3,4-b]pyridine-5-carbonitrile (374); 1-(4-(((1R,2S)-2-fluorocyclopentyl)amino)-5-(4-(3-hydroxy-3-methylbutyl)-1H-1,2,3-triazol-1-yl)pyridin-2-yl)-1H-pyrazolo[3,4-b]pyridine-5-carbonitrile (375); (S)-1-(5-(4-(3-hydroxy-3-methylbutyl)-1H-1,2,3-triazol-1-yl)-4-((1-hydroxypropan-2-yl)amino)pyridin-2-yl)-1H-pyrazolo[3,4-b]pyridine-5-carbonitrile (376); 1-(4-((1,3-difluoropropan-2-yl)amino)-5-(4-(3-hydroxy-3-methylbutyl)-1H-1,2,3-triazol-1-yl)pyridin-2-yl)-1H-pyrazolo[3,4-b]pyridine-5-carbonitrile (377); 4-(1-(6-(5-cyano-1H-pyrazolo[3,4-b]pyridin-1-yl)-4-(isopropylamino)pyridin-3-yl)-1H-1,2,3-triazol-4-yl)-2-methylbutan-2-yl glycinate (378); 1-(4-((4-fluorotetrahydrofuran-3-yl) amino)-5-(4-(3-hydroxy-3-methylbutyl)-1H-1,2,3-triazol-1-yl)pyridin-2-yl)-1H-pyrazolo [3,4-b]pyridine-5-carbonitrile (379); 4-(1-(6-(6-amino-1H-pyrazolo[3,4-d]pyrimidin-1-yl)-4-(isopropylamino)pyridin-3-yl)-1H-1,2,3-triazol-4-yl)-2-methylbutan-2-ol (380); 1-(4-((1-hydroxy-2-methylpropan-2-yl)amino)-5-(4-(3-hydroxy-3-methylbutyl)-1H-1,2,3-triazol-1-yl)pyridin-2-yl)-1H-pyrazolo[3,4-b]pyridine-5-carbonitrile (381); 4-(1-(6-(5-cyano-1H-pyrazolo[3,4-b]pyridin-1-yl)-4-(isopropylamino)pyridin-3-yl)-1H-1,2,3-triazol-4-yl)-2-methylbutan-2-yl cyclopropanecarboxylate (382); 1-(5-(4-(3-hydroxy-3-methylbutyl)-1H-1,2,3-triazol-1-yl)-4-((1-methylcyclopropyl)amino)pyridin-2-yl)-1H-pyrazolo[3,4-b]pyridine-5-carbonitrile (383); 4-(1-(6-(5-cyano-1H-pyrazolo[3,4-b]pyridin-1-yl)-4-(isopropylamino)pyridin-3-yl)-1H-1,2,3-triazol-4-yl)-2-methylbutan-2-yl dimethylglycinate (384); 1-(5-(4-(3-hydroxy-3-methylbutyl)-1H-1,2,3-triazol-1-yl)-4-(((1 s,4s)-4-hydroxycyclohexyl)amino)pyridin-2-yl)-1H-pyrazolo[3,4-b]pyridine-5-carbonitrile (385); 1-(4-(isopropylamino)-5-(4-(1-(2,2,2-trifluoroacetyl)piperidin-4-yl)-1H-1,2,3-triazol-1-yl)pyridin-2-yl)-1H-pyrazolo[3,4-b]pyridine-5-carbonitrile (386); (S)-1-(5-(4-(3,4-dihydroxy-3-methylbutyl)-1H-1,2,3-triazol-1-yl)-4-(isopropylamino)pyridin-2-yl)-1H-pyrazolo[3,4-b]pyridine-5-carbonitrile (387); (R)-1-(5-(4-(3,4-dihydroxy-3-methylbutyl)-1H-1,2,3-triazol-1-yl)-4-(isopropylamino)pyridin-2-yl)-1H-pyrazolo[3,4-b]pyridine-5-carbonitrile (388); 1-(5-(4-(3-hydroxy-3-methylbutyl)-1H-1,2,3-triazol-1-yl)-4-(propylamino)pyridin-2-yl)-1H-pyrazolo[3,4-b]pyridine-5-carbonitrile (389); 1-(5-(4-(3-hydroxy-3-methylbutyl)-1H-pyrazol-1-yl)-4-(isopropylamino)pyridin-2-yl)-1H-pyrazolo[3,4-b]pyridine-5-carbonitrile (390); 1-(5-(1-(1-acetylazetidin-3-yl)-1H-1,2,3-triazol-4-yl)-4-(isopropylamino)pyridin-2-yl)-1H-pyrazolo[3,4-b]pyridine-5-carbonitrile (391); 1-(5-(1-(((1r,4r)-4-aminocyclohexyl)-1H-1,2,3-triazol-4-yl)-4-(isopropylamino) pyridin-2-yl)-1H-pyrazolo[3,4-b]pyridine-5-carbonitrile (392); methyl ((1r,4r)-4-(4-(6-(5-cyano-1H-pyrazolo[3,4-b]pyridin-1-yl)-4-(isopropylamino)pyridin-3-yl)-1H-1,2,3-triazol-1-yl)cyclohexyl)carbamate (393); 1-(5-(1-(((1r,4r)-4-((2,2-difluoroethyl)amino) cyclohexyl)-1H-1,2,3-triazol-4-yl)-4-(isopropylamino)pyridin-2-yl)-1H-pyrazolo[3,4-b]pyridine-5-carbonitrile (394); ethyl ((1r,4r)-4-(4-(6-(5-cyano-1H-pyrazolo[3,4-b]pyridin-1-yl)-4-(isopropylamino)pyridin-3-yl)-1H-1,2,3-triazol-1-yl)cyclohexyl)carbamate (395); (S)-3-(4-((1-hydroxypropan-2-yl)amino)-5-(1-propyl-1H-1,2,3-triazol-1-yl)pyridin-2-yl)-3H-imidazo[4,5-b]pyridine-6-carbonitrile (396); 1-(5-(3-(azetidin-3-yl)isoxazol-5-yl)-4-(isopropylamino)pyridin-2-yl)-1H-pyrazolo[3,4-b]pyridine-5-carbonitrile (397); 1-(5-(3-(1-acetylazetidin-3-yl)isoxazol-5-yl)-4-(isopropylamino)pyridin-2-yl)-1H-pyrazolo[3,4-b]pyridine-5-carbonitrile (398); 1-(5-(3-(1,3-dihydroxypropan-2-yl)isoxazol-5-yl)-4-(isopropylamino)pyridin-2-yl)-1H-pyrazolo[3,4-b]pyridine-5-carbonitrile (399); 1-(4-(isopropylamino)-5-(3-(morpholin-3-yl)isoxazol-5-yl)pyridin-2-yl)-1H-pyrazolo[3,4-b]pyridine-5-carbonitrile (400); methyl 3-(5-(6-(5-cyano-1H-pyrazolo[3,4-b]pyridin-1-yl)-4-(isopropylamino)pyridin-3-yl)isoxazol-3-yl)azetidine-1-carboxylate (401); 1-(5-(3-(1-acetylpiperidin-4-yl)isoxazol-5-yl)-4-(isopropylamino)pyridin-2-yl)-1H-pyrazolo[3,4-b]pyridine-5-carbonitrile (402); 1-(4-(isopropylamino)-5-(3-(piperidin-4-yl)isoxazol-5-yl) pyridin-2-yl)-1H-pyrazolo[3,4-b]pyridine-5-carbonitrile (403); (S)-1-(4-(isopropylamino)-5-(3-(pyrrolidin-3-yl)isoxazol-5-yl)pyridin-2-yl)-1H-pyrazolo[3,4-b]pyridine-5-carbonitrile (404); (S)-1-(5-(3-(1-acetylpyrrolidin-3-yl)isoxazol-5-yl)-4-(isopropylamino)pyridin-2-yl)-1H-pyrazolo[3,4-b]pyridine-5-carbonitrile (405); (R)-1-(5-(3-(1-acetylpyrrolidin-3-yl)isoxazol-5-yl)-4-(isopropylamino)pyridin-2-yl)-1H-pyrazolo [3,4-b]pyridine-5-carbonitrile (406); (R)-1-(5-(3-(1-acetylpiperidin-3-yl)isoxazol-5-yl)-4-(isopropylamino)pyridin-2-yl)-1H-pyrazolo[3,4-b]pyridine-5-carbonitrile (407); methyl (R)-3-(5-(6-(5-cyano-1H-pyrazolo[3,4-b]pyridin-1-yl)-4-(isopropylamino)pyridin-3-yl)isoxazol-3-yl)piperidine-1-carboxylate (408); (R)-1-(5-(3-(1-acetylpiperidin-3-yl) isoxazol-5-yl)-4-(isopropylamino)pyridin-2-yl)-1H-pyrazolo[3,4-b]pyridine-5-carbonitrile (409); N-((1s,4s)-4-(5-(6-(5-cyano-1H-pyrazolo[3,4-b]pyridin-1-yl)-4-(isopropylamino)pyridin-3-yl)isoxazol-3-yl)cyclohexyl)acetamide (410); methyl ((1s,4s)-4-(5-(6-(5-cyano-1H-pyrazolo[3,4-b]pyridin-1-yl)-4-(isopropylamino)pyridin-3-yl) isoxazol-3-yl)cyclohexyl)carbamate (411); (S)-1-(4-(isopropylamino)-5-(3-(piperidin-2-yl)isoxazol-5-yl)pyridin-2-yl)-1H-pyrazolo[3,4-b]pyridine-5-carbonitrile (412); (S)-1-(4-(isopropylamino)-5-(3-(piperidin-2-yl)isoxazol-5-yl)pyridin-2-yl)-1H-pyrazolo[3,4-b]pyridine-5-carbonitrile (413); 1-(4-(isopropylamino)-5-(3-(3-(methylamino)propyl) isoxazol-5-yl)pyridin-2-yl)-1H-pyrazolo[3,4-b]pyridine-5-carbonitrile (414); N-(3-(5-(6-(5-cyano-1H-pyrazolo[3,4-b]pyridin-1-yl)-4-(isopropylamino)pyridin-3-yl)isoxazol-3-yl) propyl)-N-methylacetamide (415); 1-(4-(isopropylamino)-5-(3-(tetrahydro-2H-pyran-3-yl)isoxazol-5-yl)pyridin-2-yl)-1H-pyrazolo[3,4-b]pyridine-5-carbonitrile (416); (R)-1-(5-(3-(1-acetylpyrrolidin-2-yl) isoxazol-5-yl)-4-(isopropylamino)pyridin-2-yl)-1H-pyrazolo [3,4-b]pyridine-5-carbonitrile (417); 1-(4-(isopropylamino)-5-(3-(tetrahydro-2H-pyran-4-yl)isoxazol-5-yl)pyridin-2-yl)-1H-pyrazolo[3,4-b]pyridine-5-carbonitrile (418); 1-(5-(3-(8-acetyl-8-azabicyclo[3.2.1]octan-3-yl)isoxazol-5-yl)-4-(isopropylamino)pyridin-2-yl)-1H-pyrazolo[3,4-b]pyridine-5-carbonitrile (419); (R)-1-(5-(3-(2,2-dimethyl-1,3-dioxolan-4-yl)isoxazol-5-yl)-4-(isopropylamino)pyridin-2-yl)-1H-pyrazolo[3,4-b]pyridine-5-carbonitrile (420); 1-(5-(3-(1-acetyl-4-fluoropiperidin-4-yl)isoxazol-5-yl)-4-(isopropylamino)pyridin-2-yl)-1H-pyrazolo[3,4-b]pyridine-5-carbonitrile (421); 1-(5-(3-(4,4-difluoropiperidin-2-yl)isoxazol-5-yl)-4-(isopropylamino) pyridin-2-yl)-1H-pyrazolo [3,4-b]pyridine-5-carbonitrile (422); 1-(5-(3-(6,6-dimethylmorpholin-3-yl)isoxazol-5-yl)-4-(isopropylamino)pyridin-2-yl)-1H-pyrazolo[3,4-b]pyridine-5-carbonitrile (423); 1-(5-(3-((2S,4R)-4-hydroxypiperidin-2-yl)isoxazol-5-yl)-4-(isopropylamino)pyridin-2-yl)-1H-pyrazolo[3,4-b]pyridine-5-carbonitrile (424); 1-(5-(3-((2R,4S)-4-hydroxypiperidin-2-yl)isoxazol-5-yl)-4-(isopropylamino)pyridin-2-yl)-1H-pyrazolo[3,4-b]pyridine- 5-carbonitrile (425); 1-(5-(3-(3-hydroxy-3-methylbutyl) isoxazol-5-yl)-4-(isopropylamino) pyridin-2-yl)-1H-pyrazolo[3,4-b]pyridine-5-carbonitrile (426); (S)-1-(5-(3-(1-acetylazetidin-2-yl)isoxazol-5-yl)-4-(isopropylamino) pyridin-2-yl)-1H-pyrazolo[3,4-b]pyridine-5-carbonitrile (427); (S)-1-(4-(isopropylamino)-5-(5-(morpholin-3-yl) isoxazol-3-yl)pyridin-2-yl)-1H-pyrazolo[3,4-b]pyridine-5-carbonitrile (428); 1-(5-(5-(3-hydroxy-3-methylbutyl)isoxazol-3-yl)-4-(isopropylamino)pyridin-2-yl)-1H-pyrazolo[3,4-b]pyridine-5-carbonitrile (429); (S)-1-(4-(isopropylamino)-5-(5-(piperidin-2-yl)isoxazol-3-yl) pyridin-2-yl)-1H-pyrazolo[3,4-b]pyridine-5-carbonitrile (430); (S)-1-(5-(5-(4-ethylmorpholin-3-yl)isoxazol-3-yl)-4-(isopropylamino)pyridin-2-yl)-1H-pyrazolo[3,4-b]pyridine-5-carbonitrile (431); (S)-1-(4-(isopropylamino)-5-(5-(1-(methylsulfonyl) piperidin-2-yl)isoxazol-3-yl)pyridin-2-yl)-1H-pyrazolo[3,4-b]pyridine-5-carbonitrile (432); 1-(4-(isopropylamino)-5-(5-(morpholine-4-carbonyl)-1,3,4-oxadiazol-2-yl)pyridin-2-yl)-1H-pyrazolo[3,4-b]pyridine-5-carbonitrile (433); 1-(5-(5-(((1r,4r)-4-aminocyclohexyl) amino)-1,3,4-oxadiazol-2-yl)-4-(isopropylamino)pyridin-2-yl)-1H-pyrazolo[3,4-b]pyridine-5-carbonitrile (434); 1-(5-(5-(3-hydroxy-3-methylbutyl)-4,5-dihydroisoxazol-3-yl)-4-(isopropylamino)pyridin-2-yl)-1H-pyrazolo[3,4-b]pyridine-5-carbonitrile (435); methyl ((3-(6-(5-cyano-1H-pyrazolo[3,4-b]pyridin-1-yl)-4-(isopropylamino)pyridin-3-yl)-4,5-dihydroisoxazol-5-yl)methyl)carbamate (436); 1-(5-(5-(3-hydroxy-3-methylbutyl)-4,5-dihydroisoxazol-3-yl)-4-(isopropylamino)pyridin-2-yl)-1H-pyrazolo[3,4-b]pyridine-5-carbonitrile (437); 1-(5-(5-(2-hydroxy-2-methylpropyl) isoxazol-3-yl)-4-(isopropylamino)pyridin-2-yl)-1H-pyrazolo[3,4-b]pyridine-5-carbonitrile (438 and 439); 1-(4-(ethylamino)-5-(5-(3-hydroxy-3-methylbutyl)-4,5-dihydroisoxazol-3-yl)pyridin-2-yl)-1H-pyrazolo[3,4-b]pyridine-5-carbonitrile (440 and 441); and 1-(4-((2,2-difluoroethyl) amino)-5-(5-(3-hydroxy-3-methylbutyl)-4,5-dihydroisoxazol-3-yl)pyridin-2-yl)-1H-pyrazolo[3,4-b] pyridine-5-carbonitrile (442 and 443).

One embodiment provides compounds of the Formula (I) having IRAK4 IC$_{50}$ values of ≤0.6 μM.

One embodiment provides compounds of the Formula (I) having IRAK4 IC$_{50}$ values of ≤0.1 μM.

One embodiment provides compounds of the Formula (I) having IRAK4 IC$_{50}$ values of ≤0.05 μM.

One embodiment provides compounds of the Formula (I) having IRAK4 IC$_{50}$ values of ≤0.025 μM.

One embodiment provides compounds of the Formula (I) having IRAK4 IC$_{50}$ values of ≤0.015 μM.

One embodiment provides compounds of the Formula (I) having IRAK4 IC$_{50}$ values of ≤0.01 μM.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "cyano" refers to the group —CN.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "C$_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "C$_{1-4}$ fluoroalkyl" is intended to include C$_1$, C$_2$, C$_3$, and C$_4$ alkyl groups substituted with one or more fluorine atoms. Representative examples of fluoroalkyl groups include, but are not limited to, —CF$_3$ and —CH$_2$CF$_3$.

The term "cyanoalkyl" includes both branched and straight-chain saturated alkyl groups substituted with one or more cyano groups. For example, "cyanoalkyl" includes —CH$_2$CN, —CH$_2$CH$_2$CN, and C$_{1-4}$ cyanoalkyl.

The term "aminoalkyl" includes both branched and straight-chain saturated alkyl groups substituted with one or more amino groups. For example, "aminoalkyl" includes —CH$_2$NH$_2$, —CH$_2$CH$_2$NH$_2$, and C$_{1-4}$ aminoalkyl.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —$CHFCH_2OH$, —$CH_2CHFC(CH_3)_2OH$, and $C_{1-4}$ hydroxy-fluoroalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and insoluble solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to IRAK4; or effective to treat or prevent autoimmune and/or inflammatory disease states, such as multiple sclerosis and rheumatoid arthritis; or effective to treat cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Utility

The compounds of the invention modulate kinase activity, including the modulation of IRAK-4. Other types of kinase activity that may be modulated by the compounds of the instant invention include, but are not limited to, the Pelle/IRAK family and mutants thereof.

Accordingly, compounds of Formula (I) have utility in treating conditions associated with the modulation of kinase activity, and particularly the selective inhibition of IRAK-4 activity or the inhibition of IRAK and other Pelle family kinases. Such conditions include TLR/IL-1 family receptor associated diseases in which cytokine levels are modulated as a consequence of intracellular signaling. Moreover, the compounds of Formula (I) have advantageous selectivity for IRAK-4 activity, preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors IRAK-4, compounds of Formula (I) are useful in treating TLR/IL-1 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemia or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgia due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemia or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the kinase inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional IRAK-4-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

When the terms "IRAK-4-associated condition" or "IRAK-4-associated disease or disorder" are used herein, each is intended to encompass all of the conditions identified above as if repeated at length, as well as any other condition that is affected by IRAK-4 kinase activity.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit IRAK-4 and/or treat diseases.

The methods of treating IRAK-4 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit IRAK-4 and/or treat diseases associated with IRAK-4.

Exemplary of such other therapeutic agents include corticosteroids, rolipram, calphostin, cytokine-suppressive anti-inflammatory drugs (i), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IRAK-4 kinase-associated conditions, including TLR and IL-1 family receptor mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular disorder, diuresis, and/or natriuresis. In another embodiment, the package insert states that the pharmaceutical composition can be used in combination (as defined previously) with a second therapeutic agent to treat cardiovascular disorder, diuresis, and/or natriuresis. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, or other written sheet that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of the Formula (I) can be prepared according to the methods outlined in the following schemes. For example, in Scheme 1, the dichloride 1 can be reacted with an amine to form the mono-chlorinated ester 1.1. Subsequent reaction with a heterocyclic nucleophile, forms the disubstituted intermediate 1.2. Reduction of the ester to alcohol 1.3 followed by oxidation forms the aldehyde 1.4. Reaction of the aldehyde with a variety of reagents, such as carbon tetrabromide and DBU, forms the terminal bromoalkyne, which can be converted to alkyne 1.5 upon treatment with methyl magnesium bromide and an appropriate proton source. Conversion to compound 1.6 can be achieved upon reaction of 1.5 with an appropriate alkyl azide in the presence of copper and a suitable reaction solvent, such as tert-butanol and water.

SCHEME 1

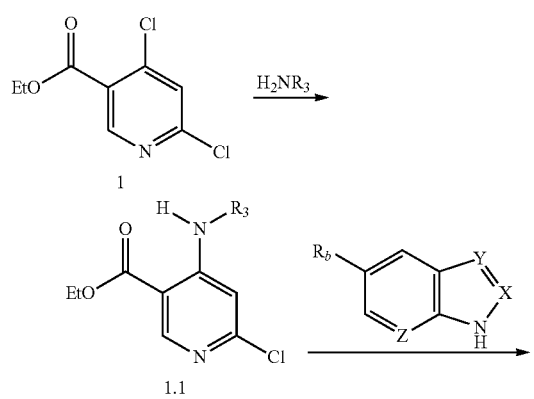

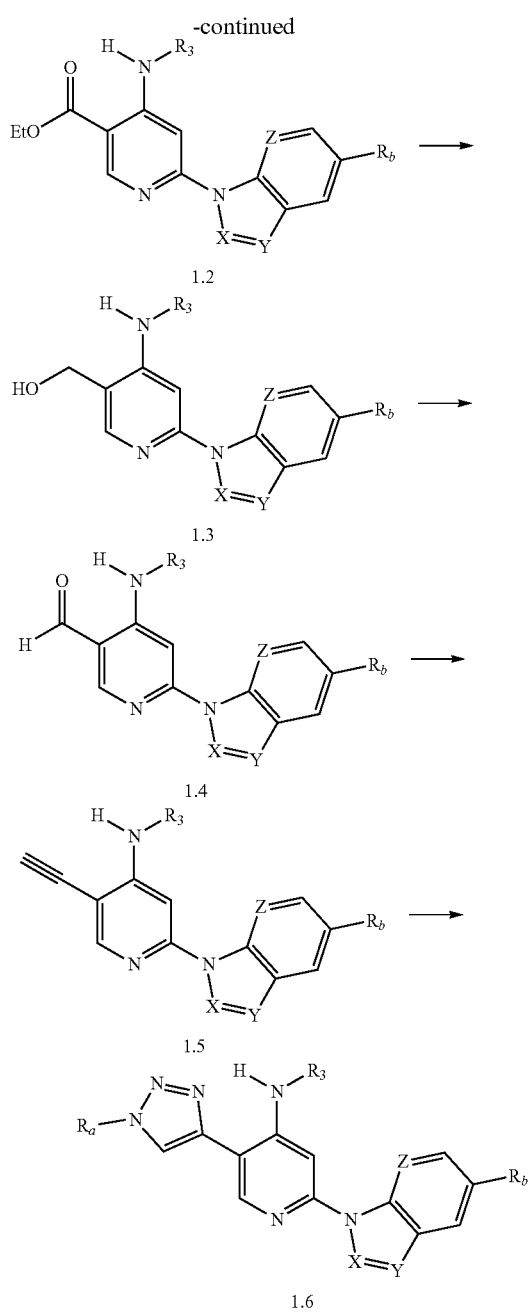

Alternatively, the order of reactions can be modified to change the overall synthesis to allow for variations at different positions of the molecule at different stages of the preparation.

An additional variation on the order of substitution is shown in Scheme 2. As in Scheme 1, reacting the dichloride with an amine affords compound 1.1. Reduction of the ester with an appropriate reducing agent, such as LAH, affords the alcohol 2.2. Oxidation of 2.2 to the aldehyde 2.3 is followed by conversion to the alkyne 2.4 by reacting with dimethyl (1-diazo-2-oxopropyl)phosphonate and a base. Triazole 2.5 can be prepared by reacting alkyne 2.4 with an appropriate alkyl azide in the presence of copper and sodium ascorbate to provide 2.5. Compound 2.5 can be reacted with a variety of heterocycles containing a reactive NH to afford compounds of the general formula 2.6.

SCHEME 2

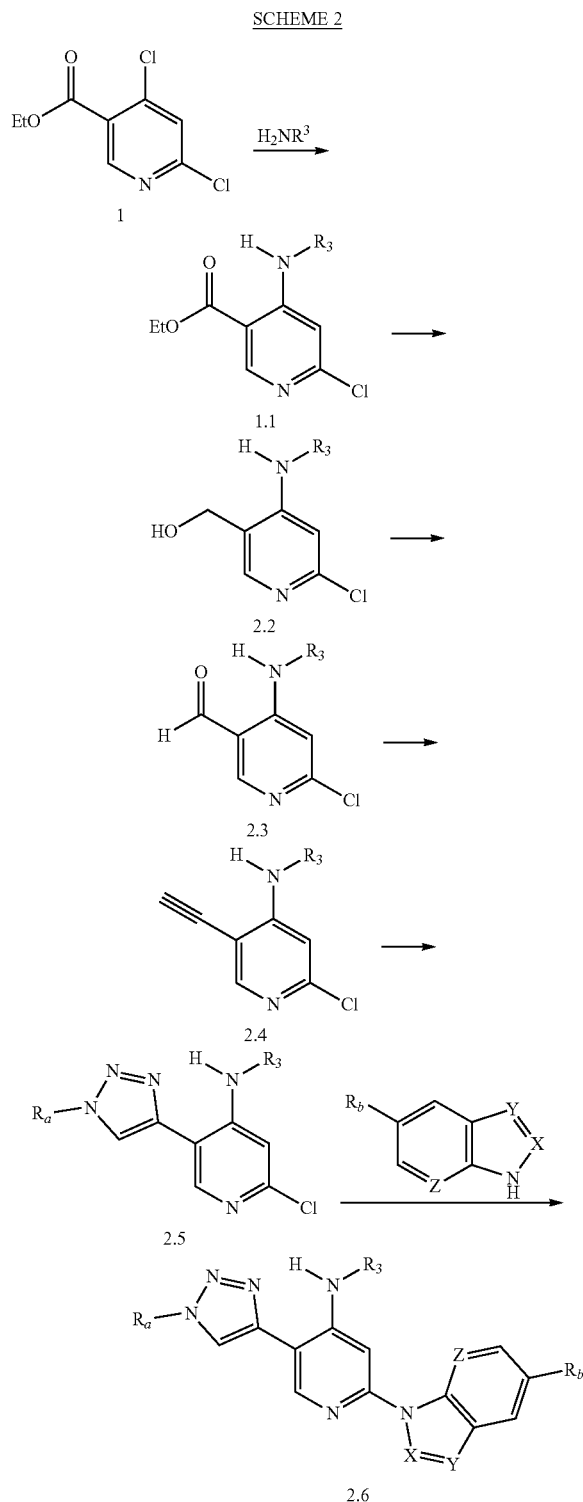

Additional functionalization of the pendant pyridine substituents can be provided. For example, Scheme 3 demonstrates that a compound including an amine or an alcohol off of the triazole substituent. The group can be further reacted with a variety of reagents to provide, but not limited to, amides, esters, halides, alkyl amines and ethers. An example of this process would be the conversion of compound 3.6 to compound 3.7 upon reacting with a fluorinating reagent such as DAST. Additionally, the pendant amine 3.8, could be reacted with an amide forming reagent, such as acetic anhydride, to form the amide 3.9. These are limited examples of the large variety of reactions that can be performed on compounds with pendant reactive functionality and further examples can be found in the tables. Additionally, these types of transformations are not limited to the heterocycle substituent shown in Scheme 3 but could also involve functionalization $R^3$ in addition to $R^a$.

SCHEME 3

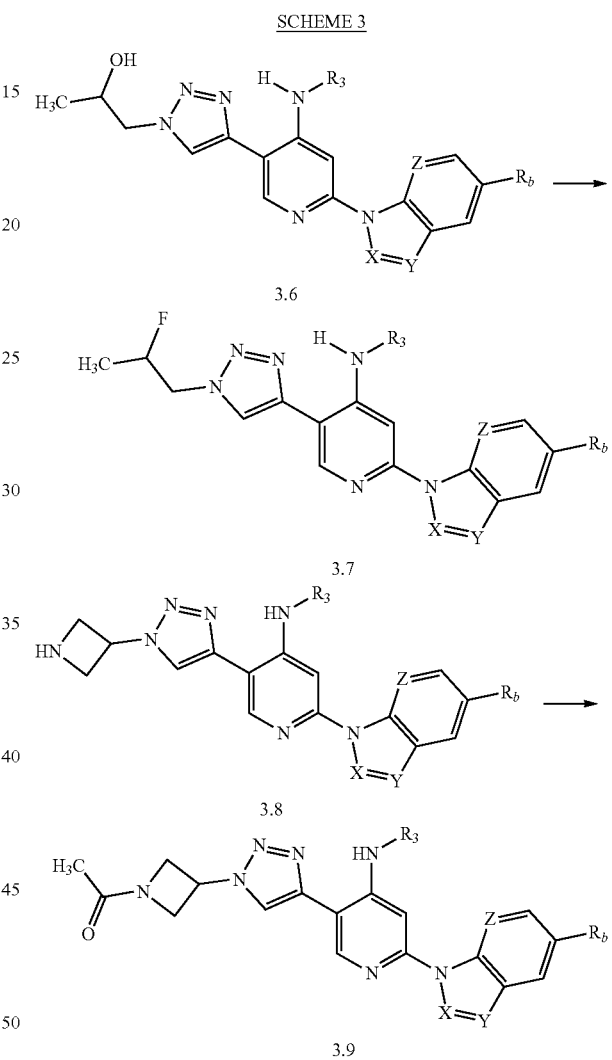

Alternative heterocycles, such as imidazoles or pyrazoles in Scheme 4, can be appended to the pyridine core by first converting the acid 4.1 to the corresponding iodide 4.2 with diacetoxyiodo benzene. Iodide 4.2 can be reacted with a variety of substituted heterocycles (W equals boronic acid, boronic ester or stannane) in the presence of a catalyst, such as palladium, to form compounds of the general formula 4.3. Iodides of the general formula 4.2 can be used to prepare other examples containing different connectivity points to the core pyridine. For Example, reaction of 4.2 with a 1,2-pyrazole in the presence of a metal, such as copper, can afford compounds of the general formula 4.4. In a further series of reactions, the intermediate 4.2 can be converted to the TMS protected acetylene by reaction with TMS acetylene in the presence of copper and a palladium catalyst. Further reaction with a base, such as $K_2CO_3$, in a protic solvent can provide the alkyne 1.5. The utility of this alkyne was demonstrated in Scheme 1.

SCHEME 4

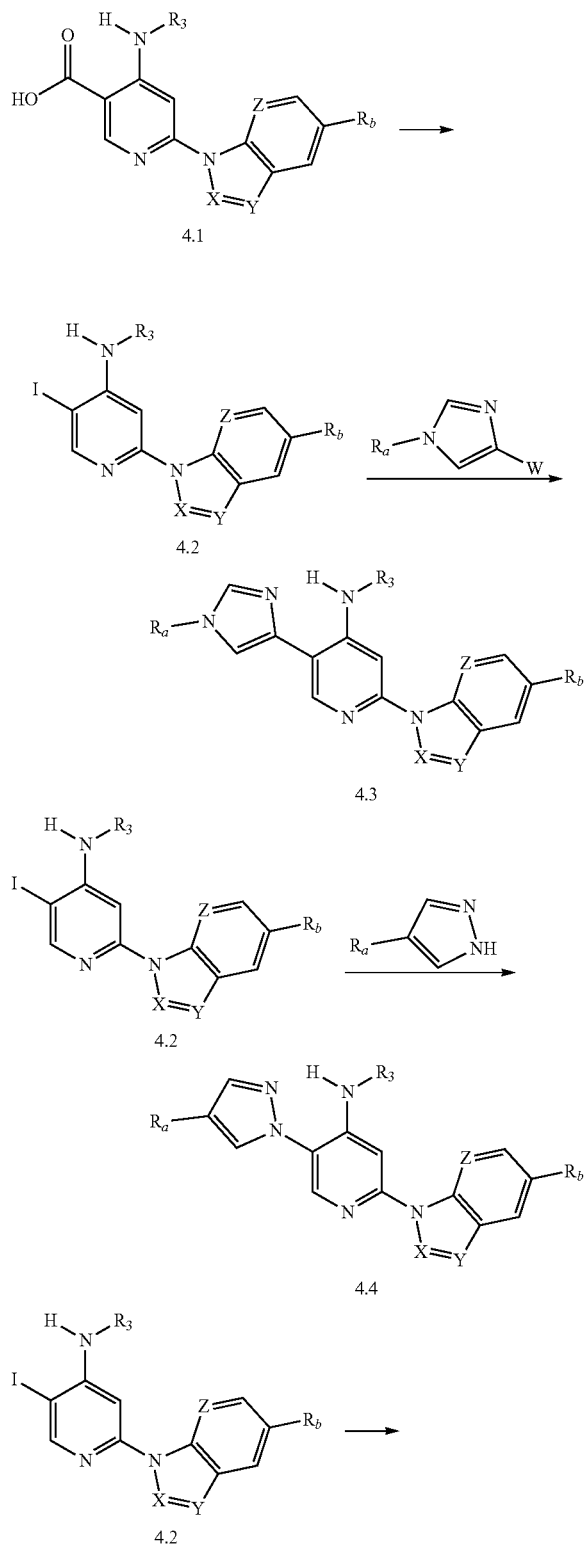

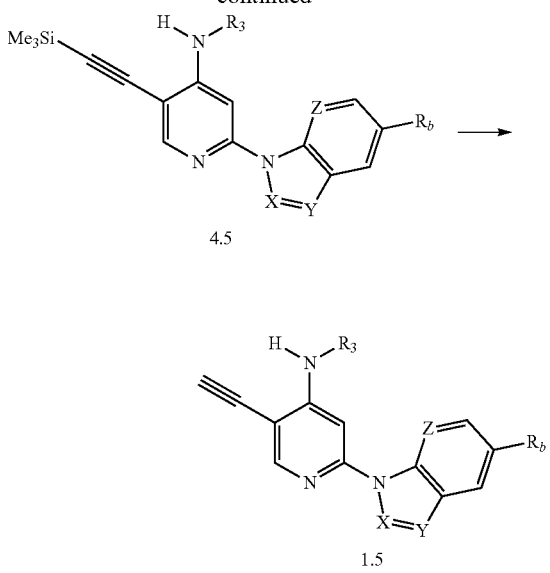

An alternative sequence of steps is outlined in Scheme 5. Triazoles of the general formula 5.3 can be prepared by reacting an appropriate halide, such as 5.1, with sodium azide and an alkyne in the presence of a metal such as copper to provide triazole 5.2. Further reaction of 5.2 with an appropriate heterocycle in the presence of a catalyst, such as palladium, can afford compounds of the formula 5.3. The functionalized iodide 4.2 may also go through the last coupling sequence to provide compounds of the formula 5.3.

SCHEME 5

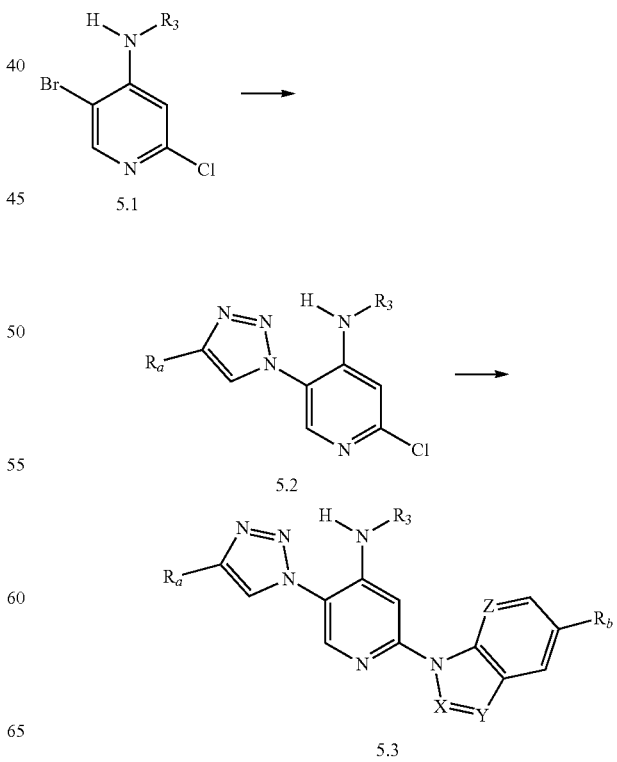

-continued 4.2

5.3

EXAMPLES

Compounds of the current invention and intermediates used in the preparation of compounds of the current invention can be prepared using procedures shown in the following examples and related procedures. The methods and conditions used in these examples, and the actual compounds prepared in these examples, are not meant to be limiting, but are meant to demonstrate how the compounds of the current invention can be prepared. Starting materials and reagents used in these examples, when not prepared by a procedure described herein, are generally either commercially available, or are reported in the chemical literature, or may be prepared by using procedures described in the chemical literature. The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In the examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters Sunfire $C_{18}$, Waters Xbridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:

aq. aqueous
BISPIN bis(pinacolato)diboron
brine saturated aqueous sodium chloride
DCM dichloromethane
DMA N,N-dimethylacetamide
DMF N,N-dimethylformamide
DMSO dimethyl sulfoxide
DPPF 1,1'-bis(diphenylphosphino)ferrocene
EtOAc ethyl acetate
EtOH ethanol
g gram(s)
h hour(s)
HPLC High Performance Liquid Chromatography
KOAc potassium acetate
LAH lithium aluminum hydride
LCMS Liquid Chromatography-Mass Spectroscopy
MeCN acetonitrile
MeMgBr methyl magnesium bromide
MeOH methanol
MPLC medium pressure liquid chromatography
MTBE methyl t-butyl ether
NBS N-bromosuccinimide
$NH_4OAc$ ammonium acetate
NIS N-iodosuccinimide
$Pd_2(dba)_3$ tris-(dibenzylideneacetone)dipalladium
pet ether petroleum ether
t-BuOH tert-butanol
TFA trifluoroacetic acid
THF tetrahydrofuran
HPLC Conditions:

A. Sunfire C18 (3×150 mm), 3.5 micron, mobile phase A: 95:5 water/MeCN, 0.05% TFA; mobile phase B: 95:5 MeCN/water, 0.05% TFA; 1 mL\min, 12 min gradient.

B. Xbridge Phenyl (3×150 mm), 3.5 micron, mobile phase A: 95:5 water/MeCN, 0.05% TFA; mobile phase B: 95:5 MeCN/water, 0.05% TFA; 1 mL\min, 12 min gradient.

C. Waters Acquity UPLC BEH C18 column (2.1×50 mm), mobile phase A: 5:95 MeCN/10 mM aq. ammonium acetate; mobile phase B: 95:5 10 mM aq. ammonium acetate/MeCN; Gradient 0-100% B over 3 minutes, then 0.75 min hold @ 100% B; 50° C. column temperature.

D. Waters Acquity UPLC BEH C18 column (2.1×50 mm), mobile phase A: 5:95 MeCN/0.1% TFA; mobile phase B: 95:5 0.1% TFA/MeCN; Gradient 0-100% B over 3 minutes, then 0.75 min hold @ 100% B; 50° C. column temperature.

E. Ascentis Express $C_{18}$ (2.1×50 mm), 2.7 micron, mobile phase A: 98:2 water/MeCN, 10 mM $NH_4OAc$; mobile phase B: 2:98 water/MeCN, 10 mM $NH_4OAc$; 1.1 mL\min, 3 min gradient.

F. Ascentis Express $C_{18}$ (2.1×50 mm), 2.7 micron, mobile phase A: 95:5 water/MeCN, 0.01% TFA; mobile phase B: 5:95 water/MeCN, 0.01% TFA; 1.1 mL\min, 3 min gradient iPAC column.

G. Xbridge C18 (4.6×30 mm), 2.5 micron, mobile phase A: 95:5 water/MeCN, 10 mM NH4OAc; mobile phase B: 95:5 MeCN/water, 10 mM NH4OAc; 5 mL\min, 2.5 min gradient.

Example 1

2-(4-(4-(isopropylamino)-6-(7H-pyrrolo[2,3-d]pyrimidin-7-yl)pyridin-3-yl)-1H-1,2,3-triazol-1-yl)ethanol

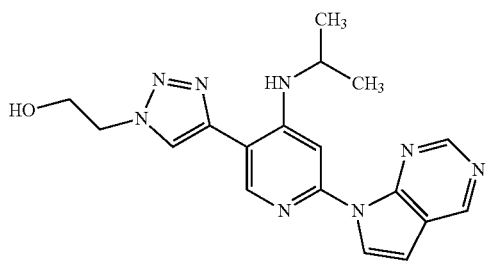

(1)

Intermediate 1A: Ethyl 4-(isopropylamino)-6-(7H-pyrrolo[2,3-d]pyrimidin-7-yl) nicotinate

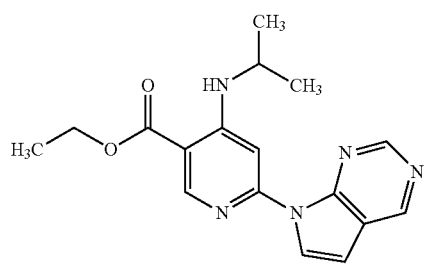

(1A)

In a 5 mL vial, a mixture of ethyl 6-chloro-4-(isopropylamino)nicotinate (0.72 g, 2.97 mmol), 7H-pyrrolo[2,3-d]pyrimidine (0.424 g, 3.56 mmol), and potassium carbonate (0.820 g, 5.93 mmol) in DMA (5 mL) was degassed with bubbling nitrogen for 5 minutes. The mixture was treated with Xantphos (0.343 g, 0.593 mmol) and Pd$_2$(dba)$_3$ (0.271 g, 0.297 mmol), degassed for another 5 minutes, and the vial was sealed. The reaction mixture was heated with stirring at 140° C. for 60 minutes, at which point it was judged to be complete by LCMS. The solids were removed by filtration and rinsed 3× with DMF (5 mL), and the combined filtrate and rinsings were concentrated in vacuo. The residue was taken up in ethyl acetate (75 mL), and the solution was washed twice with 10% lithium chloride, dried over sodium sulfate, and concentrated in vacuo. The residue was chromatographed via MPLC over a 40 g silica gel column, eluting at 40 mL/min with 25% to 60% ethyl acetate/hexanes. Fractions containing the desired product were pooled and concentrated in vacuo to yield ethyl 4-(isopropylamino)-6-(7H-pyrrolo[2,3-d]pyrimidin-7-yl)nicotinate (746 mg, 77% yield) as an off-white solid. $^1$H NMR (400 MHz, CHLOROFORM-d) δ 9.04 (s, 1H), 9.02 (s, 1H), 8.85 (s, 1H), 8.46 (d, J=4.0 Hz, 1H), 8.34 (s, 1H), 8.18 (d, J=7.0 Hz, 1H), 6.72 (d, J=3.7 Hz, 1H), 4.39 (q, J=7.0 Hz, 2H), 3.98 (dq, J=13.1, 6.5 Hz, 1H), 1.50-1.38 (m, 9H); LCMS 326.3 (M+H)$^+$.

Intermediate 1B: (4-(isopropylamino)-6-(7H-pyrrolo[2,3-d]pyrimidin-7-yl)pyridin-3-yl) methanol

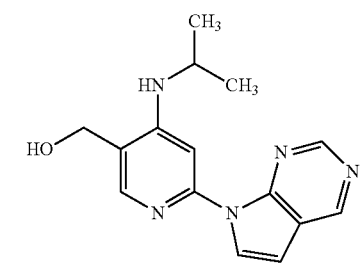

(1B)

A stirring solution of ethyl 4-(isopropylamino)-6-(7H-pyrrolo[2,3-d]pyrimidin-7-yl)nicotinate (726 mg, 2.231 mmol) was cooled to −78° C., and treated drop wise with 1M LAH in THF (6.381 mL, 6.38 mmol) over 10 minutes. When the addition was complete, the reaction mixture was stirred at −78° C. for 30 minutes, then at room temperature for 1 hour, at which point it was judged to be complete by LCMS. The mixture was cooled to 0° C., and treated carefully with water (0.2 mL) followed by 1 M NaOH (0.8 mL). After stirring for 1 hour, the resulting insoluble powder was removed by filtration, rinsed thoroughly with THF, and the combined filtrate and rinsings were concentrated in vacuo to yield (4-(isopropylamino)-6-(5H-pyrrolo[2,3-d]pyrimidin-7(6H)-yl)pyridin-3-yl) methanol (657 mg, 2.302 mmol, 103% yield) as a colorless solid, which was used as-is in the next step. LCMS 286.4 (M+H)$^+$.

Intermediate 1C: 4-(isopropylamino)-6-(7H-pyrrolo[2,3-d]pyrimidin-7-yl) nicotinaldehyde

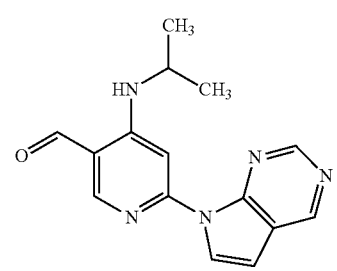

(1C)

A stirring solution of (4-(isopropylamino)-6-(5H-pyrrolo[2,3-d]pyrimidin-7(6H)-yl)pyridin-3-yl)methanol (657 mg, 2.302 mmol) in THF (10 mL) was treated with manganese dioxide (1.9 g, 21.85 mmol). The reaction mixture was stirred at reflux for 3 hours, at which point it was judged to be complete by LCMS. The mixture was heated to boiling, filtered hot through fiberglass filter paper (Whitman GF/A, 3 layers), and the solids were rinsed thoroughly with hot THF. The combined filtrate and rinsings were concentrated in vacuo, and the residue was chromatographed via MPLC over a 40 g silica gel column, eluting at 40 mL/min with 25-60% ethyl acetate/hexanes. Fractions containing only the desired product were pooled and concentrated in vacuo. Fractions containing a mixture of the desired product and impurities were pooled and concentrated in vacuo. The residue was chromatographed via MPLC over a 24 g silica gel column, eluting at 40 mL/min with 35% ethyl acetate/hexanes. Fractions containing only the desired product were pooled and concentrated in vacuo, and the material was combined with the pure material from the first column to yield 4-(isopropylamino)-6-(7H-pyrrolo[2,3-d]pyrimidin-7-yl)nicotinaldehyde (485 mg, 75% yield) as a colorless solid. $^1$H NMR (400 MHz, CHLOROFORM-d) δ 9.86 (s, 1H), 9.05 (s, 1H), 9.04 (s, 1H), 8.65 (d, J=5.3 Hz, 1H), 8.50 (d, J=4.0 Hz, 1H), 8.42 (s, 2H), 6.74 (d, J=4.0 Hz, 1H), 4.02 (dq, J=13.4, 6.5 Hz, 1H), 1.44 (d, J=6.4 Hz, 6H); LCMS 282.2 (M+H)$^+$.

Intermediate 1D: 5-(2,2-dibromovinyl)-N-isopropyl-2-(7H-pyrrolo[2,3-d]pyrimidin-7-yl)pyridin-4-amine

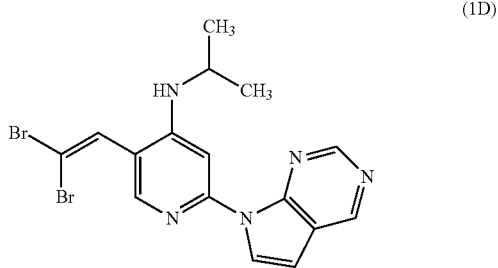 [SMILES: CC(C)Nc1cc(-n2ccc3cncnc32)ncc1C=C(Br)Br]

(1D)

A stirring solution of carbon tetrabromide (236 mg, 0.711 mmol) in dichloromethane (5 mL) was cooled to −20° C. and treated with a solution of triphenylphosphine (373 mg, 1.422 mmol) in dichloromethane (5 mL). After 20 minutes at −20° C., the mixture was cooled to −60° C. and treated drop wise with a solution of 4-(isopropylamino)-6-(7H-pyrrolo[2,3-d]pyrimidin-7-yl)nicotinaldehyde (100 mg, 0.355 mmol) and triethylamine (0.104 mL, 0.747 mmol) in dichloromethane (5 mL). The reaction mixture was stirred at −60° C. for 1 hour, then allowed to come to room temperature. The reaction mixture was concentrated in vacuo, and the residue was taken up in ethyl acetate (50 mL). The turbid solution was washed once with water, once with saturated sodium bicarbonate, and once with brine, then dried over sodium sulfate and concentrated in vacuo. The residue was chromatographed via MPLC over a 40 g silica gel column, eluting at 40 mL/min with 0-50% ethyl acetate/hexanes. Fractions containing the desired product were pooled and concentrated in vacuo to yield 5-(2,2-dibromovinyl)-N-isopropyl-2-(7H-pyrrolo[2,3-d]pyrimidin-7-yl)pyridin-4-amine (130 mg, 74.9% yield). $^1$H NMR (400 MHz, CHLOROFORM-d) δ 9.02 (s, 1H), 8.99 (s, 1H), 8.39 (d, J=4.0 Hz, 1H), 8.21 (s, 1H), 8.15 (s, 1H), 7.19 (s, 1H), 6.69 (d, J=4.0 Hz, 1H), 4.13 (d, J=7.3 Hz, 1H), 3.95 (dq, J=13.1, 6.4 Hz, 1H), 1.39 (d, J=6.4 Hz, 6H); LCMS 438.0 (M+H)$^+$.

Intermediate 1E: 5-(bromoethynyl)-N-isopropyl-2-(7H-pyrrolo[2,3-d]pyrimidin-7-yl)pyridin-4-amine

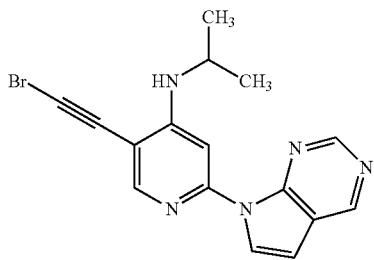

(1E)

A stirring solution of 5-(2,2-dibromovinyl)-N-isopropyl-2-(7H-pyrrolo[2,3-d]pyrimidin-7-yl)pyridin-4-amine (74 mg, 0.169 mmol) in DMSO (2 mL) was placed into an ice/water bath. When the DMSO began to freeze, the mixture was treated with DBU (0.077 mL, 0.508 mmol). The reaction mixture was allowed to slowly warm to room temperature and stirred for 1 hour, at which point it was judged to be complete by LCMS. The mixture was cooled to 5° C. and treated with 0.05 M HCl until the pH=5. The mixture was extracted 3× with ethyl acetate (10 mL), and the combined organic phases were washed once with saturated sodium bicarbonate, 3× with water, and once with 10% lithium chloride solution. The organic phase was dried over sodium sulfate and concentrated in vacuo. The residue was chromatographed via MPLC over a 12 g silica gel column, eluting at 30 mL/min with 20-35% ethyl acetate/hexanes. Fractions containing the desired product were pooled and concentrated in vacuo to yield 5-(bromoethynyl)-N-isopropyl-2-(7H-pyrrolo[2,3-d]pyrimidin-7-yl)pyridin-4-amine (47 mg, 0.132 mmol, 78% yield) as a colorless solid. $^1$H NMR (400 MHz, chloroform-d) δ 9.03 (s, 1H), 9.00 (s, 1H), 8.39 (d, J=4.0 Hz, 1H), 8.23 (s, 1H), 8.21 (s, 1H), 6.70 (d, J=4.0 Hz, 1H), 4.96 (d, J=7.0 Hz, 1H), 3.97 (dq, J=13.3, 6.6 Hz, 1H), 1.41 (d, J=6.4 Hz, 6H); LCMS 357.9 (M+H)$^+$.

Intermediate 1F: 5-Ethynyl-N-isopropyl-2-(7H-pyrrolo[2,3-d]pyrimidin-7-yl)pyridin-4-amine

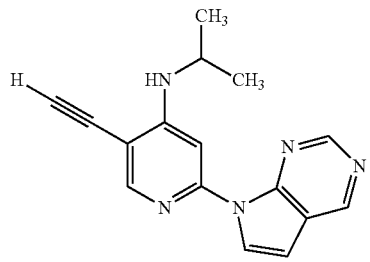

(1F)

In a dried flask, under nitrogen atmosphere, a stirring solution of 5-(bromoethynyl)-N-isopropyl-2-(7H-pyrrolo[2,3-d]pyrimidin-7-yl)pyridin-4-amine (224 mg, 0.629 mmol) in anhydrous THF (5 mL) was cooled to −80° C. and treated with methylmagnesium bromide (1.4 M in THF/toluene) (1.078 mL, 1.509 mmol) over 5 minutes. When the addition was complete, the reaction mixture was stirred at −80° C. for 10 minutes, then quenched with methanol (0.5 mL) and water (0.5 mL). The mixture was allowed to slowly warm to room temperature, stirred for 10 minutes, then diluted with ethyl acetate (20 mL). The turbid solution was washed twice with water (3 mL), and the combined washings were extracted once with ethyl acetate (5 mL). The combined ethyl acetate phases were washed once with 10% lithium chloride solution, dried over sodium sulfate, and concentrated in vacuo. The residue was chromatographed via MPLC over a 24 g silica gel column, eluting at 40 mL/min with 15-100% ethyl acetate/hexanes. Fractions containing the desired product were pooled and concentrated in vacuo to yield 5-ethynyl-N-isopropyl-2-(7H-pyrrolo[2,3-d]pyrimidin-7-yl)pyridin-4-amine (167 mg, 0.602 mmol, 96% yield) as a colorless solid. $^1$H NMR (400 MHz, chloroform-d) δ 9.03 (s, 1H), 9.00 (s, 1H), 8.39 (d, J=4.0 Hz, 1H), 8.27 (s, 1H), 8.22 (s, 1H), 6.70 (d, J=4.0 Hz, 1H), 5.07 (d, J=7.3 Hz, 1H), 3.97 (dq, J=13.3, 6.5 Hz, 1H), 3.54 (s, 1H), 1.41 (d, J=6.4 Hz, 6H); LCMS 357.9 (M+H)$^+$.

Example 1

In a sealed vial, a mixture of 5-ethynyl-N-isopropyl-2-(7H-pyrrolo[2,3-d]pyrimidin-7-yl)pyridin-4-amine (30 mg, 0.108 mmol), 2-azidoethanol (18.84 mg, 0.216 mmol), and copper powder (30 mg, 0.472 mmol) in 1:1 tBuOH/water (1 mL) was stirred at room temperature for 18 hours, at which point the reaction was judged to be complete by LCMS. The mixture was diluted with DMF (5 mL), the copper was removed by filtration, and the filtrate was concentrated in vacuo. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 20 minutes, then a 5-minute hold at 100% B; Flow: 20 mL/min. Fractions containing the desired product were combined and dried to yield 2-(4-(4-(isopropylamino)-6-(7H-pyrrolo[2,3-d]pyrimidin-7-yl)pyridin-3-yl)-1H-1,2,3-triazol-1-yl)ethanol (33 mg, 83% yield). $^1$H NMR (500 MHz, DMSO-d$_6$) δ 9.18 (br. s., 1H), 8.99 (br. s., 1H), 8.75 (s, 1H), 8.54 (br. s., 1H), 8.42 (d, J=4.3 Hz, 1H), 8.32 (d, J=7.3 Hz, 1H), 8.16 (br. s., 1H), 6.88 (br. s., 1H), 5.15 (br. s., 1H), 4.51 (t, J=5.2 Hz, 2H), 3.96-3.84 (m, 3H), 1.38 (d, J=6.1 Hz, 6H); LCMS 365.3 (M+H)$^+$; HPLC rt 1.32 min (Conditions C).

The Examples in Table 1 were prepared using the methods outlined for Example 1 using the appropriate starting material.

TABLE 1

| Ex. No. | Structure | HPLC rt (min) | HPLC cond. | LCMS |
|---|---|---|---|---|
| 2 | 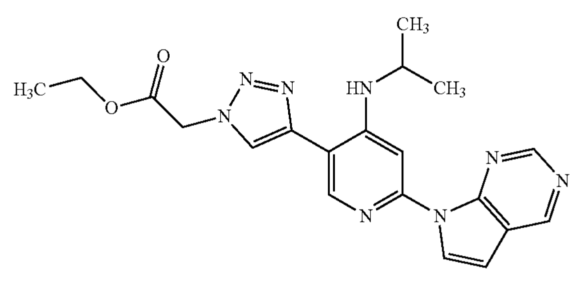 [SMILES: CCOC(=O)Cn1cc(-c2cnc(-n3ccc4cncnc43)cc2NC(C)C)nn1] | 1.77 | C | 407.2 |
| 3 | 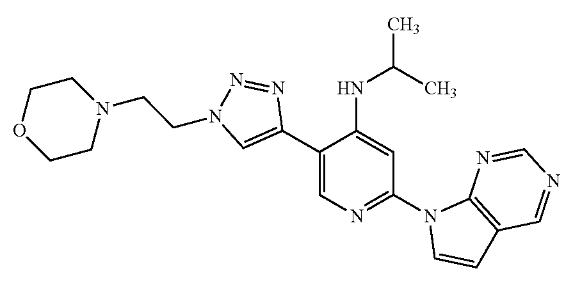 [SMILES: CC(C)Nc1cc(-n2ccc3cncnc32)ncc1-c1cn(CCN2CCOCC2)nn1] | 1.59 | C | 434.3 |
| 4 | 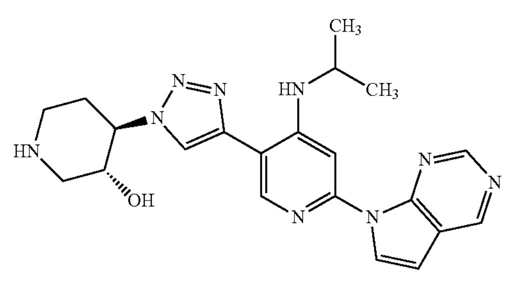 [SMILES: CC(C)Nc1cc(-n2ccc3cncnc32)ncc1-c1cn([C@@H]2CCNC[C@H]2O)nn1] | 1.16 | C | 420.3 |

TABLE 1-continued
| Ex. No. | Structure | HPLC rt (min) | HPLC cond. | LCMS |
|---|---|---|---|---|
| 5 | 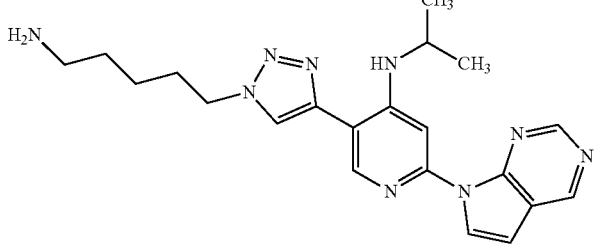 | 1.26 | C | 406.3 |
| 6 | 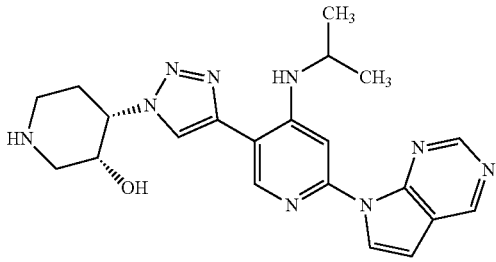 [SMILES: CC(C)Nc1cc(-n2ccc3cncnc32)ncc1-c1cn([C@H]2CCNC[C@H]2O)nn1] | 1.07 | C | 420.4 |
| 7 | 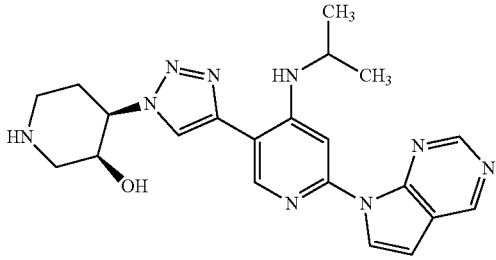 [SMILES: CC(C)Nc1cc(-n2ccc3cncnc32)ncc1-c1cn([C@@H]2CCNC[C@@H]2O)nn1] | 1.15 | C | 420.3 |
| 8 | 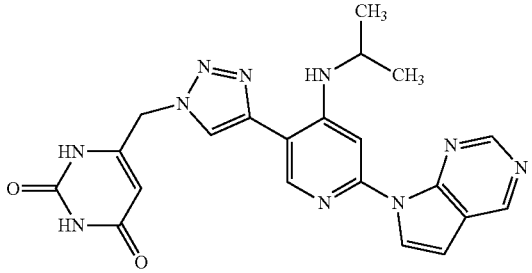 [SMILES: CC(C)Nc1cc(-n2ccc3cncnc32)ncc1-c1cn(Cc2cc(=O)[nH]c(=O)[nH]2)nn1] | 1.20 | C | 445.3 |
| 9 | 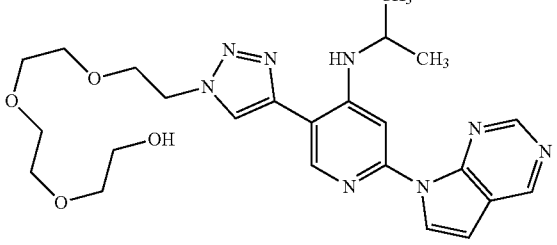 | 1.38 | C | 497.4 |

Example 10

1-(5-(1-isopentyl-1H-1,2,3-triazol-4-yl)-4-(isopropylamino)pyridin-2-yl)-1H-pyrazolo[3,4-b]pyridine-5-carbonitrile, TFA

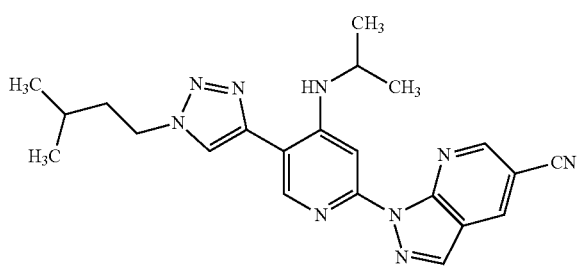

(10)

Intermediate 10A: Ethyl 6-chloro-4-(isopropylamino)nicotinate

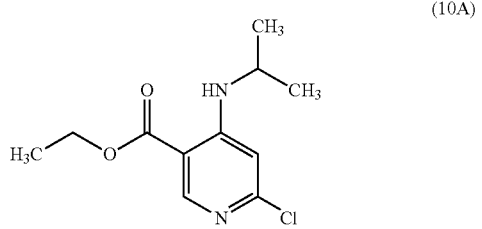 [SMILES: CCOC(=O)c1cnc(Cl)cc1NC(C)C]

(10A)

In a heavy-walled flask equipped with a Teflon screw-cap, a mixture of ethyl 4,6-dichloronicotinate (12.3 g, 55.9 mmol), and isopropylamine (14.37 mL, 168 mmol) in ethanol (100 mL) stirred at 80° C. for 18 hours, at which point the reaction was judged to be complete by LCMS. The mixture was concentrated to dryness, and the crude material was chromatographed via MPLC over a 330 g silica gel column eluting with 0-10% ethyl acetate/hexanes. Fractions containing the product were pooled and concentrated in vacuo to yield ethyl 6-chloro-4-(isopropylamino)nicotinate (12.3 g, 90% yield) as a colorless solid. $^1$H NMR (400 MHz, chloroform-d) δ 8.69 (s, 1H), 8.11 (br. s., 1H), 6.56 (s, 1H), 4.36 (q, J=7.1 Hz, 2H), 3.71 (dq, J=13.3, 6.5 Hz, 1H), 1.41 (t, J=7.2 Hz, 3H), 1.31 (d, J=6.4 Hz, 6H); LCMS 243.1 (M+H)$^+$.

Intermediate 10B: (6-Chloro-4-(isopropylamino)pyridin-3-yl)methanol

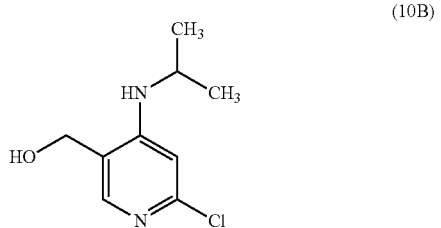

(10B)

A stirring solution of ethyl 6-chloro-4-(isopropylamino)nicotinate (1.42 g, 5.85 mmol) was cooled to −78° C., and treated drop wise with 1 M LAH in THF (18.14 mL, 18.14 mmol) over 10 minutes. When the addition was complete, the reaction mixture was stirred at −78° C. for 60 minutes, then allowed to warm to 0° C. The vessel was placed in an ice/water bath, and the reaction was carefully quenched with water (0.7 mL) followed by 1 M NaOH (2.8 mL). After stirring for 1 hour, the resulting insoluble powder was removed by filtration, rinsed thoroughly with THF, and the combined filtrate and rinsings were concentrated in vacuo to yield (6-chloro-4-(isopropylamino)pyridin-3-yl)methanol (1.14 g, 97% yield) as a colorless solid. LCMS 201.2 (M+H)$^+$.

Intermediate 10C: 6-chloro-4-(isopropylamino)nicotinaldehyde

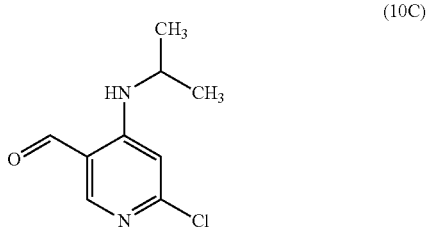

(10C)

A stirring solution of (6-chloro-4-(isopropylamino)pyridin-3-yl)methanol (1.14 g, 5.68 mmol) was treated with manganese dioxide (2.469 g, 28.4 mmol). The reaction mixture was stirred at room temperature for 60 hours (weekend), at which point it was judged to be complete by LCMS. The mixture was filtered, the solids were rinsed twice with THF and once with methylene chloride, and the combined filtrate and rinsings were concentrated in vacuo. The residue was chromatographed via MPLC over a 40 g silica gel column, eluting at 40 mL/min with 15-50% ethyl acetate/hexanes. Fractions containing the desired product were pooled and concentrated in vacuo to yield 6-chloro-4-(isopropylamino)nicotinaldehyde (967 mg, 86% yield) as a colorless oil. $^1$H NMR (400 MHz, chloroform-d) δ 9.84 (d, J=0.7 Hz, 1H), 8.56 (br. s., 1H), 8.30 (s, 1H), 6.60 (s, 1H), 3.81-3.66 (m, 1H), 1.33 (d, J=6.4 Hz, 6H); LCMS 199.2 (M+H)$^+$.

Intermediate 10D: 2-chloro-5-ethynyl-N-isopropylpyridin-4-amine

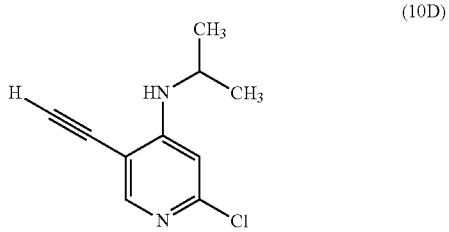

(10D)

A stirring mixture of 6-chloro-4-(isopropylamino)nicotinaldehyde (3.16 g, 15.91 mmol) and potassium carbonate (5.50 g, 39.8 mmol) in anhydrous methanol (30 mL) was cooled to 5° C. and treated with dimethyl (1-diazo-2-oxopropyl)phosphonate (7.64 mL, 31.8 mmol). The reaction mixture was allowed to come to room temperature and stirred for 6 hours. LCMS showed that the reaction had not gone to completion, so the mixture was treated with potassium carbonate (1.646 g, 11.93 mmol) and dimethyl (1-diazo-2-oxopropyl)phosphonate (1.5 g, 7.81 mmol). The reaction mixture was stirred at room temperature for 3 days, at which point it was judged to be complete by LCMS. Most of the methanol was evaporated with a stream of nitrogen, and the remaining mixture was poured into ethyl acetate (75 mL). The turbid solution was washed once with water, 2× with saturated sodium bicarbonate, and once with brine, then the organic phase was dried over sodium sulfate and concentrated in vacuo. The residue was chromatographed via MPLC over a 80 g silica gel column, eluting at 60 mL/min with a 15% to 50% ethyl acetate/hexanes gradient over 10 column volumes. Fractions containing the desired product were pooled and concentrated in vacuo to yield 2-chloro-5-ethynyl-N-isopropylpyridin-4-amine (2.26 g, 73% yield) as a purple solid. $^1$H NMR (400 MHz, chloroform-d) δ 8.13 (s, 1H), 6.48 (s, 1H), 4.97 (br. s., 1H), 3.70 (dq, J=13.5, 6.5 Hz, 1H), 3.53 (s, 1H), 1.30 (d, J=6.4 Hz, 6H); LCMS 194.9 (M+H)$^+$.

Intermediate 10E: 2-Chloro-5-(1-isopentyl-1H-1,2,3-triazol-4-yl)-N-isopropylpyridin-4-amine

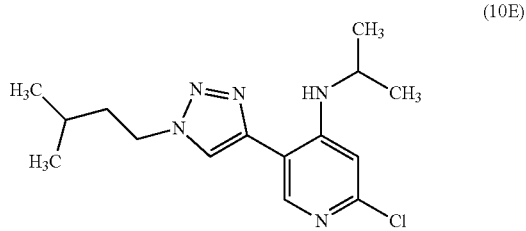 [SMILES: CC(C)CCn1cc(-c2cnc(Cl)cc2NC(C)C)nn1]

(10E)

In a sealed vial, a mixture of 1-azido-3-methylbutane (73.2 mg, 0.647 mmol), 2-chloro-5-ethynyl-N-isopropylpyridin-4-amine (84 mg, 0.432 mmol), sodium ascorbate (17.10 mg, 0.086 mmol), and copper(II) sulfate (6.89 mg, 0.043 mmol) was stirred at 60° C. for 2 hours, at which point the reaction was judged to be complete by LCMS. The mixture was diluted with ethyl acetate (15 mL), and the turbid solution was washed 3× with water and once with brine, then dried over sodium sulfate and concentrated in vacuo. The residue was chromatographed via MPLC over a 12 g silica gel column, eluting at 30 mL/min with a 0.5% to 10% methanol/methylene chloride gradient over 20 column volumes. Fractions containing the desired product were pooled and concentrated in vacuo to yield 2-chloro-5-(1-isopentyl-1H-1,2,3-triazol-4-yl)-N-isopropylpyridin-4-amine (120 mg, 90% yield) as a colorless solid. $^1$H NMR (400 MHz, chloroform-d) δ 8.25 (d, J=6.8 Hz, 1H), 8.20 (s, 1H), 7.85 (s, 1H), 6.59 (s, 1H), 4.51-4.43 (m, 2H), 3.75 (dq, J=13.0, 6.5 Hz, 1H), 1.94-1.85 (m, 2H), 1.67 (dquin, J=13.4, 6.8 Hz, 1H), 1.35 (d, J=6.4 Hz, 6H), 1.03 (d, J=6.6 Hz, 6H); LCMS 308.3 (M+H)$^+$.

Example 10

In a 20 mL microwave vial, a mixture of 2-chloro-5-(1-isopentyl-1H-1,2,3-triazol-4-yl)-N-isopropylpyridin-4-amine (25 mg, 0.081 mmol), 1H-pyrazolo[3,4-b]pyridine-5-carbonitrile (17.56 mg, 0.122 mmol), and potassium phosphate, tribasic (51.7 mg, 0.244 mmol) in dioxane (1 mL) was degassed with bubbling nitrogen for 5 minutes. In a separate vial, a stirring, degassed mixture of tetramethyl t-BuXphos (8.59 mg, 0.018 mmol) and Pd$_2$(dba)$_3$ (7.44 mg, 8.12 μmol) in 5:1 toluene/dioxane (0.5 mL) was heated at 120° C. for 3 minutes. After this mixture cooled to room temperature, it was added to the vial containing the reaction mixture, and the vial was sealed. The reaction mixture was heated with stirring at 90° C. for 18 hours, at which point it was judged to be complete by LCMS. The solvents were evaporated, and the residue was taken up in dichloromethane (5 mL). After stirring for 5 minutes, solids were removed by filtration and rinsed thoroughly with dichloromethane, and the combined filtrate and rinsings were concentrated in vacuo. The crude material was purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-100% B over 20 minutes, then a 5-minute hold at 100% B; Flow: 20 mL/min. Fractions containing the desired product were combined and dried via centrifugal evaporation to yield 1-(5-(1-isopentyl-1H-1,2,3-triazol-4-yl)-4-(isopropylamino)pyridin-2-yl)-1H-pyrazolo[3,4-b]pyridine-5-carbonitrile, TFA (17 mg, 37% yield). $^1$H NMR (500 MHz, DMSO-d$_6$) δ 9.07 (s, 1H), 9.01 (s, 1H), 8.84 (s, 1H), 8.70 (s, 1H), 8.56 (s, 1H), 7.59 (s, 1H), 4.49 (t, J=7.2 Hz, 2H), 3.92 (d, J=6.4 Hz, 1H), 1.80 (q, J=7.1 Hz, 2H), 1.51 (dt, J=13.2, 6.7 Hz, 1H), 1.34 (d, J=6.4 Hz, 6H), 0.93 (d, J=6.7 Hz, 6H); LCMS 416.4 (M+H)$^+$; HPLC rt 2.06 min (Conditions C).

The Examples in Table 2 were prepared using the methods outlined for Example 10, substituting the appropriate amine for isopropylamine, the appropriate organoazide for 1-azido-3-methylbutane, and the appropriate heterocycle for 1H-pyrazolo[3,4-b] pyridine-5-carbonitrile.

TABLE 2

| Ex. No. | Structure | HPLC rt (min) | HPLC cond. | LCMS |
|---|---|---|---|---|
| 11 | (structure) | 1.43 | C | 390.2 |
| 12 | (structure) | 1.57 | C | 459.4 |
| 13 | (structure) | 1.43 | C | 457.3 |
| 14 | (structure) | 5.11 | A | 388.3 |
| 15 | (structure) | 1.50 | C | 402.3 |

TABLE 2-continued

| Ex. No. | Structure | HPLC rt (min) | HPLC cond. | LCMS |
|---|---|---|---|---|
| 16 | 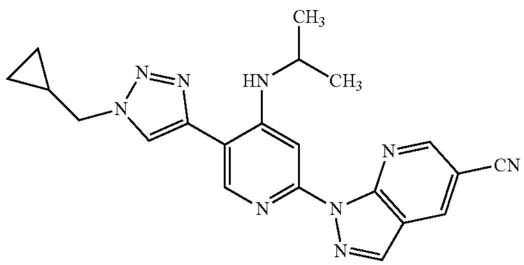 [SMILES: CC(C)Nc1cc(-n2ncc3cc(C#N)cnc32)ncc1-c1cn(CC2CC2)nn1] | 1.92 | C | 400.2 |
| 17 | 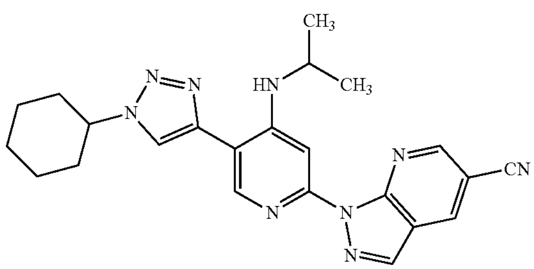 [SMILES: CC(C)Nc1cc(-n2ncc3cc(C#N)cnc32)ncc1-c1cn(C2CCCCC2)nn1] | 2.09 | C | 428.3 |
| 18 | 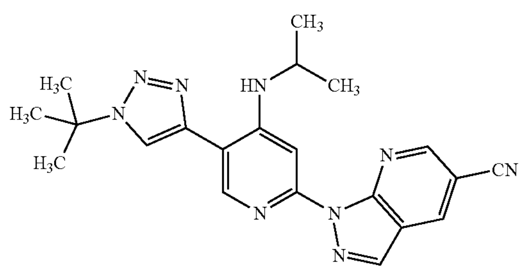 [SMILES: CC(C)Nc1cc(-n2ncc3cc(C#N)cnc32)ncc1-c1cn(C(C)(C)C)nn1] | 1.89 | C | 402.3 |
| 19 | 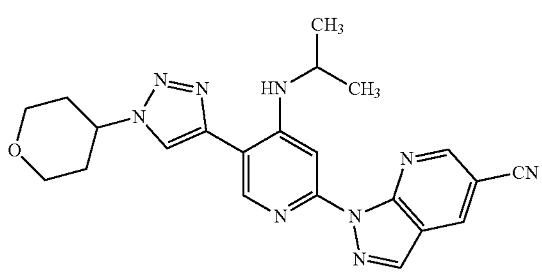 [SMILES: CC(C)Nc1cc(-n2ncc3cc(C#N)cnc32)ncc1-c1cn(C2CCOCC2)nn1] | 1.64 | C | 430.1 |
| 20 | 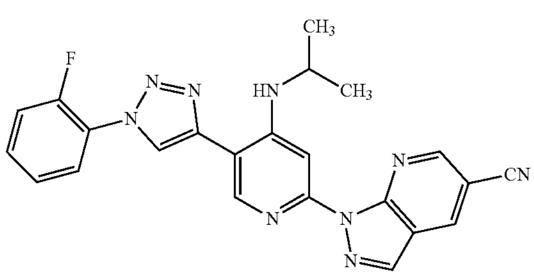 [SMILES: CC(C)Nc1cc(-n2ncc3cc(C#N)cnc32)ncc1-c1cn(-c2ccccc2F)nn1] | 2.00 | C | 440.1 |

TABLE 2-continued

| Ex. No. | Structure | HPLC rt (min) | HPLC cond. | LCMS |
|---|---|---|---|---|
| 21 | Isomer 1 | 1.48 | C | 443.0 |
| 22 | Isomer 2 | 1.50 | C | 443.3 |
| 23 | 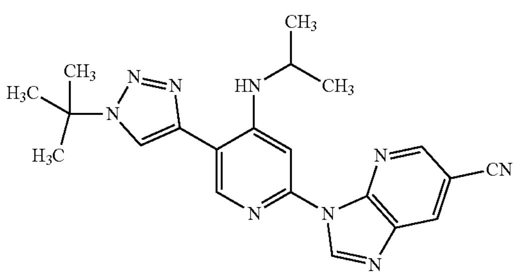 [SMILES: CC(C)Nc1cc(-n2cnc3cc(C#N)cnc32)ncc1-c1cn(C(C)(C)C)nn1] | 2.02 | C | 402.2 |
| 24 | 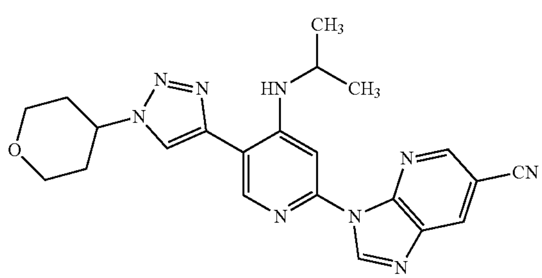 [SMILES: CC(C)Nc1cc(-n2cnc3cc(C#N)cnc32)ncc1-c1cn(C2CCOCC2)nn1] | 1.70 | C | 430.2 |
| 25 | 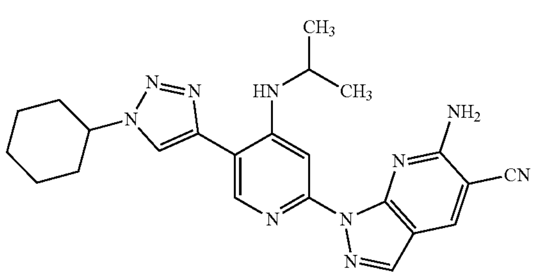 [SMILES: CC(C)Nc1cc(-n2ncc3cc(C#N)c(N)nc32)ncc1-c1cn(C2CCCCC2)nn1] | 1.95 | C | 443.3 |

TABLE 2-continued

| Ex. No. | Structure | HPLC rt (min) | HPLC cond. | LCMS |
|---|---|---|---|---|
| 26 | 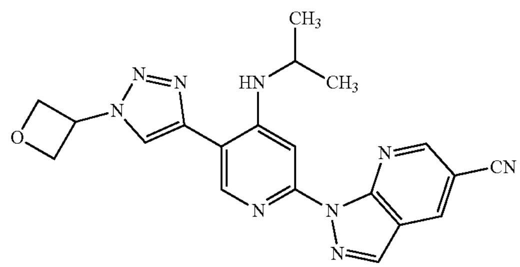 [SMILES: CC(C)Nc1cc(-n2ncc3cc(C#N)cnc32)ncc1-c1cn(C2COC2)nn1] | 1.76 | C | 411.3 |
| 27 | 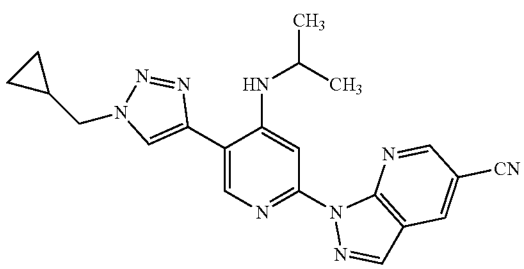 [SMILES: CC(C)Nc1cc(-n2ncc3cc(C#N)cnc32)ncc1-c1cn(CC2CC2)nn1] | 2.05 | C | 409.3 |
| 28 | 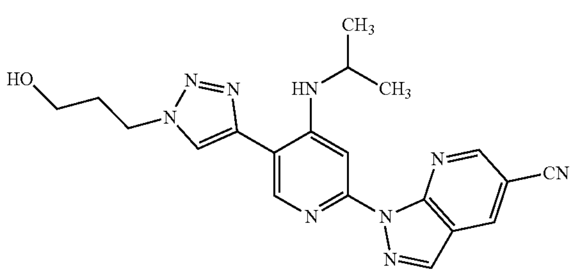 [SMILES: CC(C)Nc1cc(-n2ncc3cc(C#N)cnc32)ncc1-c1cn(CCCO)nn1] | 1.40 | C | 404.2 |
| 29 | 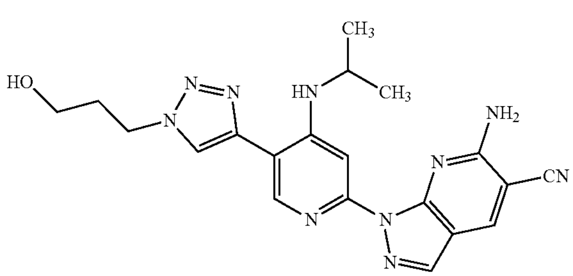 [SMILES: CC(C)Nc1cc(-n2ncc3cc(C#N)c(N)nc32)ncc1-c1cn(CCCO)nn1] | 1.29 | C | 419.3 |

Example 30

1-(4-(isopropylamino)-5-(1-propyl-1H-1,2,3-triazol-4-yl)pyridin-2-yl)-1H-pyrazolo[3,4-b]pyridine-5-carbonitrile

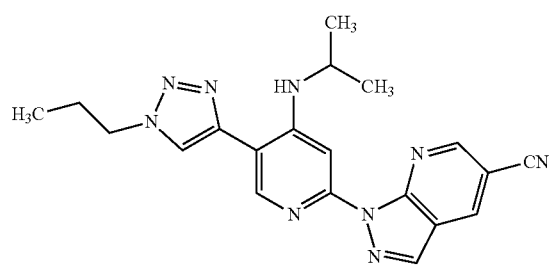

(30)

Intermediate 30A: 2-Chloro-N-isopropyl-5-(1-propyl-1H-1,2,3-triazol-4-yl)pyridin-4-amine

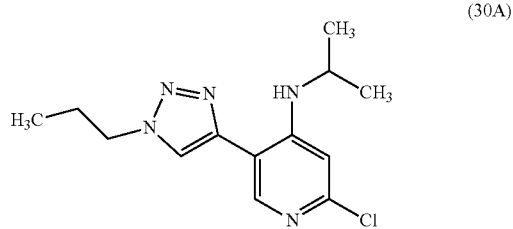 [SMILES: CCCn1cc(-c2cnc(Cl)cc2NC(C)C)nn1]

(30A)

A stirring solution of sodium azide (401 mg, 6.16 mmol) in water (0.8 mL) was treated with a solution of 1-bromopropane (0.421 mL, 4.62 mmol) in THF (0.2 mL). The reaction mixture was heated at 80° C. for 1 hour, then allowed to come to room temperature and stand until the organic and aqueous layers had separated. The top phase was transferred via pipette to a vial containing a mixture of 2-chloro-5-ethynyl-N-isopropylpyridin-4-amine (60 mg, 0.308 mmol), sodium ascorbate (12.21 mg, 0.062 mmol) and 1:1 tBuOH/water (1 mL). This mixture was treated with copper(II) sulfate (4.92 mg, 0.031 mmol), the vial was sealed, and the reaction mixture was stirred at 60° C. for 2 hours, at which point it was judged to be complete by LCMS. The mixture was diluted with ethyl acetate (15 mL), and the turbid solution was washed twice with water and once with brine. The organic phase was dried over sodium sulfate and concentrated in vacuo, and the residue was chromatographed via MPLC over a 12 g silica gel column, eluting at 30 mL/min with a 0.5% to 10% methanol/methylene chloride gradient over 20 column volumes. Fractions containing the desired product were pooled and concentrated in vacuo to yield 2-chloro-N-isopropyl-5-(1-propyl-1H-1,2,3-triazol-4-yl)pyridin-4-amine (73 mg, 85% yield) as a colorless solid. $^1$H NMR (400 MHz, CHLOROFORM-d) δ 8.26 (d, J=6.2 Hz, 1H), 8.20 (s, 1H), 7.85 (s, 1H), 6.59 (s, 1H), 4.42 (t, J=7.2 Hz, 2H), 3.76 (dq, J=13.0, 6.5 Hz, 1H), 2.04 (sxt, J=7.3 Hz, 2H), 1.36 (d, J=6.4 Hz, 6H), 1.04 (t, J=7.4 Hz, 3H); LCMS 280.0 (M+H)$^+$.

Example 30

In a 20 mL microwave vial, a mixture of 2-chloro-N-isopropyl-5-(1-propyl-1H-1,2,3-triazol-4-yl)pyridin-4-amine (33 mg, 0.118 mmol), 1H-pyrazolo[3,4-b]pyridine-5-carbonitrile (25.5 mg, 0.177 mmol), and potassium phosphate, tribasic (75 mg, 0.354 mmol) in dioxane (1 mL) was degassed with bubbling nitrogen for 5 minutes. In a separate vial, a stirring, degassed mixture of tetramethyl t-BuXphos (12.48 mg, 0.026 mmol) and Pd$_2$(dba)$_3$ (10.80 mg, 0.012 mmol) in 5:1 toluene/dioxane (0.5 mL) was heated at 120° C. for 3 minutes. After this mixture cooled to room temperature, it was added to the vial containing the reaction mixture, and the vial was sealed. The reaction mixture was heated with stirring at 90° C. for 18 hours, at which point it was judged to be complete by LCMS. The solvents were evaporated, and the residue was taken up in dichloromethane (5 mL). After stirring for 5 minutes, solids were removed by filtration and rinsed thoroughly with dichloromethane, and the combined filtrate and rinsings were concentrated in vacuo. The crude material was purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-70% B over 20 minutes, then a 5-minute hold at 100% B; Flow: 20 mL/min. Fractions containing the desired product were combined and dried via centrifugal evaporation to yield 1-(4-(isopropylamino)-5-(1-propyl-1H-1,2,3-triazol-4-yl)pyridin-2-yl)-1H-pyrazolo[3,4-b]pyridine-5-carbonitrile, TFA (18 mg, 30% yield). $^1$H NMR (500 MHz, DMSO-d$_6$) δ 9.01 (s, 1H), 8.91 (s, 1H), 8.68 (s, 1H), 8.66 (s, 1H), 8.45 (s, 1H), 7.68 (s, 1H), 4.40 (t, J=6.9 Hz, 2H), 1.89 (sxt, J=7.1 Hz, 2H), 1.33 (d, J=6.4 Hz, 6H), 0.86 (t, J=7.2 Hz, 3H); LCMS 388.3 (M+H)$^+$, HPLC rt 1.78 min (Conditions C).

The Examples in Table 3 were prepared using the methods outlined for Example 30, substituting the appropriate amine for isopropylamine in Intermediate 10A, the appropriate alkyl halide or alkyl mesylate for 1-bromopropane, and the appropriate heterocycle for 1H-pyrazolo[3,4-b]pyridine-5-carbonitrile.

TABLE 3
| Ex. No. | Structure | HPLC rt (min) | HPLC cond. | LCMS |
|---|---|---|---|---|
| 31 | 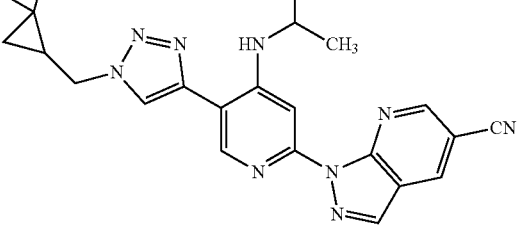 Isomer 1 | 1.80 | C | 436.2 |
| 32 | 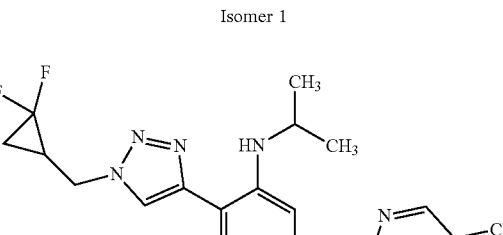 Isomer 2 | 1.80 | C | 436.2 |
| 33 | 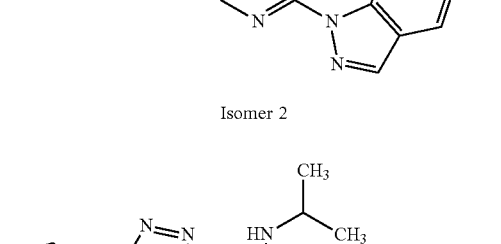 | 1.63 | C | 403.3 |
| 34 | 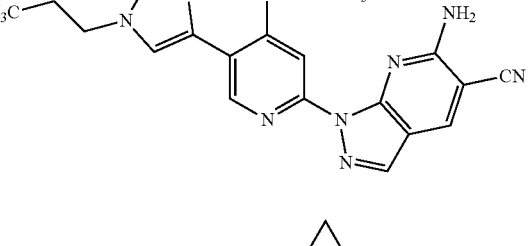 | 1.69 | C | 386.2 |
| 35 | 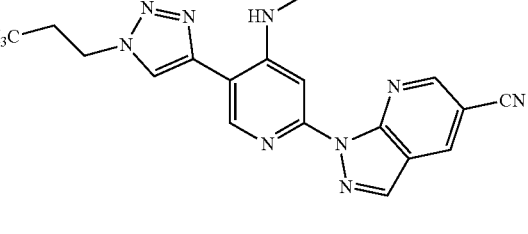 | 1.57 | C | 401.2 |

TABLE 3-continued

| Ex. No. | Structure | HPLC rt (min) | HPLC cond. | LCMS |
|---|---|---|---|---|
| 36 | 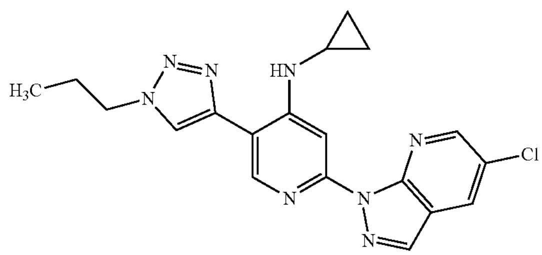 [SMILES: CCCn1cc(-c2cnc(-n3ncc4cc(Cl)cnc43)cc2NC2CC2)nn1] | 1.94 | C | 395.2 |
| 37 | 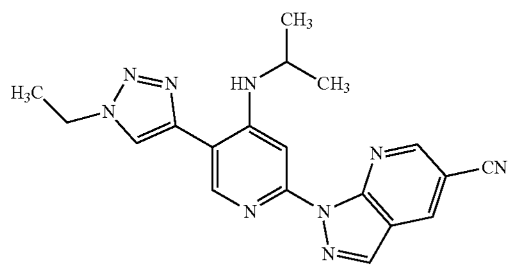 [SMILES: CCn1cc(-c2cnc(-n3ncc4cc(C#N)cnc43)cc2NC(C)C)nn1] | 1.62 | C | 374.2 |
| 38 | 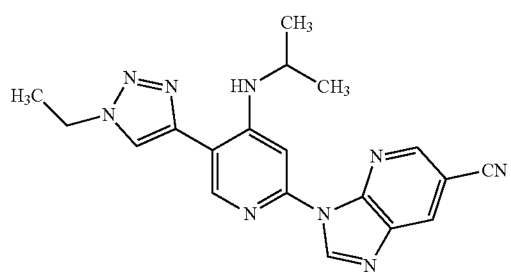 [SMILES: CCn1cc(-c2cnc(-n3cnc4cc(C#N)cnc43)cc2NC(C)C)nn1] | 1.75 | C | 374.2 |
| 39 | 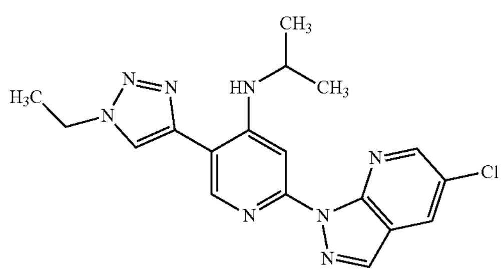 [SMILES: CCn1cc(-c2cnc(-n3ncc4cc(Cl)cnc43)cc2NC(C)C)nn1] | 1.89 | C | 383.2 |
| 40 | 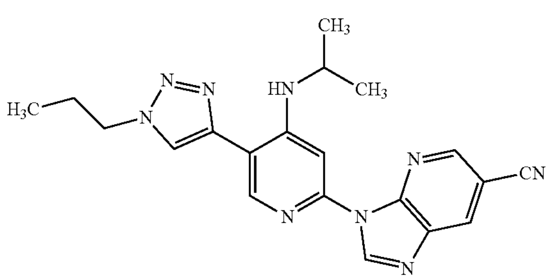 [SMILES: CCCn1cc(-c2cnc(-n3cnc4cc(C#N)cnc43)cc2NC(C)C)nn1] | 1.90 | C | 388.3 |

TABLE 3-continued
| Ex. No. | Structure | HPLC rt (min) | HPLC cond. | LCMS |
|---|---|---|---|---|
| 41 | 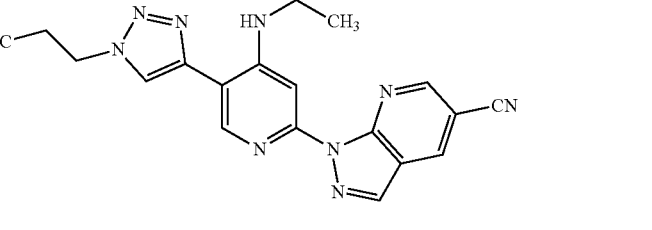 | 1.82 | C | 442.2 |
| 42 | 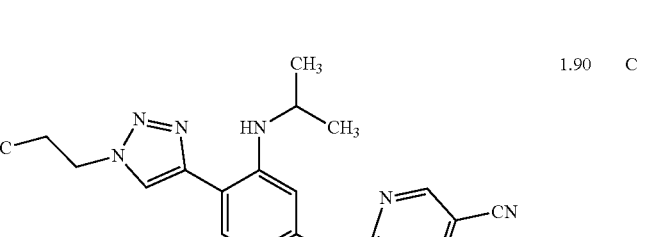 | 1.90 | C | 442.2 |
| 43 | 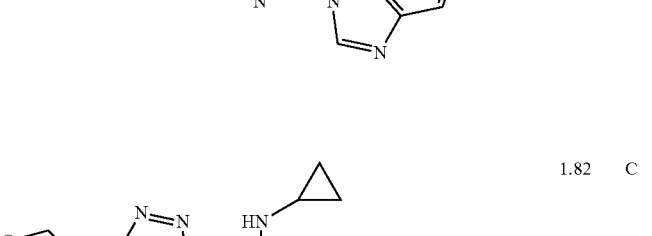 | 1.82 | C | 386.3 |
| 44 | 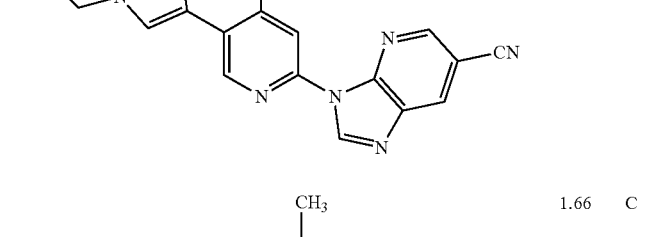 | 1.66 | C | 406.3 |
| 45 | 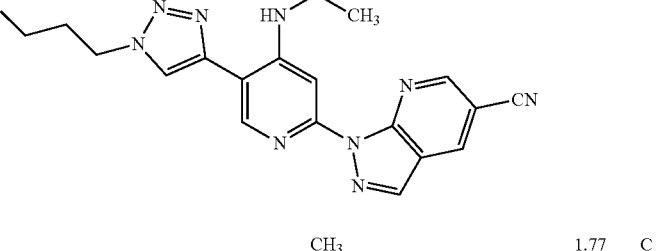 | 1.77 | C | 406.2 |

TABLE 3-continued

| Ex. No. | Structure | HPLC rt (min) | HPLC cond. | LCMS |
|---|---|---|---|---|
| 46 | 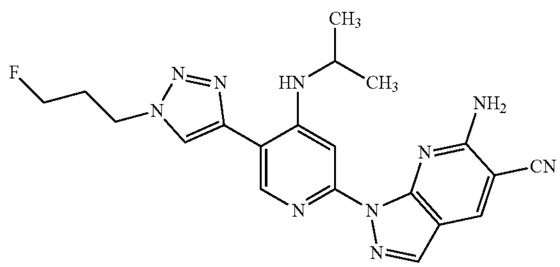 [SMILES: CC(C)Nc1cc(-n2ncc3cc(C#N)c(N)nc32)ncc1-c1cn(CCCF)nn1] | 1.53 | C | 421.3 |
| 47 | 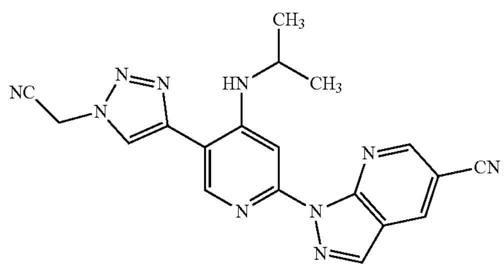 [SMILES: CC(C)Nc1cc(-n2ncc3cc(C#N)cnc32)ncc1-c1cn(CC#N)nn1] | 1.53 | C | 385.3 |
| 48 | 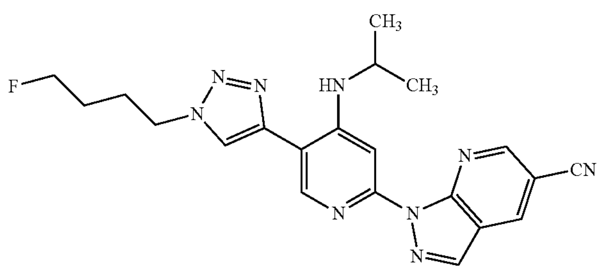 [SMILES: CC(C)Nc1cc(-n2ncc3cc(C#N)cnc32)ncc1-c1cn(CCCCF)nn1] | 1.78 | C | 420.3 |
| 49 | 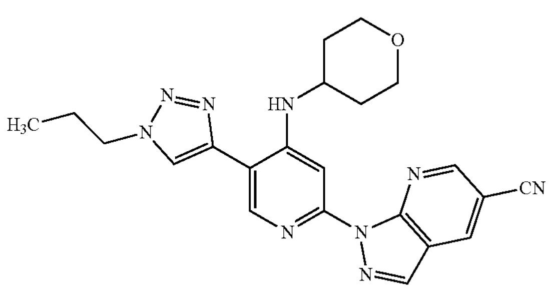 [SMILES: CCCn1cc(-c2cnc(-n3ncc4cc(C#N)cnc43)cc2NC2CCOCC2)nn1] | 1.50 | C | 430.1 |
| 50 | 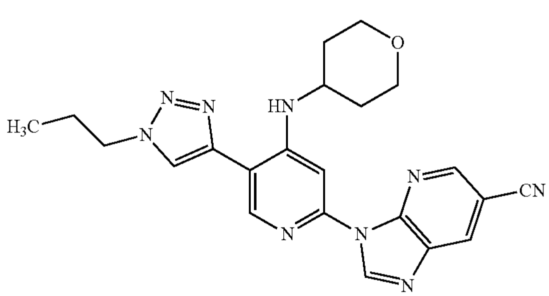 [SMILES: CCCn1cc(-c2cnc(-n3cnc4cc(C#N)cnc43)cc2NC2CCOCC2)nn1] | 1.61 | C | 430.1 |

TABLE 3-continued

| Ex. No. | Structure | HPLC rt (min) | HPLC cond. | LCMS |
|---|---|---|---|---|
| 51 | 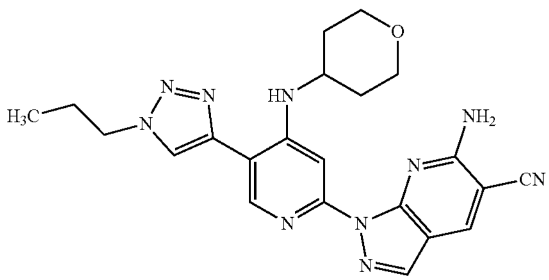 [SMILES: CCCn1cc(-c2cnc(-n3ncc4cc(C#N)c(N)nc43)cc2NC2CCOCC2)nn1] | 1.41 | C | 445.1 |
| 52 | 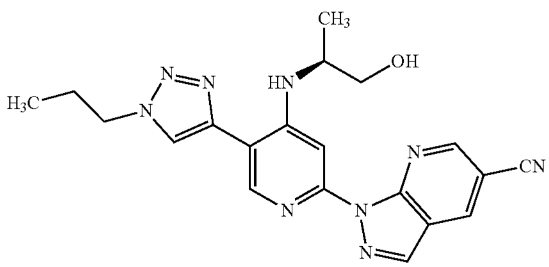 [SMILES: CCCn1cc(-c2cnc(-n3ncc4cc(C#N)cnc43)cc2N[C@@H](C)CO)nn1] | 5.14 | A | 404.1 |
| 53 | 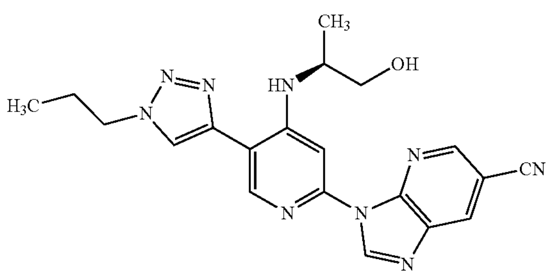 [SMILES: CCCn1cc(-c2cnc(-n3cnc4cc(C#N)cnc43)cc2N[C@@H](C)CO)nn1] | 6.73 | A | 404.1 |
| 54 | 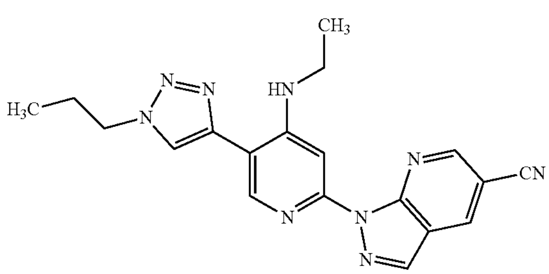 [SMILES: CCCn1cc(-c2cnc(-n3ncc4cc(C#N)cnc43)cc2NCC)nn1] | 1.10 | C | 374.7 |
| 55 | 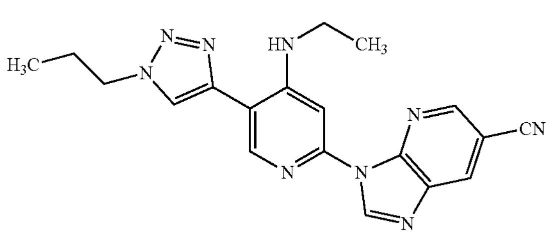 [SMILES: CCCn1cc(-c2cnc(-n3cnc4cc(C#N)cnc43)cc2NCC)nn1] | 1.43 | D | 374.1 |

TABLE 3-continued

| Ex. No. | Structure | HPLC rt (min) | HPLC cond. | LCMS |
|---------|-----------|---------------|------------|------|
| 56 | 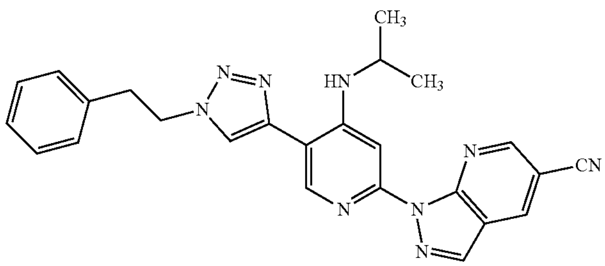 [SMILES: CC(C)Nc1cc(-n2ncc3cc(C#N)cnc32)ncc1-c1cn(CCc2ccccc2)nn1] | 1.94 | C | 450.3 |
| 57 | 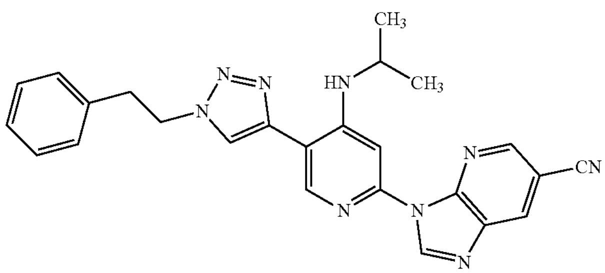 [SMILES: CC(C)Nc1cc(-n2cnc3cc(C#N)cnc32)ncc1-c1cn(CCc2ccccc2)nn1] | 2.05 | C | 450.3 |
| 58 | 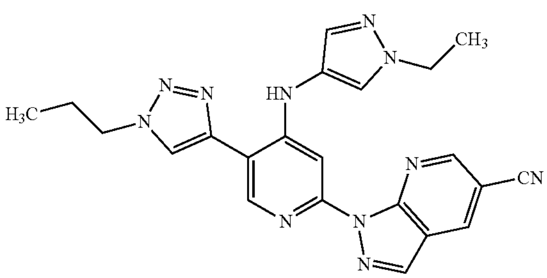 [SMILES: CCCn1cc(-c2cnc(-n3ncc4cc(C#N)cnc43)cc2Nc2cnn(CC)c2)nn1] | 1.51 | C | 440.3 |
| 59 | 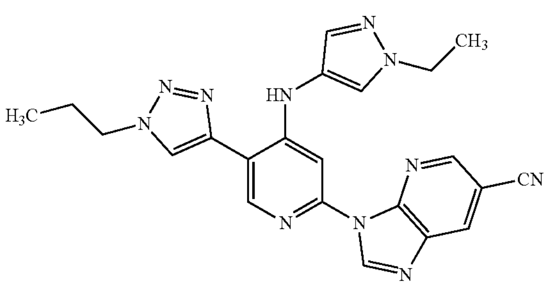 [SMILES: CCCn1cc(-c2cnc(-n3cnc4cc(C#N)cnc43)cc2Nc2cnn(CC)c2)nn1] | 1.63 | C | 440.3 |
| 60 | 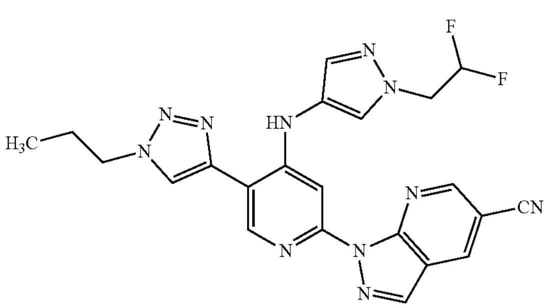 [SMILES: CCCn1cc(-c2cnc(-n3ncc4cc(C#N)cnc43)cc2Nc2cnn(CC(F)F)c2)nn1] | 1.45 | C | 476.2 |

TABLE 3-continued

| Ex. No. | Structure | HPLC rt (min) | HPLC cond. | LCMS |
|---|---|---|---|---|
| 61 | 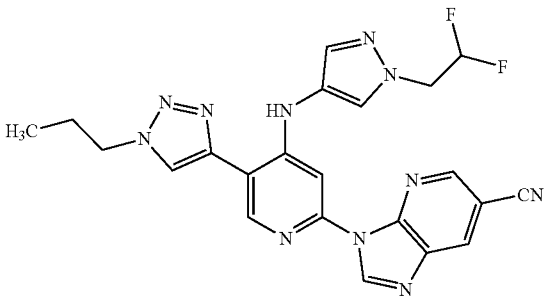 [SMILES: CCCn1cc(-c2cnc(-n3cnc4cc(C#N)cnc43)cc2Nc2cnn(CC(F)F)c2)nn1] | 1.57 | C | 476.2 |
| 62 | 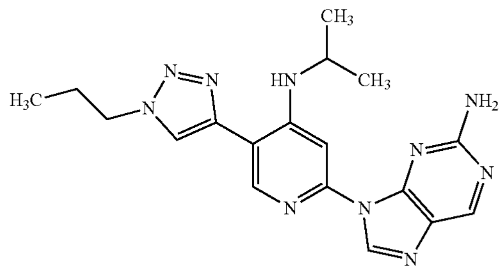 [SMILES: CCCn1cc(-c2cnc(-n3cnc4cnc(N)nc43)cc2NC(C)C)nn1] | 1.46 | C | 379.2 |

Example 63

1-(5-(1-(2-hydroxy-2-methylpropyl)-1H-1,2,3-triazol-4-yl)-4-(isopropylamino)pyridin-2-yl)-1H-pyrazolo[3,4-b]pyridine-5-carbonitrile (63)

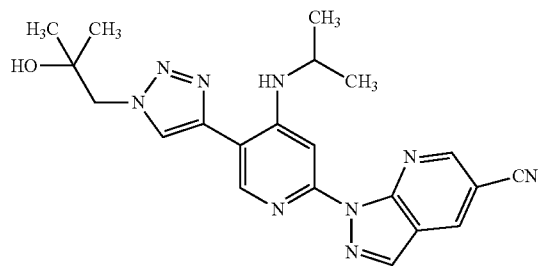

Intermediate 63A: 1-(4-(6-chloro-4-(isopropylamino)pyridin-3-yl)-1H-1,2,3-triazol-1-yl)-2-methylpropan-2-ol (63A)

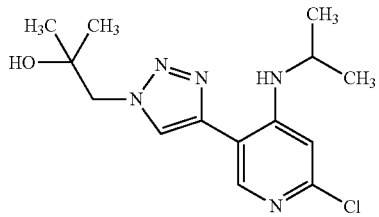

In a sealed vial, a mixture of 2,2-dimethyloxirane (0.316 mL, 3.60 mmol) and sodium azide (134 mg, 2.055 mmol) in 1:1 tBuOH/water (3 mL) was stirred at 90° C. for 4 hours. The mixture was allowed to come to room temperature, and treated with 2-chloro-5-ethynyl-N-isopropylpyridin-4-amine (100 mg, 0.514 mmol), sodium ascorbate (20.35 mg, 0.103 mmol), and copper(II) sulfate (8.20 mg, 0.051 mmol). The reaction mixture was stirred at 45° C. for 45 minutes, then at room temperature for 18 hours, at which point it was judged to be complete by LCMS. The mixture was diluted with ethyl acetate (20 mL), and the turbid solution was washed 2× with 10% lithium chloride solution and once with brine. The organic phase was dried over sodium sulfate, filtered, and concentrated in vacuo. The residue was chromatographed via MPLC over a 24 g silica gel column, eluting at 40 mL/min with a 0% to 10% methanol/methylene chloride gradient over 10 column volumes. Fractions containing the desired product were pooled and concentrated in vacuo to yield 1-(4-(6-chloro-4-(isopropylamino)pyridin-3-yl)-1H-1,2,3-triazol-1-yl)-2-methylpropan-2-ol (125 mg, 0.403 mmol, 79% yield) as a colorless solid. $^1$H NMR (400 MHz, chloroform-d) δ 8.28 (d, J=7.0 Hz, 1H), 8.20 (s, 1H), 8.08 (s, 1H), 6.59 (s, 1H), 4.43 (s, 2H), 3.76 (dq, J=13.1, 6.5 Hz, 1H), 2.90 (br. s., 1H), 1.36 (d, J=6.4 Hz, 6H), 1.33 (s, 6H); LCMS 310.1 (M+H)$^+$.

Example 63

The title compound was synthesized from 1-(4-(6-chloro-4-(isopropylamino) pyridin-3-yl)-1H-1,2,3-triazol-1-yl)-2-methylpropan-2-ol (43 mg, 0.139 mmol) and 1H-pyrazolo[3,4-b]pyridine-5-carbonitrile (30.0 mg, 0.208 mmol) using the conditions described in Example 10. $^1$H NMR (500 MHz, DMSO-d$_6$) δ 9.04 (s, 1H), 9.01 (s, 1H), 8.69 (s, 1H), 8.64 (s, 1H), 8.63 (s, 1H), 8.37 (d, J=7.1 Hz, 1H), 7.33 (s, 1H), 5.00 (s, 1H), 4.39 (s, 2H), 3.87 (dq, J=12.8, 6.5 Hz, 1H), 1.33 (d, J=6.4 Hz, 6H), 1.16 (s, 6H); LCMS 418.3 (M+H)$^+$, HPLC rt=1.55 min (conditions C).

The Examples in Table 4 were prepared using the methods outlined for Example 63, substituting the appropriate amine for isopropylamine in Intermediate 10A, the appropriate epoxide for 2,2-dimethyloxirane, and the appropriate heterocycle for 1H-pyrazolo[3,4-b]pyridine-5-carbonitrile.

TABLE 4
| Ex. No. | Structure | HPLC rt (min) | HPLC cond. | LCMS |
|---|---|---|---|---|
| 64 | 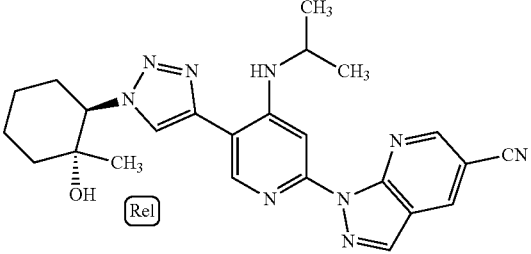 [SMILES: CC(C)Nc1cc(-n2ncc3cc(C#N)cnc32)ncc1-c1cn([C@@H]2CCCC[C@@]2(C)O)nn1] | 7.82 | A | 458.2 |
| 65 | 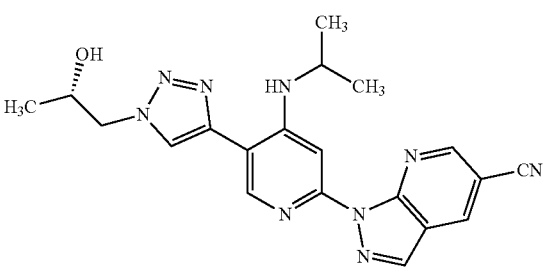 [SMILES: CC(C)Nc1cc(-n2ncc3cc(C#N)cnc32)ncc1-c1cn(C[C@H](C)O)nn1] | 5.45 | A | 404.1 |
| 66 | 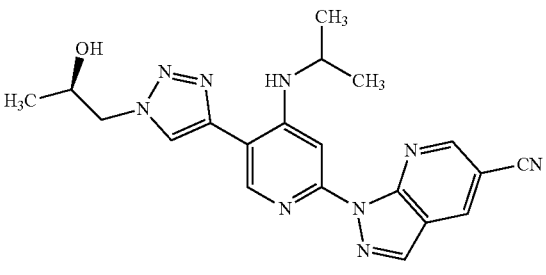 [SMILES: CC(C)Nc1cc(-n2ncc3cc(C#N)cnc32)ncc1-c1cn(C[C@@H](C)O)nn1] | 1.38 | C | 404.0 |
| 67 | 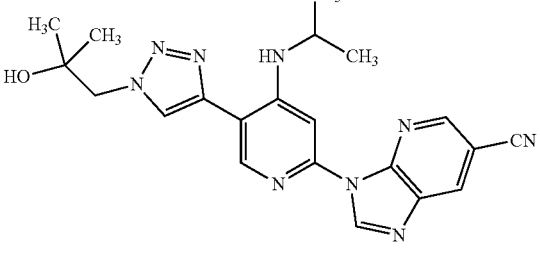 | 1.57 | C | 418.3 |
| 68 | 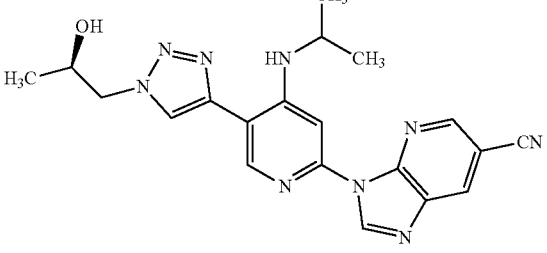 | 1.47 | C | 404.2 |

TABLE 4-continued

| Ex. No. | Structure | HPLC rt (min) | HPLC cond. | LCMS |
|---|---|---|---|---|
| 69 | 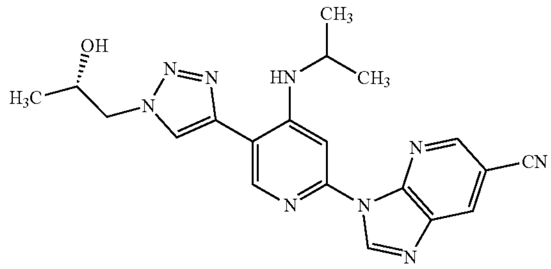 [SMILES: CC(C)Nc1cc(-n2cnc3cc(C#N)cnc32)ncc1-c1cn(C[C@H](C)O)nn1] | 1.47 | C | 404.2 |
| 70 | 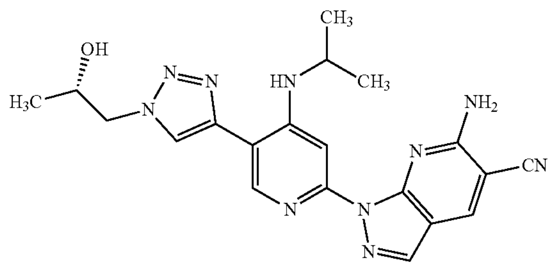 [SMILES: CC(C)Nc1cc(-n2ncc3cc(C#N)c(N)nc32)ncc1-c1cn(C[C@H](C)O)nn1] | 1.30 | C | 419.2 |
| 71 | 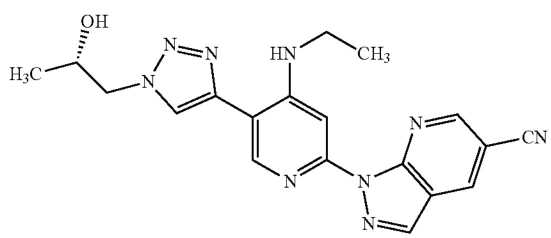 [SMILES: CCNc1cc(-n2ncc3cc(C#N)cnc32)ncc1-c1cn(C[C@H](C)O)nn1] | 1.21 | C | 390.3 |
| 72 | 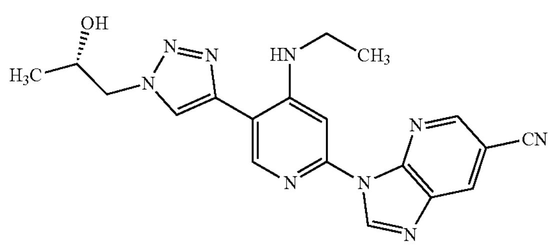 [SMILES: CCNc1cc(-n2cnc3cc(C#N)cnc32)ncc1-c1cn(C[C@H](C)O)nn1] | 1.36 | C | 390.1 |
| 73 | Isomer 1 | 1.40 | C | 432.3 |

TABLE 4-continued
| Ex. No. | Structure | HPLC rt (min) | HPLC cond. | LCMS |
|---|---|---|---|---|
| 74 | 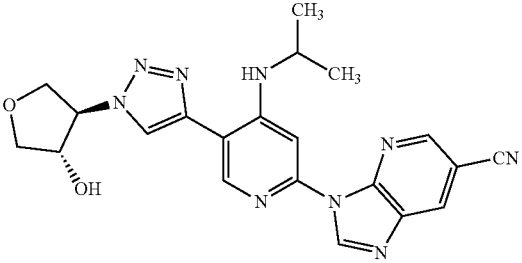 [SMILES: CC(C)Nc1cc(-n2cnc3cc(C#N)cnc32)ncc1-c1cn([C@@H]2COC[C@H]2O)nn1] Isomer 1 | 1.47 | C | 432.1 |
| 75 | 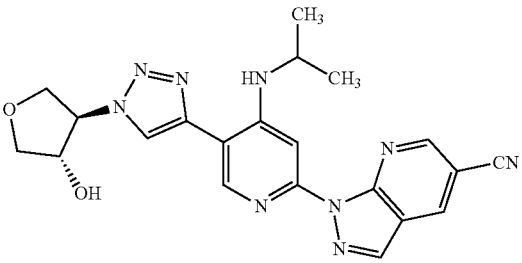 [SMILES: CC(C)Nc1cc(-n2ncc3cc(C#N)cnc32)ncc1-c1cn([C@@H]2COC[C@H]2O)nn1] Isomer 2 | 1.41 | C | 432.1 |
| 76 | 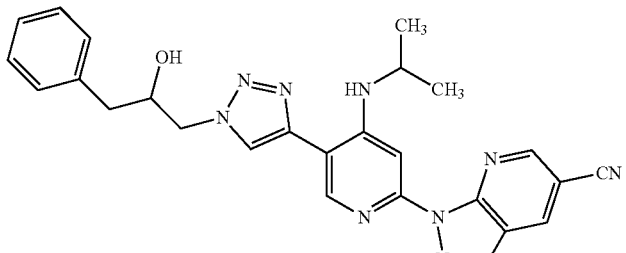 Isomer 1 | 1.84 | C | 480.1 |
| 77 | 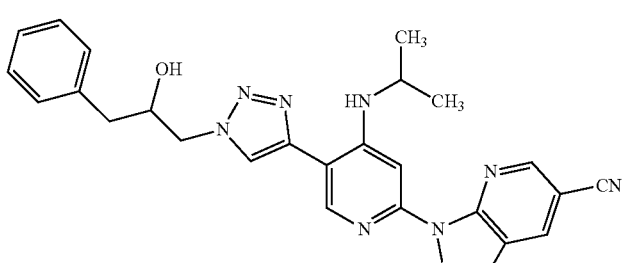 Isomer 2 | 1.84 | C | 480.3 |

TABLE 4-continued
| Ex. No. | Structure | HPLC rt (min) | HPLC cond. | LCMS |
|---|---|---|---|---|
| 78 | 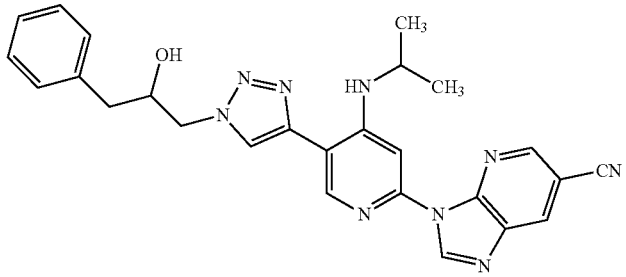 [SMILES: CC(C)Nc1cc(-n2cnc3cc(C#N)cnc32)ncc1-c1cn(CC(O)Cc2ccccc2)nn1] Isomer 1 | 1.92 | C | 480.3 |
| 79 | 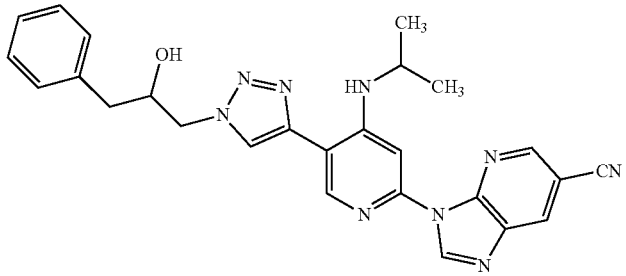 [SMILES: CC(C)Nc1cc(-n2cnc3cc(C#N)cnc32)ncc1-c1cn(CC(O)Cc2ccccc2)nn1] Isomer 2 | 2.05 | C | 479.9 |
| 80 | 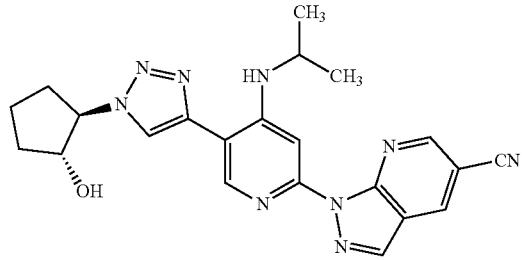 [SMILES: CC(C)Nc1cc(-n2ncc3cc(C#N)cnc32)ncc1-c1cn([C@@H]2CCC[C@H]2O)nn1] Isomer 1 | 1.61 | C | 430.2 |
| 81 | 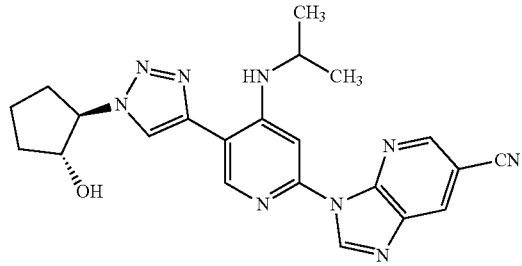 [SMILES: CC(C)Nc1cc(-n2cnc3cc(C#N)cnc32)ncc1-c1cn([C@@H]2CCC[C@H]2O)nn1] Isomer 1 | 1.69 | C | 430.3 |

TABLE 4-continued
| Ex. No. | Structure | HPLC rt (min) | HPLC cond. | LCMS |
|---|---|---|---|---|
| 82 | 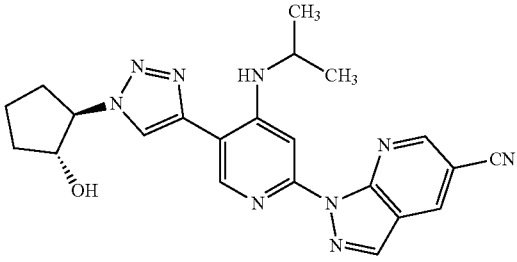 [SMILES: CC(C)Nc1cc(-n2ncc3cc(C#N)cnc32)ncc1-c1cn([C@@H]2CCC[C@H]2O)nn1] Isomer 2 | 1.61 | C | 430.2 |
| 83 | 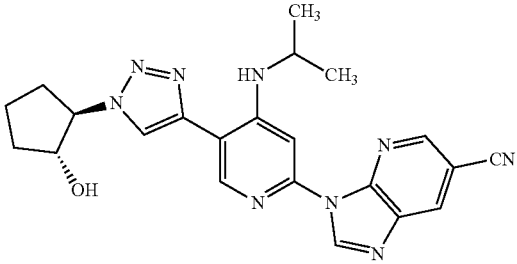 [SMILES: CC(C)Nc1cc(-n2cnc3cc(C#N)cnc32)ncc1-c1cn([C@@H]2CCC[C@H]2O)nn1] Isomer 2 | 1.69 | C | 430.1 |
| 84 | 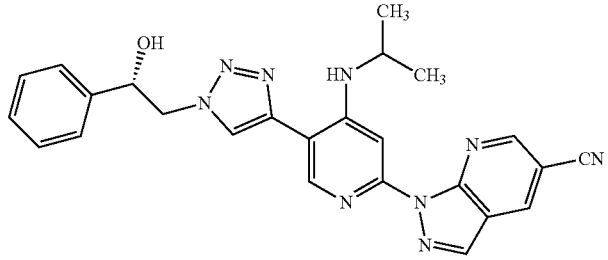 [SMILES: CC(C)Nc1cc(-n2ncc3cc(C#N)cnc32)ncc1-c1cn(C[C@@H](O)c2ccccc2)nn1] | 1.43 | C | 466.0 |
| 85 | 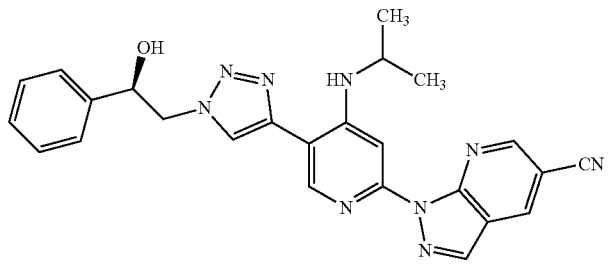 [SMILES: CC(C)Nc1cc(-n2ncc3cc(C#N)cnc32)ncc1-c1cn(C[C@H](O)c2ccccc2)nn1] | 1.75 | C | 466.3 |
| 86 | 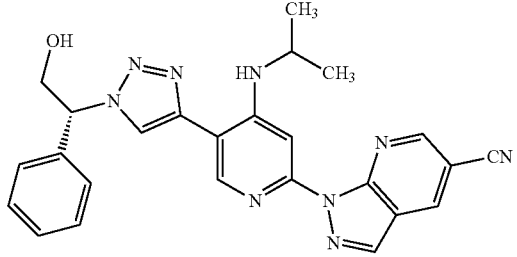 [SMILES: CC(C)Nc1cc(-n2ncc3cc(C#N)cnc32)ncc1-c1cn([C@@H](CO)c2ccccc2)nn1] | 1.45 | C | 466.2 |

TABLE 4-continued

| Ex. No. | Structure | HPLC rt (min) | HPLC cond. | LCMS |
|---|---|---|---|---|
| 87 | 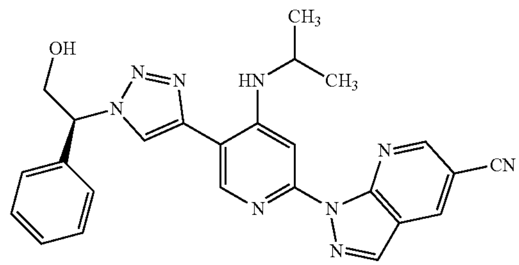 [SMILES: CC(C)Nc1cc(-n2ncc3cc(C#N)cnc32)ncc1-c1cn([C@H](CO)c2ccccc2)nn1] | 1.46 | C | 466.2 |
| 88 | Isomer 2 | 1.30 | D | 418.0 |
| 89 | Isomer 1 | 1.51 | C | 418.0 |
| 90 | Isomer 1 | 1.30 | D | 418.0 |
| 91 | Isomer 2 | 1.59 | C | 418.3 |

TABLE 4-continued
| Ex. No. | Structure | HPLC rt (min) | HPLC cond. | LCMS |
|---|---|---|---|---|
| 92 | 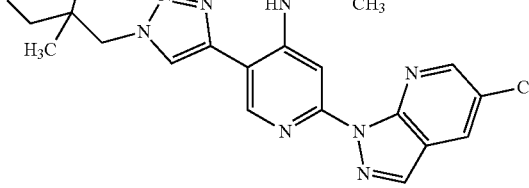 Isomer 1 | 1.64 | C | 432.2 |
| 93 | 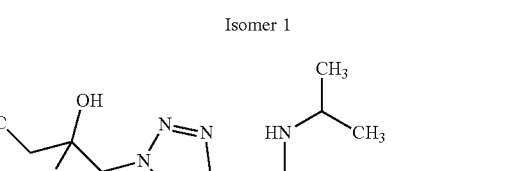 Isomer 2 | 1.63 | C | 432.3 |
| 94 | 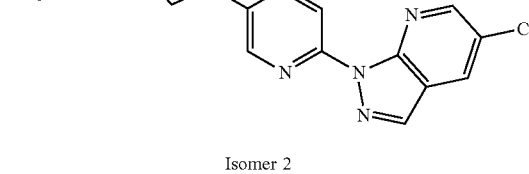 Isomer 1 | 1.72 | C | 432.2 |
| 95 | 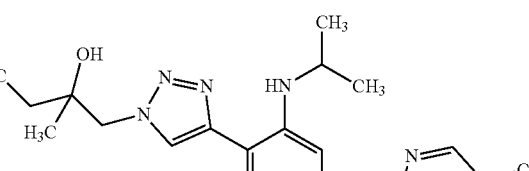 Isomer 2 | 1.72 | C | 432.2 |
| 96 | 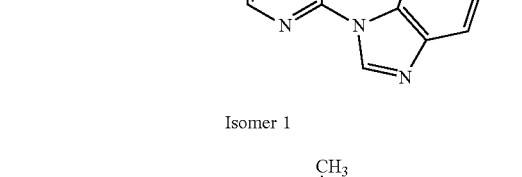 | 7.49 | A | 444.1 |

TABLE 4-continued

| Ex. No. | Structure | HPLC rt (min) | HPLC cond. | LCMS |
|---|---|---|---|---|
| 97 | 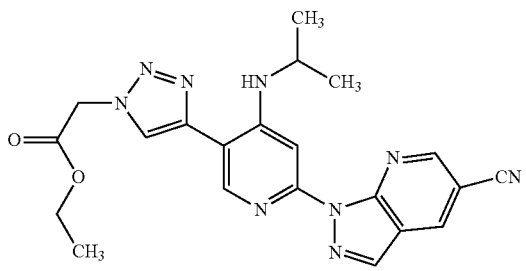 | 1.38 | C | 433.1 |

Examples 98 and 99

Ethyl 2-(4-(6-(5-cyano-1H-pyrazolo[3,4-b]pyridin-1-yl)-4-(isopropylamino)pyridin-3-yl)-1H-1,2,3-triazol-1-yl)acetate (98) and (R)-tert-butyl 2-((4-(6-(5-cyano-1H-pyrazolo[3,4-b]pyridin-1-yl)-4-(isopropylamino)pyridin-3-yl)-1H-1,2,3-triazol-1-yl)methyl)pyrrolidine-1-carboxylate (99)

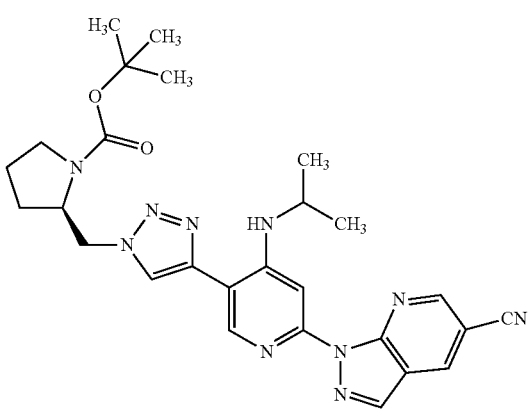

Intermediate 98A: 1-(4-(isopropylamino)-5-((trimethylsilyl)ethynyl)pyridin-2-yl)-1H-pyrazolo[3,4-b]pyridine-5-carbonitrile

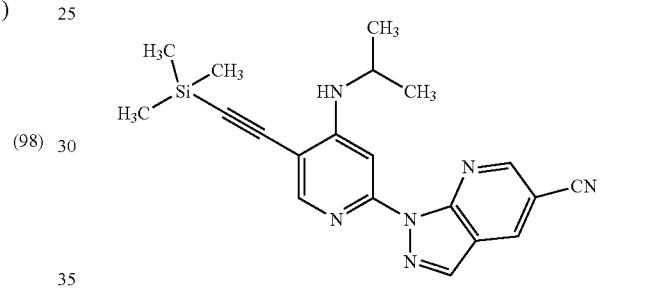

In a 25 mL vial, a solution of 1-(5-iodo-4-(isopropylamino)pyridin-2-yl)-1H-pyrazolo[3,4-b]pyridine-5-carbonitrile (1.17 g, 2.89 mmol) and copper(I) iodide (71 mg, 0.373 mmol) in DMF (10 mL) was degassed with bubbling nitrogen for 10 minutes. The mixture was treated with bis(triphenylphosphine)palladium(II) dichloride (0.264 g, 0.376 mmol) and triethylamine (8.07 mL, 57.9 mmol), and degassed for 5 minutes. Trimethylsilylacetylene (0.521 mL, 3.76 mmol) was added, the vial was sealed, and the reaction mixture was heated at 120° C. via microwave for 25 minutes, at which point it was judged to be complete by LCMS. The mixture was concentrated in vacuo, and the residue was taken up in ethyl acetate (35 mL). The solution was filtered, then washed twice with 10% lithium chloride and once with brine, dried over sodium sulfate, and concentrated in vacuo. The residue was chromatographed via MPLC over a 80 g silica gel column, eluting at 60 mL/min with 0.5%-2% methanol/dichloromethane. Fractions containing the desired product were pooled and concentrated in vacuo to yield 1-(4-(isopropylamino)-5-((trimethylsilyl)ethynyl)pyridin-2-yl)-1H-pyrazolo[3,4-b]pyridine-5-carbonitrile (1.07 g, 99% yield) as an amber solid. $^1$H NMR (400 MHz, chloroform-d) δ 8.94 (d, J=2.0 Hz, 1H), 8.50 (d, J=2.0 Hz, 1H), 8.41 (s, 1H), 8.37 (s, 1H), 7.50 (s, 1H), 5.14 (d, J=7.0 Hz, 1H), 3.89 (dq, J=13.3, 6.5 Hz, 1H), 1.38 (d, J=6.2 Hz, 6H), 0.33 (s, 9H); LCMS 375.0 (M+H)$^+$.

Intermediate 98B: 1-(5-ethynyl-4-(isopropylamino) pyridin-2-yl)-1H-pyrazolo[3,4-b]pyridine-5-carbonitrile

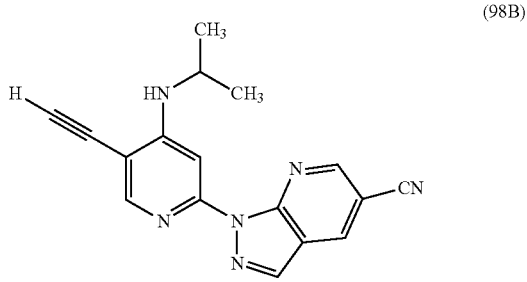 [SMILES: C#Cc1cnc(-n2ncc3cc(C#N)cnc32)cc1NC(C)C]

(98B)

A stirring solution of 1-(4-(isopropylamino)-5-((trimethylsilyl)ethynyl)pyridin-2-yl)-1H-pyrazolo[3,4-b]pyridine-5-carbonitrile (1.07 g, 2.86 mmol) in anhydrous methanol (5 mL) was cooled to 0° C. and treated with potassium carbonate (0.395 g, 2.86 mmol). The reaction mixture was stirred at 0° C. for 15 minutes, at which point it was judged to be complete by LCMS. Most of the methanol was evaporated with a stream of nitrogen, and the residue was taken up in ethyl acetate (100 mL). Solids were removed by filtration, and the filtrate was washed twice with water and once with brine, then dried over sodium sulfate and concentrated in vacuo. The residue was chromatographed via MPLC over a 40 g silica gel column, eluting at 40 mL/min with 2% methanol/dichloromethane. Fractions containing the desired product were pooled and concentrated in vacuo to yield 1-(5-ethynyl-4-(isopropylamino)pyridin-2-yl)-1H-pyrazolo[3,4-b]pyridine-5-carbonitrile (625 mg, 72% yield) as an amber solid. $^1$H NMR (400 MHz, chloroform-d) δ 8.95 (d, J=2.0 Hz, 1H), 8.51 (d, J=2.0 Hz, 1H), 8.46 (s, 1H), 8.38 (s, 1H), 7.50 (s, 1H), 5.13 (d, J=7.3 Hz, 1H), 3.91 (dq, J=13.4, 6.5 Hz, 1H), 3.58 (s, 1H), 1.38 (d, J=6.2 Hz, 6H); LCMS 303.0 (M+H)$^+$.

Example 98

In a sealed vial, a mixture of ethyl 2-azidoacetate (41.5 mg, 0.112 mmol), 1-(5-ethynyl-4-(isopropylamino)pyridin-2-yl)-1H-pyrazolo[3,4-b]pyridine-5-carbonitrile (17 mg, 0.056 mmol), and copper powder (17.87 mg, 0.281 mmol) in 1:1 t-BuOH/water (0.4 mL) was stirred at room temperature for 60 hours, at which point it was judged to be complete by LCMS. The mixture was filtered, and the crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-100% B over 20 minutes, then a 5-minute hold at 100% B; Flow: 20 mL/min. Fractions containing the desired product were combined and dried via centrifugal evaporation to yield ethyl 2-(4-(6-(5-cyano-1H-pyrazolo[3,4-b]pyridin-1-yl)-4-(isopropylamino)pyridin-3-yl)-1H-1,2,3-triazol-1-yl) acetate, TFA (2.6 mg, 8.3% yield). $^1$H NMR (500 MHz, DMSO-d$_6$) δ 9.05 (s, 1H), 9.02 (s, 1H), 8.83 (s, 1H), 8.64 (s, 1H), 8.60 (s, 1H), 8.23 (d, J=7.3 Hz, 1H), 7.35 (s, 1H), 5.55 (s, 2H), 4.24 (q, J=7.3 Hz, 2H), 3.88 (d, J=6.7 Hz, 1H), 1.33 (d, J=6.1 Hz, 6H), 1.26 (t, J=7.3 Hz, 3H); LCMS 432.3 (M+H)$^+$, HPLC rt=1.71 min (conditions C).

Example 99

In a 2-dram vial, a mixture of (S)-tert-butyl 2-(azidomethyl)pyrrolidine-1-carboxylate (71.8 mg, 0.318 mmol), 1-(5-ethynyl-4-(isopropylamino)pyridin-2-yl)-1H-pyrazolo[3,4-b]pyridine-5-carbonitrile (32 mg, 0.106 mmol), and sodium ascorbate (4.19 mg, 0.021 mmol) was treated with copper(II) sulfate (1.689 mg, 10.58 μmol) (100 mg/mL aqueous solution). The vial was sealed, and the reaction mixture was stirred at 50° C. for 2 hours, at which point it was judged to be complete by LCMS. The mixture was allowed to come to room temperature and treated with 0.5 mL of a 9:1 mixture of saturated NH$_4$C$_1$ and 10% NH$_4$OH, and stirred for 20 minutes. Ethyl acetate (3 mL) was added, and the mixture was stirred for 5 minutes. The bright blue bottom phase was separated, and the organic phase was washed once with water and concentrated in vacuo. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to yield (S)-tert-butyl 2-((4-(6-(5-cyano-1H-pyrazolo[3,4-b] pyridin-1-yl)-4-(isopropylamino)pyridin-3-yl)-1H-1,2,3-triazol-1-yl)methyl)pyrrolidine-1-carboxylate (36 mg, 62% yield). $^1$H NMR (500 MHz, DMSO-d$_6$)(rotomeric) δ 9.05 (s, 1H), 9.03 (d, J=1.8 Hz, 1H), 8.77 (s, 1H), 8.64 (s, 1H), 8.61 (br. s., 1H), 8.38-8.25 (m, 1H), 7.33 (s, 1H), 4.66-4.45 (m, 2H), 4.20 (br. s., 1H), 3.92-3.79 (m, 1H), 3.32-3.18 (m, 2H), 1.94 (br. s., 1H), 1.86-1.59 (m, 3H), 1.45-1.27 (m, 15H); LCMS 529.2 (M+H)$^+$, rt=2.068 min (Conditions C).

The Examples in Table 5 were prepared using the methods outlined for Examples 98 and 99, substituting the appropriate organoazide for 2-azido-1-morpholinoethanone.

TABLE 5

| Ex. No. | Structure | Step 3 Method | HPLC rt (min) | HPLC cond. | LCMS |
|---|---|---|---|---|---|
| 100 | 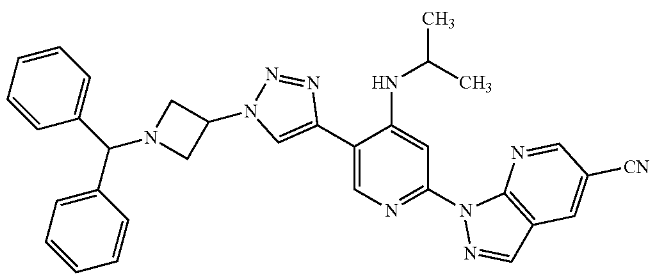 [SMILES: CC(C)Nc1cc(-n2ncc3cc(C#N)cnc32)ncc1-c1cn(C2CN(C(c3ccccc3)c3ccccc3)C2)nn1] | A | 2.29 | C | 567.3 |
| 101 | 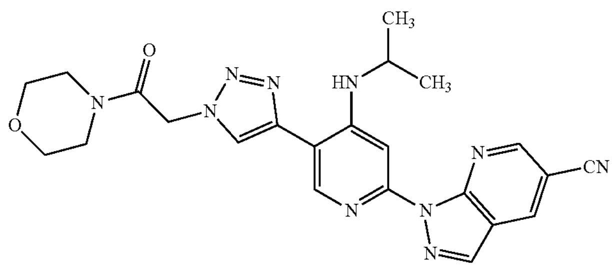 [SMILES: CC(C)Nc1cc(-n2ncc3cc(C#N)cnc32)ncc1-c1cn(CC(=O)N2CCOCC2)nn1] | A | 1.42 | C | 473.3 |
| 102 | 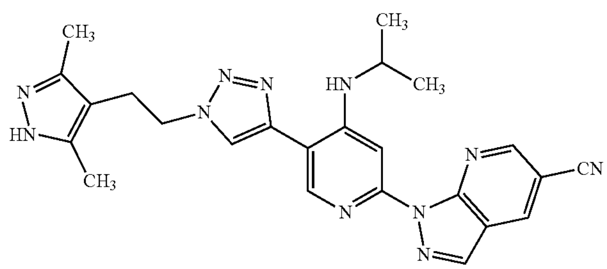 [SMILES: Cc1n[nH]c(C)c1CCn1cc(-c2cnc(-n3ncc4cc(C#N)cnc43)cc2NC(C)C)nn1] | A | 1.57 | C | 468.3 |
| 103 | 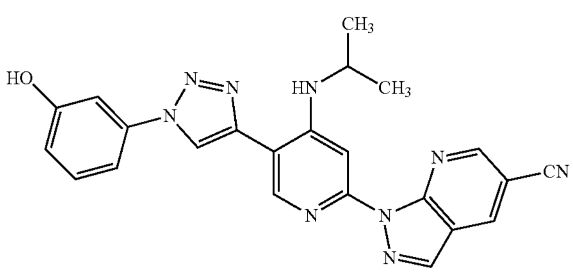 [SMILES: CC(C)Nc1cc(-n2ncc3cc(C#N)cnc32)ncc1-c1cn(-c2cccc(O)c2)nn1] | A | 1.71 | C | 438.2 |
| 104 | 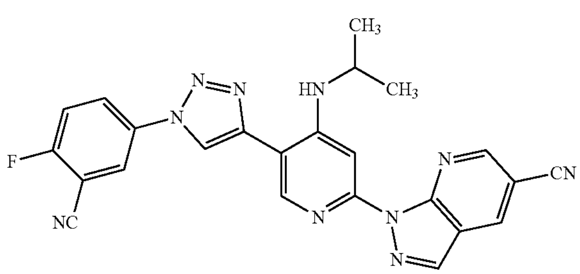 [SMILES: CC(C)Nc1cc(-n2ncc3cc(C#N)cnc32)ncc1-c1cn(-c2ccc(F)c(C#N)c2)nn1] | A | 1.92 | C | 465.3 |

TABLE 5-continued

| Ex. No. | Structure | Step 3 Method | HPLC rt (min) | HPLC cond. | LCMS |
|---|---|---|---|---|---|
| 105 | 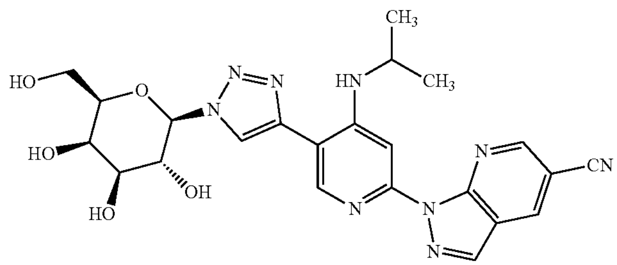 [SMILES: CC(C)Nc1cc(-n2ncc3cc(C#N)cnc32)ncc1-c1cn([C@@H]2O[C@H](CO)[C@H](O)[C@H](O)[C@H]2O)nn1] | A | 1.07 | C | 508.3 |
| 106 | 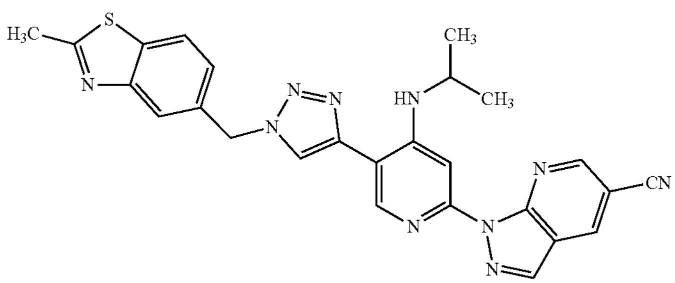 [SMILES: Cc1nc2cc(Cn3cc(-c4cnc(-n5ncc6cc(C#N)cnc65)cc4NC(C)C)nn3)ccc2s1] | A | 1.83 | C | 507.3 |
| 107 | 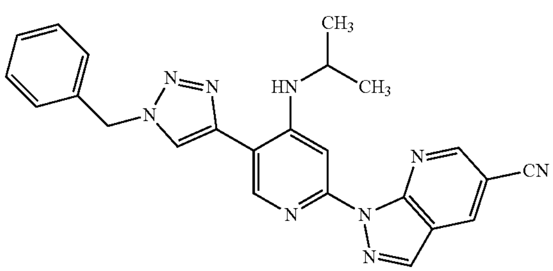 [SMILES: CC(C)Nc1cc(-n2ncc3cc(C#N)cnc32)ncc1-c1cn(Cc2ccccc2)nn1] | A | 1.87 | C | 436.3 |
| 108 | 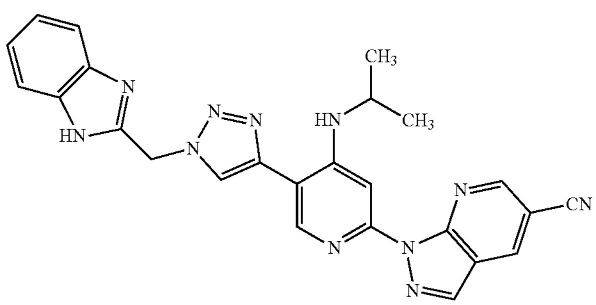 [SMILES: CC(C)Nc1cc(-n2ncc3cc(C#N)cnc32)ncc1-c1cn(Cc2nc3ccccc3[nH]2)nn1] | A | 1.52 | C | 476.3 |
| 109 | 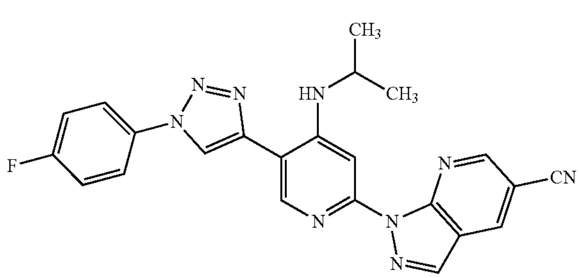 [SMILES: CC(C)Nc1cc(-n2ncc3cc(C#N)cnc32)ncc1-c1cn(-c2ccc(F)cc2)nn1] | A | 1.97 | C | 440.3 |

TABLE 5-continued
| Ex. No. | Structure | Step 3 Method | HPLC rt (min) | HPLC cond. | LCMS |
|---|---|---|---|---|---|
| 110 | 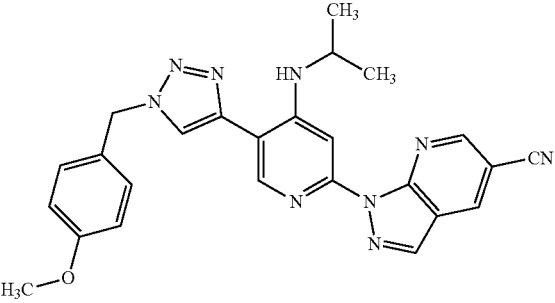 [SMILES: COc1ccc(Cn2cc(-c3cnc(-n4ncc5cc(C#N)cnc54)cc3NC(C)C)nn2)cc1] | A | 1.96 | C | 466.3 |
| 111 | 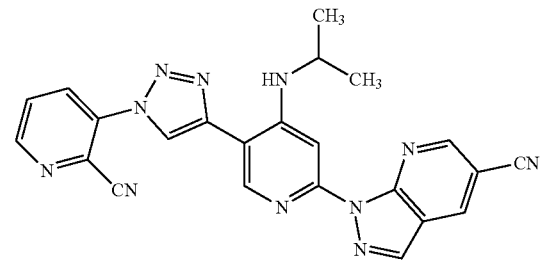 [SMILES: CC(C)Nc1cc(-n2ncc3cc(C#N)cnc32)ncc1-c1cn(-c2cccnc2C#N)nn1] | A | 1.65 | C | 448.3 |
| 112 | 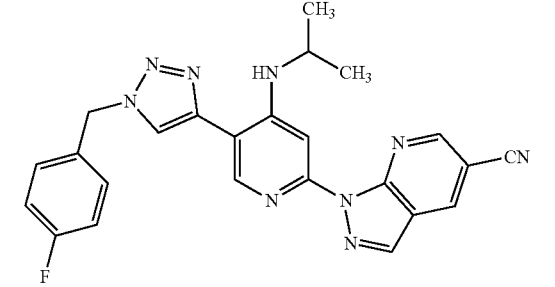 [SMILES: CC(C)Nc1cc(-n2ncc3cc(C#N)cnc32)ncc1-c1cn(Cc2ccc(F)cc2)nn1] | A | 1.60 | D | 454.3 |
| 113 | 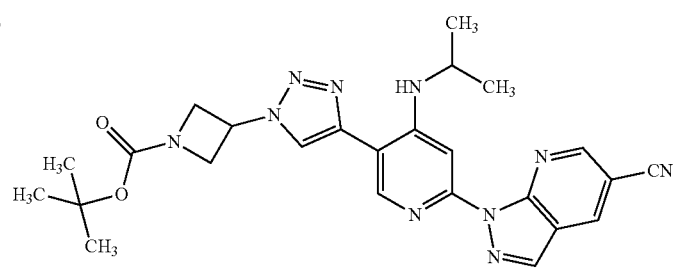 [SMILES: CC(C)Nc1cc(-n2ncc3cc(C#N)cnc32)ncc1-c1cn(C2CN(C(=O)OC(C)(C)C)C2)nn1] | B | 2.01 | C | 501.3 |
| 114 | 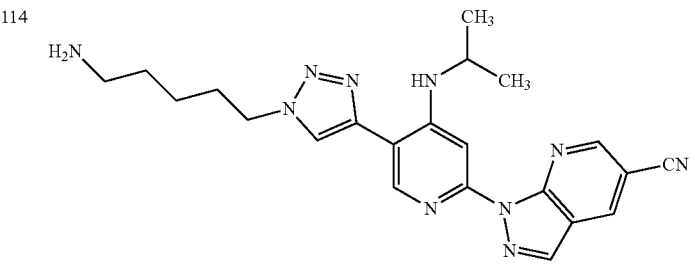 | B | 1.25 | C | 431.1 |

TABLE 5-continued

| Ex. No. | Structure | Step 3 Method | HPLC rt (min) | HPLC cond. | LCMS |
|---|---|---|---|---|---|
| 115 | 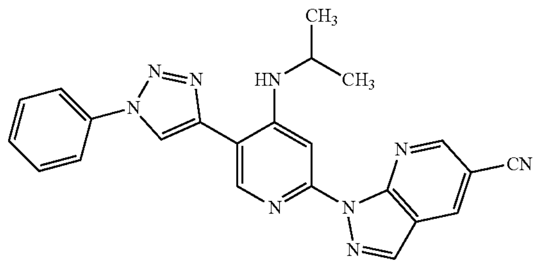 [SMILES: CC(C)Nc1cc(-n2ncc3cc(C#N)cnc32)ncc1-c1cn(-c2ccccc2)nn1] | B | 1.70 | D | 422.3 |
| 116 | 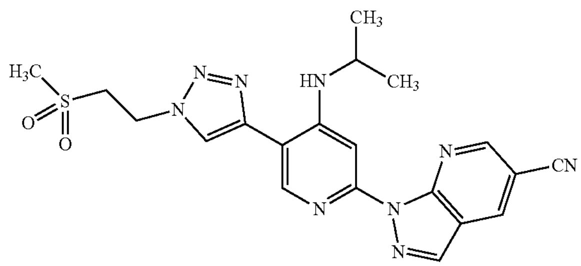 [SMILES: CC(C)Nc1cc(-n2ncc3cc(C#N)cnc32)ncc1-c1cn(CCS(C)(=O)=O)nn1] | B | 1.45 | C | 452.0 |

Example 117

1-(5-(1-(cyclobutylmethyl)-1H-1,2,3-triazol-4-yl)-4-(isopropylamino)pyridin-2-yl)-1H-pyrazolo[3,4-b]pyridine-5-carbonitrile

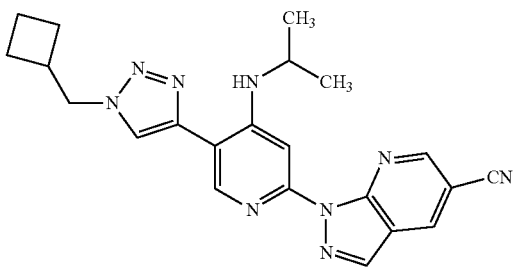

(117)

A stirring solution of sodium azide (21 mg, 0.323 mmol) and (bromomethyl) cyclobutane (0.033 mL, 0.295 mmol) in DMF (0.1 mL) was stirred at 100° C. for 2 hours, then allowed to come to room temperature. The mixture was filtered into a vial containing a mixture of 1-(5-ethynyl-4-(isopropylamino)pyridin-2-yl)-1H-pyrazolo[3,4-b]pyridine-5-carbonitrile (28 mg, 0.093 mmol), THF (0.5 mL) and water (0.3 mL). This mixture was treated with sodium ascorbate (0.51 M in water) (0.054 mL, 0.028 mmol) and copper(II) sulfate (0.62 M in water) (0.015 mL, 9.26 µmol), the vial was sealed, and the reaction mixture was stirred at 65° C. for 2 hours, at which point it was judged to be complete by LCMS. The mixture was allowed to come to room temperature, and treated with 1 mL of 0.5 M EDTA (pH 8). The heterogeneous mixture was vigorously stirred for 30 minutes, then the blue aqueous phase was removed and extracted once with THF (0.5 mL) and once with ethyl acetate (1 mL). The organic phases were combined and diluted to 4 mL with ethyl acetate, then washed once with 0.5 M EDTA (pH 8), once with 10% lithium chloride, and once with brine, then dried over sodium sulfate and concentrated in vacuo. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-70% B over 20 minutes, then a 5-minute hold at 100% B; Flow: 20 mL/min. Fractions containing the desired product were combined and dried via centrifugal evaporation to yield 1-(5-(1-(cyclobutylmethyl)-1H-1,2,3-triazol-4-yl)-4-(isopropylamino)pyridin-2-yl)-1H-pyrazolo[3,4-b]pyridine-5-carbonitrile, TFA (37 mg, 73% yield). $^1$H NMR (500 MHz, DMSO-$d_6$) δ 9.07 (d, J=1.7 Hz, 1H), 9.01 (d, J=1.8 Hz, 1H), 8.80 (s, 1H), 8.70 (s, 1H), 8.57 (s, 1H), 7.56 (s, 1H), 4.50 (d, J=7.4 Hz, 2H), 3.91 (dd, J=12.6, 6.4 Hz, 1H), 2.85 (dt, J=15.0, 7.6 Hz, 1H), 2.12-1.97 (m, 2H), 1.94-1.77 (m, 4H), 1.34 (d, J=6.3 Hz, 6H); LCMS 414.3 (M+H)$^+$, HPLC rt=1.69 min (conditions D).

The Examples in Table 6 were prepared using the method outlined for Example 117, substituting the appropriate organohalide or mesylate for (bromomethyl) cyclobutane. In cases where the organohalide was obtained as a HCl or HBr salt, an equimolar amount of potassium carbonate was used during the organoazide formation step.

TABLE 6

| Ex. No. | Structure | HPLC rt (min) | HPLC cond. | LCMS |
|---|---|---|---|---|
| 118 | 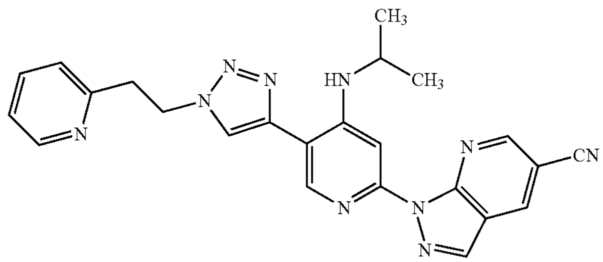 [SMILES: CC(C)Nc1cc(-n2ncc3cc(C#N)cnc32)ncc1-c1cn(CCc2ccccn2)nn1] | 1.03 | D | 451.3 |
| 119 | 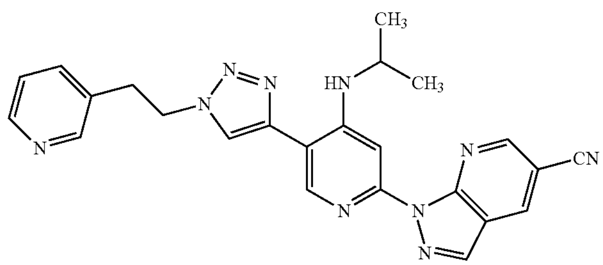 [SMILES: CC(C)Nc1cc(-n2ncc3cc(C#N)cnc32)ncc1-c1cn(CCc2cccnc2)nn1] | 1.63 | C | 451.3 |
| 120 | 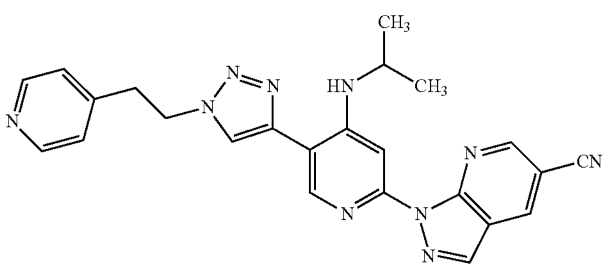 [SMILES: CC(C)Nc1cc(-n2ncc3cc(C#N)cnc32)ncc1-c1cn(CCc2ccncc2)nn1] | 1.65 | C | 451.1 |
| 121 | 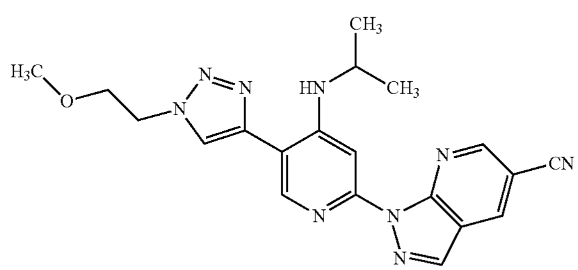 [SMILES: COCCn1cc(-c2cnc(-n3ncc4cc(C#N)cnc43)cc2NC(C)C)nn1] | 1.33 | D | 404.0 |
| 122 | 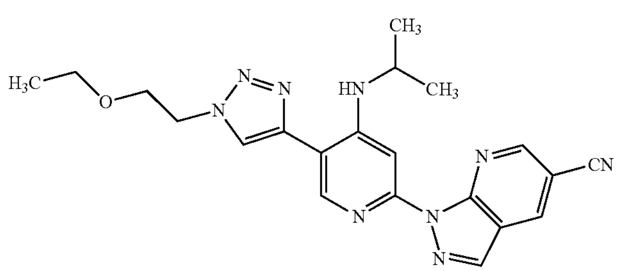 [SMILES: CCOCCn1cc(-c2cnc(-n3ncc4cc(C#N)cnc43)cc2NC(C)C)nn1] | 1.73 | C | 418.1 |

TABLE 6-continued

| Ex. No. | Structure | HPLC rt (min) | HPLC cond. | LCMS |
|---|---|---|---|---|
| 123 | 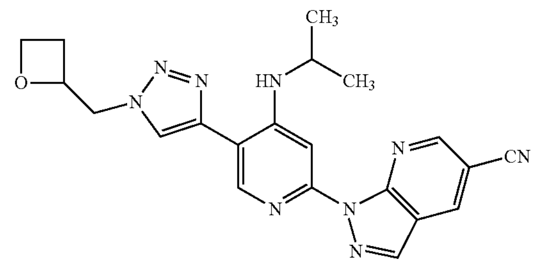 [SMILES: CC(C)Nc1cc(-n2ncc3cc(C#N)cnc32)ncc1-c1cn(CC2CCO2)nn1] | 1.59 | C | 416.2 |
| 124 | 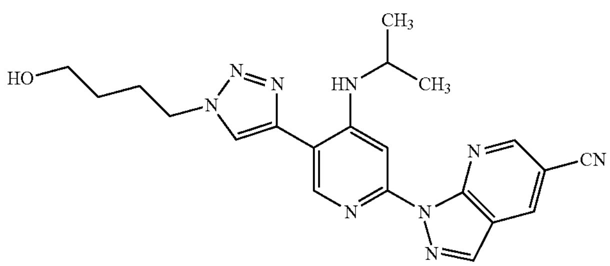 [SMILES: CC(C)Nc1cc(-n2ncc3cc(C#N)cnc32)ncc1-c1cn(CCCCO)nn1] | 1.47 | C | 418.2 |
| 125 | 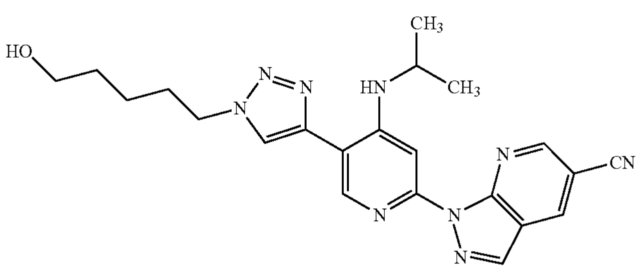 [SMILES: CC(C)Nc1cc(-n2ncc3cc(C#N)cnc32)ncc1-c1cn(CCCCCO)nn1] | 1.59 | C | 432.3 |
| 126 | 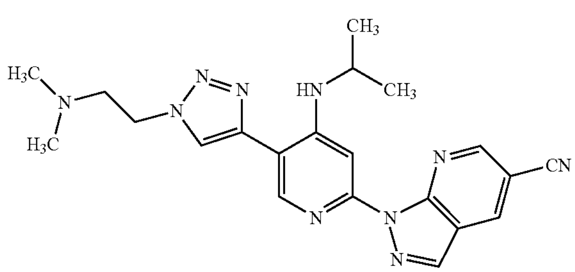 [SMILES: CC(C)Nc1cc(-n2ncc3cc(C#N)cnc32)ncc1-c1cn(CCN(C)C)nn1] | 1.45 | C | 417.0 |
| 127 | 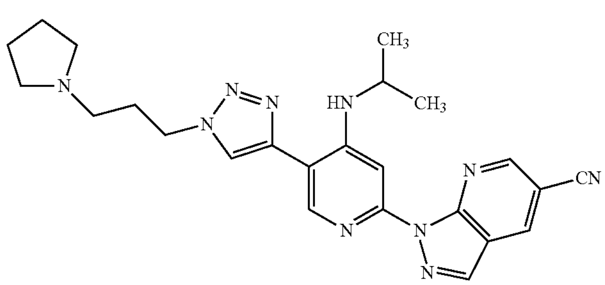 [SMILES: CC(C)Nc1cc(-n2ncc3cc(C#N)cnc32)ncc1-c1cn(CCCN2CCCC2)nn1] | 1.28 | C | 457.1 |

TABLE 6-continued

| Ex. No. | Structure | HPLC rt (min) | HPLC cond. | LCMS |
|---|---|---|---|---|
| 128 | 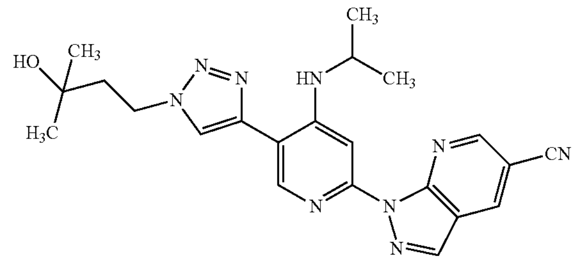 [SMILES: CC(C)Nc1cc(-n2ncc3cc(C#N)cnc32)ncc1-c1cn(CCC(C)(C)O)nn1] | 5.96 | A | 432.1 |
| 129 | 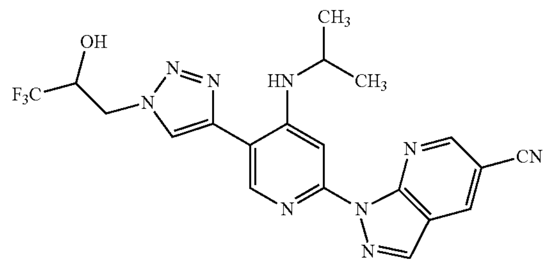 [SMILES: CC(C)Nc1cc(-n2ncc3cc(C#N)cnc32)ncc1-c1cn(CC(O)C(F)(F)F)nn1] | 1.71 | C | 458.3 |
| 130 | 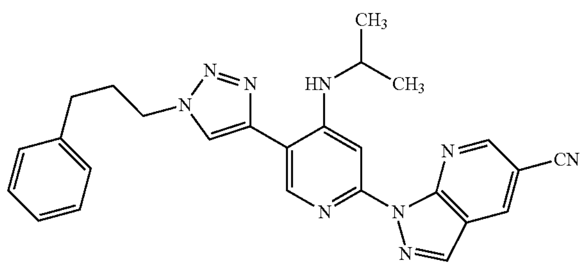 [SMILES: CC(C)Nc1cc(-n2ncc3cc(C#N)cnc32)ncc1-c1cn(CCCc2ccccc2)nn1] | 2.14 | C | 464.0 |

Example 131

1-(5-(1-(2,3-dihydroxypropyl)-1H-1,2,3-triazol-4-yl)-4-(isopropylamino)pyridin-2-yl)-1H-pyrazolo[3,4-b]pyridine-5-carbonitrile (131)

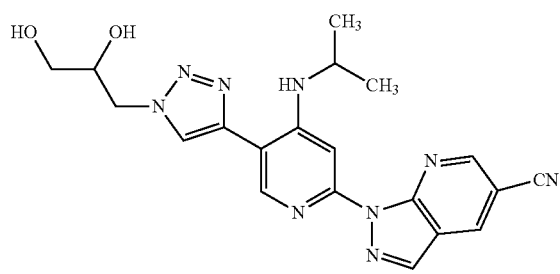

In a sealed vial, a mixture of glycidol (0.026 mL, 0.397 mmol) and sodium azide (26.7 mg, 0.410 mmol) in 1:1 tBuOH/water (0.5 mL) was stirred at 50° C. for 2 hours. The mixture was allowed to come to room temperature, and treated with 1-(5-ethynyl-4-(isopropylamino)pyridin-2-yl)-1H-pyrazolo[3,4-b]pyridine-5-carbonitrile (40 mg, 0.132 mmol), sodium ascorbate (11.4 mg, 0.058 mmol), copper(II) sulfate (5.28 mg, 0.033 mmol), and THF (0.2 mL). The reaction mixture was stirred at 50° C. for 20 minutes, then at room temperature for 1 hour, at which point it was judged to be complete by LCMS. The mixture was concentrated in vacuo, and the crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 25 minutes, then a 5-minute hold at 100% B; Flow: 20 mL/min. Fractions containing the desired product were combined and dried via centrifugal evaporation to yield 1-(5-(1-(2,3-dihydroxypropyl)-1H-1,2,3-triazol-4-yl)-4-(isopropylamino)pyridin-2-yl)-1H-pyrazolo[3,4-b]pyridine-5-carbonitrile (9 mg, 16% yield). $^1$H NMR (500 MHz, DMSO-$d_6$) δ 9.04 (s, 1H), 9.02 (s, 1H), 8.76 (s, 1H), 8.63 (s, 1H), 8.62 (s, 1H), 8.35 (d, J=7.2 Hz, 1H), 7.32 (s, 1H), 5.29 (d, J=5.3 Hz, 1H), 4.97 (t, J=5.4 Hz, 1H), 4.61 (dd, J=13.8, 2.9 Hz, 1H), 4.34 (dd, J=13.8, 8.5 Hz, 1H), 3.94 (br. s., 1H), 3.91-3.82 (m, 1H), 1.32 (d, J=6.1 Hz, 6H); LCMS 420.3 (M+H)$^+$, HPLC rt=1.29 min (Conditions C).

The Examples in Table 7 were prepared using the method outlined for Example 131, substituting the appropriate epoxide for glycidol.

TABLE 7

| Ex. No. | Structure | HPLC rt (min) | HPLC cond. | LCMS |
|---|---|---|---|---|
| 132 | 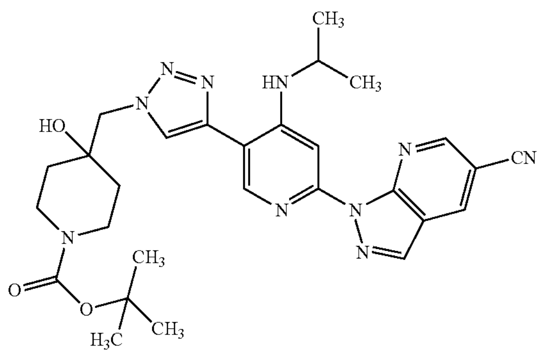 [SMILES: CC(C)Nc1cc(-n2ncc3cc(C#N)cnc32)ncc1-c1cn(CC2(O)CCN(C(=O)OC(C)(C)C)CC2)nn1] | 1.93 | C | 559.4 |
| 133 | 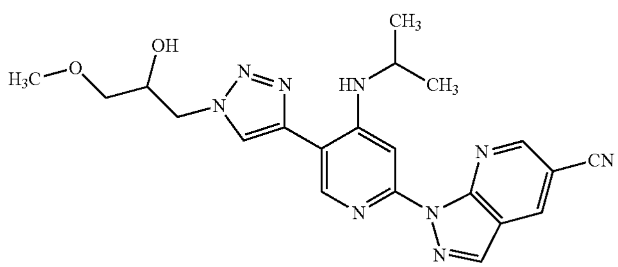 [SMILES: COCC(O)Cn1cc(-c2cnc(-n3ncc4cc(C#N)cnc43)cc2NC(C)C)nn1] | 1.45 | C | 434.0 |
| 134 | 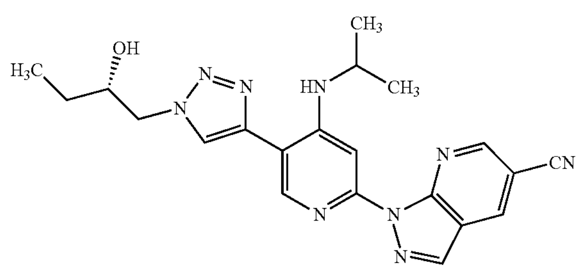 [SMILES: CC[C@H](O)Cn1cc(-c2cnc(-n3ncc4cc(C#N)cnc43)cc2NC(C)C)nn1] | 1.33 | D | 418.3 |
| 135 | 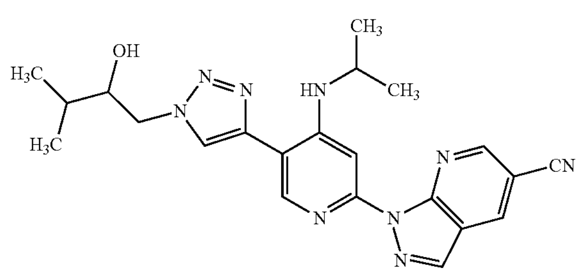 [SMILES: CC(C)Nc1cc(-n2ncc3cc(C#N)cnc32)ncc1-c1cn(CC(O)C(C)C)nn1] | 1.44 | D | 432.3 |
| 136 | 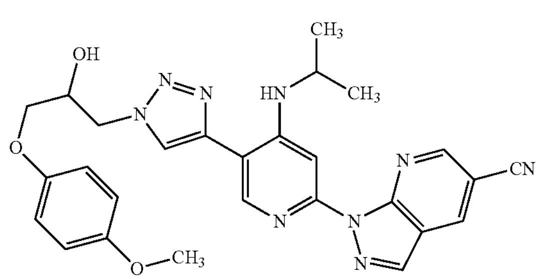 [SMILES: COc1ccc(OCC(O)Cn2cc(-c3cnc(-n4ncc5cc(C#N)cnc54)cc3NC(C)C)nn2)cc1] | 1.57 | D | 526.0 |

TABLE 7-continued

| Ex. No. | Structure | HPLC rt (min) | HPLC cond. | LCMS |
|---|---|---|---|---|
| 137 | (structure shown) | 1.32 | D | 448.0 |

Example 138

1-(5-(1-(azetidin-3-yl)-1H-1,2,3-triazol-4-yl)-4-(isopropylamino)pyridin-2-yl)-1H-pyrazolo[3,4-b]pyridine-5-carbonitrile

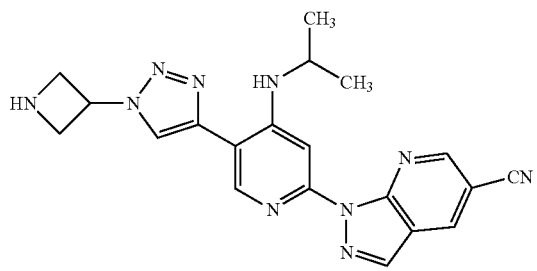

(138)

A solution of tert-butyl 3-(4-(6-(5-cyano-1H-pyrazolo[3,4-b]pyridin-1-yl)-4-(isopropylamino)pyridin-3-yl)-1H-1,2,3-triazol-1-yl)azetidine-1-carboxylate (415 mg, 0.829 mmol) in dichloromethane/TFA (2:1) (9 mL) was stirred under a nitrogen atmosphere for 1 hour, at which point the reaction was judged to be complete by LCMS. The reaction mixture was concentrated in vacuo, and the residue was concentrated 3× from dichloromethane (10 mL) to remove residual TFA. The residue was taken up in dichloromethane (30 mL), and the turbid solution was treated with half-saturated sodium bicarbonate (20 mL), resulting in the precipitation of a colorless solid. Addition of more dichloromethane and vigorous stirring failed to dissolve the precipitate, so the solids were collected by filtration, washed twice with water and once with diethyl ether, then dried under high vacuum to yield 1-(5-(1-(azetidin-3-yl)-1H-1,2,3-triazol-4-yl)-4-(isopropylamino)pyridin-2-yl)-1H-pyrazolo[3,4-b]pyridine-5-carbonitrile (285 mg, 0.712 mmol, 86% yield) as a colorless solid. $^1$H NMR (500 MHz, DMSO-$d_6$) δ 9.05 (d, J=1.2 Hz, 1H), 9.03 (d, J=1.3 Hz, 1H), 8.97 (s, 1H), 8.66 (s, 1H), 8.59 (s, 1H), 8.22 (d, J=7.2 Hz, 1H), 7.39 (s, 1H), 5.73 (t, J=7.4 Hz, 1H), 4.55 (br. s., 4H), 3.99-3.83 (m, 1H), 1.33 (d, J=6.3 Hz, 6H); LCMS 401.3 (M+H)$^+$; HPLC rt=1.21 min (conditions C).

Example 139

1-(5-(1-(1-(2-cyclopropylacetyl)azetidin-3-yl)-1H-1,2,3-triazol-4-yl)-4-(isopropylamino)pyridin-2-yl)-1H-pyrazolo[3,4-b]pyridine-5-carbonitrile

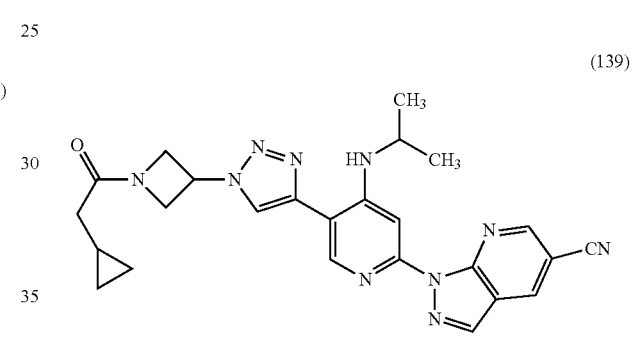

(139)

In a 5 mL vial, a stirring mixture of 1-(5-(1-(azetidin-3-yl)-1H-1,2,3-triazol-4-yl)-4-(isopropylamino)pyridin-2-yl)-1H-pyrazolo[3,4-b]pyridine-5-carbonitrile (21 mg, 0.052 mmol) and triethylamine (0.022 mL, 0.157 mmol) in dichloromethane (1 mL) was treated with 2-cyclopropylacetyl chloride (6.84 mg, 0.058 mmol). The vial was sealed, and the reaction mixture was stirred for 30 minutes, at which point it was judged to be complete by LCMS. A drop of methanol was added to quench any remaining acid chloride. The solvent was evaporated with a stream of nitrogen, and the crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation to yield 1-(5-(1-(1-(2-cyclopropylacetyl)azetidin-3-yl)-1H-1,2,3-triazol-4-yl)-4-(isopropylamino)pyridin-2-yl)-1H-pyrazolo[3,4-b]pyridine-5-carbonitrile (19 mg, 74% yield). $^1$H NMR (500 MHz, DMSO-$d_6$) δ 8.90 (s, 1H), 8.89 (s, 1H), 8.86 (s, 1H), 8.48 (s, 1H), 8.46 (s, 1H), 8.08 (d, J=6.7 Hz, 1H), 7.20 (s, 1H), 5.56-5.43 (m, 1H), 4.59 (t, J=8.7 Hz, 1H), 4.43-4.37 (m, 1H), 4.34 (t, J=9.1 Hz, 1H), 4.22-4.09 (m, 1H), 3.81-3.66 (m, 1H), 1.95 (d, J=6.6 Hz, 2H), 1.17 (d, J=5.7 Hz, 6H), 0.92-0.78 (m, 1H), 0.33 (d, J=7.7 Hz, 2H), 0.00 (d, J=4.1 Hz, 2H); LCMS 483.3 (M+H)$^+$, HPLC rt=1.65 min (Conditions C).

The Examples in Table 8 were prepared using the method outlined for Example 139, substituting the appropriate acid chloride, chloroformate, or cyanogen bromide for 2-cyclopropylacetyl chloride.

TABLE 8

| Ex. No. | Structure | HPLC rt (min) | HPLC cond. | LCMS |
|---|---|---|---|---|
| 140 | 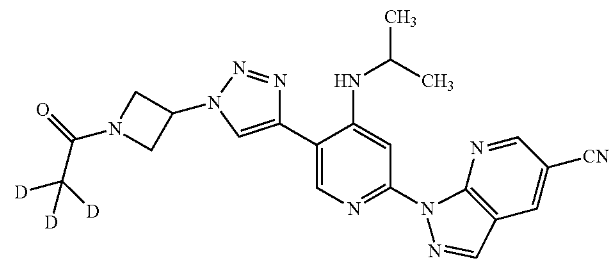 [SMILES: [2H]C([2H])([2H])C(=O)N1CC(n2cc(-c3cnc(-n4ncc5cc(C#N)cnc54)cc3NC(C)C)nn2)C1] | 1.08 | D | 446.1 |
| 141 | 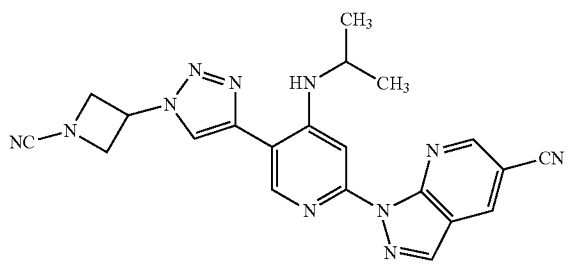 [SMILES: CC(C)Nc1cc(-n2ncc3cc(C#N)cnc32)ncc1-c1cn(C2CN(C#N)C2)nn1] | 1.20 | C | 426.2 |
| 142 | 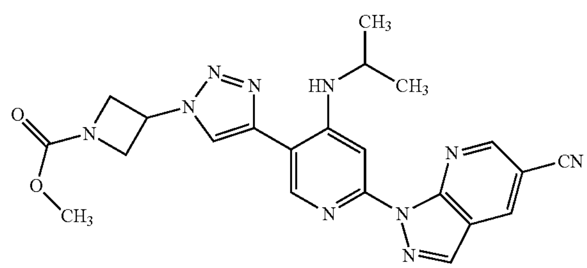 [SMILES: COC(=O)N1CC(n2cc(-c3cnc(-n4ncc5cc(C#N)cnc54)cc3NC(C)C)nn2)C1] | 1.26 | D | 459.0 |
| 143 | 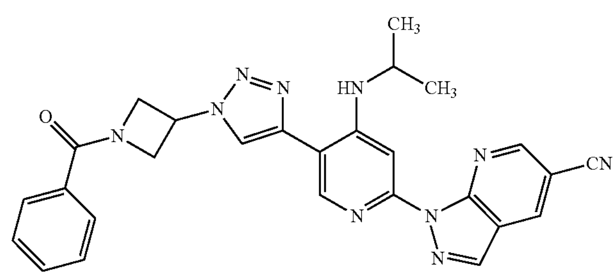 [SMILES: CC(C)Nc1cc(-n2ncc3cc(C#N)cnc32)ncc1-c1cn(C2CN(C(=O)c3ccccc3)C2)nn1] | 1.63 | C | 505.2 |
| 144 | 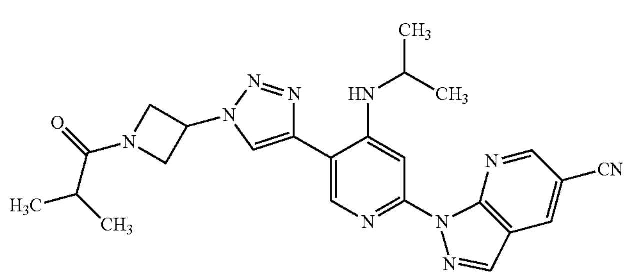 [SMILES: CC(C)Nc1cc(-n2ncc3cc(C#N)cnc32)ncc1-c1cn(C2CN(C(=O)C(C)C)C2)nn1] | 1.29 | C | 471.2 |

| Ex. No. | Structure | HPLC rt (min) | HPLC cond. | LCMS |
|---|---|---|---|---|
| 145 | 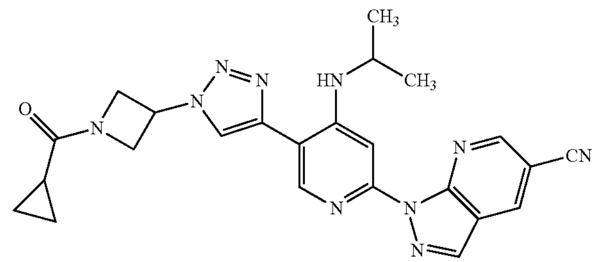 [SMILES: CC(C)Nc1cc(-n2ncc3cc(C#N)cnc32)ncc1-c1cn(C2CN(C(=O)C3CC3)C2)nn1] | 1.24 | C | 469.1 |
| 146 | 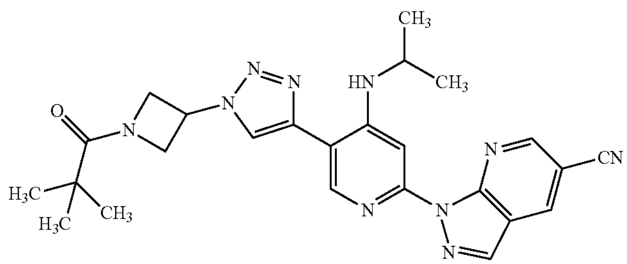 [SMILES: CC(C)Nc1cc(-n2ncc3cc(C#N)cnc32)ncc1-c1cn(C2CN(C(=O)C(C)(C)C)C2)nn1] | 1.41 | C | 485.1 |

Example 147

1-(4-(isopropylamino)-5-(1-(1-(pyrimidin-2-yl)azetidin-3-yl)-1H-1,2,3-triazol-4-yl)pyridin-2-yl)-1H-pyrazolo[3,4-b]pyridine-5-carbonitrile (147)

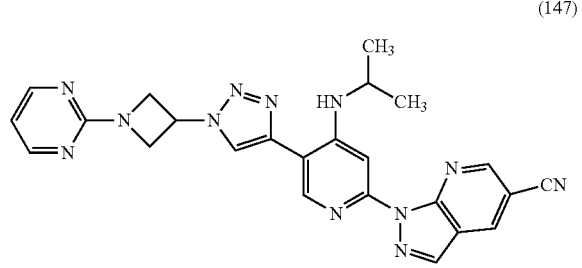 [SMILES: CC(C)Nc1cc(-n2ncc3cc(C#N)cnc32)ncc1-c1cn(C2CN(c3ncccn3)C2)nn1]

In a 2 dram vial, a solution of 1-(5-(1-(azetidin-3-yl)-1H-1,2,3-triazol-4-yl)-4-(isopropylamino)pyridin-2-yl)-1H-pyrazolo[3,4-b]pyridine-5-carbonitrile (43 mg, 0.107 mmol) and Hunig's Base (0.056 mL, 0.322 mmol) in DMF (0.5 mL) was treated with 2-chloropyrimidine (16 mg, 0.140 mmol). The vial was sealed, and the reaction mixture was stirred at 80° C. for 2 hours, at which point it was judged to be essentially complete by LCMS. The mixture was cooled to room temperature, and the crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 4-minute hold at 100% B; Flow: 20 mL/min. Fractions containing the desired product were combined and dried via centrifugal evaporation to yield 1-(4-(isopropylamino)-5-(1-(1-(pyrimidin-2-yl)azetidin-3-yl)-1H-1,2,3-triazol-4-yl)pyridin-2-yl)-1H-pyrazolo[3,4-b]pyridine-5-carbonitrile (11 mg, 20% yield). LCMS (method D) detects 479.3 (M+H)+, rt=1.24 min. $^1$H NMR (500 MHz, DMSO-d$_6$) δ 9.15 (s, 1H), 9.05 (s, 1H), 9.02 (s, 1H), 8.64 (br. s., 2H), 8.45 (d, J=4.6 Hz, 2H), 8.26 (d, J=7.1 Hz, 1H), 7.34 (s, 1H), 6.81 (t, J=4.6 Hz, 1H), 5.77 (br. s., 1H), 4.68 (t, J=8.7 Hz, 2H), 4.47 (dd, J=9.2, 5.0 Hz, 2H), 4.01-3.77 (m, 1H), 1.32 (d, J=6.1 Hz, 6H); LCMS 479.3 (M+H)+, HPLC rt=1.24 min (Conditions D).

Example 148

1-(4-(isopropylamino)-5-(1-(1-(5-methyl-1,3,4-oxadiazol-2-yl)azetidin-3-yl)-1H-1,2,3-triazol-4-yl)pyridin-2-yl)-1H-pyrazolo[3,4-b]pyridine-5-carbonitrile (148)

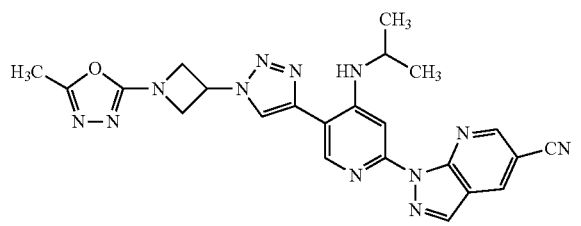

tert-Butyl 3-(4-(6-(5-cyano-1H-pyrazolo[3,4-b]pyridin-1-yl)-4-(isopropylamino) pyridin-3-yl)-1H-1,2,3-triazol-1-yl)azetidine-1-carboxylate (60 mg, 0.120 mmol) was taken up in 1:1 dichloromethane/TFA (2 mL), and the reaction mixture was stirred at room temperature for 30 minutes, at which point LCMS showed the complete removal of the Boc-group. The mixture was concentrated in vacuo, and the residue was concentrated 3× from dichloromethane to remove residual TFA. The residue was taken up in DMF (2 mL), and the mixture was treated with Hunig's Base (0.105 mL, 0.6 mmol) followed by 2-bromo-5-methyl-1,3,4-oxadiazole (29.3 mg, 0.180 mmol). The reaction mixture was stirred at 100° C. for 1 hour, at which point it was judged to be complete by LCMS. The solution was allowed to come to room temperature, and the crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 5-minute hold at 100% B; Flow: 20 mL/min. Fractions containing the desired product were combined and dried via centrifugal evaporation to yield 1-(4-(isopropylamino)-5-(1-(1-(5-methyl-1,3,4-oxadiazol-2-yl)azetidin-3-yl)-1H-1,2,3-triazol-4-yl)pyridin-2-yl)-1H-pyrazolo[3,4-b]pyridine-5-carbonitrile (24 mg, 41% yield). $^1$H NMR (500 MHz, DMSO-$d_6$) δ 9.13 (s, 1H), 9.05 (s, 1H), 9.02 (d, J=1.8 Hz, 1H), 8.63 (d, J=9.7 Hz, 2H), 8.22 (d, J=7.2 Hz, 1H), 7.35 (s, 1H), 5.81 (quint, J=5.5, 2.4 Hz, 1H), 4.70 (t, J=8.5 Hz, 2H), 4.54 (dd, J=8.8, 5.3 Hz, 2H), 3.88 (dsxt, J=13.0, 6.5 Hz, 1H), 2.39 (s, 3H), 1.32 (d, J=6.2 Hz, 6H); LCMS 483.0 (M+H)$^+$, HPLC rt=1.27 min (conditions D).

Example 149

1-(5-(1-(1-ethylazetidin-3-yl)-1H-1,2,3-triazol-4-yl)-4-(isopropylamino)pyridin-2-yl)-1H-pyrazolo[3,4-b]pyridine-5-carbonitrile

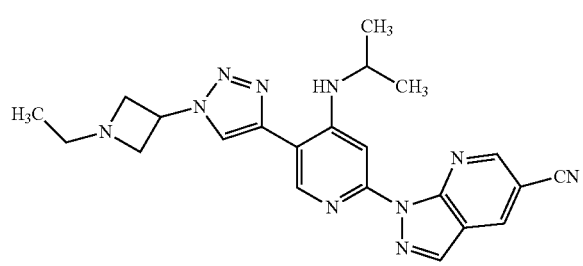

(149)

Intermediate 149A: 1-(5-(1-(azetidin-3-yl)-1H-1,2,3-triazol-4-yl)-4-(isopropylamino) pyridin-2-yl)-1H-pyrazolo[3,4-b]pyridine-5-carbonitrile, diHCl

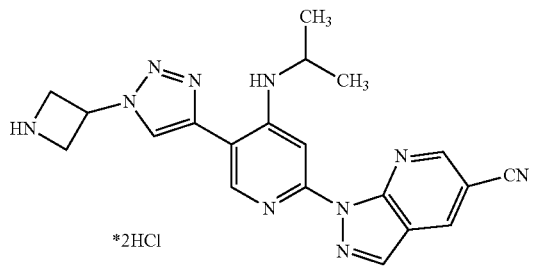

(149A)

*2HCl

A solution of tert-butyl 3-(4-(6-(5-cyano-1H-pyrazolo[3,4-b]pyridin-1-yl)-4-(isopropylamino)pyridin-3-yl)-1H-1,2,3-triazol-1-yl)azetidine-1-carboxylate (82 mg, 0.164 mmol) in dichloromethane (1 mL) was treated with HCl (4 M in dioxane) (1 mL, 4.00 mmol). The reaction mixture was stirred under a nitrogen atmosphere for 1 hour, at which point it was judged to be complete by LCMS and a colorless precipitate was observed. The reaction mixture was concentrated in vacuo, and the residue was concentrated three times from dichloromethane to yield 1-(5-(1-(azetidin-3-yl)-1H-1,2,3-triazol-4-yl)-4-(isopropylamino)pyridin-2-yl)-1H-pyrazolo[3,4-b]pyridine-5-carbonitrile, 2 HCl as a colorless solid. LCMS 401.1 (M+H)$^+$.

Example 149

A stirring suspension of 1-(5-(1-(azetidin-3-yl)-1H-1,2,3-triazol-4-yl)-4-(isopropylamino)pyridin-2-yl)-1H-pyrazolo[3,4-b]pyridine-5-carbonitrile, 2 HCl (39 mg, 0.082 mmol), acetaldehyde (5M solution in THF) (0.066 mL, 0.330 mmol), and potassium acetate (24.26 mg, 0.247 mmol) in methanol (1 mL) was treated with sodium cyanoborohydride (10.36 mg, 0.165 mmol). The reaction mixture was stirred at room temperature for 2 hours, at which point it was judged to be complete by LCMS. The mixture was treated with a few drops of 1 M sodium hydroxide, stirred for 5 minutes, then concentrated in vacuo. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation to yield 1-(5-(1-(1-ethylazetidin-3-yl)-1H-1,2,3-triazol-4-yl)-4-(isopropylamino)pyridin-2-yl)-1H-pyrazolo[3,4-b]pyridine-5-carbonitrile (4 mg, 9.15 μmol, 11.10% yield). $^1$H NMR (500 MHz, DMSO-$d_6$) δ 9.02 (d, J=1.7 Hz, 1H), 8.99 (d, J=1.8 Hz, 1H), 8.97 (s, 1H), 8.62 (s, 1H), 8.61 (s, 1H), 8.24 (d, J=7.2 Hz, 1H), 7.32 (s, 1H), 5.33 (quin, J=6.6 Hz, 1H), 3.91-3.82 (m, 1H), 3.79 (t, J=7.6 Hz, 2H), 3.49 (t, J=7.2 Hz, 1H), 2.55 (q, J=7.3 Hz, 2H), 1.30 (d, J=6.3 Hz, 6H), 0.94 (t, J=7.2 Hz, 3H); LCMS 429.3 (M+H)$^+$, HPLC rt=1.53 min (conditions C).

Example 150

1-(4-(isopropylamino)-5-(1-(1-isopropylazetidin-3-yl)-1H-1,2,3-triazol-4-yl)pyridin-2-yl)-1H-pyrazolo[3,4-b]pyridine-5-carbonitrile

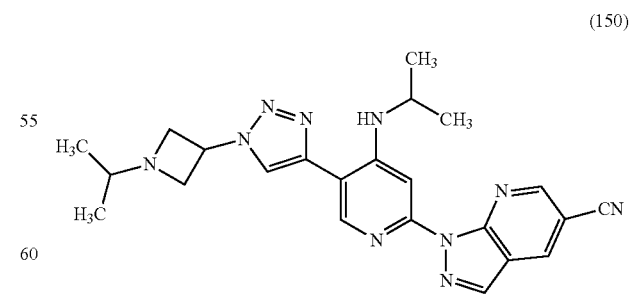

(150)

The title compound was prepared using the method described in Example 149, substituting acetone for acetaldehyde. LCMS 443.1 (M+H)$^+$, HPLC rt=1.68 min (conditions C).

Example 151

1-(4-(isopropylamino)-5-(1-(1-methylazetidin-3-yl)-1H-1,2,3-triazol-4-yl)pyridin-2-yl)-1H-pyrazolo[3,4-b]pyridine-5-carbonitrile, 2TFA

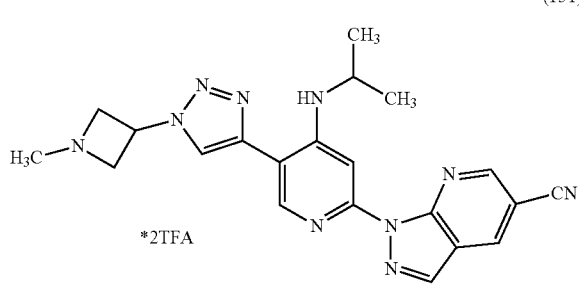

Intermediate 151A: tert-butyl 3-(4-(6-chloro-4-(isopropylamino)pyridin-3-yl)-1H-1,2,3-triazol-1-yl)azetidine-1-carboxylate

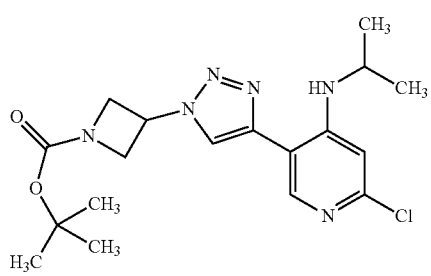

tert-Butyl 3-(4-(6-chloro-4-(isopropylamino)pyridin-3-yl)-1H-1,2,3-triazol-1-yl) azetidine-1-carboxylate was prepared from tert-butyl 3-azidoazetidine-1-carboxylate and 2-chloro-5-ethynyl-N-isopropylpyridin-4-amine using the conditions described in Intermediate 10E. LCMS 393.4 (M+H)⁺.

Intermediate 151B: 5-(1-(azetidin-3-yl)-1H-1,2,3-triazol-4-yl)-2-chloro-N-isopropylpyridin-4-amine

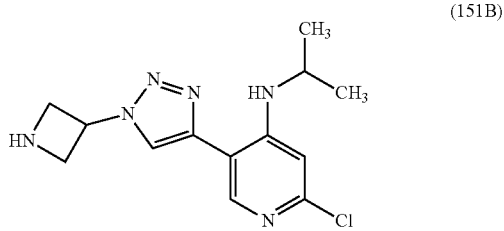 [SMILES: CC(C)Nc1cc(Cl)ncc1-c1cn(C2CNC2)nn1]

tert-Butyl 3-(4-(6-chloro-4-(isopropylamino)pyridin-3-yl)-1H-1,2,3-triazol-1-yl) azetidine-1-carboxylate (150 mg, 0.382 mmol) was dissolved in 2:1 DCM/TFA (3 mL). The reaction mixture was stirred under a nitrogen atmosphere for 1 hour, at which point it was judged to be complete by LCMS. The mixture was concentrated in vacuo, and the residue was concentrated 3× from dichloromethane to remove residual TFA. The residue was taken up in water (2 mL), and the stirring solution was treated with 1 M sodium hydroxide, causing a colorless solid to precipitate. The mixture was extracted 3 times with dichloromethane (4 mL), and the combined organic phases were washed once with 1 M sodium hydroxide and once with water, then dried over sodium sulfate and concentrated in vacuo to yield 5-(1-(azetidin-3-yl)-1H-1,2,3-triazol-4-yl)-2-chloro-N-isopropylpyridin-4-amine (93 mg, 0.318 mmol, 83% yield) as a colorless solid. LCMS 293.3 (M+H)⁺.

Intermediate 151C: 2-chloro-N-isopropyl-5-(1-(1-methylazetidin-3-yl)-1H-1,2,3-triazol-4-yl)pyridin-4-amine

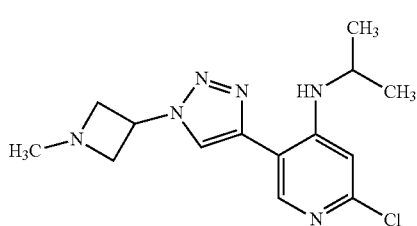

A mixture of 5-(1-(azetidin-3-yl)-1H-1,2,3-triazol-4-yl)-2-chloro-N-isopropylpyridin-4-amine (68 mg, 0.232 mmol) and formaldehyde (37%, aq) (0.026 mL, 0.348 mmol) in methanol (1.5 mL) was stirred under a nitrogen atmosphere for 20 minutes. The mixture was treated with sodium cyanoborohydride (29.2 mg, 0.465 mmol), and the reaction mixture was stirred at room temperature for 1 hour, at which point it was judged to be complete by LCMS. The methanol was evaporated with a stream of nitrogen, and the residue was taken up in ethyl acetate (2 mL). The turbid solution was washed 3× with water (0.5 mL), and once with brine, then dried over sodium sulfate and concentrated in vacuo. The residue was chromatographed via MPLC over a 4 g silica gel column, eluting at 18 mL/min with 3% then 8% methanol/methylene chloride. Fractions containing the desired product were pooled and concentrated in vacuo to yield 2-chloro-N-isopropyl-5-(1-(1-methylazetidin-3-yl)-1H-1,2,3-triazol-4-yl)pyridin-4-amine (63 mg, 88% yield) as a colorless solid. LCMS 307.1 (M+H)⁺.

Example 151

Example 151 was prepared from 2-chloro-N-isopropyl-5-(1-(1-methylazetidin-3-yl)-1H-1,2,3-triazol-4-yl)pyridin-4-amine and 1H-pyrazolo[3,4-b]pyridine-5-carbonitrile using the conditions described in Example 10. ¹H NMR (500 MHz, DMSO-d₆) δ 9.06 (s, 1H), 9.05-8.97 (m, 2H), 8.67 (s, 1H), 8.60 (s, 1H), 8.30 (br. s., 1H), 7.43 (s, 1H), 5.71 (br. s., 1H), 5.11-4.37 (m, 4H), 4.05-3.80 (m, 1H), 3.04 (br. s., 3H), 1.33 (d, J=6.2 Hz, 6H); LCMS 415.3 (M+H)⁺, HPLC rt=1.39 min (Conditions C).

Example 152

3-(4-(isopropylamino)-5-(1-(1-methylazetidin-3-yl)-1H-1,2,3-triazol-4-yl)pyridin-2-yl)-3H-imidazo[4,5-b]pyridine-6-carbonitrile

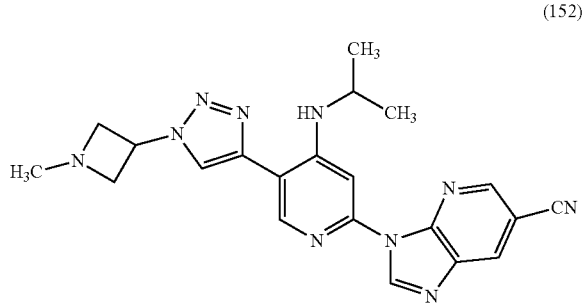 [SMILES: CC(C)Nc1cc(-n2cnc3cc(C#N)cnc32)ncc1-c1cn(C2CN(C)C2)nn1]

(152)

Example 152 was prepared according to the general conditions described in Example 151, substituting 3H-imidazo[4,5-b]pyridine-6-carbonitrile for 1H-pyrazolo[3,4-b]pyridine-5-carbonitrile. LCMS 415.2 (M+H)$^+$, HPLC rt=1.47 min.

Example 153

3-(5-(1-(1-(2,2-difluoroethyl)azetidin-3-yl)-1H-1,2,3-triazol-4-yl)-4-(isopropylamino)pyridin-2-yl)-3H-imidazo[4,5-b]pyridine-6-carbonitrile

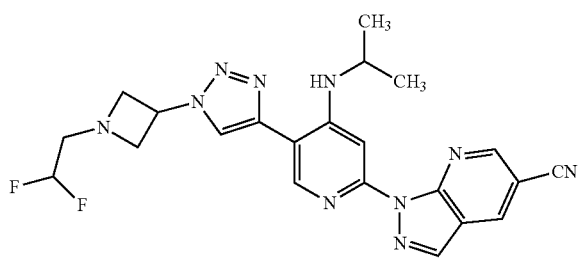

(153)

Intermediate 153A: 2-Chloro-5-(1-(1-(2,2-difluoroethyl)azetidin-3-yl)-1H-1,2,3-triazol-4-yl)-N-isopropylpyridin-4-amine (153A)

A solution of tert-butyl 3-(4-(6-chloro-4-(isopropylamino)pyridin-3-yl)-1H-1,2,3-triazol-1-yl)azetidine-1-carboxylate (154 mg, 0.392 mmol) in dichloromethane (2 mL) was treated with TFA (1 mL, 12.98 mmol). The reaction mixture was stirred under a nitrogen atmosphere for 1 hour, at which point it was judged to be complete by LCMS. The reaction mixture was concentrated in vacuo, and the residue was concentrated 2× from isopropanol and 3× from dichloromethane to remove residual TFA. The residue was dissolved in anhydrous DMF (2 mL) and transferred to a 5 mL microwave vial, and the solution was treated with potassium carbonate (179 mg, 1.294 mmol) followed by 2-iodo-1,1-difluoroethane (0.041 mL, 0.470 mmol). The vial was sealed, and the reaction mixture was heated at 110° C. for 1 hour. LCMS indicated that the reaction had not gone to completion, so it was heated at 110° C. via microwave for an additional 30 minutes. LCMS was unchanged, so the reaction mixture was worked up at this time. The reaction mixture was filtered and concentrated in vacuo, and the residue was taken up in ethyl acetate (15 mL). The turbid solution was washed twice with 10% lithium chloride solution and once with brine, then dried over sodium sulfate and concentrated in vacuo. The residue was chromatographed via MPLC over a 24 g silica gel column, eluting at 40 mL/min with a 1% to 10% methanol/dichloromethane gradient over 14 column volumes. Fractions containing the desired product were pooled and concentrated in vacuo to yield 2-chloro-5-(1-(1-(2,2-difluoroethyl)azetidin-3-yl)-1H-1,2,3-triazol-4-yl)-N-isopropylpyridin-4-amine (39 mg, 28% yield) as a colorless solid. LCMS 357.0 (M+H)$^+$. $^1$H NMR (400 MHz, CHLOROFORM-d) δ 8.22 (s, 1H), 8.15 (d, J=6.4 Hz, 1H), 8.11 (s, 1H), 6.60 (s, 1H), 5.86 (tt, J=55.7, 4.2 Hz, 1H), 5.33 (tt, J=7.1, 5.5 Hz, 1H), 4.03 (t, J=8.0 Hz, 2H), 3.86-3.71 (m, 3H), 3.00 (td, J=15.0, 4.3 Hz, 2H), 1.37-1.33 (m, 6H).

Example 153

Example 153 was prepared from 2-chloro-5-(1-(1-(2,2-difluoroethyl)azetidin-3-yl)-1H-1,2,3-triazol-4-yl)-N-isopropylpyridin-4-amine and 1H-pyrazolo[3,4-b]pyridine-5-carbonitrile using the conditions described in Example 10. LCMS 465.2 (M+H)$^+$, HPLC rt=1.84 min (Conditions C). $^1$H NMR (500 MHz, DMSO-d$_6$) δ 9.04 (br. s., 2H), 9.02 (s, 1H), 8.64 (br. s., 2H), 8.26 (d, J=7.0 Hz, 1H), 7.34 (br. s., 1H), 6.04 (tt, J=55.9, 3.3 Hz, 1H), 5.41 (quin, J=6.5 Hz, 1H), 3.95 (t, J=7.5 Hz, 2H), 3.87 (dd, J=12.7, 6.3 Hz, 1H), 3.74 (t, J=7.0 Hz, 2H), 3.02 (td, J=16.2, 3.8 Hz, 2H), 1.32 (d, J=6.2 Hz, 6H).

Example 154

1-(5-(1-(1-acetylazetidin-3-yl)-1H-1,2,3-triazol-4-yl)-4-(isopropylamino)pyridin-2-yl)-1H-pyrazolo[3,4-b]pyridine-5-carbonitrile

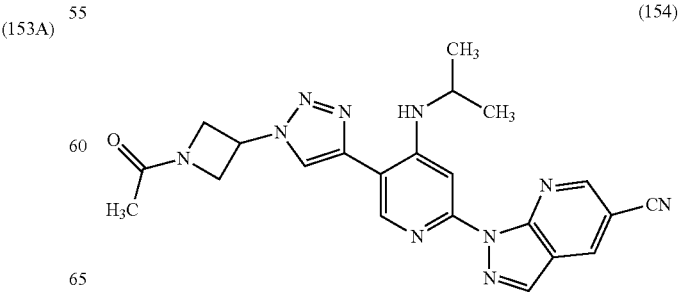

(154)

Intermediate 154A: 1-(3-(4-(6-chloro-4-(isopropylamino)pyridin-3-yl)-1H-1,2,3-triazol-1-yl)azetidin-1-yl)ethanone

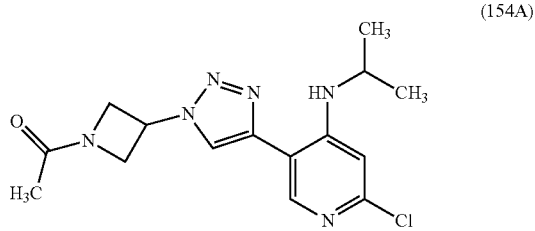 [SMILES: CC(=O)N1CC(n2cc(-c3cnc(Cl)cc3NC(C)C)nn2)C1]

(154A)

A solution of tert-butyl 3-(4-(6-chloro-4-(isopropylamino)pyridin-3-yl)-1H-1,2,3-triazol-1-yl)azetidine-1-carboxylate (307 mg, 0.781 mmol) in dichloromethane/TFA (2:1) (9 mL) was stirred under a nitrogen atmosphere for 1 hour, at which point the reaction was judged to be complete by LCMS. The reaction mixture was concentrated in vacuo, and the residue was concentrated 3× from dichloromethane (10 mL) to remove residual TFA. The residue was taken up in dichloromethane (5 mL), and treated with TEA (0.545 mL, 3.91 mmol) followed by acetic anhydride (0.081 mL, 0.860 mmol). The reaction mixture was stirred under a nitrogen atmosphere for 1 hour, at which point it was judged to be complete by LCMS. The residue was chromatographed via MPLC over a 40 g silica gel column, eluting at 40 mL/min with 8.5% then 10% methanol/dichloromethane. Fractions containing the desired product were pooled and concentrated in vacuo to yield 365 mg of a sticky solid. The material was taken up in ethyl acetate (15 mL), and the solution was washed 3× with 10% lithium chloride solution (to remove some Et$_3$N.TFA which had co-eluted with the product), and once with brine. The organic phase was dried over sodium sulfate and concentrated in vacuo to yield 1-(3-(4-(6-chloro-4-(isopropylamino)pyridin-3-yl)-1H-1,2,3-triazol-1-yl)azetidin-1-yl)ethanone (233 mg, 89% yield) as a colorless solid. LCMS 335.0 (M+H)$^+$. $^1$H NMR (400 MHz, CHLOROFORM-d) δ 8.21 (s, 1H), 8.09 (d, J=6.4 Hz, 1H), 8.04 (s, 1H), 6.61 (s, 1H), 5.47 (tt, J=7.9, 5.3 Hz, 1H), 4.80-4.61 (m, 3H), 4.50 (dd, J=10.7, 5.2 Hz, 1H), 3.77 (dq, J=13.1, 6.5 Hz, 1H), 2.00 (s, 3H), 1.36 (d, J=6.4 Hz, 6H).

Example 154

Example 154 was prepared from 1-(3-(4-(6-chloro-4-(isopropylamino)pyridin-3-yl)-1H-1,2,3-triazol-1-yl)azetidin-1-yl)ethanone and 1H-pyrazolo[3,4-b]pyridine-5-carbonitrile using the conditions described in Example 10. LCMS 443.5 (M+H)$^+$; HPLC rt 5.34 min (Conditions A). $^1$H NMR (400 MHz, CHLOROFORM-d) δ 8.96 (d, J=2.0 Hz, 1H), 8.53 (s, 1H), 8.52 (d, J=2.0 Hz, 1H), 8.39 (s, 1H), 8.24 (d, J=7.0 Hz, 1H), 8.05 (s, 1H), 7.59 (s, 1H), 5.55-5.43 (m, 1H), 4.77 (d, J=6.4 Hz, 2H), 4.71-4.63 (m, 1H), 4.54 (dd, J=10.6, 5.3 Hz, 1H), 3.96 (dq, J=13.0, 6.5 Hz, 1H), 2.02 (s, 3H), 1.44 (d, J=6.4 Hz, 6H).

The Examples in Table 9 were prepared using the general method outlined for Example 154, substituting the appropriate 6-chloropyridine for 1-(3-(4-(6-chloro-4-(isopropylamino)pyridin-3-yl)-1H-1,2,3-triazol-1-yl)azetidin-1-yl) ethanone, and the appropriate heterocycle for 1H-pyrazolo[3,4-b]pyridine-5-carbonitrile.

TABLE 9

| Ex. No. | Structure | HPLC rt (min) | HPLC cond. | LCMS |
|---|---|---|---|---|
| 155 | 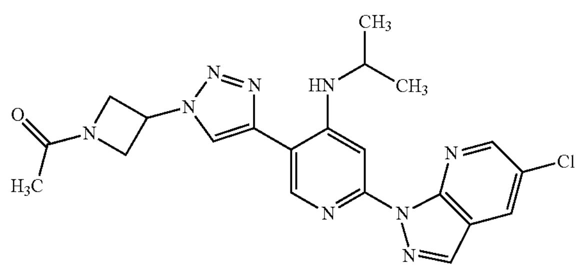 [SMILES: CC(=O)N1CC(n2cc(-c3cnc(-n4ncc5cc(Cl)cnc54)cc3NC(C)C)nn2)C1] | 1.65 | C | 452.1 |
| 156 | 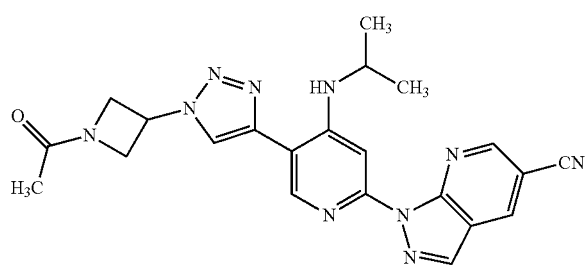 [SMILES: CC(=O)N1CC(n2cc(-c3cnc(-n4ncc5cc(C#N)cnc54)cc3NC(C)C)nn2)C1] | 1.40 | C | 443.1 |

TABLE 9-continued

| Ex. No. | Structure | HPLC rt (min) | HPLC cond. | LCMS |
|---|---|---|---|---|
| 157 | Enantiomer 1 | 1.20 | D | 457.3 |
| 158 | Enantiomer 2 | 1.20 | D | 457.3 |
| 159 | 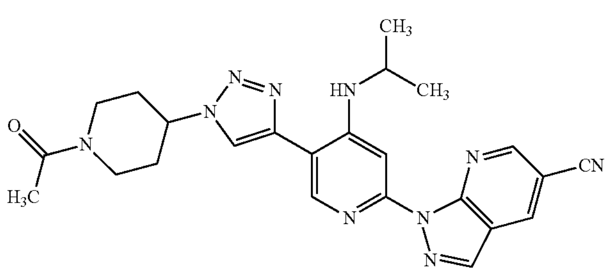 [SMILES: CC(=O)N1CCC(n2cc(-c3cnc(-n4ncc5cc(C#N)cnc54)cc3NC(C)C)nn2)CC1] | 1.49 | C | 471.2 |
| 160 | Enantiomer 1 | 1.31 | D | 471.3 |

TABLE 9-continued

| Ex. No. | Structure | HPLC rt (min) | HPLC cond. | LCMS |
|---|---|---|---|---|
| 161 | 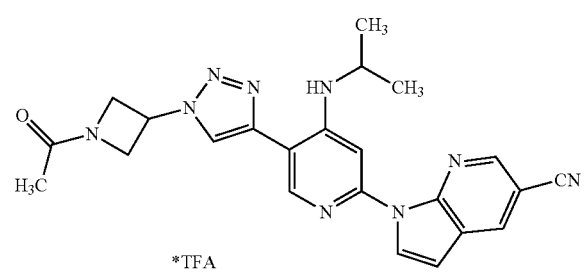<br>Enantiomer 2 | 1.31 | D | 471.3 |

Example 162

1-(5-(1-(1-acetylazetidin-3-yl)-1H-1,2,3-triazol-4-yl)-4-(isopropylamino)pyridin-2-yl)-1H-pyrrolo[2,3-b]pyridine-5-carbonitrile, TFA (162)

*TFA

In a 5 mL microwave vial, a mixture of 1-(3-(4-(6-chloro-4-(isopropylamino) pyridin-3-yl)-1H-1,2,3-triazol-1-yl)azetidin-1-yl)ethanone (31 mg, 0.093 mmol), 1H-pyrrolo[2,3-b]pyridine-5-carbonitrile (19.88 mg, 0.139 mmol), and potassium carbonate (25.6 mg, 0.185 mmol) in DMA (2 mL) was degassed with bubbling nitrogen for 5 minutes, then treated with Xantphos (10.72 mg, 0.019 mmol) and $Pd_2$(dba)$_3$ (8.48 mg, 9.26 μmol). The mixture was degassed for an additional 5 minutes, the vial was sealed, and the reaction mixture was heated via microwave at 140° C. for 30 minutes. LCMS showed that the reaction had not gone to completion, so it was heated via microwave at 140° C. for an additional 30 minutes. LCMS indicated that the reaction had not progressed much further, so heating was stopped. The reaction mixture was allowed to come to room temperature, and the crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 minutes, then a 5-minute hold at 100% B; Flow: 20 mL/min. Fractions containing the desired product were combined and dried via centrifugal evaporation to yield 1-(5-(1-(1-acetylazetidin-3-yl)-1H-1,2,3-triazol-4-yl)-4-(isopropylamino)pyridin-2-yl)-1H-pyrrolo[2,3-b]pyridine-5-carbonitrile, TFA (9 mg, 0.015 mmol, 16.62% yield). LCMS 442.2 (M+H)$^+$, HPLC rt=1.64 min (Conditions C); $^1$H NMR (500 MHz, DMSO-d$_6$) δ 9.07 (br. s., 1H), 8.82 (br. s., 1H), 8.69 (br. s., 1H), 8.58 (br. s., 1H), 8.52 (br. s., 1H), 8.08 (br. s., 1H), 6.90 (br. s., 1H), 5.62 (br. s., 1H), 4.75 (br. s., 1H), 4.55 (br. s., 1H), 4.46 (br. s., 1H), 4.27 (br. s., 1H), 3.91 (br. s., 1H), 1.87 (br. s., 3H), 1.37 (br. s., 6H).

Example 163

1-(4-(isopropylamino)-5-(1-(2-morpholinoethyl)-1H-1,2,3-triazol-4-yl)pyridin-2-yl)-1H-pyrrolo[2,3-b]pyridine-5-carbonitrile, 2TFA (163)

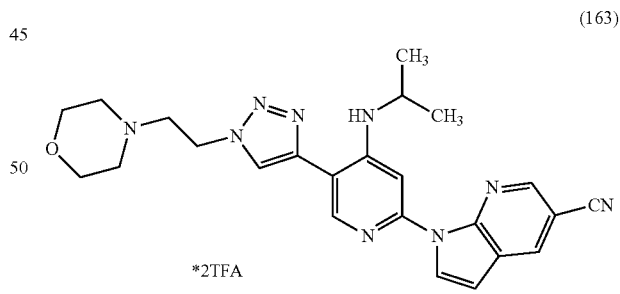

*2TFA

Example 163 was prepared using the conditions described for Example 162, substituting 2-chloro-N-isopropyl-5-(1-(2-morpholinoethyl)-1H-1,2,3-triazol-4-yl)pyridin-4-amine for 1-(3-(4-(6-chloro-4-(isopropylamino)pyridin-3-yl)-1H-1,2,3-triazol-1-yl)azetidin-1-yl)ethanone. LCMS (method C) detected 458.3 (M+H)$^+$, rt=1.87 min. $^1$H NMR (500 MHz, DMSO-d$_6$) δ 8.86-8.79 (m, 2H), 8.68 (d, J=1.8 Hz, 1H), 8.54 (s, 1H), 8.52 (d, J=3.7 Hz, 1H), 8.24 (d, J=6.7 Hz, 1H), 8.11 (s, 1H), 6.90 (d, J=3.7 Hz, 1H), 4.93-4.85 (m, 1H), 3.94-3.87 (m, 1H), 3.79 (br. s., 3H), 3.63 (br. s., 3H), 3.19 (d, J=15.3 Hz, 5H), 1.36 (d, J=6.7 Hz, 6H).

Example 164

1-(4-(isopropylamino)-5-(1-methyl-1H-1,2,3-triazol-4-yl)pyridin-2-yl)-1H-pyrazolo[3,4-b]pyridine-5-carbonitrile

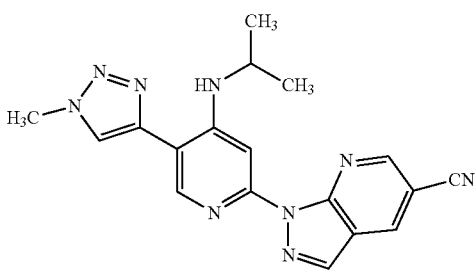

(164)

Intermediate 164A: 2-chloro-N-isopropyl-5-(1-(((trimethylsilyl)methyl)-1H-1,2,3-triazol-4-yl)pyridin-4-amine

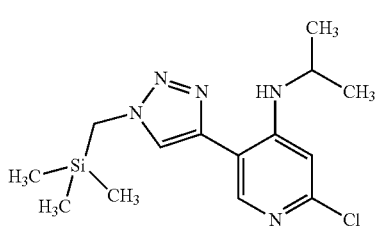

(164A)

2-chloro-N-isopropyl-5-(1-((trimethylsilyl)methyl)-1H-1,2,3-triazol-4-yl)pyridin-4-amine was prepared from 2-chloro-5-ethynyl-N-isopropylpyridin-4-amine and trimethylsilylmethyl azide using the conditions described in Intermediate 10E. LCMS 324.2 (M+H)+.

Intermediate 164B: 2-chloro-N-isopropyl-5-(1-methyl-1H-1,2,3-triazol-4-yl)pyridin-4-amine

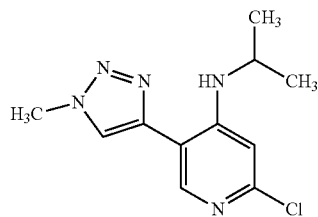

(164B)

A stirring mixture of 2-chloro-N-isopropyl-5-(1-((trimethylsilyl)methyl)-1H-1,2,3-triazol-4-yl)pyridin-4-amine (160 mg, 0.494 mmol) and water (0.018 mL, 0.988 mmol) in THF (5 mL) was cooled to 5° C. and treated with tetrabutylammonium fluoride (1 M solution in THF) (0.593 mL, 0.593 mmol). The reaction mixture was stirred for 1 hour, then allowed to come to warm temperature and stirred for 1 hour, at which point it was judged to be complete by LCMS. The reaction mixture was concentrated in vacuo, and the residue was chromatographed via MPLC over a 12 g silica gel column, eluting with a 0-5% methanol/dichloromethane gradient over 9 column volumes. Fractions containing the desired product were pooled and concentrated in vacuo to yield 2-chloro-N-isopropyl-5-(1-methyl-1H-1,2,3-triazol-4-yl)pyridin-4-amine (84 mg, 67% yield). LCMS 252.1 (M+H)+.

Example 164

Example 164 was prepared from 2-chloro-N-isopropyl-5-(1-methyl-1H-1,2,3-triazol-4-yl)pyridin-4-amine and 1H-pyrazolo[3,4-b]pyridine-5-carbonitrile using the conditions described in Example 10. LCMS 360.2 (M+H)+, HPLC rt=1.49 min (Conditions C); $^1$H NMR (500 MHz, DMSO-$d_6$) δ 9.02 (d, J=1.7 Hz, 1H), 8.98 (d, J=1.7 Hz, 1H), 8.71 (s, 1H), 8.62 (s, 1H), 8.55 (s, 1H), 8.23 (d, J=7.1 Hz, 1H), 7.32 (s, 1H), 4.16 (s, 3H), 3.85 (dq, J=12.8, 6.4 Hz, 1H), 1.30 (d, J=6.1 Hz, 6H).

Example 165

2-(5-chloro-1H-pyrazolo[3,4-b]pyridin-1-yl)-N-isopropyl-5-(1-methyl-1H-1,2,3-triazol-4-yl)pyridin-4-amine

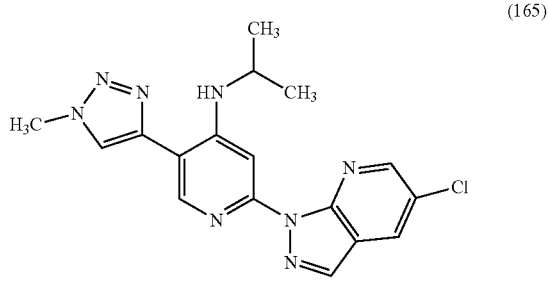 [SMILES: CC(C)Nc1cc(-n2ncc3cc(Cl)cnc32)ncc1-c1cn(C)nn1]

(165)

Example 165 was prepared using the general methods described for Example 164, substituting 5-chloro-1H-pyrazolo[3,4-b]pyridine for 1H-pyrazolo[3,4-b]pyridine-5-carbonitrile. LCMS 369.1 (M+H)+; HPLC rt=1.76 min (Conditions C). $^1$H NMR (500 MHz, DMSO-$d_6$) δ 8.82 (s, 1H), 8.80 (d, J=2.0 Hz, 1H), 8.62 (s, 2H), 8.52 (br. s., 1H), 7.78 (br. s., 1H), 4.18 (s, 3H), 4.01-3.91 (m, 1H), 1.37 (d, J=6.4 Hz, 6H).

Examples 166 and 167

1-(5-(1-(2-fluoropropyl)-1H-1,2,3-triazol-4-yl)-4-(isopropylamino)pyridin-2-yl)-1H-pyrazolo[3,4-b]pyridine-5-carbonitrile, enantiomer 1 (166) and 1-(5-(1-(2-fluoropropyl)-1H-1,2,3-triazol-4-yl)-4-(isopropylamino)pyridin-2-yl)-1H-pyrazolo[3,4-b]pyridine-5-carbonitrile, enantiomer 2 (167)

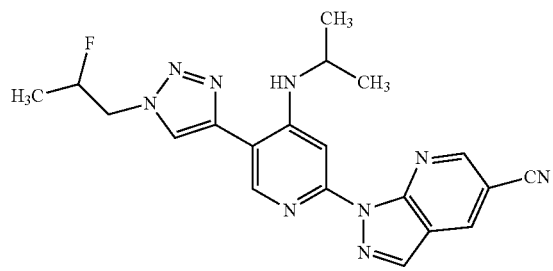

Enantiomer 1 (166)

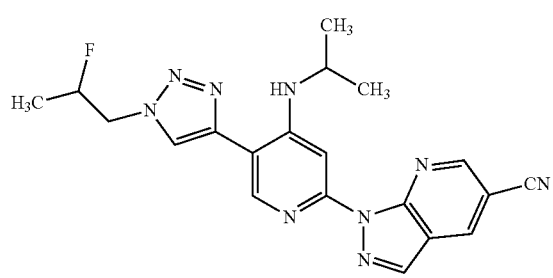

Enantiomer 2 (167)

Intermediates 166A and 167A

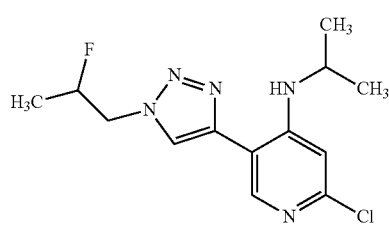

Enantiomer 1 (166A)

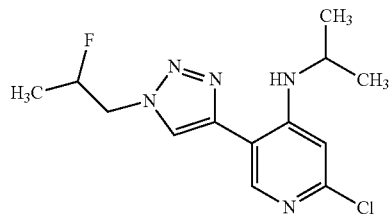

Enantiomer 2 (167A)

Under a nitrogen atmosphere, a stirring solution of 1-(4-(6-chloro-4-(isopropylamino)pyridin-3-yl)-1H-1,2,3-triazol-1-yl)propan-2-ol (prepared from 2-methyloxirane and 2-chloro-5-ethynyl-N-isopropylpyridin-4-amine using the conditions described in Intermediate 63A) (0.26 g, 0.879 mmol) in anhydrous dichloromethane (10 mL) was cooled to −78° C. and treated with diethylaminosulfur trifluoride (0.139 mL, 1.055 mmol). The reaction mixture was stirred at −78° C. for 1 hour, then allowed to come to room temperature and stirred for 1 hour, at which point it was judged to be complete by LCMS. Two drops of methanol were added to quench any residual DAST, then the reaction mixture was washed twice with saturated sodium carbonate, once with water, and once with brine. The organic phase was dried over sodium sulfate and concentrated in vacuo, and the residue was chromatographed via MPLC over a 12 g silica gel column, eluting with a 0-6% methanol/dichloromethane gradient over 19 column volumes. Fractions containing the desired product were pooled and concentrated in vacuo to yield 2-chloro-5-(1-(2-fluoropropyl)-1H-1,2,3-triazol-4-yl)-N-isopropylpyridin-4-amine (0.15 g, 57% yield). LCMS 298.1 (M+H)$^+$. $^1$H NMR (400 MHz, CHLOROFORM-d) δ 8.22 (s, 1H), 8.16 (d, J=6.6 Hz, 1H), 7.97 (d, J=1.3 Hz, 1H), 6.60 (s, 1H), 5.10 (dqd, J=48.4, 6.7, 2.3 Hz, 1H), 4.71 (ddd, J=26.3, 14.5, 2.8 Hz, 1H), 4.62-4.47 (m, 1H), 3.76 (dq, J=13.1, 6.6 Hz, 1H), 1.46 (dd, J=23.4, 6.4 Hz, 3H), 1.36 (d, J=6.4 Hz, 6H).

The enantiomers were resolved by chiral HPLC. Analytical Conditions: Analytical Column: AD-H (0.46×25 cm, 5 μm); BPR pressure: 100 bars; temperature: 35° C.; Flow rate: 3.0 mL/min; Mobile Phase: CO$_2$/MeOH w 0.1% NH$_4$OH (80/20); Detector Wavelength: UV 200-400 nm. Preparative Conditions: Preparative Column: AD-H (5×25 cm, 5 μm, #810291); BPR pressure: 100 bars; temperature: 35° C.; Flow rate: 250 mL/min; Mobile Phase: CO$_2$/MeOH w 0.1% NH$_4$OH (75/25); Detector Wavelength: 220 nm; Separation Program: Stack injection; Injection: 2.5 mL with cycle time 4 mins; Sample preparation: 156 mg in 10 mL MeOH:DCM (1:1), 15.6 mg/mL; Throughput: 585 mg/hr. Fractions containing the first-eluting enantiomer were pooled and concentrated to yield 2-chloro-5-(1-(2-fluoropropyl)-1H-1,2,3-triazol-4-yl)-N-isopropylpyridin-4-amine, enantiomer 1 (62 mg, 79% yield). LCMS 298.3 (M+H)$^+$. Fractions containing the second-eluting enantiomer were pooled and concentrated to yield 2-chloro-5-(1-(2-fluoropropyl)-1H-1,2,3-triazol-4-yl)-N-isopropylpyridin-4-amine, enantiomer 2 (61 mg, 78% yield). LCMS 298.1 (M+H)$^+$.

Example 166

Example 166 was prepared from 2-chloro-5-(1-(2-fluoropropyl)-1H-1,2,3-triazol-4-yl)-N-isopropylpyridin-4-amine, enantiomer 1 and 1H-pyrazolo[3,4-b]pyridine-5-carbonitrile using the conditions described in Example 10. LCMS 406.3 (M+H)$^+$, HPLC rt=1.67 min (Conditions C); $^1$H NMR (500 MHz, DMSO-d$_6$) δ 9.02 (s, 1H), 8.99 (s, 1H), 8.81 (s, 1H), 8.62 (s, 1H), 8.60 (s, 1H), 8.28 (d, J=7.2 Hz, 1H), 7.34 (s, 1H), 5.27-5.06 (m, 1H), 4.87-4.62 (m, 2H), 3.86 (dq, J=12.9, 6.5 Hz, 1H), 1.38 (dd, J=23.9, 6.1 Hz, 3H), 1.32 (d, J=6.2 Hz, 6H).

Example 167

Example 167 was prepared using the conditions described in Example 166, substituting 2-chloro-5-(1-(2-fluoropropyl)-1H-1,2,3-triazol-4-yl)-N-isopropylpyridin-4-amine, enantiomer 2 for 2-chloro-5-(1-(2-fluoropropyl)-1H-1,2,3- triazol-4-yl)-N-isopropylpyridin-4-amine, enantiomer 1. LCMS (method C) detects 406.3 (M+H)+, rt=1.67 min. $^1$H NMR (500 MHz, DMSO-$d_6$) δ 9.02 (s, 1H), 8.99 (s, 1H), 8.81 (s, 1H), 8.62 (s, 1H), 8.60 (s, 1H), 8.28 (d, J=7.2 Hz, 1H), 7.34 (s, 1H), 5.27-5.06 (m, 1H), 4.87-4.62 (m, 2H), 3.86 (dq, J=12.9, 6.5 Hz, 1H), 1.38 (dd, J=23.9, 6.1 Hz, 3H), 1.32 (d, J=6.2 Hz, 6H).

Example 168

(S)-1-(5-(1-(2-amino-3-phenylpropyl)-1H-1,2,3-triazol-4-yl)-4-(isopropylamino)pyridin-2-yl)-1H-pyrazolo[3,4-b]pyridine-5-carbonitrile

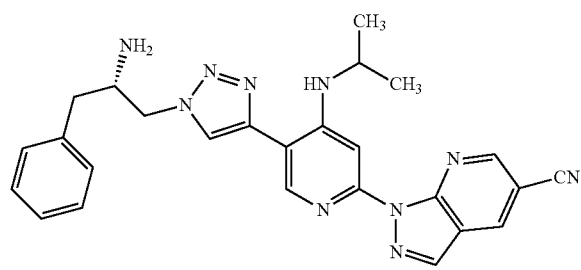
(168)

Intermediate 168A: (S)-2-((tert-butoxycarbonyl)amino)-3-phenylpropyl methanesulfonate

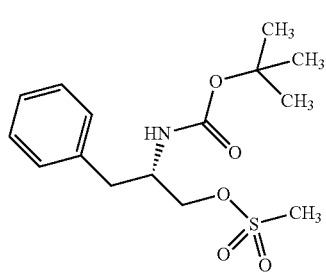
(168A)

In a 2-dram vial, a stirring solution of (S)-tert-butyl(1-hydroxy-3-phenylpropan-2-yl)carbamate (283 mg, 1.126 mmol) and triethylamine (0.314 mL, 2.252 mmol) in dichloromethane (5 mL) was cooled to 5° C. and treated with methanesulfonyl chloride (0.097 mL, 1.239 mmol). The vial was sealed, and the reaction mixture was allowed to come to room temperature and stirred for 3 hours, at which point it was judged to be complete by LCMS. The solvent was evaporated with a stream of nitrogen, and the residue was taken up in ethyl acetate (10 mL). The turbid solution was washed once with water, twice with 1 N sodium hydroxide, twice with 1 N HCl, and once with brine, then the organic phase was dried over sodium sulfate and concentrated in vacuo to yield (S)-2-((tert-butoxycarbonyl)amino)-3-phenylpropyl methanesulfonate (290 mg, 78% yield) as a colorless solid. LCMS 229.9 (M-Boc+H)+.

Intermediate 168B: (S)-tert-Butyl (1-azido-3-phenylpropan-2-yl)carbamate

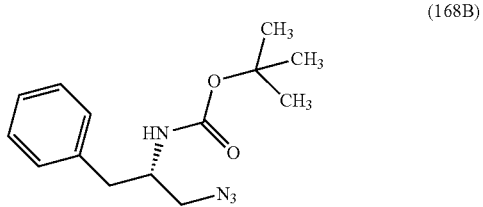 [SMILES: CC(C)(C)OC(=O)N[C@H](CN=[N+]=[N-])Cc1ccccc1]
(168B)

In a sealed vial, a stirring mixture of (S)-2-((tert-butoxycarbonyl)amino)-3-phenylpropyl methanesulfonate (290 mg, 0.880 mmol) and sodium azide (68.7 mg, 1.056 mmol) in anhydrous DMF (2 mL) was stirred at 80° C. for 3 hours, at which point the reaction was judged to be complete by LCMS. The mixture was concentrated in vacuo, and the residue was taken up in ethyl acetate (15 mL). The turbid solution was washed once with water, and 3× with 10% lithium chloride solution, then dried over sodium sulfate and concentrated in vacuo to yield 223 mg of a colorless oil. The residue was chromatographed via MPLC over a 24 g silica gel column, eluting at 40 mL/min with a 0% to 100% ethyl acetate/hexanes gradient over 10 column volumes. Fractions containing the desired product were pooled and concentrated in vacuo to yield (S)-tert-butyl (1-azido-3-phenylpropan-2-yl)carbamate (130 mg, 53% yield) as a colorless oil. $^1$H NMR (400 MHz, CHLOROFORM-d) δ 7.37-7.30 (m, 2H), 7.28-7.18 (m, 3H), 4.66 (br. s., 1H), 3.99 (br. s., 1H), 3.51-3.40 (m, 1H), 3.38-3.26 (m, 1H), 2.98-2.85 (m, 1H), 2.85-2.75 (m, 1H), 1.45 (s, 9H).

Intermediate 168C: (S)-tert-butyl (1-(4-(6-chloro-4-(isopropylamino)pyridin-3-yl)-1H-1,2,3-triazol-1-yl)-3-phenylpropan-2-yl)carbamate

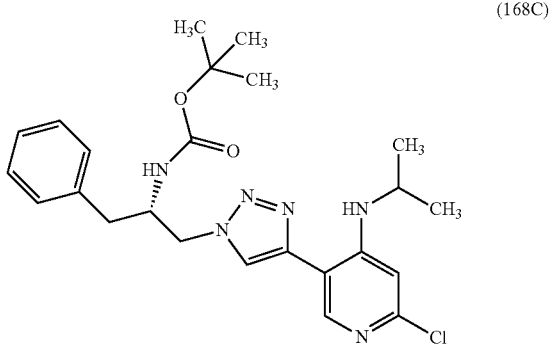 [SMILES: CC(C)Nc1cc(Cl)ncc1-c1cn(C[C@H](Cc2ccccc2)NC(=O)OC(C)(C)C)nn1]
(168C)

(S)-tert-butyl (1-(4-(6-chloro-4-(isopropylamino)pyridin-3-yl)-1H-1,2,3-triazol-1-yl)-3-phenylpropan-2-yl)carbamate was prepared from (S)-tert-butyl (1-azido-3-phenylpropan-2-yl)carbamate and 2-chloro-5-ethynyl-N-isopropylpyridin-4-amine using the conditions described in Intermediate 10E. LCMS 471.2 (M+H)+.

155

Intermediate 168D: (S)-tert-butyl (1-(4-(6-(5-cyano-1H-pyrazolo[3,4-b]pyridin-1-yl)-4-(isopropylamino)pyridin-3-yl)-1H-1,2,3-triazol-1-yl)-3-phenylpropan-2-yl)carbamate

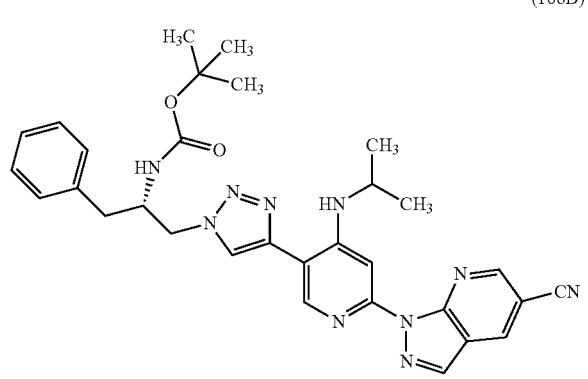

(168D)

(S)-tert-butyl (1-(4-(6-(5-cyano-1H-pyrazolo[3,4-b]pyridin-1-yl)-4-(isopropylamino)pyridin-3-yl)-1H-1,2,3-triazol-1-yl)-3-phenylpropan-2-yl)carbamate was prepared (S)-tert-butyl (1-(4-(6-chloro-4-(isopropylamino)pyridin-3-yl)-1H-1,2,3-triazol-1-yl)-3-phenylpropan-2-yl)carbamate and 1H-pyrazolo[3,4-b]pyridine-5-carbonitrile using the conditions described in Example 10. LCMS 579.3 (M+H)$^+$.

Example 168

(S)-tert-butyl (1-(4-(6-(5-cyano-1H-pyrazolo[3,4-b]pyridin-1-yl)-4-(isopropylamino)pyridin-3-yl)-1H-1,2,3-triazol-1-yl)-3-phenylpropan-2-yl)carbamate (45 mg, 0.078 mmol) was dissolved in 1:1 TFA/dichloromethane (3 mL), and the reaction mixture was stirred at room temperature for 1 hour, at which point it was judged to be complete by LCMS. The reaction mixture was concentrated in vacuo, and the residue was concentrated twice from dichloromethane to remove residual TFA. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-100% B over 20 minutes, then a 5-minute hold at 100% B; Flow: 20 mL/min. Fractions containing the desired product were combined and dried via centrifugal evaporation to yield (S)-1-(5-(1-(2-amino-3-phenylpropyl)-1H-1,2,3-triazol-4-yl)-4-(isopropylamino)pyridin-2-yl)-1H-pyrazolo[3,4-b]pyridine-5-carbonitrile, 2 TFA (25 mg, 45% yield). LCMS 479.3 (M+H)$^+$, HPLC rt=1.14 min (Conditions D); $^1$H NMR (500 MHz, DMSO-$d_6$) δ 9.05 (br. s., 1H), 9.02 (s, 1H), 8.75 (s, 1H), 8.65 (br. s., 1H), 8.57 (br. s., 1H), 8.30-8.16 (m, 2H), 7.46-7.27 (m, 6H), 4.67 (br. s., 2H), 4.08 (br. s., 1H), 3.90 (s, 1H), 3.07-2.92 (m, 2H), 1.32 (d, J=6.1 Hz, 6H).

Example 169

(R)-1-(5-(1-(2-amino-3-phenylpropyl)-1H-1,2,3-triazol-4-yl)-4-(isopropylamino)pyridin-2-yl)-1H-pyrazolo[3,4-b]pyridine-5-carbonitrile

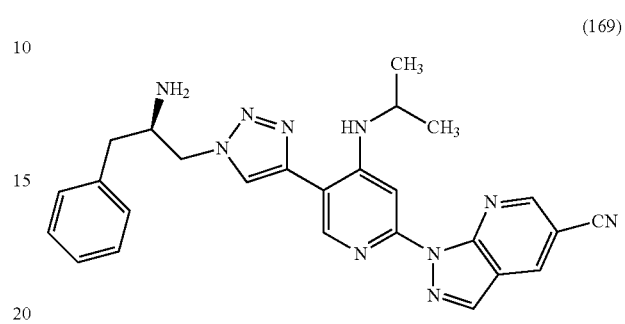

(169)

Example 169 was prepared according to the general methods described in Example 168, substituting (R)-tert-butyl (1-hydroxy-3-phenylpropan-2-yl)carbamate for (S)-tert-butyl (1-hydroxy-3-phenylpropan-2-yl)carbamate. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 10-minute hold at 100% B; Flow: 20 mL/min. Fractions containing the desired product were combined and dried via centrifugal evaporation to yield the title compound. LCMS 479.3 (M+H)$^+$, HPLC rt=1.75 min (conditions C); $^1$H NMR (500 MHz, DMSO-$d_6$) δ 9.04 (s, 1H), 9.01 (s, 1H), 8.78 (s, 1H), 8.63 (s, 1H), 8.59 (s, 1H), 8.29 (d, J=7.1 Hz, 1H), 7.40-7.22 (m, 6H), 4.57-4.47 (m, 1H), 4.42 (dd, J=13.8, 7.7 Hz, 1H), 3.87 (dq, J=12.6, 6.5 Hz, 1H), 2.87-2.78 (m, 1H), 2.77-2.69 (m, 1H), 1.32 (d, J=6.0 Hz, 6H).

Example 170

1-(4-(isopropylamino)-5-(1-(2-oxopropyl)-1H-1,2,3-triazol-4-yl)pyridin-2-yl)-1H-pyrazolo[3,4-b]pyridine-5-carbonitrile

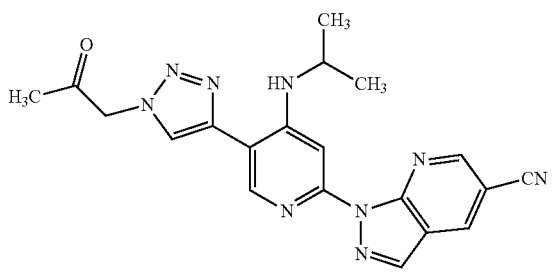

(170)

In a 2-dram vial, a stirring suspension of (S)-1-(5-(1-(2-hydroxypropyl)-1H-1,2,3-triazol-4-yl)-4-(isopropylamino)pyridin-2-yl)-1H-pyrazolo[3,4-b]pyridine-5-carbonitrile (40 mg, 0.099 mmol) in dichloromethane (2 mL) was treated with Dess-Martin Periodinane (63.1 mg, 0.149 mmol). The vial was filled with nitrogen and sealed, and the reaction mixture was stirred at room temperature for 1 hour, at which point it was judged to be complete by LCMS. Saturated sodium bicarbonate (0.5 mL) was added, and the mixture was stirred until gas evolution had ceased. The layers were separated, the aqueous phase was extracted twice with dichloromethane (1 mL), then the combined organic phases were dried over sodium sulfate and concentrated in vacuo. The residue was chromatographed via MPLC over a 24 g silica gel column, eluting at 40 mL/min with 2% then 4% methanol/dichloromethane. Fractions containing the desired product were pooled and concentrated in vacuo. The residue was taken up in dichloromethane (5 mL), and the solution was washed twice with 1 M NaOH (1 mL) and once with brine. The combined aqueous phases were extracted once with dichloromethane (2 mL), and the combined dichloromethane phases were dried over sodium sulfate and concentrated in vacuo. The residue was chromatographed via MPLC over a 24 g silica gel column, eluting at 40 mL/min with 2% then 3.5% methanol/dichloromethane. Fractions containing the desired product were pooled and concentrated in vacuo to yield 1-(4-(isopropylamino)-5-(1-(2-oxopropyl)-1H-1,2,3-triazol-4-yl)pyridin-2-yl)-1H-pyrazolo[3,4-b]pyridine-5-carbonitrile (17 mg, 42% yield) as a colorless solid. LCMS 402.1 (M+H)$^+$, HPLC rt=5.80 min (conditions A). $^1$H NMR (400 MHz, chloroform-d) δ 8.96 (d, J=2.2 Hz, 1H), 8.55 (s, 1H), 8.51 (d, J=2.0 Hz, 1H), 8.38 (s, 1H), 8.25 (d, J=7.0 Hz, 1H), 7.98 (s, 1H), 7.56 (s, 1H), 5.34 (s, 2H), 3.96 (dq, J=13.0, 6.5 Hz, 1H), 2.36 (s, 3H), 1.43 (d, J=6.4 Hz, 6H).

Example 171

1-(5-(1-(3-aminopropyl)-1H-1,2,3-triazol-4-yl)-4-(isopropylamino)pyridin-2-yl)-1H-pyrazolo[3,4-b]pyridine-5-carbonitrile (171)

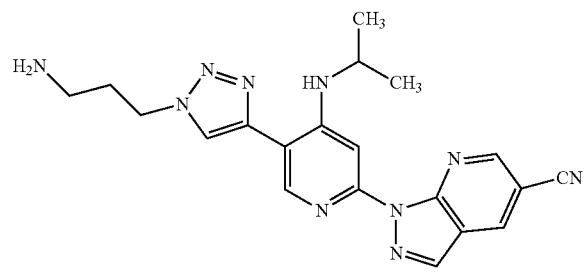

In a sealed vial, a stirring solution of sodium azide (43.0 mg, 0.662 mmol) and tert-butyl (3-bromopropyl)carbamate (158 mg, 0.662 mmol) in DMF (0.2 mL) was heated at 80° C. for 16 hours, then allowed to come to room temperature. The mixture was filtered and transferred to a vial containing a mixture of 1-(5-ethynyl-4-(isopropylamino) pyridin-2-yl)-1H-pyrazolo[3,4-b]pyridine-5-carbonitrile (40 mg, 0.132 mmol), sodium ascorbate (5.24 mg, 0.026 mmol) and 1:1 tBuOH/water (1 mL). This mixture was treated with copper (II) sulfate (2.112 mg, 0.013 mmol), the vial was sealed, and the reaction mixture was stirred at 50° C. for 40 minutes, then at room temperature for 3 hours at which time it was judged to be complete by LCMS. The reaction mixture was concentrated in vacuo, and the residue was taken up in dichloromethane (3 mL). The solution was filtered, then treated with TFA (2 mL). The reaction mixture was stirred at room temperature for 1 hour, at which point it was judged to be complete by LCMS. The mixture was concentrated in vacuo, and the residue was concentrated 3× from dichloromethane to remove residual TFA. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the desired product were combined and dried via centrifugal evaporation to yield 1-(5-(1-(3-aminopropyl)-1H-1,2,3-triazol-4-yl)-4-(isopropylamino)pyridin-2-yl)-1H-pyrazolo[3,4-b]pyridine-5-carbonitrile (20 mg, 0.048 mmol, 36.1% yield). NMR and LCMS are consistent with the expected product. LCMS 403.3 (M+H)$^+$; HPLC rt=1.15 min (Conditions C); $^1$H NMR (500 MHz, DMSO-d$_6$) δ 9.05 (br. s., 1H), 9.03 (s, 1H), 8.85 (br. s., 1H), 8.64 (br. s., 2H), 8.33 (d, J=6.7 Hz, 1H), 7.34 (br. s., 1H), 4.73-4.41 (m, 2H), 3.92-3.82 (m, 1H), 3.46 (br. s., 1H), 2.06 (br. s., 4H), 1.32 (d, J=6.2 Hz, 6H).

Example 172

1-(5-(1-(2-aminoethyl)-1H-1,2,3-triazol-4-yl)-4-(isopropylamino)pyridin-2-yl)-1H-pyrazolo[3,4-b]pyridine-5-carbonitrile (172)

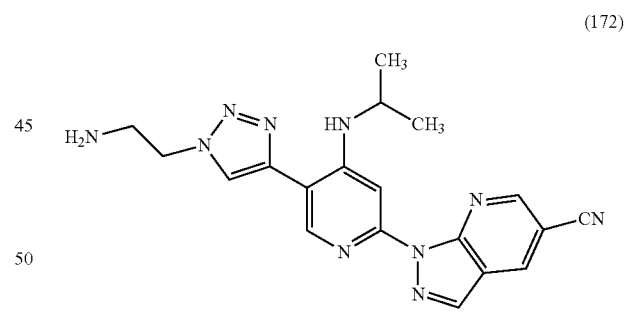

Example 172 was prepared using the conditions described in Example 171, substituting tert-butyl (2-bromoethyl)carbamate for tert-butyl (3-bromopropyl)carbamate. LCMS 403.3 (M+H)$^+$, HPLC rt=1.15 min (Conditions C); $^1$H NMR (500 MHz, DMSO-d$_6$) δ 9.05 (br. s., 1H), 9.02 (s, 1H), 8.82 (br. s., 1H), 8.64 (br. s., 2H), 8.31 (d, J=6.9 Hz, 1H), 7.34 (br. s., 1H), 4.53 (br. s., 2H), 3.90-3.82 (m, 1H), 1.92 (br. s., 2H), 1.32 (d, J=6.2 Hz, 6H).

In Table 10, Examples 173 and 174 were prepared from 1-(5-ethynyl-4-(isopropylamino)pyridin-2-yl)-1H-pyrazolo[3,4-b]pyridine-5-carbonitrile and the appropriate arylboronic acid using a procedure described in Tetrahedron Letters 48 (2007) 3525-3529. Example 175 was isolated as a side-product from the reaction that produced Example 173.

TABLE 10

| Ex. No. | Structure | HPLC rt (min) | HPLC cond. | LCMS |
|---|---|---|---|---|
| 173 | 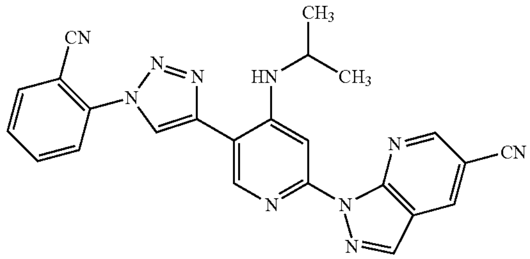 [SMILES: CC(C)Nc1cc(-n2ncc3cc(C#N)cnc32)ncc1-c1cn(-c2ccccc2C#N)nn1] | 1.79 | C | 447.3 |
| 174 | 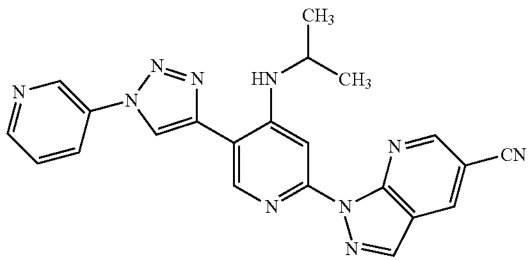 [SMILES: CC(C)Nc1cc(-n2ncc3cc(C#N)cnc32)ncc1-c1cn(-c2cccnc2)nn1] | 1.63 | C | 423.1 |
| 175 | 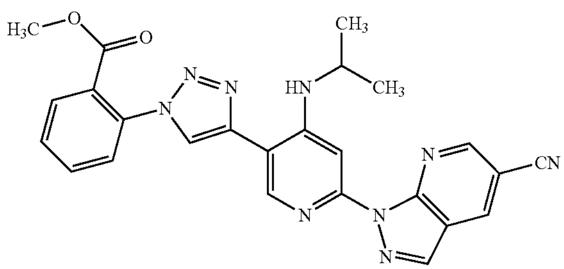 [SMILES: COC(=O)c1ccccc1-n1cc(-c2cnc(-n3ncc4cc(C#N)cnc43)cc2NC(C)C)nn1] | 1.83 | | 480.3 |

Example 176

(3R,4S)-tert-butyl 4-(4-(6-(5-cyano-1H-pyrazolo[3,4-b]pyridin-1-yl)-4-(isopropylamino)pyridin-3-yl)-1H-1,2,3-triazol-1-yl)-3-hydroxypiperidine-1-carboxylate (176)

Intermediate 176A: (3R,4S)-tert-butyl 4-(4-(6-chloro-4-(isopropylamino)pyridin-3-yl)-1H-1,2,3-triazol-1-yl)-3-hydroxypiperidine-1-carboxylate (176A)

In a sealed vial, a mixture of (3R,4S)-4-azidopiperidin-3-ol (146 mg, 1.027 mmol) (WO 2005/066176), 2-chloro-5-ethynyl-N-isopropylpyridin-4-amine (200 mg, 1.027 mmol), 1 M sodium ascorbate solution (30.5 mg, 0.154 mmol), and copper(II) sulfate (8.20 mg, 0.051 mmol) was stirred at room temperature for 24 hours, at which point the reaction was judged to be complete by LCMS. The mixture was poured into ethyl acetate (100 mL), and the turbid solution was washed twice with water and once with brine. The organic phase was dried over sodium sulfate and concentrated in vacuo to afford 395 mg of an amber solid. LCMS 337.3 (M+H)$^+$. The residue was dissolved in dichloromethane, and the solution was treated with triethylamine (0.196 mL, 1.407 mmol) and BOC-Anhydride (0.300 mL, 1.290 mmol). The reaction mixture was stirred at room temperature for 18 hours, at which point it was judged to be complete by LCMS. The reaction mixture was concentrated in vacuo, and the residue was chromatographed via MPLC over a 40 g silica gel column, eluting at 40 mL/min with 0-10% methanol/methylene chloride. The product eluted in 5% methanol. Fractions containing the desired product were pooled and concentrated in vacuo to yield (3R,4S)-tert-butyl 4-(4-(6-chloro-4-(isopropylamino)pyridin-3-yl)-1H-1,2,3-triazol-1-yl)-3-hydroxypiperidine-1-carboxylate (411 mg, 80% yield) as an off-white solid. LCMS 437.3 (M+H)$^+$.

Example 176

Example 176 was prepared from (3R,4S)-tert-butyl 4-(4-(6-chloro-4-(isopropylamino)pyridin-3-yl)-1H-1,2,3-triazol-1-yl)-3-hydroxypiperidine-1-carboxylate and 1H-pyrazolo[3,4-b]pyridine-5-carbonitrile using the conditions described in Example 10. LCMS 545.3 (M+H)$^+$, HPLC rt=1.77 min (Conditions C); $^1$H NMR (500 MHz, DMSO-d$_6$) δ 9.04 (s, 1H), 9.01 (d, J=1.7 Hz, 1H), 8.85 (s, 1H), 8.65 (s, 1H), 8.63 (s, 1H), 8.41 (d, J=6.7 Hz, 1H), 7.33 (s, 1H), 4.89 (d, J=10.8 Hz, 1H), 4.23-3.95 (m, 3H), 3.88 (dt, J=13.0, 6.8 Hz, 1H), 3.26-2.87 (m, 2H), 2.46-2.35 (m, 1H), 1.91 (d, J=8.8 Hz, 1H), 1.43 (br. s., 9H), 1.32 (dd, J=6.1, 2.7 Hz, 6H).

Example 177

1-(5-(1-((3R,4S)-3-hydroxypiperidin-4-yl)-1H-1,2,3-triazol-4-yl)-4-(isopropylamino)pyridin-2-yl)-1H-pyrazolo[3,4-b]pyridine-5-carbonitrile

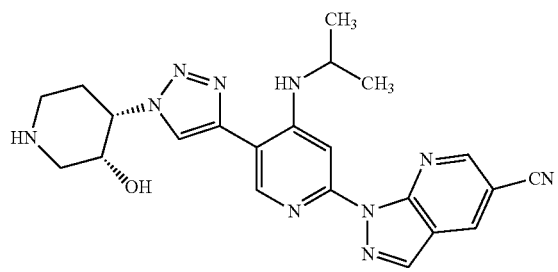

(177)

A stirring solution of (3R,4S)-tert-butyl 4-(4-(6-(5-cyano-1H-pyrazolo[3,4-b]pyridin-1-yl)-4-(isopropylamino)pyridin-3-yl)-1H-1,2,3-triazol-1-yl)-3-hydroxypiperidine-1-carboxylate (250 mg, 0.459 mmol) in dichloromethane (1 mL) was treated with TFA (1 mL, 12.98 mmol). The reaction mixture was stirred at room temperature for 30 minutes, at which point it was judged to be complete by LCMS. The reaction mixture was concentrated in vacuo, and the residue was concentrated twice from dichloromethane, once from isopropanol, and once from methanol to remove residual TFA. A portion of the crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min. Fractions containing the desired product were combined and dried via centrifugal evaporation to yield 1-(5-(1-((3R,4S)-3-hydroxypiperidin-4-yl)-1H-1,2,3-triazol-4-yl)-4-(isopropylamino)pyridin-2-yl)-1H-pyrazolo[3,4-b]pyridine-5-carbonitrile. LCMS 445.3 (M+H)$^+$; HPLC rt=1.22 min (Conditions C); $^1$H NMR (500 MHz, DMSO-d$_6$) δ 9.04 (s, 1H), 9.02 (s, 1H), 8.78 (s, 1H), 8.66 (br. s., 1H), 8.63 (s, 1H), 8.39 (d, J=7.1 Hz, 1H), 7.32 (s, 1H), 4.82 (d, J=11.8 Hz, 1H), 3.97 (br. s., 1H), 3.93-3.80 (m, 1H), 3.20-3.06 (m, 1H), 3.04-2.94 (m, 1H), 2.90 (s, 1H), 2.74 (br. s., 1H), 2.42-2.28 (m, 1H), 1.99-1.80 (m, 3H), 1.32 (dd, J=5.9, 3.2 Hz, 6H).

Example 178

1-(5-(1-((3R,4S)-1-acetyl-3-hydroxypiperidin-4-yl)-1H-1,2,3-triazol-4-yl)-4-(isopropylamino)pyridin-2-yl)-1H-pyrazolo[3,4-b]pyridine-5-carbonitrile

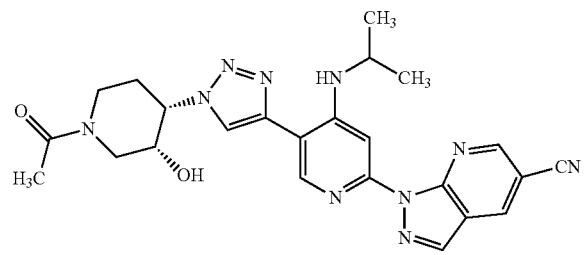

(178)

In a 1-dram vial, a stirring mixture of 1-(5-(1-((3R,4S)-3-hydroxypiperidin-4-yl)-1H-1,2,3-triazol-4-yl)-4-(isopropylamino)pyridin-2-yl)-1H-pyrazolo[3,4-b]pyridine-5-carbonitrile, 2 TFA (25 mg, 0.037 mmol) and triethylamine (0.021 mL, 0.149 mmol) in dichloromethane (0.5 mL) was treated with acetic anhydride (3.86 μl, 0.041 mmol). The vial was sealed, and the reaction mixture was stirred at room temperature for 1 hour, at which point it was judged to be complete by LCMS. The solvent was evaporated with a stream of nitrogen, and the crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 12-52% B over 20 minutes, then a 5-minute hold at 100% B; Flow: 20 mL/min. Fractions containing the desired product were combined and dried via centrifugal evaporation to yield 1-(5-(1-((3R,4S)-1-acetyl-3-hydroxypiperidin-4-yl)-1H-1,2,3-triazol-4-yl)-4-(isopropylamino) pyridin-2-yl)-1H-pyrazolo[3,4-b]pyridine-5-carbonitrile (9 mg, 0.018 mmol, 49.8% yield). LCMS 487.2 (M+H)$^+$; HPLC rt=1.29 min (Conditions C); $^1$H NMR (500 MHz, DMSO-d$_6$) δ 9.06 (s, 1H), 9.03 (s, 1H), 8.87 (br. s., 1H), 8.66 (s, 2H), 8.51 (br. s., 1H), 7.40 (br. s., 1H), 4.99 (d, J=11.1 Hz, 1H), 4.65-4.38 (m, 1H), 4.18-3.79 (m, 3H), 3.55-3.24 (m, 2H (partially suppressed), 2.79 (t, J=12.6 Hz, 1H), 2.40-2.25 (m, 1H), 2.18-1.86 (m, 4H), 1.33 (d, J=2.0 Hz, 6H).

The Examples in Table 11 were prepared using the general methods outlined for Examples 176-178, substituting the appropriate azidopiperidin-ol for (3R,4S)-4-azidopiperidin-3-ol, and the appropriate acid chloride, chloroformate, anhydride, or sulfonyl chloride for acetic anhydride. Example 182 was isolated as a side-product from the reaction that produced Example 181. Example 187 was isolated as a side-product from the reaction that produced Example 186.

TABLE 11

| Ex. No. | Structure | HPLC rt (min) | HPLC cond. | LCMS |
|---|---|---|---|---|
| 179 | 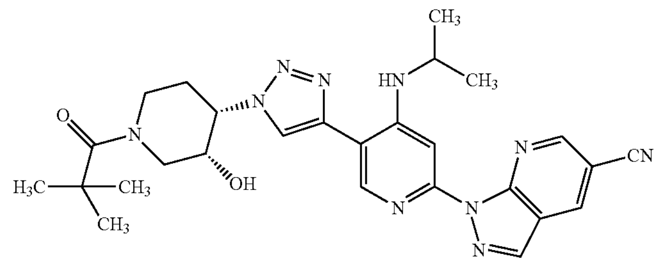 [SMILES: CC(C)Nc1cc(-n2ncc3cc(C#N)cnc32)ncc1-c1cn([C@H]2CCN(C(=O)C(C)(C)C)C[C@H]2O)nn1] | 1.59 | C | 529.3 |
| 180 | 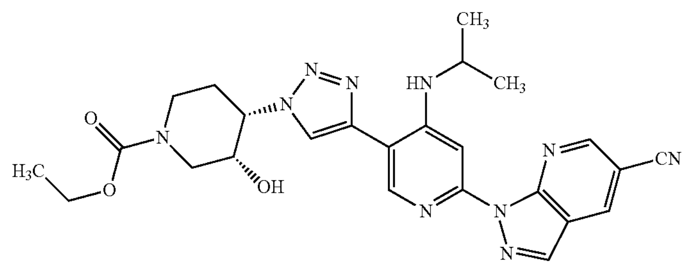 [SMILES: CCOC(=O)N1CC[C@H](n2cc(-c3cnc(-n4ncc5cc(C#N)cnc54)cc3NC(C)C)nn2)[C@H](O)C1] | 1.54 | C | 517.3 |
| 181 | 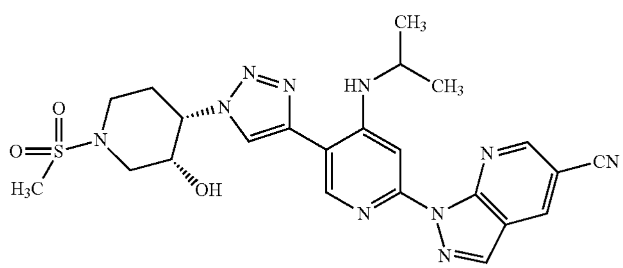 [SMILES: CC(C)Nc1cc(-n2ncc3cc(C#N)cnc32)ncc1-c1cn([C@H]2CCN(S(C)(=O)=O)C[C@H]2O)nn1] | 1.37 | C | 523.3 |
| 182 | 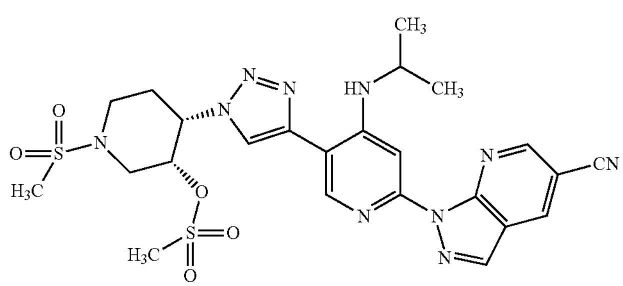 [SMILES: CC(C)Nc1cc(-n2ncc3cc(C#N)cnc32)ncc1-c1cn([C@H]2CCN(S(C)(=O)=O)C[C@H]2OS(C)(=O)=O)nn1] | 1.46 | C | 601.2 |
| 183 | 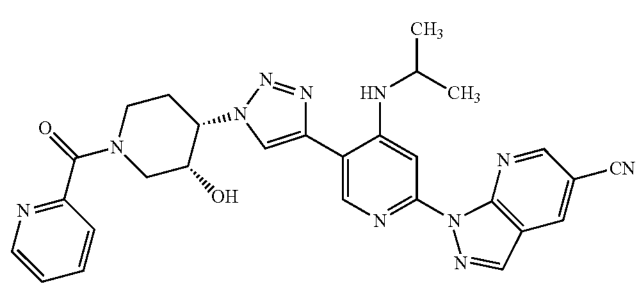 [SMILES: CC(C)Nc1cc(-n2ncc3cc(C#N)cnc32)ncc1-c1cn([C@H]2CCN(C(=O)c3ccccn3)C[C@H]2O)nn1] | 1.34 | C | 550.3 |

TABLE 11-continued
| Ex. No. | Structure | HPLC rt (min) | HPLC cond. | LCMS |
|---|---|---|---|---|
| 184 | 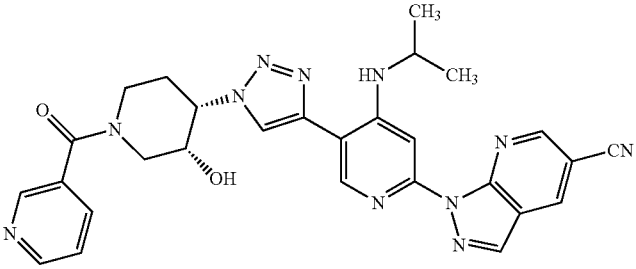 [SMILES: CC(C)Nc1cc(-n2ncc3cc(C#N)cnc32)ncc1-c1cn([C@H]2CCN(C(=O)c3cccnc3)C[C@H]2O)nn1] | 1.40 | C | 550.3 |
| 185 | 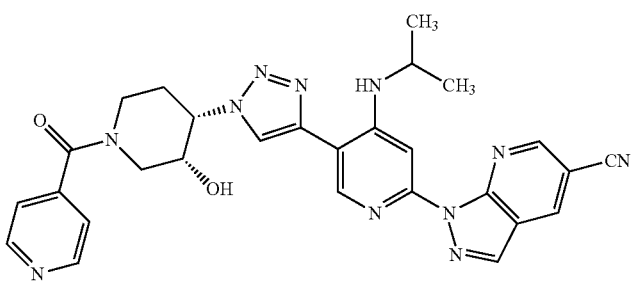 [SMILES: CC(C)Nc1cc(-n2ncc3cc(C#N)cnc32)ncc1-c1cn([C@H]2CCN(C(=O)c3ccncc3)C[C@H]2O)nn1] | 1.42 | C | 550.4 |
| 186 | 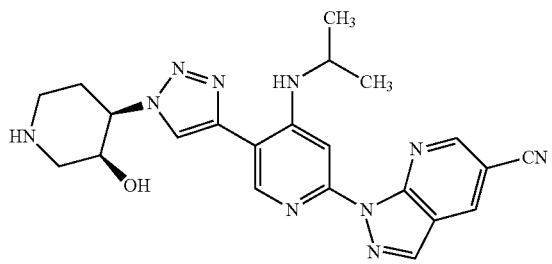 [SMILES: CC(C)Nc1cc(-n2ncc3cc(C#N)cnc32)ncc1-c1cn([C@@H]2CCNC[C@@H]2O)nn1] | 1.23 | C | 445.3 |
| 187 | 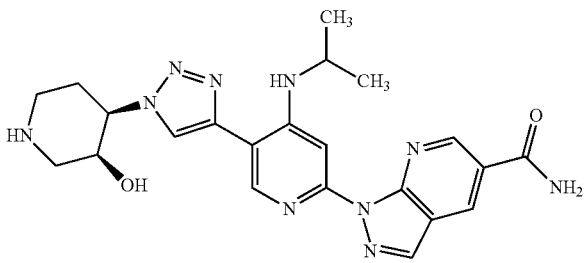 [SMILES: CC(C)Nc1cc(-n2ncc3cc(C(N)=O)cnc32)ncc1-c1cn([C@@H]2CCNC[C@@H]2O)nn1] | 0.83 | C | 463.3 |
| 188 | 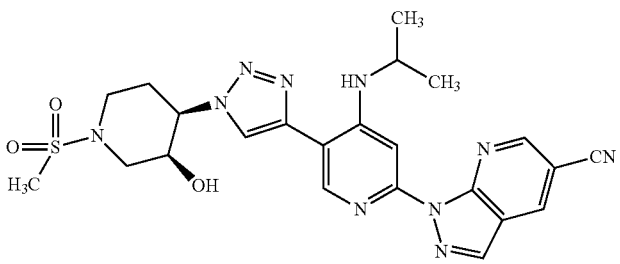 [SMILES: CC(C)Nc1cc(-n2ncc3cc(C#N)cnc32)ncc1-c1cn([C@@H]2CCN(S(C)(=O)=O)C[C@@H]2O)nn1] | 1.36 | C | 523.3 |

TABLE 11-continued

| Ex. No. | Structure | HPLC rt (min) | HPLC cond. | LCMS |
|---|---|---|---|---|
| 189 | 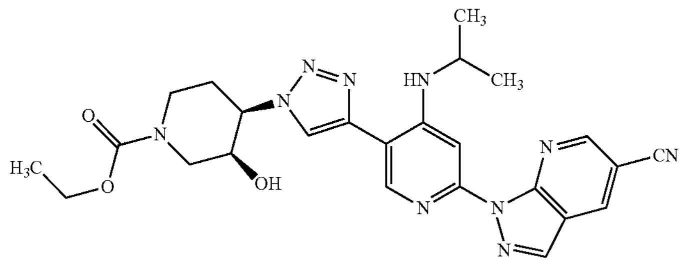 [SMILES: CCOC(=O)N1CC[C@@H](n2cc(-c3cnc(-n4ncc5cc(C#N)cnc54)cc3NC(C)C)nn2)[C@@H](O)C1] | 1.64 | C | 517.4 |
| 190 | 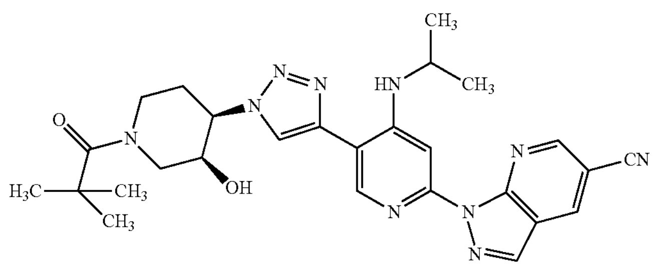 [SMILES: CC(C)Nc1cc(-n2ncc3cc(C#N)cnc32)ncc1-c1cn([C@@H]2CCN(C(=O)C(C)(C)C)C[C@@H]2O)nn1] | 1.64 | C | 516.2 |
| 191 | 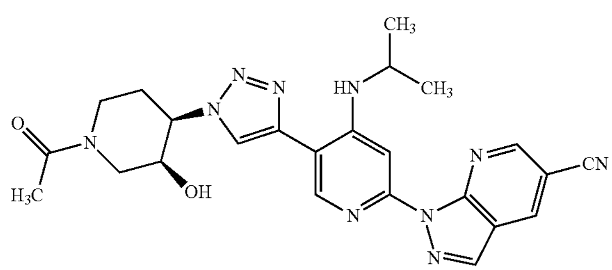 [SMILES: CC(=O)N1CC[C@@H](n2cc(-c3cnc(-n4ncc5cc(C#N)cnc54)cc3NC(C)C)nn2)[C@@H](O)C1] | 1.29 | C | 487.3 |
| 192 | 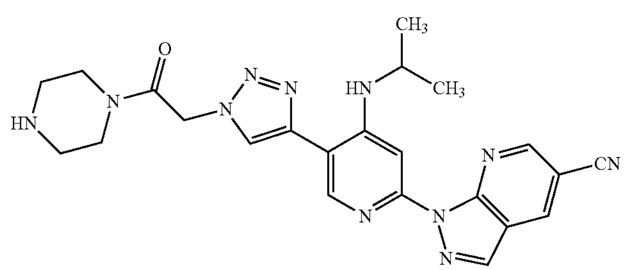 [SMILES: CC(C)Nc1cc(-n2ncc3cc(C#N)cnc32)ncc1-c1cn(CC(=O)N2CCNCC2)nn1] | 1.12 | C | 472.2 |
| 193 | 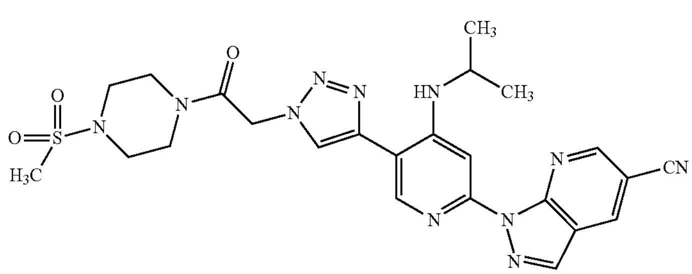 [SMILES: CC(C)Nc1cc(-n2ncc3cc(C#N)cnc32)ncc1-c1cn(CC(=O)N2CCN(S(C)(=O)=O)CC2)nn1] | 1.37 | C | 550.1 |

TABLE 11-continued
| Ex. No. | Structure | HPLC rt (min) | HPLC cond. | LCMS |
|---|---|---|---|---|
| 194 | 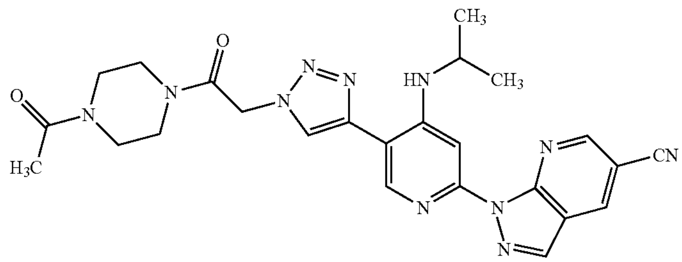 [SMILES: CC(=O)N1CCN(C(=O)Cn2cc(-c3cnc(-n4ncc5cc(C#N)cnc54)cc3NC(C)C)nn2)CC1] | 1.27 | C | 514.2 |
| 195 | 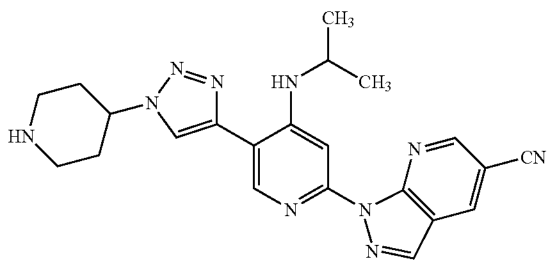 [SMILES: CC(C)Nc1cc(-n2ncc3cc(C#N)cnc32)ncc1-c1cn(C2CCNCC2)nn1] | 1.27 | C | 429.3 |
| 196 | 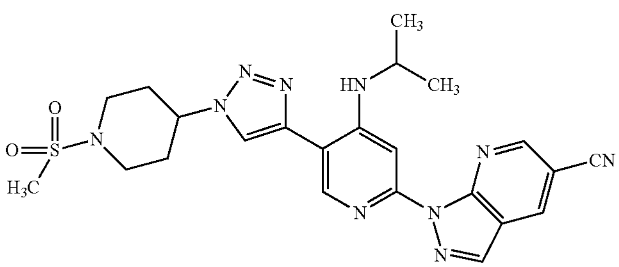 [SMILES: CC(C)Nc1cc(-n2ncc3cc(C#N)cnc32)ncc1-c1cn(C2CCN(S(C)(=O)=O)CC2)nn1] | 1.68 | C | 507.3 |
Example 197
1-(5-(1-((trans)-1-acetyl-3-hydroxypiperidin-4-yl)-1H-1,2,3-triazol-4-yl)-4-(isopropylamino)pyridin-2-yl)-1H-pyrazolo[3,4-b]pyridine-5-carbonitrile, isomer 1
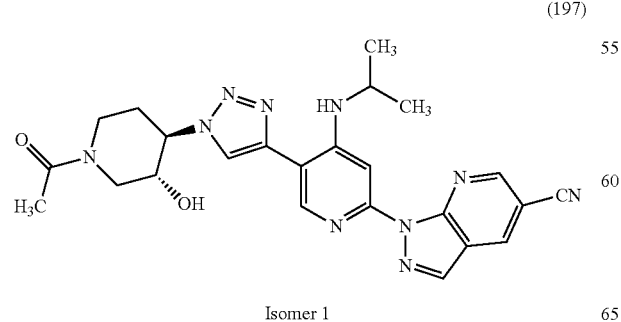
(197)
Isomer 1
Intermediates 197A and 197B: (3R,4R)-tert-butyl 4-azido-3-hydroxypiperidine-1-carboxylate (197A) and (3S,4S)-tert-butyl 3-azido-4-hydroxypiperidine-1-carboxylate (197B)
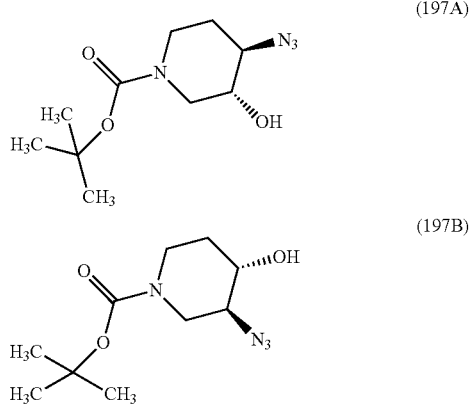

(1.1 g, 5.52 mmol) in DMF (7 mL) was treated with a solution of sodium azide (0.538 g, 8.28 mmol) in 1:1 acetone/water (7 mL). The vial was sealed, and the reaction mixture was heated to 80° C. and stirred for 18 hours. The mixture was concentrated in vacuo, and the residue was taken up in ethyl acetate (20 mL). The turbid solution was washed once with water and 3× with 10% lithium chloride solution, then the organic phase was dried over sodium sulfate and concentrated in vacuo. The residue was chromatographed via MPLC over a 80 g silica gel column, eluting at 60 mL/min with a 10% to 40% acetone/hexanes gradient over 13 column volumes. Fractions containing the first-eluting product were pooled and concentrated in vacuo to yield (trans)-tert-butyl 4-azido-3-hydroxypiperidine-1-carboxylate, Intermediate 197A (0.70 g, 52% yield) as a colorless oil. $^1$H NMR (400 MHz, chloroform-d) δ 4.18-4.10 (m, 1H), 4.00 (br. s., 1H), 3.53 (br. s., 1H), 3.45-3.36 (m, 1H), 2.93 (br. s., 1H), 2.82 (dd, J=13.4, 9.2 Hz, 1H), 2.28 (br. s., 1H), 2.04 (dq, J=13.4, 3.8 Hz, 1H), 1.48 (s, 9H). Fractions containing the second-eluting product were pooled and concentrated in vacuo to yield (trans)-tert-butyl 3-azido-4-hydroxypiperidine-1-carboxylate, Intermediate 197B (0.20 g, 15% yield) as a colorless oil. $^1$H NMR (400 MHz, chloroform-d) δ 4.44-4.09 (m, 1H), 4.02 (d, J=14.5 Hz, 1H), 3.58 (br. s., 1H), 3.35-3.24 (m, 1H), 2.99-2.63 (m, 2H), 2.20 (d, J=2.4 Hz, 1H), 1.99 (dq, J=13.2, 3.7 Hz, 1H), 1.52-1.46 (m, 9H).

Intermediate 197B: (3R,4R)-tert-butyl 4-(4-(6-chloro-4-(isopropylamino)pyridin-3-yl)-1H-1,2,3-triazol-1-yl)-3-hydroxypiperidine-1-carboxylate

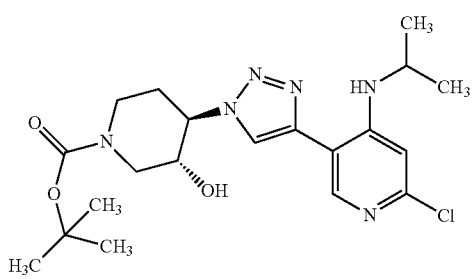

(197B)

(trans)-tert-butyl 4-(4-(6-chloro-4-(isopropylamino)pyridin-3-yl)-1H-1,2,3-triazol-1-yl)-3-hydroxypiperidine-1-carboxylate was prepared from (trans)-tert-butyl 4-azido-3-hydroxypiperidine-1-carboxylate and 2-chloro-5-ethynyl-N-isopropylpyridin-4-amine using the procedure described in Intermediate 10E. LCMS 437.3 (M+H)$^+$.

Intermediates 197C and 197D: (3R,4R)-tert-butyl 4-(4-(6-(5-cyano-1H-pyrazolo[3,4-b]pyridin-1-yl)-4-(isopropylamino)pyridin-3-yl)-1H-1,2,3-triazol-1-yl)-3-hydroxypiperidine-1-carboxylate (197C) and (3R,4R)-tert-butyl 4-(4-(6-(5-cyano-1H-pyrazolo[3,4-b]pyridin-1-yl)-4-(isopropylamino)pyridin-3-yl)-1H-1,2,3-triazol-1-yl)-3-hydroxypiperidine-1-carboxylate (197D) were prepared using the cross coupling procedure outlined for Example 10.

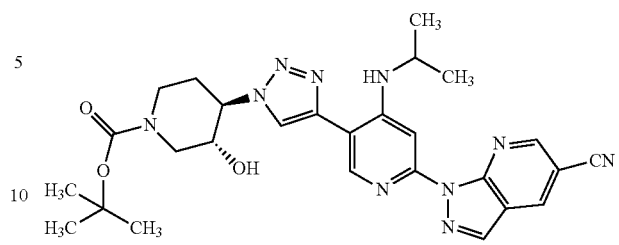

(197C)

Isomer 1

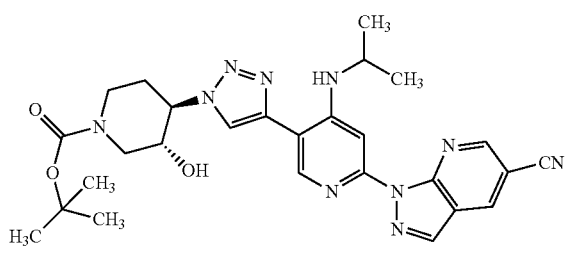

(197D)

Isomer 2

Racemic (trans)-tert-butyl 4-(4-(6-chloro-4-(isopropylamino)pyridin-3-yl)-1H-1,2,3-triazol-1-yl)-3-hydroxypiperidine-1-carboxylate was prepared from (trans)-tert-butyl 4-(4-(6-chloro-4-(isopropylamino)pyridin-3-yl)-1H-1,2,3-triazol-1-yl)-3-hydroxypiperidine-1-carboxylate and 1H-pyrazolo[3,4-b]pyridine-5-carbonitrile using the conditions described in Example 10. The enantiomers were resolved from 350 mg of racemate by chiral HPLC. Analytical Conditions: Analytical Column: ID (0.46×25 cm, 5 μm); BPR pressure: 100 bars; temperature: 35° C.; Flow rate: 3.0 mL/min; Mobile Phase: CO$_2$/MeOH w 0.2% NH$_4$OH (50/50); Detector Wavelength: UV 200-400 nm. Preparative Conditions: Preparative Column: ID (3×25 cm, 5 μm); BPR pressure: 100 bars; Temperature: 45° C.; Flow rate: 140 mL/min; Mobile Phase: CO$_2$/MeOH w 0.2% NH$_4$OH (40/60); Detector Wavelength: 254 nm; Separation Program: Stack injection-Injection: 1 mL with cycle time 4 mins; sample preparation: 350 mg in 23 mL MeOH:DCM (1:1), 15.2 mg/mL. Fractions containing the first-eluting peak were pooled and concentrated to yield (trans)-tert-butyl 4-(4-(6-(5-cyano-1H-pyrazolo[3,4-b]pyridin-1-yl)-4-(isopropylamino)pyridin-3-yl)-1H-1,2,3-triazol-1-yl)-3-hydroxypiperidine-1-carboxylate, isomer 1 (131 mg, 75% yield). LCMS 545.2 (M+H)$^+$. Fractions containing the second-eluting peak were pooled and concentrated to yield (trans)-tert-butyl 4-(4-(6-(5-cyano-1H-pyrazolo[3,4-b]pyridin-1-yl)-4-(isopropylamino)pyridin-3-yl)-1H-1,2,3-triazol-1-yl)-3-hydroxypiperidine-1-carboxylate, isomer 2 (147 mg, 84% yield). LCMS 545.2 (M+H)$^+$.

Example 197

1-(5-(1-((trans)-3-hydroxypiperidin-4-yl)-1H-1,2,3-triazol-4-yl)-4-(isopropylamino)pyridin-2-yl)-1H-pyrazolo[3,4-b]pyridine-5-carbonitrile, isomer 1, 2TFA was prepared from (trans)-tert-butyl 4-(4-(6-(5-cyano-1H-pyrazolo[3,4-b]pyridin-1-yl)-4-(isopropylamino)pyridin-3-yl)-1H-1,2,3-triazol-1-yl)-3-hydroxypiperidine-1-carboxylate, isomer 1 using the conditions described in Example 177.

The Examples in Table 12 were prepared from 1-(5-(1-((trans)-3-hydroxypiperidin-4-yl)-1H-1,2,3-triazol-4-yl)-4-(isopropylamino)pyridin-2-yl)-1H-pyrazolo[3,4-b]pyridine-5-carbonitrile, isomer 1, 2TFA or 1-(5-(1-((trams)-3-hydroxypiperidin-4-yl)-1H-1,2,3-triazol-4-yl)-4-(isopropylamino)pyridin-2-yl)-1H-pyrazolo[3,4-b]pyridine-5-carbonitrile, isomer 2, 2TFA using the general methods described in Examples 177 and 178, substituting the appropriate acid chloride, chloroformate, anhydride, or sulfonyl chloride for acetic anhydride. Example 202 was isolated as a side-product from the reaction that produced Example 199.

TABLE 12

| Ex. No. | Structure | HPLC rt (min) | HPLC cond. | LCMS |
|---|---|---|---|---|
| 198 | Isomer 1 | 1.35 | C | 487.2 |
| 199 | Isomer 1 | 1.41 | C | 523.2 |
| 200 | Isomer 1 | 1.61 | C | 529.3 |
| 201 | Isomer 1 | 1.50 | C | 503.1 |

TABLE 12-continued

| Ex. No. | Structure | HPLC rt (min) | HPLC cond. | LCMS |
|---|---|---|---|---|
| 202 | Isomer 1 | 1.55 | C | 601.2 |
| 203 | Isomer 2 | 1.34 | C | 487.2 |
| 204 | Isomer 2 | 1.47 | C | 523.1 |
| 205 | Isomer 2 | 1.46 | C | 503.2 |

TABLE 12-continued

| Ex. No. | Structure | HPLC rt (min) | HPLC cond. | LCMS |
|---|---|---|---|---|
| 206 | <br>Isomer 2 | 1.61 | C | 529.3 |

Example 207

1-(4-(cyclopropylamino)-5-(1-((trans)-4-hydroxypiperidin-3-yl)-1H-1,2,3-triazol-4-yl)pyridin-2-yl)-1H-pyrazolo[3,4-b]pyridine-5-carbonitrile (207)

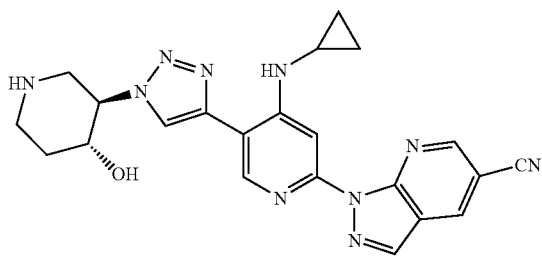

Example 207 was prepared from (trans)-tert-butyl 3-azido-4-hydroxypiperidine-1-carboxylate, 2-chloro-N-cyclopropyl-5-ethynylpyridin-4-amine and 1H-pyrazolo[3,4-b]pyridine-5-carbonitrile using the methods described in Examples 176 and 177. LCMS 487.2 (M+H)+; HPLC rt=1.29 min (conditions C); $^1$H NMR (500 MHz, DMSO-d$_6$) δ 9.06 (s, 1H), 9.02 (d, J=1.7 Hz, 1H), 8.88 (s, 1H), 8.65 (s, 1H), 8.61 (s, 1H), 8.48 (s, 1H), 7.71 (s, 1H), 4.34 (td, J=10.3, 4.4 Hz, 1H), 3.96 (td, J=10.2, 4.9 Hz, 1H), 3.26 (dd, J=11.9, 3.9 Hz, 1H), 3.04 (d, J=12.8 Hz, 1H), 2.96 (t, J=11.8 Hz, 1H), 2.72-2.58 (m, 3H), 2.00 (d, J=13.8 Hz, 1H), 1.58-1.45 (m, 1H), 0.91 (d, J=5.0 Hz, 2H), 0.61 (br. s., 2H).

Example 208

(trans)-methyl 4-(4-(6-(5-cyano-1H-pyrazolo[3,4-b]pyridin-1-yl)-4-(cyclopropylamino) pyridin-3-yl)-1H-1,2,3-triazol-1-yl)-3-hydroxy-3-methylpiperidine-1-carboxylate (208)

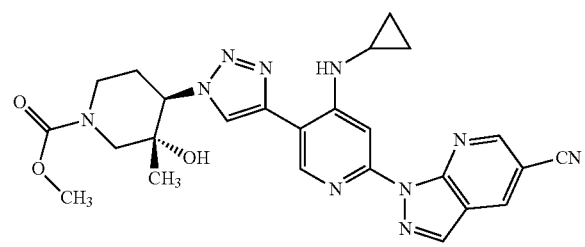

Example 208 was prepared using the general methods described in Example 195, substituting methyl 1-methyl-7-oxa-3-azabicyclo[4.1.0]heptane-3-carboxylate (WO 2005/066176) for tert-butyl 7-oxa-3-azabicyclo[4.1.0]heptane-3-carboxylate, and 2-chloro-N-cyclopropyl-5-ethynylpyridin-4-amine for 2-chloro-N-isopropyl-5-ethynylpyridin-4-amine, and omitting steps 3 and 4. LCMS 515.3 (M+H)+; HPLC rt=1.50 min (conditions C). $^1$H NMR (500 MHz, DMSO-d$_6$) δ 9.11 (d, J=1.3 Hz, 1H), 9.05 (d, J=1.7 Hz, 1H), 8.82 (s, 1H), 8.73 (s, 1H), 8.65 (s, 1H), 7.95 (d, J=3.4 Hz, 1H), 4.63 (dd, J=12.1, 4.0 Hz, 1H), 4.15 (br. s., 1H), 4.03-3.79 (m, 1H), 3.65 (s, 1H), 3.17-2.92 (m, 2H), 2.33 (d, J=9.1 Hz, 1H), 2.10 (d, J=10.4 Hz, 1H), 1.06-0.87 (m, 5H), 0.68 (br. s., 2H).

Example 209

1-(5-(1-((cis)-3-fluoropiperidin-4-yl)-1H-1,2,3-triazol-4-yl)-4-(isopropylamino)pyridin-2-yl)-1H-pyrazolo[3,4-b]pyridine-5-carbonitrile (209)

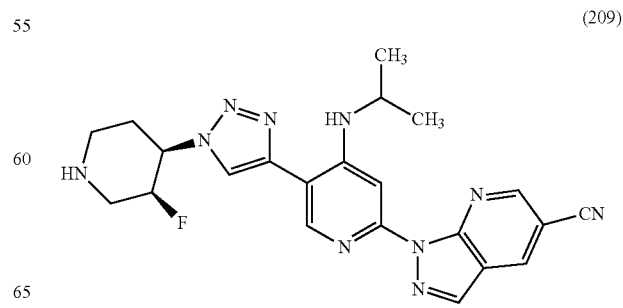

Intermediate 209A: tert-butyl 4-(4-(6-chloro-4-(isopropylamino)pyridin-3-yl)-1H-1,2,3-triazol-1-yl)-3-fluoropiperidine-1-carboxylate (209A)

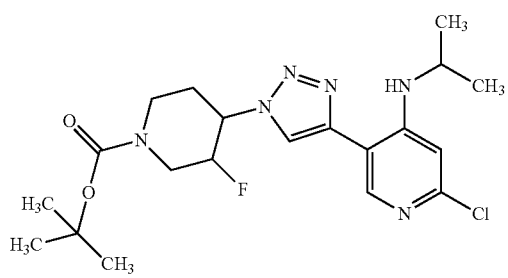

A stirring solution of (trans)-tert-butyl 4-azido-3-hydroxypiperidine-1-carboxylate (Intermediate 198A) (117 mg, 0.483 mmol) in anhydrous dichloromethane (5 mL) was cooled to −78° C. and treated with diethylaminosulfur trifluoride (0.096 mL, 0.724 mmol). The mixture was stirred at −78° C. for 2 hours, then allowed to come to room temperature and stirred for 18 hours. The reaction mixture was poured into stirring, ice-cold saturated sodium carbonate solution (10 mL). The mixture was allowed to come to room temperature and stirred for 48 hours. The layers were separated, the aqueous phase was extracted twice with dichloromethane (5 mL), and the combined organic phases were dried over sodium sulfate and concentrated in vacuo. In a 2-dram vial, a stirring mixture of the crude material (108 mg, 0.44 mmol), 2-chloro-5-ethynyl-N-isopropylpyridin-4-amine (79 mg, 0.41 mmol), and sodium ascorbate (12 mg, 0.06 mmol) in 1:1 tBuOH/water (1 mL) was treated with copper(II) sulfate (3 mg, 0.02 mmol). The vial was sealed, and the reaction mixture was stirred at 50° C. for 2 hours, at which point it was judged to be complete by LCMS. The reaction mixture was diluted with ethyl acetate (15 mL), and the turbid mixture was washed 3× with water and once with brine. The organic phase was dried over sodium sulfate and concentrated in vacuo. LCMS of the crude material detected a ~4:1 mixture of cis- and trans-isomers. The residue was chromatographed via MPLC over a 24 g silica gel column, eluting at 40 mL/min with a 0.5% to 10% methanol/methylene chloride gradient over 10 column volumes. The chromatography did not resolve the two isomers. Fractions containing the desired product were pooled and concentrated in vacuo to yield tert-butyl 4-(4-(6-chloro-4-(isopropylamino)pyridin-3-yl)-1H-1,2,3-triazol-1-yl)-3-fluoropiperidine-1-carboxylate (134 mg, 77% yield). LCMS 439.4 (M+H)$^+$.

Intermediate 209B: tert-butyl 4-(4-(6-(5-cyano-1H-pyrazolo[3,4-b]pyridin-1-yl)-4-(isopropylamino)pyridin-3-yl)-1H-1,2,3-triazol-1-yl)-3-fluoropiperidine-1-carboxylate tert-Butyl 4-(4-(6-(5-cyano-1H-pyrazolo[3,4-b]pyridin-1-yl)-4-(isopropylamino) pyridin-3-yl)-1H-1,2,3-triazol-1-yl)-3-fluoropiperidine-1-carboxylate was prepared from tert-butyl 4-(4-(6-chloro-4-(isopropylamino)pyridin-3-yl)-1H-1,2,3-triazol-1-yl)-3-fluoropiperidine-1-carboxylate and 1H-pyrazolo[3,4-b]pyridine-5-carbonitrile using the conditions described in Intermediate 10E. LCMS 547.4 (M+H)$^+$.

Example 209

A stirring solution of tert-butyl 4-(4-(6-(5-cyano-1H-pyrazolo[3,4-b]pyridin-1-yl)-4-(isopropylamino)pyridin-3-yl)-1H-1,2,3-triazol-1-yl)-3-fluoropiperidine-1-carboxylate (91 mg, 0.166 mmol) in dichloromethane (2 mL) was cooled to 5° C. and treated with TFA (1 mL). The reaction mixture was allowed to come to room temperature and stirred for 1 hour, at which point it was judged to be complete by LCMS. The reaction mixture was concentrated in vacuo, and the residue was concentrated 3× from dichloromethane (10 mL) to remove residual TFA. The bulk of the crude material was used as-is in the next step. A portion of the crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-100% B over 25 minutes, then a 5-minute hold at 100% B; Flow: 20 mL/min. Fractions containing the desired product were combined and dried via centrifugal evaporation to yield 1-(5-(1-((cis)-3-fluoropiperidin-4-yl)-1H-1,2,3-triazol-4-yl)-4-(isopropylamino)pyridin-2-yl)-1H-pyrazolo[3,4-b]pyridine-5-carbonitrile, 2 TFA. LCMS 515.3 (M+H)$^+$, HPLC rt=1.50 min (Conditions C); $^1$H NMR (500 MHz, DMSO-d$_6$) δ 9.05 (s, 1H), 9.03 (s, 1H), 8.99 (s, 1H), 8.69-8.58 (m, 2H), 8.34-8.21 (m, 1H), 7.39 (s, 1H), 5.57-5.07 (m, 2H), 4.08-3.73 (m, 2H), 3.72-3.32 (m, 1H), 3.28-3.18 (m, 1H), 2.47-2.28 (m, 1H), 1.33 (d, J=6.4 Hz, 6H). Peaks for several protons are absent from this spectrum, possibly due to the water suppression algorithm used during data processing.

Examples 210 and 211

1-(5-(1-((trans)-3-fluoro-1-(methylsulfonyl)piperidin-4-yl)-1H-1,2,3-triazol-4-yl)-4-(isopropylamino) pyridin-2-yl)-1H-pyrazolo[3,4-b]pyridine-5-carbonitrile, Isomer 1 (210)

1-(5-(1-((trans)-3-fluoro-1-(methylsulfonyl)piperidin-4-yl)-1H-1,2,3-triazol-4-yl)-4-(isopropylamino) pyridin-2-yl)-1H-pyrazolo[3,4-b]pyridine-5-carbonitrile, Isomer 2 (211)

(209B)

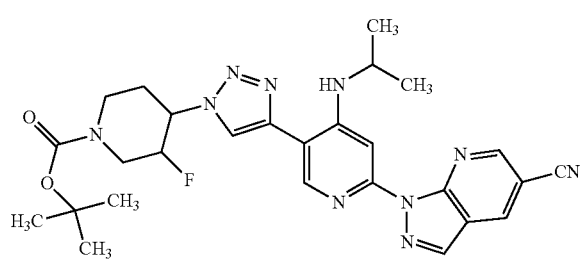

(210)

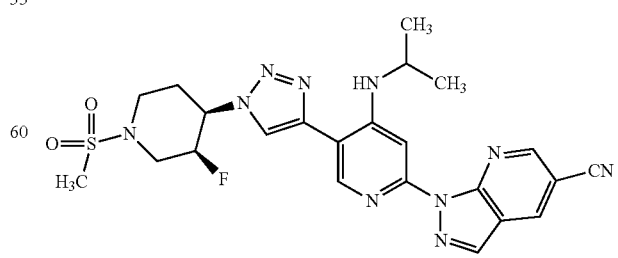

Isomer 1

(211)

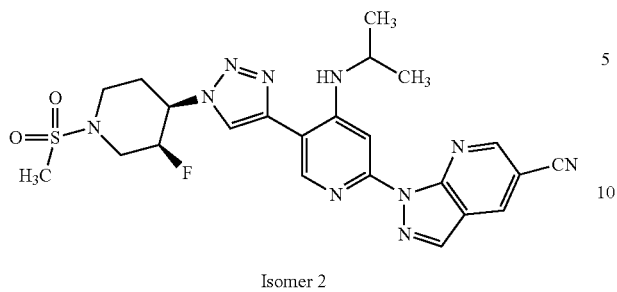

Isomer 2

A stirring solution of 1-(5-(1-(3-fluoropiperidin-4-yl)-1H-1,2,3-triazol-4-yl)-4-(isopropylamino)pyridin-2-yl)-1H-pyrazolo[3,4-b]pyridine-5-carbonitrile, 2 TFA (74.2 mg, 0.11 mmol) in dichloromethane (2 mL) and triethylamine (80 µL, 0.55 mmol) was cooled to 5° C. and treated with methanesulfonyl chloride (8.6 µL, 0.11 mmol). The reaction mixture was allowed to come to room temperature and stirred for 1 hour, at which point it was judged to be complete by LCMS. The reaction mixture was concentrated in vacuo, and the residue was chromatographed via MPLC over a 24 g silica gel column, eluting at 40 mL/min with 5% methanol/methylene chloride. The two isomers eluted close together. Fractions containing only the second-eluting (major) peak were pooled and set aside. Fractions containing both peaks were pooled and concentrated in vacuo. The residue was chromatographed via MPLC over a 24 g silica gel column, eluting at 40 mL/min with 4% methanol/methylene chloride. Fractions containing only the second-eluting peak were combined with those from the first run and concentrated in vacuo to yield 1-(5-(1-((cis)-3-fluoro-1-(methylsulfonyl)piperidin-4-yl)-1H-1,2,3-triazol-4-yl)-4-(isopropylamino)pyridin-2-yl)-1H-pyrazolo[3,4-b]pyridine-5-carbonitrile (22 mg, 0.041 mmol, 37.0% yield) as a yellow solid. LCMS 525.4 (M+H)⁺. The enantiomers were resolved from 18 mg of racemate by chiral HPLC, using the following conditions: Column: Chiral IC 3×25 cm, 5 µm; Column Temp. 35° C.; Flow rate: 150 ml/min; Mobile Phase: CO₂/[MEOH/CH₃CN/NH₄OH=50/50/0.01]=50/50; Detector wavelength: 254 nm; Injection: 0.5 mL (1.8 mg/ml); Separation Program: Stacked Injection (3.0 min each cycle).

Fractions containing the first-eluting peak were pooled and concentrated to yield Example 210. LCMS 525.0 (M+H)⁺; HPLC rt=7.64 min (conditions A). ¹H NMR (400 MHz, chloroform-d) δ 8.96 (d, J=2.0 Hz, 1H), 8.54 (s, 1H), 8.52 (d, J=2.0 Hz, 1H), 8.39 (s, 1H), 8.28 (d, J=6.8 Hz, 1H), 8.03 (s, 1H), 7.57 (s, 1H), 5.06 (dtd, J=48.4, 9.2, 5.5 Hz, 1H), 4.74-4.61 (m, 1H), 4.40-4.29 (m, 1H), 4.05 (d, J=12.8 Hz, 1H), 3.96 (dq, J=13.0, 6.5 Hz, 1H), 3.13-3.02 (m, 2H), 2.97 (s, 3H), 2.68-2.46 (m, 2H), 1.44 (d, J=6.4 Hz, 6H).

Fractions containing the second-eluting peak were pooled and concentrated to yield Example 211. LCMS 525.0 (M+H)⁺, HPLC rt=7.70 min (conditions A); ¹H NMR (400 MHz, chloroform-d) δ 8.96 (d, J=2.0 Hz, 1H), 8.54 (s, 1H), 8.52 (d, J=2.0 Hz, 1H), 8.39 (s, 1H), 8.28 (d, J=6.8 Hz, 1H), 8.03 (s, 1H), 7.57 (s, 1H), 5.06 (dtd, J=48.4, 9.2, 5.5 Hz, 1H), 4.74-4.61 (m, 1H), 4.40-4.29 (m, 1H), 4.05 (d, J=12.8 Hz, 1H), 3.96 (dq, J=13.0, 6.5 Hz, 1H), 3.13-3.02 (m, 2H), 2.97 (s, 3H), 2.68-2.46 (m, 2H), 1.44 (d, J=6.4 Hz, 6H).

Example 212 tert-butyl ((trans)-4-(4-(6-(5-cyano-1H-pyrazolo[3,4-b]pyridin-1-yl)-4-(isopropylamino)pyridin-3-yl)-1H-1,2,3-triazol-1-yl)cyclohexyl)carbamate

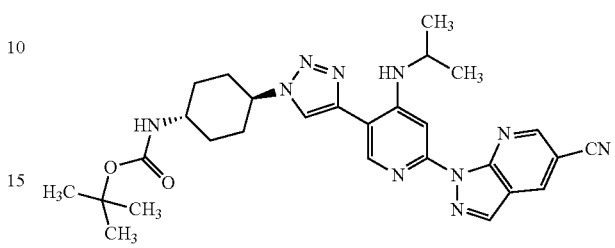

Intermediate 212A: (1 s,4s)-4-((tert-butoxycarbonyl)amino)cyclohexyl methanesulfonate

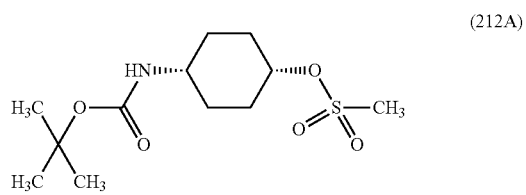 [SMILES: CC(C)(C)OC(=O)N[C@H]1CC[C@@H](OS(C)(=O)=O)CC1]

(212A)

(cis)-4-((tert-butoxycarbonyl)amino)cyclohexyl methanesulfonate was prepared from methanesulfonyl chloride and tert-butyl ((cis)-4-hydroxycyclohexyl)carbamate using the conditions described in Intermediate 168A. ¹H NMR (400 MHz, chloroform-d) δ 4.93-4.88 (m, 1H), 4.48 (br. s., 1H), 3.55 (br. s., 1H), 3.03 (s, 3H), 2.16-2.01 (m, 2H), 1.95-1.81 (m, 2H), 1.80-1.69 (m, 2H), 1.65-1.53 (m, 2H+water), 1.47 (s, 9H).

Intermediate 212B: tert-butyl ((1r,4r)-4-azidocyclohexyl)carbamate

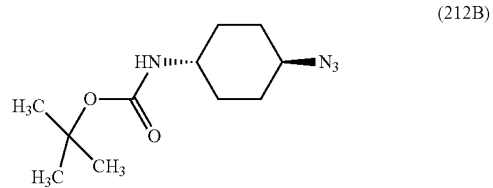 [SMILES: CC(C)(C)OC(=O)N[C@H]1CC[C@H](N=[N+]=[N-])CC1]

(212B)

In a 20 mL vial, a solution of (cis)-4-((tert-butoxycarbonyl)amino) cyclohexyl methanesulfonate (815 mg, 2.78 mmol) in DMF (5 mL) was treated with sodium azide (199 mg, 3.06 mmol). The vial was sealed, and the reaction mixture was stirred at 90° C. for 18 hours, at which point it was judged to be complete by TLC. The reaction mixture was concentrated in vacuo, and the residue was taken up in ethyl acetate (15 mL). The turbid solution was washed once with water, 3× with 10% lithium chloride solution, and once with brine, then dried over sodium sulfate and concentrated in vacuo to yield tert-butyl ((trans)-4-azidocyclohexyl)carbamate (615 mg, 92% yield) as a colorless solid. ¹H NMR (400 MHz, chloroform-d) δ 4.39 (br. s., 1H), 3.45 (br. s., 1H), 3.29 (tt, J=11.2, 4.1 Hz, 1H), 2.20-1.97 (m, 4H), 1.56-1.36 (m, 11H), 1.27-1.12 (m, 2H). The crude material was used as-is in the next step.

Example 212

Example 212 was prepared from 1-(5-ethynyl-4-(isopropylamino)pyridin-2-yl)-1H-pyrazolo[3,4-b]pyridine-5-carbonitrile and tert-butyl ((trans)-4-azidocyclohexyl) carbamate using the conditions described in Example 99 (method B). LCMS 543.2 (M+H)⁺, HPLC rt=2.07 min (Conditions C); ¹H NMR (500 MHz, DMSO-d₆) δ 9.05 (d, J=1.9 Hz, 1H), 9.03 (d, J=1.9 Hz, 1H), 8.90 (s, 1H), 8.64 (s, 1H), 8.60 (s, 1H), 8.37 (d, J=7.2 Hz, 1H), 7.33 (s, 1H), 6.91 (d, J=7.9 Hz, 1H), 4.55 (t, J=11.4 Hz, 1H), 3.87 (dq, J=13.0, 6.4 Hz, 1H), 2.21 (d, J=11.2 Hz, 2H), 2.03-1.85 (m, 4H), 1.51-1.36 (m, 11H), 1.32 (d, J=6.3 Hz, 6H).

Additional compounds prepared according to the procedures outlined for the above examples are shown in Table 13.

TABLE 13

| Ex. No. | Structure | HPLC rt (min) | HPLC cond. | LCMS |
|---|---|---|---|---|
| 213 | 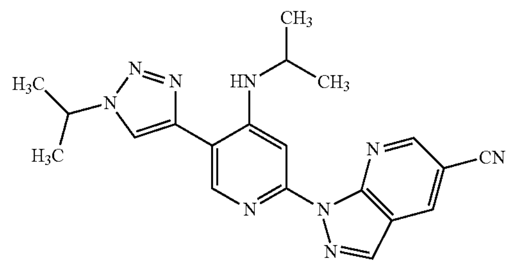 [SMILES: CC(C)Nc1cc(-n2ncc3cc(C#N)cnc32)ncc1-c1cn(C(C)C)nn1] | 1.73 | E | 388.3 |
| 214 | Isomer 1 | 7.18 | A | 416.1 |
| 215 | Isomer 2 | 7.16 | A | 416.1 |
| 216 | 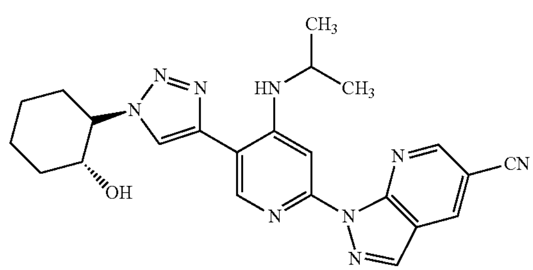 | 7.49 | D | 444.1 |

TABLE 13-continued

| Ex. No. | Structure | HPLC rt (min) | HPLC cond. | LCMS |
|---|---|---|---|---|
| 217 | 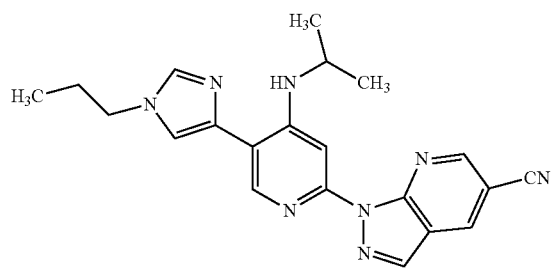 | 2.30 | C | 425.3 |
| 218 | 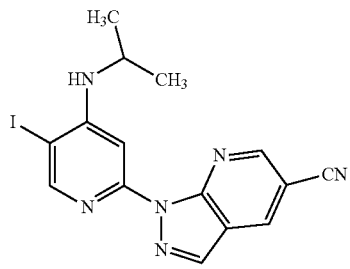 | 2.02 | C | 397.3 |

Example 219

1-(4-(Isopropylamino)-5-(1-propyl-1H-imidazol-4-yl)pyridin-2-yl)-1H-indazole-5-carbonitrile (219)

Intermediate 219A: 1-(5-iodo-4-(isopropylamino)pyridin-2-yl)-1H-pyrazolo[3,4-b]pyridine-5-carbonitrile (219A)

To a solution of potassium 6-(5-cyano-1H-pyrazolo[3,4-b]pyridin-1-yl)-4-(isopropylamino)nicotinate (400 mg, 1.11 mmol) in DMF (3 mL) and water (1 mL), was added (diacetoxyiodo)benzene (214 mg, 0.67 mmol). The mixture was heated at 60° C. for 0.5 h, then added NIS (275 mg, 1.22 mmol), and heating was continued overnight. The reaction mixture was cooled, added water, and extracted with EtOAc. The extracts were washed with Na$_2$S$_2$O$_3$ (sat. aq.) and brine. The organic extracts were then dried (Na$_2$SO$_4$), filtered, and concentrated. The crude was purified via column chromatography to afford 1-(5-iodo-4-(isopropylamino)pyridin-2-yl)-1H-pyrazolo[3,4-b]pyridine-5-carbonitrile (376 mg, 84% yield) as a yellow solid. $^1$H-NMR (400 MHz, CHLOROFORM-d) δ 8.92 (d, J=2.0 Hz, 1H), 8.60 (s, 1H), 8.49 (d, J=2.0 Hz, 1H), 8.36 (s, 1H), 7.42 (s, 1H), 4.79 (d, J=6.8 Hz, 1H), 3.89 (d, J=6.6 Hz, 1H), 1.38 (d, J=6.4 Hz, 6H). LCMS: 405.2 (M+H).

Intermediate 219B:
1-propyl-4-(tributylstannyl)-1H-imidazole

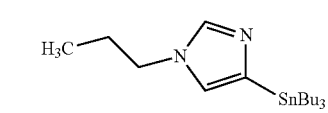

(219B)

To a solution of 4-iodo-1-propyl-1H-imidazole (165 mg, 0.7 mmol) in dry THF (3 mL), was added ethyl magnesium bromide (1.4 mL, 1.4 mmol, 1M in THF) at room temperature. The mixture was stirred at room temperature for 1 h then added tributylchlorostannane (228 mg, 0.7 mmol). The mixture was stirred at room temperature overnight. LC-MS confirmed the formation of the product. The mixture was concentrated under vacuum, no further purification was done at this step.

Example 219

To a solution of 1-(5-iodo-4-(isopropylamino)pyridin-2-yl)-1H-pyrazolo[3,4-b]pyridine-5-carbonitrile (20 mg, 0.05 mmol) in dry DMF (0.5 mL), was added 1-propyl-4-(tributylstannyl)-1H-imidazole (39.5 mg, 0.1 mmol), tetrakistriphenylphosphine palladium (5 mg, 5 μmol), and copper(I) iodide (0.94 mg, 5 μmol). The mixture was purged with $N_2$ then heated at 80° C. overnight. After cooling to room temperature, the reaction mixture was purified directly via preparative HPLC to afford 1-(4-(isopropylamino)-5-(1-propyl-1H-imidazol-4-yl)pyridin-2-yl)-1H-indazole-5-carbonitrile (4.4 mg, 23% yield). $^1$H-NMR (500 MHz, DMSO-$d_6$) δ 8.97 (d, J=11.4 Hz, 2H), 8.58 (s, 1H), 8.06 (d, J=3.1 Hz, 2H), 7.73 (s, 1H), 7.17 (s, 1H), 3.99 (br m, 2H), 1.78 (br, 2H), 1.38 (br m, 6H), 0.85 (br s, 3H); LCMS: 387.2 (M+H); HPLC rt 1.73 min, conditions C.

Example 220

1-(5-(1H-imidazol-4-yl)-4-(isopropylamino)pyridin-2-yl)-1H-indazole-5-carbonitrile

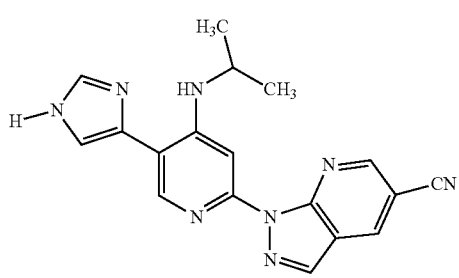

(220)

To a mixture of 1-(5-iodo-4-(isopropylamino)pyridin-2-yl)-1H-pyrazolo[3,4-b]pyridine-5-carbonitrile (50 mg, 0.124 mmol) and 4-(tributylstannyl)-1-trityl-1H-imidazole (82 mg, 0.136 mmol) in 1,4-dioxane (1 mL), was added tetrakistriphenylphosphine palladium (0)(14.3 mg, 0.012 mmol). The reaction vessel was purged with $N_2$, sealed, and heated at 100° C. overnight. The reaction mixture was cooled to room temperature and purified directly via column chromatography. The product was concentrated and treated with TFA (1 mL) in DCM (1 mL) overnight. The reaction mixture was concentrated and purified via column chromatography to afford 1-(5-(1H-imidazol-4-yl)-4-(isopropylamino)pyridin-2-yl)-1H-indazole-5-carbonitrile (23 mg, 53% yield) as a yellow solid. $^1$H NMR (400 MHz, METHANOL-$d_4$) δ 9.02 (s, 1H), 8.81 (s, 1H), 8.60 (s, 1H), 8.43-8.26 (m, 1H), 7.94 (s, 1H), 7.86 (s, 1H), 7.59 (s, 2H), 7.33-7.21 (m, 1H), 4.06-3.94 (m, 1H), 1.46 (d, J=6.4 Hz, 6H); LC/MS: 354.3 (M+H); HPLC rt 4.08 min, conditions A.

Example 221

1-(5-(1-isobutyl-1H-imidazol-4-yl)-4-(isopropylamino)pyridin-2-yl)-1H-pyrazolo[3,4-b]pyridine-5-carbonitrile

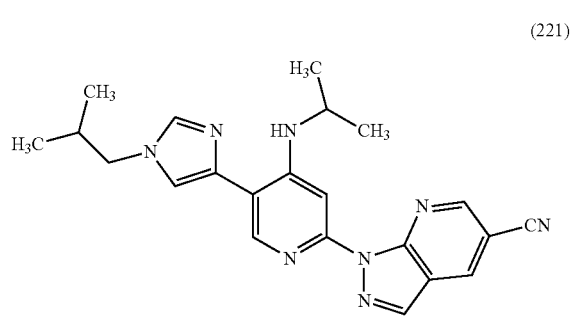 [SMILES: CC(C)Cn1cnc(-c2cnc(-n3ncc4cc(C#N)cnc43)cc2NC(C)C)c1]

(221)

To a solution of 1-(5-(1H-imidazol-4-yl)-4-(isopropylamino)pyridin-2-yl)-1H-indazole-5-carbonitrile (6 mg, 0.017 mmol) and 1-iodo-2-methylpropane (3.85 mg, 0.021 mmol) in DMF (0.1 mL) was added potassium tert-butoxide (3.91 mg, 0.035 mmol). The mixture was stirred at room temperature overnight and the product isolated directly via preparative HPLC to afford 1-(5-(1-isobutyl-1H-imidazol-4-yl)-4-(isopropylamino) pyridin-2-yl)-1H-pyrazolo[3,4-b]pyridine-5-carbonitrile (3.1 mg, 44% yield). $^1$H NMR (400 MHz, DMSO-$d_6$) δ 9.11 (s, 1H), 9.07 (s, 1H), 8.74 (s, 1H), 8.47 (s, 1H), 7.99 (m, 2H), 7.51 (br s, 1H), 3.90 (m, 3H), 2.10 (M, 1H), 1.33 (m, 6H), 0.90 (m, 6H); LC/MS: 401.2 (M+H); HPLC rt 1.91 min, conditions C.

Example 222

(S)-1-(5-(1-(2-hydroxypropyl)-1H-imidazol-4-yl)-4-(isopropylamino)pyridin-2-yl)-1H-pyrazolo[3,4-b]pyridine-5-carbonitrile

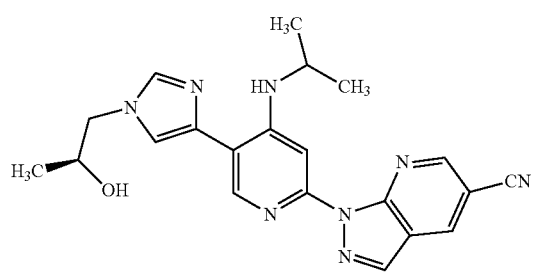

(222)

To a solution of 1-(5-(1H-imidazol-4-yl)-4-(isopropylamino)pyridin-2-yl)-1H-indazole-5-carbonitrile (10 mg, 0.03 mmol) in DMF (0.1 mL) was added (S)-2-methyloxirane (3.4 mg, 0.06 mmol) and sodium hydride (2.3 mg, 0.06 mmol, 60%). The mixture was stirred at room temperature overnight and the product isolated directly via preparative HPLC to afford (S)-1-(5-(1-(2-hydroxypropyl)-1H-imidazol-4-yl)-4-(isopropylamino)pyridin-2-yl)-1H-pyrazolo[3,4-b]pyridine-5-carbonitrile (0.9 mg, 7% yield). $^1$H NMR (400 MHz, DMSO-$d_6$) δ 9.02 (m, 3H), 8.61 (s, 1H), 8.48 (s, 1H), 7.84 (m, 2H), 7.16 (s, 1H), 4.05-3.77 (m, 4H), 1.28 (m, 6H), 1.10 (m, 3H); LC/MS: 403.2 (M+H); HPLC rt 1.36 min, conditions C.

Example 223

1-(5-(1-(1-acetylazetidin-3-yl)-1H-imidazol-4-yl)-4-(isopropylamino)pyridin-2-yl)-1H-pyrazolo[3,4-b]pyridine-5-carbonitrile

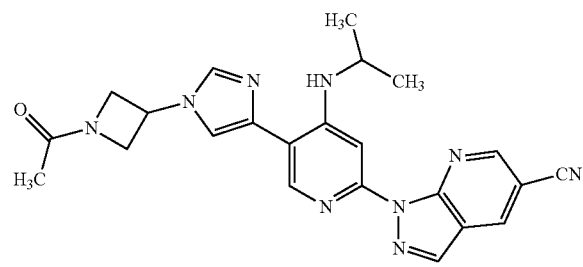

(223)

Intermediate 223A: tert-butyl 3-(4-(6-(5-cyano-1H-pyrazolo[3,4-b]pyridin-1-yl)-4-(isopropylamino)pyridin-3-yl)-1H-imidazol-1-yl)azetidine-1-carboxylate

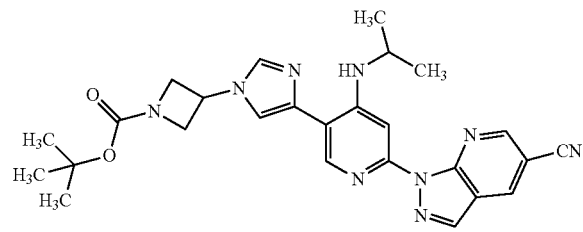

(223A)

To a solution of 1-(5-(1H-imidazol-4-yl)-4-(isopropylamino)pyridin-2-yl)-1H-pyrazolo[3,4-b]pyridine-5-carbonitrile (20 mg, 0.06 mmol) in DMF (0.5 mL), was added potassium tert-butoxide (6.5 mg, 0.06 mmol) and tert-butyl 3-iodoazetidine-1-carboxylate (38 mg, 0.134 mmol). The mixture was stirred at room temperature overnight. The mixture was added water, stirred, and filtered to give tert-butyl 3-(4-(6-(5-cyano-1H-pyrazolo[3,4-b]pyridin-1-yl)-4-(isopropylamino)pyridin-3-yl)-1H-imidazol-1-yl) azetidine-1-carboxylate (16 mg, 55% yield) which was used directly in the next step.

Example 223

To a solution of tert-butyl 3-(4-(6-(5-cyano-1H-pyrazolo[3,4-b]pyridin-1-yl)-4-(isopropylamino)pyridin-3-yl)-1H-imidazol-1-yl)azetidine-1-carboxylate (10 mg, 10 mol) in DCM (1 mL), was added 4N HCl in 1,4-dioxane (0.5 mL). The mixture was stirred at room temperature for 1 h then concentrated. DMF (0.5 mL) was added followed by HOBt (1.5 mg, 0.011 mmol), EDCI (2.1 mg, 0.011 mmol), triethylamine (2.5 mg, 0.025 mmol) and acetic acid (0.60 mg, 10 µmol). The mixture was stirred at room temperature overnight and the product was purified directly via preparative HPLC to afford 1-(5-(1-(1-acetylazetidin-3-yl)-1H-imidazol-4-yl)-4-(isopropylamino)pyridin-2-yl)-1H-pyrazolo[3,4-b]pyridine-5-carbonitrile (0.7 mg, 15%). $^1$H NMR (500 MHz, DMSO-$d_6$) δ 9.02 (d, J=5.6 Hz, 2H), 8.84 (d, J=7.4 Hz, 1H), 8.60 (s, 1H), 8.54 (s, 1H), 8.20 (s, 1H), 8.12-8.0 (m, 1H), 7.18 (s, 1H), 5.24 (br. s., 1H), 4.68-4.58 (m, 1H), 4.45-4.31 (m, 2H), 4.16-4.07 (m, 1H), 3.77 (d, J=6.6 Hz, 1H), 1.84 (s, 3H), 1.27 (d, J=6.2 Hz, 6H); LC/MS: 442.2 (M+H); HPLC rt 1.32 min, conditions C.

Example 224

1-(4-(isopropylamino)-5-(1-(pyridin-3-yl)-1H-imidazol-4-yl)pyridin-2-yl)-1H-pyrazolo[3,4-b]pyridine-5-carbonitrile

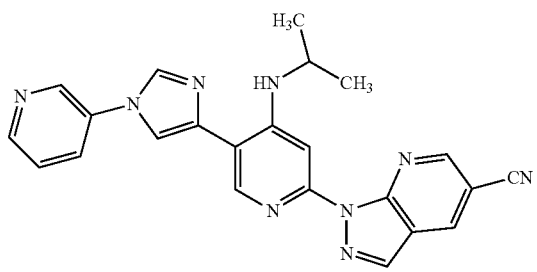

(224)

To a solution of 1-(5-(1H-imidazol-4-yl)-4-(isopropylamino)pyridin-2-yl)-1H-pyrazolo[3,4-b]pyridine-5-carbonitrile (10 mg, 0.03 mmol) in MeOH (0.5 mL), was added 3-(4,4,5,5-tetramethyl-1,3,2-dioxaborolan-2-yl)pyridine (6 mg, 0.03 mmol) and Cu$_2$O (0.80 mg, 5.8 µmol). The mixture was stirred at room temperature in the air overnight. The product was purified directly via preparative HPLC to afford 1-(4-(isopropylamino)-5-(1-(pyridin-3-yl)-1H-imidazol-4-yl)pyridin-2-yl)-1H-pyrazolo[3,4-b]pyridine-5-carbonitrile (0.8 mg, 6% yield). $^1$H NMR (500 MHz, DMSO-$d_6$) δ 9.12-8.99 (m, 3H), 8.79-8.73 (m, 1H), 8.69-8.59 (m, 3H), 8.57-8.49 (m, 1H), 8.26-8.19 (m, 1H), 7.68-7.58 (m, 1H), 7.26 (br. s., 1H), 7.15 (s, 1H), 7.05 (s, 1H), 3.87-3.75 (m, 1H), 1.30 (d, J=6.1 Hz, 6H); LC/MS: 421.8 (M+); HPLC rt 1.23 min, conditions D.

The Examples in Table 14 were prepared using the methods outlined for Example 224 using the appropriate starting material.

TABLE 14
| Ex. No. | Structure | HPLC rt (min) | HPLC cond. | LCMS |
|---|---|---|---|---|
| 225 | 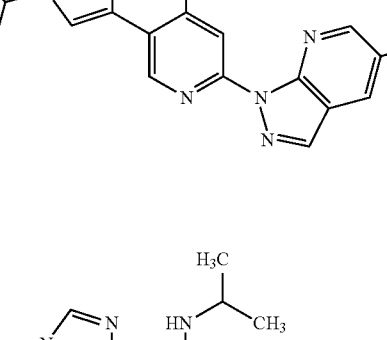 | 1.76 | C | 387.2 |
| 226 | 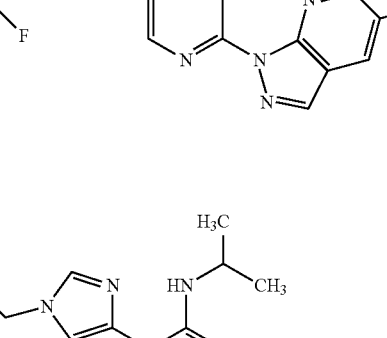 | 1.62 | C | 409.1 |
| 227 | 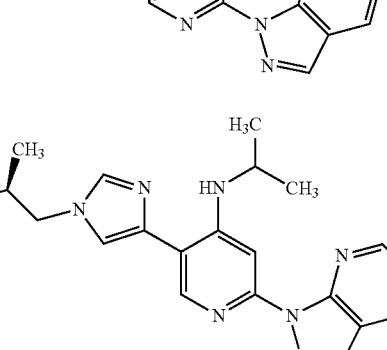 | 1.64 | C | 373.2 |
| 228 | 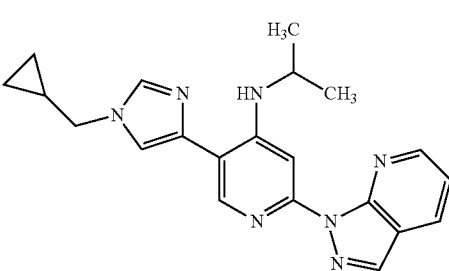 | 1.50 | C | 417.1 |
| 229 | 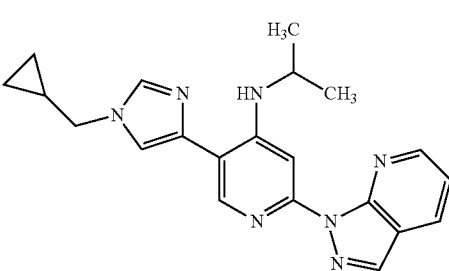 | 1.82 | C | 399.1 |

TABLE 14-continued
| Ex. No. | Structure | HPLC rt (min) | HPLC cond. | LCMS |
|---|---|---|---|---|
| 230 | 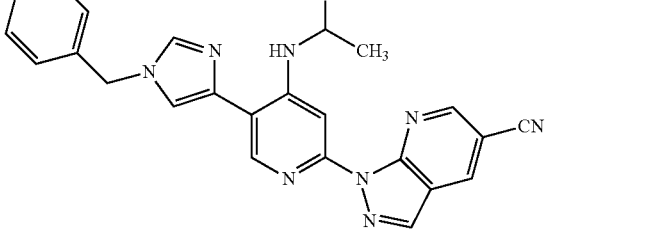 | 1.93 | C | 435.1 |
| 231 | 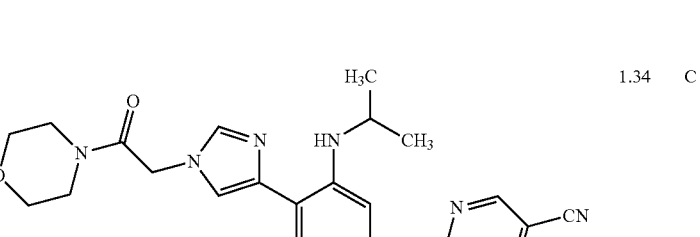 | 1.34 | C | 472.2 |
| 232 | 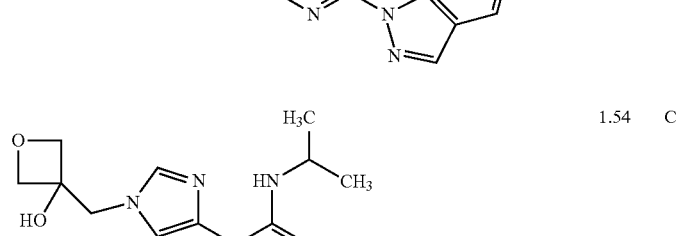 | 1.54 | C | 429.1 |
| 233 | 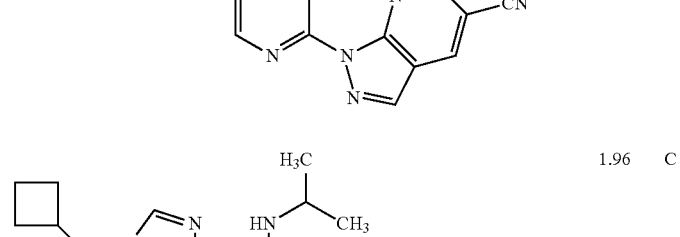 | 1.96 | C | 413.3 |
| 234 | 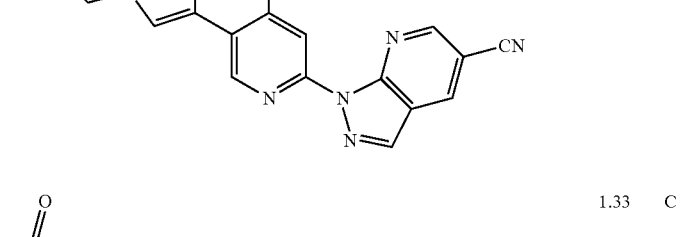 | 1.33 | C | 456.3 |

TABLE 14-continued

| Ex. No. | Structure | HPLC rt (min) | HPLC cond. | LCMS |
|---|---|---|---|---|
| 235 | 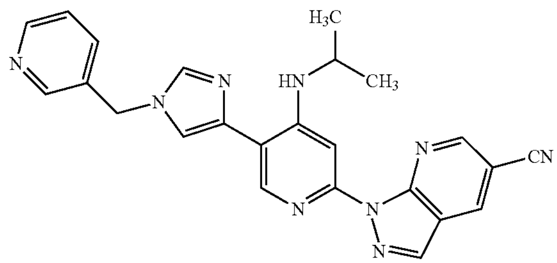 [SMILES: CC(C)Nc1cc(-n2ncc3cc(C#N)cnc32)ncc1-c1cn(Cc2cccnc2)cn1] | 1.00 | D | 436.2 |
| 236 | 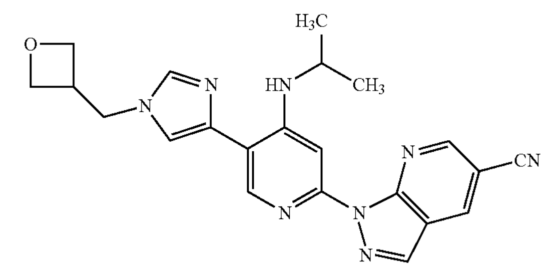 [SMILES: CC(C)Nc1cc(-n2ncc3cc(C#N)cnc32)ncc1-c1cn(CC2COC2)cn1] | 1.41 | D | 415.2 |
| 237 | 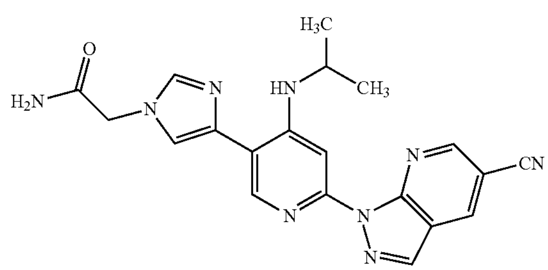 [SMILES: CC(C)Nc1cc(-n2ncc3cc(C#N)cnc32)ncc1-c1cn(CC(N)=O)cn1] | 1.27 | C | 402.2 |
| 238 | 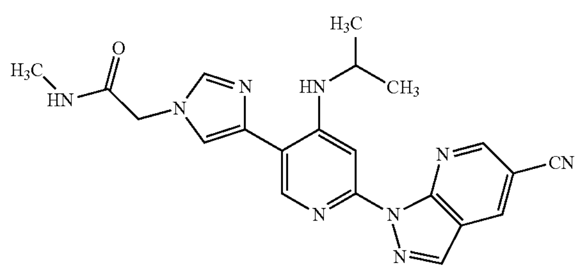 [SMILES: CNC(=O)Cn1cnc(-c2cnc(-n3ncc4cc(C#N)cnc43)cc2NC(C)C)c1] | 1.00 | D | 416.0 |
| 239 | 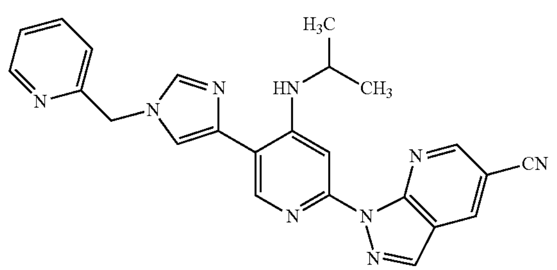 [SMILES: CC(C)Nc1cc(-n2ncc3cc(C#N)cnc32)ncc1-c1cn(Cc2ccccn2)cn1] | 1.17 | D | 436.2 |

TABLE 14-continued

| Ex. No. | Structure | HPLC rt (min) | HPLC cond. | LCMS |
|---|---|---|---|---|
| 240 | 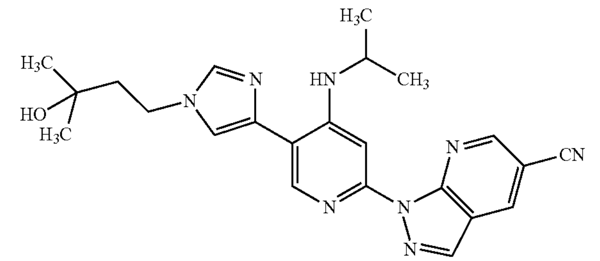 [SMILES: CC(C)Nc1cc(-n2ncc3cc(C#N)cnc32)ncc1-c1cn(CCC(C)(C)O)cn1] | 1.15 | D | 431.0 |
| 241 | 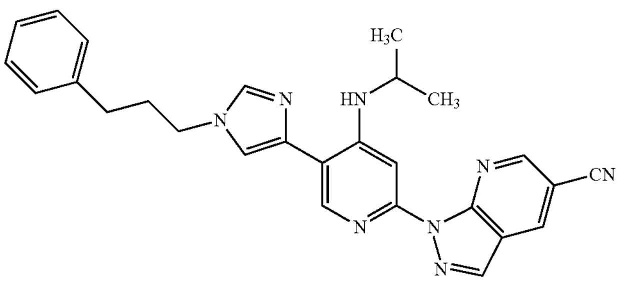 [SMILES: CC(C)Nc1cc(-n2ncc3cc(C#N)cnc32)ncc1-c1cn(CCCc2ccccc2)cn1] | 1.64 | D | 463.3 |

Example 242

1-(5-(4-(2-hydroxyethyl)-1H-pyrazol-1-yl)-4-(isopropylamino)pyridin-2-yl)-1H-pyrazolo[3,4-b]pyridine-5-carbonitrile

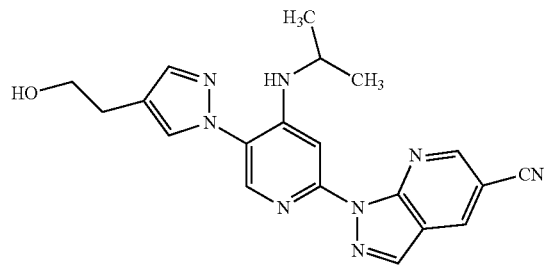

(242)

In a 20 mL microwave vial, 1-(5-iodo-4-(isopropylamino)pyridin-2-yl)-1H-pyrazolo[3,4-b]pyridine-5-carbonitrile (50 mg, 0.12 mmol), 2-(1H-pyrazol-4-yl)ethanol (13.9 mg, 0.12 mmol), potassium carbonate (51.3 mg, 0.37 mmol) and N1,N2-dimethylethane-1,2-diamine (6.54 mg, 0.074 mmol) were mixed in 1,4-dioxane (1 mL) at room temperature with stirring. While bubbling in nitrogen, copper(I) iodide (4.71 mg, 0.025 mmol) was added and the mixture was capped and heated with stirring at 110° C. for 5 hours. After cooling, the reaction mixture was filtered, and the filtrate was concentrated under high vacuum and the residue was dissolved in DMF for purification. The product was purified via preparative HPLC to afford 1-(5-(4-(2-hydroxyethyl)-1H-pyrazol-1-yl)-4-(isopropylamino)pyridin-2-yl)-1H-pyrazolo[3,4-b]pyridine-5-carbonitrile (4.4 mg, 8% yield). $^1$H NMR (500 MHz, DMSO-d$_6$) δ 9.11-8.97 (m, 2H), 8.65 (br s, 1H), 8.36 (br s, 1H), 8.17 (s, 1H), 7.77 (s, 1H), 7.39 (br s, 1H), 7.26 (d, J=7.3 Hz, 1H), 4.76 (br s, 1H), 3.84-3.74 (m, 1H), 3.67-3.59 (m, 2H), 2.67 (t, J=6.9 Hz, 2H), 1.24 (d, J=6.2 Hz, 6H); LC/MS: 389.0 (M+H); HPLC rt 1.37 min, conditions C.

Example 243

1-(5-(4-benzyl-1H-pyrazol-1-yl)-4-(isopropylamino)pyridin-2-yl)-1H-pyrazolo[3,4-b]pyridine-5-carbonitrile

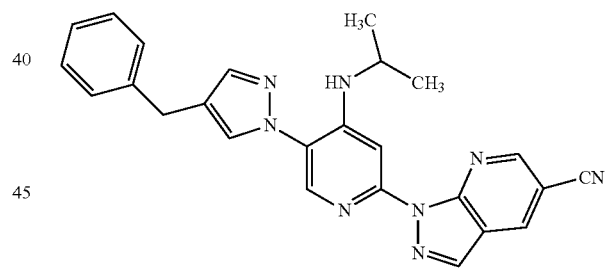

(243)

To a solution of 1-(5-iodo-4-(isopropylamino)pyridin-2-yl)-1H-pyrazolo[3,4-b]pyridine-5-carbonitrile (10 mg, 0.025 mmol) in 1,4-dioxane (0.5 mL), was added 4-benzyl-1H-pyrazole (4.70 mg, 0.030 mmol), Pd$_2$(dba)$_3$ (1.13 mg, 1.24 μmol) and Xantphos (1.43 mg, 2.5 μmol). The mixture was purged with N$_2$ then heated at 85° C. for 3 h. The mixture was cooled and the product purified directly via preparative HPLC to afford 1-(5-(4-benzyl-1H-pyrazol-1-yl)-4-(isopropylamino)pyridin-2-yl)-1H-pyrazolo[3,4-b]pyridine-5-carbonitrile (1.0 mg, 9% yield). $^1$H NMR (500 MHz, DMSO-d$_6$) δ 8.98 (dd, J=11.4, 1.8 Hz, 2H), 8.59 (s, 1H), 8.22 (s, 1H), 8.08 (s, 1H), 7.78 (s, 1H), 7.42-7.25 (m, 5H), 7.18 (s, 1H), 5.39 (s, 2H), 5.34 (d, J=7.7 Hz, 1H), 3.74 (d, J=7.0 Hz, 1H), 1.21 (d, J=6.3 Hz, 6H); LC/MS: 435.3 (M+H); HPLC rt 1.76 min, conditions C.

The Examples in Table 15 were prepared using the methods outlined for Example 243 using the appropriate starting material.

TABLE 15

| Ex. No. | Structure | HPLC rt (min) | HPLC cond. | LCMS |
|---|---|---|---|---|
| 244 | 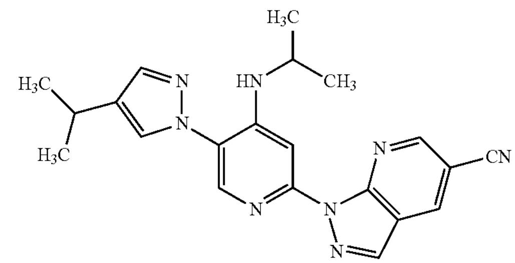 [SMILES: CC(C)Nc1cc(-n2ncc3cc(C#N)cnc32)ncc1-n1cc(C(C)C)cn1] | 2.05 | C | 387.2 |
| 245 | 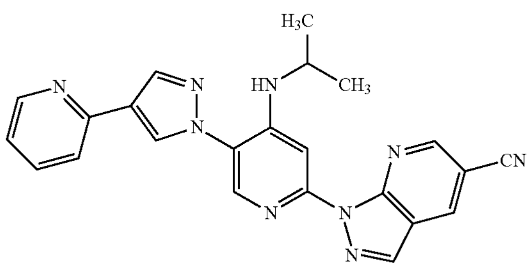 [SMILES: CC(C)Nc1cc(-n2ncc3cc(C#N)cnc32)ncc1-n1cc(-c2ccccn2)cn1] | 1.72 | C | 422.2 |
| 246 | 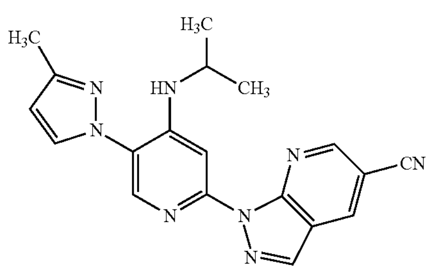 [SMILES: CC(C)Nc1cc(-n2ncc3cc(C#N)cnc32)ncc1-n1ccc(C(F)(F)F)n1] | 1.72 | C | 359.1 |
| 247 | 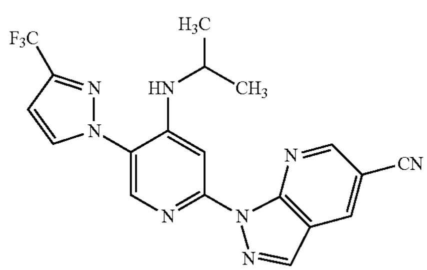 | 1.96 | C | 413.1 |
| 248 | 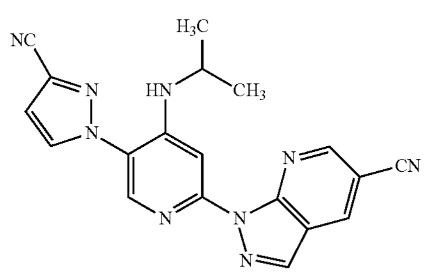 [SMILES: CC(C)Nc1cc(-n2ncc3cc(C#N)cnc32)ncc1-n1ccc(C#N)n1] | 1.36 | D | 370.0 |

TABLE 15-continued

| Ex. No. | Structure | HPLC rt (min) | HPLC cond. | LCMS |
|---|---|---|---|---|
| 249 | 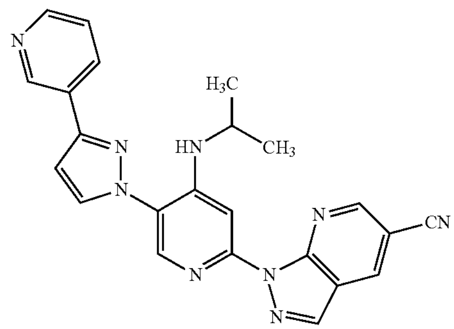 [SMILES: CC(C)Nc1cc(-n2ncc3cc(C#N)cnc32)ncc1-n1ccc(-c2cccnc2)n1] | 1.63 | C | 422.1 |
| 250 | 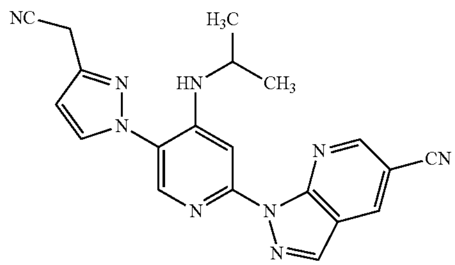 [SMILES: CC(C)Nc1cc(-n2ncc3cc(C#N)cnc32)ncc1-n1ccc(CC#N)n1] | 1.52 | C | 384.1 |
| 251 | 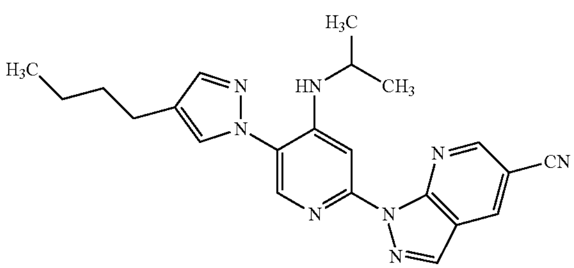 [SMILES: CCCCc1cnn(-c2cnc(-n3ncc4cc(C#N)cnc43)cc2NC(C)C)c1] | 1.45 | C | 402.3 |

Example 252

1-(5-(1-(2-hydroxyethyl)-1H-pyrazol-4-yl)-4-(isopropylamino)pyridin-2-yl)-1H-pyrazolo[3,4-b]pyridine-5-carbonitrile (252)

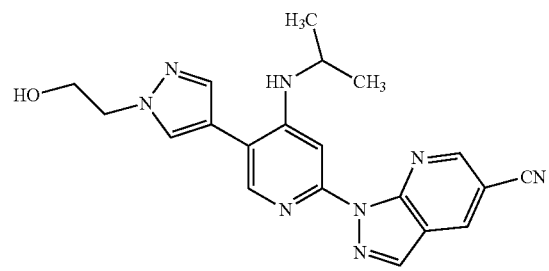

Intermediate 252A: 2-chloro-5-iodopyridin-4-amine

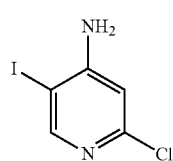

(252A)

To a stirred solution of 2-chloropyridin-4-amine (5 g, 39 mmol) in DMF (50 mL) was added NIS (8.75 g, 39 mmol). The reaction mixture was then heated at 80° C. for 3 h. The mixture was cooled and the DMF removed in vacuo. The residue was partitioned between EtOAc and water and the layers were separated. The organic layer was dried over $Na_2SO_4$, filtered, and concentrated. The product was purified via column chromatography (10% EtOAc/pet ether) to afford 2-chloro-5-iodopyridin-4-amine (4 g, 39% yield).

LCMS: 254.8 (M+). Further elution with 12% EtOAc/pet ether afforded 2-chloro-3-iodopyridin-4-amine (4 g, 39% yield).

Intermediate 252B:
2-chloro-5-iodo-N-isopropylpyridin-4-amine

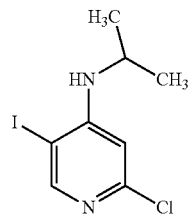

(252B)

To a stirred solution of 2-chloro-5-iodopyridin-4-amine (4 g, 15.7 mmol) in DMF (40 mL), was added NaH (2.26 g, 47.2 mmol) at 0° C. The mixture was allowed to warm to room temperature then was heated at 80° C. 2-Iodopropane (3.14 mL, 31.4 mmol) in 4 mL of DMF was added drop wise and heating continued 4 hours. The mixture was cooled to room temperature and quenched with crushed ice. The product was extracted with DCM (2×20 mL) and the organic layer was dried over $Na_2SO_4$, filtered, and concentrated. Purification via column chromatography (10% EA/pet ether) afforded 2-chloro-5-iodo-N-isopropylpyridin-4-amine (2.8 g, 60% yield) as a colorless liquid. $^1$H NMR (400 MHz, CDCl3) δ 8.28 (s, 1H), 6.42 (s, 1H), 4.65-4.63 (m, 1H), 3.75-3.64 (m, 1H), 1.32-1.27 (m, 6H); LC/MS: 296.6 (M+).

Intermediate 252C: 2-chloro-N-isopropyl-5-(1H-pyrazol-4-yl)pyridin-4-amine

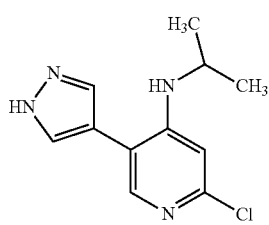

(252C)

To a stirred solution of 2-chloro-5-iodo-N-isopropylpyridin-4-amine (500 mg, 1.7 mmol) in DMF (10 mL) and water (1 mL) was added tert-butyl 4-(4,4,5,5-tetramethyl-1,3,2-dioxaborolan-2-yl)-1H-pyrazole-1-carboxylate (496 mg, 1.7 mmol) and $K_2CO_3$ (700 mg, 5.06 mmol). The mixture was degassed via nitrogen bubble for 2 min and 2nd generation Xphos precatalyst (133 mg, 0.169 mmol) was added and the degassing was continued for another 2 mins. The mixture was sealed and heated at 100° C. for 3 h. The reaction mixture was cooled and concentrated. EtOAc (150 mL) was added and the organic layer was washed with ice cold water (2×20 mL). The organic layer was dried over $Na_2SO_4$, filtered and concentrated. The product was purified via column chromatography (30% EtOAc/pet ether) to afford 2-chloro-N-isopropyl-5-(1H-pyrazol-4-yl)pyridin-4-amine (250 mg, 63% yield). $^1$H NMR (400 MHz, DMSO-d$_6$) δ 13.14 (br s, 1H) 7.94-8.03 (m, 1H) 7.80 (br s, 1H) 7.70 (s, 1H) 6.61 (s, 1H) 5.76 (s, 1H) 5.29 (d, J=8.53 Hz, 3H) 3.74 (dq, J=14.37, 6.42 Hz, 1H) 1.01-1.35 (m, 6H); LC/MS: 236.9 (M+).

Intermediate 252D: Ethyl 2-(4-(6-chloro-4-(isopropylamino)pyridin-3-yl)-1H-pyrazol-1-yl)acetate

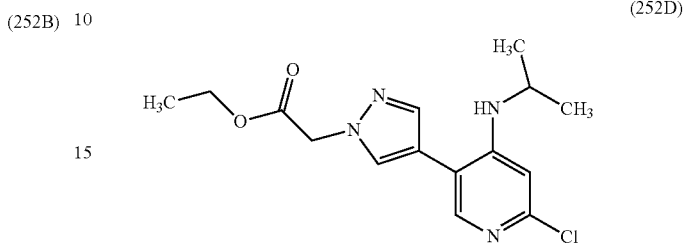

(252D)

To a stirred solution of 2-chloro-N-isopropyl-5-(1H-pyrazol-4-yl)pyridin-4-amine (150 mg, 0.63 mmol) in DMF (2 mL), was added $Cs_2CO_3$ (310 mg, 0.95 mmol) and ethyl bromoacetate (0.085 mL, 0.76 mmol). The reaction mixture was heated at 100° C. for 15 hours in a sealed tube. The reaction mixture was cooled and the DMF was removed. The residue was diluted with 50 mL of ethyl acetate and washed with ice water (2×20 mL). The organic layer was dried over $Na_2SO_4$, filtered, and concentrated. The residue was purified via column chromatography (25% EtOAc/pet ether) to afford ethyl 2-(4-(6-chloro-4-(isopropylamino)pyridin-3-yl)-1H-pyrazol-1-yl)acetate (140 mg, 68% yield). $^1$H NMR (400 MHz, DMSO-d$_6$) δ 8.06 (s, 1H) 7.81-7.87 (m, 1H) 7.72 (s, 1H) 6.64 (s, 1H) 5.17-5.24 (m, 1H) 5.12 (s, 2H) 4.12-4.25 (m, 2H) 3.76 (dq, J=14.49, 6.38 Hz, 1H) 1.20-1.29 (m, 3H) 1.12-1.18 (m, 6H); LC/MS: 322.7 (M+).

Intermediate 252E: 2-(4-(6-Chloro-4-(isopropylamino)pyridin-3-yl)-1H-pyrazol-1-yl) ethanol

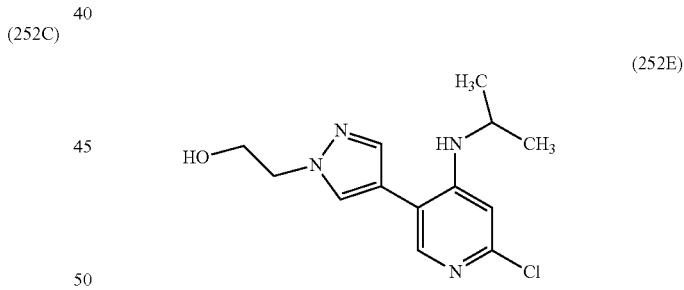

(252E)

To a stirred solution of ethyl 2-(4-(6-chloro-4-(isopropylamino)pyridin-3-yl)-1H-pyrazol-1-yl)acetate (140 mg, 0.43 mmol) in THF (6 mL) was added LAH in THF (0.88 mL, 0.88 mmol) drop wise at 0° C. The reaction mixture was allowed to warm to room temperature and stir for 1 h. The reaction mixture was quenched with sat. sodium sulfate solution, filtered through celite, and washed with ethyl acetate. The filtrate was evaporated to afford 2-(4-(6-chloro-4-(isopropylamino)pyridin-3-yl)-1H-pyrazol-1-yl) ethanol (100 mg, 82% yield) which was used directly in the next step.

Example 252

A stirred solution of 2-(4-(6-chloro-4-(isopropylamino)pyridin-3-yl)-1H-pyrazol-1-yl)ethanol (50 mg, 0.18 mmol), 1H-pyrazolo[3,4-b]pyridine-5-carbonitrile (25.7 mg, 0.18 mmol), XANTPHOS (30.9 mg, 0.05 mmol), K$_2$CO$_3$ (73.8 mg, 0.534 mmol), LiCl (7.6 mg, 0.18 mmol) and ZnCl$_2$ (7.3 mg, 0.05 mmol) in 1,4-dioxane (5 mL) was degassed with N$_2$ for 5 mins then Pd$_2$(dba)$_3$ (50 mg, 0.053 mmol) was added. The reaction mixture was further degassed for 5 min then heated at 120° C. for 20 hours in a sealed tube. The reaction mixture was cooled to room temperature and filtered through celite with EtOAc. The EtOAc washings were washed with 20 mL of 1.5N HCl and extracted with DCM for (2×20 mL). The aqueous layer was basified with NaHCO$_3$ solution and extracted with 10% MeOH/Chloroform for (4×50 mL) and the organic layer was dried over Na$_2$SO$_4$, filtered, and concentrated. The compound was further purified by preparative HPLC and lyophilized to afford 1-(5-(1-(2-hydroxyethyl)-1H-pyrazol-4-yl)-4-isopropylamino) pyridin-2-yl)-1H-pyrazolo[3,4-b]pyridine-5-carbonitrile (3 mg, 4% yield) as off white solid. $^1$H NMR (400 MHz, methanol-d$_4$) δ 8.97 (d, J=2.01 Hz, 1H) 8.84 (d, J=2.01 Hz, 1H) 8.53 (s, 1H) 8.02-8.10 (m, 1H) 7.96 (s, 1H) 7.73-7.78 (m, 1H) 7.62 (br s, 1H) 4.31-4.39 (m, 2H) 3.96-4.02 (m, 2H) 3.90 (dt, J=12.93, 6.34 Hz, 1H) 1.28-1.36 (m, 6H); LC/MS: 389.2 (M+H); HPLC rt 2.59 min, conditions E.

Example 253

1-(5-(1-ethyl-1H-pyrazol-4-yl)-4-(isopropylamino) pyridin-2-yl)-1H-pyrazolo[3,4-b]pyridine-5-carbonitrile

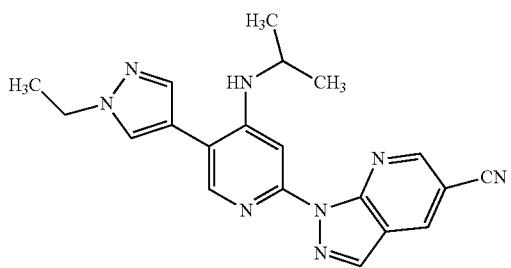

(253)

A mixture of 1-(5-iodo-4-(isopropylamino)pyridin-2-yl)-1H-pyrazolo[3,4-b]pyridine-5-carbonitrile (10 mg, 0.025 mmol), (1-ethyl-1H-pyrazol-4-yl)boronic acid (3.5 mg, 0.025 mmol), Pd(dppf)Cl$_2$ (1.8 mg, 0.003 mmol), and K$_3$PO$_4$ in dioxane (1 mL) was purged with N$_2$ and heated in a sealed microwave vial at 125° C. for 45 min. The mixture was cooled to room temperature and purified directly via preparative HPLC to afford 1-(5-(1-ethyl-1H-pyrazol-4-yl)-4-(isopropylamino)pyridin-2-yl)-1H-pyrazolo[3,4-b]pyridine-5-carbonitrile (4.3 mg, 46% yield). $^1$H NMR (500 MHz, DMSO-d$_6$) δ 8.97 (d, J=11.4 Hz, 2H), 8.58 (s, 1H), 8.06 (d, J=3.1 Hz, 2H), 7.73 (s, 1H), 7.17 (s, 1H), 5.36 (d, J=7.8 Hz, 1H), 4.20 (q, J=7.2 Hz, 2H), 1.43 (t, J=7.3 Hz, 3H), 1.21 (d, J=6.3 Hz, 6H); LC/MS: 373.2 (M+H); HPLC rt 1.60 min, conditions C.

Example 254

1-(4-(isopropylamino)-5-(1-(oxetan-3-ylmethyl)-1H-pyrazol-4-yl)pyridin-2-yl)-1H-pyrazolo[3,4-b]pyridine-5-carbonitrile

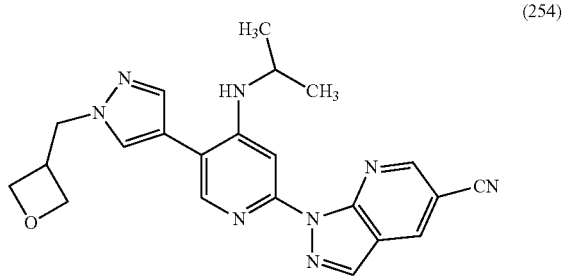 [SMILES: CC(C)Nc1cc(-n2ncc3cc(C#N)cnc32)ncc1-c1cnn(CC2COC2)c1]

(254)

To a solution of 4-(4,4,5,5-tetramethyl-1,3,2-dioxaborolan-2-yl)-1H-pyrazole (4.8 mg, 0.0255 mmol) in DMF (0.5 mL), was added K$_2$CO$_3$ (10.3 mg, 0.074 mmol) and 3-(bromomethyl)oxetane (7.47 mg, 0.05 mmol). The mixture was purged with N$_2$, sealed, and heated at 80° C. for 3 h. The reaction mixture was checked by LC-MS to confirm alkylation of the boronate. Then the mixture was added 1-(5-iodo-4-(isopropylamino) pyridin-2-yl)-1H-pyrazolo[3,4-b]pyridine-5-carbonitrile (10 mg, 0.025 mmol) and Pd(dppf)Cl$_2$ (1.8 mg, 2.5 µmol), purged with N$_2$, and heated at 90° C. for 2 h. The mixture was then cooled to room temperature and purified directly via preparative HPLC to afford 1-(4-(isopropylamino)-5-(1-(oxetan-3-ylmethyl)-1H-pyrazol-4-yl)pyridin-2-yl)-1H-pyrazolo[3,4-b]pyridine-5-carbonitrile (0.6 mg, 6% yield). $^1$H NMR (500 MHz, DMSO-d$_6$) δ 9.04 (s, 2H), 8.75-8.58 (m, 1H), 8.11 (s, 2H), 7.80 (s, 1H), 7.44-7.29 (m, 1H), 5.17-4.96 (m, 1H), 4.59-4.32 (m, 4H), 4.29-3.94 (m, 2H), 2.76-2.61 (m, 1H), 1.24 (d, J=6.2 Hz, 6H); LC/MS: 415.1 (M+H); HPLC rt 1.42 min, conditions C.

Example 255

1-(4-(isopropylamino)-5-(1-(2,2,2-trifluoroethyl)-1H-pyrazol-4-yl)pyridin-2-yl)-1H-pyrazolo[3,4-b]pyridine-5-carbonitrile

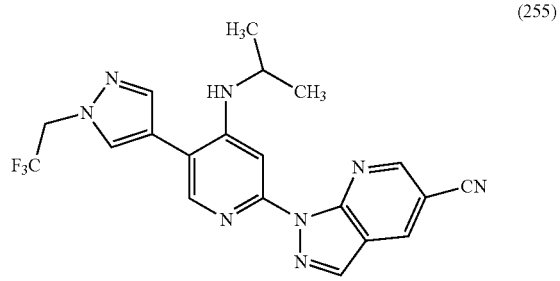 [SMILES: CC(C)Nc1cc(-n2ncc3cc(C#N)cnc32)ncc1-c1cnn(CC(F)(F)F)c1]

(255)

Intermediate 255A: 4-(4,4,5,5-tetramethyl-1,3,2-dioxaborolan-2-yl)-1-(2,2,2-trifluoroethyl)-1H-pyrazole

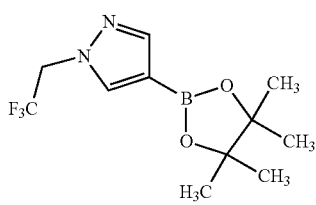

(255A)

To a stirred solution of 4-(4,4,5,5-tetramethyl-1,3,2-dioxaborolan-2-yl)-1H-pyrazole (400 mg, 2.06 mmol) in DMF (2 mL) was added $Cs_2CO_3$ (1.0 g mg, 3.1 mmol) and 2,2,2-trifluoroethyl triflate (0.58 mL, 4.1 mmol). The mixture was heated at 100° C. for 2 hours. After cooling, the mixture was concentrated to dryness then partitioned between EtOAc and water. The layers were separated and the organic layer was dried over $Na_2SO_4$, filtered, and concentrated to afford the crude product which was used directly in the next step. $^1$H NMR (400 MHz, CHLOROFORM-d) δ 7.85 (s, 1H) 7.80 (s, 1H) 4.64-4.76 (m, 2H), 1.32 (s, 12H).

Intermediate 255B: 2-Chloro-N-isopropyl-5-(1-(2,2,2-trifluoroethyl)-1H-pyrazol-4-yl) pyridin-4-amine

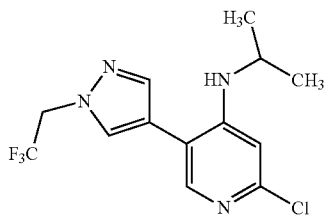

(255B)

To a stirred solution of 5-bromo-2-chloro-N-isopropylpyridin-4-amine (300 mg, 1.202 mmol) in DMF (10 mL) and water (1 mL) was added 4-(4,4,5,5-tetramethyl-1,3,2-dioxaborolan-2-yl)-1-(2,2,2-trifluoroethyl)-1H-pyrazole (498 mg, 1.8 mmol) and $K_2CO_3$ (498 mg, 3.6 mmol). The mixture was degassed by bubbling nitrogen for 2 mins. 2nd generation Xphos precatalyst (95 mg, 0.12 mmol) was added and the mixture was further degassed for 2 min. The mixture was sealed and heated at 100° C. for 3 hours. After cooling, the mixture was concentrated to dryness then partitioned between EtOAc (150 mL) and ice water (20 mL). The layers were separated and the organic layer washed again with cold water. The organic layer was dried over $Na_2SO_4$, filtered, and concentrated. The product was purified via column chromatography (30% EtOAc/pet ether) to afford 2-chloro-N-isopropyl-5-(1-(2,2,2-trifluoroethyl)-1H-pyrazol-4-yl)pyridin-4-amine (170 mg, 44% yield). LCMS: 319.3 (M+H).

Example 255

A stirred solution of 2-chloro-N-isopropyl-5-(1-(2,2,2-trifluoroethyl)-1H-pyrazol-4-yl)pyridin-4-amine (40 mg, 0.13 mmol), 1H-pyrazolo[3,4-b]pyridine-5-carbonitrile (18.1 mg, 0.13 mmol), Xantphos (73 mg, 0.13 mmol), $K_2CO_3$ (52 mg, 0.38 mmol), LiCl (5.3 mg, 0.13 mmol) and $ZnCl_2$ (5.1 mg, 0.04 mmol) in 1,4-dioxane (5 mL) was degassed with $N_2$ for 5 mins. $Pd_2(dba)_3$ (58 mg, 0.063 mmol) was added and the mixture was degassed further with $N_2$ for 5 mins then heated at 120° C. for 20 hours in a sealed tube. The reaction mixture was cooled and filtered through a bed of celite. The celite was rinsed with 50 mL of EtOAc and the concentrated organic filtrates were purified via preparative HPLC to afford 1-(4-(isopropylamino)-5-(1-(2,2,2-trifluoroethyl)-1H-pyrazol-4-yl)pyridin-2-yl)-1H-pyrazolo[3,4-b]pyridine-5-carbonitrile (6 mg, 11% yield). $^1$H NMR: (400 MHz, DMSO-$d_6$) δ 9.08-8.96 (m, 2H), 8.62 (br s, 1H), 8.23 (s, 1H), 8.13 (d, J=10.5 Hz, 1H), 7.91 (s, 1H), 7.22 (br s, 1H), 5.38 (d, J=8.0 Hz, 1H), 5.28-5.14 (m, 2H), 3.77 (dq, J=13.4, 6.6 Hz, 1H), 1.29-1.18 (m, 6H); LCMS 427.3 (M+H); HPLC rt 1.60 min, Conditions E.

Example 256

1-(4-((1-(2,2-difluoroethyl)-1H-pyrazol-4-yl)amino)-5-(1-propyl-1H-pyrazol-4-yl) pyridin-2-yl)-1H-pyrazolo[3,4-b]pyridine-5-carbonitrile

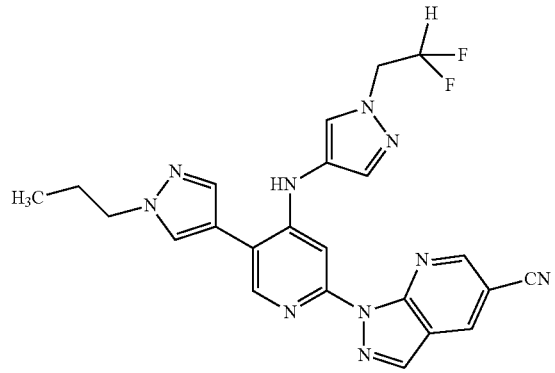

(256)

Intermediate 256A: 5-bromo-2-chloro-N-(1-(2,2-difluoroethyl)-1H-pyrazol-4-yl)pyridin-4-amine

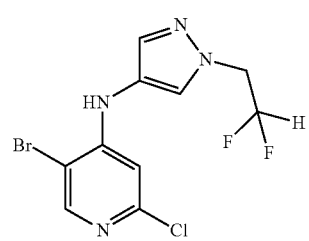

(256A)

To a stirred solution of 5-bromo-2,4-dichloropyridine (1 g, 4.41 mmol) in DMA (10 mL) was added 1-(2,2-difluoroethyl)-1H-pyrazol-4-amine (0.648 g, 4.41 mmol) and DIPEA (3.08 mL, 17.6 mmol). The reaction mixture was heated at 120° C. for 14 hours. After cooling, the mixture was concentrated to dryness then partitioned between EtOAc and water. The layers were separated and the organic layer was dried over Na$_2$SO$_4$, filtered, and concentrated. The product was purified via column chromatography (15% EtOAc/pet ether) to afford 5-bromo-2-chloro-N-(1-(2,2-difluoroethyl)-1H-pyrazol-4-yl) pyridin-4-amine (0.55 g, 35% yield). $^1$H NMR: (300 MHz, DMSO-d$_6$) δ 8.12-8.28 (m, 2H) 7.95 (s, 1H) 7.61 (s, 1H) 6.13-6.66 (m, 2H) 4.64 (td, J=15.11, 3.40 Hz, 2H); LCMS 338.9 (M+2).

Intermediate 256B: 2-chloro-N-(1-(2,2-difluoro-ethyl)-1H-pyrazol-4-yl)-5-(1-propyl-1H-pyrazol-4-yl)pyridin-4-amine (256B)

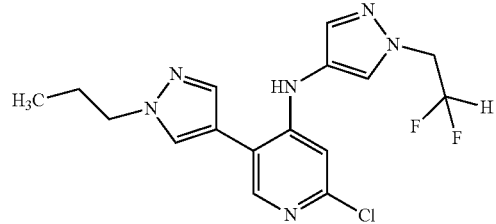

To a stirred solution of 5-bromo-2-chloro-N-(1-(2,2-difluoroethyl)-1H-pyrazol-4-yl)pyridin-4-amine (500 mg, 1.481 mmol) in DMF (10 mL) and water (1 mL) was added 1-propyl-4-(4,4,5,5-tetramethyl-1,3,2-dioxaborolan-2-yl)-1H-pyrazole (350 mg, 1.481 mmol) and K$_2$CO$_3$ (614 mg, 4.44 mmol). The mixture was degassed by bubbling nitrogen for 2 min. 2nd generation Xphos precatalyst (117 mg, 0.15 mmol) was added and the mixture was further degassed for 2 min. The mixture was sealed and heated at 100° C. for 6 hours. After cooling, the mixture was concentrated to dryness then partitioned between EtOAc (150 mL) and ice water (20 mL). The layers were separated and the organic layer washed again with cold water. The organic layer was dried over Na$_2$SO$_4$, filtered, and concentrated. The product was purified via column chromatography (30% EtOAc/pet ether) to afford 2-chloro-N-(1-(2,2-difluoroethyl)-1H-pyrazol-4-yl)-5-(1-propyl-1H-pyrazol-4-yl)pyridin-4-amine (155 mg, 27% yield). $^1$H NMR: (300 MHz, DMSO-d$_6$) δ 7.92-7.99 (m, 2H), 7.87 (s, 1H), 7.71 (s, 1H), 7.51-7.59 (m, 2H), 6.51-6.19 (m, 2H), 4.63 (td, J=15.11, 3.78 Hz, 2H), 4.05-4.19 (m, 2H), 1.84 (sxt, J=7.25 Hz, 2H), 0.80-0.96 (m, 3H); LCMS: 367.2 (M+H).

Example 256

A stirred solution of 2-chloro-N-(1-(2,2-difluoroethyl)-1H-pyrazol-4-yl)-5-(1-propyl-1H-pyrazol-4-yl)pyridin-4-amine (50 mg, 0.136 mmol), 1H-pyrazolo[3,4-b]pyridine-5-carbonitrile (20 mg, 0.14 mmol), Xantphos (47 mg, 0.08 mmol), K$_2$CO$_3$ (57 mg, 0.41 mmol), LiCl (5.8 mg, 0.14 mmol) and ZnCl$_2$ (5.6 mg, 0.04 mmol) in 1,4-dioxane (5 mL) was degassed with N$_2$ for 5 mins. Pd$_2$(dba)$_3$ (37 mg, 0.04 mmol) was added and the mixture was degassed further with N$_2$ for 5 mins then heated at 120° C. for 20 hours in a sealed tube. The reaction mixture was cooled and filtered through a bed of celite. The celite was rinsed with 50 mL of EtOAc and the concentrated organic filtrates were purified via preparative HPLC to afford 1-(4-((1-(2,2-difluoroethyl)-1H-pyrazol-4-yl)amino)-5-(1-propyl-1H-pyrazol-4-yl)pyridin-2-yl)-1H-pyrazolo[3,4-b]pyridine-5-carbonitrile (20 mg, 30% yield). $^1$H NMR: (400 MHz, DMSO-d$_6$) δ 9.00 (s, 2H), 8.61 (s, 1H), 8.20 (br s, 1H), 8.14 (s, 1H), 7.89 (s, 1H), 7.79 (s, 1H), 7.73 (br s, 1H), 7.61 (s, 1H), 7.51-7.42 (m, 1H), 6.54-6.19 (m, 1H), 4.64 (td, J=15.2, 3.5 Hz, 2H), 4.19-4.08 (m, 2H), 1.95-1.78 (m, 2H), 0.98-0.84 (m, 3H); LCMS 475.2 (M+H); HPLC rt 1.66 min, Conditions E.

The Examples in Table 16 were prepared using the methods outlined for Example 256 using the appropriate starting material.

TABLE 16

| Ex. No. | Structure | HPLC rt (min) | HPLC cond. | LCMS |
|---|---|---|---|---|
| 257 | 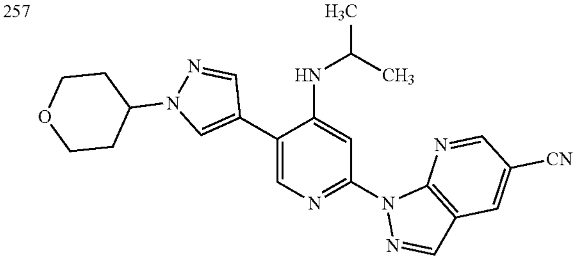 | 1.82 | E | 429.2 |
| 258 | 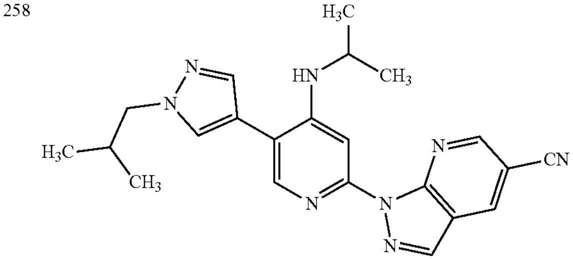 | 1.88 | C | 398.8 |

TABLE 16-continued

| Ex. No. | Structure | HPLC rt (min) | HPLC cond. | LCMS |
|---|---|---|---|---|
| 259 | 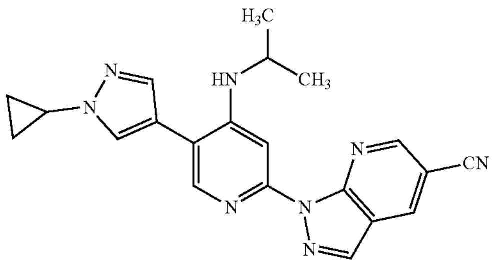 [SMILES: CC(C)Nc1cc(-n2ncc3cc(C#N)cnc32)ncc1-c1cnn(C2CC2)c1] | 1.58 | C | 385.2 |
| 260 | 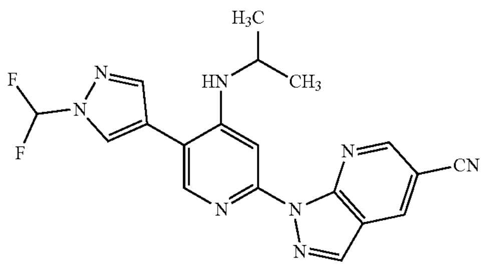 [SMILES: CC(C)Nc1cc(-n2ncc3cc(C#N)cnc32)ncc1-c1cnn(C(F)F)c1] | 1.59 | C | 395.1 |
| 261 | 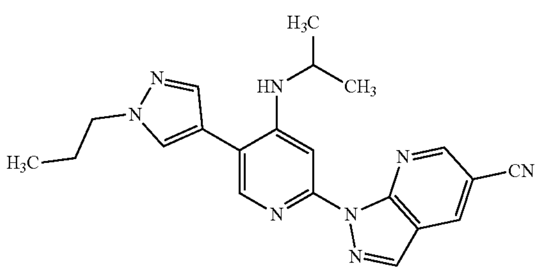 [SMILES: CCCn1cc(-c2cnc(-n3ncc4cc(C#N)cnc43)cc2NC(C)C)cn1] | 1.64 | C | 387.2 |
| 262 | 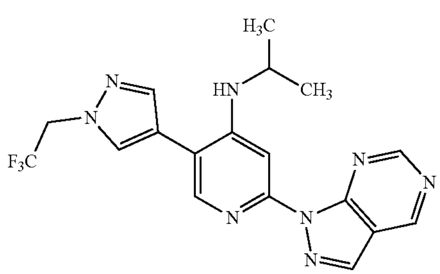 [SMILES: CC(C)Nc1cc(-n2ncc3cncnc32)ncc1-c1cnn(CC(F)(F)F)c1] | 1.35 | E | 403.3 |

Example 263

1-(4-(isopropylamino)-5-(4-propyl-1H-1,2,3-triazol-1-yl)pyridin-2-yl)-1H-pyrazolo[3,4-b]pyridine-5-carbonitrile

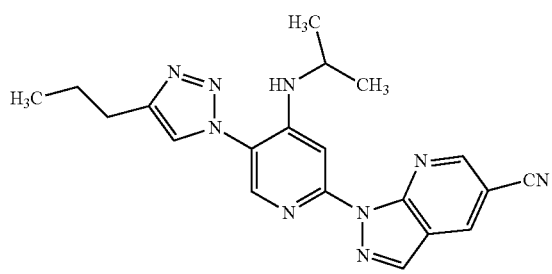

(263)

Intermediate 263A:
5-bromo-2-chloro-N-isopropylpyridin-4-amine

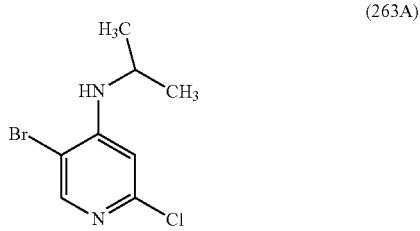

(263A)

To a stirred solution of 5-bromo-2,4-dichloropyridine (3.0 g, 13.22 mmol), isopropylamine (1.7 mL, 19.83 mmol), and Hunig's Base (11.6 mL, 66.1 mmol) in DMF (5 mL) at room temperature was then heated at 120° C. behind a safety shield for 4 hours, at which point it was judged to be complete by LCMS. The reaction mixture was diluted with ethyl acetate and washed 10% LiCl (3×). The organic layer was dried over $Na_2SO_4$, filtered and concentrated to afford the crude product. The product was purified by column chromatography (hexanes/EtOAc) to afford 5-bromo-2-chloro-N-isopropylpyridin-4-amine (1.29 g, 37% yield) as a colorless oil. LCMS m/z 249.0 (M+H).

Intermediate 263B: 2-chloro-N-isopropyl-5-(4-propyl-1H-1,2,3-triazol-1-yl)pyridin-4-amine (263B)

To a stirred suspension of 5-bromo-2-chloro-N-isopropylpyridin-4-amine (100 mg, 0.401 mmol), sodium azide (52.1 mg, 0.801 mmol), sodium ascorbate (7.94 mg, 0.040 mmol), N1,N2-dimethylethane-1,2-diamine (10.60 mg, 0.120 mmol) in ethanol (1.4 ml) and $H_2O$ (0.600 ml) at room temperature was bubbled nitrogen for 5 minutes then copper (I) iodide (15.26 mg, 0.080 mmol) and pent-1-yne (136 mg, 2.0 mmol) were added. The reaction mixture was heated at 90° C. for 2 hours, cooled to 25° C. and added another set of reagents as above. Heating was continued for 16 hours at which point the reaction was judged to be complete by LCMS. The reaction mixture was diluted with ethyl acetate (2 mL), filtered, and concentrated in vacuo. Purified by MPLC (hexanes/EtOAc) to afford 2-chloro-N-isopropyl-5-(4-propyl-1H-1,2,3-triazol-1-yl) pyridin-4-amine (46 mg, 37% yield). LCMS 252.2 $(M-N_2)^+$.

Example 263

In a 20 mL microwave vial, a mixture of 2-chloro-N-isopropyl-5-(4-propyl-1H-1,2,3-triazol-1-yl)pyridin-4-amine (24 mg, 0.086 mmol), 1H-pyrazolo[3,4-b]pyridine-5-carbonitrile (18.55 mg, 0.129 mmol), and potassium phosphate, tribasic (54.6 mg, 0.257 mmol) in dioxane (1 mL) was degassed with bubbling nitrogen for 5 minutes. In a separate vial, a stirring, degassed mixture of tetramethyl t-BuXphos (9.07 mg, 0.019 mmol) and $Pd_2(dba)_3$ (7.86 mg, 8.58 µmol) in 5:1 toluene/dioxane (0.5 mL) was heated at 120° C. for 3 minutes. After this mixture cooled to room temperature, it was added to the vial containing the reaction mixture, and the vial was sealed. The reaction mixture was heated with stirring at 90° C. for 18 hours at which point it was judged to be complete by LCMS. The reaction mixture was diluted with ethyl acetate (2 mL), filtered, and concentrated in vacuo. The product was purified by preparative HPLC to afford 1-(4-(isopropylamino)-5-(4-propyl-1H-1,2,3-triazol-1-yl)pyridin-2-yl)-1H-pyrazolo[3,4-b]pyridine-5-carbonitrile, TFA (15 mg, 34% yield). $^1$H NMR (500 MHz, DMSO-$d_6$) δ 9.05 (s, 1H), 9.01 (s, 1H), 8.66 (br. s., 1H), 8.38 (s, 1H), 8.32 (br. s., 1H), 7.50 (br. s., 1H), 6.58 (d, J=7.3 Hz, 1H), 3.87-3.76 (m, 1H), 2.72 (t, J=7.5 Hz, 2H), 1.72 (sxt, J=7.4 Hz, 2H), 1.23 (d, J=6.3 Hz, 6H), 0.99 (t, J=7.3 Hz, 3H). LCMS 388.3 $(M+H)^+$. HPLC rt 1.65 min, conditions C.

Example 264

1-(4-((2-hydroxy-2-methylpropyl)amino)-5-(4-(2-hydroxypropyl)-1H-1,2,3-triazol-1-yl)pyridin-2-yl)-1H-pyrazolo[3,4-b]pyridine-5-carbonitrile

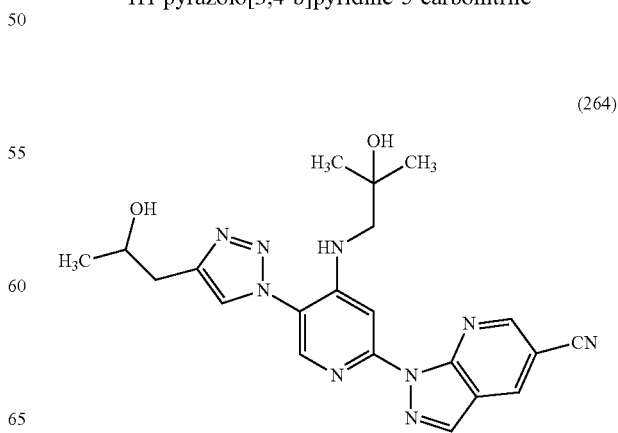

(264)

Intermediate 264A: 1-((5-bromo-2-chloropyridin-4-yl)amino)-2-methylpropan-2-ol

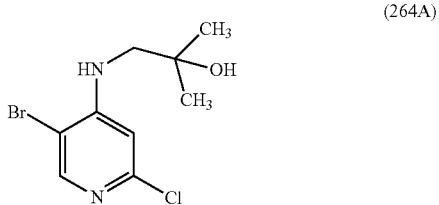

(264A)

A stirred solution of 5-bromo-2,4-dichloropyridine (500 mg, 2.20 mmol), 1-amino-2-methylpropan-2-ol (196 mg, 2.20 mmol) and Hunig's Base (1.155 mL, 6.61 mmol) in DMA (10 mL) at room temperature was then heated at 100° C. behind a safety shield for 2 hours. The reaction mixture was cooled and diluted with ethyl acetate and washed 10% LiCl (3×). The organic layer was dried over $Na_2SO_4$, filtered and concentrated to afford 1-((5-bromo-2-chloropyridin-4-yl)amino)-2-methylpropan-2-ol (650 mg, 1.744 mmol, 79% yield) as an amber oil. LCMS m/z 278.8 (M+H).

Intermediate 264B: 1-((2-chloro-5-(4-(2-hydroxypropyl)-1H-1,2,3-triazol-1-yl)pyridin-4-yl)amino)-2-methylpropan-2-ol

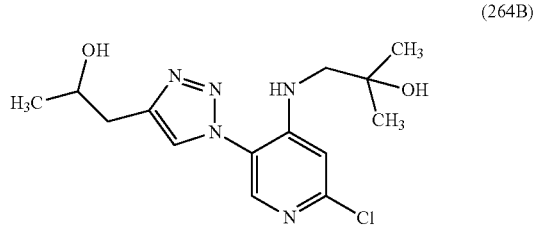 [SMILES: CC(O)Cc1cn(-c2cnc(Cl)cc2NCC(C)(C)O)nn1]

(264B)

To a stirred suspension of 1-((5-bromo-2-chloropyridin-4-yl)amino)-2-methylpropan-2-ol (400 mg, 1.43 mmol), sodium azide (98 mg, 1.50 mmol), sodium ascorbate (28.3 mg, 0.14 mmol), (1S,2S)—N1,N2-dimethylcyclohexane-1,2-diamine (30.5 mg, 0.22 mmol) in DMSO (10 ml) and $H_2O$ (2 ml) at room temperature was bubbled nitrogen for 5 minutes then copper(I) iodide (27.2 mg, 0.14 mmol) and pent-4-yn-2-ol (120 mg, 1.43 mmol) were mixed together at room temperature with stirring. Nitrogen was bubbled through the mixture for 5 minutes and then heated at 70° C. for 16 hours. The reaction mixture was cooled to 25° C. and another set of reagents was added as above. Heating at 70° C. was continued for 16 hours, at which point the reaction was judged to be complete by LCMS. The reaction mixture was diluted with ethyl acetate (50 mL) and washed with water (3×). The organic layer was dried over $Na_2SO_4$, filtered and concentrated to afford 1-((2-chloro-5-(4-(2-hydroxypropyl)-1H-1,2,3-triazol-1-yl) pyridin-4-yl)amino)-2-methylpropan-2-ol (74 mg, 11% yield). LCMS 326.0 $(M+H)^+$.

Example 264

In a 20 mL microwave vial, a mixture of 1-((2-chloro-5-(4-(2-hydroxypropyl)-1H-1,2,3-triazol-1-yl)pyridin-4-yl) amino)-2-methylpropan-2-ol (60 mg, 0.184 mmol), 1H-pyrazolo[3,4-b]pyridine-5-carbonitrile (26.5 mg, 0.184 mmol) and potassium phosphate, tribasic (117 mg, 0.552 mmol) in dioxane (1 mL) was degassed with bubbling nitrogen for 5 minutes. In a separate vial, a stirring, degassed mixture of tetramethyl t-BuXphos (19.48 mg, 0.041 mmol) and $Pd_2(dba)_3$ (16.86 mg, 0.018 mmol) in 5:1 toluene/dioxane (0.5 mL) was heated at 120° C. for 3 minutes. After this mixture cooled to room temperature, it was added to the vial containing the reaction mixture, and the vial was sealed. The reaction mixture was heated with stirring at 90° C. for 18 hours at which point it was judged to be complete by LCMS. The reaction mixture was diluted with ethyl acetate (2 mL), filtered, and concentrated in vacuo. The product was purified by preparative HPLC to afford 1-(4-((2-hydroxy-2-methylpropyl)amino)-5-(4-(2-hydroxypropyl)-1H-1,2,3-triazol-1-yl)pyridin-2-yl)-1H-pyrazolo[3,4-b]pyridine-5-carbonitrile, TFA (15 mg, 13% yield). $^1$H NMR (500 MHz, DMSO-$d_6$) δ 9.06 (d, J=18.0 Hz, 2H), 8.67 (br. s., 1H), 8.46 (s, 1H), 8.41 (br. s., 1H), 7.53 (br. s., 1H), 6.87 (br. s., 1H), 4.05-3.95 (m, 1H), 3.21 (d, J=5.2 Hz, 2H), 2.93-2.70 (m, 3H), 2.55 (s, 2H), 1.16 (s, 9H). LCMS 434.2 $(M+H)^+$. HPLC rt 1.02 min, conditions C.

The Examples in Table 17 were prepared using the methods outlined above using the appropriate starting material.

TABLE 17

| Ex. No. | Structure | HPLC rt (min) | HPLC cond. | LCMS |
|---|---|---|---|---|
| 265 single enantiomer | 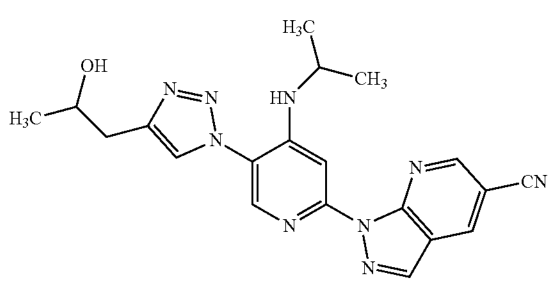 [SMILES: CC(O)Cc1cn(-c2cnc(-n3ncc4cc(C#N)cnc43)cc2NC(C)C)nn1] | 1.22 | C | 404.2 |

TABLE 17-continued

| Ex. No. | Structure | HPLC rt (min) | HPLC cond. | LCMS |
|---|---|---|---|---|
| 266 | 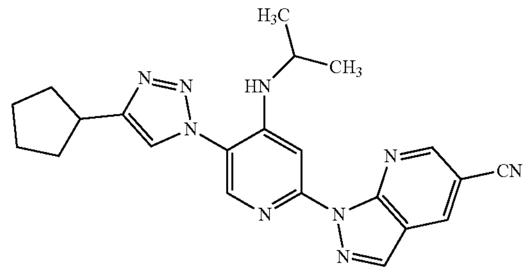 [SMILES: CC(C)Nc1cc(-n2ncc3cc(C#N)cnc32)ncc1-n1cc(C2CCCC2)nn1] | 1.85 | C | 414.1 |
| 267 | 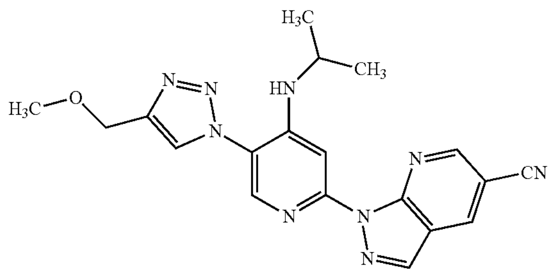 [SMILES: COCc1cn(-c2cnc(-n3ncc4cc(C#N)cnc43)cc2NC(C)C)nn1] | 1.39 | C | 390.2 |
| 268 | 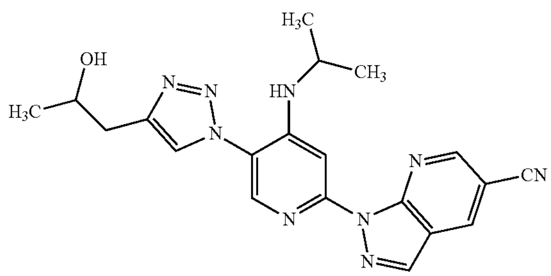 [SMILES: CC(O)Cc1cn(-c2cnc(-n3ncc4cc(C#N)cnc43)cc2NC(C)C)nn1] | 1.22 | C | 404.2 |
| 269 | 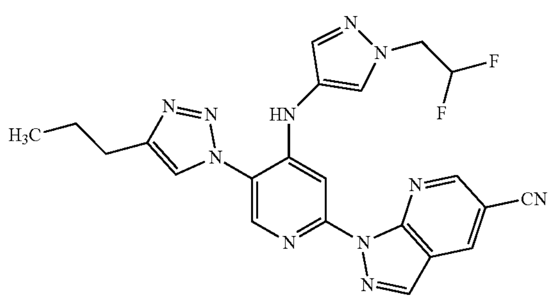 [SMILES: CCCc1cn(-c2cnc(-n3ncc4cc(C#N)cnc43)cc2Nc2cnn(CC(F)F)c2)nn1] | 1.40 | C | 476.2 |
| 270 | 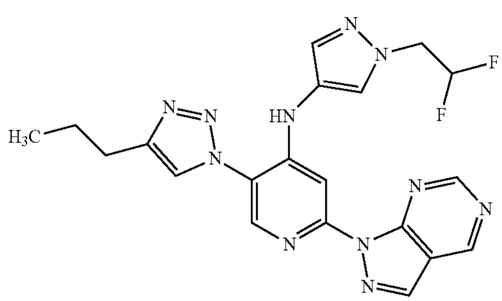 [SMILES: CCCc1cn(-c2cnc(-n3ncc4cncnc43)cc2Nc2cnn(CC(F)F)c2)nn1] | 1.22 | C | 452.2 |

TABLE 17-continued

| Ex. No. | Structure | HPLC rt (min) | HPLC cond. | LCMS |
|---|---|---|---|---|
| 271 | 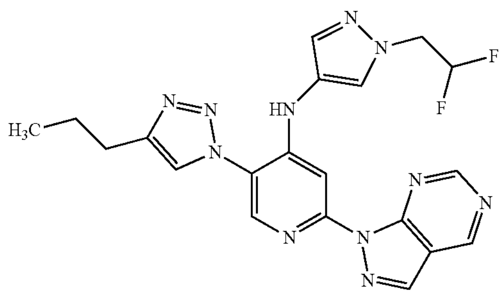 [SMILES: CCCc1cn(-c2cnc(-n3ncc4cncnc43)cc2Nc2cnn(CC(F)F)c2)nn1] | 1.34 | C | 452.0 |
| 272 | 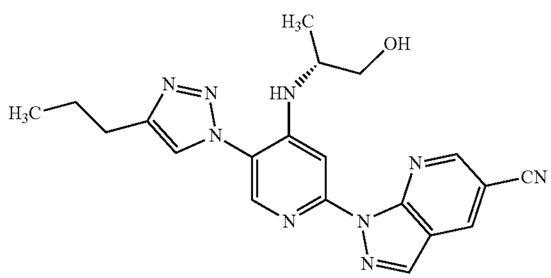 [SMILES: CCCc1cn(-c2cnc(-n3ncc4cc(C#N)cnc43)cc2N[C@H](C)CO)nn1] | 1.28 | C | 404.2 |
| 273 | 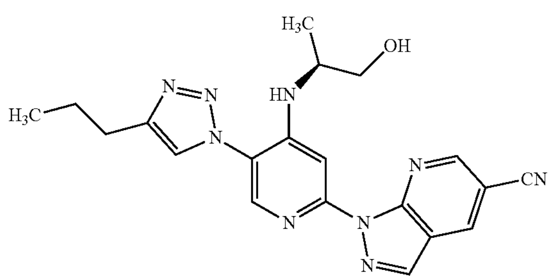 [SMILES: CCCc1cn(-c2cnc(-n3ncc4cc(C#N)cnc43)cc2N[C@@H](C)CO)nn1] | 1.28 | C | 404.0 |
| 274 single enantiomer | 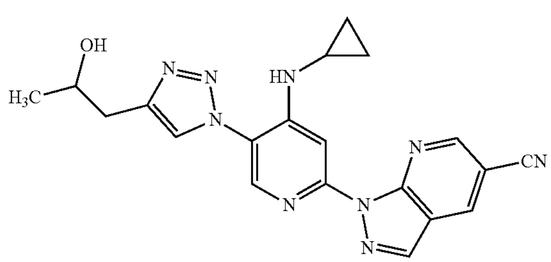 [SMILES: CC(O)Cc1cn(-c2cnc(-n3ncc4cc(C#N)cnc43)cc2NC2CC2)nn1] | 1.02 | G | 402.1 |
| 275 single enantiomer | 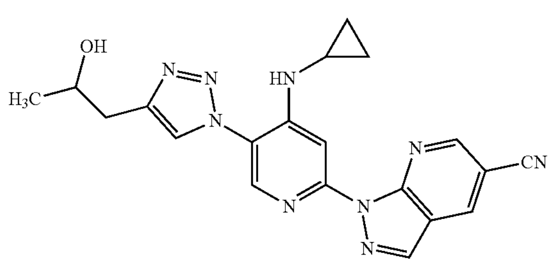 [SMILES: CC(O)Cc1cn(-c2cnc(-n3ncc4cc(C#N)cnc43)cc2NC2CC2)nn1] | 0.52 | D | 402.1 |

TABLE 17-continued

| Ex. No. | Structure | HPLC rt (min) | HPLC cond. | LCMS |
|---|---|---|---|---|
| 276 | 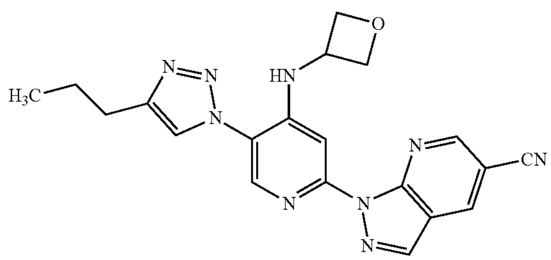 [SMILES: CCCc1cn(-c2cnc(-n3ncc4cc(C#N)cnc43)cc2NC2COC2)nn1] | 1.29 | C | 402.0 |
| 277 | 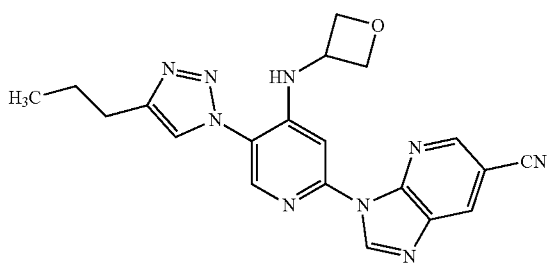 [SMILES: CCCc1cn(-c2cnc(-n3cnc4cc(C#N)cnc43)cc2NC2COC2)nn1] | 1.4 | C | 402.2 |
| 278 | 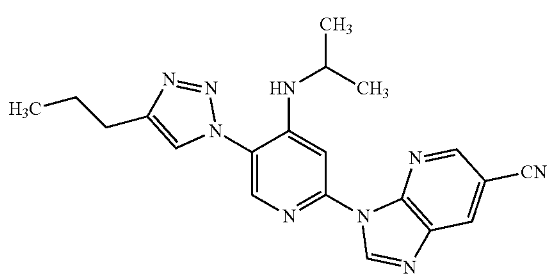 [SMILES: CCCc1cn(-c2cnc(-n3cnc4cc(C#N)cnc43)cc2NC(C)C)nn1] | 1.98 | C | 388.2 |
| 279 | 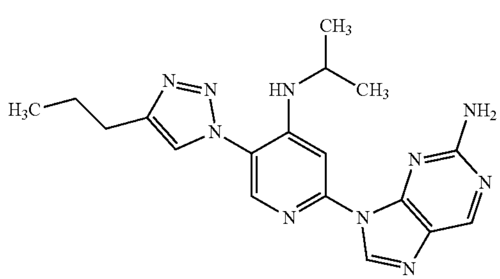 [SMILES: CCCc1cn(-c2cnc(-n3cnc4cnc(N)nc43)cc2NC(C)C)nn1] | 1.39 | C | 379.3 |
| 280 | 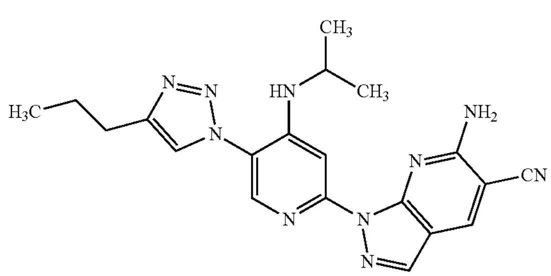 [SMILES: CCCc1cn(-c2cnc(-n3ncc4cc(C#N)c(N)nc43)cc2NC(C)C)nn1] | 1.53 | C | 403.3 |

TABLE 17-continued

| Ex. No. | Structure | HPLC rt (min) | HPLC cond. | LCMS |
|---|---|---|---|---|
| 281 | 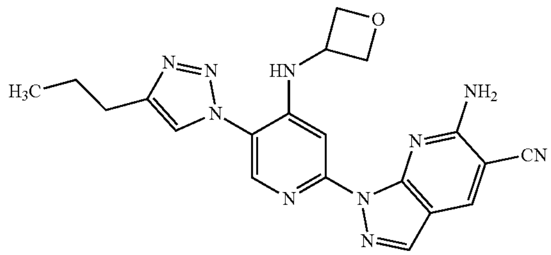 [SMILES: CCCc1cn(-c2cnc(-n3ncc4cc(C#N)c(N)nc43)cc2NC2COC2)nn1] | 1.21 | C | 417.3 |
| 282 | 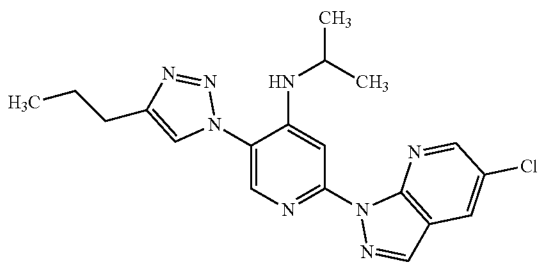 [SMILES: CCCc1cn(-c2cnc(-n3ncc4cc(Cl)cnc43)cc2NC(C)C)nn1] | 1.92 | C | 397.1 |
| 283 | 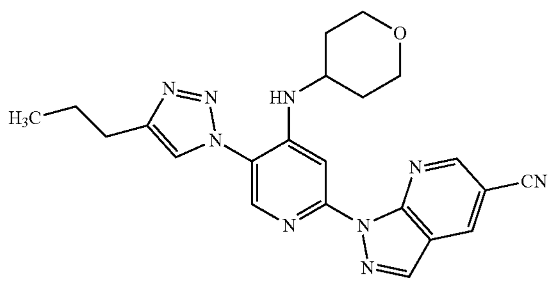 [SMILES: CCCc1cn(-c2cnc(-n3ncc4cc(C#N)cnc43)cc2NC2CCOCC2)nn1] | 1.46 | C | 430.1 |
| 284 | 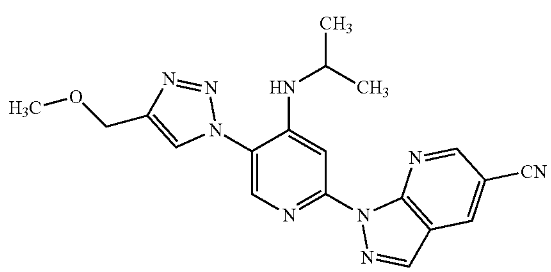 [SMILES: COCc1cn(-c2cnc(-n3ncc4cc(C#N)cnc43)cc2NC(C)C)nn1] | 1.40 | C | 390.2 |
| 285 | 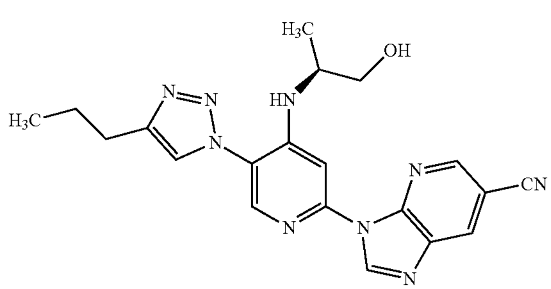 [SMILES: CCCc1cn(-c2cnc(-n3cnc4cc(C#N)cnc43)cc2N[C@@H](C)CO)nn1] | 1.43 | C | 404.1 |

TABLE 17-continued

| Ex. No. | Structure | HPLC rt (min) | HPLC cond. | LCMS |
|---|---|---|---|---|
| 286 | 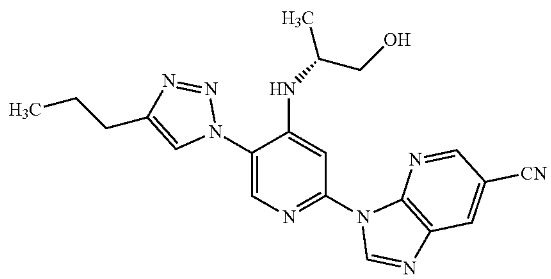 [SMILES: CCCc1cn(-c2cnc(-n3cnc4cc(C#N)cnc43)cc2N[C@H](C)CO)nn1] | 1.43 | C | 404.2 |
| 287 | 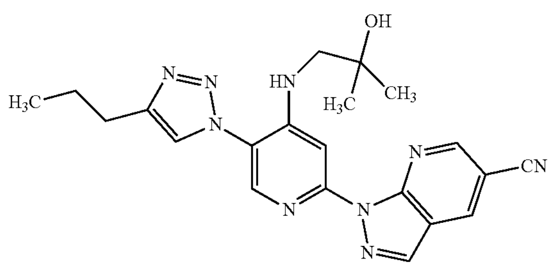 [SMILES: CCCc1cn(-c2cnc(-n3ncc4cc(C#N)cnc43)cc2NCC(C)(C)O)nn1] | 1.38 | C | 418.0 |
| 288 | 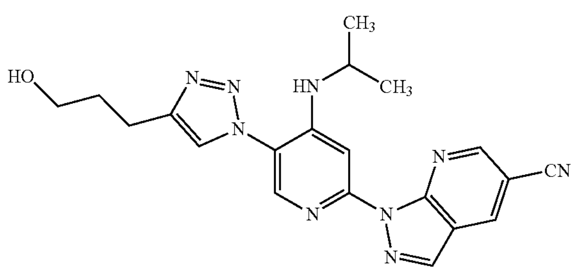 | 1.35 | C | 404.2 |
| 289 single enantiomer | 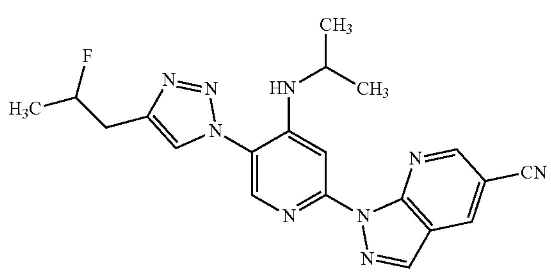 [SMILES: CC(F)Cc1cn(-c2cnc(-n3ncc4cc(C#N)cnc43)cc2NC(C)C)nn1] | 1.53 | C | 406.1 |
| 290 single enantiomer | 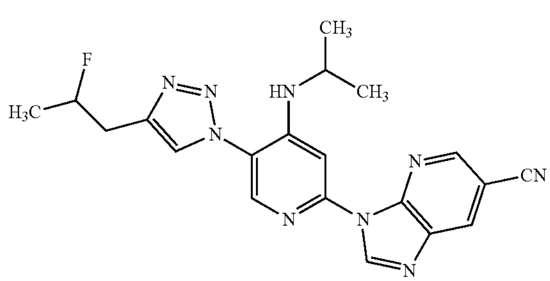 [SMILES: CC(F)Cc1cn(-c2cnc(-n3cnc4cc(C#N)cnc43)cc2NC(C)C)nn1] | 1.62 | C | 406.1 |

TABLE 17-continued

| Ex. No. | Structure | HPLC rt (min) | HPLC cond. | LCMS |
|---|---|---|---|---|
| 291 single enantiomer | 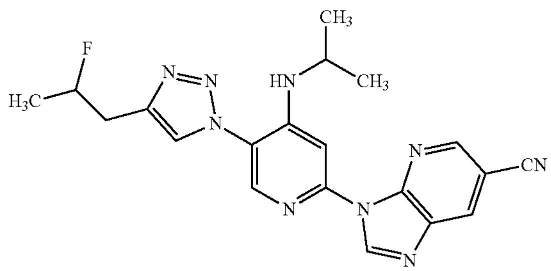 [SMILES: CC(F)Cc1cn(-c2cnc(-n3cnc4cc(C#N)cnc43)cc2NC(C)C)nn1] | 1.53 | C | 406.1 |
| 292 single enantiomer | 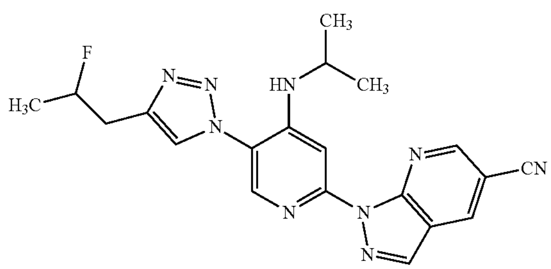 [SMILES: CC(F)Cc1cn(-c2cnc(-n3ncc4cc(C#N)cnc43)cc2NC(C)C)nn1] | 1.62 | C | 406.1 |
| 293 single enantiomer | 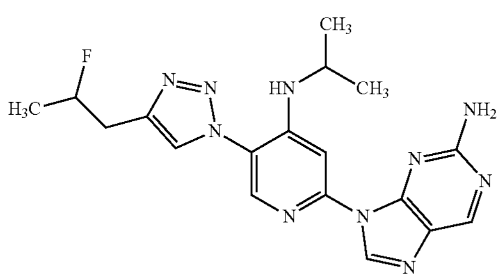 [SMILES: CC(F)Cc1cn(-c2cnc(-n3cnc4cnc(N)nc43)cc2NC(C)C)nn1] | 1.24 | C | 397.2 |
| 294 | 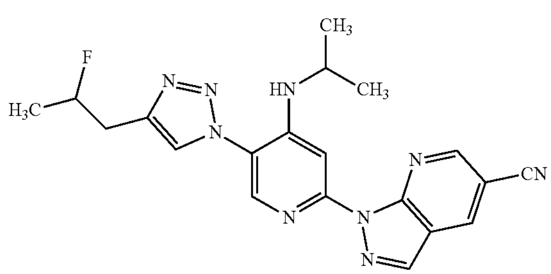 [SMILES: CC(F)Cc1cn(-c2cnc(-n3ncc4cc(C#N)cnc43)cc2NC(C)C)nn1] | 1.65 | C | 403.3 |

Example 295

1-(5-(4-(hydroxymethyl)-1H-1,2,3-triazol-1-yl)-4-(isopropylamino)pyridin-2-yl)-1H-pyrazolo[3,4-b]pyridine-5-carbonitrile (295)

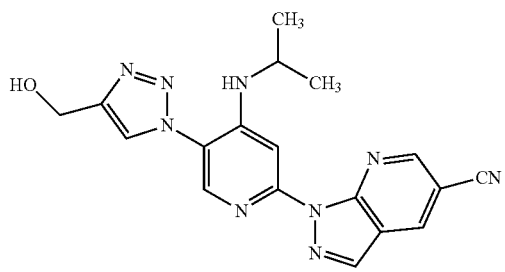

To a stirred suspension of 1-(5-iodo-4-(isopropylamino)pyridin-2-yl)-1H-pyrazolo[3,4-b]pyridine-5-carbonitrile (50 mg, 0.124 mmol), sodium azide (8.44 mg, 0.130 mmol), sodium ascorbate (2.450 mg, 0.012 mmol), (1S,2S)—N1,N2-dimethylcyclohexane-1,2-diamine (2.64 mg, 0.019 mmol) in DMSO (2 ml) and H$_2$O (0.400 ml) at room temperature was bubbled nitrogen for 5 minutes then copper (I) iodide (2.356 mg, 0.012 mmol) and prop-2-yn-1-ol (6.93 mg, 0.124) were added. The reaction mixture was stirred at room temperature for 60 hours, at which point it was judged to be complete by LCMS. The reaction mixture was diluted with ethyl acetate (2 mL), filtered, and concentrated in vacuo. The product was purified via column chromatography (hexanes/EtOAc) to afford 1-(5-(4-(hydroxymethyl)-1H-1,2,3-triazol-1-yl)-4-(isopropylamino)pyridin-2-yl)-1H-pyrazolo[3,4-b]pyridine-5-carbonitrile (10 mg, 19% yield). $^1$H NMR (500 MHz, DMSO-d$_6$) δ 9.03 (d, J=18.3 Hz, 2H), 8.65 (s, 1H), 8.46 (s, 1H), 8.29 (s, 1H), 7.48 (s, 1H), 6.48 (d, J=7.4 Hz, 1H), 5.45 (d, J=5.2 Hz, 1H), 4.65 (d, J=5.4 Hz, 2H), 3.87-3.75 (m, 1H), 1.21 (d, J=6.3 Hz, 6H). LCMS 376.2 (M+H)$^+$. HPLC rt 1.13 min, conditions C.

The Examples in Table 18 were prepared using the methods outlined for Example 295 using the appropriate starting material.

TABLE 18

| Ex. No. | Structure | HPLC rt (min) | HPLC cond. | LCMS |
|---|---|---|---|---|
| 296 | 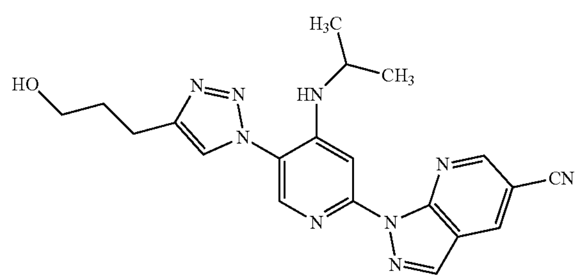 [SMILES: CC(C)Nc1cc(-n2ncc3cc(C#N)cnc32)ncc1-n1cc(CCCO)nn1] | 1.22 | C | 404.2 |
| 297 | 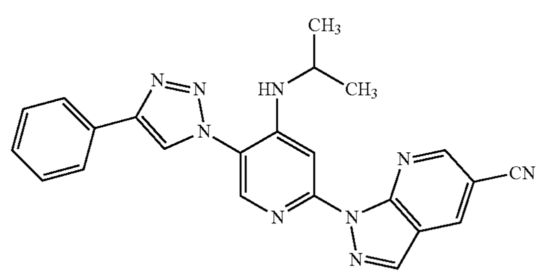 [SMILES: CC(C)Nc1cc(-n2ncc3cc(C#N)cnc32)ncc1-n1cc(-c2ccccc2)nn1] | 1.77 | D | 421.9 |
| 298 | 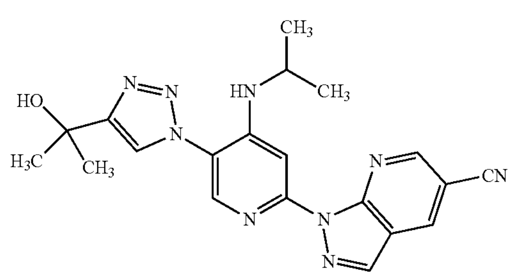 [SMILES: CC(C)Nc1cc(-n2ncc3cc(C#N)cnc32)ncc1-n1cc(C(C)(C)O)nn1] | 1.17 | D | 404.2 |

TABLE 18-continued

| Ex. No. | Structure | HPLC rt (min) | HPLC cond. | LCMS |
|---|---|---|---|---|
| 299 | 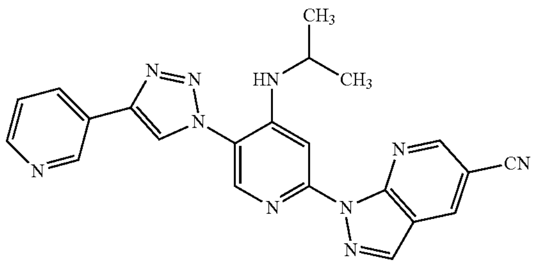 [SMILES: CC(C)Nc1cc(-n2ncc3cc(C#N)cnc32)ncc1-n1cc(-c2cccnc2)nn1] | 1.48 | C | 423.1 |
| 300 | 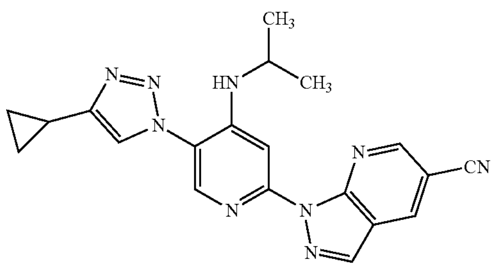 [SMILES: CC(C)Nc1cc(-n2ncc3cc(C#N)cnc32)ncc1-n1cc(C2CC2)nn1] | 1.42 | D | 386.1 |
| 301 | 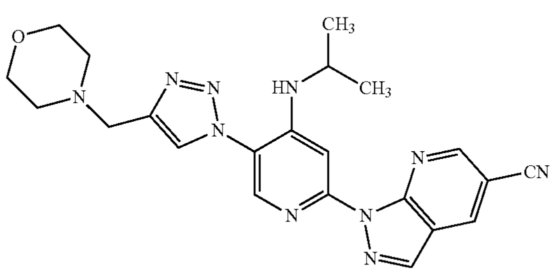 [SMILES: CC(C)Nc1cc(-n2ncc3cc(C#N)cnc32)ncc1-n1cc(CN2CCOCC2)nn1] | 1.25 | C | 445.1 |
| 302 | 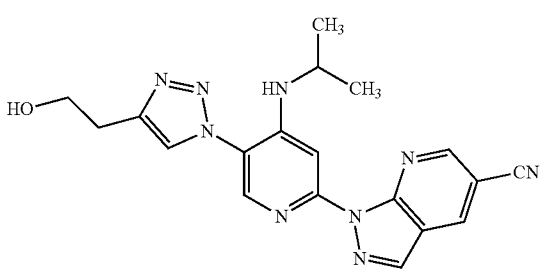 | 1.13 | C | 390.2 |
| 303 | 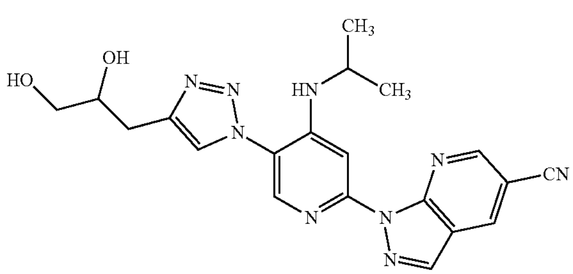 [SMILES: CC(C)Nc1cc(-n2ncc3cc(C#N)cnc32)ncc1-n1cc(CC(O)CO)nn1] | 1.47 | C | 418.3 |

TABLE 18-continued

| Ex. No. | Structure | HPLC rt (min) | HPLC cond. | LCMS |
|---|---|---|---|---|
| 304 | 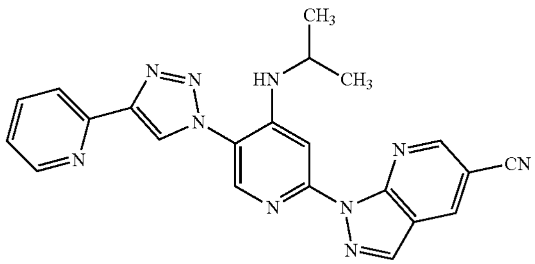 [SMILES: CC(C)Nc1cc(-n2ncc3cc(C#N)cnc32)ncc1-n1cc(-c2ccccn2)nn1] | 1.54 | C | 423.0 |
| 305 | 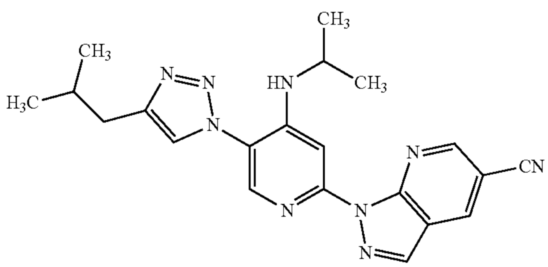 [SMILES: CC(C)Cc1cn(-c2cnc(-n3ncc4cc(C#N)cnc43)cc2NC(C)C)nn1] | 1.60 | D | 402.1 |
| 306 | 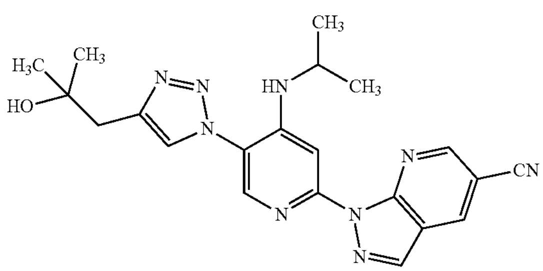 [SMILES: CC(C)Nc1cc(-n2ncc3cc(C#N)cnc32)ncc1-n1cc(CC(C)(C)O)nn1] | 1.29 | C | 418.1 |
| 307 | 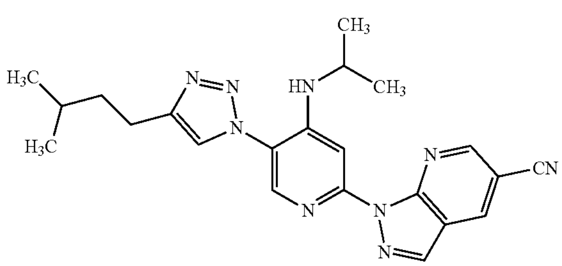 [SMILES: CC(C)CCc1cn(-c2cnc(-n3ncc4cc(C#N)cnc43)cc2NC(C)C)nn1] | 2.08 | C | 416.3 |
| 308 | 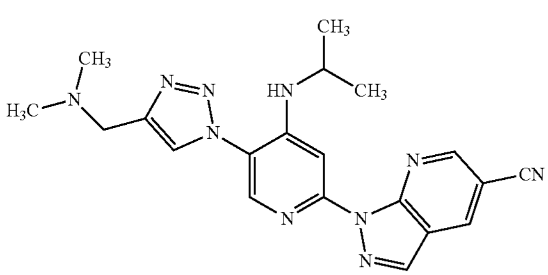 | 0.96 | D | 403.3 |

TABLE 18-continued

| Ex. No. | Structure | HPLC rt (min) | HPLC cond. | LCMS |
|---|---|---|---|---|
| 309 | 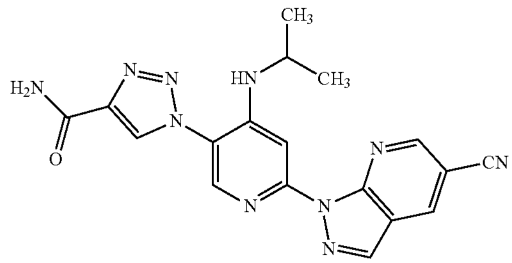 [SMILES: CC(C)Nc1cc(-n2ncc3cc(C#N)cnc32)ncc1-n1cc(C(N)=O)nn1] | 1.29 | C | 389.2 |
| 310 | 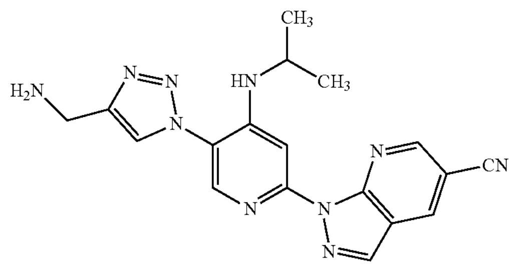 [SMILES: CC(C)Nc1cc(-n2ncc3cc(C#N)cnc32)ncc1-n1cc(CN)nn1] | 1.21 | C | 375.2 |
| 311 | 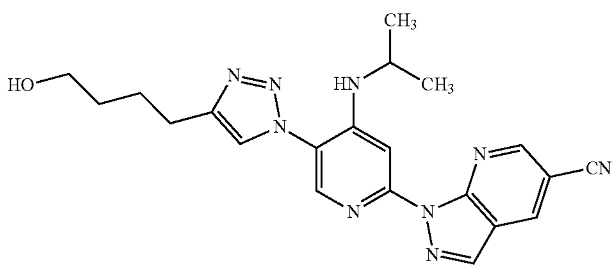 [SMILES: CC(C)Nc1cc(-n2ncc3cc(C#N)cnc32)ncc1-n1cc(CCCCO)nn1] | 1.60 | C | 418.2 |
| 312 | 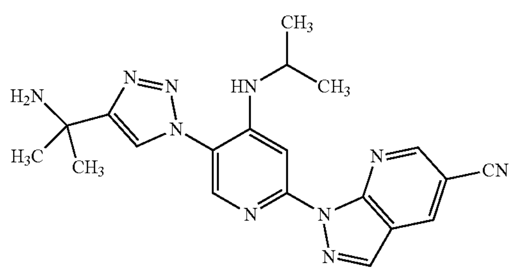 [SMILES: CC(C)Nc1cc(-n2ncc3cc(C#N)cnc32)ncc1-n1cc(C(C)(C)N)nn1] | 1.03 | C | 403.1 |
| 313 | 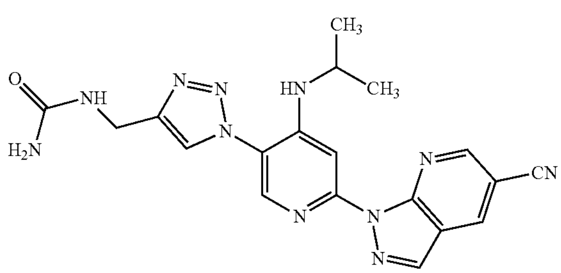 [SMILES: CC(C)Nc1cc(-n2ncc3cc(C#N)cnc32)ncc1-n1cc(CNC(N)=O)nn1] | 0.95 | D | 418.2 |

TABLE 18-continued
| Ex. No. | Structure | HPLC rt (min) | HPLC cond. | LCMS |
|---|---|---|---|---|
| 314 | 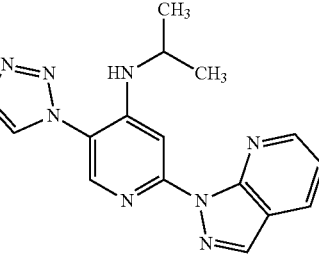 | 0.97 | C | 389.0 |
| 315 | 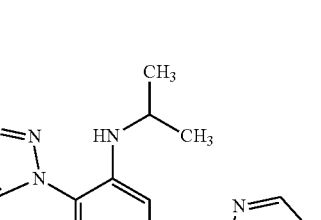 | 1.39 | D | 466.1 |
| 316 | 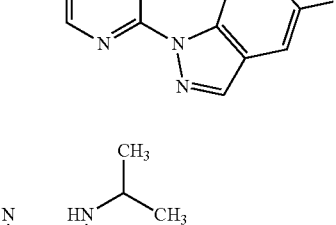 | 1.89 | C | 482.1 |
| 317 | 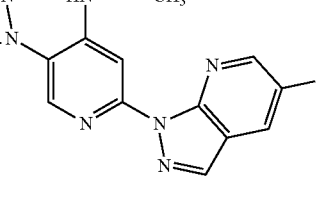 | 1.32 | C | 426.0 |
| 318 | 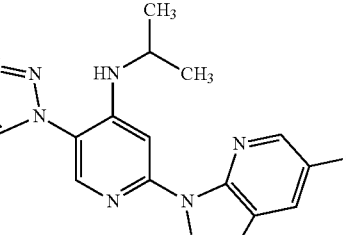 | 1.51 | C | 432.3 |

TABLE 18-continued

| Ex. No. | Structure | HPLC rt (min) | HPLC cond. | LCMS |
|---|---|---|---|---|
| 319 | 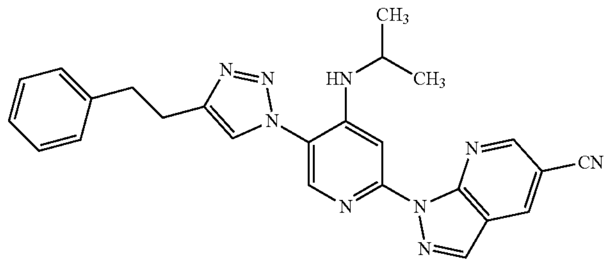 [SMILES: CC(C)Nc1cc(-n2ncc3cc(C#N)cnc32)ncc1-n1cc(CCc2ccccc2)nn1] | 2.00 | C | 450.3 |
| 320 | 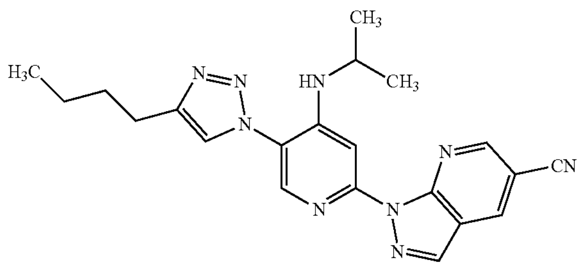 [SMILES: CCCCc1cn(-c2cnc(-n3ncc4cc(C#N)cnc43)cc2NC(C)C)nn1] | 1.84 | C | 402.1 |
| 321 | 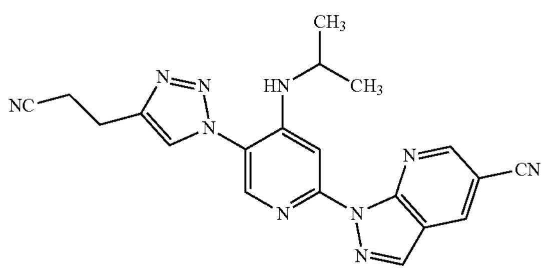 [SMILES: CC(C)Nc1cc(-n2ncc3cc(C#N)cnc32)ncc1-n1cc(CCC#N)nn1] | 1.34 | C | 399.0 |
| 322 | 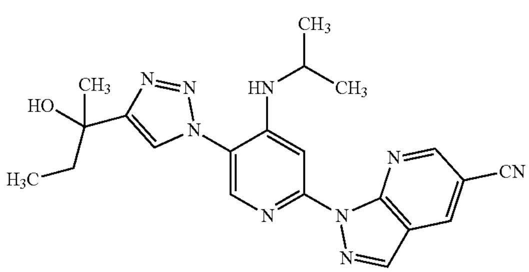 [SMILES: CCC(C)(O)c1cn(-c2cnc(-n3ncc4cc(C#N)cnc43)cc2NC(C)C)nn1] | 1.43 | C | 418.0 |
| 323 | 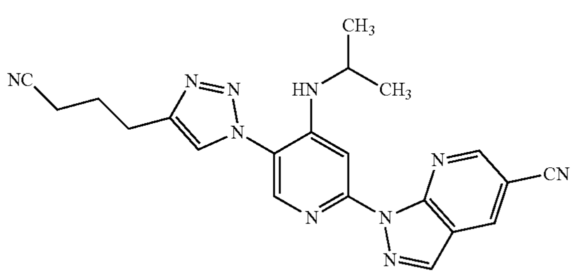 [SMILES: CC(C)Nc1cc(-n2ncc3cc(C#N)cnc32)ncc1-n1cc(CCCC#N)nn1] | 1.54 | C | 413.2 |

TABLE 18-continued

| Ex. No. | Structure | HPLC rt (min) | HPLC cond. | LCMS |
|---|---|---|---|---|
| 324 | 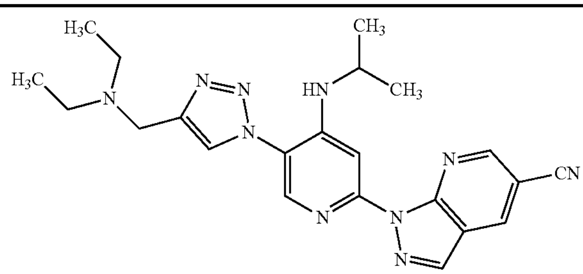 | 1.12 | D | 431.1 |
| 325 | 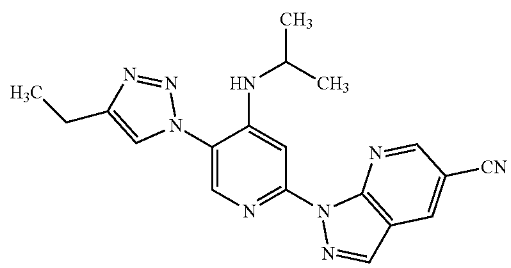 [SMILES: CCc1cn(-c2cnc(-n3ncc4cc(C#N)cnc43)cc2NC(C)C)nn1] | 1.32 | D | 374.0 |
| 326 | 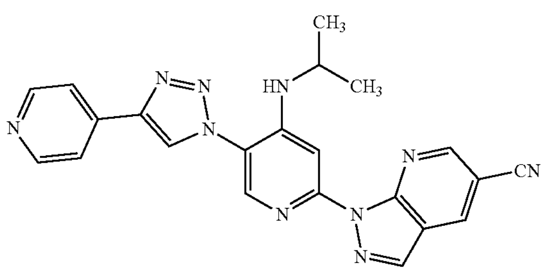 [SMILES: CC(C)Nc1cc(-n2ncc3cc(C#N)cnc32)ncc1-n1cc(-c2ccncc2)nn1] | 1.56 | C | 423.2 |
| 327 | 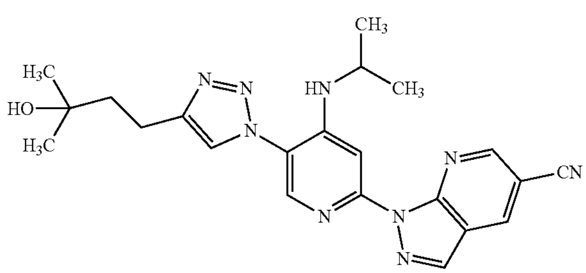 [SMILES: CC(C)Nc1cc(-n2ncc3cc(C#N)cnc32)ncc1-n1cc(CCC(C)(C)O)nn1] | 1.43 | C | 432.0 |
| 328 | 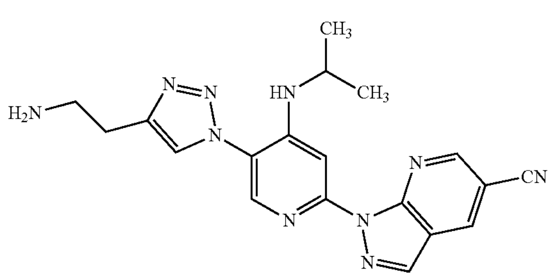 [SMILES: CC(C)Nc1cc(-n2ncc3cc(C#N)cnc32)ncc1-n1cc(CCN)nn1] | 0.91 | D | 389.2 |

Example 329

1-(5-(4-(fluoromethyl)-1H-1,2,3-triazol-1-yl)-4-(isopropylamino)pyridin-2-yl)-1H-pyrazolo[3,4-b]pyridine-5-carbonitrile

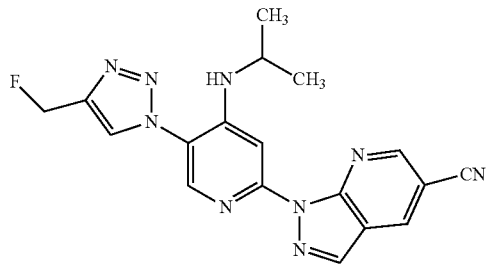

(329)

A stirring suspension of 1-(5-(4-(hydroxymethyl)-1H-1,2,3-triazol-1-yl)-4-(isopropylamino)pyridin-2-yl)-1H-pyrazolo[3,4-b]pyridine-5-carbonitrile (8 mg, 0.021 mmol) in anhydrous dichloromethane (10 mL) under nitrogen was cooled to −78° C. and treated with DAST (0.08 mL, 0.61 mmol). The reaction mixture was stirred at −78° C. for 1 hour, then at room temperature for 5 hours, at which point it was judged to be complete by LCMS. Methanol was added carefully to quench the reaction and then the contents were concentrated. The product was purified by preparative HPLC to afford 1-(5-(4-(fluoromethyl)-1H-1,2,3-triazol-1-yl)-4-(isopropylamino)pyridin-2-yl)-1H-pyrazolo[3,4-b]pyridine-5-carbonitrile (3.2 mg, 38% yield). $^1$H NMR (500 MHz, DMSO-$d_6$) δ 9.04 (d, J=16.4 Hz, 2H), 8.78 (br. s., 1H), 8.66 (s, 1H), 8.27 (s, 1H), 7.48 (s, 1H), 6.47 (d, J=7.6 Hz, 1H), 5.68-5.50 (m, 2H), 3.86-3.75 (m, 1H), 1.21 (d, J=6.3 Hz, 6H). LCMS 378.0 (M+H)$^+$. HPLC rt 1.46 min, conditions C.

Example 330

1-(5-(4-allyl-1H-1,2,3-triazol-1-yl)-4-(isopropylamino)pyridin-2-yl)-1H-pyrazolo[3,4-b]pyridine-5-carbonitrile

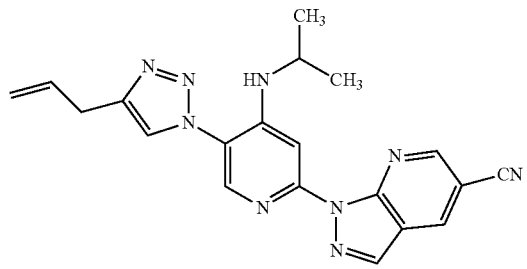

(330)

A stirring suspension of 1-(5-(4-(hydroxymethyl)-1H-1,2,3-triazol-1-yl)-4-(isopropylamino)pyridin-2-yl)-1H-pyrazolo[3,4-b]pyridine-5-carbonitrile (8 mg, 0.021 mmol) in anhydrous dichloromethane (10 mL) under nitrogen was cooled to −78° C. and treated with DAST (0.080 mL, 0.609 mmol). The reaction mixture was stirred at −78° C. for 1 hour, then at room temperature for 5 hours, at which point it was judged to be complete by LCMS. Methanol was added carefully to quench the reaction and then the contents were concentrated. The product was purified by preparative HPLC to afford 1-(5-(4-(fluoromethyl)-1H-1,2,3-triazol-1-yl)-4-(isopropylamino)pyridin-2-yl)-1H-pyrazolo [3,4-b]pyridine-5-carbonitrile (3.2 mg, 38% yield). $^1$H NMR (500 MHz, DMSO-$d_6$) δ 9.04 (d, J=16.4 Hz, 2H), 8.78 (br. s., 1H), 8.66 (s, 1H), 8.27 (s, 1H), 7.48 (s, 1H), 6.47 (d, J=7.6 Hz, 1H), 5.68-5.50 (m, 2H), 3.86-3.75 (m, 1H), 1.21 (d, J=6.3 Hz, 6H). LCMS 378.0 (M+H)$^+$. HPLC rt 1.46 min, conditions C.

Example 331

1-(4-(isopropylamino)-5-(4-(2-oxopropyl)-1H-1,2,3-triazol-1-yl)pyridin-2-yl)-1H-pyrazolo[3,4-b]pyridine-5-carbonitrile

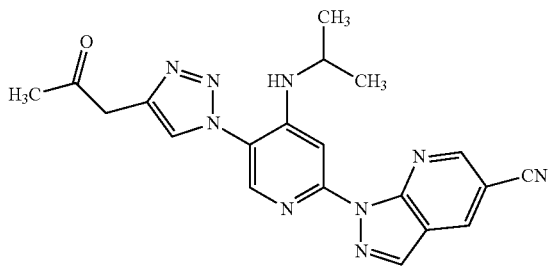

(331)

In a 2-dram vial, a stirring suspension of 1-(5-(4-(2-hydroxypropyl)-1H-1,2,3-triazol-1-yl)-4-(isopropylamino)pyridin-2-yl)-1H-pyrazolo[3,4-b]pyridine-5-carbonitrile (110 mg, 0.273 mmol) in dichloromethane (5 mL) was treated with Dess-Martin Periodinane (173 mg, 0.409 mmol). The vial was filled with nitrogen, sealed, and the reaction mixture was stirred at room temperature for 1 hour. Saturated sodium bicarbonate (0.5 mL) was added and the mixture was stirred until gas evolution had ceased. The layers were separated, and the aqueous phase was extracted with dichloromethane (3×). The organic layer was dried over Na$_2$SO$_4$, filtered and concentrated to afford 1-(4-(isopropylamino)-5-(4-(2-oxopropyl)-1H-1,2,3-triazol-1-yl) pyridin-2-yl)-1H-pyrazolo[3,4-b]pyridine-5-carbonitrile (110 mg, 100% yield). $^1$H NMR (500 MHz, DMSO-$d_6$) δ 9.03 (d, J=18.0 Hz, 2H), 8.66 (s, 1H), 8.45 (s, 1H), 8.31 (s, 1H), 7.49 (s, 1H), 6.50 (d, J=7.3 Hz, 1H), 4.01 (s, 2H), 3.86-3.75 (m, 1H), 2.24 (s, 3H), 1.22 (d, J=6.2 Hz, 6H). LCMS 402.2 (M+H)$^+$. HPLC rt 1.37 min, conditions C.

Example 332

1-(4-(isopropylamino)-5-(4-((phenylsulfonyl)methyl)-1H-1,2,3-triazol-1-yl)pyridin-2-yl)-1H-pyrazolo[3,4-b]pyridine-5-carbonitrile

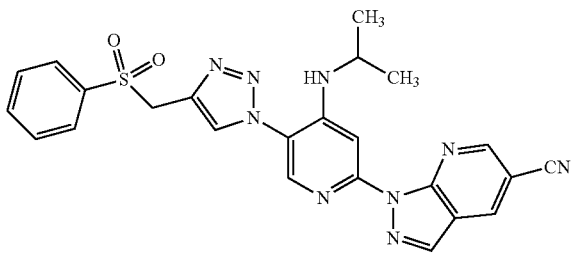

(332)

Intermediate 332A: 1-(4-(isopropylamino)-5-(4-((phenylthio)methyl)-1H-1,2,3-triazol-1-yl)pyridin-2-yl)-1H-pyrazolo[3,4-b]pyridine-5-carbonitrile

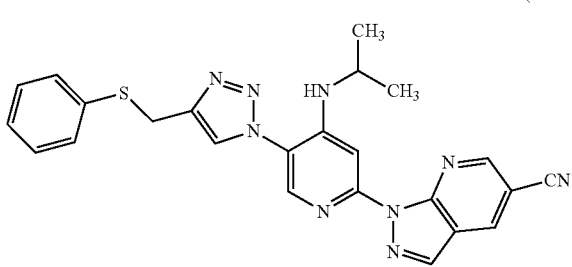

(332A)

To a stirred suspension of 1-(5-iodo-4-(isopropylamino)pyridin-2-yl)-1H-pyrazolo[3,4-b]pyridine-5-carbonitrile (50 mg, 0.124 mmol), sodium azide (8.44 mg, 0.130 mmol), sodium ascorbate (2.45 mg, 0.012 mmol), (1S,2S)—N1,N2-dimethylcyclohexane-1,2-diamine (2.64 mg, 0.019 mmol) in DMSO (2 mL) and H$_2$O (0.4 mL) at room temperature was bubbled nitrogen for 5 minutes then copper(I) iodide (2.36 mg, 0.012 mmol), and phenyl(prop-2-yn-1-yl)sulfane (18.34 mg, 0.124 mmol) were mixed together at room temperature with stirring. Nitrogen was bubbled through the mixture for 5 minutes and stirring at room temperature was continued for 16 hours. The reaction mixture was diluted with ethyl acetate (50 mL) and washed with water (3×). The organic layer was dried over Na$_2$SO$_4$, filtered and concentrated to afford 1-(4-(isopropylamino)-5-(4-((phenylthio)methyl)-1H-1,2,3-triazol-1-yl)pyridin-2-yl)-1H-pyrazolo[3,4-b]pyridine-5-carbonitrile (50 mg, 78% yield). LCMS 468.0 (M+H)$^+$.

Example 332

To a stirred suspension of 1-(4-(isopropylamino)-5-(4-((phenylthio)methyl)-1H-1,2,3-triazol-1-yl)pyridin-2-yl)-1H-pyrazolo[3,4-b]pyridine-5-carbonitrile (50 mg, 0.107 mmol) in MeOH (7 mL) at room temperature, then cooled to 0° C., was added Oxone (131 mg, 0.214 mmol) and water (3 mL). The mixture was stirred at room temperature for 1 hour then added additional Oxone (131 mg, 0.214 mmol) as above. The reaction mixture was at room temperature for 1 hour, at which point it was judged to be complete by LCMS. The solids were collected and rinsed with methanol and discarded. The filtrate was concentrated to afford 1-(4-(isopropylamino)-5-(4-((phenylsulfonyl)methyl)-1H-1,2,3-triazol-1-yl)pyridin-2-yl)-1H-pyrazolo[3,4-b]pyridine-5-carbonitrile (15 mg, 28% yield). $^1$H NMR (500 MHz, DMSO-d$_6$) δ 9.04 (d, J=17.2 Hz, 2H), 8.66 (s, 1H), 8.43 (s, 1H), 8.19 (s, 1H), 7.82 (d, J=7.7 Hz, 2H), 7.79-7.73 (m, 1H), 7.68-7.61 (m, 2H), 7.49 (s, 1H), 6.30 (d, J=7.5 Hz, 1H), 4.93 (s, 2H), 3.78 (dd, J=13.0, 6.5 Hz, 1H), 1.19 (d, J=6.2 Hz, 6H). LCMS 499.9 (M+H)$^+$. HPLC rt 1.77 min, conditions C.

Example 333 tert-butyl 4-(1-(6-(5-cyano-1H-pyrazolo[3,4-b]pyridin-1-yl)-4-(isopropylamino)pyridin-3-yl)-1H-1,2,3-triazol-4-yl)piperidine-1-carboxylate

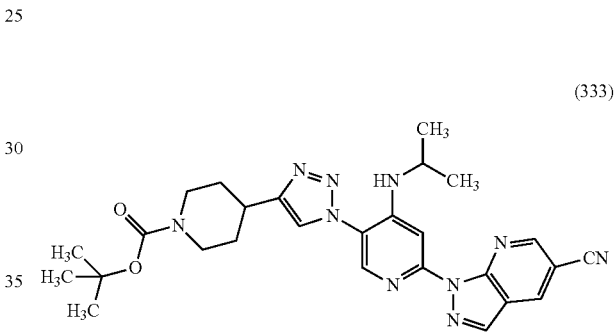

(333)

A stirred suspension of 1-(5-iodo-4-(isopropylamino)pyridin-2-yl)-1H-pyrazolo[3,4-b]pyridine-5-carbonitrile (500 mg, 1.237 mmol), sodium azide (84 mg, 1.3 mmol), sodium ascorbate (24.5 mg, 0.124 mmol), (1S,2S)—N1,N2-dimethylcyclohexane-1,2-diamine (26.4 mg, 0.186 mmol), in DMSO (6 mL) and H$_2$O (1.2 mL) at room temperature was bubbled nitrogen for 5 minutes then copper(I) iodide (23.56 mg, 0.124 mmol), and tert-butyl 4-ethynylpiperidine-1-carboxylate (259 mg, 1.237 mmol) were added. The mixture was stirred at room temperature for 20 hours, at which point it was judged to be incomplete by LCMS. Another set of reagents was added and the reaction mixture was stirred at room temperature for 60 hours, at which point the reaction was judged to be complete by LCMS. Ethyl acetate was added and the solids were removed by filtration. The filtrate was diluted with ethyl acetate and washed with water (3×). The organic layer was dried over Na$_2$SO$_4$, filtered and concentrated to afford the crude product which was purified by column chromatography (hexanes/EtOAc) to afford tert-butyl 4-(1-(6-(5-cyano-1H-pyrazolo[3,4-b]pyridin-1-yl)-4-(isopropylamino)pyridin-3-yl)-1H-1,2,3-triazol-4-yl)piperidine-1-carboxylate (165 mg, 23% yield). $^1$H NMR (400 MHz, DMSO-d$_6$) δ 9.05 (d, J=12.6 Hz, 2H), 8.66 (br. s., 1H), 8.47 (br. s., 1H), 8.35 (br. s., 1H), 7.50 (br. s., 1H), 6.61 (br. s., 1H), 5.76 (d, J=2.4 Hz, 1H), 3.99 (br. s., 2H), 3.81 (d, J=7.0 Hz, 1H), 3.30, 2.97 (br. s., 2H), 2.02 (d, J=11.7 Hz, 2H), 1.57 (d, J=13.1 Hz, 2H), 1.42 (d, J=2.4 Hz, 9H), 1.24 (br. s., 6H). LCMS 529.2 (M+H)$^+$. HPLC rt 1.61 min, Conditions G.

Example 334

1-(4-(isopropylamino)-5-(4-(piperidin-4-yl)-1H-1,2,3-triazol-1-yl)pyridin-2-yl)-1H-pyrazolo[3,4-b]pyridine-5-carbonitrile, 2 HCl

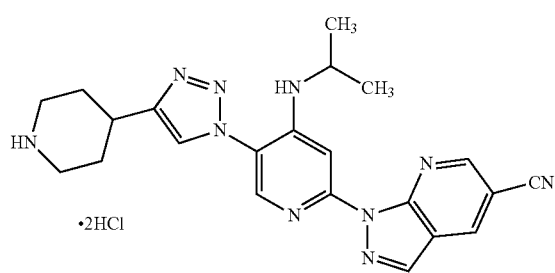

(334)

To a stirred room temperature solution of tert-butyl 4-(1-(6-(5-cyano-1H-pyrazolo [3,4-b]pyridin-1-yl)-4-(isopropylamino)pyridin-3-yl)-1H-1,2,3-triazol-4-yl)piperidine-1-carboxylate (160 mg, 0.303 mmol) in $CH_2Cl_2$ (2 mL) was added 4N HCl in dioxane (0.757 mL, 3.03 mmol). After 4 h, the reaction mixture was concentrated to afford 1-(4-(isopropylamino)-5-(4-(piperidin-4-yl)-1H-1,2,3-triazol-1-yl)pyridin-2-yl)-1H-pyrazolo[3,4-b]pyridine-5-carbonitrile, 2 HCl (150 mg, 89% yield). LCMS 429.1 $(M+H)^+$. HPLC rt 0.47 min, Conditions D.

Example 335

1-(5-(4-(1-acetylpiperidin-4-yl)-1H-1,2,3-triazol-1-yl)-4-(isopropylamino)pyridin-2-yl)-1H-pyrazolo[3,4-b]pyridine-5-carbonitrile

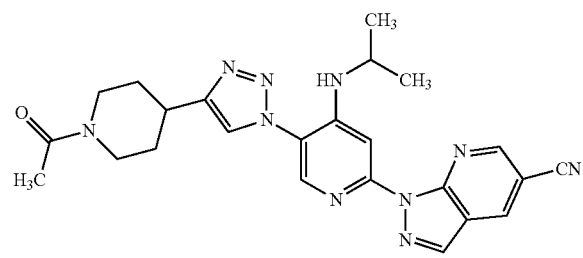

(335)

To a stirred suspension of 1-(4-(isopropylamino)-5-(4-(piperidin-4-yl)-1H-1,2,3-triazol-1-yl)pyridin-2-yl)-1H-pyrazolo[3,4-b]pyridine-5-carbonitrile, 2 HCl (20 mg, 0.040 mmol) in DMF (2 mL) was added triethylamine (0.017 mL, 0.120 mmol) followed by acetic anhydride (4.14 µl, 0.044 mmol). The mixture was stirred at room temperature for 1 hour, at which point it was judged to be complete by LCMS. The reaction mixture was diluted with ethyl acetate (2 mL), filtered, and concentrated in vacuo. The product was purified by preparative HPLC to afford 1-(5-(4-(1-acetylpiperidin-4-yl)-1H-1,2,3-triazol-1-yl)-4-(isopropylamino)pyridin-2-yl)-1H-pyrazolo[3,4-b]pyridine-5-carbonitrile (13 mg, 65% yield). $^1$H NMR (500 MHz, DMSO-$d_6$) δ 9.04 (d, J=15.3 Hz, 2H), 8.66 (s, 1H), 8.46 (s, 1H), 8.33 (s, 1H), 7.48 (s, 1H), 6.61 (d, J=7.5 Hz, 1H), 4.40 (d, J=12.7 Hz, 1H), 3.95-3.75 (m, 2H), 3.22 (t, J=11.7 Hz, 1H), 3.07 (t, J=11.4 Hz, 1H), 2.81-2.69 (m, 1H), 2.03 (s, 4H), 1.71-1.59 (m, 1H), 1.58-1.45 (m, 1H), 1.23 (d, J=6.3 Hz, 6H). LCMS 471.2 $(M+H)^+$. HPLC rt 1.59 min, conditions C.

Example 336

1-(5-(4-(1-(2,2-difluoroethyl)piperidin-4-yl)-1H-1,2,3-triazol-1-yl)-4-(isopropylamino)pyridin-2-yl)-1H-pyrazolo[3,4-b]pyridine-5-carbonitrile

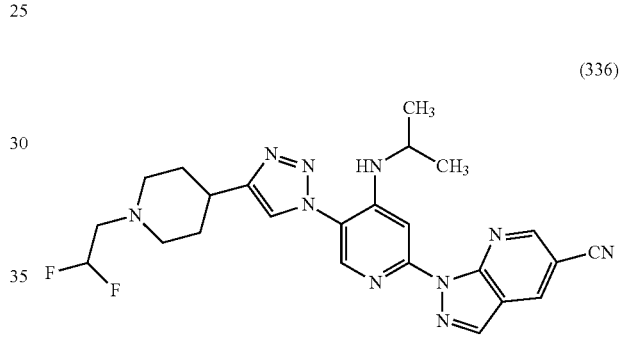

(336)

To a stirred suspension of 1-(4-(isopropylamino)-5-(4-(piperidin-4-yl)-1H-1,2,3-triazol-1-yl)pyridin-2-yl)-1H-pyrazolo[3,4-b]pyridine-5-carbonitrile, 2 HCl (20 mg, 0.040 mmol) in DMF (2 mL) at room temperature was added potassium carbonate (5.51 mg, 0.040 mmol) followed by 1,1-difluoro-2-iodoethane (7.66 mg, 0.040 mmol). After stirring for 1 h the reaction mixture was heated at 100° C. for 1 hour and then stirred at room temperature for 60 hours, at which point it was judged to be complete by LCMS. The product was purified by preparative HPLC to afford 1-(5-(4-(1-(2,2-difluoroethyl) piperidin-4-yl)-1H-1,2,3-triazol-1-yl)-4-(isopropylamino)pyridin-2-yl)-1H-pyrazolo[3,4-b]pyridine-5-carbonitrile (3.9 mg, 19% yield). $^1$H NMR (500 MHz, DMSO-$d_6$) δ 9.04 (d, J=15.7 Hz, 2H), 8.66 (s, 1H), 8.45 (s, 1H), 8.34 (s, 1H), 7.48 (s, 1H), 6.63 (d, J=7.3 Hz, 1H), 6.29-6.00 (m, 1H), 3.87-3.76 (m, 1H), 3.45 (br. s., 1H), 2.98 (d, J=10.9 Hz, 2H), 2.83-2.70 (m, 2H), 2.32 (t, J=11.1 Hz, 2H), 2.00 (d, J=11.9 Hz, 2H), 1.79-1.66 (m, 2H), 1.23 (d, J=6.3 Hz, 6H). LCMS 493.3 $(M+H)^+$. HPLC rt 1.72 min, conditions C.

Example 337

1-(4-(isopropylamino)-5-(4-(1-isopropylpiperidin-4-yl)-1H-1,2,3-triazol-1-yl)pyridin-2-yl)-1H-pyrazolo[3,4-b]pyridine-5-carbonitrile

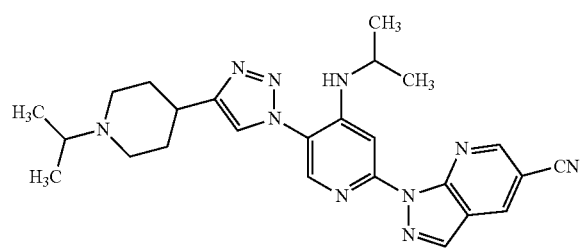

(337)

To a stirred suspension of 1-(4-(isopropylamino)-5-(4-(piperidin-4-yl)-1H-1,2,3-triazol-1-yl)pyridin-2-yl)-1H-pyrazolo[3,4-b]pyridine-5-carbonitrile, 2 HCl (20 mg, 0.040 mmol), was added acetone (0.012 mL, 0.160 mmol), sodium acetate (9.82 mg, 0.120 mmol), sodium cyanoborohydride (5.01 mg, 0.080 mmol) and methanol (1 mL) at room temperature. The mixture was stirred at room temperature for 3 hours at which point it was judged to be complete by LCMS. 1N NaOH (few drops) were added and the mixture was stirred for 5 minutes. The reaction mixture was filtered, concentrated, and purified by preparative HPLC to afford 1-(4-(isopropylamino)-5-(4-(1-isopropylpiperidin-4-yl)-1H-1,2,3-triazol-1-yl)pyridin-2-yl)-1H-pyrazolo[3,4-b]pyridine-5-carbonitrile (19 mg, 100% yield). LCMS 471.1 (M+H)$^+$. HPLC rt 1.09 min, conditions D.

Example 338 methyl 4-(1-(6-(5-cyano-1H-pyrazolo[3,4-b]pyridin-1-yl)-4-(isopropylamino)pyridin-3-yl)-1H-1,2,3-triazol-4-yl)piperidine-1-carboxylate

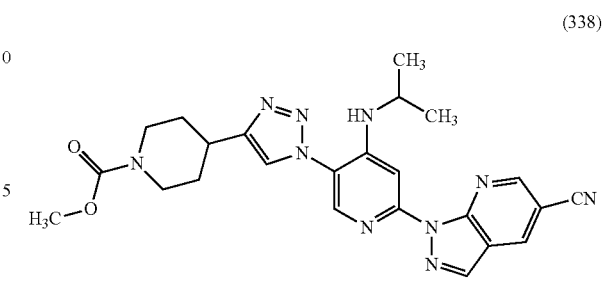

(338)

To a stirred suspension of 1-(4-(isopropylamino)-5-(4-(piperidin-4-yl)-1H-1,2,3-triazol-1-yl)pyridin-2-yl)-1H-pyrazolo[3,4-b]pyridine-5-carbonitrile, 2 HCl (20 mg, 0.040 mmol) in THF (5 mL) at room temperature was added triethylamine (0.011 mL, 0.080 mmol) followed by methyl chloroformate (3.09 µl, 0.040 mmol). The reaction mixture was filtered, concentrated, and purified by preparative HPLC to afford methyl 4-(1-(6-(5-cyano-1H-pyrazolo[3,4-b]pyridin-1-yl)-4-(isopropylamino)pyridin-3-yl)-1H-1,2,3-triazol-4-yl)piperidine-1-carboxylate (12 mg, 62% yield). $^1$H NMR (500 MHz, DMSO-d$_6$) δ 9.11-8.98 (m, 2H), 8.66 (br. s., 1H), 8.46 (s, 1H), 8.34 (br. s., 1H), 7.49 (br. s., 1H), 6.62 (d, J=7.6 Hz, 1H), 4.03 (br. s., 3H), 3.86-3.76 (m, 1H), 3.61 (s, 2H), 3.07-2.98 (m, 2H), 2.04 (d, J=11.5 Hz, 2H), 1.59 (qd, J=12.2, 4.1 Hz, 2H), 1.23 (d, J=6.4 Hz, 6H). LCMS 487.2 (M+H)$^+$. HPLC rt 1.61 min, conditions C.

The Examples in Table 19 were prepared using the methods outlined above using the appropriate starting material.

TABLE 19

| Ex. No. | Structure | HPLC rt (min) | HPLC cond. | LCMS |
|---|---|---|---|---|
| 339 | ![structure] | 1.25 | C | 443.1 |
| 340 | ![structure] | 0.5 | D | 443.1 |

TABLE 19-continued

| Ex. No. | Structure | HPLC rt (min) | HPLC cond. | LCMS |
|---|---|---|---|---|
| 341 | 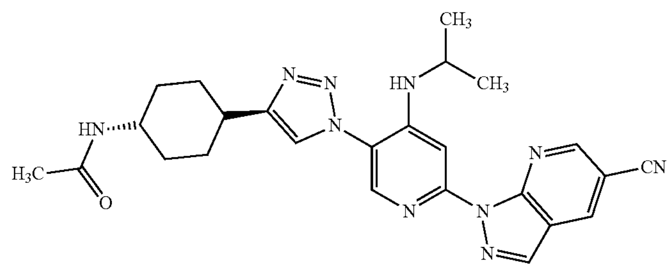 | 1.41 | C | 485.0 |
| 342 | 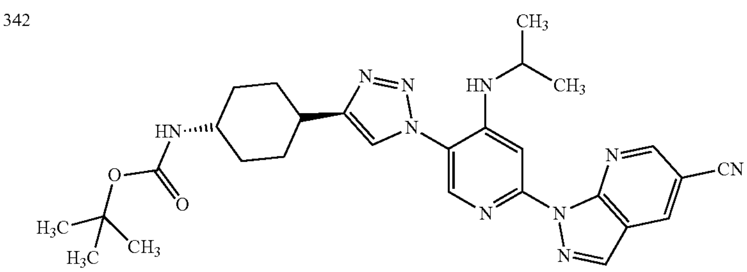 | 1.62 | G | 543.2 |
| 343 | 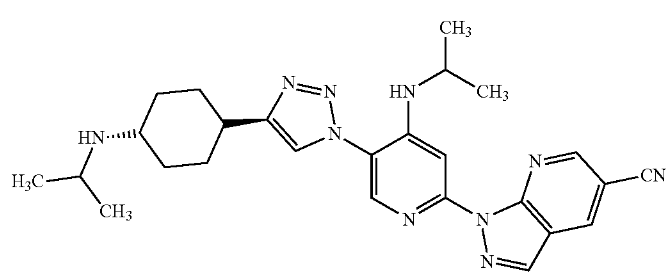 | 1.24 | C | 485.1 |
| 344 | 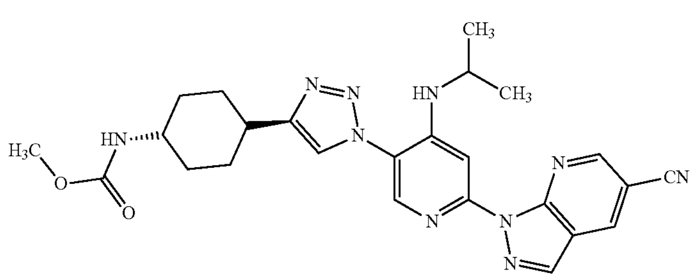 | 1.61 | C | 501.0 |

Example 345

(±)-1-(5-(4-(2-fluoro-3-hydroxy-3-methylbutyl)-1H-1,2,3-triazol-1-yl)-4-(isopropylamino)pyridin-2-yl)-1H-pyrazolo[3,4-b]pyridine-5-carbonitrile (Racemic)

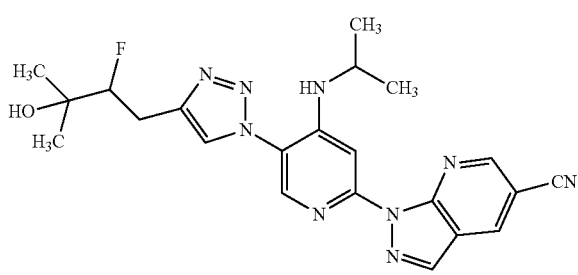
(345)

Intermediate 345A: Methyl 2-fluoropent-4-ynoate

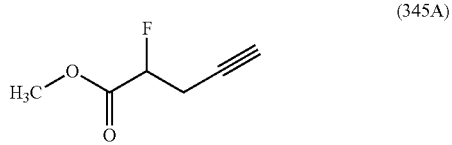
(345A)

In a 20 mL microwave vial, a mixture of dimethyl 2-fluoromalonate (900 mg, 6.0 mmol) in DMA (5 mL) at room temperature with stirring, was treated with the slow addition of sodium hydride (240 mg, 6 mmol, 60%) at 0° C. The mixture was stirred for 10 minutes, then added 3-bromoprop-1-yne (743 mg, 5.0 mmol, 80% in xylenes) and the mixture was stirred vigorously at 25° C. for 1.5 hours. TLC shows consumption of the bromide. A syringe needle was placed through the septum to allow gases to vent, then the mixture was heated at 90° C. for 20 hours. The reaction was quenched with the careful addition under nitrogen of saturated NH$_4$C$_1$ solution (0.5 mL), and extracted with ethyl acetate (3×25 mL). The combined extracts were dried over Na$_2$SO$_4$ to give a few ml of a brown oil as crude product. The crude product was dissolved in ethyl acetate and rinsed 3 times with 10% LiCl to remove DMA. The organic layer was dried over sodium sulfate, and then concentrated to give an amber oil which was purified over silica gel in 9:1 to 3:1 hexanes/EtOAc to afford methyl 2-fluoropent-4-ynoate (600 mg, 69% yield). $^1$H NMR (400 MHz, CHLOROFORM-d) δ 3.84 (s, 3H), 2.92-2.74 (m, 2H), 2.14-2.00 (m, 1H), 1.27 (d, J=5.3 Hz, 1H). LCMS 130.2 (M+H)$^+$.

Intermediate 345B: 3-Fluoro-2-methylhex-5-yn-2-ol (345B)

Methyl 2-fluoropent-4-ynoate (350 mg, 2.7 mmol) was dissolved in THF (5 mL) at room temperature with stirring under nitrogen. Then reaction mixture was cooled to 0° C. and 3M methylmagnesium chloride in THF (1.97 ml, 5.9 mmol) was added dropwise over 10 minutes. The mixture was slowly allowed to warm and stirred at room temperature for 1 hour. The reaction was carefully quenched under nitrogen with a saturated NH$_4$C$_1$ solution then extracted 2 times with methylene chloride. The organic layers were combined, dried over sodium sulfate and concentrated to afford 3-fluoro-2-methylhex-5-yn-2-ol (350 mg, 50% yield) of a light amber oil. $^1$H NMR (400 MHz, CDCl$_3$) δ 5.29 (s, 1H), 3.78-3.68 (m, 2H), 2.67-2.51 (m, 1H), 1.88-1.78 (m, 3H), 1.29-1.19 (m, 3H). LCMS 130.2 (M+H)$^+$.

Example 345

A stirred suspension of 1-(5-iodo-4-(isopropylamino)pyridin-2-yl)-1H-pyrazolo [3,4-b]pyridine-5-carbonitrile (155 mg, 0.38 mmol), sodium azide (26 mg, 0.40 mmol), sodium ascorbate (7.61 mg, 0.04 mmol), and (1S,2S)—N1,N2-dimethylcyclohexane-1,2-diamine (8.2 mg, 0.06 mmol) were mixed in DMSO (4 mL) and H$_2$O (0.8 mL) with stirring at room temperature. Nitrogen was bubbled into the mixture for 5 minutes then copper(I) iodide (7.32 mg, 0.038 mmol) and 3-fluoro-2-methylhex-5-yn-2-ol (50 mg, 0.38 mmol) were added. The mixture was stirred at room temperature for 20 h, at which point the reaction was judged to be complete by LCMS. Ethyl acetate was added and the solids were removed by filtration. The filtrate was diluted with ethyl acetate and washed with water (3×). The organic layer was dried over Na$_2$SO$_4$, filtered, and concentrated to afford the crude product which was purified by column chromatography (hexanes/EtOAc) to afford (±)-1-(5-(4-(2-fluoro-3-hydroxy-3-methylbutyl)-1H-1,2,3-triazol-1-yl)-4-(isopropylamino)pyridin-2-yl)-1H-pyrazolo[3,4-b]pyridine-5-carbonitrile (45 mg, 23% yield). $^1$H NMR (400 MHz, DMSO-d$_6$) δ 9.07 (d, J=2.0 Hz, 1H), 9.04 (d, J=2.0 Hz, 1H), 8.67 (s, 1H), 8.47 (s, 1H), 8.34 (s, 1H), 7.50 (s, 1H), 6.55 (d, J=7.9 Hz, 1H), 4.87 (s, 1H), 4.72-4.42 (m, 2H), 3.83 (dd, J=13.6, 6.5 Hz, 2H), 1.27-1.18 (m, 12H). LCMS 450.0 (M+H)$^+$.

The individual enantiomers were separated via preparative chiral supercritical fluid chromatography. Second eluting enantiomer, Example 345, isomer 2: $^1$H NMR (400 MHz, CDCl$_3$) δ 8.96 (br s, 1H), 8.52 (s, 1H), 8.40 (br s, 2H), 7.84 (s, 1H), 7.75 (br s, 1H), 6.58 (d, J=6.8 Hz, 1H), 4.71 (dd, J=9.9, 2.0 Hz, 1H), 4.59 (dd, J=8.3, 4.3 Hz, 1H), 3.91 (dq, J=12.9, 6.3 Hz, 1H), 3.39-3.28 (m, 1H), 3.29-3.14 (m, 2H), 1.41-1.31 (m, 12H). LCMS 450.3 (M+H)$^+$.

Example 346

1-(5-(4-(1-(ethylsulfonyl)piperidin-4-yl)-1H-1,2,3-triazol-1-yl)-4-(isopropylamino)pyridin-2-yl)-1H-pyrazolo[3,4-b]pyridine-5-carbonitrile

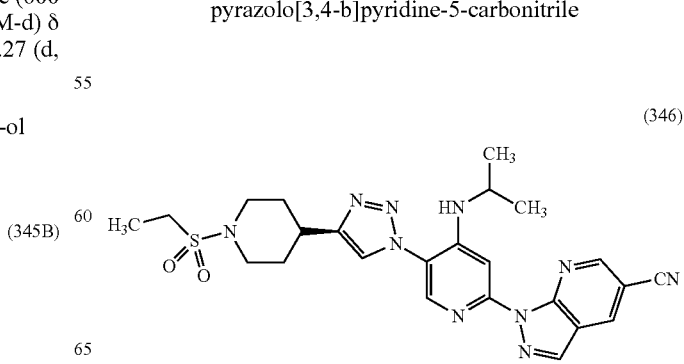
(346)

A stirring solution of 1-(4-(isopropylamino)-5-(4-(piperidin-4-yl)-1H-1,2,3-triazol-1-yl)pyridin-2-yl)-1H-pyrazolo[3,4-b]pyridine-5-carbonitrile, 2 HCl (30 mg, 0.06 mmol) and triethylamine (80 µL, 0.55 mmol) in DMF (1 mL) was treated with ethanesulfonyl chloride (7.7 mg, 0.06 mmol). The reaction mixture was stirred for 1 hour, at which point it was judged to be complete by LCMS. The reaction mixture was filtered and purified by preparative HPLC to afford 1-(5-(4-(1-(ethylsulfonyl)piperidin-4-yl)-1H-1,2,3-triazol-1-yl)-4-(isopropylamino)pyridin-2-yl)-1H-pyrazolo[3,4-b]pyridine-5-carbonitrile (6.2 mg, 19% yield). ¹H NMR (500 MHz, DMSO-d₆) δ 9.02 (s, 1H), 8.98 (s, 1H), 8.63 (s, 1H), 8.43 (s, 1H), 8.30 (s, 1H), 7.48 (s, 1H), 6.57 (d, J=7.4 Hz, 1H), 3.68-3.56 (m, 3H), 3.10-2.91 (m, 5H), 2.12 (d, J=12.2 Hz, 2H), 1.76-1.63 (m, 2H), 1.26-1.17 (m, 9H). LCMS 520.9 (M+H)⁺. HPLC rt 1.60 min, conditions C.

Example 347

1-(4-((3,3-difluorocyclopentyl)amino)-5-(4-(3-hydroxy-3-methylbutyl)-1H-1,2,3-triazol-1-yl)pyridin-2-yl)-1H-pyrazolo[3,4-b]pyridine-5-carbonitrile

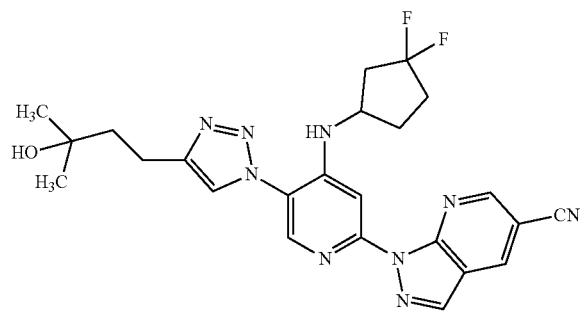

(347)

Intermediate 347A: 2-Chloro-N-(3,3-difluorocyclopentyl)-5-nitropyridin-4-amine

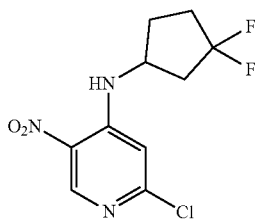

(347)

To a stirred solution of 2,4-dichloro-5-nitropyridine (1 g, 5.2 mmol) in acetonitrile (20 mL) were added 3,3-difluorocyclopentanamine (0.63 g, 5.2 mmol) and DIPEA (2.71 mL, 15.6 mmol) at room temperature and stirred for 3 h. The reaction mixture was evaporated to dryness and extracted between ethyl acetate and water. The organic layer was dried over Na₂SO₄, filtered and concentrated to an oil. The crude residue purified by silica gel column chromatography (10% ethyl acetate/pet ether) to afford 2-chloro-N-(3,3-difluorocyclopentyl)-5-nitropyridin-4-amine (1.2 g, 82% yield) as pale yellow solid. ¹H NMR (300 MHz, DMSO-d₆) δ 8.86-8.92 (m, 1H), 8.27 (d, J=8.7 Hz, 1H), 7.24 (s, 1H), 4.28-4.48 (m, 1H), 2.57-2.76 (m, 1H), 1.75-2.40 (m, 5H); LCMS m/z 279.3 (M+H).

Intermediate 347B: 6-Chloro-N4-(3,3-difluorocyclopentyl)pyridine-3,4-diamine

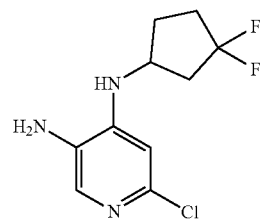

(347B)

A solution of 2-chloro-N-(3,3-difluorocyclopentyl)-5-nitropyridin-4-amine (1.8 g, 6.5 mmol) in ethyl acetate (20 mL) was added platinum(II) oxide (1.37 g, 6.5 mmol). The reaction mixture was stirred under a hydrogen atmosphere for 14 h. The reaction mixture was filtered through celite and evaporated to afford 6-chloro-N4-(3,3-difluorocyclopentyl)pyridine-3,4-diamine (1.5 g, 74% yield) as brown liquid which was used in the next step without purification. LCMS m/z 248.3 (M+H).

Intermediate 347C: 5-azido-2-chloro-N-(3,3-difluorocyclopentyl)pyridin-4-amine

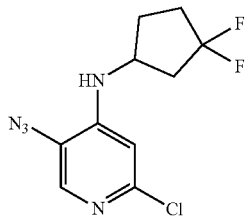

(347C)

A solution of 6-chloro-N4-(3,3-difluorocyclopentyl)pyridine-3,4-diamine (1.5 g, 6.1 mmol) in acetonitrile (20 mL) was added DMAP (1.1 g, 9.1 mmol) followed by a solution of 2-azido-1,3-dimethylimidazolinium hexafluorophosphate (3.45 g, 12.1 mmol) in acetonitrile (10 mL). The reaction mixture was stirred for 3 h. The reaction mixture was quenched by the addition of saturated NaHCO₃ solution and extracted between 30% ethyl acetate and water. The organic extracts were dried over Na₂SO₄, filtered, and evaporated to afford 5-azido-2-chloro-N-(3,3-difluorocyclopentyl)pyridin-4-amine (1.3 g, 37% yield) as brown liquid, which was used without further purification. LCMS m/z 246.3 (M−N₂).

257

Intermediate 347D: 4-(1-(6-chloro-4-((3,3-difluoro-cyclopentyl)amino)pyridin-3-yl)-1H-1,2,3-triazol-4-yl)-2-methylbutan-2-ol

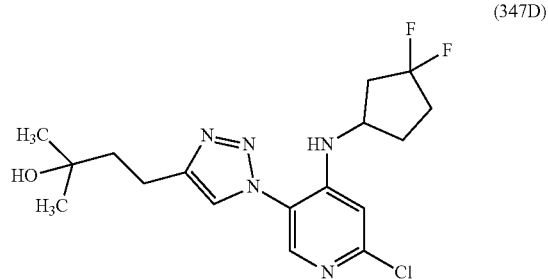 [SMILES: CC(C)(O)CCc1cn(-c2cnc(Cl)cc2NC2CCC(F)(F)C2)nn1]

(347D)

To stirred suspension of 5-azido-2-chloro-N-(3,3-difluorocyclopentyl)pyridin-4-amine (1.3 g, 4.8 mmol) in t-BuOH (10 mL) and water (10 mL) were added 2-methylhex-5-yn-2-ol (0.64 g, 5.7 mmol), copper(II) sulfate (0.174 g, 1.1 mmol), and sodium ascorbate (0.38 g, 1.9 mmol). Stirring was continued for 14 h at which time the reaction mixture was filtered through celite and concentrated. The crude residue was diluted with water and extracted ethyl acetate and the combined organic extracts were dried over $Na_2SO_4$, filtered and evaporated. The product was purified by silica gel chromatography (5% methanol/dichloromethane) to give 4-(1-(6-chloro-4-((3,3-difluorocyclopentyl) amino)pyridin-3-yl)-1H-1,2,3-triazol-4-yl)-2-methylbutan-2-ol (1 g, 55% yield) as a black solid. $^1$H NMR (300 MHz, DMSO-$d_6$) δ 8.23 (s, 1H), 8.04 (s, 1H), 7.01 (s, 1H), 6.76 (d, J=7.6 Hz, 1H), 4.15-4.26 (m, 1H), 2.69-2.82 (m, 2H), 2.56-2.66 (m, 1H), 1.91-2.36 (m, 4H), 1.63-1.84 (m, 2H), 1.52-1.61 (m, 1H), 1.02-1.20 (m, 6H); LCMS m/z 386.4 (M+H).

Example 347

To a solution of 4-(1-(6-chloro-4-((3,3-difluorocyclopentyl)amino)pyridin-3-yl)-1H-1,2,3-triazol-4-yl)-2-methylbutan-2-ol (120 mg, 0.31 mmol) in 1,4-dioxane (20 mL) in a pressure tube, were added 1H-pyrazolo[3,4-b]pyridine-5-carbonitrile (45 mg, 0.31 mmol), Xantphos (180 mg, 0.31 mmol), $K_2CO_3$ (129 mg, 0.93 mmol), lithium chloride (13.2 mg, 0.31 mmol) and zinc chloride (12.7 mg, 0.093 mmol). The mixture was degassed by bubbling nitrogen gas for 5 mins. $Pd_2(dba)_3$ (142 mg, 0.156 mmol) was added to the reaction mixture and degassing was continued for an additional 5 min. The reaction tube was sealed and heated at 120° C. for 20 h. After cooling to room temperature, the reaction mixture was filtered through celite and the bed was washed with 50 mL of ethyl acetate. The filtrate was concentrated and the product was purified by silica gel using 2% methanol/chloroform to isolate the partially pure product. The product was further purified via preparative HPLC to get afford (±)-1-(4-((3,3-difluorocyclopentyl)amino)-5-(4-(3-hydroxy-3-methylbutyl)-1H-1,2,3-triazol-1-yl) pyridin-2-yl)-1H-pyrazolo[3,4-b]pyridine-5-carbonitrile. The enantiomers were separated using chiral SFC to provide the desired enantiomer. $^1$H NMR (400 MHz, DMSO-$d_6$) δ 9.06 (dd, J=13.1, 2.0 Hz, 2H), 8.68 (s, 1H), 8.33 (d, J=11.0 Hz, 2H), 7.54 (s, 1H), 6.86 (d, J=7.5 Hz, 1H), 4.33 (s, 1H), 4.26-4.13 (m, 1H), 2.89-2.76 (m, 2H), 2.63 (d, J=8.0 Hz, 1H), 2.32-2.05 (m, 5H), 1.89-1.76 (m, 4H), 1.19 (s, 6H); LCMS m/z 494.3 (M+H).

258

Example 348

1-(4-(cyclopropylamino)-5-(4-(tetrahydro-2H-pyran-4-yl)-1H-1,2,3-triazol-1-yl)pyridin-2-yl)-1H-pyrazolo[3,4-b]pyridine-5-carbonitrile

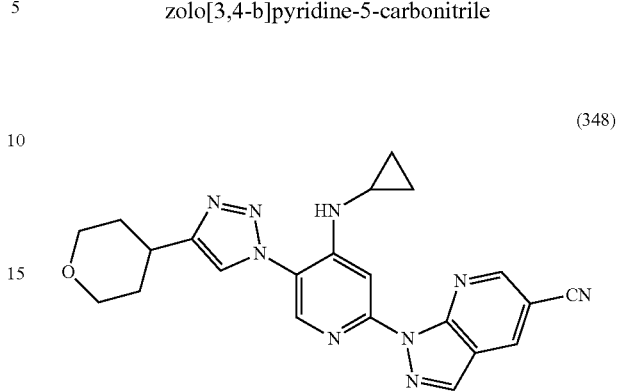

(348)

In a 20 mL microwave vial, a mixture of 2-chloro-N-cyclopropyl-5-(4-(tetrahydro-2H-pyran-4-yl)-1H-1,2,3-triazol-1-yl)pyridin-4-amine (100 mg, 0.31 mmol), 1H-pyrazolo[3,4-b]pyridine-5-carbonitrile (45.1 mg, 0.31 mmol), and potassium phosphate, tribasic (199 mg, 0.94 mmol) in dioxane (2 mL) was degassed with bubbling nitrogen for 5 minutes. In a separate vial, a stirring, degassed mixture of $Pd_2(dba)_3$ (14.3 mg, 0.016 mmol) and tetramethyl t-BuXphos (18.0 mg, 0.038 mmol) in 5:1 toluene/dioxane (0.2 mL) was heated at 120° C. for 3 minutes. After this mixture cooled to room temperature, it was added to the vial containing the reaction mixture, and the vial was sealed. The reaction mixture was heated with stirring at 80° C. for 18 hours at which point it was judged to be complete by LCMS. The reaction mixture was filtered and the product was purified by preparative HPLC to afford 1-(4-(cyclopropylamino)-5-(4-(tetrahydro-2H-pyran-4-yl)-1H-1,2,3-triazol-1-yl)pyridin-2-yl)-1H-pyrazolo[3,4-b]pyridine-5-carbonitrile (14.2 mg, 7% yield). $^1$H NMR (500 MHz, DMSO-$d_6$) δ 9.12-9.06 (m, 1H), 9.04 (s, 1H), 8.98-8.97 (m, 1H), 8.68 (br s, 1H), 8.35 (s, 1H), 8.29 (br s, 1H), 7.84 (br s, 1H), 7.10 (s, 1H), 3.94 (d, J=10.2 Hz, 2H), 3.53-3.44 (m, 1H), 3.09-2.96 (m, 1H), 1.96 (d, J=14.1 Hz, 2H), 1.80-1.67 (m, 2H), 0.82 (d, J=5.4 Hz, 2H), 0.58 (br. s., 2H). LCMS 428.3 (M+H)$^+$. HPLC rt 1.42 min, conditions C.

Example 349

1-(4-(isopropylamino)-5-(4-(2-morpholinoethyl)-1H-1,2,3-triazol-1-yl)pyridin-2-yl)-1H-pyrazolo[3,4-b]pyridine-5-carbonitrile

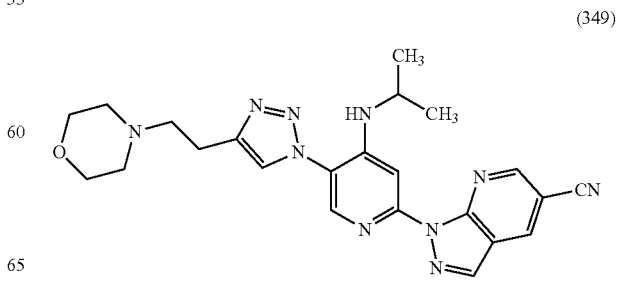

(349)

Intermediate 349A: 2-Chloro-N-isopropyl-5-(4-(2-morpholinoethyl)-1H-1,2,3-triazol-1-yl)pyridin-4-amine

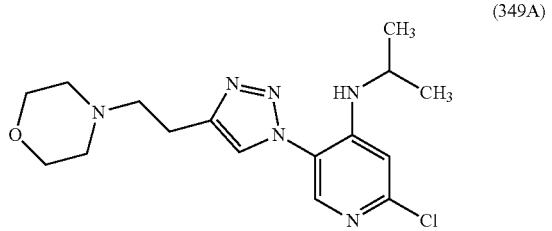 [SMILES: CC(C)Nc1cc(Cl)ncc1-n1cc(CCN2CCOCC2)nn1]

(349A)

In a 20 mL microwave vial, a mixture of 5-bromo-2-chloro-N-isopropylpyridin-4-amine (200 mg, 0.80 mmol), sodium azide (54.7 mg, 0.84 mmol), sodium ascorbate (16 mg, 0.08 mmol), copper(I) iodide (15.3 mg, 0.08 mmol), (1S,2S)—N1,N2-dimethylcyclohexane-1,2-diamine (17.1 mg, 0.12 mmol), and 4-(but-3-yn-1-yl)morpholine (112 mg, 0.80 mmol) in DMSO (20 mL) and $H_2O$ (4 mL) was heated at 70° C. for 24 hours. After cooling to room temperature, the reaction mixture was filtered and the filtrate was taken up in ethyl acetate (15 mL). The turbid solution was washed with water (3×) then dried over sodium sulfate and concentrated. The product was purified by column chromatography (hexanes/EtOAc) to afford 2-chloro-N-isopropyl-5-(4-(2-morpholinoethyl)-1H-1,2,3-triazol-1-yl)pyridin-4-amine (64 mg, 17% yield). LCMS 351.0 $(M+H)^+$.

Example 348

In a 20 mL microwave vial, a mixture of 2-chloro-N-isopropyl-5-(4-(2-morpholinoethyl)-1H-1,2,3-triazol-1-yl)pyridin-4-amine (30 mg, 0.09 mmol), 1H-pyrazolo[3,4-b]pyridine-5-carbonitrile (12.3 mg, 0.09 mmol), and potassium phosphate, tribasic (54.5 mg, 0.26 mmol) in dioxane (2 mL) was degassed with bubbling nitrogen for 5 minutes. In a separate vial, a stirring, degassed mixture of tetramethyl t-BuXphos (4.5 mg, 9.4 µmol) and $Pd_2(dba)_3$ (3.9 mg, 4.3 µmol) in 5:1 toluene/dioxane (0.2 mL) was heated at 120° C. for 3 minutes. After this mixture cooled to room temperature, it was added to the vial containing the reaction mixture, and the vial was sealed. The reaction mixture was heated with stirring at 80° C. for 18 hours behind a safety shield. The reaction mixture was filtered and purified by preparative HPLC to afford 1-(4-(isopropylamino)-5-(4-(2-morpholinoethyl)-1H-1,2,3-triazol-1-yl)pyridin-2-yl)-1H-pyrazolo[3,4-b]pyridine-5-carbonitrile (6.1 mg, 14% yield). $^1$H NMR (400 MHz, DMSO-$d_6$) δ 9.06 (d, J=1.8 Hz, 1H), 9.03 (d, J=2.0 Hz, 1H), 8.67 (s, 1H), 8.42 (s, 1H), 8.32 (br. s., 1H), 7.49 (s, 1H), 6.53 (d, J=7.5 Hz, 1H), 3.82 (dq, J=13.3, 6.6 Hz, 1H), 3.61 (br. s., 4H), 2.93 (br. s., 2H), 2.67 (d, J=2.0 Hz, 2H), 2.54 (s, 1H), 2.48-2.43 (m, 2H), 1.23 (d, J=6.4 Hz, 6H). LCMS 459.3 (M+H)+. HPLC rt 1.27 min, conditions C.

Example 350

4-(1-(6-(6-amino-1H-pyrazolo[3,4-d]pyrimidin-1-yl)-4-(isopropylamino)pyridin-3-yl)-1H-1,2,3-triazol-4-yl)-2-methylbutan-2-ol

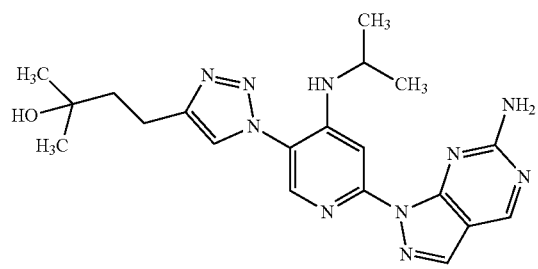

(350)

Intermediate 350A: 4-(1-(6-chloro-4-(isopropylamino)pyridin-3-yl)-1H-1,2,3-triazol-4-yl)-2-methylbutan-2-ol

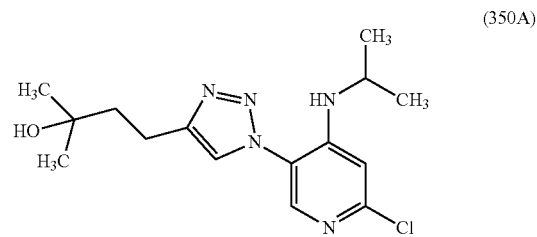 [SMILES: CC(C)Nc1cc(Cl)ncc1-n1cc(CCC(C)(C)O)nn1]

(350A)

In a 20 mL microwave vial, a mixture of 5-bromo-2-chloro-N-isopropylpyridin-4-amine (2.00 g, 8.0 mmol), sodium azide (0.547 g, 8.4 mmol), sodium ascorbate (0.159 g, 0.80 mmol), copper(I) iodide (0.153 g, 0.80 mmol), (1S,2S)—N1,N2-dimethylcyclohexane-1,2-diamine (0.171 g, 1.20 mmol), and 2-methylhex-5-yn-2-ol (0.899 g, 8.0 mmol) were mixed in DMSO (20 mL) and $H_2O$ (4 mL) at room temperature with stirring. Nitrogen was bubbled through the mixture for 5 minutes. The reaction mixture was then heated behind a safety shield at 70° C. for 16 hours at which point the reaction was judged to be complete by LCMS. After cooling to room temperature, the reaction mixture was partitioned between water (500 mL) and ethyl acetate (500 mL). The mixture was filtered to remove solids and the layers were separated. The organic layer was rinsed three times more with water. The organic layer was dried over sodium sulfate and concentrated in vacuo. The product was purified by column chromatography (hexanes/EtOAc) to afford 4-(1-(6-chloro-4-(isopropylamino)pyridin-3-yl)-1H-1,2,3-triazol-4-yl)-2-methylbutan-2-ol (1.8 g, 69% yield). $^1$H NMR (400 MHz, CDCl$_3$) δ 8.05 (s, 1H), 7.65-7.62 (m, 1H), 6.69 (s, 1H), 6.51-6.43 (m, 1H), 3.77-3.63 (m, 1H), 2.99-2.90 (m, 2H), 2.01-1.93 (m, 2H), 1.34 (s, 6H), 1.30-1.25 (m, 7H). LCMS 324.3 (M+H)$^+$.

Example 350

In a 20 mL microwave vial, a mixture of 4-(1-(6-chloro-4-(isopropylamino) pyridin-3-yl)-1H-1,2,3-triazol-4-yl)-2-methylbutan-2-ol (40 mg, 0.12 mmol), 9H-purin-2-amine (16.7 mg, 0.12 mmol) and potassium phosphate, tribasic (79 mg, 0.37 mmol) in dioxane (2 mL) was degassed with bubbling nitrogen for 5 minutes. In a separate vial, a stirring, degassed mixture of tetramethyl t-BuXphos (6.5 mg, 0.014 mmol) and Pd$_2$(dba)$_3$ (5.7 mg, 6.18 μmol) in 5:1 toluene/dioxane (0.2 mL) was heated at 120° C. for 3 minutes. After this mixture cooled to room temperature, it was added to the vial containing the reaction mixture, and the vial was sealed. The reaction mixture was heated with stirring at 80° C. for 18 hours at which point it was judged to be complete by LCMS. The reaction mixture was filtered and purified by preparative HPLC to afford 4-(1-(6-(2-amino-9H-purin-9-yl)-4-(isopropylamino)pyridin-3-yl)-1H-1,2,3-triazol-4-yl)-2-methylbutan-2-ol (29 mg, 51% yield). $^1$H NMR (500 MHz, DMSO-d$_6$) δ 8.76 (s, 1H), 8.70 (s, 1H), 8.30 (s, 1H), 8.20 (s, 1H), 8.08 (s, 1H), 6.52 (d, J=7.7 Hz, 1H), 3.92 (dq, J=13.1, 6.5 Hz, 1H), 3.50 (br. s., 1H), 2.81-2.73 (m, 2H), 1.83-1.74 (m, 2H), 1.24 (d, J=6.3 Hz, 7H), 1.16 (s, 7H). LCMS 422.9 (M+H)$^+$.

Example 351

1-(5-(4-(3-fluoro-3-methylbutyl)-1H-1,2,3-triazol-1-yl)-4-(isopropylamino)pyridin-2-yl)-1H-pyrazolo[3,4-d]pyrimidin-6-amine (351)

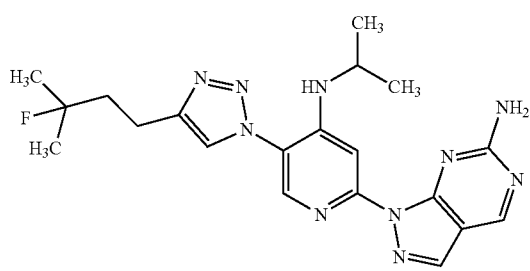

Intermediate 351A: 2-chloro-5-(4-(3-fluoro-3-methylbutyl)-1H-1,2,3-triazol-1-yl)-N-isopropylpyridin-4-amine

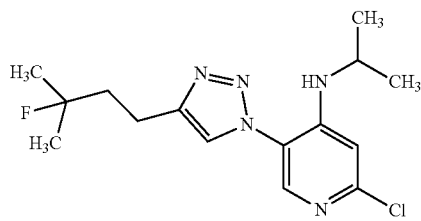 [SMILES: CC(C)Nc1cc(Cl)ncc1-n1cc(CCC(C)(C)F)nn1]

A stirring suspension of 4-(1-(6-chloro-4-(isopropylamino)pyridin-3-yl)-1H-1,2,3-triazol-4-yl)-2-methylbutan-2-ol (500 mg, 1.54 mmol) in anhydrous dichloromethane (10 mL) under nitrogen was cooled to −78° C. and treated with DAST (0.20 mL, 1.54 mmol). The reaction mixture was stirred at −78° C. for 1 hour, then at room temperature for 5 hours, at which point the reaction was judged to be complete by LCMS. Methanol was added carefully to quench the reaction and then the contents were concentrated. The residue was purified by column chromatography (hexanes/EtOAc) to afford 2-chloro-5-(4-(3-fluoro-3-methylbutyl)-1H-1,2,3-triazol-1-yl)-N-isopropylpyridin-4-amine (254 mg, 45% yield). LCMS 326.1 (M+H)$^+$.

Example 351

In a 20 mL microwave vial, a mixture of 2-chloro-5-(4-(3-fluoro-3-methylbutyl)-1H-1,2,3-triazol-1-yl)-N-isopropylpyridin-4-amine (40 mg, 0.123 mmol), 9H-purin-2-amine (16.6 mg, 0.123 mmol), and potassium phosphate, tribasic (78 mg, 0.37 mmol) in dioxane (2 mL) was degassed with bubbling nitrogen for 5 minutes. In a separate vial, a stirring, degassed mixture of tetramethyl t-BuXphos (6.5 mg, 0.014 mmol) and Pd$_2$(dba)$_3$ (5.6 mg, 6.14 μmol) in 5:1 toluene/dioxane (0.2 mL) was heated at 120° C. for 3 minutes. After this mixture cooled to room temperature, it was added to the vial containing the reaction mixture, and the vial was sealed. The reaction mixture was heated with stirring at 80° C. for 18 hours at which point the reaction was judged to be complete by LCMS. The reaction mixture was filtered and the product was purified by preparative HPLC to afford 2-chloro-5-(4-(3-fluoro-3-methylbutyl)-1H-1,2,3-triazol-1-yl)-N-isopropylpyridin-4-amine (26 mg, 51% yield). $^1$H NMR (500 MHz, DMSO-d$_6$) δ 8.76 (s, 1H), 8.71 (s, 1H), 8.36 (s, 1H), 8.20 (s, 1H), 8.11 (s, 1H), 6.80 (br. s., 2H), 6.50 (d, J=7.7 Hz, 1H), 3.99-3.84 (m, 1H), 2.86-2.78 (m, 2H), 2.10-1.97 (m, 2H), 1.44-1.35 (m, 6H), 1.25 (d, J=6.3 Hz, 6H). LCMS 424.9 (M+H)$^+$. HPLC rt 1.59 min, conditions C.

The Examples in Table 20 were prepared using the methods outlined for Examples 345-350 using the appropriate starting material.

TABLE 20

| Ex. No. | Structure | HPLC rt (min) | HPLC cond. | LCMS |
|---|---|---|---|---|
| 352 | 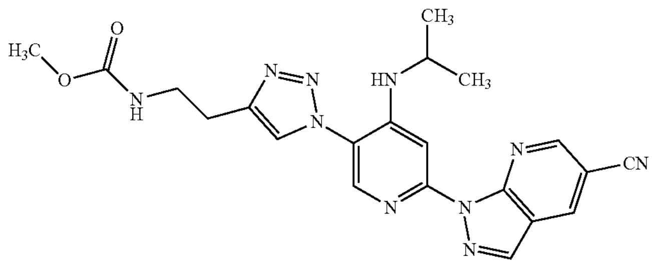 [SMILES: COC(=O)NCCc1cn(-c2cnc(-n3ncc4cc(C#N)cnc43)cc2NC(C)C)nn1] | 1.37 | C | 447.2 |
| 353 | Enantiomer 1 | 1.5 | C | 404 |
| 354 | Enantiomer 2 | 1.49 | C | 404.2 |
| 355 | 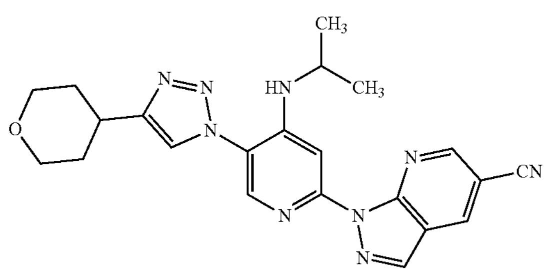 [SMILES: CC(C)Nc1cc(-n2ncc3cc(C#N)cnc32)ncc1-n1cc(C2CCOCC2)nn1] | 0.81 | D | 430.6 |
| 356 | 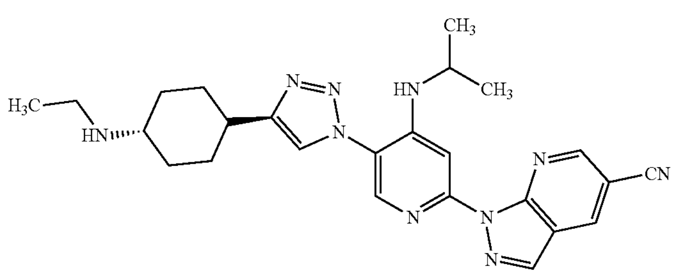 | 1.19 | C | 471.1 |

TABLE 20-continued

| Ex. No. | Structure | HPLC rt (min) | HPLC cond. | LCMS |
|---|---|---|---|---|
| 357 | 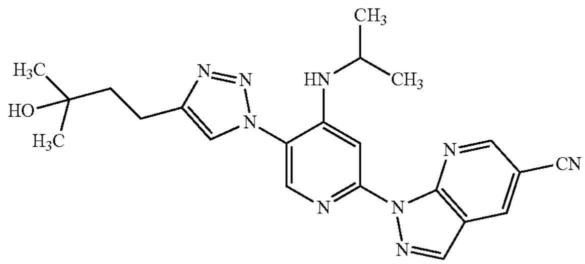 [SMILES: CC(C)Nc1cc(-n2ncc3cc(C#N)cnc32)ncc1-n1cc(CCC(C)(C)O)nn1] | 1.19 | C | 471.1 |
| 358 | 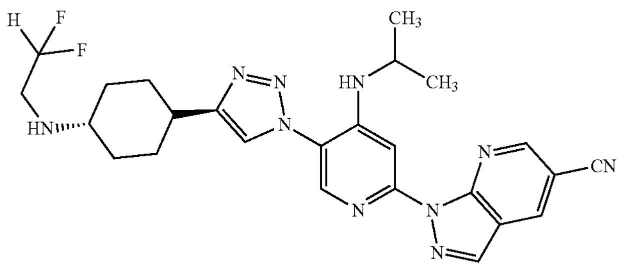 | 1.21 | C | 422.1 |
| 359 | 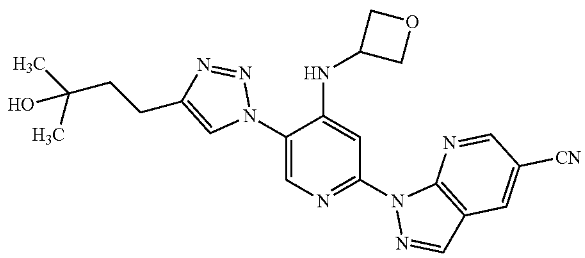 [SMILES: CC(C)(O)CCc1cn(-c2cnc(-n3ncc4cc(C#N)cnc43)cc2NC2COC2)nn1] | 1.66 | C | 507.3 |
| 360 | 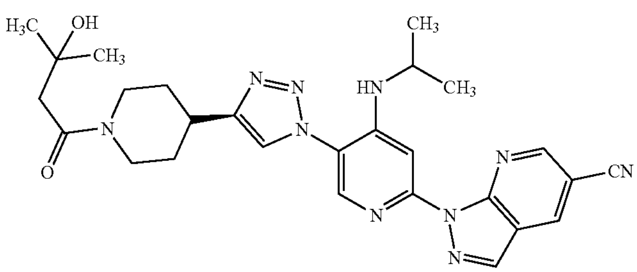 | 1.12 | C | 446.3 |
| 361 | 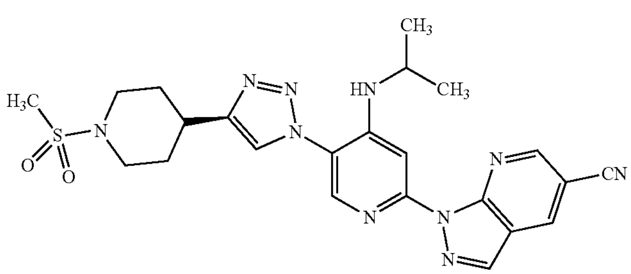 | 1.34 | C | 507.3 |
| 362 | 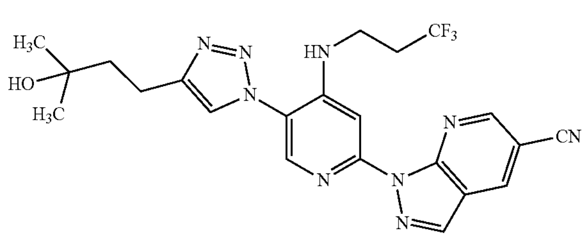 | 1.53 | F | 486.2 |

TABLE 20-continued

| Ex. No. | Structure | HPLC rt (min) | HPLC cond. | LCMS |
|---|---|---|---|---|
| 363 | 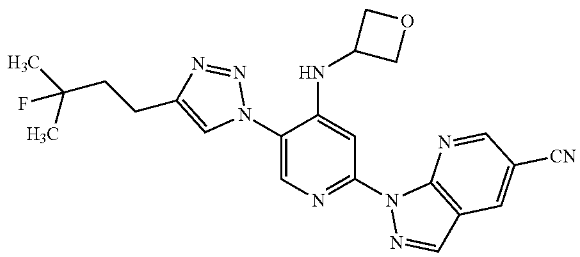 [SMILES: CC(C)(F)CCc1cn(-c2cnc(-n3ncc4cc(C#N)cnc43)cc2NC2COC2)nn1] | 1.4 | C | 447.9 |
| 364 | Enantiomer 1 | 1.64 | F | 476.2 |
| 365 | 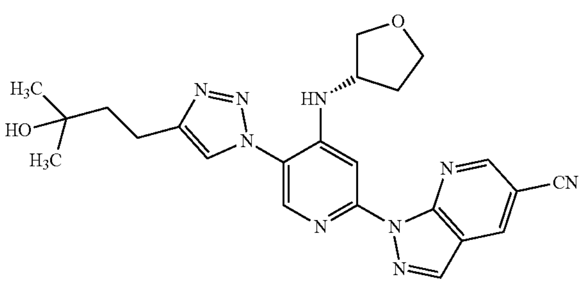 | 1.22 | C | 460 |
| 366 | 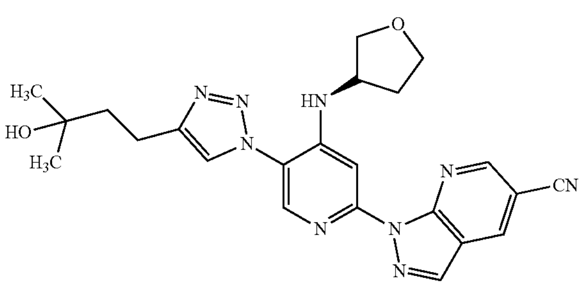 | 1.22 | C | 460.3 |
| 367 | 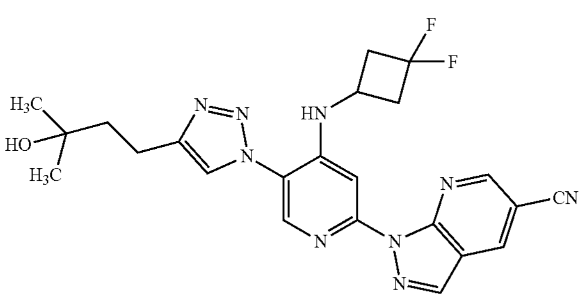 [SMILES: CC(C)(O)CCc1cn(-c2cnc(-n3ncc4cc(C#N)cnc43)cc2NC2CC(F)(F)C2)nn1] | 1.68 | F | 480.2 |

TABLE 20-continued

| Ex. No. | Structure | HPLC rt (min) | HPLC cond. | LCMS |
|---|---|---|---|---|
| 368 | 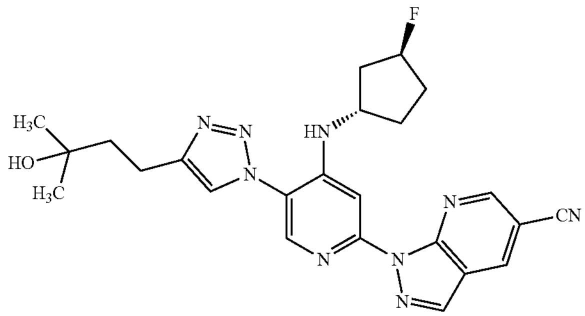 [SMILES: CC(C)(O)CCc1cn(-c2cnc(-n3ncc4cc(C#N)cnc43)cc2N[C@H]2CC[C@H](F)C2)nn1] | 1.64 | F | 476.2 |
| 369 | 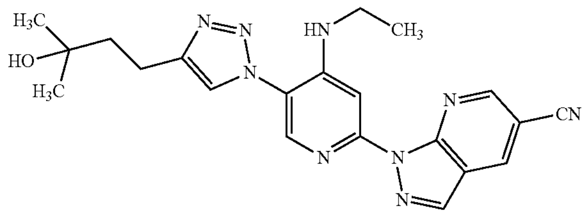 [SMILES: CCNc1cc(-n2ncc3cc(C#N)cnc32)ncc1-n1cc(CCC(C)(C)O)nn1] | 1.41 | F | 418.2 |
| 370 | 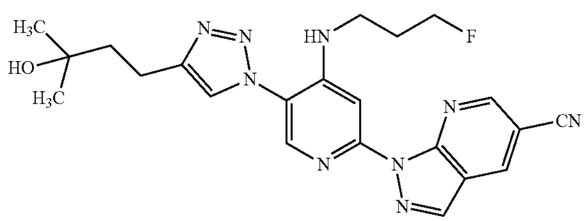 [SMILES: CC(C)(O)CCc1cn(-c2cnc(-n3ncc4cc(C#N)cnc43)cc2NCCCF)nn1] | 1.44 | C | 450.3 |
| 371 | 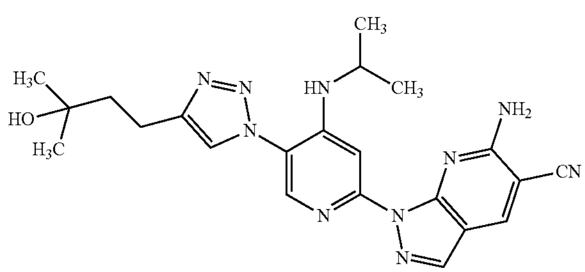 [SMILES: CC(C)Nc1cc(-n2ncc3cc(C#N)c(N)nc32)ncc1-n1cc(CCC(C)(C)O)nn1] | 1.57 | C | 447.3 |
| 372 | 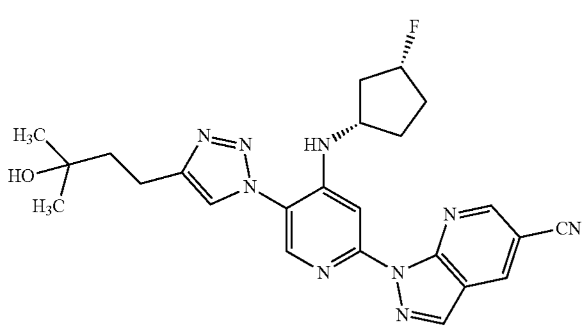 [SMILES: CC(C)(O)CCc1cn(-c2cnc(-n3ncc4cc(C#N)cnc43)cc2N[C@H]2CC[C@@H](F)C2)nn1] | 1.39 | F | 476.3 |

TABLE 20-continued

| Ex. No. | Structure | HPLC rt (min) | HPLC cond. | LCMS |
|---|---|---|---|---|
| 373 | 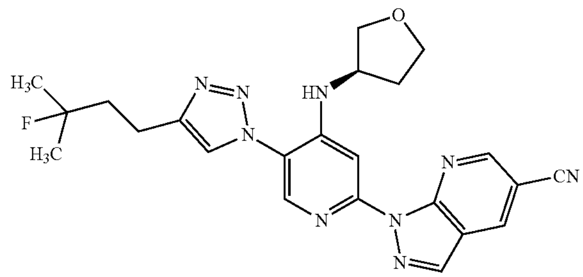 [SMILES: CC(C)(F)CCc1cn(-c2cnc(-n3ncc4cc(C#N)cnc43)cc2N[C@@H]2CCOC2)nn1] | 1.58 | C | 462.1 |
| 374 | 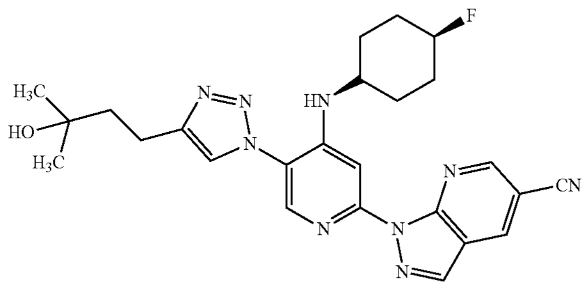 | 1.60 | E | 490.1 |
| 375 | 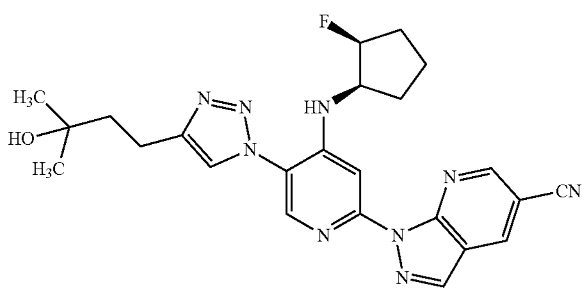 [SMILES: CC(C)(O)CCc1cn(-c2cnc(-n3ncc4cc(C#N)cnc43)cc2N[C@@H]2CCC[C@@H]2F)nn1] | 1.61 | F | 476.1 |
| 376 | 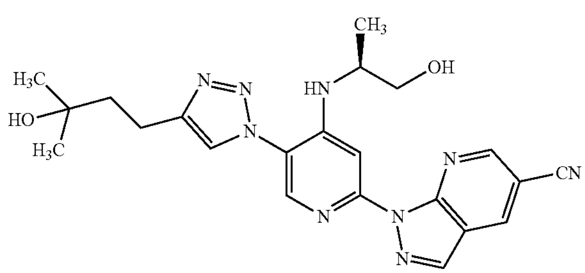 [SMILES: C[C@@H](CO)Nc1cc(-n2ncc3cc(C#N)cnc32)ncc1-n1cc(CCC(C)(C)O)nn1] | 1.41 | F | 450.1 |
| 377 | 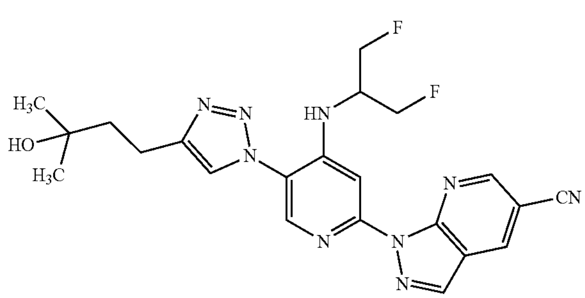 [SMILES: CC(C)(O)CCc1cn(-c2cnc(-n3ncc4cc(C#N)cnc43)cc2NC(CF)CF)nn1] | 1.43 | F | 468.1 |

TABLE 20-continued

| Ex. No. | Structure | HPLC rt (min) | HPLC cond. | LCMS |
|---|---|---|---|---|
| 378 | 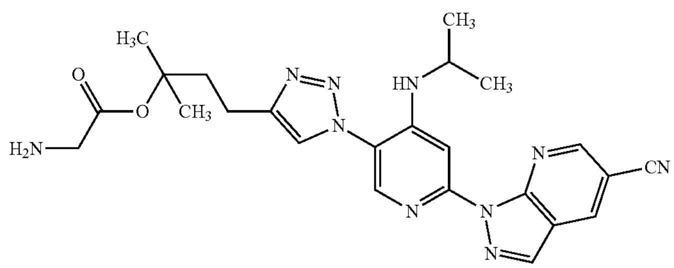 [SMILES: CC(C)Nc1cc(-n2ncc3cc(C#N)cnc32)ncc1-n1cc(CCC(C)(C)OC(=O)CN)nn1] | 1.35 | C | 489.2 |
| 379 | Enantiomer 1 | 1.36 | F | 478.2 |
| 380 | 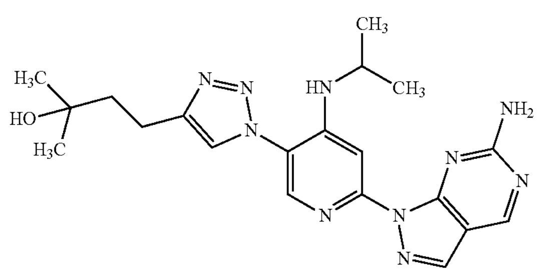 [SMILES: CC(C)Nc1cc(-n2ncc3cnc(N)nc32)ncc1-n1cc(CCC(C)(C)O)nn1] | 1.19 | C | 423.1 |
| 381 | 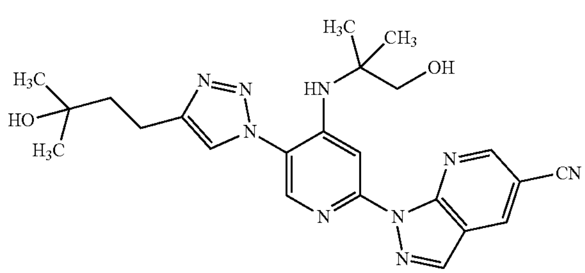 [SMILES: CC(C)(O)CCc1cn(-c2cnc(-n3ncc4cc(C#N)cnc43)cc2NC(C)(C)CO)nn1] | 1.33 | F | 462.2 |
| 382 | 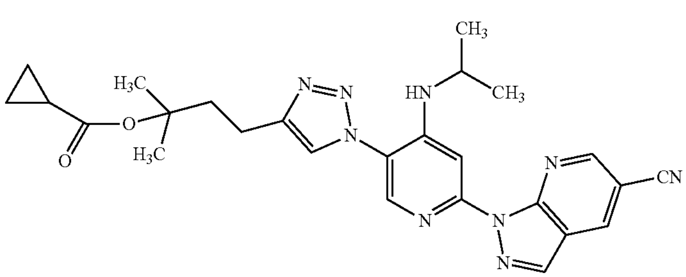 [SMILES: CC(C)Nc1cc(-n2ncc3cc(C#N)cnc32)ncc1-n1cc(CCC(C)(C)OC(=O)C2CC2)nn1] | 2.00 | C | 500.2 |

TABLE 20-continued

| Ex. No. | Structure | HPLC rt (min) | HPLC cond. | LCMS |
|---|---|---|---|---|
| 383 | 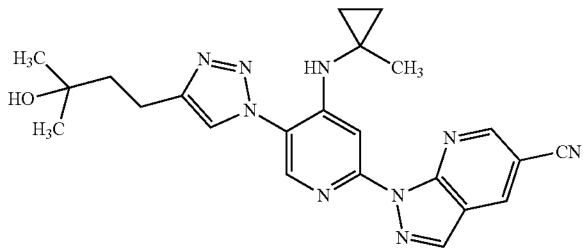 [SMILES: CC(C)(O)CCc1cn(-c2cnc(-n3ncc4cc(C#N)cnc43)cc2NC2(C)CC2)nn1] | 1.53 | F | 444.2 |
| 384 | 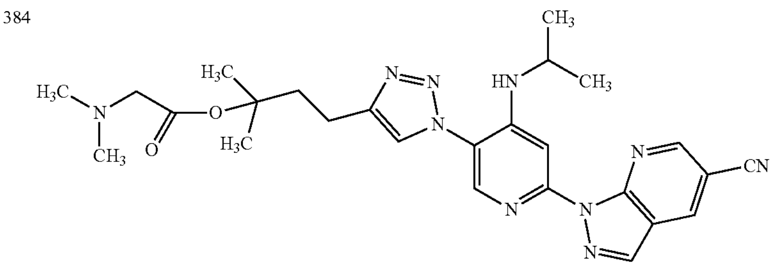 | 1.71 | C | 517.3 |
| 385 | 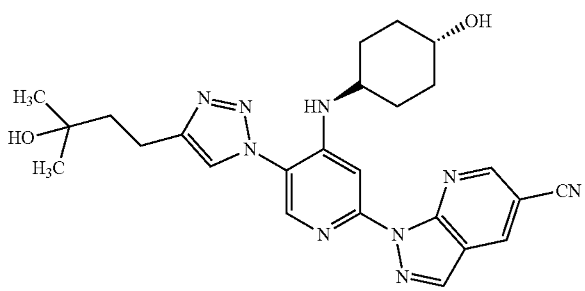 | 1.13 | F | 488.2 |
| 386 | 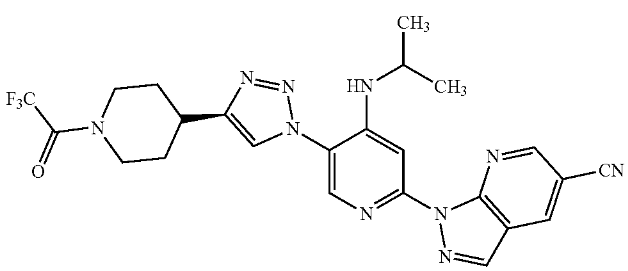 | 1.81 | C | 525.3 |
| 387 | 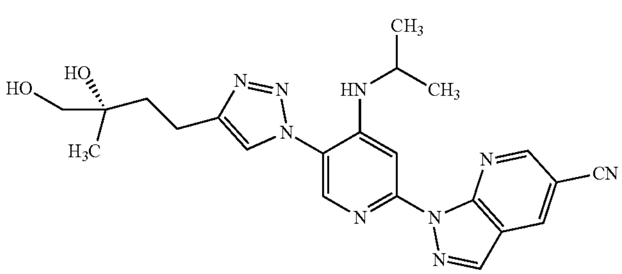 [SMILES: CC(C)Nc1cc(-n2ncc3cc(C#N)cnc32)ncc1-n1cc(CC[C@](C)(O)CO)nn1] | 1.34 | C | 448.3 |

| Ex. No. | Structure | HPLC rt (min) | HPLC cond. | LCMS |
|---|---|---|---|---|
| 388 | 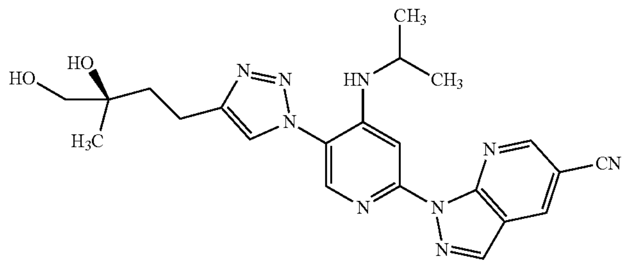 [SMILES: CC(C)Nc1cc(-n2ncc3cc(C#N)cnc32)ncc1-n1cc(CC[C@@](C)(O)CO)nn1] | 1.34 | C | 448.3 |
| 389 | 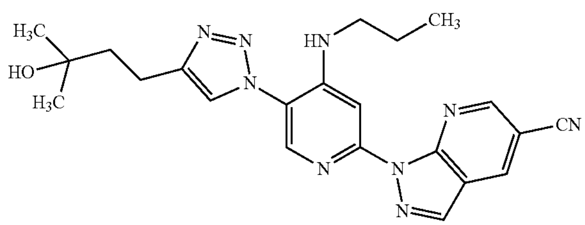 [SMILES: CCCNc1cc(-n2ncc3cc(C#N)cnc32)ncc1-n1cc(CCC(C)(C)O)nn1] | 1.58 | C | 432.2 |

Example 390

1-(5-(4-(3-hydroxy-3-methylbutyl)-1H-pyrazol-1-yl)-4-(isopropylamino)pyridin-2-yl)-1H-pyrazolo[3,4-b]pyridine-5-carbonitrile

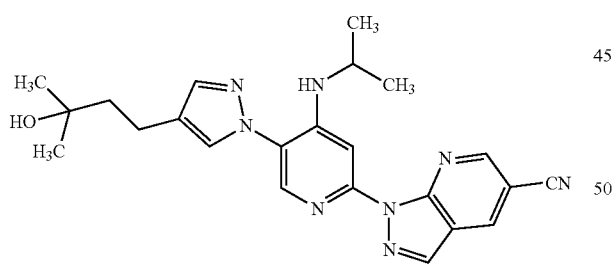
(390)

Intermediate 390A: Ethyl (E)-3-(1H-pyrazol-4-yl)acrylate

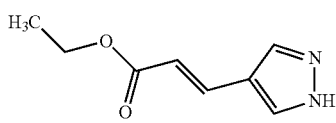
(390A)

To a stirred solution of 1H-pyrazole-4-carbaldehyde (2 g, 20.8 mmol) in THF (30 mL) was added (carboxymethylene)triphenylphosphorane (8 g, 22.9 mmol). The reaction mixture was then heated at 70° C. for 14 h. The reaction mixture was cooled to room temperature and concentrated. The residue was purified by silica gel chromatography (3% methanol/chloroform) to isolate ethyl 3-(1H-pyrazol-4-yl)acrylate (2.5 g, 73% yield). $^1$H NMR (400 MHz, DMSO-$d_6$) δ 13.14 (br s, 1H), 8.18 (s, 1H), 7.93 (s, 1H), 7.57 (d, J=15.6 Hz, 1H), 6.32 (d, J=16.1 Hz, 1H), 4.15 (q, J=7.0 Hz, 2H), 1.24 (t, J=7.3 Hz, 3H); LCMS m/z 165 (M−H).

Intermediate 390B: ethyl 3-(1H-pyrazol-4-yl)propanoate

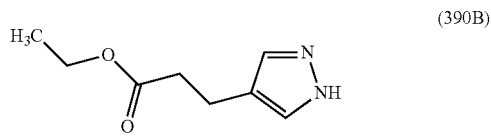
(390B)

To a stirred solution of ethyl 3-(1H-pyrazol-4-yl)acrylate (2.3 g, 13.8 mmol) in methanol (30 mL) was added palladium on carbon 10% (430 mg, 4.0 mmol). The reaction mixture was stirred under hydrogen atmosphere for 14 h. The reaction mixture was filtered through celite and the celite bed was washed with additional methanol (50 mL). The filtrate was evaporated to afford ethyl 3-(1H-pyrazol-4-yl)propanoate which was used further without purification. $^1$H NMR (400 MHz, DMSO-$d_6$) δ 12.53 (br s, 1H), 7.40 (br s, 2H), 4.05 (q, J=7.0 Hz, 2H), 2.63-2.78 (m, 2H), 2.53-2.58 (m, 2H), 1.13-1.23 (m, 3H); LCMS m/z 169.3 (M+H).

Intermediate 390C: ethyl 3-(1-(6-chloro-4-(isopropylamino)pyridin-3-yl)-1H-pyrazol-4-yl)propanoate

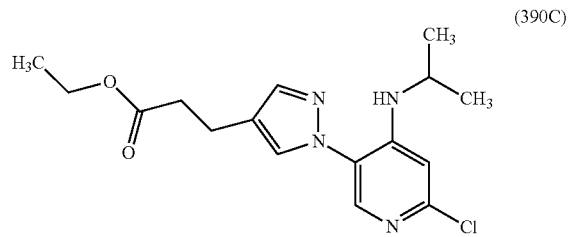 [SMILES: CCOC(=O)CCc1cnn(-c2cnc(Cl)cc2NC(C)C)c1]

(390C)

To a stirred solution of 2-chloro-5-iodo-N-isopropylpyridin-4-amine (700 mg, 2.36 mmol) in 1,4-dioxane (20 mL) in a pressure tube were added ethyl 3-(1H-pyrazol-4-yl)propanoate (397 mg, 2.36 mmol), copper(I) iodide (90 mg, 0.47 mmol), $K_2CO_3$ (652 mg, 4.72 mmol), and trans-N,N'-dimethylcyclohexane-1,2-diamine (201 mg, 1.42 mmol). The tube was sealed and heated at 110° C. for 14 h. After cooling to room temperature, the mixture was filtered through celite and the celite bed was washed with ethyl acetate (150 mL). The filtrate was concentrated and the product was purified by silica gel chromatography (10% ethyl acetate/pet ether) to provide ethyl 3-(1-(6-chloro-4-(isopropylamino)pyridin-3-yl)-1H-pyrazol-4-yl)propanoate (450 mg, 57% yield). $^1$H NMR (300 MHz, DMSO-d$_6$) δ 8.06-8.15 (m, 1H), 7.74 (s, 1H), 7.25-7.55 (m, 1H), 7.11 (d, J=7.6 Hz, 1H), 6.82 (s, 1H), 3.99-4.17 (m, 2H), 3.79 (dd, J=6.2, 13.8 Hz, 1H), 2.57-2.83 (m, 4H), 1.06-1.25 (m, 9H); LCMS m/z 337.4 (M+H).

Intermediate 390D: 4-(1-(6-chloro-4-(isopropylamino)pyridin-3-yl)-1H-pyrazol-4-yl)-2-methylbutan-2-ol

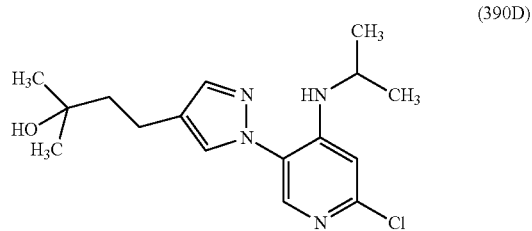 [SMILES: CC(C)Nc1cc(Cl)ncc1-n1cc(CCC(C)(C)O)cn1]

(390D)

To a stirred solution of ethyl 3-(1-(6-chloro-4-(isopropylamino)pyridin-3-yl)-1H-pyrazol-4-yl)propanoate (450 mg, 1.336 mmol) in THF (30 mL) at 0° C. was added methyl magnesium chloride (2.23 mL, 6.68 mmol). The reaction mixture was stirred for 2 h then quenched with NH$_4$C$_1$ solution and extracted with ethyl acetate (2×30 mL). The combined organic extracts were dried over Na$_2$SO$_4$, filtered, and concentrated. The crude material was purified by silica gel column chromatography (50% ethyl acetate/pet ether) to isolate 4-(1-(6-chloro-4-(isopropylamino)pyridin-3-yl)-1H-pyrazol-4-yl)-2-methylbutan-2-ol (310 mg, 72% yield). $^1$H NMR (400 MHz, DMSO-d$_6$) δ 8.03-8.17 (m, 1H), 7.50 (br s, 1H), 7.31 (br s, 1H), 7.17 (d, J=7.5 Hz, 1H), 6.80 (s, 1H), 4.23 (s, 1H), 3.78 (m, 1H), 2.52-2.76 (m, 2H), 1.63-1.77 (m, 2H), 1.08-1.26 (m, 12H); LCMS m/z 323.2 (M+H).

Example 390

A solution of 4-(1-(6-chloro-4-(isopropylamino)pyridin-3-yl)-1H-pyrazol-4-yl)-2-methylbutan-2-ol (150 mg, 0.47 mmol) in 1,4-dioxane (10 mL) in a pressure tube was added 1H-pyrazolo[3,4-b]pyridine-5-carbonitrile (67 mg, 0.47 mmol), Xantphos (269 mg, 0.47 mmol), $K_2CO_3$ (193 mg, 1.4 mmol), lithium chloride (19.7 mg, 0.47 mmol), and zinc chloride (19 mg, 0.14 mmol). The mixture was degassed by bubbling nitrogen for 5 min. Pd$_2$(dba)$_3$ (213 mg, 0.23 mmol) was added and degassed for additional 5 min. The reaction tube was sealed and heated at 120° C. for 20 h. After cooling, the mixture was filtered through celite and the filtrate was concentrated then purified by silica gel column chromatography using 3% methanol/chloroform. The product was further purified by preparative HPLC to provide 1-(5-(4-(3-hydroxy-3-methylbutyl)-1H-pyrazol-1-yl)-4-(isopropylamino)pyridin-2-yl)-1H-pyrazolo[3,4-b]pyridine-5-carbonitrile (22 mg, 11% yield). $^1$H NMR: (400 MHz, DMSO-d$_6$) δ 9.03 (dd, J=11.5, 2.0 Hz, 2H), 8.64 (s, 1H), 8.36 (s, 1H), 8.16 (d, J=0.7 Hz, 1H), 7.75 (s, 1H), 7.39 (s, 1H), 7.27 (d, J=7.3 Hz, 1H), 4.28 (s, 1H), 3.80 (dd, J=13.2, 6.4 Hz, 1H), 2.64-2.54 (m, 2H), 1.78-1.65 (m, 2H), 1.30-1.20 (m, 6H), 1.19-1.11 (m, 6H); LCMS m/z 431.3 (M+H).

The Examples in Table 21 were prepared using the methods outlined for Examples 149-162 using the appropriate starting material.

TABLE 21

| Ex. No. | Structure | HPLC rt (min) | HPLC cond. | LCMS |
|---|---|---|---|---|
| 392 | 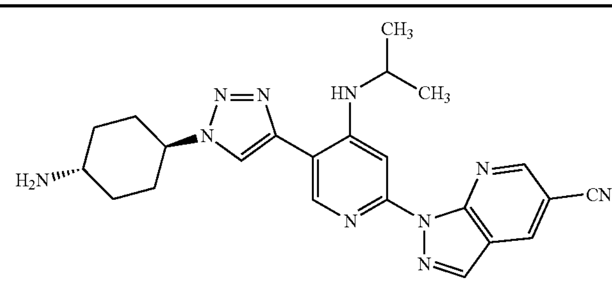 | 1.04 | D | 443.3 |

TABLE 21-continued

| Ex. No. | Structure | HPLC rt (min) | HPLC cond. | LCMS |
|---|---|---|---|---|
| 393 | 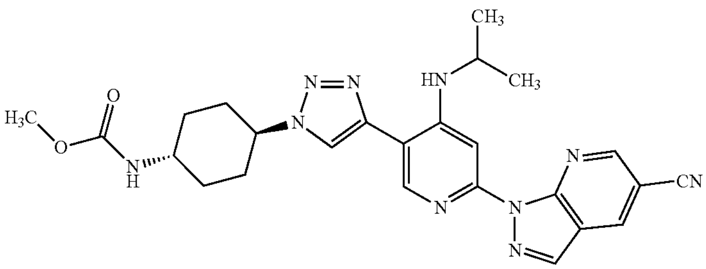 [SMILES: COC(=O)N[C@H]1CC[C@H](n2cc(-c3cnc(-n4ncc5cc(C#N)cnc54)cc3NC(C)C)nn2)CC1] | 1.44 | D | 501.3 |
| 394 | 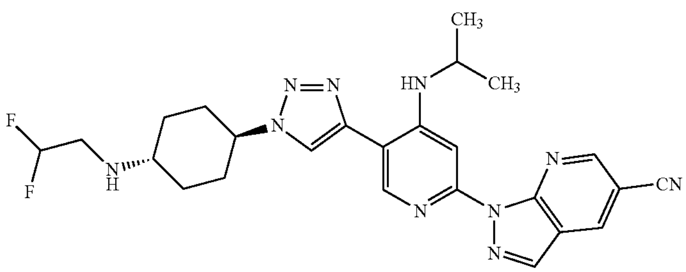 [SMILES: CC(C)Nc1cc(-n2ncc3cc(C#N)cnc32)ncc1-c1cn([C@H]2CC[C@H](NCC(F)F)CC2)nn1] | 1.11 | D | 507.4 |
| 395 | 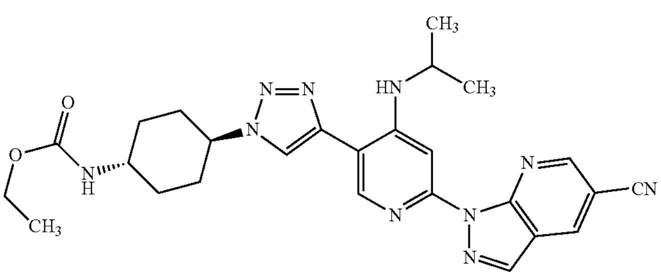 [SMILES: CCOC(=O)N[C@H]1CC[C@H](n2cc(-c3cnc(-n4ncc5cc(C#N)cnc54)cc3NC(C)C)nn2)CC1] | 1.61 | D | 515.4 |
| 396 | 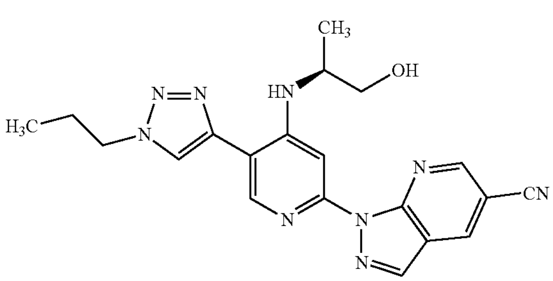 [SMILES: CCCn1cc(-c2cnc(-n3ncc4cc(C#N)cnc43)cc2N[C@@H](C)CO)nn1] | 6.73 | A | 404.1 |

Example 397

1-(5-(3-(azetidin-3-yl)isoxazol-5-yl)-4-(isopropylamino)pyridin-2-yl)-1H-pyrazolo[3,4-b]pyridine-5-carbonitrile

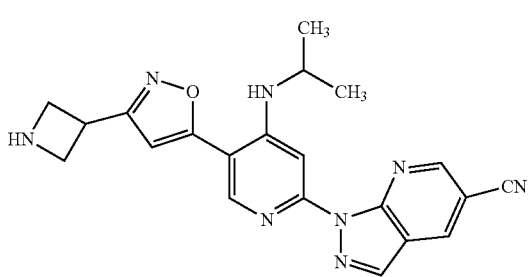

(397)

Intermediate 397A: tert-butyl 3-((hydroxyimino)methyl)azetidine-1-carboxylate

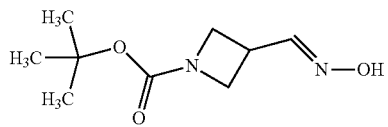

(397A)

In a 50 mL round bottom flask, a stirring mixture of tert-butyl 3-formylazetidine-1-carboxylate (0.518 g, 2.8 mmol), potassium carbonate (0.271 g, 1.96 mmol), and hydroxylamine hydrochloride (0.292 g, 4.2 mmol) in THF (5 mL) was treated with water (3 mL). The reaction mixture was stirred at room temperature under a nitrogen atmosphere for 18 hours, at which point it was judged to be complete by TLC (1:1 EtOAc/hex, KMnO$_4$). The mixture was extracted three times with ethyl acetate (5 mL), and the combined organic phases were washed twice with water and once with brine, then dried over sodium sulfate and concentrated in vacuo to yield tert-butyl 3-((hydroxyimino)methyl)azetidine-1-carboxylate (535 mg, 96% yield) as a colorless solid. $^1$H NMR (400 MHz, CHLOROFORM-d) δ 7.77 (br. s., 0.4H), 7.61 (d, J=6.6 Hz, 0.6H), 7.53 (br. s., 0.6H), 7.00 (d, J=5.3 Hz, 0.4H), 4.28-4.20 (m, 0.8H), 4.18-4.11 (m, 1.2H), 3.97 (dd, J=8.8, 5.9 Hz, 1.2H), 3.92-3.86 (m, 0.8H), 3.86-3.75 (m, 0.4H), 3.38 (tq, J=8.6, 6.1 Hz, 0.6H), 1.47 (s, 9H).

Intermediate 397B: tert-butyl 3-(chloro(hydroxyimino)methyl)azetidine-1-carboxylate

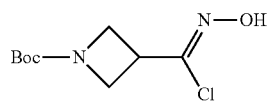

(397B)

In 40 mL vial, a solution of tert-butyl 3-((hydroxyimino)methyl)azetidine-1-carboxylate (142 mg, 0.71 mmol) in anhydrous DMF (2 mL) was treated with freshly crystallized N-chlorosuccinimide (95 mg, 0.71 mmol). The vial was filled with nitrogen and sealed, and the reaction mixture was stirred at 50° C. for 2 hours. The mixture was allowed to come to room temperature and diluted with diethyl ether (25 mL), and the turbid solution was washed three times with 10% lithium chloride and once with brine. The organic phase was dried over sodium sulfate and concentrated in vacuo to yield tert-butyl 3-(chloro(hydroxyimino)methyl)azetidine-1-carboxylate (158 mg, 95% yield) as a colorless solid. $^1$H NMR (400 MHz, CHLOROFORM-d) δ 9.13 (s, 1H), 4.47-3.99 (m, 4H), 3.58 (dt, J=14.7, 7.3 Hz, 1H), 1.47 (s, 9H).

Intermediate 397C: tert-butyl 3-(5-(6-(5-cyano-1H-pyrazolo[3,4-b]pyridin-1-yl)-4-(isopropylamino)pyridin-3-yl)isoxazol-3-yl)azetidine-1-carboxylate

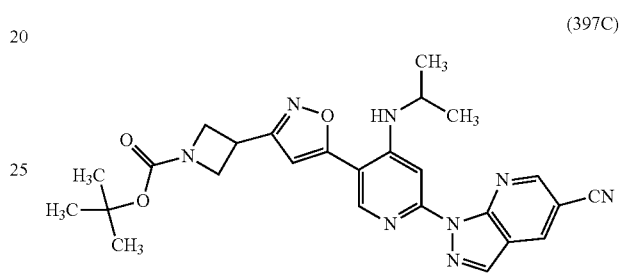

(397C)

In a 2 dram vial, a stirring mixture of tert-butyl 3-(chloro(hydroxyimino)methyl) azetidine-1-carboxylate (155 mg, 0.660 mmol) and 1-(5-ethynyl-4-(isopropylamino) pyridin-2-yl)-1H-pyrazolo[3,4-b]pyridine-5-carbonitrile (119 mg, 0.394 mmol) in dichloroethane (3 mL) was treated with triethylamine (0.219 mL, 1.574 mmol). The vial was sealed, and the reaction mixture was stirred at 75° C. for 75 minutes, at which point the reaction was judged to be complete by LCMS. The mixture was diluted with dichloromethane (1 mL), and washed twice with water, once with a pH 8 ammonia solution, and once with brine. The organic phase was dried over sodium sulfate and concentrated in vacuo, and the residue was chromatographed via MPLC over a 40 g silica gel column, eluting at 40 mL/min with a 2% to 10% methanol/dichloromethane gradient over 11 column volumes. Fractions containing the desired product were pooled and concentrated in vacuo to yield tert-butyl 3-(5-(6-(5-cyano-1H-pyrazolo[3,4-b]pyridin-1-yl)-4-(isopropylamino) pyridin-3-yl)isoxazol-3-yl)azetidine-1-carboxylate (135 mg, 69% yield) as a colorless solid. LCMS (ES+) detects 501.1 (M+H)$^+$.

Example 397

A solution of tert-butyl 3-(5-(6-(5-cyano-1H-pyrazolo[3,4-b]pyridin-1-yl)-4-(isopropylamino)pyridin-3-yl)isoxazol-3-yl)azetidine-1-carboxylate (30 mg, 0.060 mmol) in dichloromethane/TFA (2:1) (3 mL) was stirred under a nitrogen atmosphere for 30 minutes, at which point the reaction was judged to be complete by LCMS. The reaction mixture was concentrated in vacuo, and the residue was concentrated three times from dichloromethane (10 mL) to remove residual TFA. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 3-minute hold at 100% B; Flow: 20 mL/min. Fractions containing the desired product were combined and dried via centrifugal evaporation to yield 1-(5-(3-(azetidin-3-yl)isoxazol-5-yl)-4-(isopropylamino)pyridin-2-yl)-1H-pyrazolo[3,4-b]pyridine-5-carbonitrile (20 mg, 71% yield). LCMS (ES+) detects 401.3 (M+H)+. $^1$H NMR (500 MHz, DMSO-$d_6$) δ 9.03 (d, J=1.6 Hz, 1H), 8.99 (d, J=1.6 Hz, 1H), 8.64 (s, 1H), 8.50 (s, 1H), 7.44 (s, 1H), 7.09 (s, 1H), 6.21 (d, J=7.6 Hz, 1H), 4.16-4.07 (m, 1H), 4.03 (t, J=8.6 Hz, 1H), 3.97-3.91 (m, 1H), 3.90-3.81 (m, 1H), 3.70-3.63 (m, 1H), 1.87 (s, 3H), 1.29 (d, J=6.3 Hz, 6H).

Example 398

1-(5-(3-(1-acetylazetidin-3-yl)isoxazol-5-yl)-4-(isopropylamino)pyridin-2-yl)-1H-pyrazolo[3,4-b]pyridine-5-carbonitrile (398)

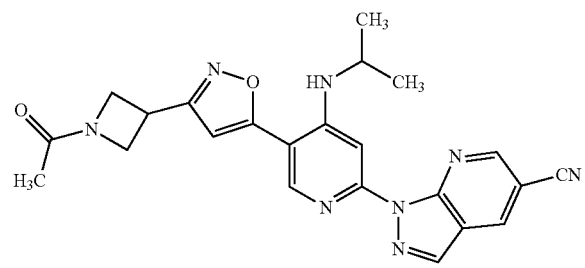

A solution of tert-butyl 3-(5-(6-(5-cyano-1H-pyrazolo[3,4-b]pyridin-1-yl)-4-(isopropylamino)pyridin-3-yl)isoxazol-3-yl)azetidine-1-carboxylate (31 mg, 0.062 mmol) in dichloromethane/TFA (2:1) (3 mL) was stirred under a nitrogen atmosphere for 20 minutes, at which point the reaction was judged to be complete by LCMS. The reaction mixture was concentrated in vacuo, and the residue was concentrated three times from dichloromethane (10 mL) to remove residual TFA. The residue was taken up in dichloromethane (1 mL), and treated with TEA (0.043 mL, 0.310 mmol) followed by acetic anhydride (6.43 µL, 0.068 mmol). The reaction mixture was stirred under a nitrogen atmosphere for 20 minutes, at which point the reaction was judged to be complete by LCMS. The reaction mixture was treated with a few drops of methanol and stirred for 5 minutes to quench any residual acetic anhydride, then the mixture was concentrated in vacuo. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 20 minutes, then a 3-minute hold at 100% B; Flow: 20 mL/min. Fractions containing the desired product were combined and dried via centrifugal evaporation to yield the titled compound (23 mg, 80% yield). LCMS (ES+) detects 443.1 (M+H)+. $^1$H NMR (500 MHz, DMSO-$d_6$) δ 9.06 (d, J=1.7 Hz, 1H), 9.02 (d, J=1.7 Hz, 1H), 8.66 (s, 1H), 8.52 (s, 1H), 7.44 (s, 1H), 7.13 (s, 1H), 6.25 (d, J=7.6 Hz, 1H), 4.63-4.50 (m, 1H), 4.37-4.21 (m, 2H), 4.11-3.97 (m, 2H), 3.93-3.81 (m, 1H), 1.81 (s, 3H), 1.30 (d, J=6.3 Hz, 6H).

Example 399

1-(5-(3-(1,3-dihydroxypropan-2-yl)isoxazol-5-yl)-4-(isopropylamino)pyridin-2-yl)-1H-pyrazolo[3,4-b]pyridine-5-carbonitrile (399)

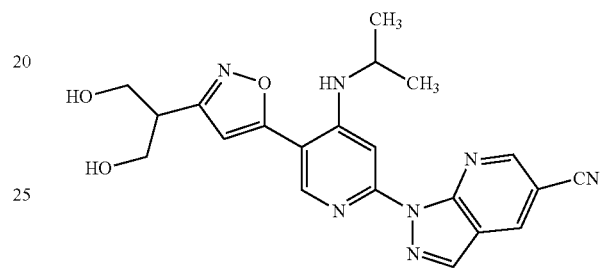

In a 2 dram vial, a stirring mixture of N-hydroxyoxetane-3-carbimidoyl chloride (71 mg, 0.314 mmol) (prepared from oxetane-3-carbaldehyde using the methods described previously) and 1-(5-ethynyl-4-(isopropylamino)pyridin-2-yl)-1H-pyrazolo[3,4-b]pyridine-5-carbonitrile (28 mg, 0.093 mmol) in dichloroethane (1 mL) was treated with TEA (0.09 mL, 0.65 mmol). The vial was sealed, and the reaction mixture was stirred at 70° C. for 2 hours, at which point the reaction was judged to be complete by LCMS. The solvent was evaporated with a stream of nitrogen, and the crude material was purified via preparative LC/MS with the following conditions: Column: Xbridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation to yield 1-(5-(3-(1,3-dihydroxypropan-2-yl)isoxazol-5-yl)-4-(isopropylamino)pyridin-2-yl)-1H-pyrazolo[3,4-b]pyridine-5-carbonitrile (12 mg, 30% yield). LCMS (ES+) detects 420.0 (M+H)+. $^1$H NMR (500 MHz, DMSO-$d_6$) δ 9.06 (br. s., 1H), 9.01 (s, 1H), 8.67 (br. s., 1H), 7.58-7.34 (m, 1H), 7.26 (br. s., 1H), 7.16 (br. s., 1H), 6.30-6.14 (m, 1H), 5.04-4.90 (m, 1H), 4.79 (t, J=6.3 Hz, 1H), 4.44 (quin, J=7.5 Hz, 1H), 3.95-3.80 (m, 1H), 3.80-3.67 (m, 1H), 3.06 (t, J=6.3 Hz, 1H), 1.30 (d, J=5.9 Hz, 6H).

Example 400, Isomers 1 & 2

1-(4-(isopropylamino)-5-(3-(morpholin-3-yl)isoxazol-5-yl)pyridin-2-yl)-1H-pyrazolo[3,4-b]pyridine-5-carbonitrile (Isomers 1 and 2)

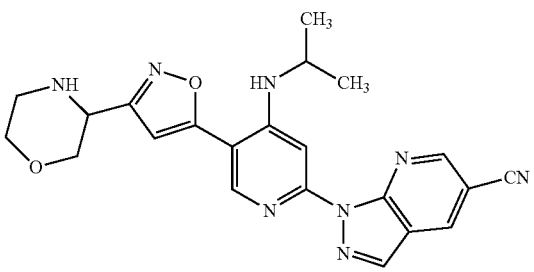

(400)

Intermediates 400A (Isomers 1 and 2): tert-butyl 3-(5-(6-(5-cyano-1H-pyrazolo[3,4-b]pyridin-1-yl)-4-(isopropylamino)pyridin-3-yl)isoxazol-3-yl)morpholine-4-carboxylate

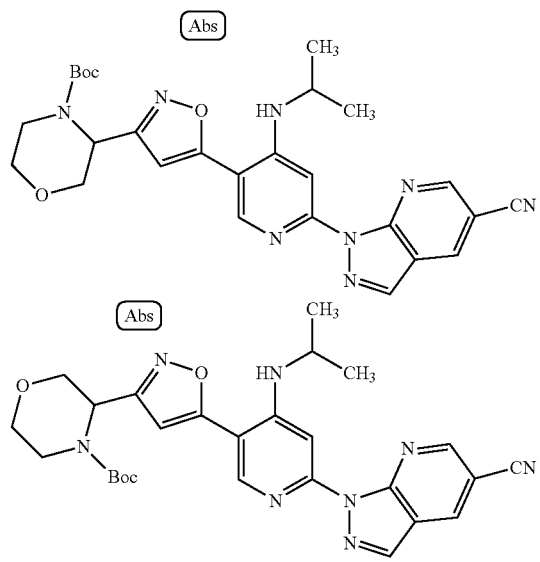

In a 2 dram vial, a stirring mixture of tert-butyl 3-(chloro(hydroxyimino)methyl) morpholine-4-carboxylate (144 mg, 0.54 mmol) (prepared from tert-butyl 3-formylmorpholine-4-carboxylate using the methods previously disclosed) and 1-(5-ethynyl-4-(isopropylamino)pyridin-2-yl)-1H-pyrazolo[3,4-b]pyridine-5-carbonitrile (98 mg, 0.324 mmol) in chloroform (3 mL) was treated with TEA (0.181 mL, 1.3 mmol). The vial was sealed, and the reaction mixture was stirred at 60° C. for 2 hours, at which point the reaction was judged to be complete by LCMS. The mixture was diluted with dichloromethane (10 mL), and washed twice with water, and once with brine. The organic phase was dried over sodium sulfate and concentrated in vacuo, and the residue was chromatographed via MPLC over a 40 g silica gel column, eluting at 40 mL/min with 1% then 1.5% then 2% methanol/dichloromethane. Fractions containing the desired product were pooled and concentrated in vacuo to yield tert-butyl 3-(5-(6-(5-cyano-1H-pyrazolo[3,4-b]pyridin-1-yl)-4-(isopropylamino)pyridin-3-yl)isoxazol-3-yl)morpholine-4-carboxylate (85 mg, 49% yield) as a colorless solid. LCMS (ES+) detects 531.3 $(M+H)^+$. The two enantiomers were resolved by chiral HPLC using the conditions shown below to yield tert-butyl 3-(5-(6-(5-cyano-1H-pyrazolo[3,4-b]pyridin-1-yl)-4-(isopropylamino)pyridin-3-yl)isoxazol-3-yl)morpholine-4-carboxylate, Isomer 1 (38 mg, 89% yield), LCMS $(ES^+)$ detected 531.3 $(M+H)^+$; and tert-butyl 3-(5-(6-(5-cyano-1H-pyrazolo[3,4-b]pyridin-1-yl)-4-(isopropylamino)pyridin-3-yl)isoxazol-3-yl)morpholine-4-carboxylate, ISOMER 2 (37 mg, 87% yield), LCMS (ES+) detects 531.3 $(M+H)^+$.

Preparative Conditions: First pass; Preparative Column: AD-H (3×25 cm, 5 µm, #122090) BPR pressure: 100 bars; Temperature: 35° C.; Flow rate: 150 mL/min; Mobile Phase: $CO_2$/MeOH w 0.1% $NH_4OH$ (60/40); Detector Wavelength: 254 nm; Separation Program: single injection; Injection: 2.5 mL with cycle time: mins. Sample preparation: 78 mg/6 mL MeOH:DCM (2:1), 13 mg/mL

Example 400, Isomer 1

A solution of tert-butyl 3-(5-(6-(5-cyano-1H-pyrazolo[3,4-b]pyridin-1-yl)-4-(isopropylamino)pyridin-3-yl)isoxazol-3-yl)morpholine-4-carboxylate, Isomer 1 (37 mg, 0.070 mmol) in chloroform (1 mL) was cooled to room temperature and treated with TFA (1 mL, 12.98 mmol). The reaction mixture was stirred at room temperature for 30 minutes, at which point the reaction was judged to be complete by LCMS. The reaction mixture was concentrated in vacuo, and the residue was concentrated twice from dichloromethane to remove residual TFA. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation to yield the titled compound (24 mg, 0.06 mmol, 76% yield). LCMS $(ES^+)$ detects 430.9 $(M+H)^+$. $^1$H NMR (500 MHz, DMSO-$d_6$) δ 9.05 (s, 1H), 9.01 (s, 1H), 8.65 (s, 1H), 8.52 (s, 1H), 7.43 (s, 1H), 7.01 (s, 1H), 6.19 (d, J=7.2 Hz, 1H), 4.03 (dd, J=9.3, 2.7 Hz, 1H), 3.92 (dd, J=11.0, 2.3 Hz, 1H), 3.86 (dd, J=13.0, 6.6 Hz, 1H), 3.74 (d, J=10.9 Hz, 1H), 3.55 (t, J=10.5 Hz, 1H), 2.88 (br. s., 2H), 1.30 (d, J=5.7 Hz, 6H).

Example 400, Isomer 2

Example 400, Isomer 2 was prepared from tert-butyl 3-(5-(6-(5-cyano-1H-pyrazolo[3,4-b]pyridin-1-yl)-4-(isopropylamino)pyridin-3-yl)isoxazol-3-yl)morpholine-4-carboxylate, Isomer 2 using the method described for the preparation of Example 400, Isomer 1. LCMS $(ES^+)$ detects 431.1 $(M+H)^+$. $^1$H NMR (500 MHz, DMSO-$d_6$) δ 9.05 (s, 1H), 9.01 (s, 1H), 8.65 (s, 1H), 8.52 (s, 1H), 7.43 (s, 1H), 7.02 (s, 1H), 6.19 (d, J=7.5 Hz, 1H), 4.03 (dd, J=9.1, 2.9 Hz, 1H), 3.92 (dd, J=10.9, 2.8 Hz, 1H), 3.86 (dd, J=13.0, 6.5 Hz, 1H), 3.75 (d, J=11.0 Hz, 1H), 3.61-3.47 (m, 1H), 3.46-3.36 (m, 1H), 2.88 (d, J=4.6 Hz, 2H), 1.30 (d, J=5.9 Hz, 6H).

The Examples in Table 22 were prepared using the methods outlined for Examples 397-400 using the appropriate starting material.

TABLE 22

| Ex. No. | Structure | HPLC rt (min) | HPLC cond. | LCMS |
|---|---|---|---|---|
| 401 | 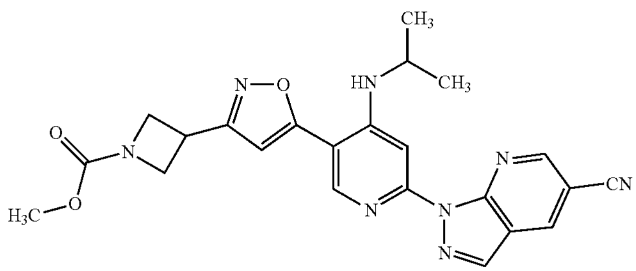 [SMILES: COC(=O)N1CC(c2cc(-c3cnc(-n4ncc5cc(C#N)cnc54)cc3NC(C)C)on2)C1] | 1.34 | D | 459 |
| 402 | 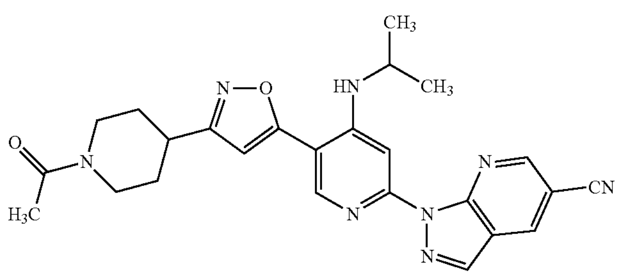 [SMILES: CC(=O)N1CCC(c2cc(-c3cnc(-n4ncc5cc(C#N)cnc54)cc3NC(C)C)on2)CC1] | 1.28 | D | 471.4 |
| 403 | 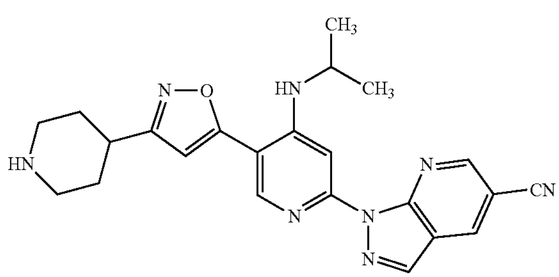 [SMILES: CC(C)Nc1cc(-n2ncc3cc(C#N)cnc32)ncc1-c1cc(C2CCNCC2)no1] | 1.01 | D | 429.1 |
| 404 | 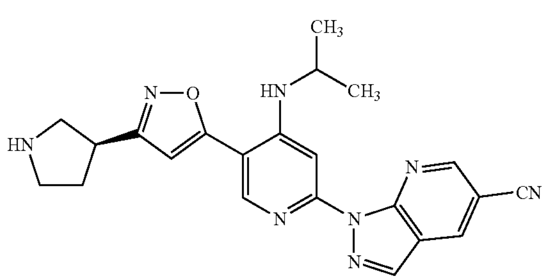 [SMILES: CC(C)Nc1cc(-n2ncc3cc(C#N)cnc32)ncc1-c1cc([C@H]2CCNC2)no1] | 0.96 | D | 415.0 |
| 405 | 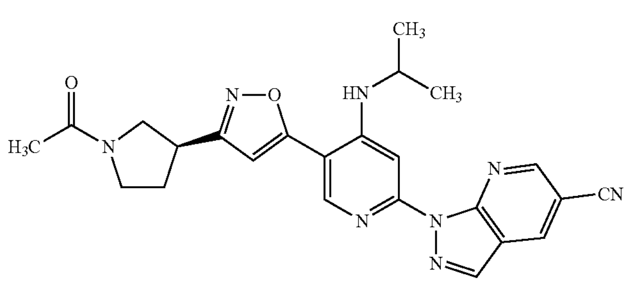 [SMILES: CC(=O)N1CC[C@H](c2cc(-c3cnc(-n4ncc5cc(C#N)cnc54)cc3NC(C)C)on2)C1] | 1.18 | D | 457.0 |

TABLE 22-continued
| Ex. No. | Structure | HPLC rt (min) | HPLC cond. | LCMS |
|---|---|---|---|---|
| 406 | 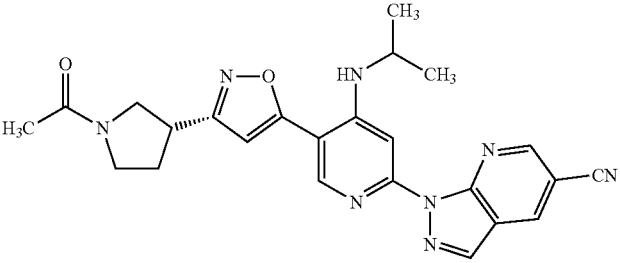 | 1.18 | D | 456.9 |
| 407 | 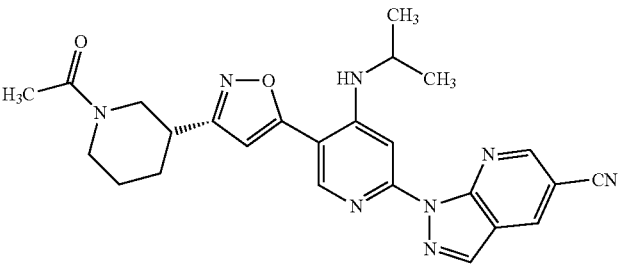 | 1.34 | D | 471.4 |
| 408 | 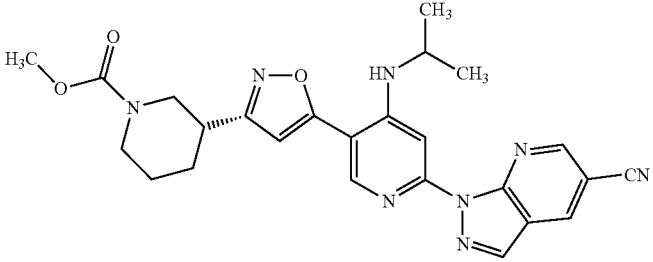 | 1.55 | D | 487.1 |
| 409 | 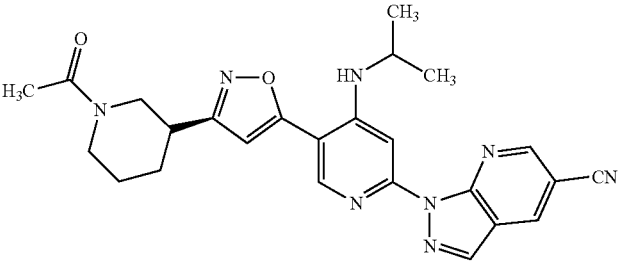 | 1.33 | D | 471.2 |
| 410 | 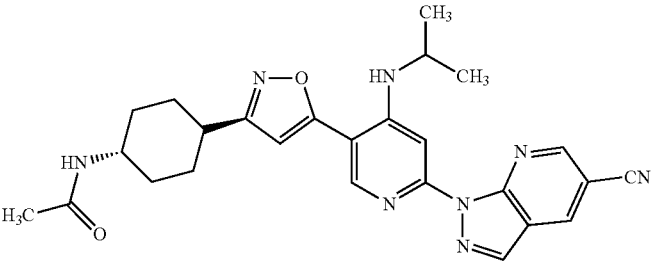 | 1.32 | D | 485.4 |

TABLE 22-continued

| Ex. No. | Structure | HPLC rt (min) | HPLC cond. | LCMS |
|---|---|---|---|---|
| 411 | 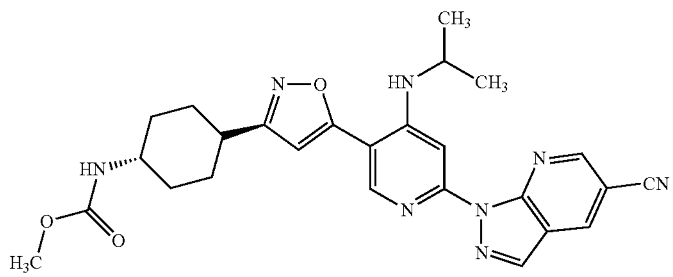 | 1.50 | D | 501.2 |
| 412 | 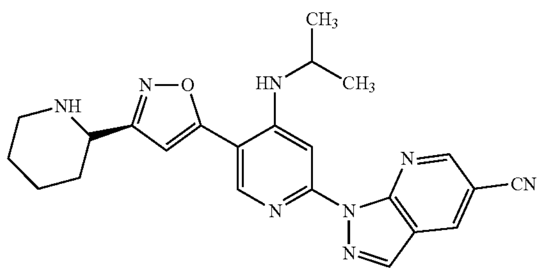 | 1.05 | D | 429.0 |
| 413 | 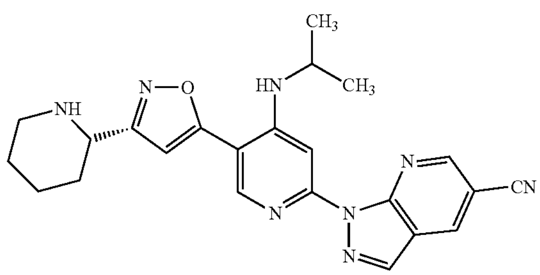 | 1.05 | D | 429.2 |
| 414 | 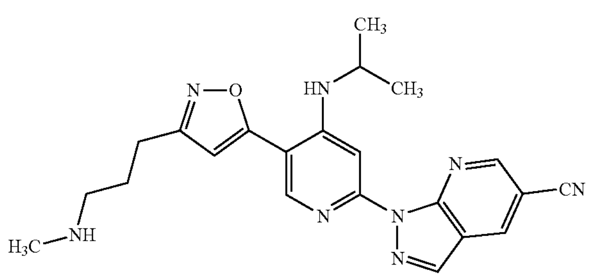 [SMILES: CNCCCc1cc(-c2cnc(-n3ncc4cc(C#N)cnc43)cc2NC(C)C)on1] | 0.96 | D | 417.0 |
| 415 | 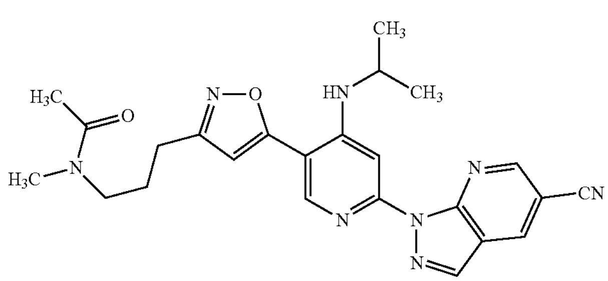 [SMILES: CC(=O)N(C)CCCc1cc(-c2cnc(-n3ncc4cc(C#N)cnc43)cc2NC(C)C)on1] | 1.21 | D | 459.1 |

TABLE 22-continued

| Ex. No. | Structure | HPLC rt (min) | HPLC cond. | LCMS |
|---|---|---|---|---|
| 416 | 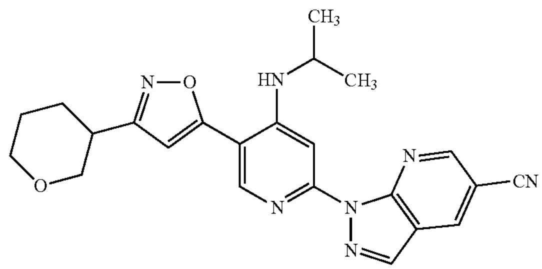 [SMILES: CC(C)Nc1cc(-n2ncc3cc(C#N)cnc32)ncc1-c1cc(C2CCCOC2)no1] | 1.36 | D | 429.9 |
| 417 | 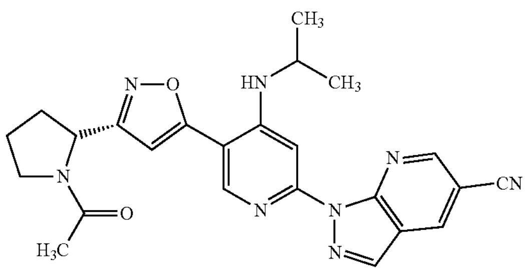 | 1.17 | D | 457.0 |
| 418 | 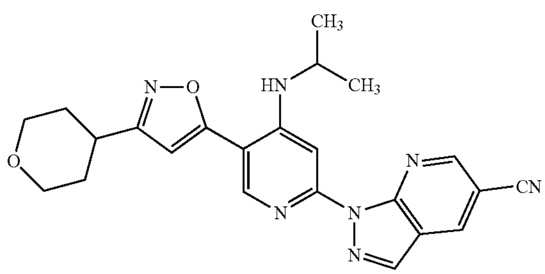 [SMILES: CC(C)Nc1cc(-n2ncc3cc(C#N)cnc32)ncc1-c1cc(C2CCOCC2)no1] | 1.27 | D | 430.1 |
| 419 | 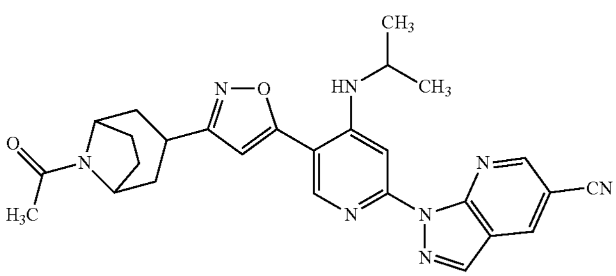 [SMILES: CC(=O)N1C2CCC1CC(c1cc(-c3cnc(-n4ncc5cc(C#N)cnc54)cc3NC(C)C)on1)C2] | 1.34 | D | 497.1 |
| 420 | 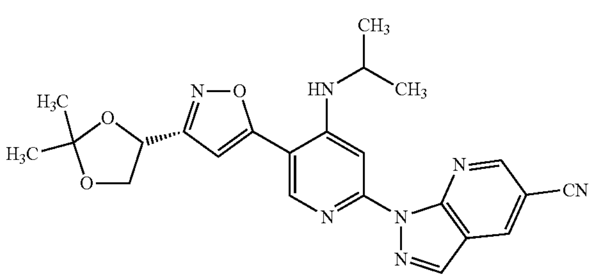 | 1.45 | D | 446.0 |

TABLE 22-continued

| Ex. No. | Structure | HPLC rt (min) | HPLC cond. | LCMS |
|---|---|---|---|---|
| 421 | 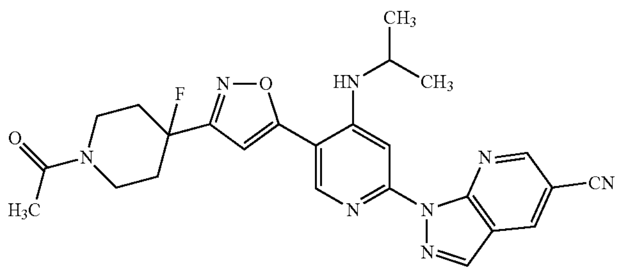 [SMILES: CC(=O)N1CCC(F)(c2cc(-c3cnc(-n4ncc5cc(C#N)cnc54)cc3NC(C)C)on2)CC1] | 1.31 | D | 489.2 |
| 422 | 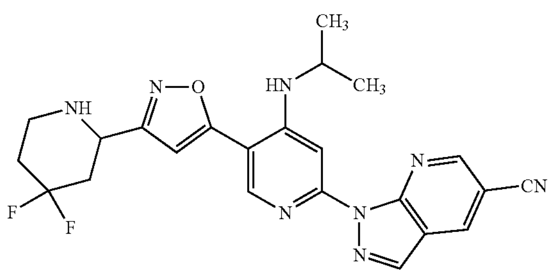 [SMILES: CC(C)Nc1cc(-n2ncc3cc(C#N)cnc32)ncc1-c1cc(C2CC(F)(F)CCN2)no1] | 1.34 | D | 465.0 |
| 423 | 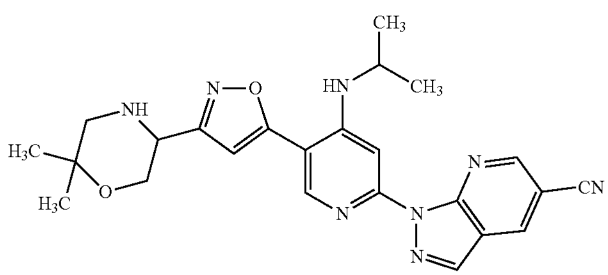 [SMILES: CC(C)Nc1cc(-n2ncc3cc(C#N)cnc32)ncc1-c1cc(C2COC(C)(C)CN2)no1] | 1.28 | D | 459.2 |
| 424 | 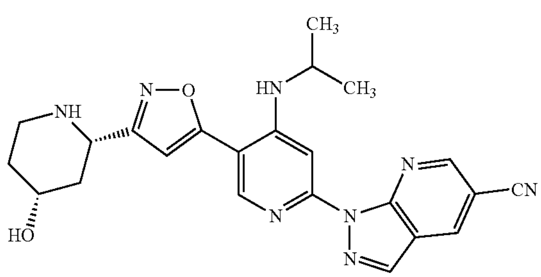 [SMILES: CC(C)Nc1cc(-n2ncc3cc(C#N)cnc32)ncc1-c1cc([C@@H]2C[C@H](O)CCN2)no1] | 0.93 | D | 445.3 |
| 425 | 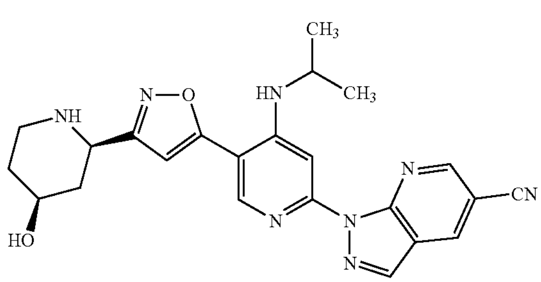 [SMILES: CC(C)Nc1cc(-n2ncc3cc(C#N)cnc32)ncc1-c1cc([C@H]2C[C@@H](O)CCN2)no1] | 0.92 | D | 445.2 |

TABLE 22-continued

| Ex. No. | Structure | HPLC rt (min) | HPLC cond. | LCMS |
|---|---|---|---|---|
| 426 | 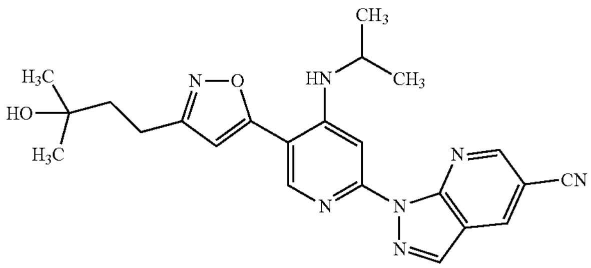 [SMILES: CC(C)Nc1cc(-n2ncc3cc(C#N)cnc32)ncc1-c1cc(CCC(C)(C)O)no1] | 1.40 | D | 432.0 |
| 427 | 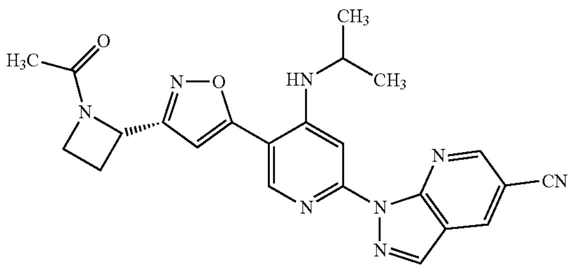 | 1.24 | D | 443.0 |

Example 428

(S)-1-(4-(isopropylamino)-5-(5-(morpholin-3-yl)isoxazol-3-yl)pyridin-2-yl)-1H-pyrazolo[3,4-b]pyridine-5-carbonitrile (428)

Intermediate 428A: 6-chloro-4-(isopropylamino)nicotinaldehyde

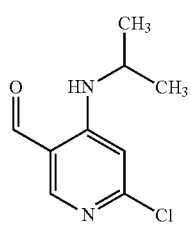

(428A)

To a solution of (6-chloro-4-(isopropylamino)pyridin-3-yl)methanol (8 g, 40 mmol) in DCM (10 mL) at 0° C. was added Dess-Martin periodinane (25.4 g, 60 mmol). The reaction mixture was stirred for 12 h. The reaction mixture was diluted with pet ether and filtered through celite. The filter cake was thoroughly washed with 15% ethyl acetate/pet ether and the combined filtrate was washed 10% NaHCO$_3$ solution, dried over Na$_2$SO$_4$, and concentrated. Purification by silica gel column chromatography using 0-15% ethyl acetate/pet ether provided 6-chloro-4-(isopropylamino)nicotinaldehyde (7.2 g, 91% yield) as pale yellow syrup. $^1$H NMR (300 MHz, DMSO-d$_6$) δ 9.85 (d, J=0.76 Hz, 1H), 8.34-8.53 (m, 2H), 6.90 (s, 1H), 3.90 (td, J=6.42, 7.93 Hz, 1H), 1.08-1.27 (m, 6H); LCMS: m/z 199 (M+H).

Intermediate 428B: 1-(5-formyl-4-(isopropylamino)pyridin-2-yl)-1H-pyrazolo[3,4-b]pyridine-5-carbonitrile

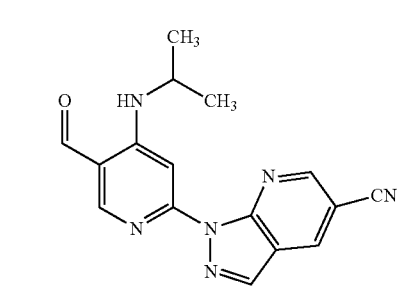

(428B)

To a solution of 6-chloro-4-(isopropylamino)nicotinaldehyde (2.2 g, 11.1 mmol) and 1H-pyrazolo[3,4-b]pyridine-5-carbonitrile (1.60 g, 11.1 mmol) in dioxane (12 mL) in a 35 mL pressure tube were added Xantphos (1.28 g, 2.22 mmol), lithium chloride (0.47 g, 11.1 mmol), zinc chloride (0.30 g, 2.22 mmol) and K$_2$CO$_3$ (4.6 g, 33 mmol). The mixture was degassed for 10 minutes followed by the addition of Pd$_2$(dba)$_3$ (1.01 g, 1.1 mmol) and degassed again for additional

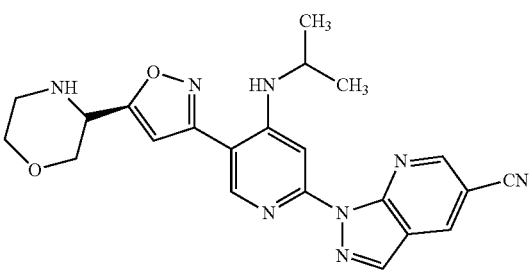

5 minutes. The pressure tube was closed and heated at 110° C. for 16 h. The reaction mixture was filtered and concentrated to an dark residue. The product was purified by silica gel column chromatography using 0-2% methanol/CHCl$_3$ to provide 1-(5-formyl-4-(isopropylamino)pyridin-2-yl)-1H-pyrazolo[3,4-b]pyridine-5-carbonitrile (700 mg, 21% yield) as off-white solid. $^1$H NMR (300 MHz, DMSO-d$_6$) δ 9.94 (s, 1H), 8.99-9.15 (m, 2H), 8.69 (s, 2H), 8.59 (br. s., 1H), 7.49 (s, 1H), 3.80-4.05 (m, 1H), 1.30 (d, J=6.42 Hz, 6H); LCMS m/z 307.2 (M+H).

Intermediate 428B: (E)-1-(5-((hydroxyimino)methyl)-4-(isopropylamino)pyridin-2-yl)-1H-pyrazolo[3,4-b]pyridine-5-carbonitrile

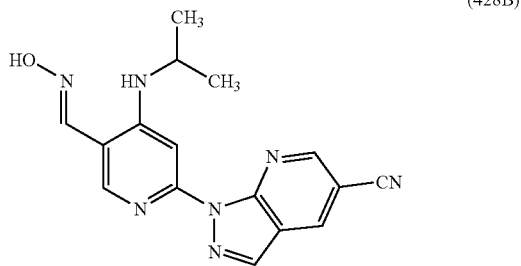

(428B)

To a stirred solution of 1-(5-formyl-4-(isopropylamino)pyridin-2-yl)-1H-pyrazolo[3,4-b]pyridine-5-carbonitrile (700 mg, 2.29 mmol) in ethanol (10 mL) was added hydroxylamine hydrochloride (191 mg, 2.74 mmol) and pyridine (0.554 mL, 6.86 mmol). The mixture was stirred for 12 h, then filtered and dried in vacuo to afford (E)-1-(5-((hydroxyimino)methyl)-4-(isopropylamino)pyridin-2-yl)-1H-pyrazolo[3,4-b]pyridine-5-carbonitrile (300 mg, 41% yield) as white solid. $^1$H NMR (300 MHz, DMSO-d$_6$) δ 11.40 (s, 1H), 8.96-9.10 (m, 2H), 8.61-8.76 (m, 1H), 8.38 (s, 1H), 8.27 (s, 1H), 7.93 (d, J=7.2 Hz, 1H), 7.32 (s, 1H), 3.86 (dd, J=6.6, 12.7 Hz, 1H), 1.18-1.38 (m, 6H); LCMS m/z 322 (M+H).

Intermediate 428C: tert-butyl (R)-3-(methoxy(methyl)carbamoyl)morpholine-4-carboxylate

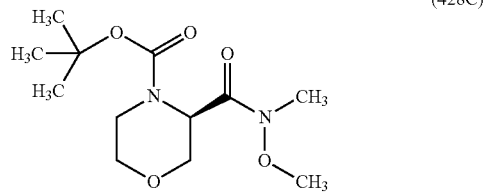

(428C)

To a stirred suspension of 4-boc-3(R)-morpholinecarboxylic acid (2.0 g, 8.65 mmol) in DCM (30 mL) was added N,O-dimethylhydroxylamine hydrochloride (2.53 g, 26 mmol). The mixture was stirred for 5 min then propylphosphonic anhydride (11.01 g, 17.3 mmol) was added drop wise at 0° C. over 5 min. The reaction mixture was allowed to reach room temperature and was stirred for 16 h. The reaction was quenched by the addition of NaHCO$_3$ solution and the organic layer was separated. The aqueous layer was further extracted with DCM (2×50 mL) and the combined organic layer was washed with brine, dried over Na$_2$SO$_4$, and concentrated. The product was purified by silica gel column chromatography using 40% ethyl acetate/pet ether to obtain (R)-tert-butyl 3-(methoxy(methyl)carbamoyl)morpholine-4-carboxylate (1.3 g, 52% yield). $^1$H NMR (300 MHz, CDCl$_3$-d) δ 4.76 (br s, 1H), 4.27 (d, J=10.95 Hz, 1H), 3.91 (m, 1H), 3.59-3.83 (m, 6H), 3.41-3.59 (m, 1H), 3.22 (s, 3H), 1.48 (s, 9H).

Intermediate 428D: tert-butyl (R)-3-formylmorpholine-4-carboxylate

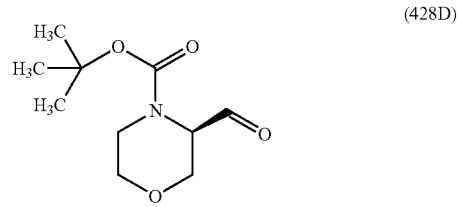

(428D)

To a stirred solution of (R)-tert-butyl 3-(methoxy(methyl)carbamoyl)morpholine-4-carboxylate (1.3 g, 4.74 mmol) in dry THF (30 mL) was added LiAlH$_4$ (4.74 mL, 4.74 mmol) solution drop wise at −10° C. over 10 min and stirred for 30 min at the same temperature. The reaction was quenched by the addition of saturated Na$_2$SO$_4$ solution at 0° C. and extracted with ethyl acetate. The combined organic layer was washed with brine, dried over Na$_2$SO$_4$, and concentrated. The product was purified by silica gel column chromatography using 20% ethyl acetate/pet ether to obtain (R)-tert-butyl 3-formylmorpholine-4-carboxylate (320 mg, 31% yield) $^1$H NMR (400 MHz, CHLOROFORM-d) δ 9.66 (br s, 1H), 4.21-4.57 (m, 2H), 3.59-3.99 (m, 3H), 3.37-3.59 (m, 2H), 3.00-3.31 (m, 1H), 1.47 (br.s., 9H).

Intermediate 428E: tert-butyl (S)-3-ethynylmorpholine-4-carboxylate

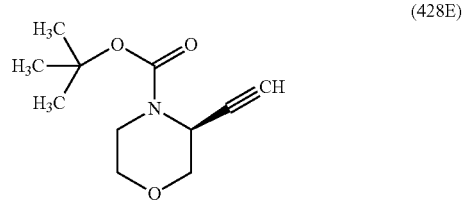

(428E)

To a stirred solution of (R)-tert-butyl 3-formylmorpholine-4-carboxylate (250 mg, 1.16 mmol), dimethyl (1-diazo-2-oxopropyl)phosphonate (335 mg, 1.74 mmol) in methanol (15 mL) was added K$_2$CO$_3$ (642 mg, 4.65 mmol). The mixture was stirred for 16 h and then concentrated. The residue was diluted with water and extracted with ethyl acetate (2×10 mL). The combined organic extracts were washed with brine, dried over Na$_2$SO$_4$, and concentrated. The residue was purified by silica gel column using 10% ethyl acetate/pet ether to afford (S)-tert-butyl 3-ethynylmorpholine-4-carboxylate (98 mg, 40% yield). $^1$H NMR (300 MHz, CDCl$_3$-d) δ 4.76 (br. s., 1H), 3.87-4.01 (m, 2H), 3.68-3.80 (m, 1H), 3.62 (dd, J=3.0, 11.3 Hz, 1H), 3.41-3.55 (m, 1H), 3.19-3.41 (m, 1H), 2.32 (d, J=2.3 Hz, 1H), 1.46-1.55 (m, 9H).

Example 428

To a stirred suspension of (E)-1-(5-((hydroxyimino)methyl)-4-(isopropylamino) pyridin-2-yl)-1H-pyrazolo[3,4-b]pyridine-5-carbonitrile (100 mg, 0.31 mmol) and (S)-tert-butyl 3-ethynylmorpholine-4-carboxylate (72 mg, 0.34 mmol) in THF (3 mL) was added bis(tri-n-butyltin) oxide (0.4 mL, 0.78 mmol) drop wise at room temperature and stirred for 5 min. This clear solution was cooled to 0° C. and NBS (166 mg, 0.93 mmol) was added portion wise followed by the addition of (S)-tert-butyl 3-ethynylmorpholine-4-carboxylate (72.3 mg, 0.342 mmol). The reaction mixture was filtered through celite bed and thoroughly washed with ethyl acetate (10 mL). The filtrate was concentrated afford crude (R)-tert-butyl 3-(3-(6-(5-cyano-1H-pyrazolo[3,4-b]pyridin-1-yl)-4-(isopropylamino)pyridin-3-yl)isoxazol-5-yl)morpholine-4-carboxylate (180 mg) which was suspended in DCM (15 mL) and treated with TFA (1.1 mL, 14.1 mmol). After being stirred for 3 h, the reaction mixture was concentrated and the residue was purified by Prep-HPLC to give (R)-1-(4-(isopropylamino)-5-(5-(morpholin-3-yl)isoxazol-3-yl) pyridin-2-yl)-1H-pyrazolo[3,4-b]pyridine-5-carbonitrile (2.3 mg, 1.7% yield). $^1$H NMR (400 MHz, DMSO-d$_6$) δ 8.98-9.11 (m, 2H), 8.77 (s, 1H), 8.60-8.71 (m, 1H), 7.62 (d, J=7.3 Hz, 1H), 7.45 (s, 1H), 7.22-7.32 (m, 1H), 4.17-4.30 (m, 1H), 3.85-4.02 (m, 1H), 3.08-3.21 (m, 1H), 2.76-2.93 (m, 1H), 1.98-2.14 (m, 1H), 1.79-1.93 (m, 1H), 1.63-1.77 (m, 1H), 1.45-1.62 (m, 2H), 1.26-1.39 (m, 6H); LCMS m/z 431.1 (M+H).

The Examples in Table 23 were prepared using the methods outlined for Examples 428 using the appropriate starting material.

TABLE 23

| Ex. No. | Structure | HPLC rt (min) | HPLC cond. | LCMS |
|---|---|---|---|---|
| 429 | 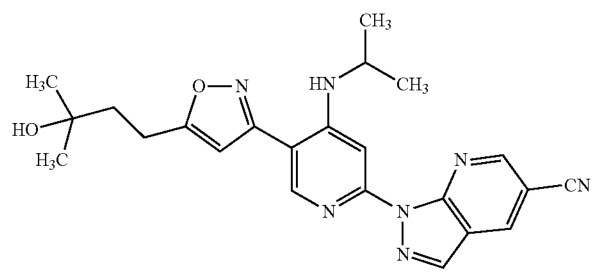 [SMILES: CC(C)Nc1cc(-n2ncc3cc(C#N)cnc32)ncc1-c1cc(CCC(C)(C)O)on1] | 1.64 | F | 432.2 |
| 430 | 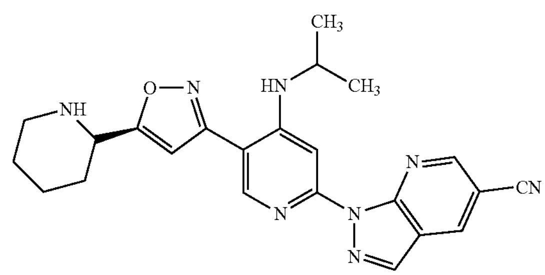 | 1.13 | F | 415.2 |
| 431 | 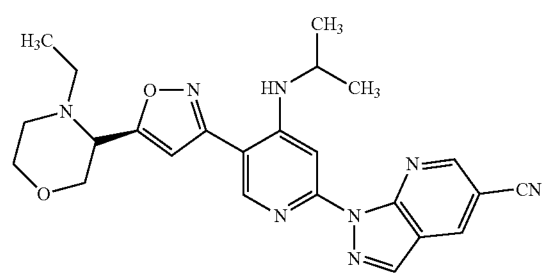 | 1.11 | F | 459.3 |
| 432 | 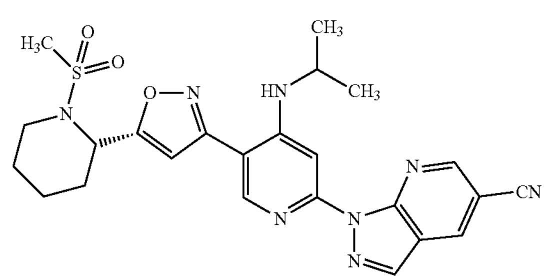 | 1.78 | F | 507 |

Example 433

1-(4-(isopropylamino)-5-(5-(morpholine-4-carbonyl)-1,3,4-oxadiazol-2-yl)pyridin-2-yl)-1H-pyrazolo[3,4-b]pyridine-5-carbonitrile (433)

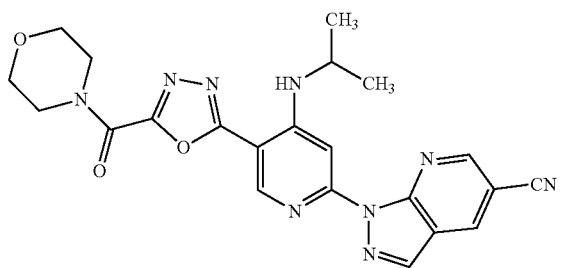

Intermediate 433A: tert-butyl 4-(5-(6-chloro-4-(isopropylamino)pyridin-3-yl)-1,3,4-oxadiazole-2-carbonyl)piperazine-1-carboxylate (433A)

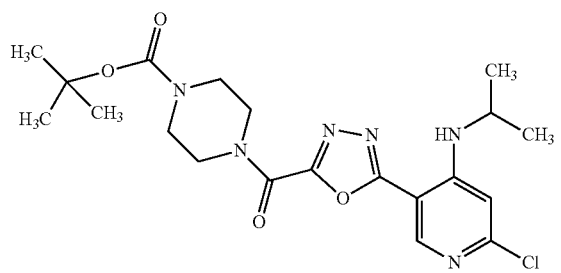

To a solution of methyl 5-(6-chloro-4-(isopropylamino)pyridin-3-yl)-1,3,4-oxadiazole-2-carboxylate (0.2 g, 0.67 mmol) in methanol (15 mL) was added tert-butyl piperazine-1-carboxylate (0.25 g, 1.35 mmol). The reaction mixture was heated at 75° C. for 6 h and then cooled to room temperature. The reaction mixture was concentrated and the crude residue was purified by silica gel column chromatography (50% ethyl acetate/pet ether) to afford tert-butyl 4-(5-(6-chloro-4-(isopropylamino)pyridin-3-yl)-1,3,4-oxadiazole-2-carbonyl)piperazine-1-carboxylate as colorless gummy liquid. LCMS m/z 451.2 (M+H).

Intermediate 433B: 1-(4-(isopropylamino)-5-(5-(piperazine-1-carbonyl)-1,3,4-oxadiazol-2-yl)pyridin-2-yl)-1H-pyrazolo[3,4-b]pyridine-5-carbonitrile (433B)

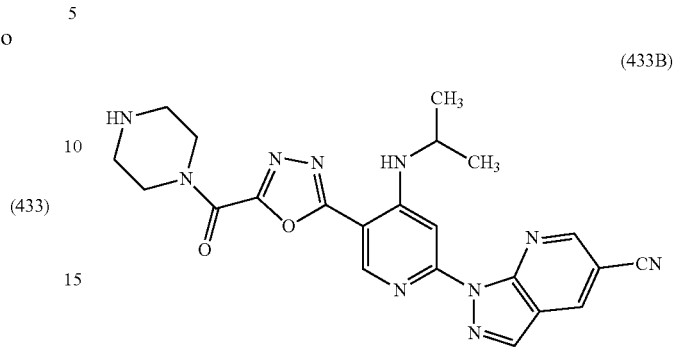

To tert-butyl 4-(5-(6-chloro-4-(isopropylamino)pyridin-3-yl)-1,3,4-oxadiazole-2-carbonyl)piperazine-1-carboxylate (0.1 g, 0.22 mmol) in a 15 mL pressure tube were added 1,4-dioxane (10 mL), 1H-pyrazolo[3,4-b]pyridine-5-carbonitrile (0.032 g, 0.22 mmol), Xantphos (0.051 g, 0.09 mmol), and cesium carbonate (0.289 g, 0.89 mmol). The mixture was degassed via nitrogen gas bubble for 10 min then Pd$_2$(dba)$_3$ (0.081 g, 0.09 mmol) was added. The mixture was again degassed, then sealed and heated at 115° C. for 16 h. After cooling, the reaction mixture was filtered through celite and concentrated to give the crude product which was purified by silica gel chromatography (4% methanol/chloroform) to afford tert-butyl 4-(5-(6-(5-cyano-1H-pyrazolo[3,4-b]pyridin-1-yl)-4-(isopropylamino)pyridin-3-yl)-1,3,4-oxadiazole-2-carbonyl)piperazine-1-carboxylate pale yellow solid. The solid material was dissolved in DCM (10 mL) and treated with TFA (5 mL). After being stirred for 3 h, the reaction mixture was concentrated and co-evaporated with chloroform (10 mL) to obtain crude compound which was purified by preparative HPLC to give 1-(4-(isopropylamino)-5-(5-(piperazine-1-carbonyl)-1,3,4-oxadiazol-2-yl)pyridin-2-yl)-1H-pyrazolo[3,4-b]pyridine-5-carbonitrile (7 mg). $^1$H NMR (400 MHz, DMSO-d$_6$) δ 9.10 (d, J=2.0 Hz, 1H), 9.05 (d, J=2.0 Hz, 1H), 8.80 (s, 1H), 8.70 (s, 1H), 7.99 (d, J=7.0 Hz, 1H), 7.63 (s, 1H), 3.94-4.10 (m, 1H), 3.49-3.79 (m, 4H), 2.03 (dd, J=7.5, 15.1 Hz, 4H), 1.38 (d, J=6.5 Hz, 6H); LCMS m/z 459.2 (M+H).

Example 434

1-(5-(5-(((1R,4R)-4-aminocyclohexyl)amino)-1,3,4-oxadiazol-2-yl)-4-(isopropylamino)pyridin-2-yl)-1H-pyrazolo[3,4-b]pyridine-5-carbonitrile (434)

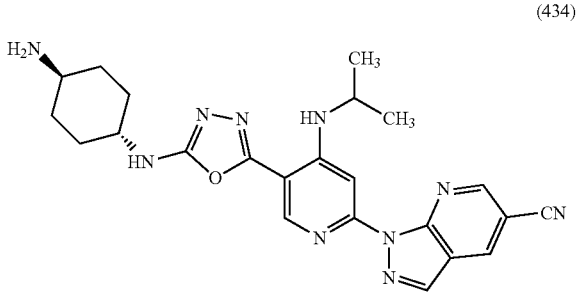 [SMILES: CC(C)Nc1cc(-n2ncc3cc(C#N)cnc32)ncc1-c1nnc(N[C@H]2CC[C@H](N)CC2)o1]

The tert-butyl ((1R,4R)-4-((5-(6-(5-cyano-1H-pyrazolo[3,4-b]pyridin-1-yl)-4-(isopropylamino)pyridin-3-yl)-1,3,4-oxadiazol-2-yl)amino)cyclohexyl)carbamate (0.1 g, 0.179 mmol) was dissolved in CH$_2$Cl$_2$ (5 mL) and added TFA (0.041 mL, 0.537 mmol) The reaction was stirred for 3 h then concentrated and azeotroped with chloroform 4 times to obtain 1-(5-(5-(((1R,4R)-4-aminocyclohexyl)amino)-1,3,4-oxadiazol-2-yl)-4-(isopropylamino)pyridin-2-yl)-1H-pyrazolo[3,4-b]pyridine-5-carbonitrile (1.3 mg, 2% yield). HPLC rt 1.46 min, Conditions E; LCMS 459.2 (M+H).

Example 435

1-(5-(5-(3-hydroxy-3-methylbutyl)-4,5-dihydroisoxazol-3-yl)-4-(isopropylamino)pyridin-2-yl)-1H-pyrazolo[3,4-b]pyridine-5-carbonitrile (Enantiomers 1 and 2)

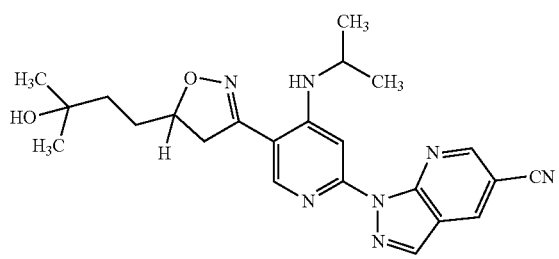

(435)

To a stirred suspension of 1-(5-((hydroxyimino)methyl)-4-(isopropylamino) pyridin-2-yl)-1H-pyrazolo[3,4-b]pyridine-5-carbonitrile (100 mg, 0.31 mmol) in THF (2 mL) was added bis(tri-n-butyltin) oxide (371 mg, 0.62 mmol). The mixture was stirred for 5 minutes and NBS (166 mg, 0.93 mmol) was added followed by 2-methylhex-5-en-2-ol (107 mg, 0.93 mmol). The reaction mixture was stirred at room temperature overnight. The reaction mixture was concentrated and the residue was purified by preparative HPLC to afford the racemic 1-(5-(5-(3-hydroxy-3-methylbutyl)-4,5-dihydroisoxazol-3-yl)-4-(isopropylamino)pyridin-2-yl)-1H-pyrazolo[3,4-b]pyridine-5-carbonitrile (60 mg). The enantiomers were separated via preparative chiral SFC to afford Enantiomer 1: 1-(5-(5-(3-hydroxy-3-methylbutyl)-4,5-dihydroisoxazol-3-yl)-4-(isopropylamino)pyridin-2-yl)-1H-pyrazolo[3,4-b]pyridine-5-carbonitrile (10 mg, 6.4% yield). $^1$H NMR (400 MHz, DMSO-d$_6$) δ 9.04 (dd, J=2.0, 11.6 Hz, 2H), 8.65 (s, 1H), 8.34 (s, 1H), 7.88 (d, J=7.0 Hz, 1H), 7.37 (s, 1H), 4.64 (m, 1H), 4.20 (s, 1H), 3.88 (m, 1H), 3.67 (dd, J=10.3, 16.8 Hz, 1H), 3.25 (d, J=8.5 Hz, 1H), 1.60-1.79 (m, 2H), 1.38-1.57 (m, 2H), 1.22-1.33 (m, 6H), 1.10 (s, 6H); LCMS m/z 434 (M+H).

Example 436

Methyl ((3-(6-(5-cyano-1H-pyrazolo[3,4-b]pyridin-1-yl)-4-(isopropylamino)pyridin-3-yl)-4,5-dihydroisoxazol-5-yl)methyl)carbamate

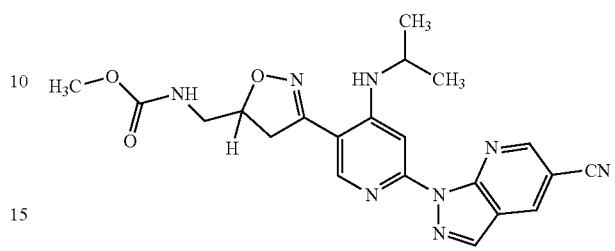

(436)

Intermediate 436A: Methyl Allylcarbamate

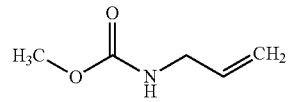

(436A)

To a stirred solution of prop-2-en-1-amine (0.5 g, 8.8 mmol) in DCM (20 mL), was added DIPEA (4.6 mL, 26.3 mmol) followed by methyl carbonochloridate (0.83 g, 8.8 mmol) at 0° C. Stirring was continued for 1 h at room temperature then the reaction mixture was evaporated to dryness and extracted between DCM and water. The organic layer was dried over Na$_2$SO$_4$, filtered and concentrated to afford methyl allylcarbamate (0.4 g, 40% yield). $^1$H NMR (400 MHz, DMSO-d$_6$) δ 7.29 (br s, 1H), 5.63-5.90 (m, 1H), 4.93-5.21 (m, 2H), 3.58-3.63 (m, 2H), 3.53 (s, 3H).

Example 436

To a stirred solution of (E)-1-(5-((hydroxyimino)methyl)-4-(isopropylamino) pyridin-2-yl)-1H-pyrazolo[3,4-b]pyridine-5-carbonitrile (50 mg, 0.16 mmol) in THF (12 mL) was added bis(tri-n-butyltin) oxide (139 mg, 0.23 mmol) at 0° C. After being stirred for 5 minutes, NBS (83 mg, 0.47 mmol) and methyl allylcarbamate (17.9 mg, 0.16 mmol) was added and the reaction mixture was stirred for 14 h at room temperature. The crude compound was filtered through celite and concentrated. This material was diluted with ethyl acetate and washed with NaHCO$_3$ solution, dried over Na$_2$SO$_4$, filtered, and concentrated. The crude residue was purified by silica gel column chromatography using 5% methanol/chloroform to give the desired compound as mixture of enantiomers which was repurified by preparative-HPLC to enrich the purity. Chiral separation by SFC provided the desired enantiomer methyl ((3-(6-(5-cyano-1H-pyrazolo[3,4-b]pyridin-1-yl)-4-(isopropylamino)pyridin-3-yl)-4,5-dihydroisoxazol-5-yl)methyl)carbamate (2.9 mg, 4.2% yield). $^1$H NMR (400 MHz, DMSO-d$_6$) δ 9.04 (dd, J=11.5, 2.0 Hz, 1H), 8.66 (s, 1H), 8.32 (s, 1H), 7.83 (d, J=7.5 Hz, 1H), 7.46-7.38 (m, 2H), 4.76-4.68 (m, 2H), 3.90 (dt, J=12.8, 6.7 Hz, 2H), 3.67 (dd, J=16.6, 10.5 Hz, 2H), 3.56 (s, 2H), 3.23 (d, J=4.0 Hz, 2H), 1.31-1.21 (m, 6H); LCMS m/z 494.4 (M+H).

The Examples in Table 24 were prepared using the methods outlined for Examples 435-436 using the appropriate starting material.

TABLE 24
| Ex. No. | Structure | HPLC rt (min) | HPLC cond. | LCMS |
|---|---|---|---|---|
| 437 | 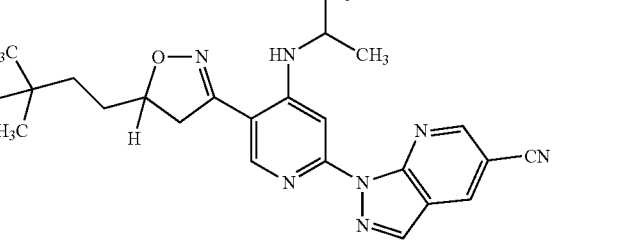<br>racemate | 1.56 | F | 434.2 |
| 438 | 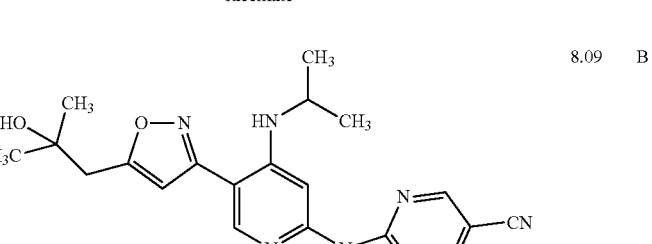<br>Enantiomer 1 | 8.09 | B | 420.2 |
| 439 | 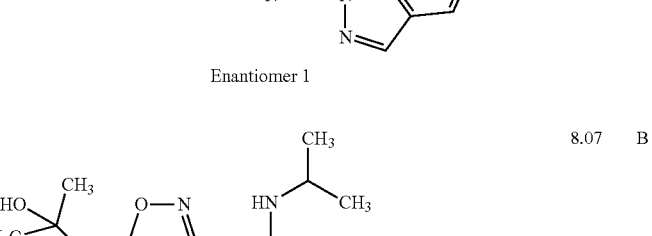<br>Enantiomer 2 | 8.07 | B | 420.2 |
| 440 | 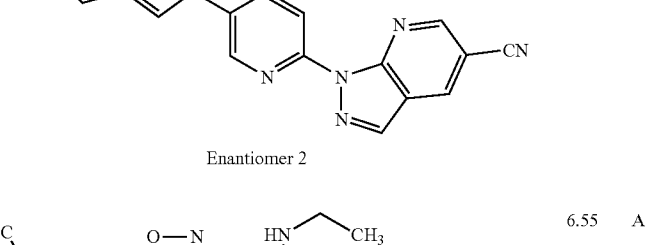<br>Enantiomer 1 | 6.55 | A | 420.2 |
| 441 | 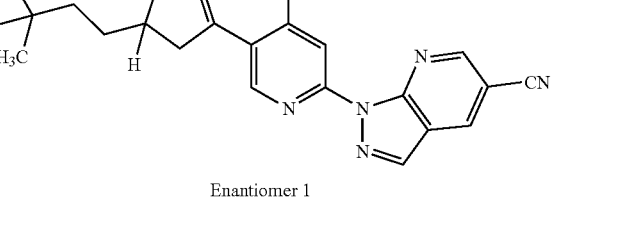<br>Enantiomer 2 | 6.55 | A | 420.2 |

TABLE 24-continued

| Ex. No. | Structure | HPLC rt (min) | HPLC cond. | LCMS |
|---|---|---|---|---|
| 442 | Enantiomer 1 | 7.26 | A | 456.2 |
| 443 | Enantiomer 2 | 7.26 | A | 456.2 |

Biological Assays

The pharmacological properties of the compounds of this invention may be confirmed by a number of biological assays. The exemplified biological assays, which follow, have been carried out with compounds of the invention.

IRAK4 Inhibition Assay

The assays were performed in U-bottom 384-well plates. The final assay volume was 30 µL prepared from 15 µL additions of enzyme and substrates (fluoresceinated peptide and ATP) and test compounds in assay buffer (20 mM HEPES pH 7.2, 10 mM $MgCl_2$, 0.015% Brij 35 and 4 mM DTT). The reaction was initiated by the combination of IRAK4 with substrates and test compounds. The reaction mixture was incubated at room temperature for 60 min. and terminated by adding 45 µL of 35 mM EDTA to each sample. The reaction mixture was analyzed on the Caliper LAB-CHIP® 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentrations of reagents in the assays are ATP, 500 µM; FL-IPTSPITT-TYFFFKKK peptide 1.5 µM; IRAK4, 0.6 nM; and DMSO, 1.6%.

Caco-2 Permeability Assay

Thirteen to 27 days prior to assay, Caco-2 cells were seeded onto collagen-coated polycarbonate filter membranes in 24-well transwell plates at a density of $1.45 \times 10^5$ cells/$cm^2$, approximately $4.8 \times 10^4$ cells per well. The cells were grown in a culture medium consisting of DMEM supplemented with 10% fetal bovine serum, 10 mM HEPES, 1% nonessential amino acids, 2 mM L-glutamine, 100 U/mL penicillin-G, and 100 µg/mL streptomycin. The culture medium was replaced every 3 days and the cells were maintained at 37° C. in a 95% relative humidity and 5% $CO_2$ atmosphere. The cells were evaluated for tight junction formation just prior to assay. The test compound was solubilized to 10 mM in 100% DMSO and diluted to 3 µM in assay buffer. Permeability studies were initiated by adding 200 µL assay buffer plus/minus compound to the apical transwell compartment and 600 µL assay buffer plus/minus compound to the basolateral compartment of the 24-well transwell low-binding cluster plate. For apical-to-basolateral (A to B) permeability (absorptive direction), buffer containing compound was placed in the apical compartment (donor wells), while buffer alone was placed in the corresponding basolateral compartments (receiver wells). For basolateral-to-apical (B to A) permeability (secretive direction), buffer containing compound was placed in the basolateral compartment (donor wells), while buffer alone was placed in the corresponding apical compartments (receiver wells). Transwells were then incubated for 2 hours at 37° C. in a 95% relative humidity and 5% $CO_2$ atmosphere with gentle agitation. Following incubation, 100 µL was removed from each apical and basolateral compartment and transferred to 96-well low binding plates that had been previously loaded with 100 µL/well of acetonitrile containing 250 nM propranolol, 250 nM diclofenac, and 500 nM tolbutamide as internal standards. The samples were subsequently analyzed by LC-MS/MS to determine concentrations of compound.

IRAK4 Whole Blood Assay

Human whole blood containing the anti-coagulant ACD-A was plated in 384-well plate (25 µL/well) and incubated with compounds for 60 minutes at 37° C. in a 5% $CO_2$ incubator. The blood was stimulated with a TLR2 agonist, 10 µg/mL final concentration of lipoteichoic acid (Invivogen, San Diego, Calif.) in 25 µL RPMI (Gibco) for 5 hours in a 5% $CO_2$ incubator. At the end of the incubation, plates were centrifuged at 2300 rpm for 5 minutes. Supernatants were harvested and analyzed for IL-6 levels by Flow Cytometry beads assay (BD Biosciences, San Jose, Calif.).

PBMC TLR2 Induced IL-6 Assay.

Peripheral blood mononuclear cells (PBMCs) were isolated from human blood containing the anti-coagulant EDTA (2.5 mM) by centrifugation over a Ficoll gradient. PBMCs (250000 cells/well) were cultured in assay media (RPMI with 10% heat inactivated FCS) with compounds for 30 minutes at 37° C. in a 5% $CO_2$ incubator. Following pretreatment with compounds, cells were stimulated for 5 hours with 10 μg/ml lipoteichoic acid (Invivogen, San Diego, Calif.), a TLR2 agonist. At the end of the culture, plates were centrifuged at 1800 rpm for 10 minutes to pellet the cells. Supernatants were harvested and analyzed for IL-6 levels by ELISA (BD Biosciences, San Jose, Calif.).

The table below lists the IRAK4 $IC_{50}$ values, the Whole Blood $EC_{50}$ values, and Caco-2 Permeability values for the following examples of this invention measured in the IRAK4 Inhibition Assay, IRAK4 Whole Blood Assay and the Caco-2 Permeability assay. The compounds of the present invention, as exemplified by the following examples, showed IRAK $IC_{50}$ inhibition values of less than 0.6 μM.

TABLE 25

IRAK4 Inhibition Data

| Example No. | IRAK4 $IC_{50}$ (μM) | Whole Blood $EC_{50}$ (μM) | Caco-2 Permeability (nm/s) |
|---|---|---|---|
| 1 | 0.007 | 0.83 | — |
| 2 | 0.001 | 10.00 | — |
| 3 | 0.002 | 0.56 | 330 |
| 4 | 0.003 | 2.53 | <15 |
| 5 | 0.003 | 2.13 | — |
| 6 | 0.005 | 1.45 | 17 |
| 7 | 0.007 | 4.12 | 39 |
| 8 | 0.007 | — | — |
| 9 | 0.003 | — | — |
| 10 | 0.003 | 0.40 | 55 |
| 11 | 0.011 | 1.95 | 28 |
| 12 | 0.004 | 0.31 | 234 |
| 13 | 0.003 | 0.27 | 229 |
| 14 | 0.003 | 0.49 | 41 |
| 15 | 0.007 | — | — |
| 16 | 0.005 | 0.85 | 140 |
| 17 | 0.005 | 1.97 | — |
| 18 | 0.017 | — | — |
| 19 | 0.001 | — | — |
| 20 | 0.007 | 20.00 | — |
| 21 | 0.004 | 0.32 | 42 |
| 22 | 0.004 | 0.49 | — |
| 23 | 0.096 | — | — |
| 24 | 0.003 | — | — |
| 25 | 0.002 | 0.80 | 49 |
| 26 | 0.027 | — | — |
| 27 | 0.016 | — | — |
| 28 | 0.006 | 1.91 | — |
| 29 | 0.004 | 0.38 | <15 |
| 30 | 0.004 | 0.16 | 225 |
| 31 | 0.007 | 1.97 | 159 |
| 32 | 0.005 | 0.37 | 162 |
| 33 | 0.003 | 3.72 | 167 |
| 34 | 0.004 | 0.66 | 481 |
| 35 | 0.003 | 0.46 | 237 |
| 36 | 0.011 | — | — |
| 37 | 0.005 | 0.16 | 339 |
| 38 | 0.010 | — | — |
| 39 | 0.014 | 4.30 | — |
| 40 | 0.003 | — | 278 |
| 41 | 0.004 | 0.32 | 278 |
| 42 | 0.005 | — | 57 |
| 43 | 0.006 | — | — |
| 44 | 0.007 | 0.63 | — |
| 45 | 0.008 | — | — |
| 46 | 0.014 | 0.49 | — |
| 47 | 0.016 | — | — |
| 48 | 0.004 | 0.92 | 300 |
| 49 | 0.004 | 0.58 | 288 |
| 50 | 0.005 | — | — |
| 51 | 0.003 | — | — |
| 52 | 0.003 | 0.43 | 34 |
| 53 | 0.002 | 0.10 | 267 |
| 54 | 0.009 | 1.18 | 408 |
| 55 | 0.008 | — | — |
| 56 | 0.003 | 0.18 | 72 |
| 57 | 0.003 | 0.61 | — |
| 58 | 0.093 | — | — |
| 59 | 0.005 | — | 200 |
| 60 | 0.002 | 0.25 | 119 |
| 61 | 0.007 | — | — |
| 62 | 0.004 | 0.14 | 321 |
| 63 | 0.014 | 0.90 | 78 |
| 64 | 0.005 | — | 148 |
| 65 | 0.009 | 0.42 | — |
| 66 | 0.016 | — | 59 |
| 67 | 0.032 | — | — |
| 68 | 0.014 | — | — |
| 69 | 0.010 | 1.37 | — |
| 70 | 0.005 | 3.96 | — |
| 71 | 0.040 | — | — |
| 72 | 0.052 | — | — |
| 73 | 0.005 | 0.50 | — |
| 74 | 0.007 | — | — |
| 75 | 0.004 | 0.39 | 16 |
| 76 | 0.007 | — | — |
| 77 | 0.021 | — | — |
| 78 | 0.043 | — | — |
| 79 | 0.026 | — | — |
| 80 | 0.003 | 0.59 | — |
| 81 | 0.004 | 1.54 | — |
| 82 | 0.005 | 1.66 | — |
| 83 | 0.005 | 0.86 | — |
| 84 | 0.005 | 0.53 | — |
| 85 | 0.005 | 0.31 | 69 |
| 86 | 0.018 | 1.77 | — |
| 87 | 0.009 | 4.53 | — |
| 88 | 0.005 | 1.29 | 71 |
| 89 | 0.007 | 0.93 | — |
| 90 | 0.004 | 0.17 | 101 |
| 91 | 0.005 | 1.92 | — |
| 92 | 0.011 | 1.12 | 124 |
| 93 | 0.010 | 0.28 | 115 |
| 94 | 0.021 | — | — |
| 95 | 0.016 | — | — |
| 96 | 0.007 | 5.56 | 57 |
| 97 | 0.008 | 1.44 | <15 |
| 98 | 0.002 | — | — |
| 99 | 0.008 | 3.37 | — |
| 100 | 0.235 | — | — |
| 101 | 0.005 | — | — |
| 102 | 0.004 | 1.11 | <15 |
| 103 | 0.172 | — | — |
| 104 | 0.399 | — | — |
| 105 | 0.055 | — | — |
| 106 | 0.321 | — | — |
| 107 | 0.015 | — | — |
| 108 | 0.035 | — | — |
| 109 | 0.217 | — | — |
| 110 | 0.075 | — | — |
| 111 | 0.013 | — | — |
| 112 | 0.076 | — | — |
| 113 | 0.013 | 1.86 | — |
| 114 | 0.003 | 0.87 | — |
| 115 | 0.033 | — | — |
| 116 | 0.003 | 0.21 | — |
| 117 | 0.004 | 1.19 | 101 |
| 118 | 0.003 | 1.09 | — |
| 119 | 0.002 | 0.43 | 50 |
| 120 | 0.001 | 0.20 | 74 |
| 121 | 0.006 | 1.74 | — |
| 122 | 0.006 | 0.59 | 322 |
| 123 | 0.005 | 0.24 | 244 |
| 124 | 0.002 | 0.29 | 29 |
| 125 | 0.003 | 1.76 | — |
| 126 | 0.004 | 0.39 | — |
| 127 | 0.010 | 2.95 | — |
| 128 | 0.001 | 0.34 | 50 |
| 129 | 0.007 | 0.83 | — |

TABLE 25-continued

IRAK4 Inhibition Data

| Example No. | IRAK4 IC$_{50}$ (μM) | Whole Blood EC$_{50}$ (μM) | Caco-2 Permeability (nm/s) |
|---|---|---|---|
| 130 | 0.005 | 10.71 | — |
| 131 | 0.012 | 1.08 | — |
| 132 | 0.051 | — | — |
| 133 | 0.010 | 0.98 | — |
| 134 | 0.006 | 0.55 | — |
| 135 | 0.004 | 1.19 | — |
| 136 | 0.027 | — | — |
| 137 | 0.008 | 1.69 | — |
| 138 | 0.025 | — | — |
| 139 | 0.004 | 1.09 | — |
| 140 | 0.003 | 0.36 | <15 |
| 141 | 0.008 | 0.96 | — |
| 142 | 0.005 | 0.56 | — |
| 143 | 0.008 | 0.97 | — |
| 144 | 0.004 | 0.49 | — |
| 145 | 0.004 | 0.74 | — |
| 146 | 0.003 | 1.09 | — |
| 147 | 0.005 | 1.06 | — |
| 148 | 0.005 | 1.90 | — |
| 149 | 0.002 | 0.73 | — |
| 150 | 0.002 | 0.45 | 91 |
| 151 | 0.002 | 1.61 | — |
| 152 | 0.004 | 0.75 | 158 |
| 153 | 0.002 | 0.27 | 179 |
| 154 | 0.004 | 0.15 | <15 |
| 155 | 0.006 | — | — |
| 156 | 0.003 | 0.66 | — |
| 157 | 0.006 | 0.28 | <15 |
| 158 | 0.002 | 0.52 | — |
| 159 | 0.004 | 0.13 | <15 |
| 160 | 0.001 | 0.29 | 18 |
| 161 | 0.002 | 0.25 | 35 |
| 162 | 0.004 | 0.44 | 171 |
| 163 | 0.002 | 0.60 | 195 |
| 164 | 0.008 | 0.60 | — |
| 165 | 0.025 | — | — |
| 166 | 0.006 | 0.11 | 361 |
| 167 | 0.007 | 1.03 | — |
| 168 | 0.024 | — | — |
| 169 | 0.017 | 2.14 | — |
| 170 | 0.002 | 0.43 | 45 |
| 171 | 0.006 | 1.16 | — |
| 172 | 0.018 | 0.95 | — |
| 173 | 0.026 | — | — |
| 174 | 0.017 | — | — |
| 175 | 0.035 | — | — |
| 176 | 0.013 | 2.10 | — |
| 177 | 0.013 | — | <15 |
| 178 | 0.006 | 0.53 | <15 |
| 179 | 0.007 | 0.68 | 18 |
| 180 | 0.011 | 2.14 | 32 |
| 181 | 0.007 | 0.40 | <15 |
| 182 | 0.005 | 0.75 | — |
| 183 | 0.010 | 0.52 | — |
| 184 | 0.020 | — | — |
| 185 | 0.008 | 1.04 | — |
| 186 | 0.016 | 1.78 | — |
| 187 | 0.302 | — | — |
| 188 | 0.018 | 0.11 | <15 |
| 189 | 0.027 | — | — |
| 190 | 0.026 | — | — |
| 191 | 0.016 | 0.39 | <15 |
| 192 | 0.003 | 0.15 | <15 |
| 193 | 0.004 | — | — |
| 194 | 0.006 | 0.62 | — |
| 195 | 0.002 | 0.45 | <15 |
| 196 | 0.004 | 1.21 | 47 |
| 197 | 0.003 | 0.17 | <15 |
| 199 | 0.004 | 0.55 | — |
| 200 | 0.005 | — | — |
| 201 | 0.004 | — | — |
| 202 | 0.005 | 0.95 | — |
| 203 | 0.004 | 0.72 | <15 |
| 204 | 0.006 | 0.71 | — |
| 205 | 0.005 | — | — |
| 206 | 0.003 | 1.90 | 20 |
| 207 | 0.006 | 1.33 | <15 |
| 208 | 0.006 | 1.51 | 26 |
| 209 | 0.002 | 0.49 | 24 |
| 210 | 0.002 | 0.51 | 43 |
| 211 | 0.002 | 0.29 | 32 |
| 212 | 0.003 | 1.40 | — |
| 213 | 0.005 | 1.75 | 193 |
| 214 | 0.007 | 0.92 | 136 |
| 215 | 0.008 | 1.31 | 104 |
| 216 | 0.002 | 1.65 | 73 |
| 217 | 0.006 | — | — |
| 218 | 0.009 | 2.09 | 125 |
| 219 | 0.010 | 1.48 | 318 |
| 220 | 0.105 | — | — |
| 221 | 0.012 | 2.21 | — |
| 222 | 0.063 | — | — |
| 223 | 0.022 | — | — |
| 224 | 0.087 | — | — |
| 225 | 0.017 | 5.59 | — |
| 226 | 0.016 | 1.48 | — |
| 227 | 0.029 | — | — |
| 228 | 0.019 | — | — |
| 229 | 0.010 | 0.59 | — |
| 230 | 0.027 | — | — |
| 231 | 0.021 | — | — |
| 232 | 0.022 | — | — |
| 233 | 0.004 | 0.53 | — |
| 234 | 0.016 | 0.44 | — |
| 235 | 0.030 | — | — |
| 236 | 0.011 | 0.99 | — |
| 237 | 0.037 | — | — |
| 238 | 0.036 | — | — |
| 239 | 0.034 | — | — |
| 240 | 0.003 | 0.74 | 57 |
| 241 | 0.035 | — | — |
| 242 | 0.047 | — | — |
| 243 | 0.062 | — | — |
| 244 | 0.061 | — | — |
| 245 | 0.334 | — | — |
| 246 | 0.336 | — | — |
| 247 | 0.202 | — | — |
| 248 | 0.066 | — | — |
| 249 | 0.047 | — | — |
| 250 | 0.196 | — | — |
| 251 | 0.039 | — | — |
| 252 | 0.119 | — | — |
| 253 | 0.065 | — | — |
| 254 | 0.190 | — | — |
| 255 | 0.039 | — | — |
| 256 | 0.014 | 0.60 | — |
| 257 | 0.020 | — | — |
| 258 | 0.052 | — | — |
| 259 | 0.153 | — | — |
| 260 | 0.146 | — | — |
| 261 | 0.029 | — | — |
| 262 | 0.288 | — | — |
| 263 | 0.015 | 0.33 | 78 |
| 264 | 0.008 | 0.33 | 225 |
| 265 | 0.005 | 0.41 | — |
| 266 | 0.014 | 0.52 | — |
| 267 | 0.083 | — | — |
| 268 | 0.038 | — | — |
| 269 | 0.004 | 0.39 | 38 |
| 270 | 0.006 | 1.17 | 372 |
| 271 | 0.108 | — | — |
| 272 | 0.529 | — | — |
| 273 | 0.078 | — | — |
| 274 | 0.023 | — | — |
| 275 | 0.030 | — | — |
| 276 | 0.017 | — | — |
| 277 | 0.087 | — | — |
| 278 | 0.015 | — | 237 |

TABLE 25-continued

IRAK4 Inhibition Data

| Example No. | IRAK4 IC$_{50}$ (μM) | Whole Blood EC$_{50}$ (μM) | Caco-2 Permeability (nm/s) |
|---|---|---|---|
| 279 | 0.017 | — | — |
| 280 | 0.003 | 0.23 | 276 |
| 281 | 0.007 | 0.38 | — |
| 282 | 0.013 | 2.26 | — |
| 283 | 0.007 | 1.28 | — |
| 284 | 0.085 | — | — |
| 285 | 0.017 | 6.40 | — |
| 286 | 0.157 | — | — |
| 287 | 0.034 | — | — |
| 288 | 0.020 | — | — |
| 289 | 0.006 | 0.20 | 474 |
| 290 | 0.025 | — | — |
| 291 | 0.014 | 0.85 | — |
| 292 | 0.029 | — | — |
| 293 | 0.028 | — | — |
| 294 | 0.004 | 1.71 | — |
| 295 | 0.048 | — | — |
| 296 | 0.011 | 0.24 | 44 |
| 297 | 0.028 | — | — |
| 298 | 0.194 | — | — |
| 299 | 0.044 | — | — |
| 300 | 0.022 | — | — |
| 301 | 0.022 | — | — |
| 302 | 0.029 | — | — |
| 303 | 0.016 | 1.18 | — |
| 304 | 0.115 | — | — |
| 305 | 0.010 | 0.55 | — |
| 306 | 0.056 | — | — |
| 307 | 0.003 | 0.58 | — |
| 308 | 0.080 | — | — |
| 309 | 0.304 | — | — |
| 310 | 0.108 | — | — |
| 311 | 0.006 | 0.12 | 64 |
| 312 | 0.213 | — | — |
| 313 | 0.115 | — | — |
| 314 | 0.093 | — | — |
| 315 | 0.005 | 1.78 | — |
| 316 | 0.244 | — | — |
| 317 | 0.060 | — | — |
| 318 | 0.025 | 0.79 | 108 |
| 319 | 0.002 | 0.92 | — |
| 320 | 0.003 | 0.93 | — |
| 321 | 0.018 | 0.57 | — |
| 322 | 0.039 | — | — |
| 323 | 0.006 | 1.31 | — |
| 324 | 0.018 | 3.41 | — |
| 325 | 0.016 | 0.99 | — |
| 326 | 0.028 | — | — |
| 327 | 0.003 | 0.20 | 74 |
| 328 | 0.026 | — | — |
| 329 | 0.034 | — | — |
| 330 | 0.298 | — | — |
| 331 | 0.010 | 2.56 | 92 |
| 332 | 0.009 | 2.05 | — |
| 333 | 0.014 | 4.70 | — |
| 334 | 0.002 | 0.07 | <15 |
| 335 | 0.006 | 0.63 | — |
| 336 | 0.007 | 0.22 | 250 |
| 337 | 0.006 | 0.28 | <15 |
| 338 | 0.006 | 0.38 | 179 |
| 339 | 0.005 | 0.39 | <15 |
| 340 | 0.004 | 0.81 | — |
| 341 | 0.003 | 0.30 | <15 |
| 342 | 0.002 | 1.12 | — |
| 343 | 0.003 | 0.52 | — |
| 344 | 0.003 | 0.65 | — |
| 345, racemic | 0.004 | 0.27 | — |
| 345, Isomer 2 | 0.002 | 0.20 | 160 |
| 346 | 0.006 | 0.46 | — |
| 347 | 0.002 | 0.43 | 97 |
| 348 | 0.013 | 0.17 | 410 |
| 349 | 0.003 | 0.27 | 186 |
| 350 | 0.006 | 0.28 | 64 |
| 351 | 0.004 | 0.37 | 306 |
| 352 | 0.020 | 0.46 | |
| 353 | 0.011 | 0.43 | |
| 354 | 0.014 | 0.15 | 360 |
| 355 | 0.007 | 0.24 | 487 |
| 356 | 0.003 | 0.27 | <15 |
| 357 | 0.020 | 0.46 | |
| 358 | 0.005 | 0.43 | 172 |
| 359 | 0.011 | 0.22 | <15 |
| 360 | 0.007 | 0.31 | 36 |
| 361 | 0.007 | 0.36 | 56 |
| 362 | 0.007 | 0.44 | |
| 363 | 0.006 | 0.33 | 156 |
| 364 | 0.003 | 0.25 | 45 |
| 365 | 0.003 | 0.41 | <15 |
| 366 | 0.009 | 0.41 | |
| 367 | 0.009 | 0.23 | 36 |
| 368 | 0.003 | 0.18 | 32 |
| 369 | 0.007 | 0.27 | 67 |
| 370 | 0.009 | 0.28 | 25 |
| 371 | 0.001 | 0.13 | <15 |
| 372 | 0.004 | 0.33 | 36 |
| 373 | 0.004 | 0.30 | 277 |
| 374 | 0.002 | 0.38 | 32 |
| 375 | 0.001 | 0.30 | 68 |
| 376 | 0.006 | 0.38 | |
| 377 | 0.007 | 0.24 | <15 |
| 378 | 0.002 | 0.16 | <15 |
| 379 | 0.005 | 0.14 | <15 |
| 380 | 0.006 | 0.46 | |
| 381 | 0.002 | 0.25 | |
| 382 | 0.002 | 0.46 | 248 |
| 383 | 0.002 | 0.37 | |
| 384 | 0.002 | 0.25 | 131 |
| 385 | 0.003 | 0.49 | |
| 386 | 0.004 | 0.20 | 248 |
| 387 | 0.008 | 0.24 | <15 |
| 388 | 0.006 | 0.26 | |
| 389 | 0.014 | 0.31 | 302 |
| 390 | 0.008 | 0.27 | 371 |
| 392 | 0.003 | 0.44 | <15 |
| 393 | 0.002 | 0.33 | 106 |
| 394 | 0.002 | 0.25 | 91 |
| 395 | 0.001 | 0.29 | 94 |
| 396 | 0.002 | 0.10 | 267 |
| 397 | 0.005 | 0.46 | |
| 398 | 0.004 | 0.30 | 69 |
| 399 | 0.010 | 0.14 | <15 |
| 400, Isomer 1 | 0.003 | 0.23 | 224 |
| 400, Isomer 2 | 0.006 | 0.27 | 530 |
| 401 | 0.004 | 0.38 | 280 |
| 402 | 0.002 | 0.25 | 192 |
| 403 | 0.004 | 0.23 | <15 |
| 404 | 0.003 | 0.23 | <15 |
| 405 | 0.004 | 0.26 | 125 |
| 406 | 0.003 | 0.47 | 163 |
| 407 | 0.001 | 0.29 | 250 |
| 408 | 0.002 | 0.49 | |
| 409 | 0.002 | 0.47 | 302 |
| 410 | 0.002 | 0.30 | 148 |
| 411 | 0.003 | 0.43 | 269 |
| 412 | 0.004 | 0.40 | 139 |
| 413 | 0.005 | 0.30 | 139 |
| 414 | 0.007 | 0.25 | <15 |
| 415 | 0.003 | 0.26 | 183 |
| 416 | 0.002 | 0.48 | |
| 417 | 0.007 | 0.34 | 292 |
| 418 | 0.003 | 0.49 | |
| 419 | 0.002 | 0.43 | 199 |
| 420 | 0.006 | 0.35 | 438 |
| 421 | 0.003 | 0.20 | 322 |
| 422 | 0.003 | 0.48 | 317 |
| 423 | 0.002 | 0.16 | 394 |
| 424 | 0.010 | 0.18 | <15 |
| 425 | 0.009 | 0.14 | <15 |

TABLE 25-continued

IRAK4 Inhibition Data

| Example No. | IRAK4 IC$_{50}$ (µM) | Whole Blood EC$_{50}$ (µM) | Caco-2 Permeability (nm/s) |
|---|---|---|---|
| 426 | 0.001 | 0.34 | |
| 427 | 0.015 | 0.25 | 80 |
| 428 | 0.004 | 0.46 | 263 |
| 429 | 0.002 | 0.45 | |
| 430 | 0.007 | 0.47 | |
| 431 | 0.002 | 0.44 | 218 |
| 432 | 0.001 | 0.37 | |
| 433 | 0.011 | 0.20 | 17 |
| 434 | 0.004 | 0.33 | |
| 435, enantiomer 1 | 0.002 | 0.42 | |
| 435, enantiomer 2 | 0.002 | 0.48 | 264 |
| 436 | 0.002 | 0.29 | 319 |
| 437 | 0.002 | 0.21 | |
| 438 | 0.005 | 0.23 | 273 |
| 439 | 0.004 | 0.25 | 310 |
| 440 | 0.004 | 0.28 | 316 |
| 441 | 0.002 | 0.26 | 317 |
| 442 | 0.004 | 0.41 | |
| 443 | 0.002 | 0.39 | 141 |

What is claimed is:

1. A compound of Formula (I)

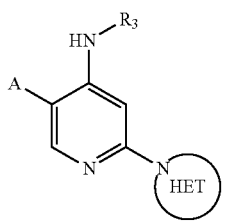

(I)

or a salt thereof, wherein:

HET is a heteroaryl selected from pyrrolo[2,3-b]pyridinyl, pyrrolo[2,3-d]pyrimidinyl, pyrazolo[3,4-b]pyridinyl, pyrazolo[3,4-d]pyrimidinyl, imidazolo[4,5-b]pyridinyl, and imidazolo[4,5-d]pyrimidinyl, wherein said heteroaryl is attached to the pyridinyl group in the compound of Formula (I) by a nitrogen ring atom in said heteroaryl and wherein said heteroaryl is substituted with zero to 2 $R_b$;

A is pyrazolyl, imidazolyl, triazolyl, isoxazolyl, oxadiazolyl or dihydroisoxazolyl, each substituted with $R_a$;

$R_3$ is $C_{2-3}$ alkyl, $C_{2-3}$ fluoroalkyl, $C_{3-4}$ hydroxyalkyl, or a cyclic group selected from $C_{3-6}$ cycloalkyl, oxetanyl, tetrahydrofuranyl, tetrahydropyranyl, and pyrazolyl, wherein said cyclic group is substituted with zero to 2 substituents independently selected from F, —OH, $C_{1-2}$ alkyl, and —CH$_2$CHF$_2$;

$R_a$ is:

(i) H, F, Cl, —OH, —CN, $C_{1-6}$ alkyl, $C_{1-6}$ fluoroalkyl, $C_{1-4}$ cyanoalkyl, $C_{1-6}$ hydroxyalkyl, $C_{1-5}$ hydroxyfluoroalkyl, $C_{2-4}$ alkenyl, $C_{1-6}$ aminoalkyl, —(CH$_2$)$_{1-3}$NHR$_y$, —(CH$_2$)$_{1-3}$NR$_y$R$_y$, —CH$_2$CH(OH)(phenyl), —CH(CH$_2$OH)(phenyl), —CH$_2$CH(OH)CH$_2$(phenyl), —CH$_2$CH(OH)CH$_2$O(methoxyphenyl), —CH$_2$CH(NH$_2$)CH$_2$(phenyl), —(CH$_2$CH$_2$O)$_4$H, —(CH$_2$)$_{1-3}$O(C$_{1-3}$ alkyl), —CH$_2$CH(OH)CH$_2$O(C$_{1-3}$ alkyl), —CH$_2$C(O)(C$_{1-3}$ alkyl), —CH$_2$C(O)NR$_y$R$_y$, —(CH$_2$)$_{1-3}$NR$_y$C(O)(C$_{1-3}$ alkyl), —CH$_2$C(O)O(C$_{1-3}$ alkyl), —C(O)NH$_2$, —CH$_2$NR$_y$C(O)NH$_2$, —(CH$_2$)$_{1-2}$NR$_y$C(O)O(C$_{1-2}$ alkyl), —(CR$_y$R$_y$)$_{1-5}$OC(O)CH$_2$NR$_y$R$_y$, —CH$_2$CH$_2$S(O)$_2$CH$_3$, —CH$_2$S(O)$_2$(C$_{1-3}$ alkyl), —CH$_2$S(O)$_2$(phenyl), or —NH(aminocyclohexyl); or (ii) —(CH$_2$)$_{0-3}$R$_z$ or —(CH$_2$)$_{0-1}$C(O)R$_z$, wherein R$_z$ is $C_{3-6}$ cycloalkyl, azetidinyl, oxetanyl, tetrahydrofuranyl, tetrahydropyranyl, piperidinyl, piperazinyl, pyrrolyl, pyrrolidinonyl, morpholinyl, pyrrolidinyl, phenyl, pyrazolyl, imidazolyl, pyridinyl, pyrimidinyl, dioxopyrimidinyl, benzo[d]imidazolyl, benzo[d]thiazolyl, 1,3-dioxolanyl, or 8-azabicyclo[3.2.1]octanyl, each substituted with zero to 4 substituents independently from F, —CN, —OH, —NR$_y$R$_y$, $C_{1-3}$ alkyl, $C_{1-3}$ fluoroalkyl, $C_{1-3}$ hydroxyalkyl, —CH(phenyl)$_2$, —O(C$_{1-4}$ alkyl), —C(O)(C$_{1-4}$ alkyl), —C(O)(C$_{1-4}$ deuteroalkyl), —C(O)(C$_{1-5}$ hydroxyalkyl), —C(O)(C$_{1-3}$ fluoroalkyl), —C(O)(C$_{3-6}$ cycloalkyl), —C(O)O(C$_{1-3}$ alkyl), —C(O)NR$_y$R$_y$, —C(O)(phenyl), —C(O)(pyridinyl), —C(O)CH$_2$(C$_{3-6}$ cycloalkyl), —C(O)O(C$_{1-4}$ alkyl), —NH(C$_{1-4}$ alkyl), —NH(C$_{1-3}$ fluoroalkyl), —NHC(O)CH$_3$, —NHC(O)O(C$_{1-3}$ alkyl), —NHC(O)OC(CH$_3$)$_3$, —S(O)$_2$(C$_{1-3}$ alkyl), —OS(O)$_2$(C$_{1-3}$ alkyl), methyl oxadiazolyl, and pyrimidinyl;

each $R_b$ is independently selected from H, Cl, —CN, —NH$_2$, and —C(O)NH$_2$; and each $R_y$ is independently H or $C_{1-2}$ alkyl.

2. The compound according to claim 1 or a salt thereof, wherein:

HET is a heteroaryl selected from pyrrolo[2,3-b]pyridinyl, pyrrolo[2,3-d]pyrimidinyl, pyrazolo[3,4-b]pyridinyl, pyrazolo[3,4-d]pyrimidinyl, imidazolo[4,5-b]pyridinyl, and imidazolo[4,5-d]pyrimidinyl, wherein said heteroaryl is attached to the pyridinyl group in the compound of Formula (I) by a nitrogen ring atom in the heteroaryl and wherein said heteroaryl is substituted with zero to 2 $R_b$;

A is pyrazolyl, imidazolyl, or triazolyl, each substituted with $R_a$;

$R_3$ is —CH$_2$CH$_3$, —CH(CH$_3$)$_2$, —CH$_2$CHF$_2$, —CH(CH$_3$)CH$_2$OH, cyclopropyl, oxetanyl, tetrahydropyranyl, ethyl pyrazolyl, or 2,2-difluoroethyl pyrazolyl;

$R_a$ is:

(i) H, F, Cl, —OH, —CN, $C_{1-6}$ alkyl, $C_{1-4}$ fluoroalkyl, $C_{1-4}$ cyanoalkyl, $C_{1-6}$ hydroxyalkyl, $C_{1-4}$ hydroxyfluoroalkyl, $C_{2-4}$ alkenyl, $C_{1-6}$ aminoalkyl, —(CH$_2$)$_{1-3}$NHR$_y$, —(CH$_2$)$_{1-3}$NR$_y$R$_y$, —CH$_2$CH(OH)(phenyl), —CH(CH$_2$OH)(phenyl), —CH$_2$CH(OH)CH$_2$(phenyl), —CH$_2$CH(OH)CH$_2$O(methoxyphenyl), —CH$_2$CH(NH$_2$)CH$_2$(phenyl), —(CH$_2$CH$_2$O)$_4$H, —(CH$_2$)$_{1-3}$O(C$_{1-3}$ alkyl), —CH$_2$CH(OH)CH$_2$O(C$_{1-3}$ alkyl), —CH$_2$C(O)(C$_{1-3}$ alkyl), —CH$_2$C(O)NR$_y$R$_y$, —CH$_2$C(O)O(C$_{1-3}$ alkyl), —C(O)NH$_2$, —CH$_2$NHC(O)NH$_2$, —CH$_2$CH$_2$S(O)$_2$CH$_3$, —CH$_2$S(O)$_2$(C$_{1-3}$ alkyl), or —CH$_2$S(O)$_2$(phenyl); or (ii) —(CH$_2$)$_{0-3}$R$_z$ or —CH$_2$C(O)R$_z$, wherein R$_z$ is $C_{3-6}$ cycloalkyl, azetidinyl, oxetanyl, tetrahydrofuranyl, tetrahydropyranyl, piperidinyl, piperazinyl, pyrrolyl, pyrrolidinonyl, morpholinyl, pyrrolidinyl, phenyl, pyrazolyl, imidazolyl, pyridinyl, pyrimidinyl, pyrimidinonyl, benzo[d]imidazolyl, or benzo[d]thiazolyl, each substituted with zero to 4 substituents independently from F, —CN, —OH, —NR$_y$R$_y$, $C_{1-3}$ alkyl, $C_{1-3}$ fluoroalkyl, —CH(phenyl)$_2$, —O(C$_{1-4}$ alkyl), —C(O)(C$_{1-4}$ alkyl), —C(O)(C$_{1-4}$ deuteroalkyl), —C(O)(C$_{3-6}$ cycloalkyl), —C(O)O(C$_{1-3}$ alkyl), —C(O)NR$_y$R$_y$, —C(O)(phenyl), —C(O)(pyridinyl), —C(O)CH$_2$(C$_{3-6}$ cycloalkyl), —C(O)O(C$_{1-4}$ alkyl), —NHCH(CH$_3$)$_2$, —NHC(O)CH$_3$, —NHC(O)OCH$_3$, —NHC(O)OC(CH$_3$)$_3$, —S(O)$_2$(C$_{1-3}$ alkyl), —OS(O)$_2$(C$_{1-3}$ alkyl), methyl oxadiazolyl, and pyrimidinyl;

each R$_b$ is independently selected from H, Cl, —CN, —NH$_2$, and —C(O)NH$_2$; and each R$_y$ is independently H or C$_{1-2}$ alkyl.

3. The compound according to claim 1 or a salt thereof, wherein:

A is

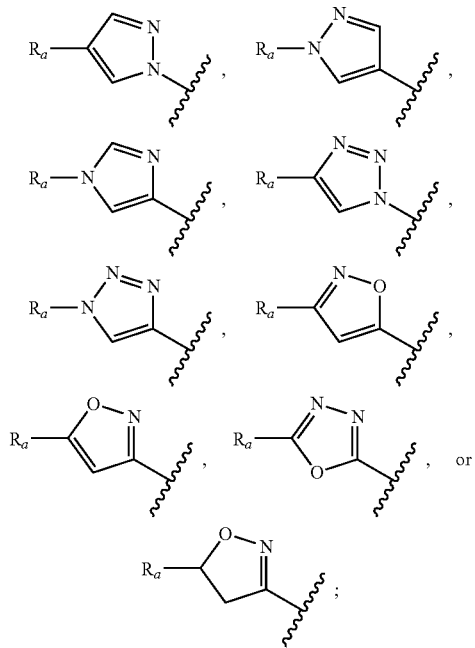

R$_a$ is:

(i) H, —CN, C$_{1-5}$ alkyl, C$_{1-5}$ fluoroalkyl, C$_{1-3}$ cyanoalkyl, C$_{1-5}$ hydroxyalkyl, —CH$_2$CH(OH)CF$_3$, —CH$_2$CHFC(CH$_3$)$_2$OH, —CH$_2$CH(OH)(phenyl), —CH(CH$_2$OH)(phenyl), —CH$_2$CH(OH)CH$_2$(phenyl), —CH$_2$CH(OH)CH$_2$O(methoxyphenyl), —CH=CH$_2$, —CH$_2$NH$_2$, —CH$_2$NHCH$_3$, —CH$_2$N(CH$_3$)$_2$, —CH$_2$CH$_2$NH$_2$, —CH$_2$CH$_2$N(CH$_3$)$_2$, —CH$_2$CH$_2$CH$_2$NHR$_y$, —C(CH$_3$)$_2$NH$_2$, —(CH$_2$)$_5$NH$_2$, —CH$_2$CH(NH$_2$)CH$_2$(phenyl), —CH$_2$N(CH$_2$CH$_3$)$_2$, —(CH$_2$CH$_2$O)$_4$H, —CH$_2$OCH$_3$, —CH$_2$CH$_2$OCH$_3$, —CH$_2$CH$_2$OCH$_2$CH$_3$, —CH$_2$CH(OH)CH$_2$OCH$_3$, —CH$_2$CH(OH)CH$_2$OCH$_2$CH$_3$, —CH$_2$C(O)CH$_3$, —CH$_2$C(O)NH$_2$, —CH$_2$C(O)NHCH$_3$, —CH$_2$C(O)OCH$_2$CH$_3$, —C(O)NH$_2$, —CH$_2$NHC(O)NH$_2$, —CH$_2$NR$_y$C(O)NH$_2$, —(CH$_2$)$_{1-2}$NR$_y$C(O)O(C$_{1-2}$ alkyl), —CH$_2$CH$_2$CH$_2$N(CH$_3$)C(O)CH$_3$, —CH$_2$CH$_2$NHC(O)OCH$_3$, —CH$_2$CH$_2$C(CH$_3$)$_2$OC(O)CH$_2$NR$_y$R, —(CH$_2$)$_{1-5}$OC(O)CH$_2$NR$_y$R$_y$, or —CH$_2$CH$_2$S(O)$_2$CH$_3$;

(ii) cyclopropyl, cyclopentyl, hydroxycyclopentyl, oxetanyl, or cyclohexyl substituted with zero or one substituent selected from —OH, C$_{1-2}$ alkyl, —NH$_2$, —NHCH(CH$_3$)$_2$, —NHC(O)CH$_3$, —NHC(O)O(C$_{1-3}$ alkyl), and —NHCH$_2$CHF$_2$;

(iii) phenyl substituted with zero to 2 substituents independently selected from F, —CN, —OH, —OCH$_3$, and —C(O)OCH$_3$;

(iv) —CH$_2$(cyclopropyl), —CH$_2$(difluorocyclopropyl), —CH$_2$(cyclobutyl), —CH$_2$(oxetanyl), —CH$_2$(hydroxyoxetanyl), —CH$_2$(morpholinyl), —CH$_2$(phenyl), —CH$_2$(fluorophenyl), —CH$_2$(methoxyphenyl), —CH$_2$(pyridinyl), —CH$_2$(butoxycarbonyl, hydroxypiperidinyl), —CH$_2$(butoxycarbonyl pyrrolidinyl), —CH$_2$(acetylazetidinyl), —CH$_2$(benzo[d]imidazolyl), —CH$_2$(methyl benzo[d]thiazolyl), —CH$_2$CH$_2$(morpholinyl), —CH$_2$CH$_2$(phenyl), —CH$_2$CH$_2$(pyridinyl), —CH$_2$CH$_2$(dimethylpyrazolyl), —CH$_2$CH$_2$CH$_2$(phenyl), —CH$_2$CH$_2$CH$_2$(pyrrolidinyl), —CH$_2$C(O)(morpholinyl), —CH$_2$C(O)(piperazinyl), —CH$_2$C(O)(acetylpiperazinyl), —CH$_2$C(O)(methylsulfonyl piperazinyl), —CH$_2$CH(NH$_2$)CH$_2$(phenyl), —CH$_2$S(O)$_2$(phenyl), —C(O)(morpholinyl), or —NH(aminocyclohexyl);

(v) pyridinyl, tetrahydrofuranyl, tetrahydropyranyl, pyrrolidinyl, morpholinyl, pyrrolidinonyl, dioxopyrimidinyl, imidazolyl, 1,3-dioxolanyl, 8-azabicyclo[3.2.1]octanyl, or azetidinyl substituted with zero to 4 substituents independently selected from —CN, —OH, —CH$_3$, —CH$_2$CH$_3$, —CH(CH$_3$)$_2$, —CH$_2$OH, —C(O)cyclopropyl, —C(O)phenyl, —C(O)CH$_3$, —C(O)CD$_3$, —C(O)CH(CH$_3$)$_2$, —C(O)C(CH$_3$)$_3$, —C(O)CH$_2$(cyclopropyl), —C(O)OCH$_3$, —C(O)OC(CH$_3$)$_3$, —CH(phenyl)$_2$, methyl oxadiazolyl, and pyrimidinyl; or (vi) piperidinyl substituted with zero to 3 substituents independently selected from F, —OH, —CH$_3$, —CH(CH$_3$)$_2$, —CH$_2$CHF$_2$, —C(O)NH$_2$, —C(O)CH$_3$, —C(O)CH$_2$CH$_3$, —C(O)C(CH$_3$)$_3$, —C(O)CH$_2$C(CH$_3$)$_2$OH, —C(O)CF$_3$, —C(O)OCH$_3$, —C(O)OCH$_2$CH$_3$, —C(O)OC(CH$_3$)$_3$, —C(O)(pyridinyl), —S(O)$_2$(C$_{1-2}$ alkyl), and —OS(O)$_2$CH$_3$.

4. The compound according to claim 1 or a salt thereof, wherein:

A is

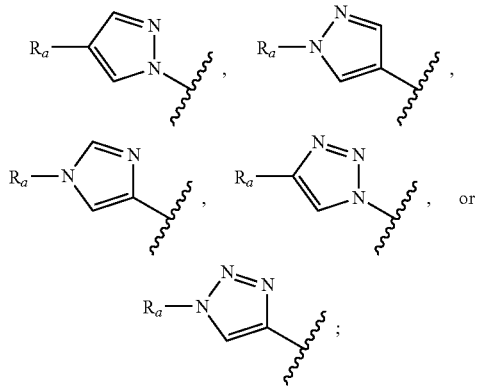

R$_a$ is:

(i) H, —CN, C$_{1-5}$ alkyl, C$_{1-3}$ fluoroalkyl, C$_{1-3}$ cyanoalkyl, C$_{1-5}$ hydroxyalkyl, —CH$_2$CH(OH)CF$_3$, —CH$_2$CH(OH)(phenyl), —CH(CH$_2$OH)(phenyl), —CH$_2$CH(OH)CH$_2$(phenyl), —CH$_2$CH(OH)CH$_2$O(methoxyphenyl), —CH=CH$_2$, —CH$_2$NH$_2$, —CH$_2$NHCH$_3$, —CH$_2$N(CH$_3$)$_2$, —CH$_2$CH$_2$NH$_2$, —CH$_2$CH$_2$N(CH$_3$)$_2$, —CH$_2$CH$_2$CH$_2$NH$_2$, —C(CH$_3$)$_2$NH$_2$, —(CH$_2$)$_5$NH$_2$, —CH$_2$CH(NH$_2$)CH$_2$(phenyl), —CH$_2$N(CH$_2$CH$_3$)$_2$, —(CH₂CH₂O)₄H, —CH₂OCH₃, —CH₂CH₂OCH₃, —CH₂CH₂OCH₂CH₃, —CH₂CH(OH)CH₂OCH₃, —CH₂CH(OH)CH₂OCH₂CH₃, —CH₂C(O)CH₃, —CH₂C(O)NH₂, —CH₂C(O)NHCH₃, —CH₂C(O)OCH₂CH₃, —C(O)NH₂, —CH₂NHC(O)NH₂, or —CH₂CH₂S(O)₂CH₃;

(ii) cyclopropyl, cyclopentyl, hydroxycyclopentyl, oxetanyl, or cyclohexyl substituted with zero or one substituent selected from —OH, —CH₃, —NH₂, —NHCH(CH₃)₂, —NHC(O)CH₃, —NHC(O)OCH₃, and —NHC(O)OC(CH₃)₃;

(iii) phenyl substituted with zero to 2 substituents independently selected from F, —CN, —OH, —OCH₃, and —C(O)OCH₃;

(iv) —CH₂(cyclopropyl), —CH₂(difluorocyclopropyl), —CH₂(cyclobutyl), —CH₂(oxetanyl), —CH₂(hydroxyoxetanyl), —CH₂(morpholinyl), —CH₂(phenyl), —CH₂(fluorophenyl), —CH₂(methoxyphenyl), —CH₂(pyridinyl), —CH₂(butoxycarbonyl, hydroxypiperidinyl), —CH₂(butoxycarbonyl pyrrolidinyl), —CH₂(acetylazetidinyl), —CH₂(benzo[d]imidazolyl), —CH₂(methyl benzo[d]thiazolyl), —CH₂CH₂(morpholinyl), —CH₂CH₂(phenyl), —CH₂CH₂(pyridinyl), —CH₂CH₂(dimethylpyrazolyl), —CH₂CH₂CH₂(phenyl), —CH₂CH₂CH₂(pyrrolidinyl), —CH₂C(O)(morpholinyl), —CH₂C(O)(piperazinyl), —CH₂C(O)(acetylpiperazinyl), —CH₂C(O)(methylsulfonyl piperazinyl), —CH₂CH(NH₂)CH₂(phenyl), or —CH₂S(O)₂(phenyl);

(v) pyridinyl, cyanopyridinyl, tetrahydrofuranyl, tetrahydropyranyl, hydroxytetrahydrofuranyl, trihydroxy(methoxy)tetrahydropyranyl, acetopyrrolidinyl, methylpyrrolidinonyl, pyrimidinonyl, methylimidazolyl, or azetidinyl substituted with zero to 1 substituent selected from —CN, —CH₃, —CH₂CH₃, —CH(CH₃)₂, —C(O)cyclopropyl, —C(O)phenyl, —C(O)CH₃, —C(O)CD₃, —C(O)CH(CH₃)₂, —C(O)C(CH₃)₃, —C(O)CH₂(cyclopropyl), —C(O)OCH₃, —C(O)OC(CH₃)₃, —CH(phenyl)₂, methyl oxadiazolyl, and pyrimidinyl; or (vi) piperidinyl substituted with zero to 3 substituents independently selected from F, —OH, —CH₃, —CH(CH₃)₂, —CH₂CHF₂, —C(O)NH₂, —C(O)CH₃, —C(O)CH₂CH₃, —C(O)C(CH₃)₃, —C(O)OCH₃, —C(O)OCH₂CH₃, —C(O)OC(CH₃)₃, —C(O)(pyridinyl), —S(O)₂CH₃, and —OS(O)₂CH₃.

5. The compound according to claim 1 or a salt thereof, wherein HET is:

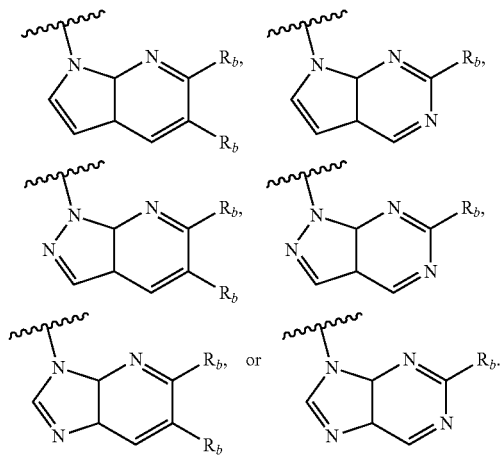

6. The compound according to claim 1 or a salt thereof, wherein $R_a$ is:

(i) H, —CN, —CH₃, —CH₂CH₃, —CH₂CH₂CH₃, —CH(CH₃)₂, —CH₂CH₂CH₂CH₃, —CH₂CH(CH₃)₂, —C(CH₃)₃, —CH₂CH₂CH(CH₃)₂, —CH₂F, —CHF₂, —CF₃, —CH₂CHF₂, —CH₂CF₃, —CH₂CHFCH₃, —CH₂CH₂CH₂F, —CH₂CH₂C(CH₃)₂F, —CH₂CN, —CH₂CH₂CN, —CH₂CH₂CH₂CN, —CH₂OH, —CH₂CH₂OH, —CH₂C(CH₃)₂OH, —C(CH₃)₂OH, —CH₂CH(CH₃)OH, —CH₂CH(OH)CH₃, —CH₂CH₂CH₂OH, —(CH₂)₄OH, —C(CH₃)(OH)CH₂CH₃, —CH₂CH(OH)CH₂OH, —CH₂CH(CH₃)CH₂OH, —CH₂CH(OH)CH₂CH₃, —CH(CH₃)CH(CH₃)OH, —CH₂CH₂C(CH₃)₂OH, —CH₂CH₂C(CH₃)(OH)CH₂OH, —CH₂CH(OH)CH(CH₃)₂, —CH₂C(CH₃)(OH)CH₂CH₃, —CH₂CH₂C(CH₃)(OH)CH₂OH, —CH(CH₂OH)₂, —CH₂CH(OH)CF₃, —CH₂CHFC(CH₃)₂OH, —CH₂CH(OH)(phenyl), —CH(CH₂OH)(phenyl), —CH₂CH(OH)CH₂(phenyl), —CH₂CH(OH)CH₂O(methoxyphenyl), —CH=CH₂, —CH₂NH₂, —CH₂NHCH₃, —CH₂N(CH₃)₂, —CH₂CH₂NH₂, —CH₂CH₂N(CH₃)₂, —CH₂CH₂CH₂NH₂, —C(CH₃)₂NH₂, —CH₂CH₂CH₂NHCH₃, —(CH₂)₅NH₂, —CH₂CH(NH₂)CH₂(phenyl), —CH₂N(CH₂CH₃)₂, —(CH₂CH₂O)₄H, —CH₂OCH₃, —CH₂CH₂OCH₃, —CH₂CH₂OCH₂CH₃, —CH₂CH(OH)CH₂OCH₃, —CH₂CH(OH)CH₂OCH₂CH₃, —CH₂C(O)CH₃, —CH₂C(O)NH₂, —CH₂C(O)NHCH₃, —CH₂C(O)OCH₂CH₃, —C(O)NH₂, —CH₂NHC(O)NH₂, —CH₂NHC(O)OCH₃, —CH₂CH₂NHC(O)OCH₃, —CH₂CH₂CH₂N(CH₃)C(O)CH₃, —CH₂CH₂C(CH₃)₂OC(O)CH₂NH₂, —CH₂CH₂C(CH₃)₂OC(O)CH₂N(CH₃)₂, or —CH₂CH₂S(O)₂CH₃;

(ii) cyclopropyl, cyclopentyl, oxetanyl, or cyclohexyl substituted with zero or one substituent selected from —OH, —CH₃, —NH₂, —NHCH₂CH₃, —NHCH(CH₃)₂, —NHCH₂CHF₂, —NHC(O)CH₃, —NHC(O)OCH₃, —NHC(O)OCH₂CH₃, and —NHC(O)OC(CH₃)₃;

(iii) phenyl substituted with zero to 2 substituents independently selected from F, —CN, —OH, —OCH₃, and —C(O)OCH₃;

(iv) —CH₂(cyclopropyl), —CH₂(difluorocyclopropyl), —CH₂(cyclobutyl), —CH₂(oxetanyl), —CH₂(hydroxyoxetanyl), —CH₂(morpholinyl), —CH₂(phenyl), —CH₂(fluorophenyl), —CH₂(methoxyphenyl), —CH₂(pyridinyl), —CH₂(butoxycarbonyl, hydroxypiperidinyl), —CH₂(butoxycarbonyl pyrrolidinyl), —CH₂(acetylazetidinyl), —CH₂(benzo[d]imidazolyl), —CH₂(methyl benzo[d]thiazolyl), —CH₂CH₂(morpholinyl), —CH₂CH₂(phenyl), —CH₂CH₂(pyridinyl), —CH₂CH₂(dimethylpyrazolyl), —CH₂CH₂CH₂(phenyl), —CH₂CH₂CH₂(pyrrolidinyl), —C(O)(morpholinyl), —CH₂C(O)(morpholinyl), —CH₂C(O)(piperazinyl), —CH₂C(O)(acetylpiperazinyl), —CH₂C(O)(methylsulfonyl piperazinyl), —CH₂CH(NH₂)CH₂(phenyl), or —CH₂S(O)₂(phenyl);

(v) pyridinyl, tetrahydrofuranyl, tetrahydropyranyl, pyrrolidinyl, pyrrolidinonyl, morpholinyl, dioxopyrimidinyl, imidazolyl, azetidinyl, 1,3-dioxolanyl, or 8-azabicyclo[3.2.1]octanyl, each substituted with zero to 4 substituents independently selected from —OH, —CN, —CH₃, —CH₂CH₃, —CH(CH₃)₂, —CH₂OH, —C(O)cyclopropyl, —C(O)phenyl, —C(O)CH₃, —C(O)CD₃, —C(O)CH(CH₃)₂, —C(O)C(CH₃)₃, —C(O)CH₂(cyclopropyl), —C(O)OCH₃, —C(O)OC(CH₃)₃, —CH(phenyl)₂, methyl oxadiazolyl, and pyrimidinyl; or
(vi) piperidinyl substituted with zero to 3 substituents independently selected from F, —OH, —CH₃, —CH(CH₃)₂, —CH₂CHF₂, —C(O)NH₂, —C(O)CH₃, —C(O)CH₂CH₃, —C(O)C(CH₃)₃, —C(O)CF₃, —C(O)OCH₃, —C(O)OCH₂CH₃, —C(O)OC(CH₃)₃, —C(O)CH₂C(CH₃)₂OH, —C(O)(pyridinyl), —S(O)₂CH₃, —S(O)₂CH₂CH₃, and —OS(O)₂CH₃.

7. The compound according to claim 1 or a salt thereof, wherein A is triazolyl.

8. The compound according to claim 1 or a salt thereof, wherein A is pyrazolyl or imidazolyl.

9. The compound according to claim 1 or a salt thereof, wherein A is isoxazolyl.

10. The compound according to claim 1 or a salt thereof, wherein said compound or said salt is selected from: 2-(4-(4-(isopropylamino)-6-(7H-pyrrolo[2,3-d]pyrimidin-7-yl)pyridin-3-yl)-1H-1,2,3-triazol-1-yl)ethanol (1); ethyl 2-(4-(4-(isopropylamino)-6-(7H-pyrrolo[2,3-d]pyrimidin-7-yl)pyridin-3-yl)-1H-1,2,3-triazol-1-yl)acetate (2); N-isopropyl-5-(1-(2-morpholinoethyl)-1H-1,2,3-triazol-4-yl)-2-(7H-pyrrolo[2,3-d]pyrimidin-7-yl)pyridin-4-amine (3); (3R,4R)-4-(4-(4-(isopropylamino)-6-(7H-pyrrolo[2,3-d]pyrimidin-7-yl) pyridin-3-yl)-1H-1,2,3-triazol-1-yl)piperidin-3-ol (4); 5-(1-(5-aminopentyl)-1H-1,2,3-triazol-4-yl)-N-isopropyl-2-(7H-pyrrolo[2,3-d]pyrimidin-7-yl)pyridin-4-amine (5); (3R,4S)-4-(4-(4-(isopropylamino)-6-(7H-pyrrolo[2,3-d]pyrimidin-7-yl)pyridin-3-yl)-1H-1,2,3-triazol-1-yl)piperidin-3-ol (6); (3S,4R)-4-(4-(4-(isopropylamino)-6-(7H-pyrrolo [2,3-d]pyrimidin-7-yl)pyridin-3-yl)-1H-1,2,3-triazol-1-yl)piperidin-3-ol (7); 6-((4-(4-(isopropylamino)-6-(7H-pyrrolo[2,3-d]pyrimidin-7-yl)pyridin-3-yl)-1H-1,2,3-triazol-1-yl)methyl)pyrimidine-2,4(1H,3H)-dione (8); 2-(2-(2-(2-(4-(4-(isopropylamino)-6-(7H-pyrrolo[2,3-d]pyrimidin-7-yl)pyridin-3-yl)-1H-1,2,3-triazol-1-yl)ethoxy)ethoxy)ethoxy)ethanol (9); 1-(5-(1-isopentyl-1H-1,2,3-triazol-4-yl)-4-(isopropylamino)pyridin-2-yl)-1H-pyrazolo[3,4-b]pyridine-5-carbonitrile, TFA (10); 1-(5-(1-(2-hydroxyethyl)-1H-1,2,3-triazol-4-yl)-4-(isopropylamino)pyridin-2-yl)-1H-pyrazolo[3,4-b]pyridine-5-carbonitrile (11); 1-(4-(isopropylamino)-5-(1-(2-morpholinoethyl)-1H-1,2,3-triazol-4-yl)pyridin-2-yl)-1H-pyrazolo[3,4-b]pyridine-5-carbonitrile (12); 1-(4-(cyclopropylamino)-5-(1-(2-morpholinoethyl)-1H-1,2,3-triazol-4-yl)pyridin-2-yl)-1H-pyrazolo[3,4-b]pyridine-5-carbonitrile (13); 1-(4-(cyclopropylamino)-5-(1-(2-hydroxyethyl)-1H-1,2,3-triazol-4-yl) pyridin-2-yl)-1H-pyrazolo[3,4-b]pyridine-5-carbonitrile (14); 1-(4-(isopropylamino)-5-(1-(oxetan-3-yl)-1H-1,2,3-triazol-4-yl)pyridin-2-yl)-1H-pyrazolo[3,4-b]pyridine-5-carbonitrile (15); 1-(5-(1-(cyclopropylmethyl)-1H-1,2,3-triazol-4-yl)-4-(isopropylamino) pyridin-2-yl)-1H-pyrazolo[3,4-b]pyridine-5-carbonitrile (16); 1-(5-(1-cyclohexyl-1H-1,2,3-triazol-4-yl)-4-(isopropylamino)pyridin-2-yl)-1H-pyrazolo[3,4-b]pyridine-5-carbonitrile (17); 1-(5-(1-(tert-butyl)-1H-1,2,3-triazol-4-yl)-4-(isopropylamino)pyridin-2-yl)-1H-pyrazolo[3,4-b]pyridine-5-carbonitrile (18); 1-(4-(isopropylamino)-5-(1-(tetrahydro-2H-pyran-4-yl)-1H-1,2,3-triazol-4-yl)pyridin-2-yl)-1H-pyrazolo[3,4-b] pyridine-5-carbonitrile (19); 1-(5-(1-(2-fluorophenyl)-1H-1,2,3-triazol-4-yl)-4-(isopropylamino)pyridin-2-yl)-1H-pyrazolo[3,4-b]pyridine-5-carbonitrile (20); 1-(4-(isopropylamino)-5-(1-(1-methyl-2-oxopyrrolidin-3-yl)-1H-1,2,3-triazol-4-yl)pyridin-2-yl)-1H-pyrazolo[3,4-b]pyridine-5-carbonitrile, isomer 1 (21) and isomer 2 (22); 3-(5-(1-(tert-butyl)-1H-1,2,3-triazol-4-yl)-4-(isopropylamino)pyridin-2-yl)-3H-imidazo[4,5-b]pyridine-6-carbonitrile (23); 3-(4-(isopropylamino)-5-(1-(tetrahydro-2H-pyran-4-yl)-1H-1,2,3-triazol-4-yl) pyridin-2-yl)-3H-imidazo[4,5-b]pyridine-6-carbonitrile (24); 6-amino-1-(5-(1-cyclohexyl-1H-1,2,3-triazol-4-yl)-4-(isopropylamino)pyridin-2-yl)-1H-pyrazolo[3,4-b] pyridine-5-carbonitrile (25); 2-(5-chloro-1H-pyrazolo[3,4-b]pyridin-1-yl)-N-isopropyl-5-(1-(oxetan-3-yl)-1H-1,2,3-triazol-4-yl)pyridin-4-amine (26); 2-(5-chloro-1H-pyrazolo [3,4-b]pyridin-1-yl)-5-(1-(cyclopropylmethyl)-1H-1,2,3-triazol-4-yl)-N-isopropylpyridin-4-amine (27); 1-(5-(1-(3-hydroxypropyl)-1H-1,2,3-triazol-4-yl)-4-(isopropylamino)pyridin-2-yl)-1H-pyrazolo[3,4-b]pyridine-5-carbonitrile (28); 6-amino-1-(5-(1-(3-hydroxypropyl)-1H-1,2,3-triazol-4-yl)-4-(isopropylamino)pyridin-2-yl)-1H-pyrazolo[3,4-b]pyridine-5-carbonitrile (29); 1-(4-(isopropylamino)-5-(1-propyl-1H-1,2,3-triazol-4-yl) pyridin-2-yl)-1H-pyrazolo[3,4-b]pyridine-5-carbonitrile (30); 1-(5-(1-((2,2-difluorocyclopropyl)methyl)-1H-1,2,3-triazol-4-yl)-4-(isopropylamino)pyridin-2-yl)-1H-pyrazolo[3,4-b]pyridine-5-carbonitrile, isomer 1 (31) and isomer 2 (32); 6-amino-1-(4-(isopropylamino)-5-(1-propyl-1H-1,2,3-triazol-4-yl)pyridin-2-yl)-1H-pyrazolo[3,4-b]pyridine-5-carbonitrile (33); 1-(4-(cyclopropylamino)-5-(1-propyl-1H-1,2,3-triazol-4-yl)pyridin-2-yl)-1H-pyrazolo[3,4-b]pyridine-5-carbonitrile (34); 6-amino-1-(4-(cyclopropylamino)-5-(1-propyl-1H-1,2,3-triazol-4-yl)pyridin-2-yl)-1H-pyrazolo[3,4-b] pyridine-5-carbonitrile (35); 2-(5-chloro-1H-pyrazolo[3,4-b]pyridin-1-yl)-N-cyclopropyl-5-(1-propyl-1H-1,2,3-triazol-4-yl)pyridin-4-amine (36); 1-(5-(1-ethyl-1H-1,2,3-triazol-4-yl)-4-(isopropylamino)pyridin-2-yl)-1H-pyrazolo[3,4-b]pyridine-5-carbonitrile (37); 3-(5-(1-ethyl-1H-1,2,3-triazol-4-yl)-4-(isopropylamino)pyridin-2-yl)-3H-imidazo[4,5-b]pyridine-6-carbonitrile (38); 2-(5-chloro-1H-pyrazolo[3,4-b]pyridin-1-yl)-5-(1-ethyl-1H-1,2,3-triazol-4-yl)-N-isopropylpyridin-4-amine (39); 3-(4-(isopropylamino)-5-(1-propyl-1H-1,2,3-triazol-4-yl)pyridin-2-yl)-3H-imidazo[4,5-b]pyridine-6-carbonitrile (40); 1-(4-(isopropylamino)-5-(1-(3,3,3-trifluoropropyl)-1H-1,2,3-triazol-4-yl)pyridin-2-yl)-1H-pyrazolo[3,4-b]pyridine-5-carbonitrile (41); 3-(4-(isopropylamino)-5-(1-(3,3,3-trifluoropropyl)-1H-1,2,3-triazol-4-yl)pyridin-2-yl)-3H-imidazo[4,5-b]pyridine-6-carbonitrile (42); 3-(4-(cyclopropylamino)-5-(1-propyl-1H-1,2,3-triazol-4-yl)pyridin-2-yl)-3H-imidazo[4,5-b]pyridine-6-carbonitrile (43); 1-(5-(1-(3-fluoropropyl)-1H-1,2,3-triazol-4-yl)-4-(isopropylamino)pyridin-2-yl)-1H-pyrazolo[3,4-b]pyridine-5-carbonitrile (44); 3-(5-(1-(3-fluoropropyl)-1H-1,2,3-triazol-4-yl)-4-(isopropylamino)pyridin-2-yl)-3H-imidazo[4,5-b]pyridine-6-carbonitrile (45); 6-amino-1-(5-(1-(3-fluoropropyl)-1H-1,2,3-triazol-4-yl)-4-(isopropylamino)pyridin-2-yl)-1H-pyrazolo[3,4-b]pyridine-5-carbonitrile (46); 1-(5-(1-(cyanomethyl)-1H-1,2,3-triazol-4-yl)-4-(isopropylamino) pyridin-2-yl)-1H-pyrazolo[3,4-b]pyridine-5-carbonitrile (47); 1-(5-(1-(4-fluorobutyl)-1H-1,2,3-triazol-4-yl)-4-(isopropylamino)pyridin-2-yl)-1H-pyrazolo[3,4-b] pyridine-5-carbonitrile (48); 1-(5-(1-propyl-1H-1,2,3-triazol-4-yl)-4-((tetrahydro-2H-pyran-4-yl) amino)pyridin-2-yl)-1H-pyrazolo[3,4-b]pyridine-5-carbonitrile (49); 3-(5-(1-propyl-1H-1,2,3-triazol-4-yl)-4-((tetrahydro-2H-pyran-4-yl)amino)pyridin-2-yl)-3H-imidazo[4,5-b] pyridine-6-carbonitrile (50); 6-amino-1-(5-(1-propyl-1H-1,2,3-triazol-4-yl)-4-((tetrahydro-2H-pyran-4-yl)amino)pyridin-2-yl)-1H-pyrazolo[3,4-b]pyridine-5-carbonitrile (51); (S)-1-(4-((1-hydroxypropan-2-yl)amino)-5-(1-propyl-1H-1,2,3-triazol-4-yl)pyridin-2-yl)-1H-pyrazolo[3,4-b]pyridine-5-carbonitrile (52); (S)-3-(4-((1-hydroxypropan-2-yl)amino)-5-(1-propyl-1H-1,2,3-triazol-4-yl)pyridin-2-yl)-3H-imidazo[4,5-b]pyridine-6-carbonitrile (53); 1-(4-(ethylamino)-5-(1- propyl-1H-1,2,3-triazol-4-yl) pyridin-2-yl)-1H-pyrazolo[3,4-b]pyridine-5-carbonitrile (54); 3-(4-(ethylamino)-5-(1-propyl-1H-1,2,3-triazol-4-yl)pyridin-2-yl)-3H-imidazo[4,5-b]pyridine-6-carbonitrile (55); 1-(4-(isopropylamino)-5-(1-phenethyl-1H-1,2,3-triazol-4-yl)pyridin-2-yl)-1H-pyrazolo[3,4-b]pyridine-5-carbonitrile (56); 3-(4-(isopropylamino)-5-(1-phenethyl-1H-1,2,3-triazol-4-yl)pyridin-2-yl)-3H-imidazo[4,5-b]pyridine-6-carbonitrile (57); 1-(4-(((1-ethyl-1H-pyrazol-4-yl)amino)-5-(1-propyl-1H-1,2,3-triazol-4-yl)pyridin-2-yl)-1H-pyrazolo [3,4-b]pyridine-5-carbonitrile (58); 3-(4-((1-ethyl-1H-pyrazol-4-yl)amino)-5-(1-propyl-1H-1,2,3-triazol-4-yl)pyridin-2-yl)-3H-imidazo[4,5-b]pyridine-6-carbonitrile (59); 1-(4-((1-(2,2-difluoroethyl)-1H-pyrazol-4-yl)amino)-5-(1-propyl-1H-1,2,3-triazol-4-yl)pyridin-2-yl)-1H-pyrazolo[3,4-b]pyridine-5-carbonitrile (60); 3-(4-((1-(2,2-difluoroethyl)-1H-pyrazol-4-yl)amino)-5-(1-propyl-1H-1,2,3-triazol-4-yl)pyridin-2-yl)-3H-imidazo[4,5-b]pyridine-6-carbonitrile (61); 9-(4-(isopropylamino)-5-(1-propyl-1H-1,2,3-triazol-4-yl)pyridin-2-yl)-9H-purin-2-amine (62); 1-(5-(1-(2-hydroxy-2-methylpropyl)-1H-1,2,3-triazol-4-yl)-4-(isopropylamino)pyridin-2-yl)-1H-pyrazolo [3,4-b]pyridine-5-carbonitrile (63); 1-(5-(1-((1R,2R)-2-hydroxy-2-methylcyclohexyl)-1H-1,2,3-triazol-4-yl)-4-(isopropylamino)pyridin-2-yl)-1H-pyrazolo[3,4-b]pyridine-5-carbonitrile (64); (S)-1-(5-(1-(2-hydroxypropyl)-1H-1,2,3-triazol-4-yl)-4-(isopropylamino)pyridin-2-yl)-1H-pyrazolo[3,4-b]pyridine-5-carbonitrile (65); (R)-1-(5-(1-(2-hydroxypropyl)-1H-1,2,3-triazol-4-yl)-4-(isopropylamino)pyridin-2-yl)-1H-pyrazolo[3,4-b]pyridine-5-carbonitrile (66); 3-(5-(1-(2-hydroxy-2-methylpropyl)-1H-1,2,3-triazol-4-yl)-4-(isopropylamino)pyridin-2-yl)-3H-imidazo[4,5-b]pyridine-6-carbonitrile (67); (R)-3-(5-(1-(2-hydroxypropyl)-1H-1,2,3-triazol-4-yl)-4-(isopropylamino)pyridin-2-yl)-3H-imidazo[4,5-b]pyridine-6-carbonitrile (68); (S)-3-(5-(1-(2-hydroxypropyl)-1H-1,2,3-triazol-4-yl)-4-(isopropylamino)pyridin-2-yl)-3H-imidazo[4,5-b]pyridine-6-carbonitrile (69); (S)-6-amino-1-(5-(1-(2-hydroxypropyl)-1H-1,2,3-triazol-4-yl)-4-(isopropylamino)pyridin-2-yl)-1H-pyrazolo[3,4-b]pyridine-5-carbonitrile (70); (S)-1-(4-(ethylamino)-5-(1-(2-hydroxypropyl)-1H-1,2,3-triazol-4-yl)pyridin-2-yl)-1H-pyrazolo[3,4-b]pyridine-5-carbonitrile (71); (S)-3-(4-(ethylamino)-5-(1-(2-hydroxypropyl)-1H-1,2,3-triazol-4-yl)pyridin-2-yl)-3H-imidazo[4,5-b]pyridine-6-carbonitrile (72); 3-(5-(1-((3R,4S)-4-hydroxytetrahydrofuran-3-yl)-1H-1,2,3-triazol-4-yl)-4-(isopropylamino)pyridin-2-yl)-3H-imidazo[4,5-b]pyridine-6-carbonitrile (74); 3-(5-(1-((3R,4S)-4-hydroxytetrahydrofuran-3-yl)-1H-1,2,3-triazol-4-yl)-4-(isopropylamino) pyridin-2-yl)-3H-imidazo[4,5-b]pyridine-6-carbonitrile, isomer 1 (73) and isomer 2 (75); 1-(5-(1-(2-hydroxy-3-phenylpropyl)-1H-1,2,3-triazol-4-yl)-4-(isopropylamino)pyridin-2-yl)-1H-pyrazolo [3,4-b]pyridine-5-carbonitrile, isomer 1 (76) and isomer 2 (77); 3-(5-(1-(2-hydroxy-3-phenylpropyl)-1H-1,2,3-triazol-4-yl)-4-(isopropylamino)pyridin-2-yl)-3H-imidazo[4,5-b]pyridine-6-carbonitrile, isomer 1 (78) and isomer 2 (79); (S)-1-(5-(1-(2-hydroxy-2-phenylethyl)-1H-1,2,3-triazol-4-yl)-4-(isopropylamino)pyridin-2-yl)-1H-pyrazolo[3,4-b] pyridine-5-carbonitrile (84); (R)-1-(5-(1-(2-hydroxy-2-phenylethyl)-1H-1,2,3-triazol-4-yl)-4-(isopropylamino)pyridin-2-yl)-1H-pyrazolo[3,4-b]pyridine-5-carbonitrile (85); (R)-1-(5-(1-(2-hydroxy-1-phenylethyl)-1H-1,2,3-triazol-4-yl)-4-(isopropylamino)pyridin-2-yl)-1H-pyrazolo[3,4-b]pyridine-5-carbonitrile (86); (S)-1-(5-(1-(2-hydroxy-1-phenylethyl)-1H-1,2,3-triazol-4-yl)-4-(isopropylamino) pyridin-2-yl)-1H-pyrazolo[3,4-b] pyridine-5-carbonitrile (87); 1-(5-(1-((2R,3S)-3-hydroxybutan-2-yl)-1H-1,2,3-triazol-4-yl)-4-(isopropylamino)pyridin-2-yl)-1H-pyrazolo[3,4-b]pyridine-5-carbonitrile, isomer 1 (89) and isomer 2 (88); 1-(5-(1-((2S,3S)-3-hydroxybutan-2-yl)-1H-1,2,3-triazol-4-yl)-4-(isopropylamino) pyridin-2-yl)-1H-pyrazolo[3,4-b]pyridine-5-carbonitrile, isomer 1 (90) and isomer 2 (91); 1-(5-(1-(2-hydroxy-2-methylbutyl)-1H-1,2,3-triazol-4-yl)-4-(isopropylamino)pyridin-2-yl)-1H-pyrazolo[3,4-b]pyridine-5-carbonitrile, isomer 1 (92) and isomer 2 (93); 3-(5-(1-(2-hydroxy-2-methylbutyl)-1H-1,2,3-triazol-4-yl)-4-(isopropylamino)pyridin-2-yl)-3H-imidazo[4,5-b]pyridine-6-carbonitrile, isomer 1 (94) and isomer 2 (95) (94 and 95); 1-(5-(1-((1R,2R)-2-hydroxycyclohexyl)-1H-1,2,3-triazol-4-yl)-4-(isopropylamino)pyridin-2-yl)-1H-pyrazolo[3,4-b]pyridine-5-carbonitrile (96); 6-amino-1-(5-(1-(2-hydroxy-2-methylpropyl)-1H-1,2,3-triazol-4-yl)-4-(isopropylamino)pyridin-2-yl)-1H-pyrazolo[3,4-b]pyridine-5-carbonitrile (97); Ethyl 2-(4-(6-(5-cyano-1H-pyrazolo [3,4-b]pyridin-1-yl)-4-(isopropylamino)pyridin-3-yl)-1H-1,2,3-triazol-1-yl) acetate (98); (R)-tert-butyl 2-((4-(6-(5-cyano-1H-pyrazolo [3,4-b]pyridin-1-yl)-4-(isopropylamino) pyridin-3-yl)-1H-1,2,3-triazol-1-yl) methyl)pyrrolidine-1-carboxylate (99); 1-(5-(1-(1-benzhydrylazetidin-3-yl)-1H-1,2,3-triazol-4-yl)-4-(isopropylamino)pyridin-2-yl)-1H-pyrazolo[3,4-b]pyridine-5-carbonitrile (100); 1-(4-(isopropylamino)-5-(1-(2-morpholino-2-oxoethyl)-1H-1,2,3-triazol-4-yl)pyridin-2-yl)-1H-pyrazolo[3,4-b]pyridine-5-carbonitrile (101); 1-(5-(1-(2-(3,5-dimethyl-1H-pyrazol-4-yl)ethyl)-1H-1,2,3-triazol-4-yl)-4-(isopropylamino)pyridin-2-yl)-1H-pyrazolo [3,4-b]pyridine-5-carbonitrile (102); 1-(5-(1-(3-hydroxyphenyl)-1H-1,2,3-triazol-4-yl)-4-(isopropylamino) pyridin-2-yl)-1H-pyrazolo[3,4-b]pyridine-5-carbonitrile (103); 1-(5-(1-(3-cyano-4-fluorophenyl)-1H-1,2,3-triazol-4-yl)-4-(isopropylamino)-pyridin-2-yl)-1H-pyrazolo[3,4-b]pyridine-5-carbonitrile (104); 1-(4-(isopropylamino)-5-(1-((2R,3R,4S,5R,6R)-3,4,5-trihydroxy-6-(hydroxymethyl)tetrahydro-2H-pyran-2-yl)-1H-1,2,3-triazol-4-yl)pyridin-2-yl)-1H-pyrazolo[3,4-b]pyridine-5-carbonitrile (105); 1-(4-(isopropylamino)-5-(1-((2-methylbenzo[d]thiazol-5-yl)methyl)-1H-1,2,3-triazol-4-yl)pyridin-2-yl)-1H-pyrazolo[3,4-b]pyridine-5-carbonitrile (106); 1-(5-(1-benzyl-1H-1,2,3-triazol-4-yl)-4-(isopropylamino) pyridin-2-yl)-1H-pyrazolo[3,4-b]pyridine-5-carbonitrile (107); 1-(5-(1-((1H-benzo[d]imidazol-2-yl)methyl)-1H-1,2,3-triazol-4-yl)-4-(isopropylamino)pyridin-2-yl)-1H-pyrazolo[3,4-b]pyridine-5-carbonitrile (108); 1-(5-(1-(4-fluorophenyl)-1H-1,2,3-triazol-4-yl)-4-(isopropylamino)pyridin-2-yl)-1H-pyrazolo[3,4-b]pyridine-5-carbonitrile (109); 1-(4-(isopropylamino)-5-(1-(4-methoxybenzyl)-1H-1,2,3-triazol-4-yl)pyridin-2-yl)-1H-pyrazolo[3,4-b]pyridine-5-carbonitrile (110); 1-(5-(1-(2-cyanopyridin-3-yl)-1H-1,2,3-triazol-4-yl)-4-(isopropylamino)pyridin-2-yl)-1H-pyrazolo[3,4-b]pyridine-5-carbonitrile (111); 1-(5-(1-(4-fluorobenzyl)-1H-1,2,3-triazol-4-yl)-4-(isopropylamino)pyridin-2-yl)-1H-pyrazolo [3,4-b]pyridine-5-carbonitrile (112); tert-butyl 3-(4-(6-(5-cyano-1H-pyrazolo [3,4-b]pyridin-1-yl)-4-(isopropylamino) pyridin-3-yl)-1H-1,2,3-triazol-1-yl)azetidine-1-carboxylate (113); 1-(5-(1-(5-aminopentyl)-1H-1,2,3-triazol-4-yl)-4-(isopropylamino) pyridin-2-yl)-1H-pyrazolo[3,4-b]pyridine-5-carbonitrile (114); 1-(4-(isopropylamino)-5-(1-phenyl-1H-1,2,3-triazol-4-yl)pyridin-2-yl)-1H-pyrazolo[3,4-b] pyridine-5-carbonitrile (115); 1-(4-(isopropylamino)-5-(1-(2-(methylsulfonyl)ethyl)-1H-1,2,3-triazol-4-yl) pyridin-2-yl)-1H-pyrazolo[3,4-b]pyridine-5-carbonitrile (116); 1-(5-(1-(cyclobutylmethyl)-1H-1,2,3-triazol-4-yl)-4-(isopropylamino)pyridin-2-yl)-1H-pyrazolo [3,4-b] pyridine-5-carbonitrile (117); 1-(4-(isopropylamino)-5-(1-(2-(pyridin-2-yl)ethyl)-1H-1,2,3-triazol-4-yl)pyridin-2-yl)-1H-pyrazolo[3,4-b]pyridine-5-carbonitrile (118); 1-(4-

(isopropylamino)-5-(1-(2-(pyridin-3-yl)ethyl)-1H-1,2,3-triazol-4-yl)pyridin-2-yl)-1H-pyrazolo[3,4-b]pyridine-5-carbonitrile (119); 1-(4-(isopropylamino)-5-(1-(2-(pyridin-4-yl)ethyl)-1H-1,2,3-triazol-4-yl)pyridin-2-yl)-1H-pyrazolo[3,4-b]pyridine-5-carbonitrile (120); 1-(4-(isopropylamino)-5-(1-(2-methoxyethyl)-1H-1,2,3-triazol-4-yl)pyridin-2-yl)-1H-pyrazolo[3,4-b]pyridine-5-carbonitrile (121); 1-(5-(1-(2-ethoxyethyl)-1H-1,2,3-triazol-4-yl)-4-(isopropylamino)pyridin-2-yl)-1H-pyrazolo[3,4-b]pyridine-5-carbonitrile (122); 1-(4-(isopropylamino)-5-(1-(oxetan-2-ylmethyl)-1H-1,2,3-triazol-4-yl)pyridin-2-yl)-1H-pyrazolo[3,4-b]pyridine-5-carbonitrile (123); 1-(5-(1-(4-hydroxybutyl)-1H-1,2,3-triazol-4-yl)-4-(isopropylamino)pyridin-2-yl)-1H-pyrazolo[3,4-b]pyridine-5-carbonitrile (124); 1-(5-(1-(5-hydroxypentyl)-1H-1,2,3-triazol-4-yl)-4-(isopropylamino)pyridin-2-yl)-1H-pyrazolo[3,4-b]pyridine-5-carbonitrile (125); 1-(5-(1-(2-(dimethylamino)ethyl)-1H-1,2,3-triazol-4-yl)-4-(isopropylamino)pyridin-2-yl)-1H-pyrazolo[3,4-b]pyridine-5-carbonitrile (126); 1-(4-(isopropylamino)-5-(1-(3-(pyrrolidin-1-yl)propyl)-1H-1,2,3-triazol-4-yl)pyridin-2-yl)-1H-pyrazolo[3,4-b]pyridine-5-carbonitrile (127); 1-(5-(1-(3-hydroxy-3-methylbutyl)-1H-1,2,3-triazol-4-yl)-4-(isopropylamino)pyridin-2-yl)-1H-pyrazolo[3,4-b]pyridine-5-carbonitrile (128); 1-(4-(isopropylamino)-5-(1-(3,3,3-trifluoro-2-hydroxypropyl)-1H-1,2,3-triazol-4-yl)pyridin-2-yl)-1H-pyrazolo[3,4-b]pyridine-5-carbonitrile (129); 1-(4-(isopropylamino)-5-(1-(3-phenylpropyl)-1H-1,2,3-triazol-4-yl) pyridin-2-yl)-1H-pyrazolo[3,4-b]pyridine-5-carbonitrile (130); 1-(5-(1-(2,3-dihydroxypropyl)-1H-1,2,3-triazol-4-yl)-4-(isopropylamino)pyridin-2-yl)-1H-pyrazolo[3,4-b]pyridine-5-carbonitrile (131); tert-butyl 4-((4-(6-(5-cyano-1H-pyrazolo[3,4-b] pyridin-1-yl)-4-(isopropylamino)pyridin-3-yl)-1H-1,2,3-triazol-1-yl)methyl)-4-hydroxypiperidine-1-carboxylate (132); 1-(5-(1-(2-hydroxy-3-methoxypropyl)-1H-1,2,3-triazol-4-yl)-4-(isopropylamino)pyridin-2-yl)-1H-pyrazolo[3,4-b]pyridine-5-carbonitrile (133); (S)-1-(5-(1-(2-hydroxybutyl)-1H-1,2,3-triazol-4-yl)-4-(isopropylamino)pyridin-2-yl)-1H-pyrazolo[3,4-b]pyridine-5-carbonitrile (134); 1-(5-(1-(2-hydroxy-3-methylbutyl)-1H-1,2,3-triazol-4-yl)-4-(isopropylamino)pyridin-2-yl)-1H-pyrazolo[3,4-b]pyridine-5-carbonitrile (135); 1-(5-(1-(2-hydroxy-3-(4-methoxyphenoxy)propyl)-1H-1,2,3-triazol-4-yl)-4-(isopropylamino)pyridin-2-yl)-1H-pyrazolo[3,4-b]pyridine-5-carbonitrile (136); 1-(5-(1-(3-ethoxy-2-hydroxypropyl)-1H-1,2,3-triazol-4-yl)-4-(isopropylamino)pyridin-2-yl)-1H-pyrazolo[3,4-b]pyridine-5-carbonitrile (137); 1-(5-(1-(azetidin-3-yl)-1H-1,2,3-triazol-4-yl)-4-(isopropylamino)pyridin-2-yl)-1H-pyrazolo[3,4-b]pyridine-5-carbonitrile (138); 1-(5-(1-(1-(2-cyclopropylacetyl)azetidin-3-yl)-1H-1,2,3-triazol-4-yl)-4-(isopropylamino)pyridin-2-yl)-1H-pyrazolo[3,4-b]pyridine-5-carbonitrile (139); 1-(5-(1-(1-trideuteroacetylazetidin-3-yl)-1H-1,2,3-triazol-4-yl)-4-(isopropylamino)pyridin-2-yl)-1H-pyrazolo[3,4-b]pyridine-5-carbonitrile (140); 1-(5-(1-(1-cyanoazetidin-3-yl)-1H-1,2,3-triazol-4-yl)-4-(isopropylamino)pyridin-2-yl)-1H-pyrazolo[3,4-b]pyridine-5-carbonitrile (141); methyl 3-(4-(6-(5-cyano-1H-pyrazolo[3,4-b]pyridin-1-yl)-4-(isopropylamino)pyridin-3-yl)-1H-1,2,3-triazol-1-yl)azetidine-1-carboxylate (142); 1-(5-(1-(1-benzoylazetidin-3-yl)-1H-1,2,3-triazol-4-yl)-4-(isopropylamino)pyridin-2-yl)-1H-pyrazolo[3,4-b]pyridine-5-carbonitrile (143); 1-(5-(1-(1-isobutyrylazetidin-3-yl)-1H-1,2,3-triazol-4-yl)-4-(isopropylamino)pyridin-2-yl)-1H-pyrazolo[3,4-b]pyridine-5-carbonitrile (144); 1-(5-(1-(1-(cyclopropanecarbonyl)azetidin-3-yl)-1H-1,2,3-triazol-4-yl)-4-(isopropylamino)pyridin-2-yl)-1H-pyrazolo[3,4-b]pyridine-5-carbonitrile (145); 1-(4-(isopropylamino)-5-(1-(1-pivaloylazetidin-3-yl)-1H-1,2,3-triazol-4-yl)pyridin-2-yl)-1H-pyrazolo[3,4-b]pyridine-5-carbonitrile (146); 1-(4-(isopropylamino)-5-(1-(1-(pyrimidin-2-yl)azetidin-3-yl)-1H-1,2,3-triazol-4-yl)pyridin-2-yl)-1H-pyrazolo[3,4-b] pyridine-5-carbonitrile (147); 1-(4-(isopropylamino)-5-(1-(1-(5-methyl-1,3,4-oxadiazol-2-yl)azetidin-3-yl)-1H-1,2,3-triazol-4-yl)pyridin-2-yl)-1H-pyrazolo[3,4-b]pyridine-5-carbonitrile (148); 1-(5-(1-(1-ethyl azetidin-3-yl)-1H-1,2,3-triazol-4-yl)-4-(isopropylamino)pyridin-2-yl)-1H-pyrazolo[3,4-b]pyridine-5-carbonitrile (149); 1-(4-(isopropylamino)-5-(1-(1-isopropylazetidin-3-yl)-1H-1,2,3-triazol-4-yl)pyridin-2-yl)-1H-pyrazolo[3,4-b]pyridine-5-carbonitrile (150); 1-(4-(isopropylamino)-5-(1-(1-methylazetidin-3-yl)-1H-1,2,3-triazol-4-yl)pyridin-2-yl)-1H-pyrazolo[3,4-b]pyridine-5-carbonitrile, 2TFA (151); 3-(4-(isopropylamino)-5-(1-(1-methylazetidin-3-yl)-1H-1,2,3-triazol-4-yl)pyridin-2-yl)-3H-imidazo[4,5-b]pyridine-6-carbonitrile (152); 3-(5-(1-(1-(2,2-difluoroethyl)azetidin-3-yl)-1H-1,2,3-triazol-4-yl)-4-(isopropylamino)pyridin-2-yl)-3H-imidazo[4,5-b]pyridine-6-carbonitrile (153); 1-(5-(1-(1-acetylazetidin-3-yl)-1H-1,2,3-triazol-4-yl)-4-(isopropylamino)pyridin-2-yl)-1H-pyrazolo[3,4-b]pyridine-5-carbonitrile (154); 1-(3-(4-(6-(5-chloro-1H-pyrazolo[3,4-b]pyridin-1-yl)-4-(isopropylamino)pyridin-3-yl)-1H-1,2,3-triazol-1-yl)azetidin-1-yl)ethanone (155); 3-(5-(1-(1-acetylazetidin-3-yl)-1H-1,2,3-triazol-4-yl)-4-(isopropylamino)pyridin-2-yl)-3H-imidazo[4,5-b]pyridine-6-carbonitrile (156); 1-(5-(1-(1-acetylpyrrolidin-3-yl)-1H-1,2,3-triazol-4-yl)-4-(isopropylamino)pyridin-2-yl)-1H-pyrazolo[3,4-b]pyridine-5-carbonitrile, enantiomer 1 (157) and enantiomer 2 (158); 1-(5-(1-(1-acetylpiperidin-4-yl)-1H-1,2,3-triazol-4-yl)-4-(isopropylamino)pyridin-2-yl)-1H-pyrazolo[3,4-b]pyridine-5-carbonitrile (159); 1-(5-(1-(1-acetylpiperidin-3-yl)-1H-1,2,3-triazol-4-yl)-4-(isopropylamino)pyridin-2-yl)-1H-pyrazolo[3,4-b]pyridine-5-carbonitrile, enantiomer 1 (160) and enantiomer 2 (161); 1-(5-(1-(1-acetylazetidin-3-yl)-1H-1,2,3-triazol-4-yl)-4-(isopropylamino)pyridin-2-yl)-1H-pyrrolo[2,3-b]pyridine-5-carbonitrile, TFA (162); 1-(4-(isopropylamino)-5-(1-(2-morpholinoethyl)-1H-1,2,3-triazol-4-yl)pyridin-2-yl)-1H-pyrrolo[2,3-b]pyridine-5-carbonitrile, 2TFA (163); 1-(4-(isopropylamino)-5-(1-methyl-1H-1,2,3-triazol-4-yl)pyridin-2-yl)-1H-pyrazolo[3,4-b]pyridine-5-carbonitrile (164); 2-(5-chloro-1H-pyrazolo[3,4-b]pyridin-1-yl)-N-isopropyl-5-(1-methyl-1H-1,2,3-triazol-4-yl)pyridin-4-amine (165); 1-(5-(1-(2-fluoropropyl)-1H-1,2,3-triazol-4-yl)-4-(isopropylamino)pyridin-2-yl)-1H-pyrazolo[3,4-b]pyridine-5-carbonitrile, enantiomer 1 (166) and enantiomer 2 (167); (S)-1-(5-(1-(2-amino-3-phenylpropyl)-1H-1,2,3-triazol-4-yl)-4-(isopropylamino)pyridin-2-yl)-1H-pyrazolo[3,4-b] pyridine-5-carbonitrile (168); (R)-1-(5-(1-(2-amino-3-phenylpropyl)-1H-1,2,3-triazol-4-yl)-4-(isopropylamino)pyridin-2-yl)-1H-pyrazolo[3,4-b]pyridine-5-carbonitrile (169); 1-(4-(isopropylamino)-5-(1-(2-oxopropyl)-1H-1,2,3-triazol-4-yl)pyridin-2-yl)-1H-pyrazolo[3,4-b]pyridine-5-carbonitrile (170); 1-(5-(1-(3-aminopropyl)-1H-1,2,3-triazol-4-yl)-4-(isopropylamino)pyridin-2-yl)-1H-pyrazolo[3,4-b]pyridine-5-carbonitrile (171); 1-(5-(1-(2-aminoethyl)-1H-1,2,3-triazol-4-yl)-4-(isopropylamino)pyridin-2-yl)-1H-pyrazolo[3,4-b]pyridine-5-carbonitrile (172); 1-(5-(1-(2-cyanophenyl)-1H-1,2,3-triazol-4-yl)-4-(isopropylamino)pyridin-2-yl)-1H-pyrazolo [3,4-b]pyridine-5-carbonitrile (173); 1-(4-(isopropylamino)-5-(1-(pyridin-3-yl)-1H-1,2,3-triazol-4-yl)pyridin-2-yl)-1H-pyrazolo[3,4-b]pyridine-5-carbonitrile (174); methyl 2-(4-(6-(5-cyano-1H-pyrazolo[3,4-b]pyridin-1-yl)-4-(isopropylamino)pyridin-3-yl)-1H-1,2,3-triazol-1-yl)benzoate (175); (3R,4S)-tert-butyl 4-(4-(6-(5-cyano-1H-pyrazolo[3,4-b] pyridin-1-yl)-4-(isopropylamino)

pyridin-3-yl)-1H-1,2,3-triazol-1-yl)-3-hydroxypiperidine-1-carboxylate (176); 1-(5-(1-((3R,4S)-3-hydroxypiperidin-4-yl)-1H-1,2,3-triazol-4-yl)-4-(isopropylamino)pyridin-2-yl)-1H-pyrazolo[3,4-b]pyridine-5-carbonitrile (177); 1-(5-(1-((3R,4S)-1-acetyl-3-hydroxypiperidin-4-yl)-1H-1,2,3-triazol-4-yl)-4-(isopropylamino)pyridin-2-yl)-1H-pyrazolo[3,4-b]pyridine-5-carbonitrile (178); 1-(5-(1-((3R,4S)-3-hydroxy-1-pivaloylpiperidin-4-yl)-1H-1,2,3-triazol-4-yl)-4-(isopropylamino)pyridin-2-yl)-1H-pyrazolo[3,4-b]pyridine-5-carbonitrile (179); (3R,4S)-ethyl 4-(4-(6-(5-cyano-1H-pyrazolo[3,4-b]pyridin-1-yl)-4-(isopropylamino)pyridin-3-yl)-1H-1,2,3-triazol-1-yl)-3-hydroxypiperidine-1-carboxylate (180); 1-(5-(1-((3R,4S)-3-hydroxy-1-(methylsulfonyl)piperidin-4-yl)-1H-1,2,3-triazol-4-yl)-4-(isopropylamino) pyridin-2-yl)-1H-pyrazolo[3,4-b]pyridine-5-carbonitrile (181); (3R,4S)-4-(4-(6-(5-cyano-1H-pyrazolo[3,4-b]pyridin-1-yl)-4-(isopropylamino) pyridin-3-yl)-1H-1,2,3-triazol-1-yl)-1-(methylsulfonyl)piperidin-3-yl methanesulfonate (182); 1-(5-(1-((3R,4S)-3-hydroxy-1-picolinoylpiperidin-4-yl)-1H-1,2,3-triazol-4-yl)-4-(isopropylamino)pyridin-2-yl)-1H-pyrazol[3,4-b]pyridine-5-carbonitrile (183); 1-(5-(1-((3R,4S)-3-hydroxy-1-nicotinoylpiperidin-4-yl)-1H-1,2,3-triazol-4-yl)-4-(isopropylamino)pyridin-2-yl)-1H-pyrazolo[3,4-b]pyridine-5-carbonitrile (184); 1-(5-(1-((3R,4 S)-3-hydroxy-1-isonicotinoylpiperidin-4-yl)-1H-1,2,3-triazol-4-yl)-4-(isopropylamino)pyridin-2-yl)-1H-pyrazolo[3,4-b]pyridine-5-carbonitrile (185); 1-(5-(1-((3 S,4R)-3-hydroxypiperidin-4-yl)-1H-1,2,3-triazol-4-yl)-4-(isopropylamino)pyridin-2-yl)-1H-pyrazolo[3,4-b]pyridine-5-carbonitrile (186); 1-(5-(1-((3 S,4R)-3-hydroxypiperidin-4-yl)-1H-1,2,3-triazol-4-yl)-4-(isopropylamino)pyridin-2-yl)-1H-pyrazolo[3,4-b]pyridine-5-carboxamide (187); 1-(5-(1-((3 S,4R)-3-hydroxy-1-(methylsulfonyl)piperidin-4-yl)-1H-1,2,3-triazol-4-yl)-4-(isopropylamino)pyridin-2-yl)-1H-pyrazolo[3,4-b]pyridine-5-carbonitrile (188); (3 S,4R)-ethyl 4-(4-(6-(5-cyano-1H-pyrazolo[3,4-b]pyridin-1-yl)-4-(isopropylamino)pyridin-3-yl)-1H-1,2,3-triazol-1-yl)-3-hydroxypiperidine-1-carboxylate (189); 1-(5-(1-((3 S,4R)-3-hydroxy-1-pivaloylpiperidin-4-yl)-1H-1,2,3-triazol-4-yl)-4-(isopropylamino)pyridin-2-yl)-1H-pyrazolo[3,4-b]pyridine-5-carbonitrile (190); 1-(5-(1-((3 S,4R)-1-acetyl-3-hydroxypiperidin-4-yl)-1H-1,2,3-triazol-4-yl)-4-(isopropylamino)pyridin-2-yl)-1H-pyrazolo[3,4-b]pyridine-5-carbonitrile (191); 1-(4-(isopropylamino)-5-(1-(2-oxo-2-(piperazin-1-yl)ethyl)-1H-1,2,3-triazol-4-yl)pyridin-2-yl)-1H-pyrazolo[3,4-b]pyridine-5-carbonitrile (192); 1-(4-(isopropylamino)-5-(1-(2-(4-(methylsulfonyl)piperazin-1-yl)-2-oxoethyl)-1H-1,2,3-triazol-4-yl)pyridin-2-yl)-1H-pyrazolo[3,4-b]pyridine-5-carbonitrile (193); 1-(5-(1-(2-(4-acetylpiperazin-1-yl)-2-oxoethyl)-1H-1,2,3-triazol-4-yl)-4-(isopropylamino)pyridin-2-yl)-1H-pyrazolo[3,4-b]pyridine-5-carbonitrile (194); 1-(4-(isopropylamino)-5-(1-(piperidin-4-yl)-1H-1,2,3-triazol-4-yl)pyridin-2-yl)-1H-pyrazolo[3,4-b]pyridine-5-carbonitrile (195); 1-(4-(isopropylamino)-5-(1-(1-(methylsulfonyl) piperidin-4-yl)-1H-1,2,3-triazol-4-yl)pyridin-2-yl)-1H-pyrazolo[3,4-b]pyridine-5-carbonitrile (196); 1-(5-(1-((trans)-1-acetyl-3-hydroxypiperidin-4-yl)-1H-1,2,3-triazol-4-yl)-4-(isopropylamino)pyridin-2-yl)-1H-pyrazolo[3,4-b]pyridine-5-carbonitrile (197); 1-(5-(1-((3R,4R)-1-acetyl-3-hydroxypiperidin-4-yl)-1H-1,2,3-triazol-4-yl)-4-(isopropylamino)pyridin-2-yl)-1H-pyrazolo[3,4-b]pyridine-5-carbonitrile, isomer 1 (198) and isomer 2 (203); 1-(5-(1-((3R,4R)-3-hydroxy-1-(methylsulfonyl)piperidin-4-yl)-1H-1,2,3-triazol-4-yl)-4-(isopropylamino)pyridin-2-yl)-1H-pyrazolo[3,4-b]pyridine-5-carbonitrile, isomer 1 (199) and isomer 2 (204); 1-(5-(1-((3R,4R)-3-hydroxy-1-pivaloylpiperidin-4-yl)-1H-1,2,3-triazol-4-yl)-4-(isopropylamino)pyridin-2-yl)-1H-pyrazolo[3,4-b]pyridine-5-carbonitrile, isomer 1 (200) and isomer 2 (206); methyl (3R,4R)-4-(4-(6-(5-cyano-1H-pyrazolo[3,4-b]pyridin-1-yl)-4-(isopropylamino)pyridin-3-yl)-1H-1,2,3-triazol-1-yl)-3-hydroxypiperidine-1-carboxylate, isomer 1 (201) and isomer 2 (205); (3R,4R)-4-(4-(6-(5-cyano-1H-pyrazolo[3,4-b]pyridin-1-yl)-4-(isopropylamino)pyridin-3-yl)-1H-1,2,3-triazol-1-yl)-1-(methylsulfonyl)piperidin-3-yl methanesulfonate (202); 1-(4-(cyclopropylamino)-5-(1-((trans)-4-hydroxypiperidin-3-yl)-1H-1,2,3-triazol-4-yl)pyridin-2-yl)-1H-pyrazolo[3,4-b]pyridine-5-carbonitrile (207); (trans)-methyl 4-(4-(6-(5-cyano-1H-pyrazolo[3,4-b] pyridin-1-yl)-4-(cyclopropylamino) pyridin-3-yl)-1H-1,2,3-triazol-1-yl)-3-hydroxy-3-methylpiperidine-1-carboxylate (208); 1-(5-(1-((cis)-3-fluoropiperidin-4-yl)-1H-1,2,3-triazol-4-yl)-4-(isopropylamino)pyridin-2-yl)-1H-pyrazolo[3,4-b]pyridine-5-carbonitrile (209); 1-(5-(1-((trans)-3-fluoro-1-(methylsulfonyl)piperidin-4-yl)-1H-1,2,3-triazol-4-yl)-4-(isopropylamino)pyridin-2-yl)-1H-pyrazolo[3,4-b]pyridine-5-carbonitrile, isomer 1 (210) and isomer 2 (211); tert-butyl ((trans)-4-(4-(6-(5-cyano-1H-pyrazolo[3,4-b]pyridin-1-yl)-4-(isopropylamino)pyridin-3-yl)-1H-1,2,3-triazol-1-yl)cyclohexyl)carbamate (212); 1-(5-(1-isopropyl-1H-1,2,3-triazol-4-yl)-4-(isopropylamino)pyridin-2-yl)-1H-pyrazolo[3,4-b]pyridine-5-carbonitrile (213); 1-(4-(isopropylamino)-5-(1-(tetrahydrofuran-3-yl)-1H-1,2,3-triazol-4-yl)pyridin-2-yl)-1H-pyrazolo[3,4-b]pyridine-5-carbonitrile, isomer 1 (214) and isomer 2 (215); 1-(5-(1-((1S,2R)-2-hydroxycyclohexyl)-1H-1,2,3-triazol-4-yl)-4-(isopropylamino) pyridin-2-yl)-1H-pyrazolo[3,4-b]pyridine-5-carbonitrile (216); 2-(5-chloro-1H-pyrazolo [3,4-b]pyridin-1-yl)-5-(1-isopentyl-1H-1,2,3-triazol-4-yl)-N-isopropylpyridin-4-amine (217); 2-(5-chloro-1H-pyrazolo[3,4-b]pyridin-1-yl)-N-isopropyl-5-(1-propyl-1H-1,2,3-triazol-4-yl)pyridin-4-amine (218); 1-(4-(Isopropylamino)-5-(1-propyl-1H-imidazol-4-yl)pyridin-2-yl)-1H-indazole-5-carbonitrile (219); 1-(5-(1H-imidazol-4-yl)-4-(isopropylamino)pyridin-2-yl)-1H-indazole-5-carbonitrile (220); 1-(5-(1-isobutyl-1H-imidazol-4-yl)-4-(isopropylamino)pyridin-2-yl)-1H-pyrazolo[3,4-b]pyridine-5-carbonitrile (221); (S)-1-(5-(1-(2-hydroxypropyl)-1H-imidazol-4-yl)-4-(isopropylamino) pyridin-2-yl)-1H-pyrazolo[3,4-b]pyridine-5-carbonitrile (222); 1-(5-(1-(1-acetylazetidin-3-yl)-1H-imidazol-4-yl)-4-(isopropylamino) pyridin-2-yl)-1H-pyrazolo[3,4-b] pyridine-5-carbonitrile (223); 1-(4-(isopropylamino)-5-(1-(pyridin-3-yl)-1H-imidazol-4-yl) pyridin-2-yl)-1H-pyrazolo[3,4-b]pyridine-5-carbonitrile (224); 1-(5-(1-isopropyl-1H-imidazol-4-yl)-4-(isopropylamino)pyridin-2-yl)-1H-pyrazolo[3,4-b]pyridine-5-carbonitrile (225); 1-(5-(1-(2,2-difluoroethyl)-1H-imidazol-4-yl)-4-(isopropylamino)pyridin-2-yl)-1H-pyrazolo[3,4-b]pyridine-5-carbonitrile (226); 1-(5-(1-ethyl-1H-imidazol-4-yl)-4-(isopropylamino)pyridin-2-yl)-1H-pyrazolo[3,4-b]pyridine-5-carbonitrile (227); (S)-1-(5-(1-(3-hydroxy-2-methylpropyl)-1H-imidazol-4-yl)-4-(isopropylamino) pyridin-2-yl)-1H-pyrazolo[3,4-b]pyridine-5-carbonitrile (228); 1-(5-(1-(cyclopropylmethyl)-1H-imidazol-4-yl)-4-(isopropylamino)pyridin-2-yl)-1H-pyrazolo[3,4-b] pyridine-5-carbonitrile (229); 1-(5-(1-benzyl-1H-imidazol-4-yl)-4-(isopropylamino)pyridin-2-yl)-1H-pyrazolo[3,4-b]pyridine-5-carbonitrile (230); 1-(4-(isopropylamino)-5-(1-(2-morpholino-2-oxoethyl)-1H-imidazol-4-yl)pyridin-2-yl)-1H-pyrazolo[3,4-b]pyridine-5-carbonitrile (231); 1-(5-(1-((3-hydroxyoxetan-3-yl)methyl)-1H-imidazol-4-yl)-4-(isopropylamino) pyridin-2-yl)-1H-pyrazolo[3,4-b] pyridine-5-carbonitrile (232); 1-(5-(1-(cyclobutylmethyl)-1H-imidazol-4-yl)-4-(isopropylamino)pyridin-2-yl)-1H- pyrazolo[3,4-b]pyridine-5-carbonitrile (233); 1-(5-(1-((1-acetylazetidin-3-yl)methyl)-1H-imidazol-4-yl)-4-(isopropylamino)pyridin-2-yl)-1H-pyrazolo[3,4-b]pyridine-5-carbonitrile (234); 1-(4-(isopropylamino)-5-(1-(pyridin-3-ylmethyl)-1H-imidazol-4-yl)pyridin-2-yl)-1H-pyrazolo[3,4-b]pyridine-5-carbonitrile (235); 1-(4-(isopropylamino)-5-(1-(oxetan-3-ylmethyl)-1H-imidazol-4-yl) pyridin-2-yl)-1H-pyrazolo[3,4-b]pyridine-5-carbonitrile (236); 2-(4-(6-(5-cyano-1H-pyrazolo[3,4-b]pyridin-1-yl)-4-(isopropylamino)pyridin-3-yl)-1H-imidazol-1-yl) acetamide (237); 2-(4-(6-(5-cyano-1H-pyrazolo[3,4-b]pyridin-1-yl)-4-(isopropylamino) pyridin-3-yl)-1H-imidazol-1-yl)-N-methylacetamide (238); 1-(4-(isopropylamino)-5-(1-(pyridin-2-ylmethyl)-1H-imidazol-4-yl)pyridin-2-yl)-1H-pyrazolo[3,4-b]pyridine-5-carbonitrile (239); 1-(5-(1-(3-hydroxy-3-methylbutyl)-1H-imidazol-4-yl)-4-(isopropylamino)pyridin-2-yl)-1H-pyrazolo[3,4-b]pyridine-5-carbonitrile (240); 1-(4-(isopropylamino)-5-(1-(3-phenylpropyl)-1H-imidazol-4-yl)pyridin-2-yl)-1H-pyrazolo[3,4-b] pyridine-5-carbonitrile (241); 1-(5-(4-(2-hydroxyethyl)-1H-pyrazol-1-yl)-4-(isopropylamino) pyridin-2-yl)-1H-pyrazolo[3,4-b]pyridine-5-carbonitrile (242); 1-(5-(4-benzyl-1H-pyrazol-1-yl)-4-(isopropylamino)pyridin-2-yl)-1H-pyrazolo[3,4-b]pyridine-5-carbonitrile (243); 1-(5-(4-isopropyl-1H-pyrazol-1-yl)-4-(isopropylamino)pyridin-2-yl)-1H-pyrazolo[3,4-b]pyridine-5-carbonitrile (244); 1-(4-(isopropylamino)-5-(4-(pyridin-2-yl)-1H-pyrazolo[3,4-b] pyridine-5-carbonitrile (245); 1-(4-(isopropylamino)-5-(3-methyl-1H-pyrazol-1-yl)pyridin-2-yl)-1H-pyrazolo[3,4-b] pyridine-5-carbonitrile (246); 1-(4-(isopropylamino)-5-(3-(trifluoromethyl)-1H-pyrazol-1-yl) pyridin-2-yl)-1H-pyrazolo[3,4-b]pyridine-5-carbonitrile (247); 1-(5-(3-cyano-1H-pyrazol-1-yl)-4-(isopropylamino)pyridin-2-yl)-1H-pyrazolo[3,4-b]pyridine-5-carbonitrile (248); 1-(4-(isopropylamino)-5-(3-(pyridin-3-yl)-1H-pyrazol-1-yl)pyridin-2-yl)-1H-pyrazolo[3,4-b]pyridine-5-carbonitrile (249); 1-(5-(3-(cyanomethyl)-1H-pyrazol-1-yl)-4-(isopropylamino)pyridin-2-yl)-1H-pyrazolo[3,4-b]pyridine-5-carbonitrile (250); 1-(5-(4-(3-aminopropyl)-1H-pyrazol-1-yl)-4-(isopropylamino)pyridin-2-yl)-1H-pyrazolo[3,4-b]pyridine-5-carbonitrile (251); 1-(5-(1-(2-hydroxyethyl)-1H-pyrazol-4-yl)-4-(isopropylamino)pyridin-2-yl)-1H-pyrazolo[3,4-b]pyridine-5-carbonitrile (252); 1-(5-(1-ethyl-1H-pyrazol-4-yl)-4-(isopropylamino)pyridin-2-yl)-1H-pyrazolo[3,4-b]pyridine-5-carbonitrile (253); 1-(4-(isopropylamino)-5-(1-(oxetan-3-ylmethyl)-1H-pyrazol-4-yl) pyridin-2-yl)-1H-pyrazolo[3,4-b]pyridine-5-carbonitrile (254); 1-(4-(isopropylamino)-5-(1-(2,2,2-trifluoroethyl)-1H-pyrazol-4-yl)pyridin-2-yl)-1H-pyrazolo[3,4-b]pyridine-5-carbonitrile (255); 1-(4-((1-(2,2-difluoroethyl)-1H-pyrazol-4-yl)amino)-5-(1-propyl-1H-pyrazol-4-yl) pyridin-2-yl)-1H-pyrazolo[3,4-b]pyridine-5-carbonitrile (256); 1-(4-(isopropylamino)-5-(1-(tetrahydro-2H-pyran-4-yl)-1H-pyrazol-4-yl)pyridin-2-yl)-1H-pyrazolo[3,4-b]pyridine-5-carbonitrile (257); 1-(5-(1-isobutyl-1H-pyrazol-4-yl)-4-(isopropylamino)pyridin-2-yl)-1H-pyrazolo[3,4-b]pyridine-5-carbonitrile (258); 1-(5-(1-cyclopropyl-1H-pyrazol-4-yl)-4-(isopropylamino) pyridin-2-yl)-1H-pyrazolo[3,4-b] pyridine-5-carbonitrile (259); 1-(5-(1-(difluoromethyl)-1H-pyrazol-4-yl)-4-(isopropylamino)pyridin-2-yl)-1H-pyrazolo[3,4-b]pyridine-5-carbonitrile (260); 1-(4-(isopropylamino)-5-(1-propyl-1H-pyrazol-4-yl)pyridin-2-yl)-1H-pyrazolo[3,4-b] pyridine-5-carbonitrile (261); N-isopropyl-2-(1H-pyrazolo[3,4-d]pyrimidin-1-yl)-5-(1-(2,2,2-trifluoroethyl)-1H-pyrazol-4-yl)pyridin-4-amine (262); 1-(4-(isopropylamino)-5-(4-propyl-1H-1,2,3-triazol-1-yl)pyridin-2-yl)-1H-pyrazolo[3,4-b]pyridine-5-carbonitrile (263); 1-(4-((2-hydroxy-2-methylpropyl)amino)-5-(4-(2-hydroxypropyl)-1H-1,2,3-triazol-1-yl)pyridin-2-yl)-1H-pyrazolo[3,4-b]pyridine-5-carbonitrile (264); 1-(5-(4-(2-hydroxypropyl)-1H-1,2,3-triazol-1-yl)-4-(isopropylamino)pyridin-2-yl)-1H-pyrazolo[3,4-b] pyridine-5-carbonitrile (268); 1-(5-(4-cyclopentyl-1H-1,2,3-triazol-1-yl)-4-(isopropylamino)pyridin-2-yl)-1H-pyrazolo[3,4-b]pyridine-5-carbonitrile (266); 1-(4-(isopropylamino)-5-(4-(methoxymethyl)-1H-1,2,3-triazol-1-yl)pyridin-2-yl)-1H-pyrazolo [3,4-b]pyridine-5-carbonitrile (267); 1-(4-((1-(2,2-difluoroethyl)-1H-pyrazol-4-yl) amino)-5-(4-propyl-1H-1,2,3-triazol-1-yl)pyridin-2-yl)-1H-pyrazolo[3,4-b] pyridine-5-carbonitrile (269); N-(1-(2,2-difluoroethyl)-1H-pyrazol-4-yl)-5-(4-propyl-1H-1,2,3-triazol-1-yl)-2-(1H-pyrazolo[3,4-d]pyrimidin-1-yl)pyridin-4-amine (270); (R)-1-(4-((1-hydroxypropan-2-yl)amino)-5-(4-propyl-1H-1,2,3-triazol-1-yl)pyridin-2-yl)-1H-pyrazolo[3,4-b]pyridine-5-carbonitrile (272); (S)-1-(4-((1-hydroxypropan-2-yl)amino)-5-(4-propyl-1H-1,2,3-triazol-1-yl)pyridin-2-yl)-1H-pyrazolo[3,4-b]pyridine-5-carbonitrile (273); 1-(4-(cyclopropylamino)-5-(4-(2-hydroxypropyl)-1H-1,2,3-triazol-1-yl)pyridin-2-yl)-1H-pyrazolo[3,4-b]pyridine-5-carbonitrile, enantiomer 1 (274) and enantiomer 2 (275); 1-(4-(oxetan-3-ylamino)-5-(4-propyl-1H-1,2,3-triazol-1-yl) pyridin-2-yl)-1H-pyrazolo[3,4-b]pyridine-5-carbonitrile (276); 3-(4-(oxetan-3-ylamino)-5-(4-propyl-1H-1,2,3-triazol-1-yl)-3H-imidazo[4,5-b]pyridine-6-carbonitrile (277); 3-(4-(isopropylamino)-5-(4-propyl-1H-1,2,3-triazol-1-yl)pyridin-2-yl)-3H-imidazo[4,5-b]pyridine-6-carbonitrile (278); 9-(4-(isopropylamino)-5-(4-propyl-1H-1,2,3-triazol-1-yl)pyridin-2-yl)-9H-purin-2-amine (279); 6-amino-1-(4-(isopropylamino)-5-(4-propyl-1H-1,2,3-triazol-1-yl)pyridin-2-yl)-1H-pyrazolo[3,4-b]pyridine-5-carbonitrile (280); 6-amino-1-(4-(oxetan-3-ylamino)-5-(4-propyl-1H-1,2,3-triazol-1-yl)pyridin-2-yl)-1H-pyrazolo[3,4-b] pyridine-5-carbonitrile (281); 2-(5-chloro-1H-pyrazolo[3,4-b]pyrazol-1-yl)-N-isopropyl-5-(4-propyl-1H-1,2,3-triazol-1-yl)pyridin-4-amine (282); 1-(5-(4-propyl-1H-1,2,3-triazol-1-yl)-4-((tetrahydro-2H-pyran-4-yl)amino)pyridin-2-yl)-1H-pyrazolo[3,4-b]pyridine-5-carbonitrile (283); 3-(4-(isopropylamino)-5-(4-(methoxymethyl)-1H-1,2,3-triazol-1-yl)pyridin-2-yl)-3H-imidazo[4,5-b]pyridine-6-carbonitrile (284); (S)-3-(4-((1-hydroxypropan-2-yl)amino)-5-(4-propyl-1H-1,2,3-triazol-1-yl)pyridin-2-yl)-3H-imidazo[4,5-b]pyridine-6-carbonitrile (285); (R)-3-(4-((1-hydroxypropan-2-yl)amino)-5-(4-propyl-1H-1,2,3-triazol-1-yl) pyridin-2-yl)-3H-imidazo[4,5-b]pyridine-6-carbonitrile (286); 1-(4-((2-hydroxy-2-methylpropyl)amino)-5-(4-propyl-1H-1,2,3-triazol-1-yl)pyridin-2-yl)-1H-pyrazolo[3,4-b] pyridine-5-carbonitrile (287); 3-(5-(4-(3-hydroxypropyl)-1H-1,2,3-triazol-1-yl)-4-(isopropylamino)pyridin-2-yl)-3H-imidazo[4,5-b]pyridine-6-carbonitrile (288); 1-(5-(4-(2-fluoropropyl)-1H-1,2,3-triazol-1-yl)-4-(isopropylamino)pyridin-2-yl)-1H-pyrazolo [3,4-b]pyridine-5-carbonitrile (289); 3-(5-(4-(2-fluoropropyl)-1H-1,2,3-triazol-1-yl)-4-(isopropylamino)pyridin-2-yl)-3H-imidazo[4,5-b]pyridine-6-carbonitrile (290); 3-(5-(4-(2-fluoropropyl)-1H-1,2,3-triazol-1-yl)-4-(isopropylamino)pyridin-2-yl)-3H-imidazo[4,5-b]pyridine-6-carbonitrile (291); 1-(5-(4-(2-fluoropropyl)-1H-1,2,3-triazol-1-yl)-4-(isopropylamino)pyridin-2-yl)-1H-pyrazolo[3,4-b]pyridine-5-carbonitrile (292); 9-(5-(4-(2-fluoropropyl)-1H-1,2,3-triazol-1-yl)-4-(isopropylamino)pyridin-2-yl)-9H-purin-2-amine (293); 1-(5-(4-(2-fluoropropyl)-1H-1,2,3-triazol-1-yl)-4-(isopropylamino)pyridin-2-yl)-1H-pyrazolo[3,4-b] pyridine-5-carbonitrile (294); 1-(5-(4-(hydroxymethyl)-1H-1,2,3-triazol-1-yl)-4-(isopropylamino)pyridin-2-yl)-1H-pyrazolo[3,4-b]pyridine-5-carbonitrile (295); 1-(5-(4-(3- hydroxypropyl)-1H-1,2,3-triazol-1-yl)-4-(isopropylamino)pyridin-2-yl)-1H-pyrazolo[3,4-b]pyridine-5-carbonitrile (296); 1-(4-(isopropylamino)-5-(4-phenyl-1H-1,2,3-triazol-1-yl)pyridin-2-yl)-1H-pyrazolo[3,4-b]pyridine-5-carbonitrile (297); 1-(5-(4-(2-hydroxypropan-2-yl)-1H-1,2,3-triazol-1-yl)-4-(isopropylamino)pyridin-2-yl)-1H-pyrazolo[3,4-b]pyridine-5-carbonitrile (298); 1-(4-(isopropylamino)-5-(4-(pyridin-3-yl)-1H-1,2,3-triazol-1-yl)pyridin-2-yl)-1H-pyrazolo[3,4-b]pyridine-5-carbonitrile (299); 1-(5-(4-cyclopropyl-1H-1,2,3-triazol-1-yl)-4-(isopropylamino)pyridin-2-yl)-1H-pyrazolo[3,4-b]pyridine-5-carbonitrile (300); 1-(4-(isopropylamino)-5-(4-(morpholinomethyl)-1H-1,2,3-triazol-1-yl)pyridin-2-yl)-1H-pyrazolo[3,4-b]pyridine-5-carbonitrile (301); 1-(5-(4-(2-hydroxyethyl)-1H-1,2,3-triazol-1-yl)-4-(isopropylamino) pyridin-2-yl)-1H-pyrazolo[3,4-b]pyridine-5-carbonitrile (302); 1-(5-(4-(2-hydroxybutyl)-1H-1,2,3-triazol-1-yl)-4-(isopropylamino)pyridin-2-yl)-1H-pyrazolo[3,4-b]pyridine-5-carbonitrile (303); 1-(4-(isopropylamino)-5-(4-(pyridin-2-yl)-1H-1,2,3-triazol-1-yl) pyridin-2-yl)-1H-pyrazolo[3,4-b]pyridine-5-carbonitrile (304); 1-(5-(4-isobutyl-1H-1,2,3-triazol-1-yl)-4-(isopropylamino)pyridin-2-yl)-1H-pyrazolo[3,4-b]pyridine-5-carbonitrile (305); 1-(5-(4-(2-hydroxy-2-methylpropyl)-1H-1,2,3-triazol-1-yl)-4-(isopropylamino)pyridin-2-yl)-1H-pyrazolo[3,4-b]pyridine-5-carbonitrile (306); 1-(5-(4-isopentyl-1H-1,2,3-triazol-1-yl)-4-(isopropylamino)pyridin-2-yl)-1H-pyrazolo[3,4-b]pyridine-5-carbonitrile (307); 1-(5-(4-((dimethylamino)methyl)-1H-1,2,3-triazol-1-yl)-4-(isopropylamino)pyridin-2-yl)-1H-pyrazolo[3,4-b]pyridine-5-carbonitrile (308); 1-(6-(5-cyano-1H-pyrazolo[3,4-b]pyridin-1-yl)-4-(isopropylamino)pyridin-3-yl)-1H-1,2,3-triazole-4-carboxamide (309); 1-(5-(4-(aminomethyl)-1H-1,2,3-triazol-1-yl)-4-(isopropylamino)pyridin-2-yl)-1H-pyrazolo[3,4-b]pyridine-5-carbonitrile (310); 1-(5-(4-(4-hydroxybutyl)-1H-1,2,3-triazol-1-yl)-4-(isopropylamino)pyridin-2-yl)-1H-pyrazolo [3,4-b]pyridine-5-carbonitrile (311); 1-(5-(4-(2-aminopropan-2-yl)-1H-1,2,3-triazol-1-yl)-4-(isopropylamino)pyridin-2-yl)-1H-pyrazolo[3,4-b]pyridine-5-carbonitrile (312); 1-((1-(6-(5-cyano-1H-pyrazolo[3,4-b]pyridin-1-yl)-4-(isopropylamino)pyridin-3-yl)-1H-1,2,3-triazol-4-yl)methyl)urea (313); 1-(4-(isopropylamino)-5-(4-((methylamino)methyl)-1H-1,2,3-triazol-1-yl)pyridin-2-yl)-1H-pyrazolo[3,4-b]pyridine-5-carbonitrile (314); (R)-1-(5-(4-(2-hydroxy-2-phenylethyl)-1H-1,2,3-triazol-1-yl)-4-(isopropylamino)pyridin-2-yl)-1H-pyrazolo[3,4-b]pyridine-5-carbonitrile (315); 1-(5-(4-(3,5-dimethoxyphenyl)-1H-1,2,3-triazol-1-yl)-4-(isopropylamino)pyridin-2-yl)-1H-pyrazolo[3,4-b]pyridine-5-carbonitrile (316); 1-(4-(isopropylamino)-5-(4-(1-methyl-1H-imidazol-5-yl)-1H-1,2,3-triazol-1-yl)pyridin-2-yl)-1H-pyrazolo[3,4-b]pyridine-5-carbonitrile (317); 1-(5-(4-(2-hydroxy-2-methylbutyl)-1H-1,2,3-triazol-1-yl)-4-(isopropylamino)pyridin-2-yl)-1H-pyrazolo[3,4-b]pyridine-5-carbonitrile (318); 1-(4-(isopropylamino)-5-(4-phenethyl-1H-1,2,3-triazol-1-yl)pyridin-2-yl)-1H-pyrazolo[3,4-b]pyridine-5-carbonitrile (319); 1-(5-(4-butyl-1H-1,2,3-triazol-1-yl)-4-(isopropylamino)pyridin-2-yl)-1H-pyrazolo[3,4-b] pyridine-5-carbonitrile (320); 1-(5-(4-(2-cyanoethyl)-1H-1,2,3-triazol-1-yl)-4-(isopropylamino)pyridin-2-yl)-1H-pyrazolo[3,4-b]pyridine-5-carbonitrile (321); 1-(5-(4-(2-hydroxybutan-2-yl)-1H-1,2,3-triazol-1-yl)-4-(isopropylamino)pyridin-2-yl)-1H-pyrazolo[3,4-b]pyridine-5-carbonitrile (322); 1-(5-(4-(3-cyanopropyl)-1H-1,2,3-triazol-1-yl)-4-(isopropylamino)pyridin-2-yl)-1H-pyrazolo[3,4-b]pyridine-5-carbonitrile (323); 1-(5-(4-((diethylamino)methyl)-1H-1,2,3-triazol-1-yl)-4-(isopropylamino)pyridin-2-yl)-1H-pyrazolo[3,4-b]pyridine-5-carbonitrile (324); 1-(5-(4-ethyl-1H-1,2,3-triazol-1-yl)-4-(isopropylamino)pyridin-2-yl)-1H-pyrazolo[3,4-b]pyridine-5-carbonitrile (325); 1-(4-(isopropylamino)-5-(4-(pyridin-4-yl)-1H-1,2,3-triazol-1-yl)pyridin-2-yl)-1H-pyrazolo [3,4-b]pyridine-5-carbonitrile (326); 1-(5-(4-(3-hydroxy-3-methylbutyl)-1H-1,2,3-triazol-1-yl)-4-(isopropylamino)pyridin-2-yl)-1H-pyrazolo[3,4-b]pyridine-5-carbonitrile (327); 1-(5-(4-(2-aminoethyl)-1H-1,2,3-triazol-1-yl)-4-(isopropylamino)pyridin-2-yl)-1H-pyrazolo[3,4-b]pyridine-5-carbonitrile (328); 1-(5-(4-(fluoromethyl)-1H-1,2,3-triazol-1-yl)-4-(isopropylamino)pyridin-2-yl)-1H-pyrazolo[3,4-b]pyridine-5-carbonitrile (329); 1-(5-(4-allyl-1H-1,2,3-triazol-1-yl)-4-(isopropylamino)pyridin-2-yl)-1H-pyrazolo[3,4-b]pyridine-5-carbonitrile (330); 1-(4-(isopropylamino)-5-(4-(2-oxopropyl)-1H-1,2,3-triazol-1-yl)pyridin-2-yl)-1H-pyrazolo[3,4-b]pyridine-5-carbonitrile (331); 1-(4-(isopropylamino)-5-(4-((phenylsulfonyl)methyl)-1H-1,2,3-triazol-1-yl)pyridin-2-yl)-1H-pyrazolo[3,4-b]pyridine-5-carbonitrile (332); tert-butyl 4-(1-(6-(5-cyano-1H-pyrazolo [3,4-b]pyridin-1-yl)-4-(isopropylamino)pyridin-3-yl)-1H-1,2,3-triazol-4-yl)piperidine-1-carboxylate (333); 1-(4-(isopropylamino)-5-(4-(piperidin-4-yl)-1H-1,2,3-triazol-1-yl) pyridin-2-yl)-1H-pyrazolo[3,4-b]pyridine-5-carbonitrile, 2 HCl (334); 1-(5-(4-(1-acetylpiperidin-4-yl)-1H-1,2,3-triazol-1-yl)-4-(isopropylamino)pyridin-2-yl)-1H-pyrazolo[3,4-b]pyridine-5-carbonitrile (335); 1-(5-(4-(1-(2,2-difluoroethyl)piperidin-4-yl)-1H-1,2,3-triazol-1-yl)-4-(isopropylamino)pyridin-2-yl)-1H-pyrazolo[3,4-b]pyridine-5-carbonitrile (336); 1-(4-(isopropylamino)-5-(4-(1-isopropylpiperidin-4-yl)-1H-1,2,3-triazol-1-yl)pyridin-2-yl)-1H-pyrazolo[3,4-b]pyridine-5-carbonitrile (337); methyl 4-(1-(6-(5-cyano-1H-pyrazolo[3,4-b]pyridin-1-yl)-4-(isopropylamino)pyridin-3-yl)-1H-1,2,3-triazol-4-yl)piperidine-1-carboxylate (338); 1-(5-(4-(1-acetylazetidin-3-yl)-1H-1,2,3-triazol-1-yl)-4-(isopropylamino)pyridin-2-yl)-1H-pyrazolo[3,4-b]pyridine-5-carbonitrile (339); 1-(5-(4-((1s,4s)-4-aminocyclohexyl)-1H-1,2,3-triazol-1-yl)-4-(isopropylamino) pyridin-2-yl)-1H-pyrazolo[3,4-b]pyridine-5-carbonitrile (340); N-((1s,4s)-4-(1-(6-(5-cyano-1H-pyrazolo[3,4-b]pyridin-1-yl)-4-(isopropylamino)pyridin-3-yl)-1H-1,2,3-triazol-4-yl) cyclohexyl)acetamide (341); tert-butyl ((1s,4s)-4-(1-(6-(5-cyano-1H-pyrazolo[3,4-b]pyridin-1-yl)-4-(isopropylamino) pyridin-3-yl)-1H-1,2,3-triazol-4-yl) cyclohexyl)carbamate (342); 1-(4-(isopropylamino)-5-(4-((1s,4s)-4-(isopropylamino) cyclohexyl)-1H-1,2,3-triazol-1-yl)pyridin-2-yl)-1H-pyrazolo[3,4-b]pyridine-5-carbonitrile (343); methyl ((1s,4s)-4-(1-(6-(5-cyano-1H-pyrazolo[3,4-b]pyridin-1-yl)-4-(isopropylamino)pyridin-3-yl)-1H-1,2,3-triazol-4-yl)cyclohexyl)carbamate (344); (+)-1-(5-(4-(2-fluoro-3-hydroxy-3-methylbutyl)-1H-1,2,3-triazol-1-yl)-4-(isopropylamino)pyridin-2-yl)-1H-pyrazolo[3,4-b]pyridine-5-carbonitrile (345); 1-(5-(4-(1-(ethylsulfonyl) piperidin-4-yl)-1H-1,2,3-triazol-1-yl)-4-(isopropylamino)pyridin-2-yl)-1H-pyrazolo [3,4-b]pyridine-5-carbonitrile (346); 1-(4-((3,3-difluorocyclopentyl)amino)-5-(4-(3-hydroxy-3-methylbutyl)-1H-1,2,3-triazol-1-yl)pyridin-2-yl)-1H-pyrazolo[3,4-b]pyridine-5-carbonitrile (347); 1-(4-(cyclopropylamino)-5-(4-(tetrahydro-2H-pyran-4-yl)-1H-1,2,3-triazol-1-yl)pyridin-2-yl)-1H-pyrazolo[3,4-b]pyridine-5-carbonitrile (348); 1-(4-(isopropylamino)-5-(4-(2-morpholinoethyl)-1H-1,2,3-triazol-1-yl)pyridin-2-yl)-1H-pyrazolo[3,4-b]pyridine-5-carbonitrile (349); 4-(1-(6-(6-amino-1H-pyrazolo[3,4-d]pyrimidin-1-yl)-4-(isopropylamino)pyridin-3-yl)-1H-1,2,3-triazol-4-yl)-2-methylbutan-2-ol (350); 1-(5-(4-(3-fluoro-3-methylbutyl)-1H-1,2,3-triazol-1-yl)-4-(isopropylamino) pyridin-2-yl)-1H-pyrazolo[3,4-d]pyrimidin-6-amine (351); methyl (2-(1-(6-(5-cyano-1H-pyrazolo[3,4-b]pyridin-1-yl)-

4-(isopropylamino)pyridin-3-yl)-1H-1,2,3-triazol-4-yl) ethyl)carbamate (352); 1-(4-(cyclopropylamino)-5-(4-(2-fluoropropyl)-1H-1,2,3-triazol-1-yl)pyridin-2-yl)-1H-pyrazolo[3,4-b]pyridine-5-carbonitrile, enantiomer 1 (353) and enantiomer 2 (354); 1-(4-(isopropylamino)-5-(4-(tetrahydro-2H-pyran-4-yl)-1H-1,2,3-triazol-1-yl)pyridin-2-yl)-1H-pyrazolo[3,4-b]pyridine-5-carbonitrile (355); 1-(5-(4-((1s,4s)-4-(ethylamino) cyclohexyl)-1H-1,2,3-triazol-1-yl)-4-(isopropylamino)pyridin-2-yl)-1H-pyrazolo[3,4-b]pyridine-5-carbonitrile (356); 4-(1-(6-(5-amino-H-pyrazolo[3,4-b]pyridin-1-yl)-4-(isopropylamino)pyridin-3-yl)-1H-1,2,3-triazol-4-yl)-2-methylbutan-2-ol (357); 1-(5-(4-((1s,4s)-4-((2,2-difluoroethyl)amino)cyclohexyl)-1H-1,2,3-triazol-1-yl)-4-(isopropylamino)pyridin-2-yl)-1H-pyrazolo[3,4-b]pyridine-5-carbonitrile (358); 1-(5-(4-(3-hydroxy-3-methylbutyl)-1H-1,2,3-triazol-1-yl)-4-(oxetan-3-ylamino)pyridin-2-yl)-1H-pyrazolo[3,4-b]pyridine-5-carbonitrile (359); 1-(5-(4-(1-(3-hydroxy-3-methylbutanoyl) piperidin-4-yl)-1H-1,2,3-triazol-1-yl)-4-(isopropylamino)pyridin-2-yl)-1H-pyrazolo[3,4-b]pyridine-5-carbonitrile (360); 1-(4-(isopropylamino)-5-(4-(1-(methylsulfonyl)piperidin-4-yl)-1H-1,2,3-triazol-1-yl)pyridin-2-yl)-1H-pyrazolo[3,4-b]pyridine-5-carbonitrile (361); 1-(5-(4-(3-hydroxy-3-methylbutyl)-1H-1,2,3-triazol-1-yl)-4-((3,3,3-trifluoropropyl)amino)pyridin-2-yl)-1H-pyrazolo[3,4-b]pyridine-5-carbonitrile (362); 1-(5-(4-(3-fluoro-3-methylbutyl)-1H-1,2,3-triazol-1-yl)-4-(oxetan-3-ylamino)pyridin-2-yl)-1H-pyrazolo[3,4-b]pyridine-5-carbonitrile (363); 1-(4-((3-fluorocyclopentyl)amino)-5-(4-(3-hydroxy-3-methylbutyl)-1H-1,2,3-triazol-1-yl)pyridin-2-yl)-1H-pyrazolo[3,4-b] pyridine-5-carbonitrile (364); (S)-1-(5-(4-(3-hydroxy-3-methylbutyl)-1H-1,2,3-triazol-1-yl)-4-((tetrahydrofuran-3-yl)amino)pyridin-2-yl)-1H-pyrazolo[3,4-b]pyridine-5-carbonitrile (365); (R)-1-(5-(4-(3-hydroxy-3-methylbutyl)-1H-1,2,3-triazol-1-yl)-4-((tetrahydrofuran-3-yl)amino)pyridin-2-yl)-1H-pyrazolo[3,4-b]pyridine-5-carbonitrile (366); 1-(4-((3,3-difluorocyclobutyl)amino)-5-(4-(3-hydroxy-3-methylbutyl)-1H-1,2,3-triazol-1-yl)pyridin-2-yl)-1H-pyrazolo[3,4-b]pyridine-5-carbonitrile (367); 1-(4-(((1 S,3 S)-3-fluorocyclopentyl)amino)-5-(4-(3-hydroxy-3-methylbutyl)-1H-1,2,3-triazol-1-yl)pyridin-2-yl)-1H-pyrazolo[3,4-b]pyridine-5-carbonitrile (368); 1-(4-(ethylamino)-5-(4-(3-hydroxy-3-methylbutyl)-1H-1,2,3-triazol-1-yl)pyridin-2-yl)-1H-pyrazolo[3,4-b] pyridine-5-carbonitrile (369); 1-(4-((3-fluoropropyl)amino)-5-(4-(3-hydroxy-3-methylbutyl)-1H-1,2,3-triazol-1-yl)pyridin-2-yl)-1H-pyrazolo[3,4-b]pyridine-5-carbonitrile (370); 6-amino-1-(5-(4-(3-hydroxy-3-methylbutyl)-1H-1,2,3-triazol-1-yl)-4-(isopropylamino)pyridin-2-yl)-1H-pyrazolo[3,4-b]pyridine-5-carbonitrile (371); 1-(4-(((1S,3R)-3-fluorocyclopentyl)amino)-5-(4-(3-hydroxy-3-methylbutyl)-1H-1,2,3-triazol-1-yl)pyridin-2-yl)-1H-pyrazolo[3,4-b]pyridine-5-carbonitrile (372); (R)-1-(5-(4-(3-fluoro-3-methylbutyl)-1H-1,2,3-triazol-1-yl)-4-((tetrahydrofuran-3-yl)amino)pyridin-2-yl)-1H-pyrazolo[3,4-b]pyridine-5-carbonitrile (373); 1-(4-(((1 r,4r)-4-fluorocyclohexyl) amino)-5-(4-(3-hydroxy-3-methylbutyl)-1H-1,2,3-triazol-1-yl)pyridin-2-yl)-1H-pyrazolo [3,4-b]pyridine-5-carbonitrile (374); 1-(4-(((1R,2S)-2-fluorocyclopentyl)amino)-5-(4-(3-hydroxy-3-methylbutyl)-1H-1,2,3-triazol-1-yl)pyridin-2-yl)-1H-pyrazolo[3,4-b]pyridine-5-carbonitrile (375); (S)-1-(5-(4-(3-hydroxy-3-methylbutyl)-1H-1,2,3-triazol-1-yl)-4-((1-hydroxypropan-2-yl)amino)pyridin-2-yl)-1H-pyrazolo[3,4-b]pyridine-5-carbonitrile (376); 1-(4-((1,3-difluoropropan-2-yl)amino)-5-(4-(3-hydroxy-3-methylbutyl)-1H-1,2,3-triazol-1-yl)pyridin-2-yl)-1H-pyrazolo[3,4-b]pyridine-5-carbonitrile (377); 4-(1-(6-(5-cyano-1H-pyrazolo[3,4-b]pyridin-1-yl)-4-(isopropylamino)pyridin-3-yl)-1H-1,2,3-triazol-4-yl)-2-methylbutan-2-yl glycinate (378); 1-(4-((4-fluorotetrahydrofuran-3-yl) amino)-5-(4-(3-hydroxy-3-methylbutyl)-1H-1,2,3-triazol-1-yl)pyridin-2-yl)-1H-pyrazolo [3,4-b]pyridine-5-carbonitrile (379); 1-(4-((1-hydroxy-2-methylpropan-2-yl)amino)-5-(4-(3-hydroxy-3-methylbutyl)-1H-1,2,3-triazol-1-yl)pyridin-2-yl)-1H-pyrazolo[3,4-b]pyridine-5-carbonitrile (381); 1-(5-(4-(3-hydroxy-3-methylbutyl)-1H-1,2,3-triazol-1-yl)-4-((1-methylcyclopropyl)amino) pyridin-2-yl)-1H-pyrazolo[3,4-b]pyridine-5-carbonitrile (383); 4-(1-(6-(5-cyano-1H-pyrazolo[3,4-b] pyridin-1-yl)-4-(isopropylamino)pyridin-3-yl)-1H-1,2,3-triazol-4-yl)-2-methylbutan-2-yl dimethylglycinate (384); 1-(5-(4-(3-hydroxy-3-methylbutyl)-1H-1,2,3-triazol-1-yl)-4-(((1 s,4s)-4-hydroxycyclohexyl)amino)pyridin-2-yl)-1H-pyrazolo[3,4-b]pyridine-5-carbonitrile (385); 1-(4-(isopropylamino)-5-(4-(1-(2,2,2-trifluoroacetyl)piperidin-4-yl)-1H-1,2,3-triazol-1-yl) pyridin-2-yl)-1H-pyrazolo[3,4-b]pyridine-5-carbonitrile (386); (S)-1-(5-(4-(3,4-dihydroxy-3-methylbutyl)-1H-1,2,3-triazol-1-yl)-4-(isopropylamino)pyridin-2-yl)-1H-pyrazolo[3,4-b]pyridine-5-carbonitrile (387); (R)-1-(5-(4-(3,4-dihydroxy-3-methylbutyl)-1H-1,2,3-triazol-1-yl)-4-(isopropylamino)pyridin-2-yl)-1H-pyrazolo[3,4-b]pyridine-5-carbonitrile (388); 1-(5-(4-(3-hydroxy-3-methylbutyl)-1H-1,2,3-triazol-1-yl)-4-(propylamino)pyridin-2-yl)-1H-pyrazolo[3,4-b]pyridine-5-carbonitrile (389); 1-(5-(4-(3-hydroxy-3-methylbutyl)-1H-pyrazol-1-yl)-4-(isopropylamino)pyridin-2-yl)-1H-pyrazolo[3,4-b]pyridine-5-carbonitrile (390); 1-(5-(1-((1r,4r)-4-aminocyclohexyl)-1H-1,2,3-triazol-4-yl)-4-(isopropylamino) pyridin-2-yl)-1H-pyrazolo[3,4-b]pyridine-5-carbonitrile (392); methyl ((1r,4r)-4-(4-(6-(5-cyano-1H-pyrazolo[3,4-b]pyridin-1-yl)-4-(isopropylamino)pyridin-3-yl)-1H-1,2,3-triazol-1-yl)cyclohexyl)carbamate (393); 1-(5-(1-((1r,4r)-4-((2,2-difluoroethyl)amino) cyclohexyl)-1H-1,2,3-triazol-4-yl)-4-(isopropylamino)pyridin-2-yl)-1H-pyrazolo[3,4-b]pyridine-5-carbonitrile (394); ethyl ((1r,4r)-4-(4-(6-(5-cyano-1H-pyrazolo[3,4-b] pyridin-1-yl)-4-(isopropylamino)pyridin-3-yl)-1H-1,2,3-triazol-1-yl)cyclohexyl)carbamate (395); 1-(5-(3-(azetidin-3-yl)isoxazol-5-yl)-4-(isopropylamino)pyridin-2-yl)-1H-pyrazolo[3,4-b] pyridine-5-carbonitrile (397); 1-(5-(3-(1-acetylazetidin-3-yl)isoxazol-5-yl)-4-(isopropylamino)pyridin-2-yl)-1H-pyrazolo[3,4-b] pyridine-5-carbonitrile (398); 1-(5-(3-(1,3-dihydroxypropan-2-yl)isoxazol-5-yl)-4-(isopropylamino) pyridin-2-yl)-1H-pyrazolo[3,4-b]pyridine-5-carbonitrile (399); 1-(4-(isopropylamino)-5-(3-(morpholin-3-yl)isoxazol-5-yl)pyridin-2-yl)-1H-pyrazolo[3,4-b]pyridine-5-carbonitrile (400); methyl 3-(5-(6-(5-cyano-1H-pyrazolo[3,4-b]pyridin-1-yl)-4-(isopropylamino)pyridin-3-yl)isoxazol-3-yl)azetidine-1-carboxylate (401); 1-(5-(3-(1-acetylpiperidin-4-yl)isoxazol-5-yl)-4-(isopropylamino) pyridin-2-yl)-1H-pyrazolo[3,4-b]pyridine-5-carbonitrile (402); 1-(4-(isopropylamino)-5-(3-(piperidin-4-yl)isoxazol-5-yl)pyridin-2-yl)-1H-pyrazolo[3,4-b]pyridine-5-carbonitrile (403); (S)-1-(4-(isopropylamino)-5-(3-(pyrrolidin-3-yl)isoxazol-5-yl)pyridin-2-yl)-1H-pyrazolo[3,4-b]pyridine-5-carbonitrile (404); (S)-1-(5-(3-(1-acetylpyrrolidin-3-yl)isoxazol-5-yl)-4-(isopropylamino)pyridin-2-yl)-1H-pyrazolo[3,4-b]pyridine-5-carbonitrile (405); (R)-1-(5-(3-(1-acetylpyrrolidin-3-yl)isoxazol-5-yl)-4-(isopropylamino)pyridin-2-yl)-1H-pyrazolo [3,4-b]pyridine-5-carbonitrile (406); (R)-1-(5-(3-(1-acetylpiperidin-3-yl)isoxazol-5-yl)-4-(isopropylamino)pyridin-2-yl)-1H-pyrazolo[3,4-b]pyridine-5-carbonitrile (407); methyl (R)-3-(5-(6-(5-cyano-1H-pyrazolo[3,4-b]pyridin-1-yl)-4-(isopropylamino)pyridin-3-yl)

isoxazol-3-yl)piperidine-1-carboxylate (408); (S)-1-(5-(3-(1-acetylpiperidin-3-yl) isoxazol-5-yl)-4-(isopropylamino)pyridin-2-yl)-1H-pyrazolo[3,4-b]pyridine-5-carbonitrile (409); N-((1s,4s)-4-(5-(6-(5-cyano-1H-pyrazolo[3,4-b]pyridin-1-yl)-4-(isopropylamino)pyridin-3-yl)isoxazol-3-yl)cyclohexyl)acetamide (410); methyl ((1s,4s)-4-(5-(6-(5-cyano-1H-pyrazolo[3,4-b]pyridin-1-yl)-4-(isopropylamino)pyridin-3-yl) isoxazol-3-yl)cyclohexyl)carbamate (411); (R)-1-(4-(isopropylamino)-5-(3-(piperidin-2-yl)isoxazol-5-yl)pyridin-2-yl)-1H-pyrazolo[3,4-b]pyridine-5-carbonitrile (412); (S)-1-(4-(isopropylamino)-5-(3-(piperidin-2-yl)isoxazol-5-yl)pyridin-2-yl)-1H-pyrazolo[3,4-b] pyridine-5-carbonitrile (413); 1-(4-(isopropylamino)-5-(3-(3-(methylamino)propyl) isoxazol-5-yl)pyridin-2-yl)-1H-pyrazolo[3,4-b]pyridine-5-carbonitrile (414); N-(3-(5-(6-(5-cyano-1H-pyrazolo[3,4-b]pyridin-1-yl)-4-(isopropylamino)pyridin-3-yl)isoxazol-3-yl) propyl)-N-methylacetamide (415); 1-(4-(isopropylamino)-5-(3-(tetrahydro-2H-pyran-3-yl)isoxazol-5-yl)pyridin-2-yl)-1H-pyrazolo[3,4-b]pyridine-5-carbonitrile (416); (R)-1-(5-(3-(1-acetylpyrrolidin-2-yl) isoxazol-5-yl)-4-(isopropylamino)pyridin-2-yl)-1H-pyrazolo [3,4-b]pyridine-5-carbonitrile (417); 1-(4-(isopropylamino)-5-(3-(tetrahydro-2H-pyran-4-yl)isoxazol-5-yl)pyridin-2-yl)-1H-pyrazolo[3,4-b]pyridine-5-carbonitrile (418); 1-(5-(3-(8-acetyl-8-azabicyclo[3.2.1] octan-3-yl)isoxazol-5-yl)-4-(isopropylamino)pyridin-2-yl)-1H-pyrazolo[3,4-b]pyridine-5-carbonitrile (419); (R)-1-(5-(3-(2,2-dimethyl-1,3-dioxolan-4-yl)isoxazol-5-yl)-4-(isopropylamino)pyridin-2-yl)-1H-pyrazolo[3,4-b]pyridine-5-carbonitrile (420); 1-(5-(3-(1-acetyl-4-fluoropiperidin-4-yl)isoxazol-5-yl)-4-(isopropylamino)pyridin-2-yl)-1H-pyrazolo[3,4-b]pyridine-5-carbonitrile (421); 1-(5-(3-(4,4-difluoropiperidin-2-yl)isoxazol-5-yl)-4-(isopropylamino)pyridin-2-yl)-1H-pyrazolo [3,4-b]pyridine-5-carbonitrile (422); 1-(5-(3-(6,6-dimethylmorpholin-3-yl)isoxazol-5-yl)-4-(isopropylamino)pyridin-2-yl)-1H-pyrazolo[3,4-b]pyridine-5-carbonitrile (423); 1-(5-(3-((2S,4R)-4-hydroxypiperidin-2-yl)isoxazol-5-yl)-4-(isopropylamino)pyridin-2-yl)-1H-pyrazolo[3,4-b]pyridine-5-carbonitrile (424); 1-(5-(3-((2R,4 S)-4-hydroxypiperidin-2-yl)isoxazol-5-yl)-4-(isopropylamino)pyridin-2-yl)-1H-pyrazolo[3,4-b]pyridine-5-carbonitrile (425); 1-(5-(3-(3-hydroxy-3-methylbutyl) isoxazol-5-yl)-4-(isopropylamino) pyridin-2-yl)-1H-pyrazolo[3,4-b]pyridine-5-carbonitrile (426); (S)-1-(5-(3-(1-acetylazetidin-2-yl)isoxazol-5-yl)-4-(isopropylamino)pyridin-2-yl)-1H-pyrazolo[3,4-b] pyridine-5-carbonitrile (427); (S)-1-(4-(isopropylamino)-5-(5-(morpholin-3-yl)isoxazol-3-yl)pyridin-2-yl)-1H-pyrazolo[3,4-b]pyridine-5-carbonitrile (428); 1-(5-(5-(3-hydroxy-3-methylbutyl)isoxazol-3-yl)-4-(isopropylamino)pyridin-2-yl)-1H-pyrazolo[3,4-b] pyridine-5-carbonitrile (429); (S)-1-(4-(isopropylamino)-5-(5-(piperidin-2-yl)isoxazol-3-yl) pyridin-2-yl)-1H-pyrazolo[3,4-b]pyridine-5-carbonitrile (430); (S)-1-(5-(5-(4-ethylmorpholin-3-yl)isoxazol-3-yl)-4-(isopropylamino)pyridin-2-yl)-1H-pyrazolo[3,4-b] pyridine-5-carbonitrile (431); (S)-1-(4-(isopropylamino)-5-(5-(1-(methylsulfonyl) piperidin-2-yl)isoxazol-3-yl)pyridin-2-yl)-1H-pyrazolo[3,4-b]pyridine-5-carbonitrile (432); 1-(4-(isopropylamino)-5-(5-(morpholine-4-carbonyl)-1,3,4-oxadiazol-2-yl)pyridin-2-yl)-1H-pyrazolo[3,4-b]pyridine-5-carbonitrile (433); 1-(5-(5-(((1r,4r)-4-aminocyclohexyl)amino)-1,3,4-oxadiazol-2-yl)-4-(isopropylamino)pyridin-2-yl)-1H-pyrazolo[3,4-b]pyridine-5-carbonitrile (434); 1-(5-(5-(3-hydroxy-3-methylbutyl)-4,5-dihydroisoxazol-3-yl)-4-(isopropylamino)pyridin-2-yl)-1H-pyrazolo[3,4-b]pyridine-5-carbonitrile (435); methyl ((3-(6-(5-cyano-1H-pyrazolo[3,4-b]pyridin-1-yl)-4-(isopropylamino)pyridin-3-yl)-4,5-dihydroisoxazol-5-yl)methyl)carbamate (436); 1-(5-(5-(2-hydroxy-2-methylpropyl) isoxazol-3-yl)-4-(isopropylamino)pyridin-2-yl)-1H-pyrazolo[3,4-b]pyridine-5-carbonitrile, enantiomer 1 and enantiomer 2; 1-(4-(ethylamino)-5-(5-(3-hydroxy-3-methylbutyl)-4,5-dihydroisoxazol-3-yl)pyridin-2-yl)-1H-pyrazolo[3,4-b] pyridine-5-carbonitrile, enantiomer 1 (440) and enantiomer 2 (441); and 1-(4-((2,2-difluoroethyl)amino)-5-(5-(3-hydroxy-3-methylbutyl)-4,5-dihydroisoxazol-3-yl)pyridin-2-yl)-1H-pyrazolo[3,4-b]pyridine-5-carbonitrile, enantiomer 1 (442) and enantiomer 2 (443).

11. A pharmaceutical composition comprising one or more compounds according to claim 1 and a pharmaceutically acceptable carrier or diluent.

12. A method of treating a disease, comprising administering to a patient a therapeutically-effective amount of a compound according to claim 1, wherein the disease is selected from Crohn's disease, ulcerative colitis, asthma, graft versus host disease, allograft rejection, chronic obstructive pulmonary disease, Graves' disease, rheumatoid arthritis, systemic lupus erythematosus, lupus nephritis, cutaneous lupus, psoriasis, cryopyrin-associated periodic syndromes, TNF receptor associated periodic syndrome, familial Mediterranean fever, adult onset stills, systemic onset juvenile idiopathic arthritis, multiple sclerosis, neuropathic pain, gout, and gouty arthritis.

13. The method according to claim 12, wherein the disease is selected from Crohn's disease, ulcerative colitis, rheumatoid arthritis, systemic lupus erythematosus, lupus nephritis, cutaneous lupus, psoriasis, gout, and gouty arthritis.

* * * * *

UNITED STATES PATENT AND TRADEMARK OFFICE
CERTIFICATE OF CORRECTION

PATENT NO. : 10,294,229 B2
APPLICATION NO. : 15/738362
DATED : May 21, 2019
INVENTOR(S) : Daniel S. Gardner et al.

Page 1 of 2

It is certified that error appears in the above-identified patent and that said Letters Patent is hereby corrected as shown below:

On the Title Page

Column 1 (Inventors), Line 9, delete "MA (US)" and insert -- MD (US) --, therefor.

Column 2 (Abstract), Line 2, delete "[2,3-b]" and insert -- [2,3b] --, therefor.

In the Specification

Column 1, Line 7, after "application" insert -- is a 371 application of International Application No. PCT/US2016/038858 filed on June 23, 2016, which --.

Column 1, Line 9, delete "which is incorporated herein in its entirety." and insert -- the content of each is hereby fully incorporated by reference in its entirety for all purposes. --, therefor.

In the Claims

Claim 10, Column 331, Line 25, delete "4 S)" and insert -- 4S) --, therefor.

Claim 10, Column 331, Line 28, delete "((3 S," and insert -- ((3S, --, therefor.

Claim 10, Column 331, Line 31, delete "((3 S," and insert -- ((3S, --, therefor.

Claim 10, Column 331, Line 33, delete "((3 S," and insert -- ((3S, --, therefor.

Claim 10, Column 331, Line 36, delete "(3 S," and insert -- (3S, --, therefor.

Claim 10, Column 331, Line 39, delete "((3 S," and insert -- ((3S, --, therefor.

Claim 10, Column 331, Line 42, delete "((3 S," and insert -- ((3S, --, therefor.

Signed and Sealed this
Seventeenth Day of September, 2019

Andrei Iancu
*Director of the United States Patent and Trademark Office*

CERTIFICATE OF CORRECTION (continued)
U.S. Pat. No. 10,294,229 B2

Claim 10, Column 333, Line 27, after "1H-" insert -- pyrazol-1-yl)pyridin-2-yl)-1H- --.

Claim 10, Column 336, Lines 46-47, delete "((1 s," and insert -- ((1s, --, therefor.

Claim 10, Column 336, Line 49, delete "(+)" and insert -- (±) --, therefor.

Claim 10, Column 337, Line 10, delete "-H-" and insert -- -1H- --, therefor.

Claim 10, Column 337, Line 40, delete "(((1 S," and insert -- (((1S, --, therefor.

Claim 10, Column 338, Line 15, delete "(((1 s," and insert -- (((1s, --, therefor.

Claim 10, Column 339, Line 40, delete "4 S)" and insert -- 4S) --, therefor.